US008084481B2

(12) United States Patent
Meier et al.

(10) Patent No.: US 8,084,481 B2
(45) Date of Patent: Dec. 27, 2011

(54) SUBSTITUTED ARYLIMIDAZOLONE AND TRIAZOLONE AS INHIBITORS OF VASOPRESSIN RECEPTORS

(75) Inventors: Heinrich Meier, Wuppertal (DE); Eckhard Bender, Langenfeld (DE); Ulf Brüggemeier, Leichlingen (DE); Ingo Flamme, Reichshof (DE); Dagmar Karthaus, Solingen (DE); Peter Kolkhof, Wuppertal (DE); Daniel Meibom, Leverkusen (DE); Dirk Schneider, Wuppertal (DE); Verena Voehringer, Wuppertal (DE); Chantal Fürstner, Mülheim/Ruhr (DE); Jörg Keldenich, Wuppertal (DE); Dieter Lang, Velbert (DE); Elisabeth Pook, Wuppertal (DE); Carsten Schmeck, Mülheim (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 195 days.

(21) Appl. No.: 12/301,616

(22) PCT Filed: May 21, 2007

(86) PCT No.: PCT/EP2007/004615
§ 371 (c)(1),
(2), (4) Date: Jun. 15, 2009

(87) PCT Pub. No.: WO2007/134862
PCT Pub. Date: Nov. 29, 2007

(65) Prior Publication Data
US 2009/0312381 A1   Dec. 17, 2009

(30) Foreign Application Priority Data
May 23, 2006 (DE) .......................... 10 2006 024 024

(51) Int. Cl.
*A61K 31/41* (2006.01)
*A61K 31/415* (2006.01)
*C07D 249/00* (2006.01)
*C07D 233/00* (2006.01)

(52) U.S. Cl. ............... 514/383; 514/385; 548/262.2; 548/300.1

(58) Field of Classification Search .............. 514/383, 514/385; 548/262.2, 300.1
See application file for complete search history.

(56) References Cited

U.S. PATENT DOCUMENTS

| 5,276,049 A | 1/1994 | Himmelsbach et al. |
| 5,468,448 A | 11/1995 | Wahi et al. |
| 5,585,394 A | 12/1996 | Di Malta et al. |
| 5,681,841 A | 10/1997 | Himmelsbach et al. |
| 6,531,142 B1 | 3/2003 | Rabe et al. |
| 6,746,989 B1 | 6/2004 | Muller et al. |
| 6,762,152 B1 | 7/2004 | Muller et al. |
| 6,838,415 B1 | 1/2005 | Muller et al. |
| 2002/0045651 A1 | 4/2002 | Brenner et al. |
| 2002/0172644 A1 | 11/2002 | Haslwanter et al. |
| 2003/0161790 A1 | 8/2003 | Wahi et al. |
| 2004/0071757 A1 | 4/2004 | Rolf et al. |
| 2006/0148779 A1* | 7/2006 | Bell et al. ............. 514/211.03 |
| 2008/0095863 A1 | 4/2008 | Kabra et al. |
| 2010/0261771 A1* | 10/2010 | Bruggemeier et al. ....... 514/376 |

FOREIGN PATENT DOCUMENTS

| CA | 2327784 A1 | 3/2008 |
| EP | 051829 | 5/1982 |
| EP | 0412594 A2 | 7/1990 |
| EP | 0533276 A1 | 3/1993 |
| WO | 9931099 A1 | 6/1999 |
| WO | 0100595 A1 | 1/2001 |
| WO | WO-02/066447 | 8/2002 |
| WO | WO-2005/006892 | 1/2005 |
| WO | WO-2005/007112 | 1/2005 |
| WO | WO-2005/086836 | 9/2005 |
| WO | WO 2005/105779 | 11/2005 |
| WO | 2006066133 A2 | 6/2006 |
| WO | 2006117657 A1 | 11/2006 |

OTHER PUBLICATIONS

R. W. Schrier, M.D. et al., "Hormones and Hemodynamics in Hear Failure," New England Journal of Medicine, vol. 341, No. 8, (1999), pp. 577-585.
L. De Luca, M.D. et al., "Hyponatremia in Patients with Heart Failure," American Journal of Cardiology 2005; 96 Supp., 19L-23L.
G. S. Francis, M.D. et al, "Comparison of Neuroendocrine Activation in Patients with Left Ventricular Dysfunction with and without Congestive Heart Failure," Circulation, 1990; pp. 1724-1929.
P. Sanghi et al., "Vasopressin Antagonism: a Future Treatment Option in Heart Failure," The European Society of Cardiology, 2005, pp. 538-543.
J. J. Bronson et al., "Discovery of the first Antibacterial Small Molecule Inhibitors of MurB," Bioorganic & Medicinal Chemistry Letters 13, 2003, pp. 873-875.
Lemmens-Gruber, et al.: Vasopressin antagonists, Cell. Mol. Life Sci. 63 (2006) 1766-1779.
Tang et al.,: Vasopressin receptor antagonists in the management of acute heart failure, Expert Opin. Investig. Drugs, 2005, 14:5, pp. 593-600.
Palm et al., Vasopressin Antagonists as Aquaretic Agents for the Treatment of Hyponatremia, Am. J. Med. (2006) vol. 119 (7A) S87-S92.
U.S. Appl. No. 13/132,897, filed Jun. 15, 2009.
U.S. Appl. No. 12/727,044, filed Feb. 16, 2011.

(Continued)

*Primary Examiner* — Susannah Chung
(74) *Attorney, Agent, or Firm* — Karen B. King

(57) ABSTRACT

The present application relates to novel, substituted 4-arylimidazol-2-ones and 5-aryl-1,2,4-triazolones, processes for the production thereof, the use thereof alone or in combinations for the treatment and/or prevention of diseases and the use thereof for the production of medicaments for the treatment and/or prevention of diseases, in particular for the treatment and/or prevention of cardiovascular diseases.

11 Claims, No Drawings

OTHER PUBLICATIONS

Francis et al., "Comparison of Neuroendocrine Activation in Patients with Left Ventricular Dysfunction with and without Congestive Heart Failure," Circulation 1990, vol. 82, 1724-1729.

English translation of WO 2001/00595, filed as U.S. Appl. No. 10/019,247 on Dec. 18, 2001.

* cited by examiner

SUBSTITUTED ARYLIMIDAZOLONE AND TRIAZOLONE AS INHIBITORS OF VASOPRESSIN RECEPTORS

RELATED APPLICATIONS/PATENTS AND INCORPORATION BY REFERENCE

This application is a National Stage Application filed under 35 U.S.C. §371 based on International Application No. PCT/EP2007/004615, filed May 21, 2007, which claims priority to German Patent Application Number 102006024024.3, filed May 23, 2006, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel, substituted 4-arylimidazol-2-ones and 5-aryl-1,2,4-triazolones, processes for the production thereof, the use thereof alone or in combinations for the treatment and/or prevention of diseases and the use thereof for the production of medicaments for the treatment and/or prevention of diseases, in particular for the treatment and/or prevention of cardiovascular diseases.

The liquid content of the human body is subject to various physiological control mechanisms the purpose whereof is to keep it constant (volume homeostasis). In the process, both the volume filling of the vascular system and also the osmolarity of the plasma are continuously recorded by appropriate sensors (baroreceptors and osmoreceptors). The information which these sensors supply to the relevant centres in the brain regulate drinking behaviour and control fluid excretion via the kidneys by means of humoral and neural signals. The peptide hormone vasopressin is of central importance in this [Schrier R. W., Abraham, W. T., *New Engl. J. Med.* 341, 577-585 (1999)].

Vasopressin is produced in specialized endocrine neurones in the *Nucleus supraopticus* and *N. paraventricularis* in the wall of the third ventricle (hypothalamus) and transported from there along its neural processes into the posterior lobes of the hypophysis (neurohypophysis). There the hormone is released into the bloodstream according to stimulus. A loss of volume, e.g. as a result of acute bleeding, heavy sweating, prolonged thirst or diarrhoea, is a stimulus for intensified outpouring of the hormone. Conversely, the secretion of vasopressin is inhibited by an increase in the intravascular volume, e.g. as result of increased fluid intake.

Vasopressin exerts its action mainly via binding to three receptors, which are classified as V1a, V1b and V2 receptors and belong to the family of G protein-coupled receptors. V1a receptors are mainly located on the cells of the vascular smooth musculature. Their activation gives rise to vasoconstriction, as a result of which the peripheral resistance and blood pressure rise. Apart from this, V1a receptors are also detectable in the liver. V1b receptors (also named V3 receptors) are detectable in the central nervous system. Together with corticotropin-releasing hormone (CRH), vasopressin regulates the basal and stress-induced secretion of adrenocorticotropic hormone (ACTH) via the V1b receptor. V2 receptors are located in the distal tubular epithelium and the epithelium of the renal collecting tubules in the kidney. Their activation renders these epithelia permeable to water. This phenomenon is due to the incorporation of aquaporins (special water channels) in the luminal membrane of the epithelial cells.

The importance of vasopressin for the reabsorption of water from the urine in the kidney becomes clear from the clinical picture of diabetes insipidus, which is caused by a deficiency of the hormone, e.g. owing to hypophysis damage. Patients who suffer from this clinical picture excrete up to 20 litres of urine per 24 hours if they are not given replacement hormone. This volume corresponds to about 10% of the primary urine. Because of its great importance for the reabsorption of water from the urine, vasopressin is also synonymously referred to as antidiuretic hormone (ADH). Logically, pharmacological inhibition of the action of vasopressin/ADH on the V2 receptor results in increased urine excretion. In contrast to the action of other diuretics (thiazides and loop diuretics), however, V2 receptor antagonists cause increased water excretion, without substantially increasing the excretion of electrolytes. This means that by means of V2 antagonist drugs, volume homeostasis can be restored, without in the process affecting electrolyte homeostasis. Hence drugs with V2 antagonist activity appear particularly suitable for the treatment of all disease conditions which are associated with an overloading of the body with water, without the electrolytes being effectively increased in parallel. A significant electrolyte abnormality is measurable in clinical chemistry as hyponatraemia (sodium concentration <135 mmol/L); it is the most important electrolyte abnormality in hospital patients, with an incidence of ca. 5% or 250,000 cases per year in the USA alone. If the plasma sodium concentration falls below 115 mmol/L, comatose states and death are imminent.

Depending on the underlying cause, a distinction is made between hypovolaemic, euvolaemic and hypervolaemic hyponatraemia. The forms of hypervolaemia with oedema formation are clinically significant. Typical examples of this are syndrome of inappropriate ADH/vasopressin secretion (SIAD) (e.g. after craniocerebral trauma or as paraneoplasia in carcinomas) and hypervolaemic hyponatraemia in liver cirrhosis, various renal diseases and cardiac insufficiency [De Luca L. et al., *Am. J. Cardiol.* 96 (suppl.), 19L-23L (2005)]. In particular, patients with cardiac insufficiency, in spite of their relative hyponatraemia and hypervolaemia, often display elevated vasopressin levels, which is seen as the consequence of generally disturbed neurohumoral regulation in cardiac insufficiency [Francis G. S. et al., *Circulation* 82, 1724-1729 (1990)].

The disturbed neurohormonal regulation essentially manifests itself in an elevation of the sympathetic tone and in appropriate activation of the renin-angiotensin-aldosterone system. While the inhibition of these components by beta receptor blockers on the one hand and by ACE inhibitors or angiotensin receptor blockers on the other is now a firm component of the pharmacological treatment of cardiac insufficiency, the inappropriate elevation of vasopressin secretion in advanced cardiac insufficiency is at present still not adequately treatable. Apart from the retention of water mediated by V2 receptors and the unfavourable haemodynamic consequences associated therewith in terms of increased backload, the emptying of the left ventricle, the pressure in the pulmonary blood vessels and cardiac output are also adversely affected by vasoconstriction mediated by V1a receptors. Furthermore, on the basis of experimental data in animals, a direct hypertrophy-promoting action on the heart muscle is also attributed to vasopressin. In contrast to the renal effect of volume expansion, which is mediated by activation of V2 receptors, the direct action on the heart muscle is triggered by activation of V1a receptors.

For these reasons, substances which inhibit the action of vasopressin on the V2 and/or on the V1a receptor appear suitable for the treatment of cardiac insufficiency. In particular, compounds with combined activity on both vasopressin receptors (V1a and V2) should both have desirable renal and also haemodynamic effects and thus offer an especially ideal profile for the treatment of patients with cardiac insufficiency. The provision of such combined vasopressin antagonists also appears to make sense inasmuch as a volume diminution mediated solely via V2 receptor blockade can entail the stimulation of osmoreceptors and as a result a further compensatory increase in vasopressin release. As a result, in the absence of a component simultaneously blocking the V1a receptor, the harmful effects of the vasopressin, such as for example vasoconstriction and heart muscle atrophy, could be further intensified [Saghi P. et al., Europ. Heart J. 26, 538-543 (2005)].

The synthesis of certain imidazolinoneacetamide derivates and their antibacterial action is reported in J. J. Bronson et al., Bioorg. Med. Chem. Lett. 13, 873-875 (2003). Imidazolinonealkanoic acids with pharmacological activity are described in EP 051 829-A1. In WO 99/54315, substituted triazolones with neuroprotective activity are disclosed, and in WO 2006/117657 triazolone derivates as anti-inflammatory agents are described. Further, in EP 503 548-A1 and EP 587 134-A2, cyclic urea derivatives and the use thereof for the treatment of thromboses are claimed. Substituted imidazole- and triazolethiones as ion channel modulators are disclosed in WO 2005/086836, WO 2005/06892 and WO 2005/097112. triazolethione derivatives are also described in WO 02/066447 as sphingomyelinase inhibitors.

An object of the present invention are compounds of the general formula (I)

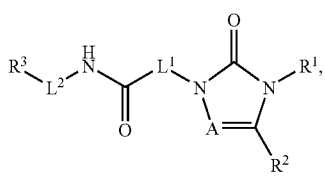

(I)

in which
A stands for N or C—$R^4$, wherein
  $R^4$ means hydrogen or $(C_1-C_4)$ alkyl,
$R^1$ stands for $(C_1-C_6)$ alkyl, $(C_2-C_6)$ alkenyl or $(C_2-C_6)$ alkynyl, which can each be singly to triply, similarly or differently, substituted with residues selected from the range halogen, cyano, oxo, trifluoromethyl, $(C_3-C_7)$ cycloalkyl, phenyl, —$OR^{10}$, —$NR^{11}R^{12}$, —$C(=O)$—$OR^{13}$ and —$C(=O)$—$NR^{14}R^{15}$, wherein
  (i) $(C_3-C_7)$ cycloalkyl can be up to doubly, similarly or differently, substituted with $(C_1-C_4)$ alkyl, oxo, hydroxy, $(C_1-C_4)$ alkoxy and/or amino,
  (ii) phenyl can be up to triply, similarly or differently, substituted with residues selected from the range halogen, cyano, nitro, $(C_1-C_4)$ alkyl, trifluoromethyl, hydroxy, hydroxymethyl, $(C_1-C_4)$ alkoxy, trifluoromethoxy, $(C_1-C_4)$ alkoxymethyl, hydroxycarbonyl, $(C_1-C_4)$ alkoxycarbonyl, aminocarbonyl, mono-$(C_1-C_4)$ alkylaminocarbonyl and di-$(C_1-C_4)$ alkylaminocarbonyl, (iii) $R^{10}$, $R^{11}$, $R^{12}$, $R^{13}$, $R^{14}$ and $R^{15}$ mutually independently on each single occurrence mean hydrogen, $(C_1-C_6)$ alkyl or $(C_3-C_7)$ cycloalkyl, wherein
    $(C_1-C_6)$ alkyl can itself be up to doubly, similarly or differently, substituted with amino, hydroxy, $(C_1-C_4)$ alkoxy, hydroxycarbonyl and/or $(C_1-C_4)$ alkoxycarbonyl
    and
    $(C_3-C_7)$ cycloalkyl can itself be up to doubly, similarly or differently, substituted with $(C_1-C_4)$ alkyl, oxo, hydroxy, $(C_1-C_4)$ alkoxy and/or amino,
  and/or
  (iv) $R^{11}$ and $R^{12}$ and also $R^{14}$ and $R^{15}$ respectively in pairs together with the nitrogen atom to which they are bound can form a 4 to 7-membered heterocycle, which can contain a further hetero atom from the range N, O and S and be up to doubly, similarly or differently, substituted with $(C_1-C_4)$ alkyl, oxo, hydroxy, $(C_1-C_4)$ alkoxy and/or amino,
or
$R^1$ stands for $(C_3-C_7)$ cycloalkyl, which can be up to doubly, similarly or differently, substituted with $(C_1-C_4)$ alkyl, $(C_1-C_4)$ alkoxy, hydroxy, amino and/or oxo,
$R^2$ stands for phenyl, naphthyl, thienyl, benzothienyl, furyl or benzofuryl, which can each be singly to triply, similarly or differently, substituted with residues selected from the range halogen, cyano, nitro, $(C_1-C_4)$ alkyl, trifluoromethyl, hydroxy, $(C_1-C_4)$ alkoxy, trifluoromethoxy and phenyl,
  wherein the last-named phenyl residue can itself be up to doubly, similarly or differently, substituted with residues selected from the range halogen, cyano, nitro, $(C_1-C_4)$ alkyl, trifluoromethyl, hydroxy, $(C_1-C_4)$ alkoxy, trifluoromethoxy, hydroxy-$(C_1-C_4)$-alkyl and $(C_1-C_4)$ alkylthio,
$L^1$ stands for a group of the formula —$(CR^{5A}R^{5B})_m$—, wherein
  m means the number 1, 2 or 3
  and
  $R^{5A}$ and $R^{5B}$ mutually independently mean hydrogen or $(C_1-C_4)$ alkyl
  or
  two residues $R^{5A}$ and $R^{5B}$ bound to the same carbon atom are linked to one another and together form a —$(CH_2)_n$— bridge, wherein
    n means the number 2, 3, 4 or 5,
  or, in the event that m stands for the number 2 or 3,
  two residues $R^{5A}$ and/or $R^{5B}$ bound to adjacent (1,2- or 2,3-) or non-adjacent (1,3-) carbon atoms are linked to one another and together form a —$(CH_2)_p$ bridge, wherein
    p means the number 1, 2, 3 or 4,
  where, in the event that the group —$CR^{5A}R^{5B}$— occurs several times, the individual meanings of $R^{5A}$ and $R^{5B}$ can in each case be the same or different,
or
$L^1$ stands for a group of the formula

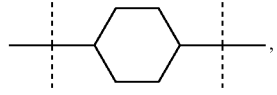

$L^2$ stands for a group of the formula *—$CR^{6A}R^{6B}$—$(CR^{7A}R^{7B})_q$— or *—$CR^{6A}R^{6B}$—$CR^{7A}R^{7B}$—O—, wherein \* means the binding site with the N atom of the amide group, q means the number 0, 1 or 2, $R^{6A}$ means hydrogen or $(C_1-C_4)$ alkyl, $R^{6B}$ means hydrogen, $(C_1-C_4)$ alkyl, trifluoromethyl, $(C_3-C_6)$ cycloalkyl or phenyl, which can be up to doubly, similarly or differently, substituted with halogen, $(C_1-C_4)$ alkyl and/or trifluoromethyl, or means a residue of the formula —C(=O)—OR$^{16}$ or —C(=O)—NR$^{17}$R$^{18}$, wherein $R^{16}$, $R^{17}$ and $R^{18}$ mutually independently represent hydrogen, $(C_1-C_4)$ alkyl or $(C_3-C_6)$ cycloalkyl or $R^{17}$ and $R^{18}$ together with the nitrogen atom to which they are bound form a 4 to 6-membered heterocycle, which can contain a further hetero atom from the range N, O and S and be up to doubly, similarly or differently, substituted with $(C_1-C_4)$ alkyl, hydroxy and/or $(C_1-C_4)$ alkoxy, or $R^{6A}$ and $R^{6B}$ are linked to one another and together form a —(CH$_2$)$_r$— bridge, wherein r means the number 2, 3, 4 or 5 and one CH$_2$ group of the bridge can be exchanged for —O—, —S— or >N—R$^{19}$, wherein $R^{19}$ represents hydrogen or $(C_1-C_4)$ alkyl, $R^{7A}$ means hydrogen, fluorine, $(C_1-C_4)$ alkyl or $(C_1-C_4)$ alkoxy, $R^{7B}$ means hydrogen, fluorine, $(C_1-C_4)$ alkyl, hydroxy-$(C_1-C_4)$ alkyl or a residue of the formula —OR$^{20}$, —NR$^{21}$R$^{22}$, —C(=O)—OR$^{23}$ or —C(=O)—NR$^{24}$R$^{25}$, wherein $R^{20}$, $R^{21}$, $R^{22}$, $R^{23}$, $R^{24}$ and $R^{25}$ mutually independently represent hydrogen, $(C_1-C_4)$ alkyl or $(C_3-C_6)$ cycloalkyl or $R^{21}$ and $R^{22}$ and also $R^{24}$ and $R^{25}$ respectively in pairs together with the nitrogen atom to which they are bound form a 4 to 6-membered heterocycle, which can contain a further hetero atom from the range N, O and S and be up to doubly, similarly or differently, substituted with $(C_1-C_4)$ alkyl, hydroxy and/or $(C_1-C_4)$ alkoxy, or $R^{7A}$ and $R^{7B}$ together form an oxo group or $R^{7A}$ and $R^{7B}$ are linked to one another and together form a —(CH$_2$)$_s$— bridge, wherein s means the number 2, 3, 4 or 5 and one CH$_2$ group of the bridge can be exchanged for —O—, —S— or >N—R$^{26}$, wherein $R^{26}$ represents hydrogen or $(C_1-C_4)$ alkyl, where, in the event that the group —CR$^{7A}$R$^{7B}$— occurs several times, the individual meanings of $R^{7A}$ and $R^{7B}$ can in each case be the same or different, or $L^2$ stands for a group of the formula

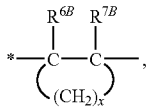

wherein means the binding site with the N atom of the amide group, x means the number 1, 2, 3 or 4, where one CH$_2$ group of the ring can be exchanged for —O—, —S— or >N—R$^{27}$, wherein $R^{27}$ represents hydrogen or $(C_1-C_4)$ alkyl, and $R^{6B}$ and $R^{7B}$ each have the aforesaid meanings, $R^3$ stands for phenyl, naphthyl or 5 to 10-membered heteroaryl with up to three hetero atoms from the range N, O and/or S, which can each be singly to triply, similarly or differently, substituted with residues selected from the range halogen, cyano, nitro, $(C_1-C_4)$ alkyl, trifluoromethyl, hydroxy, $(C_1-C_4)$ alkoxy, trifluoromethoxy, $(C_1-C_4)$ alkylthio, $(C_1-C_4)$ alkylsulfinyl, $(C_1-C_4)$ alkylsulphonyl, di-$(C_1-C_4)$ alkylamino and phenyl, wherein the last-named phenyl residue can itself be up to doubly, similarly or differently, substituted with halogen, cyano, nitro, $(C_1-C_4)$ alkyl, $(C_1-C_4)$ alkoxy, trifluoromethyl and/or trifluoromethoxy, or the grouping $L^2$-$R^3$ together forms a group of the formula

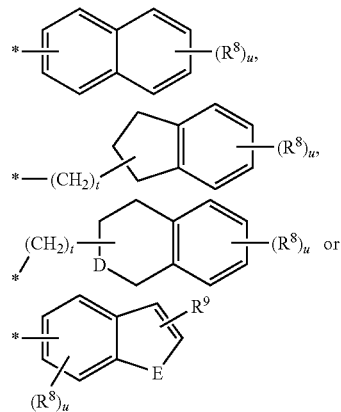

wherein

\* means the binding site with the N atom of the amide group,

D means CH$_2$ or O,

E means NH, N—CH$_3$, O or S, t means the number 0 or 1, $R^8$ means a substituent selected from the range halogen, cyano, nitro, $(C_1-C_4)$ alkyl, $(C_1-C_4)$ alkoxy, trifluoromethyl and trifluoromethoxy, u means the number 0, 1 or 2, where, in the event that the substituent $R^8$ occurs several times, its meanings can be the same or different, and $R^9$ means hydrogen or $(C_1-C_4)$ alkyl, and salts, solvates and solvates of the salts thereof.

Compounds according to the invention are the compounds of the formula (I) and salts, solvates and solvates of the salts thereof, the compounds of the formulae mentioned below covered by formula (I) and salts, solvates and solvates of the salts thereof and the compounds mentioned below as practical examples covered by formula (I) and salts, solvates and solvates of the salts thereof, insofar as the compounds of the formulae mentioned below covered by formula (I) are not already salts, solvates and solvates of the salts.

Depending on their structure, the compounds according to the invention can exist in stereoisomeric forms (enantiomers, diastereomers). The present invention therefore includes the enantiomers or diastereomers and respective mixtures thereof. From such mixtures of enantiomers and/or diastereomers, the stereoisomerically homogeneous components can be isolated in known manner.

Insofar as the compounds according to the invention can occur in tautomeric forms, the present invention includes all tautomeric forms.

As salts in the context of the present invention, physiologically harmless salts of the compounds according to the invention are preferred. Also included are salts which are not themselves suitable for pharmaceutical applications, but can for example be used for the isolation or purification of the compounds according to the invention.

Physiologically harmless salts of the compounds according to the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically harmless salts of the compounds according to the invention also include salts of usual bases, such as for example and preferably alkali metal salts (e.g. sodium and potassium salts), alkaline earth salts (e.g. calcium and magnesium salts) and ammonium salts, derived from ammonia or organic amines with 1 to 16 C atoms, such as for example and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention those forms of the compounds according to the invention which in the solid or liquid state form a complex by coordination with solvent molecules are described as solvates. Hydrates are a specific form of solvates, wherein the coordination takes place with water. Hydrates are preferred as solvates in the context of the present invention.

In addition, the present invention also includes prodrugs of the compounds according to the invention. The term "prodrugs" includes compounds which can themselves be biologically active or inactive, but are converted into compounds according to the invention (for example metabolically or hydrolytically) during their residence time in the body.

In the context of the present invention, unless otherwise specified, the substituents have the following meaning:

In the context of the invention, $(C_1-C_6)$ alkyl and $(C_1-C_4)$ alkyl stand for a linear or branched alkyl residue with 1 to 6 and 1 to 4 carbon atoms respectively. A linear or branched alkyl residue with 1 to 4 carbon atoms is preferred. For example and preferably, the following may be mentioned: methyl, ethyl, n-propyl, isopropyl, n-butyl, iso-butyl, sec.-butyl, tert.-butyl, 1-ethylpropyl, n-pentyl and n-hexyl.

In the context of the invention, hydroxy-$(C_1-C_4)$ alkyl stands for a linear or branched alkyl residue with 1 to 4 carbon atoms, which bears a hydroxy group as a substituent in the chain or in the terminal position. For example and preferably, the following may be mentioned: hydroxymethyl, 1-hydroxyethyl, 2-hydroxyethyl, 1-hydroxy-1-methylethyl, 1,1-dimethyl-2-hydroxyethyl, 1-hydroxypropyl, 2-hydroxypropyl, 3-hydroxypropyl, 1-hydroxy-2-methylpropyl, 2-hydroxy-1-methylpropyl, 2-hydroxy-2-methylpropyl, 1-hydroxybutyl, 2-hydroxybutyl, 3-hydroxybutyl and 4-hydroxybutyl.

In the context of the invention, an oxo group stands for an oxygen atom which is linked to a carbon atom via a double bond.

In the context of the invention $(C_2-C_6)$ alkenyl and $(C_2-C_4)$ alkenyl stand for a linear or branched alkenyl residue with 2 to 6 and 2 to 4 carbon atoms respectively and a double bond. A linear or branched alkenyl residue with 2 to 4 carbon atoms is preferred. For example and preferably, the following may be mentioned: vinyl, allyl, n-prop-1-en-1-yl, isopropenyl, 2-methyl-2-propen-1-yl, n-but-1-en-1-yl and n-but-2-en-1-yl.

In the context of the invention, $(C_2-C_6)$ alkynyl and $(C_2-C_4)$ alkynyl stand for a linear or branched alkynyl residue with 2 to 6 and 2 to 4 carbon atoms respectively and a triple bond. A linear or branched alkynyl residue with 2 to 4 carbon atoms is preferred. For example and preferably, the following may be mentioned: ethynyl, n-prop-1-yn-1-yl, n-prop-2-yn-1-yl, n-but-2-yn-1-yl and n-but-3-yn-1-yl.

In the context of the invention, $(C_1-C_6)$ alkoxy and $(C_1-C_4)$ alkoxy stand for a linear or branched alkoxy residue with 1 to 6 and 1 to 4 carbon atoms respectively. A linear or branched alkoxy residue with 1 to 4 carbon atoms is preferred. For example and preferably, the following may be mentioned: methoxy, ethoxy, n-propoxy, isopropoxy, n-butoxy, tert.-butoxy, n-pentoxy and n-hexoxy.

In the context of the invention, $(C_1-C_4)$ alkoxycarbonyl stands for a linear or branched alkoxy residue with 1 to 4 carbon atoms, which is linked via a carbonyl group. For example and preferably, the following may be mentioned: methoxycarbonyl, ethoxycarbonyl, n-propoxy-carbonyl, isopropoxycarbonyl, n-butoxycarbonyl and tert.-butoxycarbonyl.

In the context of the invention, mono-$(C_1-C_4)$ alkylamino stands for an amino group with one linear or branched alkyl substituent, which has 1 to 4 carbon atoms. For example and preferably, the following may be mentioned: methylamino, ethylamino, n-propylamino, isopropylamino, n-butylamino and tert.-butylamino.

In the context of the invention, di-$(C_1-C_4)$ alkylamino stands for an amino group with two linear or branched alkyl substituents, the same or different, which each have 1 to 4 carbon atoms. For example and preferably, the following may be mentioned: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino and N-tert.-butyl-N-methylamino.

In the context of the invention, mono- or di-$(C_1-C_4)$ alkylaminocarbonyl stands for an amino group which is linked via a carbonyl group and which has respectively one linear or branched two linear or branched alkyl substituents, the same or different, each with 1 to 4 carbon atoms. For example and preferably, the following may be mentioned: methylaminocarbonyl, ethylaminocarbonyl, n-propylaminocarbonyl, isopropylaminocarbonyl, n-butylaminocarbonyl, tert.-butylaminocarbonyl, N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl and N-tert.-butyl-N-methylaminocarbonyl.

In the context of the invention, $(C_1-C_4)$ alkylthio stands for a thio group with a linear or branched alkyl substituent which has 1 to 4 carbon atoms. For example and preferably, the following may be mentioned: methylthio, ethylthio, n-propylthio, isopropylthio, n-butylthio and tert.-butylthio.

In the context of the invention, $(C_1-C_4)$ alkylsulfinyl stands for a linear or branched alkylsulfinyl residue with 1 to 4 carbon atoms. For example and preferably, the following may be mentioned: methylsulfinyl, ethylsulfinyl, n-propylsulfinyl, isopropylsulfinyl, n-butylsulfinyl and tert.-butyl-sulfinyl.

In the context of the invention, $(C_1-C_4)$ alkylsulphonyl stands for a linear or branched alkylsulphonyl residue with 1 to 4 carbon atoms. For example and preferably, the following may be mentioned: methylsulphonyl, ethylsulphonyl, n-propylsulphonyl, isopropylsulphonyl, n-butylsulphonyl and tert.-butylsulphonyl.

In the context of the invention, $(C_3-C_7)$ cycloalkyl and $(C_3-C_6)$ cycloalkyl stand for a monocyclic, saturated cycloalkyl group with 3 to 7 and 3 to 6 carbon atoms respectively. A cycloalkyl residue with 3 to 6 carbon atoms is preferred. For example and preferably, the following may be mentioned: cyclopropyl, cyclobutyl, cyclopentyl, cyclohexyl and cycloheptyl.

In the context of the invention, a 4 to 7-membered or a 4 to 6-membered heterocycle stands for a monocyclic, saturated heterocycle with a total of 4 to 7 and 4 to 6 ring atoms respectively, which contains a ring nitrogen atom, is linked via this, and can contain a further ring hetero atom from the range N, O and S. For example, the following may be mentioned: azetidinyl, pyrrolidinyl, pyrazolidinyl, piperidinyl, piperazinyl, morpholinyl, thiomorpholinyl, hexahydroazepinyl and hexahydro-1,4-diazepinyl. A 4 to 6-membered heterocycle, which as well as the ring nitrogen atom can contain a further ring hetero atom from the range N and O is preferred. Pyrrolidinyl, piperidinyl, piperazinyl and morpholinyl are especially preferred.

In the context of the invention, 5 to 10-membered heteroaryl stands for a mono- or optionally bicyclic aromatic heterocycle (heteroaromatic) with a total of 5 to 10 ring atoms, which contains up to three ring hetero atoms from the range N, O and/or S and is linked via a ring carbon atom or optionally via a ring nitrogen atom. For example, the following may be mentioned: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl and pyrazolo[3,4-b]pyridinyl. Mono- or optionally bicyclic 5 to 10-membered heteroaryl residues with up to two hetero atoms from the range N, O and/or S are preferred. Monocyclic 5- or 6-membered heteroaryl residues with up to two hetero atoms from the range N, O and/or S such as for example furyl, thienyl, thiazolyl, oxazolyl, isothiazolyl, isoxazolyl, pyrazolyl, imidazolyl, pyridyl, pyrimidinyl, pyridazinyl and pyrazinyl are especially preferred.

In the context of the invention, halogen includes fluorine, chlorine, bromine and iodine. Fluorine or chlorine are preferred.

When residues in the compounds according to the invention are substituted, the residues can, unless otherwise specified, be singly or multiply substituted. In the context of the present invention, for all residues which occur several times their meaning is mutually independent. Substitution with one, two or three substituents, the same or different, is preferred. Substitution with one substituent is quite especially preferred.

Preferred in the context of the present invention are compounds of the formula (I), in which A stands for N or C—$R^4$, wherein
  $R^4$ means hydrogen or $(C_1-C_4)$ alkyl,
$R^1$ stands for $(C_1-C_6)$ alkyl, which can be substituted with hydroxy, $(C_1-C_6)$ alkoxy, $(C_3-C_7)$ cycloalkyl or phenyl, or for $(C_3-C_7)$ cycloalkyl,
  wherein the said cycloalkyl residues can themselves be up to doubly, similarly or differently, substituted with $(C_1$-$C_4)$ alkyl, $(C_1-C_4)$ alkoxy, hydroxy, amino and/or oxo and
  the phenyl residue up to triply, similarly or differently, with halogen, cyano, nitro, $(C_1-C_4)$ alkyl, $(C_1-C_4)$ alkoxy, trifluoromethyl and/or trifluoromethoxy,
$R^2$ stands for phenyl, naphthyl, thienyl, benzothienyl, furyl or benzofuryl, which can each be substituted up to triply, similarly or differently, with halogen, cyano, nitro, $(C_1-C_4)$ alkyl, $(C_1-C_4)$ alkoxy, trifluoromethyl, trifluoromethoxy and/or phenyl,
  wherein the last-named phenyl residue can itself be up to doubly, similarly or differently, substituted with halogen, cyano, nitro, $(C_1-C_4)$ alkyl, $(C_1-C_4)$ alkoxy, trifluoromethyl and/or trifluoromethoxy,
$L^1$ stands for a group of the formula —$(CR^{5A}R^{5B})_m$—,
  wherein
  m means the number 1, 2 or 3
  and
  $R^{5A}$ and $R^{5B}$ mutually independently mean hydrogen or $(C_1-C_4)$ alkyl
  or
  two residues $R^{5A}$ and $R^{5B}$ bound to the same carbon atom are linked to one another and together form a —$(CH_2)_n$— bridge, wherein
    n means the number 2, 3, 4 or 5,
  or, in the event that m stands for the number 2 or 3,
  two residues bound to adjacent (1,2- or 1,3-) or non-adjacent (1,3-) carbon atoms $R^{5A}$ and/or $R^{5B}$ are linked to one another and together form a —$(CH_2)_p$— bridge, wherein
    p means the number 1, 2, 3 or 4,
  where, in the event that the group —$CR^{5A}R^{5B}$— occurs several times, the individual meanings of $R^{5A}$ and $R^{5B}$ can in each case be the same or different,
or
$L^1$ stands for a group of the formula

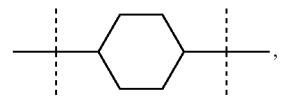

$L^2$ stands for a group of the formula *—$CR^{6A}R^{6B}$—$(CR^{7A}R^{7B})_q$— or *—$CR^{6A}R^{6B}$— $CR^{7A}R^{7B}$—O—,
  wherein
  * means the binding site with the N atom of the amide group,
  q means the number 0, 1 or 2,
  $R^{6A}$ means hydrogen or $(C_1-C_4)$ alkyl,
  $R^{6B}$ means hydrogen, $(C_1-C_4)$ alkyl, trifluoromethyl, $(C_3-C_6)$ cycloalkyl or phenyl, which can be up to doubly, similarly or differently, substituted with halogen, $(C_1-C_4)$ alkyl and/or trifluoromethyl,
  or
  $R^{6A}$ and $R^{6B}$ are linked to one another and together form a —$(CH_2)_r$— bridge, wherein
    r means the number 2, 3, 4 or 5,
  and
  $R^{7A}$ and $R^{7B}$ mutually independently mean hydrogen or $(C_1-C_4)$ alkyl,
    where, in the event that the group —$CR^{7A}R^{7B}$— occurs several times, the individual meanings of $R^{7A}$ and $R^{7B}$ can in each case be the same or different,
$R^3$ stands for phenyl, naphthyl or 5 to 10-membered heteroaryl with up to three hetero atoms from the range N, O and/or S, which can each be up to triply, similarly or differently, substituted with halogen, cyano, nitro, $(C_1-C_4)$ alkyl, $(C_1-C_4)$ alkoxy, trifluoromethyl, trifluoromethoxy, di-$(C_1-C_4)$ alkylamino and/or phenyl, wherein the last-named phenyl residue can itself be up to doubly, similarly or differently, substituted with halogen, cyano, nitro, $(C_1-C_4)$ alkyl, $(C_1-C_4)$ alkoxy, trifluoromethyl and/or trifluoromethoxy, or the grouping $L^2$-$R^3$ together forms a group of the formula

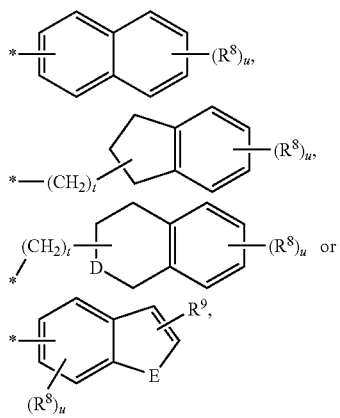

wherein

* means the binding site with the N atom of the amide group,

D means $CH_2$ or O,

E means NH, N—$CH_3$, O or S, t means the number 0 or 1, $R^8$ means a substituent selected from the range halogen, cyano, nitro, $(C_1-C_4)$ alkyl, $(C_1-C_4)$ alkoxy, trifluoromethyl and trifluoromethoxy, u means the number 0, 1 or 2, where, in the event that the substituent $R^8$ occurs several times, its meanings can be the same or different, and $R^9$ means hydrogen or $(C_1-C_4)$ alkyl, and salts, solvates and solvates of the salts thereof.

Likewise preferred in the context of the present invention are compounds of the formula (I), in which A stands for N or C—$R^4$, wherein $R^4$ means hydrogen or $(C_1-C_4)$ alkyl, $R^1$ stands for $(C_1-C_6)$ alkyl, which can be singly to triply, similarly or differently, substituted with residues selected from the range fluorine, chlorine, cyano, oxo, trifluoromethyl, $(C_3-C_6)$ cycloalkyl, phenyl, —$OR^{10}$, —$NR^{11}R^{12}$, —$C(=O)$—$OR^{13}$ and —$C(=O)$—$NR^{14}R^{15}$, wherein (i) $(C_3-C_6)$ cycloalkyl can be up to doubly, similarly or differently, substituted with $(C_1-C_4)$ alkyl, oxo, hydroxy, $(C_1-C_4)$ alkoxy and/or amino, (ii) phenyl can be up to triply, similarly or differently, substituted with residues selected from the range fluorine, chlorine, cyano, $(C_1-C_4)$ alkyl, trifluoromethyl, hydroxy, hydroxymethyl, $(C_1-C_4)$ alkoxy, trifluoromethoxy, $(C_1-C_4)$ alkoxymethyl, hydroxycarbonyl, $(C_1-C_4)$ alkoxycarbonyl, aminocarbonyl, mono-$(C_1-C_4)$ alkylaminocarbonyl and di-$(C_1-C_4)$ alkylaminocarbonyl, (iii) $R^{10}$, $R^{11}$, $R^{12}$, $R^{13}$, $R^{14}$ and $R^{15}$ mutually independently on each single occurrence mean hydrogen, $(C_1-C_4)$ alkyl or $(C_3-C_6)$ cycloalkyl, where $(C_1-C_4)$ alkyl can itself be up to doubly, similarly or differently, substituted with amino, hydroxy, $(C_1-C_4)$ alkoxy, hydroxycarbonyl and/or $(C_1-C_4)$ alkoxycarbonyl and $(C_3-C_6)$ cycloalkyl can itself be up to doubly, similarly or differently, substituted with $(C_1-C_4)$ alkyl, oxo, hydroxy, $(C_1-C_4)$ alkoxy and/or amino, and/or (iv) $R^{11}$ and $R^{12}$ and also $R^{14}$ and $R^{15}$ respectively in pairs together with the nitrogen atom to which they are bound form a 4 to 6-membered heterocycle, which can contain a further hetero atom from the range N and O and be up to doubly, similarly or differently, substituted with $(C_1-C_4)$ alkyl, oxo, hydroxy, $(C_1-C_4)$ alkoxy and/or amino, or $R^1$ stands for $(C_2-C_6)$ alkenyl, which can be substituted with hydroxy, $(C_1-C_4)$ alkoxy, hydroxycarbonyl or $(C_1-C_4)$ alkoxycarbonyl, or for $(C_3-C_6)$ cycloalkyl, which can be up to doubly, similarly or differently, substituted with $(C_1-C_4)$ alkyl, $(C_1-C_4)$ alkoxy, hydroxy, amino and/or oxo, $R^2$ stands for phenyl or thienyl, which can be singly to triply, similarly or differently, substituted with residues selected from the range fluorine, chlorine, cyano, $(C_1-C_4)$ alkyl, trifluoromethyl, hydroxy, $(C_1-C_4)$ alkoxy, trifluoromethoxy and phenyl, wherein the last-named phenyl residue can itself be up to doubly, similarly or differently, substituted with residues selected from the range fluorine, chlorine, cyano, $(C_1-C_4)$ alkyl, trifluoromethyl, $(C_1-C_4)$ alkoxy and trifluoromethoxy, $L^1$ stands for a group of the formula —$CR^{5A}R^{5B}$—, wherein $R^{5A}$ and $R^{5B}$ mutually independently mean hydrogen or $(C_1-C_4)$ alkyl, $L^2$ stands for a group of the formula *—$CR^{6A}R^{6B}$—$(CR^{7A}R^{7B})_q$—, wherein

* means the binding site with the N atom of the amide group, q means the number 0 or 1, $R^{6A}$ means hydrogen or $(C_1-C_4)$ alkyl $R^{6B}$ means hydrogen, $(C_1-C_4)$ alkyl, trifluoromethyl, $(C_3-C_6)$ cycloalkyl or phenyl, which can be up to doubly, similarly or differently, substituted with fluorine, chlorine, $(C_1-C_4)$ alkyl and/or trifluoromethyl, or a residue of the formula —$C(=O)$—$OR^{16}$ or —$C(=O)$—$NR^{17}R^{18}$, wherein $R^{16}$, $R^{17}$ and $R^{18}$ mutually independently represent hydrogen, $(C_1-C_4)$ alkyl or $(C_3-C_6)$ cycloalkyl or $R^{17}$ and $R^{18}$ together with the nitrogen atom to which they are bound form a 4 to 6-membered heterocycle, which can contain a further hetero atom from the range N and O and be up to doubly, similarly or differently, substituted with $(C_1-C_4)$ alkyl, hydroxy and/or $(C_1-C_4)$ alkoxy, or $R^{6A}$ and $R^{6B}$ are linked to one another and together form a —$(CH_2)_r$— bridge, wherein r means the number 2, 3, 4 or 5 and one $CH_2$ group of the bridge can be exchanged for —O—, $R^{7A}$ means hydrogen, fluorine or $(C_1-C_4)$ alkyl, $R^{7B}$ means hydrogen, fluorine, $(C_1-C_4)$ alkyl, hydroxy-$(C_1-C_4)$ alkyl or a residue of the formula $-OR^{20}$, $-NR^{21}R^{22}$, $-C(=O)-OR^{23}$ or $-C(=O)-NR^{24}R^{25}$, wherein $R^{20}$, $R^{21}$, $R^{22}$, $R^{23}$, $R^{24}$ and $R^{25}$ mutually independently represent hydrogen, $(C_1-C_4)$ alkyl or $(C_3-C_6)$ cycloalkyl or $R^{21}$ and $R^{22}$ and also $R^{24}$ and $R^{25}$ respectively in pairs together with the nitrogen atom to which they are bound form a 4 to 6-membered heterocycle, which can contain a further hetero atom from the range N and O and be up to doubly, similarly or differently, substituted with $(C_1-C_4)$ alkyl, hydroxy and/or $(C_1-C_4)$ alkoxy, or $R^{7A}$ and $R^{7B}$ together form an oxo group or $R^{7A}$ and $R^{7B}$ are linked to one another and together form a $-(CH_2)_s-$ bridge, wherein s means the number 2, 3, 4 or 5 and one $CH_2$ group of the bridge can be exchanged for $-O-$, or $L^2$ stands for a group of the formula

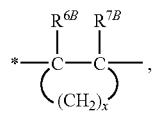

wherein

 means the binding site with the N atom of the amide group, x means the number 1, 2, 3 or 4, where one $CH_2$ group of the ring can be exchanged for $-O-$, and $R^{6B}$ and $R^{7B}$ each have the aforesaid meanings, and $R^3$ stands for phenyl, naphthyl or 5 to 10-membered heteroaryl with up to two hetero atoms from the range N, O and/or S, which can each be singly to triply, similarly or differently, substituted with residues selected from the range fluorine, chlorine, cyano, $(C_1-C_4)$ alkyl, trifluoromethyl, hydroxy, $(C_1-C_4)$ alkoxy, trifluoromethoxy, $(C_1-C_4)$ alkylthio, $(C_1-C_4)$ alkylsulphonyl, di-$(C_1-C_4)$ alkylamino and phenyl, wherein the last-named phenyl residue can itself be up to doubly, similarly or differently, substituted with fluorine, chlorine, cyano, $(C_1-C_4)$ alkyl, $(C_1-C_4)$ alkoxy, trifluoromethyl and/or trifluoromethoxy, and salts, solvates and solvates of the salts thereof.

Particularly preferred in the context of the present invention are compounds of the formula (I), in which A stands for N or $C-R^4$, wherein $R^4$ means hydrogen or $(C_1-C_4)$ alkyl, $R^1$ stands for $(C_1-C_6)$ alkyl, which can be substituted with hydroxy, $(C_1-C_4)$ alkoxy, $(C_3-C_6)$ cycloalkyl or phenyl, or for $(C_3-C_6)$ cycloalkyl, wherein the said cycloalkyl residues can themselves be up to doubly, similarly or differently, substituted with $(C_1-C_4)$ alkyl, $(C_1-C_4)$ alkoxy, hydroxy and/or amino and the phenyl residue can be up to doubly, similarly or differently, substituted with halogen, cyano, nitro, $(C_1-C_4)$ alkyl, $(C_1-C_4)$ alkoxy, trifluoromethyl and/or trifluoromethoxy, $R^2$ stands for phenyl, naphthyl, thienyl or benzothienyl, which can each be up to triply, similarly or differently, substituted with halogen, cyano, nitro, $(C_1-C_4)$ alkyl, $(C_1-C_4)$ alkoxy, trifluoromethyl, trifluoromethoxy and/or phenyl, wherein the last-named phenyl residue can itself be up to doubly, similarly or differently, substituted with halogen, cyano, nitro, $(C_1-C_4)$ alkyl, $(C_1-C_4)$ alkoxy, trifluoromethyl and/or trifluoromethoxy, $L^1$ stands for a group of the formula $-(CR^{5A}R^{5B})_m-$, wherein m means the number 1, 2 or 3 and $R^{5A}$ and $R^{5B}$ mutually independently mean hydrogen or methyl or two residues $R^{5A}$ and $R^{5B}$ bound to the same carbon atom are linked to one another and together form a $-(CH_2)_n-$ bridge, wherein n means the number 2, 3, 4 or 5, or, in the event that m stands for the number 2 or 3, two residues bound to adjacent (1,2- or 2,3-) or non-adjacent (1,3-) carbon atoms $R^{5A}$ and/or $R^{5B}$ are linked to one another and together form a $-(CH_2)_p-$ bridge, wherein p means the number 1, 2, 3 or 4, where, in the event that the group $-CR^{5A}R^{5B}-$ occurs several times, the individual meanings of $R^{5A}$ and $R^{5B}$ can in each case be the same or different, or $L^1$ stands for a group of the formula

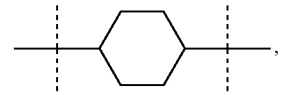

$L^2$ stands for a group of the formula $*-CR^{6A}R^{6B}-(CH_2)_q-$, wherein

* means the binding site with the N atom of the amide group, q means the number 0 or 1, $R^{6A}$ means hydrogen or methyl, $R^{6B}$ means hydrogen, $(C_1-C_4)$ alkyl, trifluoromethyl or $(C_3-C_6)$ cycloalkyl or $R^{6A}$ and $R^{6B}$ are linked to one another and together form a $-(CH_2)_r-$ bridge, wherein r means the number 2, 3, 4 or 5, and $R^3$ stands for phenyl, naphthyl or 5 to 10-membered heteroaryl with up to two hetero atoms from the range N, O and/or S, which can each be up to triply, similarly or differently, substituted with halogen, cyano, nitro, $(C_1-C_4)$ alkyl, $(C_1-C_4)$ alkoxy, trifluoromethyl, trifluoromethoxy and/or phenyl, wherein the last-named phenyl residue can itself be up to doubly, similarly or differently, substituted with halogen, cyano, nitro, $(C_1-C_4)$ alkyl, $(C_1-C_4)$ alkoxy, trifluoromethyl and/or trifluoromethoxy, and salts, solvates and solvates of the salts thereof.

Likewise particularly preferred in the context of the present invention are compounds of the formula (I), in which A stands for N or C—$R^4$, wherein
$R^4$ means hydrogen or methyl,
$R^1$ stands for $(C_1-C_6)$ alkyl, which can be singly or doubly, similarly or differently, substituted with residues selected from the range fluorine, oxo, trifluoromethyl, $(C_3-C_6)$ cycloalkyl, phenyl, —$OR^{10}$, —C(=O)—$OR^{13}$ and —C(=O)—$NR^{14}R^{15}$, wherein
  (i) $(C_3-C_6)$ cycloalkyl can be up to doubly, similarly or differently, substituted with $(C_1-C_4)$ alkyl, hydroxy and/or $(C_1-C_4)$ alkoxy,
  (ii) phenyl can be up to doubly, similarly or differently, substituted with residues selected from the range fluorine, chlorine, cyano, $(C_1-C_4)$ alkyl, trifluoromethyl, hydroxymethyl, $(C_1-C_4)$ alkoxy, hydroxycarbonyl, $(C_1-C_4)$ alkoxycarbonyl, aminocarbonyl, mono-$(C_1-C_4)$ alkylaminocarbonyl and di-$(C_1-C_4)$ alkylaminocarbonyl,
  and
  (iii) $R^{10}$, $R^{13}$, $R^{14}$ and $R^{15}$ mutually independently on each single occurrence mean hydrogen, $(C_1-C_4)$ alkyl or $(C_3-C_6)$ cycloalkyl, where
    $(C_1-C_4)$ alkyl can itself be up to doubly, similarly or differently, substituted with hydroxy, $(C_1-C_4)$ alkoxy, hydroxycarbonyl and/or $(C_1-C_4)$ alkoxycarbonyl
    and
    $(C_3-C_6)$ cycloalkyl can itself be up to doubly, similarly or differently, substituted with $(C_1-C_4)$ alkyl, hydroxy and/or $(C_1-C_4)$ alkoxy,
or
$R^1$ stands for $(C_2-C_6)$ alkenyl, which can be substituted with hydroxycarbonyl or $(C_1-C_4)$ alkoxycarbonyl,
or
  for $(C_3-C_6)$ cycloalkyl, which can be up to doubly, similarly or differently, substituted with $(C_1-C_4)$ alkyl, $(C_1-C_4)$ alkoxy and/or hydroxy,
$R^2$ stands for phenyl or thienyl, which can be singly to doubly, similarly or differently, substituted with residues selected from the range fluorine, chlorine, $(C_1-C_4)$ alkyl, trifluoromethyl, $(C_1-C_4)$ alkoxy and trifluoromethoxy,
$L^1$ stands for a group of the formula —$CR^{5A}R^{5B}$—, wherein $R^{5A}$ and $R^{5B}$ mutually independently mean hydrogen or methyl,
$L^2$ stands for a group of the formula *—$CR^{6A}R^{6B}$—$(CR^{7A}R^{7B})_q$—, wherein
  * means the binding site with the N atom of the amide group,
  q means the number 0 or 1,
  $R^{6A}$ means hydrogen or methyl,
  $R^{6B}$ means hydrogen, methyl, trifluoromethyl or a residue of the formula —C(=O)—$OR^{16}$ or —C(=O)—$NR^{17}R^{18}$, wherein
    $R^{16}$, $R^{17}$ and $R^{18}$ mutually independently represent hydrogen, $(C_1-C_4)$ alkyl or $(C_3-C_6)$ cycloalkyl
    or
    $R^{17}$ and $R^{18}$ together with the nitrogen atom to which they are bound form a 4 to 6-membered heterocycle, which can contain an O atom as a further hetero atom,
  or
  $R^{6A}$ and $R^{6B}$ are linked to one another and together form a —$(CH_2)_r$— bridge, wherein
    r means the number 2, 3, 4 or 5
    and one $CH_2$ group of the bridge can be exchanged for —O—,
  $R^{7A}$ means hydrogen, fluorine or methyl,
  $R^{7B}$ means hydrogen, fluorine, methyl or a residue of the formula —C(=O)—$OR^{23}$ or —C(=O)—$NR^{24}R^{25}$, wherein
    $R^{23}$, $R^{24}$ and $R^{25}$ mutually independently represent hydrogen, $(C_1-C_4)$ alkyl or $(C_3-C_6)$ cycloalkyl
    or
    $R^{24}$ and $R^{25}$ together with the nitrogen atom to which they are bound form a 4 to 6-membered heterocycle, which can contain an O atom as a further hetero atom,
  or
  $R^{7A}$ and $R^{7B}$ together form an oxo group
  or
  $R^{7A}$ and $R^{7B}$ are linked to one another and together form a —$(CH_2)_s$— bridge, wherein
    s means the number 2, 3, 4 or 5
    and one $CH_2$ group of the bridge can be exchanged for —O—,
or
$L^2$ stands for a group of the formula

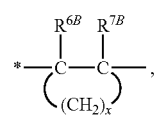

wherein
  * means the binding site with the N atom of the amide group,
  x means the number 1, 2, 3 or 4,
    where one $CH_2$ group of the ring can be exchanged for —O—,
  and
  $R^{6B}$ and $R^{7B}$ each have the aforesaid meanings,
and
$R^3$ stands for phenyl, naphthyl, pyridyl, quinolinyl or isoquinolinyl, which can each be singly to doubly, similarly or differently, substituted with residues selected from the range fluorine, chlorine, cyano, $(C_1-C_4)$ alkyl, trifluoromethyl, $(C_1-C_4)$ alkoxy, trifluoromethoxy, $(C_1-C_4)$ alkylthio and phenyl,
  wherein the last-named phenyl residue can itself be up to doubly, similarly or differently, substituted with fluorine, chlorine, cyano, $(C_1-C_4)$ alkyl, $(C_1-C_4)$ alkoxy, trifluoromethyl and/or trifluoromethoxy,
and salts, solvates and solvates of the salts thereof.

Especially preferred in the context of the present invention are compounds of the formula (I), in which
A stands for N or CH,
$R^1$ stands for $(C_1-C_6)$ alkyl, which can be singly or doubly, similarly or differently, substituted with residues selected from the range fluorine, oxo, hydroxy, $(C_1-C_4)$ alkoxy, trifluoromethyl, $(C_3-C_6)$ cycloalkyl and phenyl,
  where phenyl can itself be up to doubly, similarly or differently, substituted with residues selected from the range fluorine, chlorine, cyano, $(C_1-C_4)$ alkyl, trifluoromethyl, hydroxymethyl, $(C_1-C_4)$ alkoxy, trifluoromethoxy, hydroxycarbonyl, aminocarbonyl and di-$(C_1-C_4)$ alkylaminocarbonyl,
or
$R^1$ stands for $(C_2-C_4)$ alkenyl or $(C_3-C_6)$ cycloalkyl,
$R^2$ stands for phenyl or thienyl, which can be singly to doubly, similarly or differently, substituted with residues selected from the range fluorine, chlorine, bromine, $(C_1-C_4)$ alkyl and $(C_1-C_4)$ alkoxy,
$L^1$ stands for —$CH_2$—, —$CH(CH_3)$— or —$CH_2CH_2$—, $L^2$ stands for a group of the formula $*-CR^{6A}R^{6B}-(CR^{7A}R^{7B})_q-$, wherein
* means the binding site with the N atom of the amide group,
q means the number 0 or 1,
$R^{6A}$ means hydrogen or methyl,
$R^{6B}$ means hydrogen, methyl, trifluoromethyl or a residue of the formula $-C(=O)-NR^{17}R^{18}$, wherein
$R^{17}$ and $R^{18}$ mutually independently represent hydrogen, $(C_1-C_4)$ alkyl or $(C_3-C_6)$ cycloalkyl
or
$R^{17}$ and $R^{18}$ together with the nitrogen atom to which they are bound form a 4 to 6-membered heterocycle, which can contain an O atom as a further hetero atom,
or
$R^{6A}$ and $R^{6B}$ are linked to one another and together form a $-(CH_2)_r$ bridge, wherein
r means the number 2, 3, 4 or 5
and one $CH_2$ group of the bridge can be exchanged for $-O-$,
$R^{7A}$ means hydrogen, fluorine or methyl,
$R^{7B}$ means hydrogen, fluorine, methyl or a residue of the formula $-C(=O)-OR^{23}$ or $-C(=O)-NR^{24}R^{25}$, wherein
$R^{23}$, $R^{24}$ and $R^{25}$ mutually independently represent hydrogen or $(C_1-C_4)$ alkyl
or
$R^{24}$ and $R^{25}$ together with the nitrogen atom to which they are bound form a 4 to 6-membered heterocycle, which can contain an O atom as a further hetero atom,
or
$R^{7A}$ and $R^{7B}$ together form an oxo group
or
$R^{7A}$ and $R^{7B}$ are linked to one another and together form a $-(CH_2)_s$ bridge, wherein
s means the number 2, 3, 4 or 5
and one $CH_2$ group of the bridge can be exchanged for $-O-$,
or
$L^2$ stands for a group of the formula

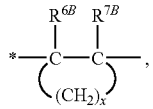

wherein
* means the binding site with the N atom of the amide group,
x means the number 1, 2, 3 or 4
and
$R^{6B}$ and $R^{7B}$ each have the aforesaid meanings,
and
$R^3$ stands for phenyl or pyridyl, which can be singly to doubly, similarly or differently, substituted with residues selected from the range fluorine, chlorine, $(C_1-C_4)$ alkyl, trifluoromethyl, $(C_1-C_4)$ alkoxy and trifluoromethoxy, or for naphthyl,
and salts, solvates and solvates of the salts thereof.

Quite especially preferred in the context of the present invention are compounds of the formula (I), in which
A stands for N or CH,
$R^1$ stands for $(C_1-C_6)$ alkyl, which can be singly or doubly, similarly or differently, substituted with residues selected from the range fluorine, oxo, hydroxy, methoxy, ethoxy, trifluoromethyl, cyclopropyl and phenyl,
where phenyl can itself be up to doubly, similarly or differently, substituted with residues selected from the range fluorine, chlorine, cyano, methyl, hydroxymethyl, methoxy, hydroxycarbonyl, aminocarbonyl and dimethylaminocarbonyl,
or
$R^1$ stands for vinyl, allyl or cyclopropyl,
$R^2$ stands for phenyl or thienyl, which can be singly to doubly, similarly or differently, substituted with residues selected from the range fluorine, chlorine, methyl and methoxy,
$L^1$ stands for $-CH_2-$,
$L^2$ stands for a group of the formula $*-CR^{6A}R^{6B}-(CR^{7A}R^{7B})_q-$, wherein
* means the binding site with the N atom of the amide group,
q means the number 0 or 1,
$R^{6A}$ means hydrogen or methyl,
$R^{6B}$ means hydrogen, methyl, trifluoromethyl or a residue of the formula $-C(=O)-NR^{17}R^{18}$, wherein
$R^{17}$ and $R^{18}$ mutually independently represent hydrogen, methyl, ethyl or cyclopropyl
or
$R^{17}$ and $R^{18}$ together with the nitrogen atom to which they are bound form an azetidine, pyrrolidine, piperidine or morpholine ring,
or
$R^{6A}$ and $R^{6B}$ are linked together and together with the carbon atom to which they are bound form a group of the formula

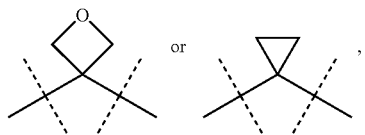

$R^{7A}$ means hydrogen, fluorine or methyl,
$R^{7B}$ means hydrogen, fluorine, methyl or a residue of the formula $-C(=O)-OR^{23}$ or $-C(=O)-NR^{24}R^{25}$, wherein
$R^{23}$, $R^{24}$ and $R^{25}$ mutually independently represent hydrogen, methyl or ethyl
or
$R^{24}$ and $R^{25}$ together with the nitrogen atom to which they are bound form an azetidine, pyrrolidine, piperidine or morpholine ring,
or
$R^{7A}$ and $R^{7B}$ together form an oxo group
or
$R^{7A}$ and $R^{7B}$ are linked to one another and together form a $-(CH_2)_s$ bridge, wherein
s means the number 2, 3, 4 or 5
and one $CH_2$ group of the bridge can be exchanged for $-O-$, or $L^2$ stands for a group of the formula

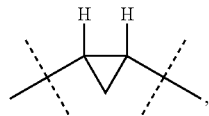

and $R^3$ stands for phenyl, which can be singly or doubly, similarly or differently, substituted with fluorine, chlorine, trifluoromethyl and/or trifluoromethoxy, or for 1-naphthyl, and salts, solvates and solvates of the salts thereof.

Quite especially preferred in the context of the present invention are also compounds of the formula (I), in which A stands for N or CH, $R^1$ stands for $(C_1-C_4)$ alkyl, 2-methoxyethyl, cyclopropyl, cyclohexylmethyl, benzyl or 1-phenethyl, where the phenyl ring in the said benzyl- and 1-phenethyl residues can be substituted with fluorine, chlorine, methyl, trifluoromethyl, methoxy or trifluoromethoxy, $R^2$ stands for phenyl or thienyl, which can each be singly or doubly, similarly or differently, substituted with fluorine, chlorine, bromine, methyl and/or methoxy, $L^1$ stands for —CH$_2$—, —CH$_2$CH$_2$— or —CH(CH$_3$)—, $L^2$ stands for —CH$_2$—, —CH(CH$_3$)— or —C(CH$_3$)$_2$— and $R^3$ stands for phenyl, which is singly or doubly, similarly or differently, substituted with fluorine, chlorine, trifluoromethyl and/or trifluoromethoxy, or for 1-naphthyl, and salts, solvates and solvates of the salts thereof.

The residue definitions stated in detail in the respective combinations or preferred combinations of residues are also replaced at will by residue definitions of other combinations, irrespective of the particular stated combinations of residues.

Quite especially preferred are combinations of two or more of the aforesaid preference ranges.

A further object of the invention is a process for the production of the compounds according to the invention of the formula (I), characterized in that

[A] a compound of the formula (II)

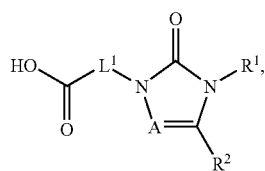

in which A, $L^1$, $R^1$ and $R^2$ each have the aforesaid meanings, is coupled with a compound of the formula (III)

in which $L^2$ and $R^3$ have the aforesaid meanings, in an inert solvent with activation of the carboxylic acid function or

[B] a compound of the formula (IV)

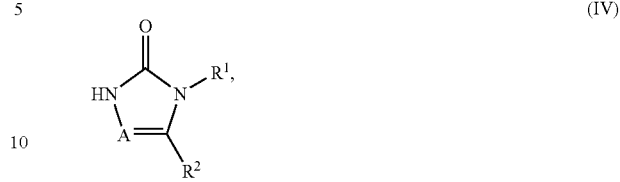

in which A, $R^1$ and $R^2$ each have the aforesaid meanings, is reacted with a compound of the formula (V)

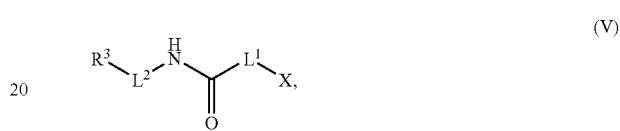

in which $L^1$, $L^2$ and $R^3$ each have the aforesaid meanings and

X stands for a leaving group, such as for example halogen, mesylate or tosylate, in an inert solvent in the presence of a base.

and the resulting compounds of the formula (I) are optionally converted into their solvates, salts and/or solvates of the salts with the appropriate (i) solvents and/or (ii) bases or acids.

Inert solvents for the process step (II)+(III)→(I) are for example ethers such as diethyl ether, dioxan, tetrahydrofuran, glycol dimethyl ether or diethylene glycol dimethyl ether, hydrocarbons such as benzene, toluene, xylene, hexane, cyclohexane or petroleum fractions, halogenated hydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethylsulphoxide, N,N-dimethylformamide, N,N'-dimethylpropyleneurea (DMPU) or N-methylpyrrolidone (NMP). Likewise it is possible to use mixtures of the said solvents. Dichloromethane, tetrahydrofuran, dimethylformamide, dimethylsulphoxide or mixtures of these solvents are preferred.

As condensation agents for the amidation in the process step (II)+(III)→(I), for example carbodiimides such as N,N'-diethyl-, N,N'-dipropyl-, N,N'-diisopropyl- or N,N'-dicyclohexylcarbodiimide (DCC) or N-(3-dimethylaminoisopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium-3 sulphate or 2-tert.-butyl-5-methyl-isoxazolium perchlorate, acylamino compounds such as 2-ethoxy-1-ethoxycarbonyl-1,2-dihydroquinoline, or isobutyl chloroformate, propanephosphonic anhydride, diethyl cyanophosphonate, bis-(2-oxo-3-oxazolidinyl)-phosphoryl chloride, benzotriazol-1-yloxy-tris(dimethylamino)phosphonium hexafluorophosphate, benzotriazol-1-yloxy-tris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2- oxo-1-(2H)-pyridyl)-1,1,3,3-tetramethyluronium tetrafluoroborate (TPTU), O-(7-Azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), optionally in combination with other additives such as 1-hydroxybenzotriazole (HOBt) or N-hydroxysuccinimide (HOSu), and, as bases, alkali metal carbonates, e.g. sodium or potassium carbonate or hydrogen carbonate, or organic bases such as trialkylamines, e.g. triethylamine, N-methylmorpholine, N-methylpiperidine or N,N-diisopropylethylamine, are suitable. Preferably EDC in combination with HOBt or TBTU in combination with N,N-diisopropylethylamine is used.

The condensation (II)+(III)→(I) is generally performed in a temperature range from −20° C. to +60° C., preferably at 0° C. to +40° C. The reaction can take place at normal, increased or reduced pressure (e.g. from 0.5 to 5 bar). The operation is generally carried out at normal pressure.

Inert solvents for the process step (IV)+(V)→(I) are for example halogenated hydrocarbons such as dichloromethane, trichloromethane, tetrachloromethane, trichloroethylene or chlorobenzene, ethers such as diethyl ether, dioxan, tetrahydrofuran, glycol dimethyl ether or diethylene glycol dimethyl ether, hydrocarbons such as benzene, toluene, xylene, hexane, cyclohexane or petroleum fractions, or other solvents such as acetone, methyl ethyl ketone, ethyl acetate, acetonitrile, N,N-dimethylformamide, dimethylsulphoxide, N,N'-dimethylpropyleneurea (DMPU), N-methylpyrrolidone (NMP) or pyridine. Likewise it is possible to use mixtures of the said solvents. Preferably, acetonitrile, acetone or dimethylformamide is used.

As bases for the process step (IV)+(V)→(I), the usual inorganic or organic bases are suitable. These preferably include alkali metal hydroxides such as for example lithium, sodium or potassium hydroxide, alkali metal or alkaline earth metal carbonates such as lithium, sodium, potassium, calcium or caesium carbonate, alkali metal alcoholates such as sodium or potassium methanolate, sodium or potassium ethanolate or sodium or potassium tert.-butylate, alkali metal hydrides such as sodium or potassium hydride, amides such as sodamide, lithium or potassium bis(trimethylsilyl)-amide or lithium diisopropylamide, or organic amines such as triethylamine, N-methylmorpholine, N-methylpiperidine N,N-diisopropylethylamine, pyridine, 1,5-diazabicyclo-[4.3.0]non-5-ene (DBN), 1,8-diazabicyclo[5.4.0]undec-7-ene (DBU) or 1,4-diazabicyclo[2.2.2]octane (DABCO®). Preferably, potassium or caesium carbonate is used.

For this, the base is used in an amount of 1 to 5 mol, preferably in an amount of 1 to 2.5 mol, based on 1 mol of the compound of the formula (IV). The reaction generally takes place in a temperature range from 0° C. to +100° C., preferably at +20° C. to +80° C. The reaction can take place at normal, increased or reduced pressure (e.g. from 0.5 to 5 bar). The operation is generally carried out at normal pressure.

The production of the compounds according to the invention can be illustrated by the following synthetic scheme:

Scheme 1

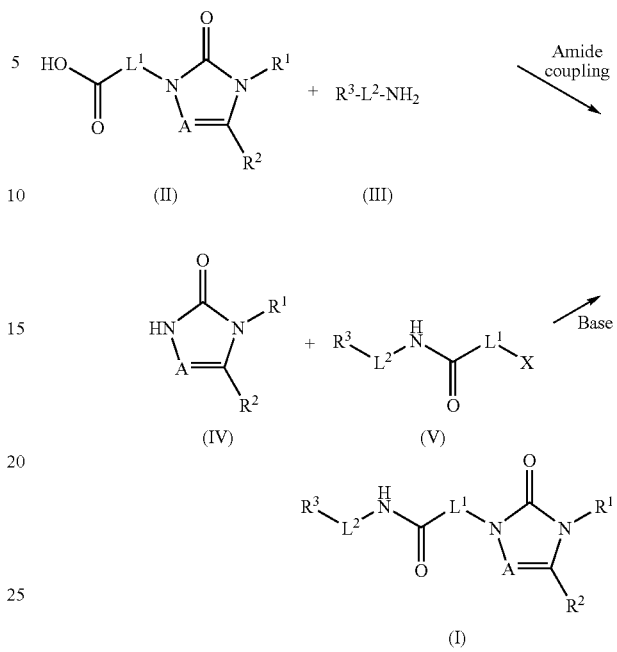

The compounds of the formula (II), in which A stands for N, can be obtained by base-induced alkylation of 5-aryl-2,4-dihydro-3H-1,2,4-triazol-3-ones of the formula (IVa) to give the $N^2$-substituted compounds (VIIa) and subsequent ester hydrolysis (see Scheme 2):

Scheme 2

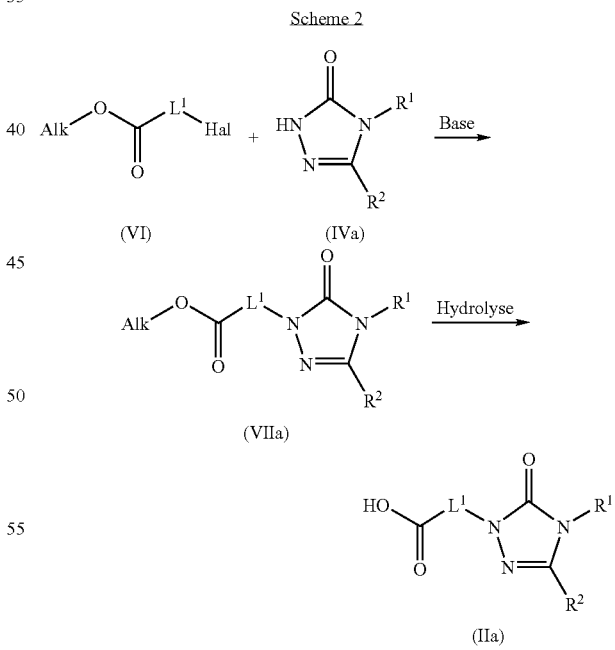

[Alk = Alkyl, Hal = Halogen].

The compounds of the formula (VIIa) can alternatively be obtained from N-(alkoxycarbonyl)-arylthioamides of the formula (IX) known in the literature [see e.g. M. Arnswald, W. P. Neumann, J. Org. Chem. 58 (25), 7022-7028 (1993); E. P. Papadopoulos, J. Org. Chem. 41 (6), 962-965 (1976)] by reaction with hydrazino esters of the formula (VIII) and subsequent alkylation on N-4 of the triazolone (Xa) (Scheme 3):

Scheme 3

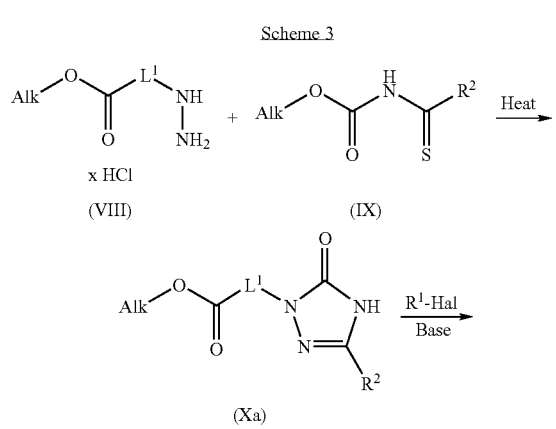

The compounds of the formula (II), in which A stands for C—R[4], are accessible by reaction of α-aminoketones of the formula (XI) with isocyanates of the formula (XII) and subsequent ester hydrolysis (Scheme 4). The compounds of the formula (XI) can themselves be synthesized in a manner known in the literature from α-bromoketones of the formula (XIV) and amino esters of the formula (XV) (Scheme 5):

Scheme 4

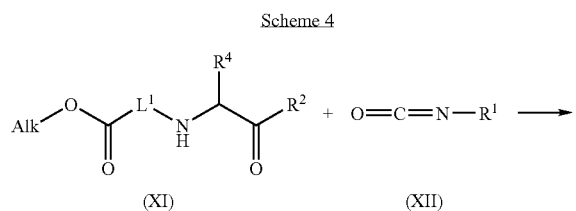

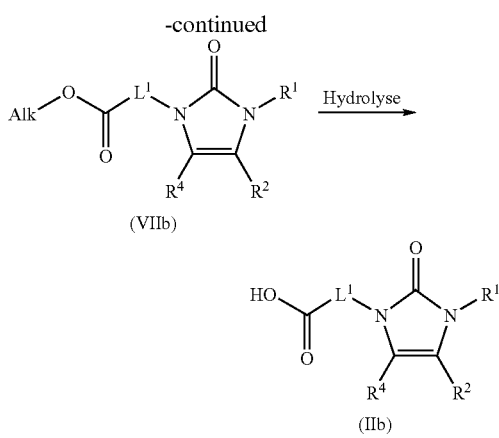

Scheme 5

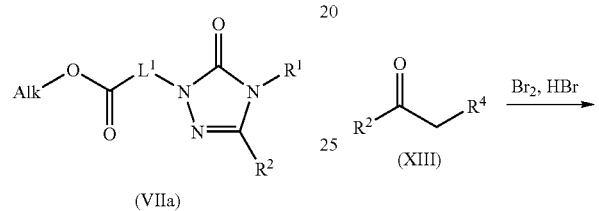

The compounds of the formula (IV), in which A stands for N, can be produced starting from carboxylic acid hydrazides of the formula (XVI) by reaction with isocyanates of the formula (XII) or nitrophenyl carbamates of the formula (XVII) and subsequent base-induced cyclization of the intermediate hydrazine carboxamides (XVIII) (Scheme 6):

Scheme 6

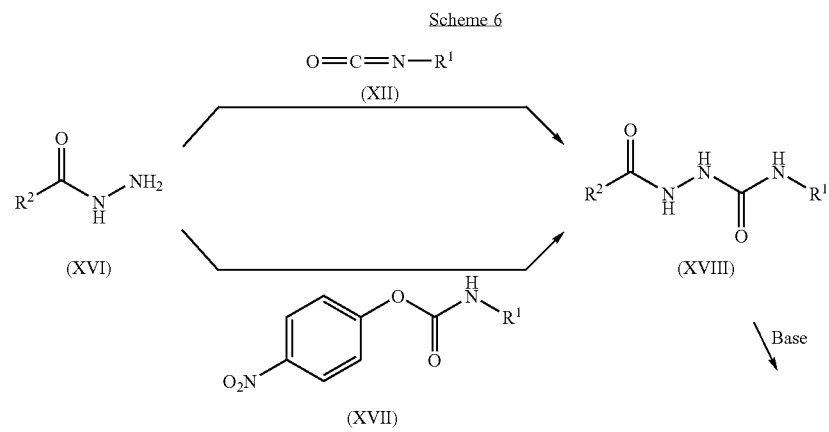

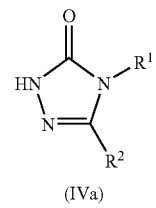

(IVa)

The compounds of the formula (V) are for example accessible by acylation of amines of formula (III) with carboxylic acid chlorides of the formula (XIX) (Scheme 7):

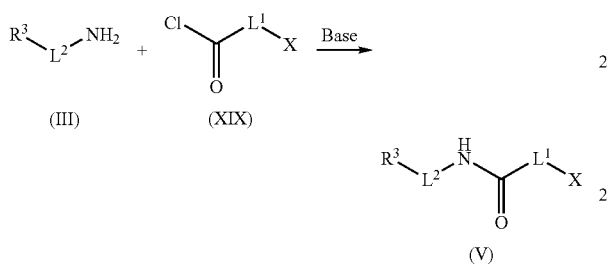

In a particular process modification, compounds of the formula (VIIa) or (VIIb) can optionally also be produced in that instead of $R^1$ in the processes described in Schemes 2, 3, 4 or 6, a temporary protective group (PG), such as for example allyl or 4-methoxybenzyl, is firstly used; after their cleavage to give compounds of the formula (X), compounds of the formula (VII) can be obtained by appropriate N-alkylation (Scheme 8):

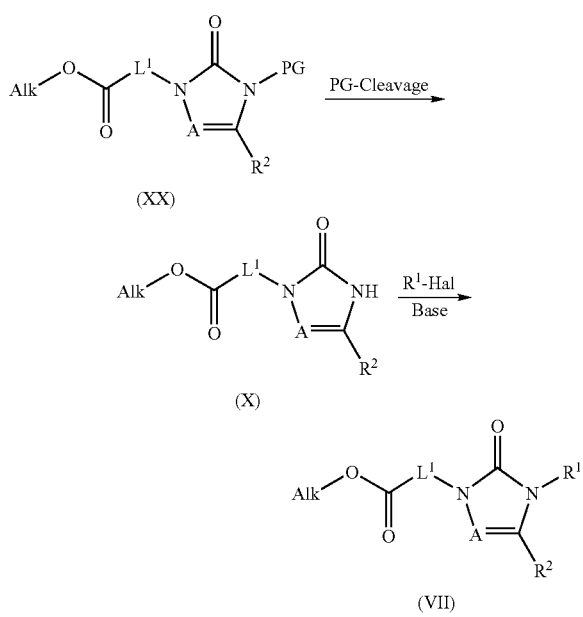

[PG = protective group, e.g. allyl or 4-methoxybenzyl].

Analogous conversions PG→$R^1$ can optionally also be effected later at the stage of the compounds of the formula (IIa), (IIb) or (I) (Scheme 9):

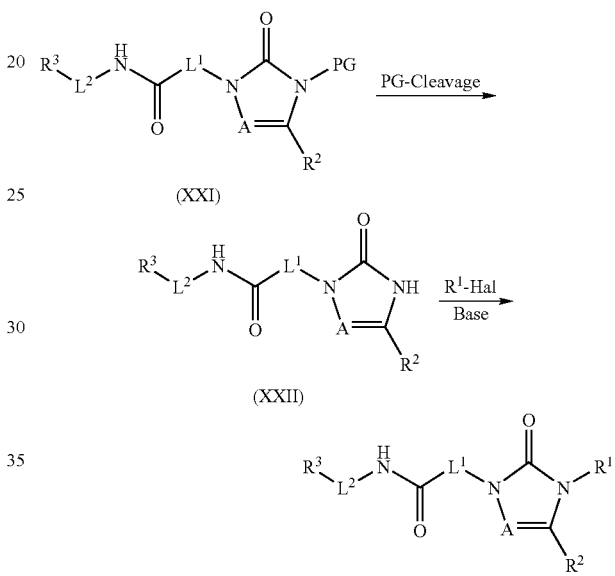

The introduction and cleavage of the protective group PG here takes place by normal literature methods [see e.g. T. W. Greene and P. G. M. Wuts, *Protective Groups in Organic Synthesis*, Wiley, New York, 1999]. Thus the allyl group is preferably removed by means of formic acid in the presence of the tetrakis(triphenylphosphine)palladium(0) catalyst and an amine base such as triethylamine. The cleavage of the p-methoxybenzyl protective group is preferably effected by means of strong acids, such as for example trifluoroacetic acid, or by an oxidative route, e.g. by treatment with 2,3-dichloro-5,6-dicyano-1,4-benzoquinone (DDQ) or ammonium cerium(IV) nitrate.

The subsequent N-alkylation (X)→(VII) or (XXII)→(I) is performed analogously to the previously described process step (IV)+(V)→(I). As inert solvents, acetone, acetonitrile, dimethylformamide, dimethylsulphoxide, toluene, tetrahydrofuran, glycol dimethyl ether or mixtures thereof are preferable. As the base, sodium hydride or potassium or caesium carbonate is preferably used. Optionally, these alkylations can advantageously be performed with the addition of catalysts such as for example lithium bromide, sodium iodide, tetra-n-butylammonium bromide or benzyltriethylammonium chloride. The reactions generally take place in a temperature range from 0° C. to +150° C., preferably at +20° C. to +80° C.

Many of the compounds of the formulae (III), (VI), (VIII), (IX), (XII), (XIII), (XV), (XVI), (XVII) and (XIX) are commercially available, known in the literature or accessible by generally known processes.

The compounds according to the invention have valuable pharmacological properties and can be used for the prophylaxis and/or treatment of various diseases and disease-induced states in humans and animals.

The compounds according to the invention are potent selective V1a, selective V2 and in particular dual V1a/V2 receptor antagonists, which inhibit vasopressin activity in vitro and in vivo. Furthermore, the compounds according to the invention also act as antagonists on the related oxytocin receptor.

The compounds according to the invention are particularly suitable for the prophylaxis and/or treatment of cardiovascular diseases. In this connection, the following may for example and preferably be mentioned as target indications: acute and chronic cardiac insufficiency, arterial hypertension, coronary heart disease, stable and unstable angina pectoris, myocardial ischaemia, myocardial infarction, shock, arteriosclerosis, atrial and ventricular arrhythmias, transitory and ischaemic attacks, stroke, inflammatory cardiovascular diseases, peripheral and cardiac vascular diseases, peripheral circulation disorders, arterial pulmonary hypertension, spasms of the coronary arteries and peripheral arteries, thromboses, thromboembolic diseases, oedema formation such as for example pulmonary oedema, cerebral oedema, renal oedema or cardiac insufficiency-related oedema, and restenosis for example after thrombolysis treatments, percutaneous-transluminal angioplasties (PTA), transluminal coronary angioplasties (PTCA), heart transplants and bypass operations.

In the sense of the present invention, the term cardiac insufficiency also includes more specific or related disease forms such as right cardiac insufficiency, left cardiac insufficiency, global insufficiency, ischaemic cardiomyopathy, dilative cardiomyopathy, congenital heart defects, heart valve defects, cardiac insufficiency with heart valve defects, mitral valve stenosis, mitral valve insufficiency, aortic valve stenosis, aortic valve insufficiency, tricuspidal stenosis, tricuspidal insufficiency, pulmonary valve stenosis, pulmonary valve insufficiency, combined heart valve defects, heart muscle inflammation (myocarditis), chronic myocarditis, acute myocarditis, viral myocarditis, diabetic cardiac insufficiency, alcohol-toxic cardiomyopathy, cardiac storage diseases, diastolic cardiac insufficiency and systolic cardiac insufficiency.

Furthermore, the compounds according to the invention are suitable for use as a diuretic for the treatment of oedemas and in electrolyte disorders, in particular in hypervolaemic and euvolaemic hyponatraemia.

The compounds according to the invention are also suitable for the prophylaxis and/or treatment of polycystic kidney disease (PCKD) and syndrome of inappropriate ADH secretion (SIADH).

In addition, the compounds according to the invention can be used for the prophylaxis and/or treatment of liver cirrhosis, ascites, diabetes mellitus and diabetic complications such as for example neuropathy and nephropathy, acute and chronic kidney failure and chronic renal insufficiency.

Further, the compounds according to the invention are suitable for the prophylaxis and/or treatment of central nervous disorders such as anxiety states and depression, of glaucoma and of cancer, in particular of pulmonary tumours.

Furthermore, the compounds according to the invention can be used for the prophylaxis and/or treatment of inflammatory diseases, asthmatic diseases, chronic-obstructive respiratory tract diseases (COPD), pain conditions, prostatic hypertrophy, incontinence, bladder inflammation, hyperactive bladder, diseases of the adrenals such as for example pheochromocytoma and adrenal apoplexy, diseases of the intestine such as for example Crohn's disease and diarrhoea, or of menstrual disorders such as for example dysmenorrhoea.

A further object of the present invention is the use of the compounds according to the invention for the treatment and/or prophylaxis of diseases, in particular of the diseases mentioned above.

A further object of the present invention is the use of the compounds according to the invention for the production of a medicament for the treatment and/or prophylaxis of diseases, in particular of the diseases mentioned above.

A further object of the present invention is a method for the treatment and/or prophylaxis of diseases, in particular of the diseases mentioned above, with the use of an effective quantity of at least one of the compounds according to the invention.

The compounds according to the invention can be used alone or if necessary in combination with other active substances. A further object of the present invention are medicaments which contain at least one of the compounds according to the invention and one or more other active substances, in particular for the treatment and/or prophylaxis of the diseases mentioned above. As combination active substances suitable for this, the following may for example and preferably be mentioned:

- organic nitrates and NO donors, such as for example sodium nitroprusside, nitroglycerine, isosorbide mononitrate, isosorbide dinitrate, molsidomine or SIN-1, and inhalational NO;
- diuretics, in particular loop diuretics and thiazides and thiazide-like diuretics;
- positive-inotropically active compounds, such as for example cardiac glycosides (digoxin), and beta-adrenergic and dopaminergic agonists such as isoproterenol, adrenalin, noradrenalin, dopamine and dobutamine;
- compounds which inhibit the degradation of cyclic guanosine monophosphate (cGMP) and/or cyclic adenosine monophosphate (cAMP), such as for example inhibitors of phosphodiesterases (PDE) 1, 2, 3, 4 and/or 5, in particular PDE 5 inhibitors such as sildenafil, vardenafil and tadalafil, and PDE 3 inhibitors such as amrinone and milrinone;
- natriuretic peptides such as for example "atrial natriuretic peptide" (ANP, anaritide), "B-type natriuretic peptide" or "brain natriuretic peptide" (BNP, nesiritide), "C-type natriuretic peptide" (CNP) and urodilatin;
- calcium sensitisers, such as for example and preferably levosimendan;
- NO- and haem-independent activators of guanylate cyclase, such as in particular the compounds described in WO 01/19355, WO 01/19776, WO 01/19778, WO 01/19780, WO 02/070462 and WO 02/070510;
- NO-independent, but haem-dependent stimulators of guanylate cyclase, such as in particular the compounds described in WO 00/06568, WO 00/06569, WO 02/42301 and WO 03/095451;
- Inhibitors of human neutrophil elastase (HNE), such as for example sivelestat or DX-890 (reltran);
- Compounds inhibiting the signal transduction cascade, such as for example tyrosine kinase inhibitors, in particular sorafenib, imatinib, gefitinib and erlotinib;

compounds influencing the energy metabolism of the heart, such as for example and preferably etomoxir, dichloracetate, ranolazine or trimetazidine;

agents with antithrombotic action, for example and preferably from the group of the thrombocyte aggregation inhibitors, anticoagulants or profibrinolytic substances;

blood pressure-lowering active substances, for example and preferably from the group of the calcium antagonists, angiotensin AII antagonists, ACE inhibitors, vasopeptidase inhibitors, inhibitors of neutral endopeptidase, endothelin antagonists, renin inhibitors, alpha receptor blockers, beta receptor blockers, mineralocorticoid receptor antagonists and rho-kinase inhibitors; and/or active substances modifying fat metabolism, for example and preferably from the group of the thyroid receptor agonists, cholesterol synthesis inhibitors such as for example and preferably HMG-CoA reductase or squalene synthesis inhibitors, ACAT inhibitors, CETP inhibitors, MTP inhibitors, PPAR-alpha-, PPAR-gamma- and/or PPAR-delta agonists, cholesterol absorption inhibitors, lipase inhibitors, polymeric gallic acid adsorbers, gallic acid reabsorption inhibitors and lipoprotein(a) antagonists.

In a preferred embodiment of the invention, the compounds according to the invention are administered in combination with a diuretic, such as for example and preferably furosemid, bumetanid, torsemid, bendroflumethiazid, chlorthiazid, hydrochlorthiazid, hydroflumethiazid, methyclothiazid, polythiazid, trichlormethiazid, chlorthalidon, indapamid, metolazon, quinethazon, acetazolamid, dichlorophenamid, methazolamid, glycerine, isosorbide, mannitol, amilorid or triamteren.

Agents with antithrombotic action are understood preferably to mean compounds from the group of the thrombocyte aggregation inhibitors, anticoagulants or profibrinolytic substances.

In a preferred embodiment of the invention, the compounds according to the invention are administered in combination with a thrombocyte aggregation inhibitor, such as for example and preferably aspirin, clopidogrel, ticlopidine or dipyridamol.

In a preferred embodiment of the invention, the compounds according to the invention are administered in combination with a thrombin inhibitor, such as for example and preferably ximelagatran, melagatran, bivalirudin or clexane.

In a preferred embodiment of the invention, the compounds according to the invention are administered in combination with a GPIIb/IIIa antagonist, such as for example and preferably tirofiban or abciximab.

In a preferred embodiment of the invention, the compounds according to the invention are administered in combination with a factor Xa inhibitor, such as for example and preferably rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as for example and preferably coumarin.

Blood pressure-lowering agents are understood preferably to mean compounds from the group of the calcium antagonists, angiotensin AII antagonists, ACE inhibitors, vasopeptidase inhibitors, inhibitors of neutral endopeptidase, endothelin antagonists, renin inhibitors, alpha receptor blockers, beta receptor blockers, mineralocorticoid receptor antagonists, rho-kinase inhibitors and diuretics.

In a preferred embodiment of the invention, the compounds according to the invention are administered in combination with a calcium antagonist, such as for example and preferably nifedipin, amlodipin, verapamil or diltiazem.

In a preferred embodiment of the invention, the compounds according to the invention are administered in combination with an angiotensin AII antagonist, such as for example and preferably losartan, candesartan, valsartan, telmisartan or embusartan.

In a preferred embodiment of the invention, the compounds according to the invention are administered in combination with an ACE inhibitor, such as for example and preferably enalapril, captopril, lisinopril, ramipril, delapril, fosinopril, quinopril, perindopril or trandopril.

In a preferred embodiment of the invention, the compounds according to the invention are administered in combination with a vasopeptidase inhibitor or inhibitor of neutral endopeptidase (NEP), such as for example and preferably omapatrilat or AVE-7688.

In a preferred embodiment of the invention, the compounds according to the invention are administered in combination with an endothelin antagonist, such as for example and preferably bosentan, darusentan, ambrisentan or sitaxsentan.

In a preferred embodiment of the invention, the compounds according to the invention are administered in combination with a renin inhibitor, such as for example and preferably aliskiren, SPP-600 or SPP-800.

In a preferred embodiment of the invention, the compounds according to the invention are administered in combination with an alpha-1 receptor blocker, such as for example and preferably prazosin.

In a preferred embodiment of the invention, the compounds according to the invention are administered in combination with a beta receptor blocker, such as for example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with a mineralocorticoid receptor antagonist, such as for example and preferably spironolactone, eplerenon, canrenon or potassium canrenoate.

In a preferred embodiment of the invention, the compounds according to the invention are administered in combination with a rho-kinase inhibitor, such as for example and preferably fasudil, Y-27632, SLx-2119, BF-66851, BF-66852, BF-66853, KI-23095 or BA-1049.

Fat metabolism-modifying agents are understood preferably to mean compounds from the group of the CETP inhibitors, thyroid receptor agonists, cholesterol synthesis inhibitors such as HMG-CoA reductase or squalene synthesis inhibitors, ACAT inhibitors, MTP inhibitors, PPAR-alpha-, PPAR-gamma- and/or PPAR-delta agonists, cholesterol absorption inhibitors, polymeric gallic acid adsorbers, gallic acid reabsorption inhibitors, lipase inhibitors and lipoprotein (a) antagonists.

In a preferred embodiment of the invention, the compounds according to the invention are administered in combination with a CETP inhibitor, such as for example and preferably torcetrapib (CP-529 414), JJT-705, BAY 60-5521, BAY 78-7499 or CETP-vaccine (avant).

In a preferred embodiment of the invention, the compounds according to the invention are administered in combination with a thyroid receptor agonist, such as for example and preferably D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of the statins, such as for example and preferably lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor, such as for example and preferably BMS-188494 or TAK-475.

In a preferred embodiment of the invention, the compounds according to the invention are administered in combination with an ACAT inhibitor, such as for example and preferably avasimibe, melinamide, pactimibe, eflucimibe or SMP-797.

In a preferred embodiment of the invention, the compounds according to the invention are administered in combination with an MTP inhibitor, such as for example and preferably implitapide, BMS-201038, R-103757 or JTT-130.

In a preferred embodiment of the invention, the compounds according to the invention are administered in combination with a PPAR-gamma agonist, such as for example and preferably pioglitazone or rosiglitazone.

In a preferred embodiment of the invention, the compounds according to the invention are administered in combination with a PPAR-delta agonist, such as for example and preferably GW-501516 or BAY 68-5042.

In a preferred embodiment of the invention, the compounds according to the invention are administered in combination with a cholesterol absorption inhibitor, such as for example and preferably ezetimibe, tiqueside or pamaqueside.

In a preferred embodiment of the invention, the compounds according to the invention are administered in combination with a lipase inhibitor, such as for example and preferably orlistat.

In a preferred embodiment of the invention, the compounds according to the invention are administered in combination with a polymeric gallic acid adsorber, such as for example and preferably cholestyramine, colestipol, colesolvam, cholestagel or colestimid.

In a preferred embodiment of the invention, the compounds according to the invention are administered in combination with a gallic acid reabsorption inhibitor, such as for example and preferably ASBT (=IBAT) inhibitors such as for example AZD-7806, S-8921, AK-105, BARI-1741, SC-435 or SC-635.

In a preferred embodiment of the invention, the compounds according to the invention are administered in combination with a lipoprotein(a) antagonist, such as for example and preferably gemcabene calcium (CI-1027) or nicotinic acid.

A further object of the present invention are medicaments which contain at least one compound according to the invention, usually together with one or more inert, non-toxic, pharmaceutically suitable additives, and the use thereof for the aforesaid purposes.

The compounds according to the invention can act systemically and/or locally. For this purpose, they can be administered in a suitable manner, such as for example by the oral, parenteral, pulmonary, nasal, sublingual, lingual, buccal, rectal, dermal, transdermal, conjunctival or aural routes or as an implant or stent.

For these administration routes, the compounds according to the invention can be administered in suitable administration forms.

For oral administration, administration forms which function according to the state of the art, releasing the compound according to the invention rapidly and/or in a modified manner, which contain the compounds according to the invention in crystalline and/or amorphized and/or dissolved form, such as for example tablets (uncoated or coated tablets, for example with gastric juice-resistant or delayed dissolution or insoluble coatings, which control the release of the compound according to the invention), tablets rapidly disintegrating in the oral cavity or films/wafers, films/lyophilisates, capsules (for example hard or soft gelatine capsules), dragees, granules, pellets, powders, emulsions, suspensions, aerosols or solutions are suitable.

Parenteral administration can be effected omitting an absorption step (e.g. intravenous, intra-arterial, intracardial, intraspinal or intralumbar administration) or involving absorption (e.g. intra-muscular, subcutaneous, intracutaneous, percutaneous or intraperitoneal administration). Suitable administration forms for parenteral administration include injection and infusion preparations in the form of solutions, suspensions, emulsions, lyophilisates or sterile powders.

For the other administration routes, for example inhalation formulations (including powder inhalers and nebulisers), nasal drops, solutions or sprays, tablets for lingual, sublingual or buccal administration, tablets, films/wafers or capsules, suppositories, oral or ophthalmic preparations, vaginal capsules, aqueous suspensions (lotions, shakable mixtures), lipophilic suspensions, ointments, creams, transdermal therapeutic systems (e.g. plasters), milk, pastes, foams, dusting powders, implants or stents are suitable.

Oral or parenteral administration, in particular oral and intravenous administration, are preferred.

The compounds according to the invention can be converted into the stated administration forms. This can be effected in a manner known per se by mixing with inert, non-toxic, pharmaceutically suitable additives. These additives include carriers (for example microcrystalline cellulose, lactose or mannitol), solvents (e.g. liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants such as for example ascorbic acid), colourants (e.g. inorganic pigments such as for example iron oxide) and flavour or odour correctors.

In general, to achieve effective results in parenteral administration it has been found advantageous to administer quantities of about 0.001 to 10 mg/kg, preferably about 0.01 to 1 mg/kg body weight. In oral administration, the dosage is about 0.01 bis 100 mg/kg, preferably about 0.01 to 20 mg/kg and quite especially preferably 0.1 to 10 mg/kg body weight.

Nonetheless it can sometimes be necessary to deviate from the said quantities, namely depending on body weight, administration route, individual response to the active substance, nature of the preparation and time or interval at which administration takes place. Thus in some cases it can be sufficient to manage with less than the aforesaid minimum quantity, while in other cases the stated upper limit must be exceeded. In the event of administration of larger quantities, it may be advisable to divide these into several individual administrations through the day.

The following practical examples illustrate the invention. The invention is not limited to the examples.

Unless otherwise stated, the percentages stated in the following tests and examples are percent by weight, parts are parts by weight, and solvent ratios, dilution ratios and concentration information about liquid/liquid solutions are each based on volume.

A. EXAMPLES

Abbreviations

| | |
|---|---|
| Alk | alkyl |
| Boc | tert.-butoxycarbonyl |
| CI | chemical ionization (in MS) |
| DCI | direct chemical ionization (in MS) |
| DME | 1,2-dimethoxyethane |
| DMF | dimethylformamide |
| DMSO | dimethylsulphoxide |
| of theory | of theory (for yields) |
| EDC | N'-(3-dimethylaminopropyl)-N-ethylcarbodiimide (hydrochloride) |
| EA | ethyl acetate |
| eq. | equivalent(s) |
| ESI | electrospray ionization (in MS) |
| FMOC | 9-fluorenylmethoxycarbonyl |
| GC/MS | gas chromatography-coupled mass spectrometry |
| sat. | saturated |
| hr(s) | hour(s) |
| Hal | halogen |
| HOBt | 1-hydroxy-1H-benzotriazole hydrate |
| HPLC | high pressure, high performance liquid chromatography |
| conc. | concentrated |
| LC/MS | liquid chromatography-coupled mass spectrometry |
| LDA | lithium diisopropylamide |
| LiHMDS | lithium hexamethyldisilazane |
| min(s) | minute(s) |
| MS | mass spectrometry |
| NMR | nuclear magnetic resonance spectrometry |
| PG | protective group |
| rac | racemic/racemate |
| $R_f$ | retention factor (in thin layer chromatography on silica gel) |
| RT | room temperature |
| $R_t$ | retention time (in HPLC) |
| TBTU | 0-(benzotriazol-1-yl)-N,N,N',N'-tetramethyluronium tetrafluoroborate |
| THF | tetrahydrofuran |
| TMOF | trimethyl orthoformate |
| UV | ultraviolet spectrometry |
| v/v | volume to volume ratio (of a solution) |

LC/MS-, HPLC- and GC/MS-Methods:

Method 1 (HPLC): Instrument: HP 1100 with DAD detection; Column: Kromasil 100 RP-18, 60 mm×2.1 mm, 3.5 µm; Eluent A: 5 ml $HClO_4$ (70%)/liter water, Eluent B: acetonitrile; Gradient: 0 min 2% B→0.5 min 2% B→4.5 min 90% B→9 min 90% B→9.2 ml 2% B 10 min 2% B; Flow rate: 0.75 ml/min; Column temperature: 30° C.; UV detection: 210 nm.

Method 2 (HPLC): Instrument: HP 1100 with DAD detection; Column: Kromasil 100 RP-18, 60 mm×2.1 mm, 3.5 µm; Eluent A: 5 ml $HClO_4$ (70%)/liter water, Eluent B: acetonitrile; Gradient: 0 min 2% B→0.5 min 2% B→4.5 min 90% B→6.5 min 90% B→6.7 min 2% B→7.5 min 2% B; Flow rate: 0.75 mL/min; Column temperature: 30° C.; UV detection: 210 nm.

Method 3 (LC/MS): Instrument: Micromass Platform LCZ with HPLC Agilent Series 1100; Column: Thermo Hypersil GOLD 31±20 mm×4 mm; Eluent A: 1 l water+0.5 ml 50% formic acid; Eluent B: 1 l acetonitrile+0.5 ml 50% formic acid; Gradient: 0.0 min 100% A→0.2 min 100% A→2.9 min 30% A→3.1 min 10% A→5.5 min 10% A; Oven: 50° C.; Flow rate: 0.8 mL/min; UV detection: 210 nm.

Method 4 (LC/MS): MS instrument type: Micromass ZQ; HPLC instrument type: HP 1100 Series; UV DAD; Column: Phenomenex Synergi 2µ Hydro-RP Mercury 20 mm×4 mm; Eluent A: 1 l water+0.5 ml 50% formic acid, Eluent B: 1 l acetonitrile+0.5 ml 50% formic acid; Gradient: 0.0 min 90% A→2.5 min 30% A→3.0 min 5% A→4.5 min 5% A; Flow rate: 0.0 min 1 mL/min→2.5 min/3.0 min/4.5 min 2 ml/min; Oven: 50° C.; UV detection: 210 nm.

Method 5 (LC/MS): Instrument: Micromass Quattro LCZ with HPLC Agilent Series 1100; Column: Phenomenex Synergi 2µ Hydro-RP Mercury 20 mm×4 mm; Eluent A: 1 l water+0.5 ml 50% formic acid, Eluent B: 1 l acetonitrile+0.5 ml 50% formic acid; Gradient: 0.0 min 90% A→2.5 min 30% A→3.0 min 5% A→4.5 min 5% A; Flow rate: 0.0 min 1 mL/min→2.5 min/3.0 min/4.5 min 2 ml/min; Oven: 50° C.; UV detection: 208-400 nm.

Method 6 (LC/MS): Instrument MS: Waters ZQ 2000; Instrument HPLC: Agilent 1100, 2-column switching; Autosampler: HTC PAL; Column: YMC-ODS-AQ, 50 mm×4.6 mm, 3.0 µm; Eluent A: water+0.1% formic acid, Eluent B: acetonitrile+0.1% formic acid; Gradient: 0.0 min 100% A→0.2 min 95% A→1.8 min 25% A→1.9 min 10% A→2.0 min 5% A→3.2 min 5% A→3.21 min 100% A→3.35 min 100% A; Oven: 40° C.; Flow rate: 3.0 mL/min; UV detection: 210 nm.

Method 7 (LC/MS): MS instrument type: Micromass ZQ; HPLC instrument type: Waters Alliance 2795; Column: Phenomenex Synergi 2µ Hydro-RP Mercury 20 mm×4 mm; Eluent A: 1 l water+0.5 ml 50% formic acid, Eluent B: 1 l acetonitrile+0.5 ml 50% formic acid; Gradient: 0.0 min 90% A→2.5 min 30% A→3.0 min 5% A→4.5 min 5% A; Flow rate: 0.0 ml/min→2.5 min/3.0 min/4.5 min 2 mL/min; Oven: 50° C.; UV detection: 210 nm.

Method 8 (LC/MS): MS instrument type: Micromass ZQ; HPLC instrument type: HP 1100 Series; UV DAD; Column: Phenomenex Gemini 3µ 30 mm×3.00 mm; Eluent A: 1 l water+0.5 ml 50% formic acid, Eluent B: 1 l acetonitrile+0.5 ml 50% formic acid; Gradient: 0.0 min 90% A→2.5 min 30% A→3.0 min 5% A→4.5 min 5% A; Flow rate: 0.0 min 1 mL/min→2.5 min/3.0 min/4.5 min 2 ml/min; Oven: 50° C.; UV detection: 210 nm.

Method 9 (preparative HPLC): Instrument: Abimed Gilson Pump 305/306, Manometric Module 806; Column: Grom-Sil 120 ODS-4HE 10 µm, 250 mm×30 mm; Eluent: A=water, B=acetonitrile; Gradient: 0.0 min 30% B, 3 min 30% B, 31 min 95% B, 44 min 95% B, 44.01 min 30% B, 45 min 30% B; Flow rate: 50 ml/min; Column temperature: RT; UV detection: 210 nm.

Method 10 (preparative HPLC): Instrument: Abimed Gilson Pump 305/306, Manometric Module 806; Column: Grom-Sil 120 ODS-4HE 10 µm, 250 mm×20 mm; Eluent: A=water, B=acetonitrile; Gradient: 0.0 min 10% B, 5 min 10% B, 30 min 95% B, 34 min 95% B, 34.01 min 10% B, 38 min 10% B; Flow rate: 25 ml/min; Column temperature: RT; UV detection: 210 nm.

Method 11 (preparative HPLC): Instrument: Abimed Gilson Pump 305/306, Manometric Module 806; Column: Grom-Sil 120 ODS-4HE 10 µm, 250 mm×20 mm; Eluent: A=water, B=acetonitrile; Gradient: 0.0 min 10% B, 3 min 10% B, 30 min 95% B, 42 min 95% B, 42.01 min 10% B, 45 min 10% B; Flow rate: 50 ml/min; Column temperature: RT; UV detection: 210 nm.

Method 12 (preparative HPLC): Instrument: Abimed Gilson Pump 305/306, Manometric Module 806; Column: Grom-Sil 120 ODS-4HE 10 µm, 250 mm×40 mm; Eluent: A=water, B=acetonitrile; Gradient: 0.0 min 10% B, 3 min 10% B, 27 min 98% B, 34 min 98% B, 38 min 10% B; Flow rate: 50 ml/min; Column temperature: RT; UV detection: 214 nm.

Method 13 (preparative HPLC): Instrument: Abimed Gilson Pump 305/306, Manometric Module 806; Column: Macherey-Nagel VP 50/21 Nucleosil 100-5 C18 Nautilus 5 µm; Eluent: A=acetonitrile, B=water+0.1% formic acid; Gradient: 0.0 min 10% A, 2.00 min 10% A, 6.00 min 90% A, 7.00 min 90% A, 7.10 min 10% A, 8 min 10% A; Run time: ca. 10 min per separation; Flow rate: 25 mL/min; Column temperature: RT; UV detection: 220 nm.

Method 14 (chiral preparative HPLC): chiral silica gel phase based on the selector poly(N-methacryloyl-L-leucine-tert.-butylamide); Column: 680 mm×40 mm; Eluent: iso-hexane/ethyl acetate 1:1 (v/v); Flow rate: 50 mL/min; Temperature: 24° C.; UV detection: 260 nm. Analytical column: 250 mm×4.6 mm; same eluent; Flow rate: 2 mL/min.

Method 15 (chiral preparative HPLC): chiral silica gel phase based on the selector poly(N-methacryloyl-L-leucine-dicyclopropylmethylamide); Column: 250 mm×30 mm; Eluent: iso-hexane/ethyl acetate 3:7 (v/v); Flow rate: 25 mL/min; Temperature: 24° C.; UV detection: 260 nm. Analytical column: 250 mm×4.6 mm; same eluent; Flow rate: 2 ml/min.

Method 16 (chiral preparative HPLC): chiral silica gel phase based on the selector poly(N-methacryloyl-D-valine-3-pentylamide); Column: 250 mm×20 mm; Eluent: iso-hexane/ethyl acetate 1:3 (v/v); Flow rate: 25 mL/min; Temperature: 24° C.; UV detection: 260 nm. Analytical column: 250 mm×4.6 mm; same eluent; Flow rate: 2 mL/min.

Method 17 (LC/MS): Instrument: Micromass Quattro LCZ with HPLC Agilent Series 1100; Column: Phenomenex Onyx Monolithic C18, 100 mm×3 mm; Eluent A: 1 l water+0.5 ml 50% formic acid, Eluent B: 1 l acetonitrile+0.5 ml 50% formic acid; Gradient: 0.0 min 90% A→2 min 65% A→4.5 min 5% A→6 min 5% A; Flow rate: 2 mL/min; Oven: 40° C.; UV detection: 208-400 nm.

Method 18 (LC/MS): Instrument: Micromass Quattro LCZ with HPLC Agilent Series 1100; Column: Phenomenex Gemini 3µ, 30 mm×3.00 mm; Eluent A: 1 l water+0.5 ml 50% formic acid, Eluent B: 1 l acetonitrile+0.5 ml 50% formic acid; Gradient: 0.0 min 90% A→2.5 min 30% A→3.0 min 5% A→4.5 min 5% A; Flow rate: 0.0 min 1 mL/min→2.5 min/3.0 min/4.5 min 2 mL/min; Oven: 50° C.; UV detection: 208-400 nm.

Method 19 (LC/MS): MS instrument type: Waters ZQ; HPLC instrument type: Waters Alliance 2795; Column: Phenomenex Onyx Monolithic C18, 100 mm×3 mm; Eluent A: 1 l water+0.5 ml 50% formic acid, Eluent B: 1 l acetonitrile+0.5 ml 50% formic acid; Gradient: 0.0 min 90% A→2 min 65% A→4.5 min 5% A→6 min 5% A; Flow rate: 2 mL/min; Oven: 40° C.; UV detection: 210 nm.

Method 20 (preparative HPLC): Column: Grom-Sil 120 ODS-4HE, 10 µm, 250 mm×30 mm; Eluent A: 0.1% formic acid in water, Eluent B: acetonitrile; Flow rate: 50 mL/min; Program: 0-3 min 10% B, 3-27 min gradient to 95% B; 27-34 min 95% B; 34.01-38 min 10% B.

Method 21 (GC/MS): Instrument: Micromass GCT, GC6890; Column: Restek RTX-35, 15 m×200 µm×0.33 µm; constant flow rate with helium: 0.88 mL/min; Oven: 70° C.; Inlet: 250° C.; Gradient: 70° C., 30° C./min→310° C. (3 min hold).

Method 22 (LC/MS): MS instrument type: Micromass ZQ; HPLC instrument type: Waters Alliance 2795; Column: Phenomenex Synergi 2.5µ MAX-RP 100A Mercury 20 mm×4 mm; Eluent A: 1 l water+0.5 ml 50% formic acid, Eluent B: 1 l acetonitrile+0.5 ml 50% formic acid; Gradient: 0.0 min 90% A→0.1 min 90% A→3.0 min 5% A→4.0 min 5% A→4.01 min 90% A; Flow rate: 2 ml/min; Oven: 50° C.; UV detection: 210 nm.

Method 23 (LC/MS): Instrument: Micromass Quattro LCZ with HPLC Agilent Series 1100; Column: Phenomenex Synergi 2.5µ MAX-RP 100A Mercury 20 mm×4 mm; Eluent A: 1 l water+0.5 ml 50% formic acid, Eluent B: 1 l acetonitrile+0.5 ml 50% formic acid; Gradient: 0.0 min 90% A→0.1 min 90% A→3.0 min 5% A→4.0 min 5% A→4.1 min 90% A; Flow rate: 2 ml/min; Oven: 50° C.; UV detection: 208-400 nm.

Method 24 (LC/MS): Instrument MS: Micromass TOF (LCT); Instrument HPLC: Waters 2690; Autosampler: Waters 2700; Column: YMC-ODS-AQ, 50 mm×4.6 mm, 3.0 µm; Eluent A: water+0.1% formic acid, Eluent B: acetonitrile+0.1% formic acid; Gradient: 0.0 min 100% A→0.2 min 95% A→1.8 min 25% A→1.9 min 10% A→2.0 min 5% A→3.2 min 5% A→3.21 min 100% A→3.35 min 100% A; Oven: 40° C.; Flow rate: 3.0 mL/min; UV detection: 210 nm.

Starting Compounds and Intermediates:

Example 1A

2-[3-(trifluoromethyl)phenyl]propan-2-amine

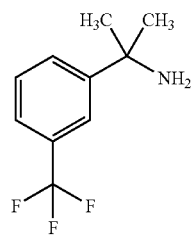

14.0 g (56.8 mmol) of anhydrous cerium(III) chloride are stirred in 60 ml tetrahydrofuran under an argon atmosphere for 2 hours at room temperature. After cooling to −50° C., 35.5 ml of a 1.6 M solution of methyllithium in diethyl ether is slowly added dropwise at this temperature and the mixture stirred for a further 30 mins at −50° C. 3.24 g (18.9 mmol) of 3-trifluoromethylbenzonitrile, dissolved in 30 ml tetrahydrofuran, is then added dropwise at −50° C., allowed to warm slowly to room temperature and then stirred overnight. For the workup, 20 ml of a 25% aqueous ammonia solution are added, the mixture filtered through kieselguhr and the eluate concentrated in vacuo. The residue is taken up in ethyl acetate and extracted twice with 1 N hydrochloric acid. The combined aqueous phases are adjusted to pH 12 with 1 N aqueous sodium hydroxide and extracted twice with ethyl acetate. After drying of the combined organic phases over magnesium sulphate and removal of the solvent in vacuo 3.41 g (98% of theory) of the target compound remain.

LC/MS [Method 3]: $R_t$=2.44 min
$^1$H-NMR (400 MHz, DMSO-$d_6$): δ=1.39 (s, 6H), 2.01 (br. s, 2H), 7.48-7.56 (m, 2H), 7.78-7.85 (m, 1H), 7.90 (s, 1H).

Example 2A 2-(4-chlorobenzoyl)-N-cyclopropylhydrazinecarboxamide

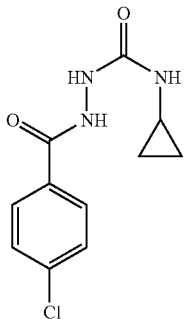

Under an argon atmosphere, 4.00 g (23.4 mmol) of 4-chlorobenzoic acid hydrazide are placed in 50 ml tetrahydrofuran. 1.95 g (23.4 mmol) of cyclopropyl isocyanate, dissolved in 50 ml tetrahydrofuran, are added dropwise at 50° C., and the mixture further stirred overnight at 50° C. The solvent is evaporated in vacuo, diethyl ether is added to the residue and the solid formed is isolated and purified by filtration and further washing with diethyl ether. 5.92 g (ca. 100% of theory) of the target compound are thus obtained.

HPLC [Method 2]: $R_t$=3.69 min

MS [CIpos]: m/z=371 (M+NH$_4$)$^+$, 354 (M+H)$^+$ $^1$H-NMR (400 MHz, DMSO-$d_6$): δ=0.33-0.46 (m, 2H), 0.51-0.65 (m, 2H), 2.44-2.52 (m, 1H), 6.69 (s, 1H), 7.55, 7.57 (AA' part of an AA'BB' system, 2H), 7.88 (s, 1H), 7.88, 7.90 (BB' part of an AA'BB' system, 2H), 10.16 (s, 1H).

The following compounds are obtained analogously:

| Example No. | Structure | LC/MS $R_t$ [Method] | $^1$H-NMR (400 MHz, DMSO-$d_6$) |
|---|---|---|---|
| 3A | 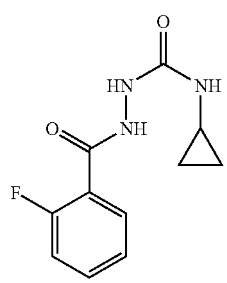 | $R_t$ = 0.86 min [7] | δ = 0.33-0.46 (m, 2H), 0.52-0.66 (m, 2H), 2.45-2.52 (m, 1H), 6.57 (s, 1H), 7.26-7.34 (m, 2H), 7.51-7.59 (m, 1H), 7.62-7.69 (m, 1H), 7.98 (s, 1H), 9.86 (s, 1H). |
| 4A | 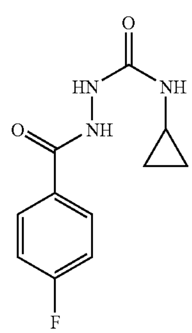 | $R_t$ = 1.00 min [7] | δ = 0.33-0.46 (m, 2H), 0.51-0.65 (m, 2H), 2.44-2.52 (m, 1H), 6.67 (d, 1H), 7.32 (t, 2H), 7.86 (s, 1H), 7.95 (dd, 1H), 10.10 (s, 1H). |
| 5A | 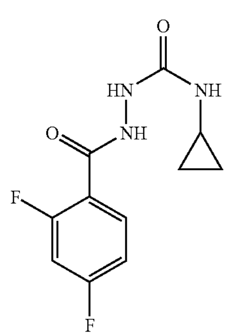 | $R_t$ = 1.00 min [7] | |

| Example No. | Structure | LC/MS $R_t$ [Method] | $^1$H-NMR (400 MHz, DMSO-d$_6$) |
|---|---|---|---|
| 6A | 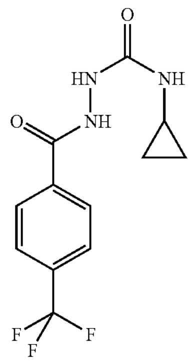 | $R_t$ = 1.48 min [7] | |
| 7A | 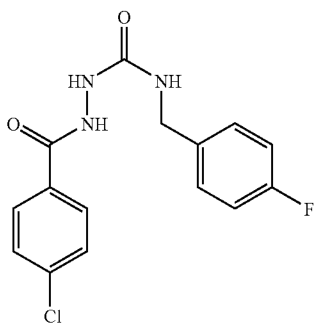 | $R_t$ = 1.78 min [7] | δ = 4.22 (d, 2H), 7.09-7.18 (m, 2H), 7.27-7.34 (m, 2H), 7.56, 7.58 (AA' part of an AA'BB' system, 2H), 7.91, 7.93 (BB' part of an AA'BB' system, 2H), 8.03 (s, 1H), 10.26 (s, 1H). |

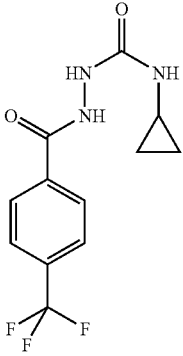

Example 8A

2-(3-chlorobenzoyl)-N-cyclopropylhydrazinecarboxamide

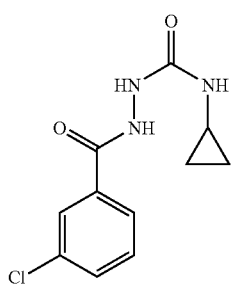

Under an argon atmosphere, 430 mg (2.52 mmol) of 3-chlorobenzoic acid hydrazide are placed in 6 ml tetrahydrofuran. 209 mg (2.52 mmol) of cyclopropyl isocyanate, dissolved in 2 ml tetrahydrofuran is added dropwise and further stirred overnight at room temperature. It is concentrated and purified by stirring the residue with diethyl ether, filtration, further washing with diethyl ether and drying in vacuo. 514 mg (80% of theory) of the target compound are thus obtained.

LC/MS [Method 5]: $R_t$=1.41 min $^1$H-NMR (400 MHz, DMSO-d$_6$): δ=0.34-0.46 (m, 2H), 0.51-0.65 (m, 2H), 2.44-2.56 (m, 1H), 6.71 (s, 1H), 7.52 (t, 1H), 7.64 (dd, 1H), 7.83 (d, 1H), 7.91 (d, 1H), 7.92 (s, 1H), 10.19 (s, 1H).

The following compound is obtained analogously:

| Example No. | Structure | LC/MS $R_t$ [Method] | $^1$H-NMR (400 MHz, DMSO-$d_6$) |
|---|---|---|---|
| 9A | 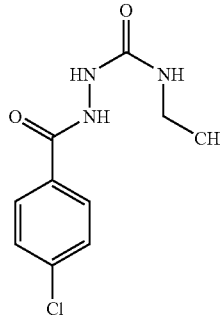 | $R_t$ = 1.44 min [8] | δ = 1.00 (t, 3H), 3.05 (dq, 2H), 6.50 (br. t, 1H), 7.55, 7.57 (AA' part of an AA'BB' system, 2H), 7.83 (s, 1H), 7.89, 7.91 (BB' part of an AA'BB' system, 2H), 10.17 (s, 1H). |

Example 10A

2-(2-chlorobenzoyl)-N-cyclopropylhydrazinecarboxamide

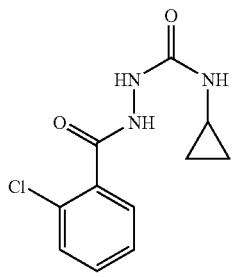

Under an argon atmosphere, 10.0 g (58.6 mmol) of 2-chlorobenzoic acid hydrazide is placed in 50 ml tetrahydrofuran. 4.87 g (58.6 mmol) of cyclopropyl isocyanate, dissolved in 50 ml tetrahydrofuran, are added dropwise at 50° C., and the mixture further stirred overnight at 50° C. The resulting precipitate is filtered off after cooling to room temperature and then washed with diethyl ether. 13.9 g (93% of theory) of the target compound are thus obtained.

LC/MS [Method 7]: $R_t$=1.01 min $^1$H-NMR (400 MHz, DMSO-$d_6$): δ=0.33-0.45 (m, 2H), 0.53-0.67 (m, 2H), 2.45-2.53 (m, 1H), 6.47 (d, 1H), 7.39-7.55 (m, 4H), 8.00 (s, 1H), 9.95 (s, 1H).

The following compounds are obtained analogously:

| Example No. | Structure | LC/MS $R_t$ [Method] | $^1$H-NMR (400 MHz, DMSO-$d_6$) |
|---|---|---|---|
| 11A | 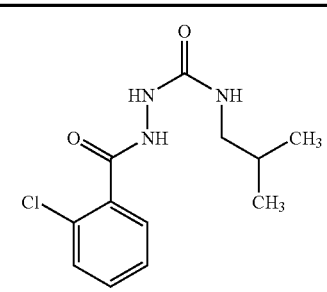 | $R_t$ = 1.41 min [7] | δ = 0.85 (d, 6H), 1.60-1.75 (m, 1H), 2.89 (t, 2H), 6.27 (t, 1H), 7.39-7.57 (m, 4H), 7.96 (s, 1H), 10.00 (s, 1H). |
| 12A | 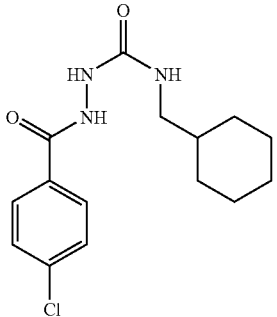 | $R_t$ = 1.93 min [7] | δ = 0.77-0.92 (m, 2H), 1.04-1.23 (m, 3H), 1.31-1.43 (m, 1H), 1.56-1.71 (m, 5H), 2.87 (t, 2H), 6.49 (br. t, 1H), 7.55, 7.57 (AA' part of an AA'BB' system, 2H), 7.78 (s, 1H), 7.89, 7.91 (BB' part of an AA'BB' system, 2H), 10.16 (s, 1H). |

| Example No. | Structure | LC/MS $R_t$ [Method] | $^1$H-NMR (400 MHz, DMSO-$d_6$) |
|---|---|---|---|
| 13A | 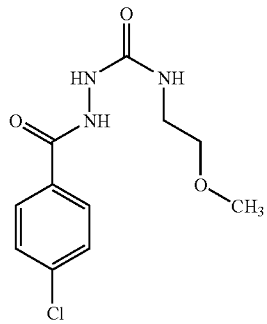 | $R_t$ = 1.18 min [7] | δ = 3.18 (dt, 2H), 3.25 (s, 3H), 3.29-3.35 (m, 2H), 6.53 (br. t, 1H), 7.56, 7.58 (AA' part of an AA'BB' system, 2H), 7.89, 7.91 (BB' part of an AA'BB' system, 2H), 7.94 (s, 1H), 10.21 (s, 1H). |

Example 14A

N-cyclopropyl-2-(2-methoxybenzoyl)-hydrazinecarboxamide

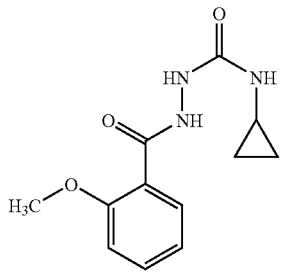

250 mg (3.01 mmol) of cyclopropyl isocyanate, dissolved in 3 ml THF, are added dropwise to 500 mg (3.01 mmol) of 2-methoxybenzoic acid hydrazide, dissolved in 7 ml THF, and the mixture stirred overnight at room temperature. The resulting precipitate is filtered off, washed with diethyl ether and dried in vacuo. 709 mg (94% of theory) of the target compound are thus obtained.

LC/MS [Method 5]: $R_t$=1.27 min $^1$H-NMR (400 MHz, DMSO-$d_6$): δ=0.32-0.45 (m, 2H), 0.53-0.66 (m, 2H), 2.45-2.53 (m, 1H), 3.88 (s, 3H), 7.05 (t, 1H), 7.15 (d, 1H), 7.50 (ddd, 1H), 6.49 (br. s, 1H), 7.72 (dd, 1H), 7.99 (d, 1H), 9.62 (d, 1H).

The following is obtained analogously:

Example 15A

N-ethyl-2-(4-methoxybenzoyl)-hydrazinecarboxamide

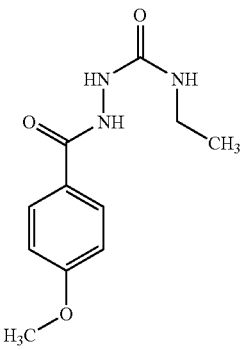

LC/MS [Method 5]: $R_t$=1.14 min $^1$H-NMR (400 MHz, DMSO-$d_6$): δ=1.00 (t, 3H), 3.05 (dq, 2H), 3.81 (s, 3H), 6.43 (br. s, 1H), 7.00, 7.02 (AA' part of an AA'BB' system, 2H), 7.73 (s, 1H), 7.86, 7.88 (BB' part of an AA'BB' system, 2H), 9.94 (s, 1H).

Example 16A 2-(2-chlorobenzoyl)-N-(4-methoxyphenylmethyl)-hydrazinecarboxamide

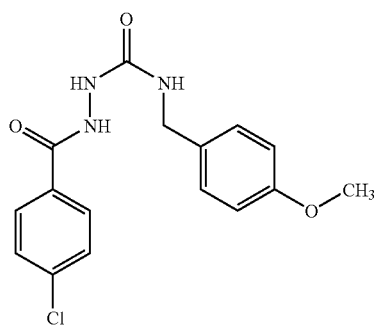

2.50 g (14.7 mmol) of 4-chlorobenzoic acid hydrazide are placed in 30 ml tetrahydrofuran at room temperature. 2.50 g (15.3 mmol) of 4-methoxyphenylmethyl isocyanate, dissolved in 6 ml tetrahydrofuran, are rapidly added dropwise with stirring to this suspension. The mixture is stirred for a further 6 hrs at room temperature and then allowed to stand for about 65 hrs. 50 ml of diethyl ether are then added with stirring, the reaction vessel cooled in an ice/water bath, and the precipitate is filtered off, further washed with cold diethyl ether and dried in vacuo. 4.80 g (98% of theory) of the target compound are thus obtained.

LC/MS [Method 5]: $R_t$=1.87 min $^1$H-NMR (400 MHz, DMSO-$d_6$): δ=3.72 (s, 3H), 4.17 (d, 2H), 6.85, 6.87 (AA' part of an AA'BB' system, 2H), 7.03 (br. t, 1H), 7.18, 7.20 (BB' part of an AA'BB' system, 2H), 7.56, 7.58 (AA' part of an AA'BB' system, 2H), 7.90, 7.93 (BB' part of an AA'BB' system, 2H), 7.96 (s, 1H), 10.24 (s, 1H).

Example 17A 2-(4-chlorobenzoyl)-N-(3-fluorophenylmethyl)-hydrazinecarboxamide

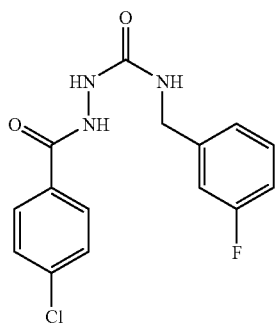

553 mg (3.24 mmol) of 4-chlorobenzoic acid hydrazide are placed in 10 ml tetrahydrofuran at room temperature. 500 mg (3.31 mmol) of 3-fluorophenylmethyl isocyanate, dissolved in 5 ml tetrahydrofuran, are rapidly added dropwise to this suspension with stirring. The mixture is further stirred overnight at room temperature. The reaction mixture is treated with 50 ml diethyl ether, and the precipitate is recovered by filtration, then washed with diethyl ether and dried in vacuo. 965 mg (92% of theory) of the target compound are thus obtained LC/MS [Method 8]: $R_t$=2.00 min $^1$H-NMR (400 MHz, DMSO-$d_6$): δ=4.26 (d, 2H), 6.98-7.12 (m, 3H), 7.20 (br. s, 1H), 7.34 (q, 1H), 7.56, 7.58 (AA' part of an AA'BB' system, 2H), 7.91, 7.94 (BB' part of an AA'BB' system, 2H), 8.08 (s, 1H), 10.28 (s, 1H).

Analogously to the three aforesaid examples, the following are obtained:

| Example No. | Structure | LC/MS $R_t$ [Method] | $^1$H-NMR (400 MHz, DMSO-$d_6$) |
|---|---|---|---|
| 18A | 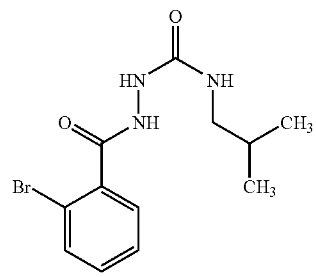 | $R_t$ = 1.46 min [7] | δ = 0.85 (d, 6H), 1.60-1.75 (m, 1H), 2.89 (t, 2H), 6.25 (t, 1H), 7.40 (td, 1H), 7.46 (td, 1H), 7.51 (dd, 1H), 7.68 (d, 1H), 7.96 (s, 1H), 10.00 (s, 1H). |
| 19A | 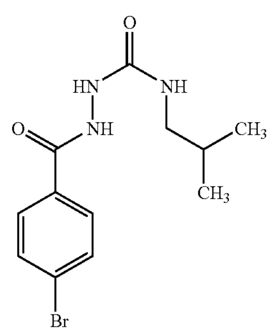 | $R_t$ = 1.63 min [7] | δ = 0.83 (d, 6H), 1.60-1.75 (m, 1H), 2.85 (t, 2H), 6.53 (t, 1H), 7.69, 7.71 (AA' part of an AA'BB' system, 2H), 7.80 (br. d, 1H), 7.82, 7.84 (BB' part of an AA'BB' system, 2H), 10.20 (br. d, 1H). |
| 20A | 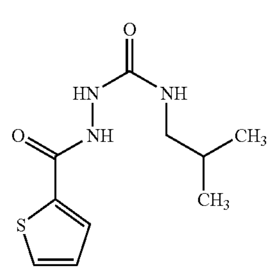 | $R_t$ = 1.39 min [5] | δ = 0.83 (d, 6H), 1.60-1.74 (m, 1H), 2.85 (t, 2H), 6.49 (br. t, 1H), 7.17 (t, 1H), 7.77-7.85 (m, 3H), 10.13 (s, 1H). |

-continued

| Example No. | Structure | LC/MS R$_t$ [Method] | $^1$H-NMR (400 MHz, DMSO-d$_6$) |
|---|---|---|---|
| 21A | (structure: 5-chlorothiophene-2-carbonyl hydrazide urea with isobutyl) | R$_t$ = 1.99 min [8] | δ = 0.82 (d, 6H), 1.59-1.74 (m, 1H), 2.84 (t, 2H), 6.53 (br. t, 1H), 7.22 (d, 1H), 7.70 (d, 1H), 7.85 (s, 1H), 10.23 (s, 1H). |
| 22A | (structure: 4-chlorobenzoyl hydrazide urea with 2-fluorobenzyl) | R$_t$ = 1.97 min [8] | δ = 4.28 (d, 2H), 7.03-7.19 (m, 3H), 7.24-7.32 (m, 1H), 7.37 (t, 1H), 7.56, 7.58 (AA' part of an AA'BB' system, 2H), 7.91, 7.93 (BB' part of an AA'BB' system, 2H), 8.08 (s, 1H), 10.29 (s, 1H). |
| 23A | (structure: 4-chlorobenzoyl hydrazide urea with (S)-1-phenylethyl) | R$_t$ = 1.97 min [5] | δ = 1.36 (d, 3H), 4.81 (dq, 1H), 6.93 (d, 1H), 7.18-7.25 (m, 1H), 7.28-7.35 (m, 4H), 7.55, 7.58 (AA' part of an AA'BB' system, 2H), 7.88 (br. s, 1H), 7.89, 7.91 (BB' part of an AA'BB' system, 2H), 10.22 (s, 1H). |
| 24A | (structure: 3-nitrobenzoyl hydrazide urea with cyclopropyl) | R$_t$ = 1.01 min [7] | |
| 25A | (structure: 4-nitrobenzoyl hydrazide urea with cyclopropyl) | R$_t$ = 1.50 min [7] | |

| Example No. | Structure | LC/MS $R_t$ [Method] | $^1$H-NMR (400 MHz, DMSO-d$_6$) |
|---|---|---|---|
| 26A | 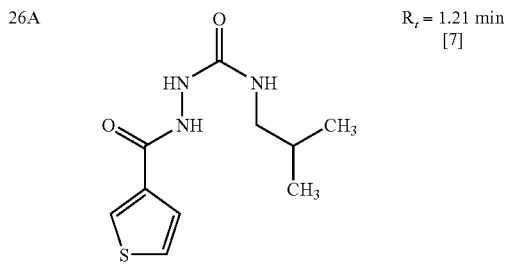 | $R_t$ = 1.21 min [7] | |
| 27A | 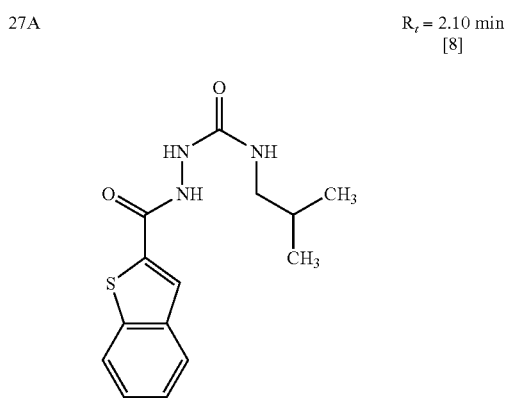 | $R_t$ = 2.10 min [8] | |
| 28A | 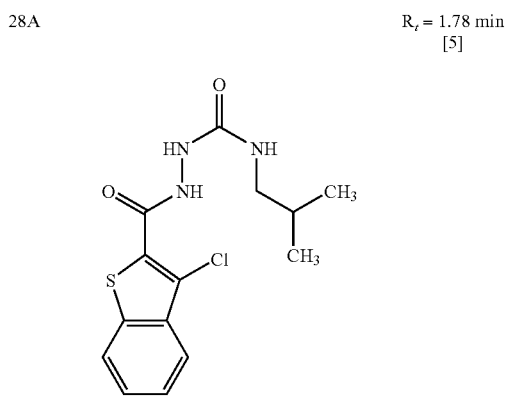 | $R_t$ = 1.78 min [5] | |
| 29A | 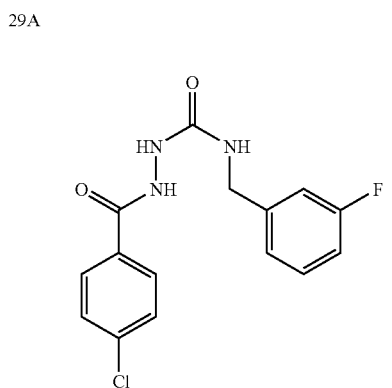 | $R_t$ = 2.00 min [8] | |

| Example No. | Structure | LC/MS $R_t$ [Method] | $^1$H-NMR (400 MHz, DMSO-$d_6$) |
|---|---|---|---|
| 30A | 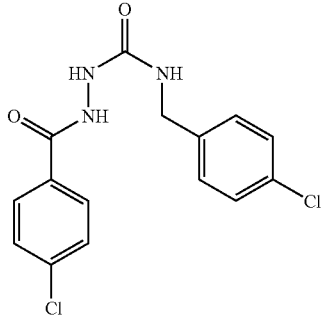 | $R_t$ = 2.06 min [5] | |
| 31A | 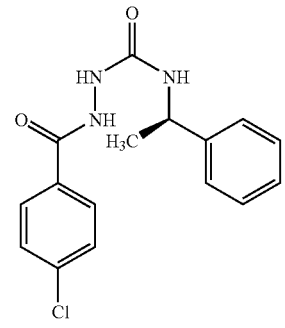 | $R_t$ = 1.97 min [5] | |

Example 32A 2-(3-bromobenzoyl)-N-isobutylhydrazinecarboxamide

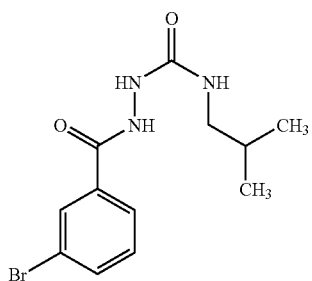

5.00 g (23.3 mmol) of 3-bromobenzoic acid hydrazide are placed in 50 ml tetrahydrofuran at room temperature. 2.70 g (27.2 mmol) of isobutyl isocyanate, dissolved in 10 ml tetrahydrofuran, are rapidly added dropwise with stirring to this suspension. The mixture is firstly further stirred at room temperature and then allowed to stand overnight. The precipitate formed after addition of 100 ml diethyl ether is filtered off and then washed with diethyl ether. An initial quantity of 1.42 g (19% of theory) of the target compound is thus obtained. The mother liquor is concentrated, and the residue again slurried in diethyl ether and filtered. After washing with diethyl ether and drying in vacuo, a further 5.62 g (77% of theory) of the target compound remain.

LC/MS [Method 5]: $R_t$=1.78 min $^1$H-NMR (400 MHz, DMSO-$d_6$): δ=0.83 (d, 6H), 2.85 (t, 2H), 6.56 (br. t, 1H), 7.46 (t, 1H), 7.77 (d, 1H), 7.82 (s, 1H), 7.88 (d, 1H), 8.07 (s, 1H), 10.22 (s, 1H).

Example 33A 2-(2-phenylbenzoyl)-N-isobutylhydrazinecarboxamide

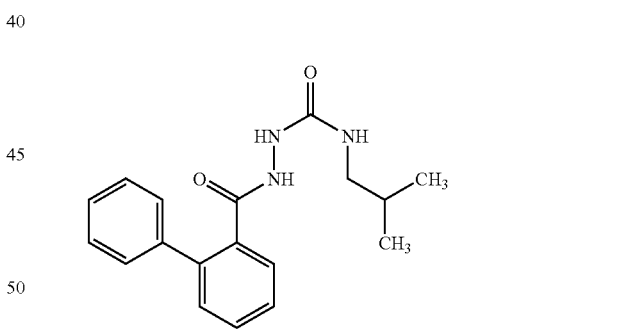

1.00 g (4.71 mmol) of 2-phenylbenzoic acid hydrazide are placed in 10 ml tetrahydrofuran at room temperature. 0.51 g (5.15 mmol) of isobutyl isocyanate, dissolved in 2 ml tetrahydrofuran, are rapidly added dropwise with stirring. The mixture is firstly stirred further at room temperature and then allowed to stand overnight. Addition of an equal volume of diethyl ether and 10 ml of cyclohexane results in separation of a small quantity of a solid, which is filtered off and discarded. Concentration of the filtrate yields 1.53 g (ca. 100% of theory) of a slightly THF-moist product, which is used further as such.

LC/MS [Method 8]: $R_t$=2.1 min.

Example 34A 2-(4-chlorobenzoyl)-N-methylhydrazinecarboxamide

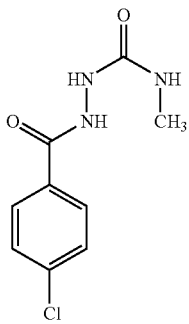

575 mg (2.93 mmol) of 4-nitrophenyl methylcarbamate and 417 mg (3.22 mmol) of N,N-diisopropylethylamine are successively added to 500 mg (2.93 mmol) of 4-chlorobenzoic acid hydrazide in 15 ml dichloromethane and the mixture stirred overnight at room temperature. It is concentrated, the residue is purified by preparative HPLC [Method 9] and 410 mg (61% of theory) of the target compound are thus obtained.

LC/MS [Method 5]: $R_t$=1.24 min $^1$H-NMR (400 MHz, DMSO-$d_6$): δ=2.57 (d, 3H), 6.45 (br. d, 1H), 7.56, 7.58 (AA' part of an AA'BB' system, 2H), 7.89 (br. s, 1H), 7.89, 7.91 (BB' part of an AA'BB' system, 2H), 10.19 (s, 1H).

Example 35A

N-methyl-2-(4-methylbenzoyl)-hydrazinecarboxamide

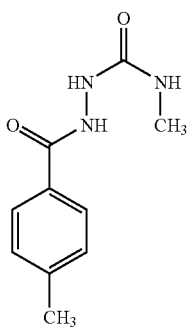

653 mg (3.33 mmol) of 4-nitrophenyl methylcarbamate and 473 mg (3.22 mmol) of N,N-diisopropylethylamine are added to 500 mg (3.33 mmol) of 4-methylbenzoic acid hydrazide in 15 ml dichloromethane and the mixture stirred overnight at room temperature. The precipitate formed is recovered by filtration, washed with diethyl ether and dried in vacuo. 602 mg (87% of theory) of the target compound are thus obtained.

LC/MS [Method 7]: $R_t$=0.94 min.

Example 36A 5-(4-chlorophenyl)-4-cyclopropyl-2,4-dihydro-3H-1,2,4-triazol-3-one

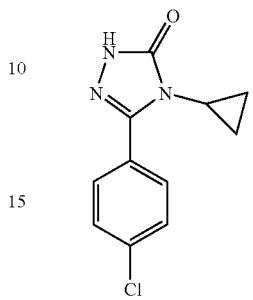

14.65 g (57.7 mmol) of 2-(4-chlorobenzoyl)-N-cyclopropylhydrazinecarboxamide from Example 2A are heated under reflux overnight in 60 ml 2 N aqueous sodium hydroxide. After cooling, the mixture is acidified to pH 1 with 2 N hydrochloric acid and extracted with ethyl acetate. The organic phase is dried over sodium sulphate, filtered and concentrated. The residue is stirred with dichloromethane, and the resulting precipitate filtered off, then washed with dichloromethane and dried in vacuo. 10.9 g (69% of theory) of the target compound are thus obtained.

LC/MS [Method 7]: $R_t$=1.57 min $^1$H-NMR (400 MHz, DMSO-$d_6$): δ=0.50-0.62 (m, 2H), 0.79-0.93 (m, 2H), 3.10 (dddd, 1H), 7.57, 7.59 (AA' part of an AA'BB' system, 2H), 7.79, 7.81 (BB' part of an AA'BB' system, 2H), 11.85 (s, 1H).

Example 37A 4-cyclopropyl-5-(2-fluorophenyl)-2,4-dihydro-3H-1,2,4-triazol-3-one

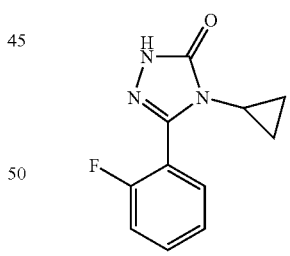

0.89 g (3.75 mmol) of 2-(2-fluorobenzoyl)-N-cyclopropylhydrazinecarboxamide from Example 3A are heated under reflux in 3.75 ml 2 N aqueous sodium hydroxide for about 45 hrs. To complete the reaction, a further 5 ml 6 N aqueous sodium hydroxide are added and the mixture heated once more under reflux for 6 hrs. After cooling, it is acidified with 1 N hydrochloric acid with stirring and the reaction mixture extracted three times with ethyl acetate. The combined organic phases are dried over magnesium sulphate and concentrated. 0.74 g (73% of theory) of the target compound are thus obtained, which is further reacted without further purification.

LC/MS [Method 4]: $R_t$=1.66 min.

Example 38A 4-cyclopropyl-5-(2,4-difluorophenyl)-2,4-dihydro-3H-1,2,4-triazol-3-one

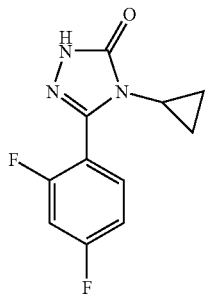

1.00 g (3.92 mmol) of N-cyclopropyl-2-(2,4-difluorobenzoyl)-hydrazinecarboxamide from Example 5A are heated under reflux in 4 ml 4 N aqueous sodium hydroxide for 28 hrs. After cooling, it is acidified to about pH 2 with 2 N hydrochloric acid, diluted with water and extracted four times with ethyl acetate. The combined organic phases are dried over magnesium sulphate, filtered, concentrated and the residue dried in vacuo. 0.415 g (31% of theory) of the target compound are thus obtained, which is further reacted as such.

LC/MS [Method 7]: $R_t$=1.38 min.

Example 39A 5-(2-chlorophenyl)-4-cyclopropyl-2,4-dihydro-3H-1,2,4-triazol-3-one

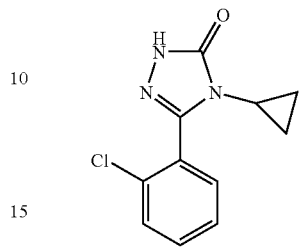

7.00 g (27.6 mmol) of 2-(2-chlorobenzoyl)-N-cyclopropylhydrazinecarboxamide from Example 10A are heated under reflux for about 60 hrs in 30 ml 3 N aqueous sodium hydroxide (conversion testing by LC/MS analysis). After cooling, it is acidified with 1 N hydrochloric acid and the mixture extracted three times with ethyl acetate. The combined organic phases are washed twice with saturated sodium hydrogen carbonate solution, dried over magnesium sulphate, filtered and concentrated. 3.32 g (48% of theory) of the target compound are thus obtained.

LC/MS [Method 7]: $R_t$=1.38 min $^1$H-NMR (400 MHz, DMSO-$d_6$): δ=0.49-0.56 (m, 2H), 0.60-0.67 (m, 2H), 2.80 (dddd, 1H), 7.46-7.67 (m, 4H), 11.86 (br. s, 1H).

The following are obtained analogously:

| Example No. | Structure | LC/MS $R_t$ [Method] | $^1$H-NMR (400 MHz, DMSO-$d_6$) |
|---|---|---|---|
| 40A | 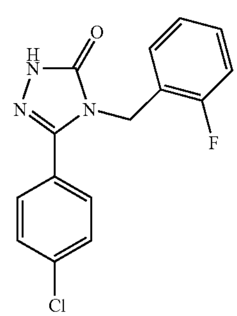 | $R_t$ = 1.97 min [7] | δ = 4.97 (s, 2H), 7.02 (t, 1H), 7.10 (t, 1H), 7.13 (t, 1H), 7.29 (q, 1H), 7.53 (centre of an AA'BB' system, 4H), 12.15 (s, 1H). |
| 41A | 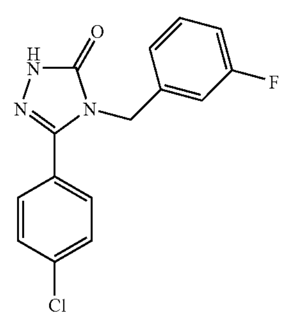 | $R_t$ = 1.98 min [7] | δ = 4.94 (s, 2H), 6.90 (t, 1H), 7.08 (td, 1H), 7.35 (dt, 1H), 7.53 (centre of an AA'BB' system, 4H), 12.19 (s, 1H). |

-continued

| Example No. | Structure | LC/MS R$_t$ [Method] | $^1$H-NMR (400 MHz, DMSO-d$_6$) |
|---|---|---|---|
| 42A | 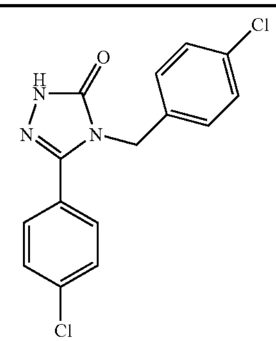 | R$_t$ = 2.33 min [8] | |
| 43A | 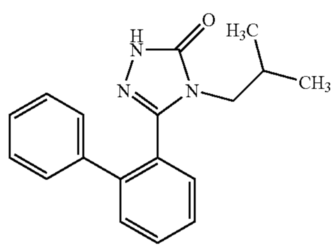 | R$_t$ = 2.17 min [5] | |
| 44A | 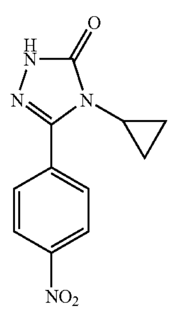 | R$_t$ = 2.01 min [8] | |

The following are obtained analogously after additional purification by preparative HPLC [Method 9]:

| Example No. | Structure | LC/MS R$_t$ [Method] | $^1$H-NMR (400 MHz, DMSO-d$_6$) |
|---|---|---|---|
| 45A | 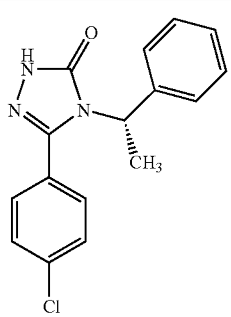 | R$_t$ = 2.21 min [5] | δ = 1.76 (d, 3H), 5.19 (q, 1H), 7.18-7.36 (m, 5H), 7.36, 7.38 (AA' part of an AA'BB' system, 2H), 7.53, 7.55 (BB' part of an AA'BB' system, 2H), 12.00 (s, 1H). |

| Example No. | Structure | LC/MS $R_t$ [Method] | $^1$H-NMR (400 MHz, DMSO-$d_6$) |
|---|---|---|---|
| 46A | 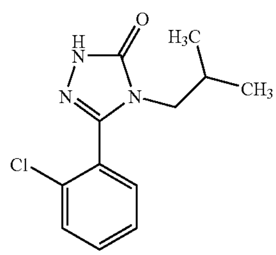 | $R_t$ = 1.70 min [7] | δ = 0.66 (d, 6H), 1.57-1.73 (m, 1H), 3.26 (d, 2H), 7.48-7.55 (m, 1H), 7.57-7.64 (m, 2H), 7.64-7.69 (m, 1H), 12.00 (s, 1H). |
| 47A | 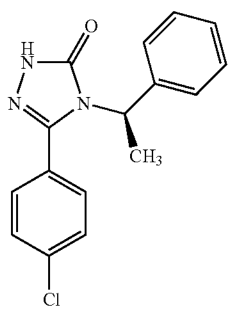 | $R_t$ = 2.21 min [5] | |
| 48A | 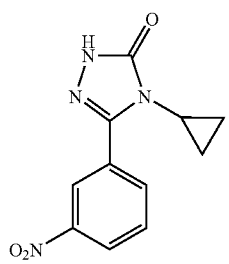 | $R_t$ = 1.60 min [8] | |

Example 49A

5-(4-chlorophenyl)-4-(2-methoxyethyl)-2,4-dihydro-3H-1,2,4-triazol-3-one

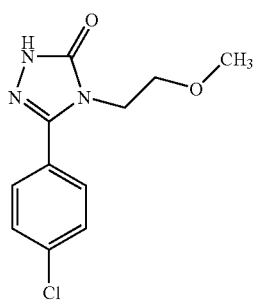

1.28 g (4.71 mmol) of 2-(4-chlorobenzoyl)-N-(2-methoxyethyl)-hydrazinecarboxamide from Example 13A are heated under reflux overnight in 10 ml 3 N aqueous sodium hydroxide. After cooling, it is acidified to about pH 2.5 with 1 N hydrochloric acid with ice-cooling and the resulting precipitate filtered off and dried in vacuo. 1.09 g (92% of theory) of the target compound, which is reacted without further purification, are thus obtained.

LC/MS [Method 7]: $R_t$=1.53 min $^1$H-NMR (400 MHz, DMSO-$d_6$): δ=3.11 (s, 3H), 3.45 (t, 2H), 3.83 (t, 2H), 7.58, 7.60 (AA' part of an AA'BB' system, 2H), 7.70, 7.72 (BB' part of an AA'BB' system, 2H), 11.98 (s, 1H).

The following are obtained analogously:

| Example No. | Structure | LC/MS $R_t$ [Method] | $^1$H-NMR (400 MHz, DMSO-$d_6$) |
|---|---|---|---|
| 50A | (5-(4-fluorophenyl)-4-cyclopropyl-2,4-dihydro-3H-1,2,4-triazol-3-one) | $R_t$ = 1.61 min [8] | δ = 0.48-0.62 (m, 2H), 0.77-0.91 (m, 2H), 3.08 (dddd, 1H), 7.35, (t, 2H,) 7.81 (dd, 2H), 11.77 (s, 1H). |
| 51A | (5-(4-trifluoromethylphenyl)-4-cyclopropyl-2,4-dihydro-3H-1,2,4-triazol-3-one) | $R_t$ = 1.94 min [8] | δ = 0.51-0.64 (m, 2H), 0.80-0.95 (m, 2H), 3.15 (dddd, 1H), 7.87, 7.89 (AA' part of an AA'BB' system, 2H), 8.01, 8.03 (BB' part of an AA'BB' system, 2H), 11.99 (s, 1H). |
| 52A | (5-(4-bromophenyl)-4-isobutyl-2,4-dihydro-3H-1,2,4-triazol-3-one) | $R_t$ = 2.27 min [4] | δ = 0.68 (d, 6H), 1.58-1.73 (m, 1H), 3.55 (d, 2H), 7.60, 7.62 (AA' part of an AA'BB' system, 2H), 7.72, 7.74 (BB' part of an AA'BB' system, 2H), 11.96 (s, 1H). |
| 53A | (5-(3-bromophenyl)-4-isobutyl-2,4-dihydro-3H-1,2,4-triazol-3-one) | $R_t$ = 1.88 min [7] | δ = 0.69 (d, 6H), 1.57-1.73 (m, 1H), 3.55 (d, 2H), 7.49 (t, 1H), 7.67 (br. d, 1H), 7.74 (br. d, 1H), 7.85 (t, 1H), 11.98 (br. s, 1H). |
| 54A | (5-(2-bromophenyl)-4-isobutyl-2,4-dihydro-3H-1,2,4-triazol-3-one) | $R_t$ = 1.75 min [7] | δ = 0.68 (d, 6H), 1.57-1.73 (m, 1H), 3.24 (d, 2H), 7.48-7.61 (m, 3H), 7.77-7.85 (m, 1H), 11.90 (s, 1H). |

-continued
| Example No. | Structure | LC/MS $R_t$ [Method] | $^1$H-NMR (400 MHz, DMSO-$d_6$) |
|---|---|---|---|
| 55A | 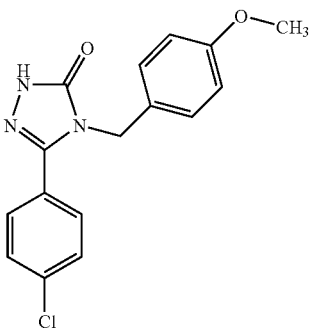 | $R_t$ = 2.10 min [5] | δ = 3.69 (s, 3H), 4.86 (s, 2H), 6.83, 6.85 (AA' part of an AA'BB' system, 2H), 6.96, 6.99 (BB' part of an AA'BB' system, 2H), 7.54 (centre of an AA'BB' system, 4H), 12.11 (br. s, 1H). |
| 56A | 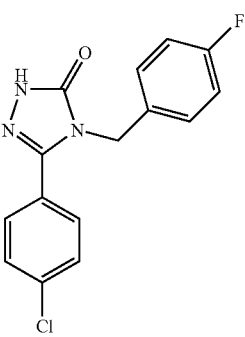 | $R_t$ = 2.22 min [8] | δ = 4.91 (s, 2H), 7.07-7.16 (m, 4H), 7.53 (s, 4H), 12.16 (br. s, 1H). |
| 57A | 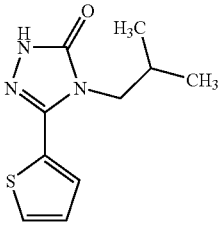 | $R_t$ = 1.56 min [5] | δ = 0.80 (d, 6H), 1.79-1.94 (m, 1H), 3.64 (d, 2H), 7.21 (dd, 1H), 7.55 (d, 1H), 7.75 (d, 1H), 11.96 (s, 1H). |
| 58A | 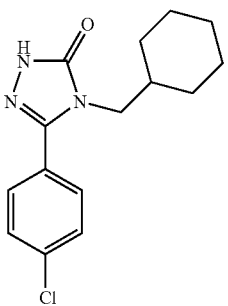 | $R_t$ = 2.18 min [7] | |
| 59A | 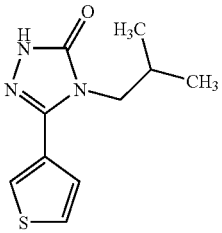 | $R_t$ = 1.54 min [7] | |

| Example No. | Structure | LC/MS R$_t$ [Method] | $^1$H-NMR (400 MHz, DMSO-d$_6$) |
|---|---|---|---|
| 60A | 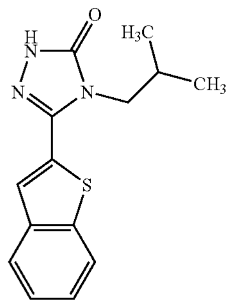 | R$_t$ = 2.14 min [5] | |

The following are obtained analogously after additional purification by preparative HPLC [Method 12]:

| Example No. | Structure | LC/MS R$_t$ [Method] |
|---|---|---|
| 61A | 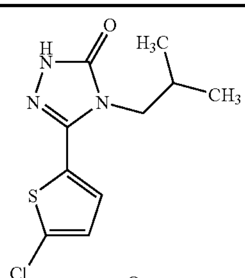 | R$_t$ = 1.88 min [7] |
| 62A | 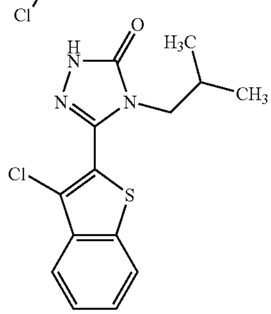 | R$_t$ = 2.45 min [8] |

Example 63A 4-cyclopropyl-5-(2-methoxyphenyl)-2,4-dihydro-3H-1,2,4-triazol-3-one

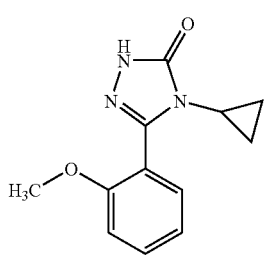

700 mg (2.81 mmol) of N-cyclopropyl-2-(2-methoxybenzoyl)-hydrazinecarboxamide from Example 14A are heated under reflux overnight in 10 ml 3 N aqueous sodium hydroxide. After cooling, it is acidified to pH 5-6 with dilute hydrochloric acid, and the mixture is concentrated and the residue purified by preparative HPLC [Method 12]. 240 mg (37% of theory) of the target compound are thus obtained.

LC/MS [Method 5]: R$_t$=1.49 min $^1$H-NMR (400 MHz, DMSO-d$_6$): δ=0.37-0.50 (m, 2H), 0.53-0.67 (m, 2H), 2.76 (dddd, 1H), 3.84 (s, 3H), 7.05 (t, 1H), 7.17 (t, 1H), 7.34 (dd, 1H), 7.53 (ddd, 1H), ca. 11.5-12 (broad, 1H).

Example 64A 5-(4-chlorophenyl)-4-methyl-2,4-dihydro-3H-1,2,4-triazol-3-one

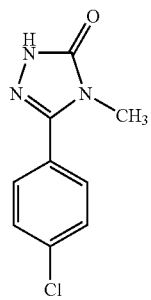

400 mg (1.78 mmol) of 2-(4-chlorobenzoyl)-N-methylhydrazinecarboxamide from Example 34A are heated under reflux overnight in 7 ml 3 N aqueous sodium hydroxide. After cooling, it is adjusted to pH ca. 11 with aqueous citric acid solution and the resulting precipitate filtered off, washed with water and dried in vacuo. 350 mg (95% of theory) of the target compound are thus obtained.

LC/MS [Method 7]: R$_t$=1.39 min $^1$H-NMR (400 MHz, DMSO-d$_6$): δ=3.24 (s, 3H), 7.59, 7.61 (AA' part of an AA'BB' system, 2H), 7.71, 7.73 (BB' part of an AA'BB' system, 2H), 11.96 (s, 1H).

The following are obtained analogously:

| Example No. | Structure | LC/MS $R_t$ [Method] | $^1$H-NMR (400 MHz, DMSO-$d_6$) |
|---|---|---|---|
| 65A | (triazolone with N-ethyl and 4-chlorophenyl) | $R_t$ = 1.55 min [7] | δ = 1.08 (t, 3H), 3.70 (q, 2H), 7.60, 7.62 (AA' part of an AA'BB' system, 2H), 7.66, 7.68 (BB' part of an AA'BB' system, 2H), 11.95 (s, 1H). |
| 66A | (triazolone with N-ethyl and 4-methoxyphenyl) | $R_t$ = 1.53 min [8] | |
| 67A | (triazolone with N-methyl and 4-methylphenyl) | $R_t$ = 1.30 min [7] | |

Example 68A

Ethyl[3-(4-chlorophenyl)-4-cyclopropyl-5-oxo-4,5-dihydro-1H-1,2,4-triazol-1-yl]acetate

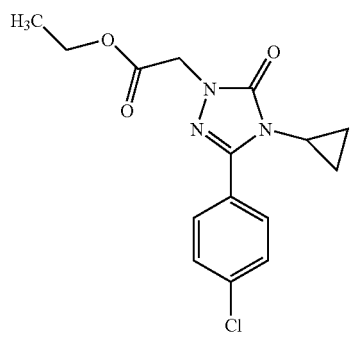

586 mg (4.24 mmol) of potassium carbonate are added to 500 mg (2.12 mmol) of 5-(4-chlorophenyl)-4-cyclopropyl-2,4-dihydro-3H-1,2,4-triazol-3-one from Example 36A and 260 mg (2.12 mmol) of ethyl chloroacetate in 10 ml acetonitrile and the mixture is heated under reflux with stirring for 2 hours. It is then concentrated, the residue taken up in water is extracted with dichloromethane, the organic phase dried over sodium sulphate and again concentrated. After purification by flash chromatography over silica gel (eluent: first dichloromethane, then dichloromethane/methanol 100:1) 448 mg (66% of theory) of the target compound are obtained.

MS [CIpos]: m/z=339 (M+NH$_4$)$^+$, 322 (M+H)$^+$ $^1$H-NMR (400 MHz, DMSO-$d_6$): δ=0.50-0.64 (m, 2H), 0.83-0.97 (m, 2H), 1.21 (t, 3H), 3.21 (dddd, 1H), 4.15 (q, 2H), 4.62 (s, 2H), 7.59, 7.61 (AA' part of an AA'BB' system, 2H), 7.81, 7.83 (BB' part of an AA'BB' system, 2H).

Example 69A

Ethyl[3-(4-chlorophenyl)-4-(2-methoxyethyl)-5-oxo-4,5-dihydro-1H-1,2,4-triazol-1-yl]acetate

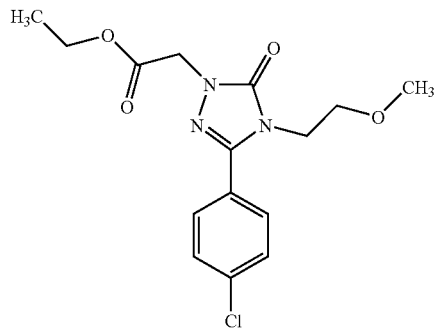

527 mg (4.30 mmol) of ethyl chloroacetate are added to 1.09 g (4.30 mmol) of 5-(4-chlorophenyl)-4-(2-methoxyethyl)-2,4-dihydro-3H-1,2,4-triazol-3-one from Example 49A and 1.19 g (8.59 mmol) of potassium carbonate in 20 ml acetonitrile and the mixture is heated under reflux for 3 hours with stirring. After purification of the resulting crude product by preparative HPLC [Method 9] 810 mg (42% of theory) of the target compound are obtained.

LC/MS [Method 5]: $R_t$=2.16 min $^1$H-NMR (400 MHz, DMSO-$d_6$): δ=1.21 (t, 3H), 3.11 (s, 3H), 3.47 (t, 2H), 3.89 (t, 2H), 4.16 (q, 2H), 4.67 (s, 2H), 7.60, 7.63 (AA' part of an AA'BB' system, 2H), 7.72, 7.74 (BB' part of an AA'BB' system, 2H).

The following are obtained analogously after purification by preparative HPLC [Method 11]:

| Example No. | Structure | LC/MS or HPLC, MS $R_t$ [Method] | $^1$H-NMR (400 MHz, DMSO-$d_6$) |
|---|---|---|---|
| 70A | 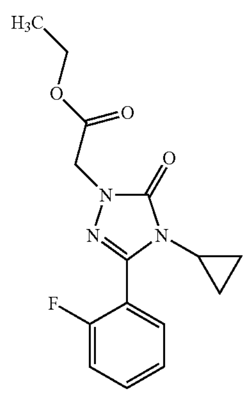 | $R_t$ = 1.74 min [7] | δ = 0.45-0.68 (m, 2H), 0.68-0.82 (m, 2H), 1.21 (t, 3H), 2.92-3.00 (m, 1H), 4.15 (q, 2H), 4.63 (s, 2H), 7.35-7.47 (m, 2H), 7.59-7.69 (m, 2H). |
| 71A | 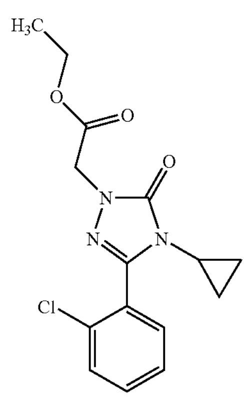 | $R_t$ = 1.84 min [7] | δ = 0.48-0.61 (m, 2H), 0.61-0.75 (m, 2H), 1.21 (t, 3H), 2.90 (dddd, 1H), 4.15 (q, 2H), 4.62 (s, 2H), 7.49-7.55 (m, 1H), 7.58-7.70 (m, 3H). |

-continued

| Example No. | Structure | LC/MS or HPLC, MS $R_t$ [Method] | $^1$H-NMR (400 MHz, DMSO-$d_6$) |
|---|---|---|---|
| 72A | (structure) | HPLC [2]: $R_t$ = 4.04 min; MS [ESIpos]: m/z = 318 (M + H)$^+$ | δ = 0.38-0.52 (m, 2H), 0.58-0.72 (m, 2H), 1.21 (t, 3H), 2.86 (dddd, 1H), 3.86 (s, 3H), 4.15 (q, 2H), 4.58 (s, 2H), 7.06 (t, 1H), 7.19 (d, 1H), 7.33 (dd, 1H), 7.56 (ddd, 1H). |
| 73A | (structure) | HPLC [1]: $R_t$ = 4.11 min; MS [CIpos]: m/z = 293 (M + NH$_4$)$^+$, 276 (M + H)$^+$ | δ = 1.21 (t, 3H), 2.38 (s, 3H), 3.30 (s, 3H), 4.16 (q, 2H), 4.65 (s, 2H), 7.35, 7.37 (AA' part of an AA'BB' system, 2H), 7.58, 7.60 (BB' part of an AA'BB' system, 2H). |
| 74A | (structure) | $R_t$ = 1.83 min [7] | |

The following are obtained analogously after purification by preparative HPLC [Method 12]:

| Example No. | Structure | LC/MS $R_t$ [Method] |
|---|---|---|
| 75A | 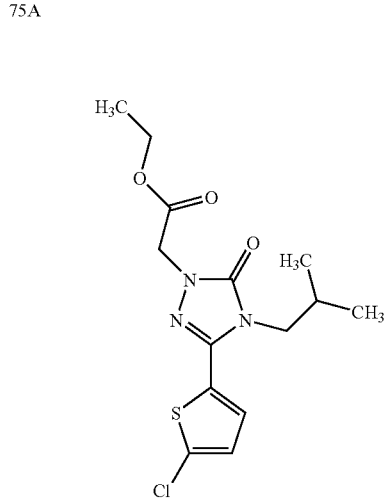 | $R_t$ = 2.36 min [7] |
| 76A | 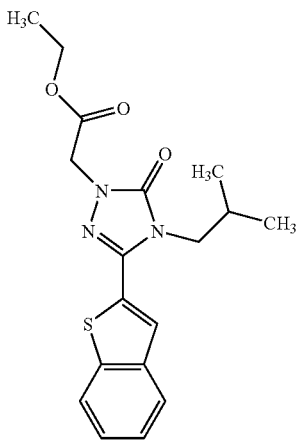 | $R_t$ = 2.43 min [7] |
| 77A | 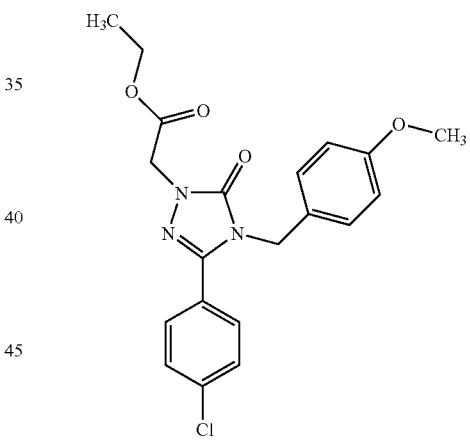 | $R_t$ = 2.56 min [7] |

Example 78A

Ethyl[3-(4-chlorophenyl)-4-(4-methoxyphenylmethyl)-5-oxo-4,5-dihydro-1H-1,2,4-triazol-1-yl]-acetate 2.54 g (18.4 mmol) of potassium carbonate are added to 2.90 g (9.18 mmol) of 5-(4-chlorophenyl)-4-(4-methoxyphenylmethyl)-2,4-dihydro-3H-1,2,4-triazol-3-one from Example 55A and 1.13 g (9.18 mmol) of ethyl chloroacetate in 60 ml acetonitrile and the mixture is heated under reflux overnight with stirring. It is then concentrated, the residue is partitioned between ethyl acetate and water and the aqueous phase extracted three times more with ethyl acetate. By evaporation of the organic phases, combined and dried over magnesium sulphate, 3.58 g (97% of theory) of the target compound are obtained.

LC/MS [Method 8]: $R_t$=2.54 min $^1$H-NMR (400 MHz, DMSO-$d_6$): δ=1.22 (t, 3H), 3.70 (s, 3H), 4.18 (q, 2H), 4.73 (s, 2H), 4.94 (s, 2H), 6.83, 6.85 (AA' part of an AA'BB' system, 2H), 6.97, 6.99 (BB' part of an AA'BB' system, 2H), 7.55 (centre of an AA'BB' system, 4H).

The following are obtained analogously:

| Example No. | Structure | LC/MS $R_t$ [Method] | $^1$H-NMR (400 MHz, DMSO-d$_6$) |
|---|---|---|---|
| 79A | (ethyl 2-(5-oxo-4-isobutyl-3-(thiophen-2-yl)-4,5-dihydro-1H-1,2,4-triazol-1-yl)acetate) | $R_t$ = 3.51 min [3] | δ = 0.81 (d, 6H), 1.20 (t, 3H), 1.80-1.95 (m, 1H), 3.71 (d, 2H), 4.15 (q, 2H), 4.67 (s, 2H), 7.24 (dd, 1H), 7.62 (d, 1H), 7.80 (d, 1H). |
| 80A | (ethyl 2-(3-(4-chlorophenyl)-4-methyl-5-oxo-4,5-dihydro-1H-1,2,4-triazol-1-yl)acetate) | $R_t$ = 1.84 min [7] | |
| 81A | (ethyl 2-(3-(4-chlorophenyl)-4-ethyl-5-oxo-4,5-dihydro-1H-1,2,4-triazol-1-yl)acetate) | $R_t$ = 1.98 min [7] | |

-continued

| Example No. | Structure | LC/MS $R_t$ [Method] | $^1$H-NMR (400 MHz, DMSO-$d_6$) |
|---|---|---|---|
| 82A | 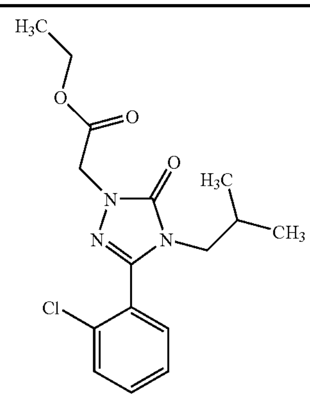 | $R_t$ = 2.13 min [7] | |
| 83A | 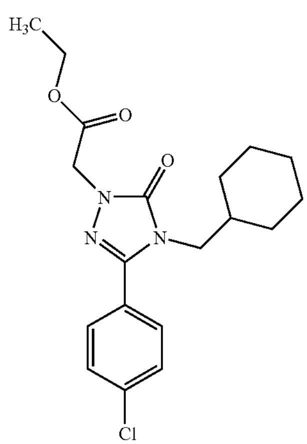 | $R_t$ = 2.80 min [5] | |

The following is obtained analogously after additional purification by preparative HPLC [Method 12]:

Example 84A

Methyl[4-isobutyl-5-oxo-3-(3-thienyl)-4,5-dihydro-1H-1,2,4-triazol-1-yl]acetate

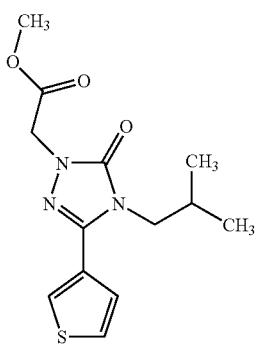

LC/MS [Method 8]: $R_t$=2.06 min.

Example 85A

Ethyl rac-2-[3-(4-chlorophenyl)-4-cyclopropyl-5-oxo-4,5-dihydro-1H-1,2,4-triazol-1-yl]propionate

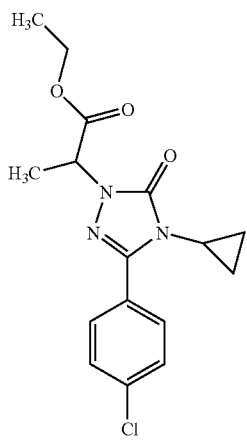

384 mg (2.12 mmol) of ethyl 2-bromopropionate and 1.38 g (4.24 mmol) of caesium carbonate are added to 500 mg (2.12 mmol) of 5-(4-chlorophenyl)-4-cyclopropyl-2,4-dihydro-3H-1,2,4-triazol-3-one from Example 36A in 5 ml acetonitrile and the reaction mixture is heated at 85° C. overnight. It is then concentrated in vacuo, the residue is partitioned between water and dichloromethane, and the separated organic phase is dried over sodium sulphate and again evaporated. After purification of the residue by flash chromatography over silica gel (eluent: first dichloromethane, then dichloromethane/methanol 200:1), 729 mg (97% of theory) of the target compound are obtained.

HPLC [Method 2]: $R_t$=4.47 min

MS [CIpos]: m/z=353 $(M+NH_4)^+$, 336 $(M+H)^+$ $^1$H-NMR (400 MHz, DMSO-$d_6$): δ=0.49-0.65 (m, 2H), 0.84-0.96 (m, 2H), 1.16 (t, 3H), 1.56 (d, 3H), 3.21 (dddd, 1H), 4.12 (q, 2H), 4.94 (q, 1H), 7.59, 7.61 (AA' part of an AA'BB' system, 2H), 7.81, 7.83 (BB' part of an AA'BB' system, 2H).

The following are obtained analogously after additional purification by preparative HPLC:

Example 86A

Ethyl 2-[3-(4-chlorophenyl)-4-cyclopropyl-5-oxo-4,5-dihydro-1H-1,2,4-triazol-1-yl]-2-methyl-propionate

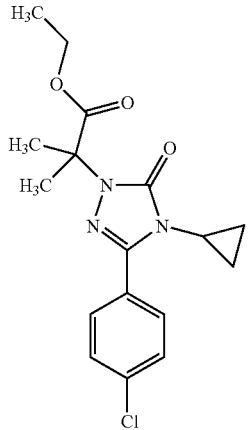

HPLC [Method 2]: $R_t$=4.75 min

MS [CIpos]: m/z=367 $(M+NH_4)^+$, 350 $(M+H)^+$ $^1$H-NMR (400 MHz, DMSO-$d_6$): δ=0.48-0.61 (m, 2H), 0.82-0.96 (m, 2H), 1.15 (t, 3H), 1.64 (s, 6H), 3.17 (dddd, 1H), 4.12 (q, 2H), 7.59, 7.61 (AA' part of an AA'BB' system, 2H), 7.81, 7.84 (BB' part of an AA'BB' system, 2H).

Example 87A

Ethyl 3-[3-(4-chlorophenyl)-4-cyclopropyl-5-oxo-4,5-dihydro-1H-1,2,4-triazol-1-yl]propionate

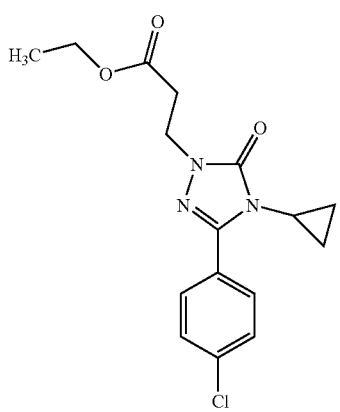

290 mg (2.12 mmol) of ethyl 3-chloropropionate and 586 mg (4.24 mmol) of potassium carbonate are added to 500 mg (2.12 mmol) of 5-(4-chlorophenyl)-4-cyclopropyl-2,4-dihydro-3H-1,2,4-triazol-3-one from Example 36A in 5 ml acetonitrile and the reaction mixture is heated at 85° C. overnight.

1.38 g (4.24 mmol) of caesium carbonate and one spatula tip of potassium iodide are added, and the mixture stirred for a further 4 hrs at 85° C. It is then concentrated in vacuo, the residue is partitioned between water and dichloromethane, and the separated organic phase dried over sodium sulphate and again evaporated. After purification of the residue by flash chromatography over silica gel (eluent: first dichloromethane, then dichloromethane/methanol 100:1), 580 mg (80% of theory) of the target compound are obtained.

HPLC [Method 2]: $R_t$=4.18 min

MS [ESIpos]: m/z=336 $(M+H)^+$ $^1$H-NMR (400 MHz, DMSO-$d_6$): δ=0.50-0.63 (m, 2H), 0.81-0.95 (m, 2H), 1.15 (t, 3H), 3.15 (dddd, 1H), 2.72 (t, 2H), 3.96 (t, 2H), 4.05 (q, 2H), 7.58, 7.60 (AA' part of an AA'BB' system, 2H), 7.78, 7.80 (BB' part of an AA'BB' system, 2H).

Example 88A

[3-(4-chlorophenyl)-4-cyclopropyl-5-oxo-4,5-dihydro-1H-1,2,4-triazol-1-yl]acetic acid

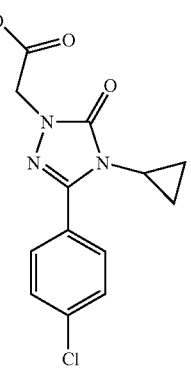

Method A:

4.84 g (15.0 mmol) of ethyl[3-(4-chlorophenyl)-4-cyclopropyl-5-oxo-4,5-dihydro-1H-1,2,4-triazol-1-yl]-acetate from Example 69A are placed in 12 ml methanol and stirred with 4 ml 20% aqueous potassium hydroxide for 2 hours at room temperature. It is concentrated and adjusted to about pH 1 with 2 N hydrochloric acid. The precipitated solid is filtered off, washed with water and dichloromethane and then dried in vacuo. 4.06 g (95% of theory) of the target compound are thus obtained.

MS [ESIpos]: m/z=294 $(M+H)^+$; [ESIneg]: m/z=292 $(M-H)^-$ $^1$H-NMR (400 MHz, DMSO-$d_6$): δ=0.50-0.64 (m, 2H), 0.82-0.97 (m, 2H), 3.20 (dddd, 1H), 4.47 (s, 2H), 7.58, 7.61 (AA' part of an AA'BB' system, 2H), 7.81, 7.83 (BB' part of an AA'BB' system, 2H).

Method B:

364 mg (2.97 mmol) of ethyl chloroacetate are added to 700 mg (2.97 mmol) of 5-(4-chloro-phenyl)-4-cyclopropyl-2,4-dihydro-3H-1,2,4-triazol-3-one from Example 49A and 821 mg (5.94 mmol) of potassium carbonate in 14.6 ml acetonitrile and the mixture is heated under reflux for 3 hours with stirring. It is then concentrated, taken up in 10 ml methanol, 1 ml 20% aqueous potassium hydroxide are added, and the is mixture stirred for 4 hrs at room temperature. For the workup, the reaction mixture is diluted with water, acidified with 2 N hydrochloric acid to pH 3 and then extracted five times with ethyl acetate. The combined organic phases are dried over magnesium sulphate and concentrated. 684 mg (79% of theory) of the target compound are thus obtained.

The following are obtained analogously to Example 88A/Method A:

| Example No. | Structure | LC/MS $R_t$ [Method] | $^1$H-NMR (400 MHz, DMSO-$d_6$) |
|---|---|---|---|
| 89A | (structure) | $R_t$ = 2.01 min [4] | δ = 0.68 (d, 6H), 1.59-1.74 (m, 1H), 4.55 (s, 2H), 7.50-7.56 (m, 1H), 7.57-7.71 (m, 3H), 13.09 (br. s, 1H). |
| 90A | (structure) | $R_t$ = 1.52 min [7] | δ = 3.11 (s, 3H), 3.47 (t, 2H), 3.89 (t, 2H), 4.54 (s, 2H), 7.60, 7.62 (AA' part of an AA'BB' system, 2H), 7.72, 7.75 (BB' part of an AA'BB' system, 2H), 13.13 (br. s, 1H). |
| 91A | (structure) | $R_t$ = 2.16 min [7] | δ = 0.67-0.80 (m, 2H), 0.93-1.10 (m, 3H), 1.35-1.63 (m, 6H), 3.64 (d, 2H), 4.55 (s, 2H), 7.60, 7.63 (AA' part of an AA'BB' system, 2H), 7.69, 7.71 (BB' part of an AA'BB' system, 2H), 13.11 (br. s, 1H). |
| 92A | (structure) | $R_t$ = 1.44 min [5] | |

| Example No. | Structure | LC/MS $R_t$ [Method] | ¹H-NMR (400 MHz, DMSO-d₆) |
|---|---|---|---|
| 93A | 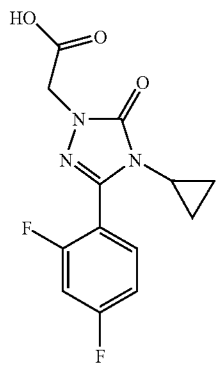 | $R_t$ = 1.64 min [4] | |
| 94A | 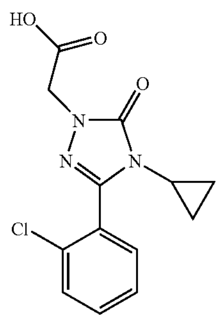 | $R_t$ = 1.65 min [4] | |

Example 95A

[4-cyclopropyl-3-(2-methoxyphenyl)-5-oxo-4,5-dihydro-1H-1,2,4-triazol-1-yl]acetic acid

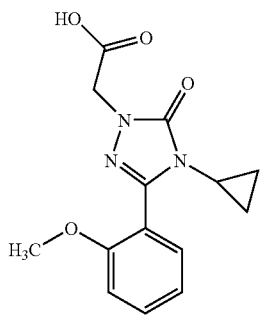

140 mg (0.44 mmol) of ethyl[4-cyclopropyl-3-(2-methoxyphenyl)-5-oxo-4,5-dihydro-1H-1,2,4-triazol-1-yl]-acetate from Example 72A are placed in 0.3 ml methanol and stirred overnight at room temperature with 0.12 ml of 20% aqueous potassium hydroxide. This is then concentrated and adjusted to about pH 1 with 1 N hydrochloric acid. The precipitated solid is filtered off, washed with diethyl ether and then dried in vacuo. 81 mg (63% of theory) of the target compound are thus obtained.

HPLC [Method 1]: $R_t$=3.61 min

MS [ESIpos]: m/z=290 (M+H)⁺; [ESIneg]: m/z=288 (M−H)⁻

¹H-NMR (400 MHz, DMSO-d₆): δ=0.38-0.51 (m, 2H), 0.57-0.72 (m, 2H), 2.86 (dddd, 1H), 3.86 (s, 3H), 4.46 (s, 2H), 7.06 (t, 1H), 7.19 (d, 1H), 7.33 (d, 1H), 7.55 (t, 1H), 13.07 (br. s, 1H).

Example 96A

[3-(4-chlorophenyl)-4-(4-methoxyphenylmethyl)-5-oxo-4,5-dihydro-1H-1,2,4-triazol-1-yl]acetic acid

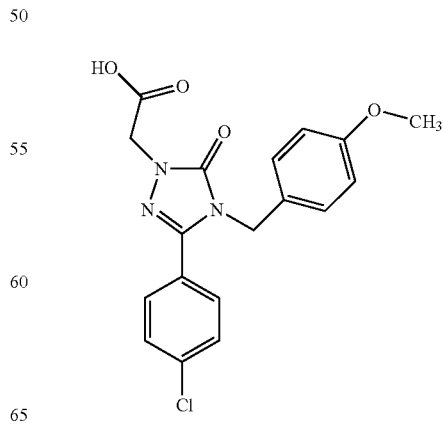

3.58 g (8.91 mmol) of ethyl[3-(4-chlorophenyl)-4-(4-methoxyphenylmethyl)-5-oxo-4,5-dihydro-1H-1,2,4-triazol-1-yl]-acetate from Example 78A are placed in 40 ml methanol and stirred overnight at room temperature with 4 ml of 20% aqueous potassium hydroxide. It is adjusted to pH 6 with 1 N hydrochloric acid and purified by preparative HPLC [Method 12]. 2.71 g (81% of theory) of the target compound are thus obtained.

LC/MS [Method 5]: $R_t$=1.94 min $^1$H-NMR (400 MHz, DMSO-$d_6$): δ=3.70 (s, 3H), 4.60 (s, 2H), 4.93 (s, 2H), 6.83, 6.85 (AA' part of an AA'BB' system, 2H), 6.98, 7.00 (BB' part of an AA'BB' system, 2H), 7.56 (centre of an AA'BB' system, 4H), 13.19 (br. s, 1H).

The following are obtained analogously:

| Example No. | Structure | LC/MS $R_t$ [Method] | $^1$H-NMR (400 MHz, DMSO-$d_6$) |
|---|---|---|---|
| 97A | 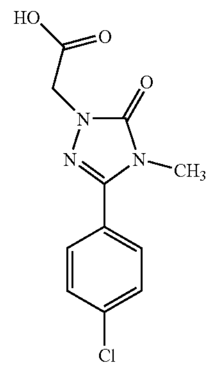 | $R_t$ = 1.56 min [5] | δ = 3.29 (s, 3H), 3.91 (s, 2H), 7.58, 7.60 (AA' part of an AA'BB' system, 2H), 7.71, 7.73 (BB' part of an AA'BB' system, 2H). |
| 98A | 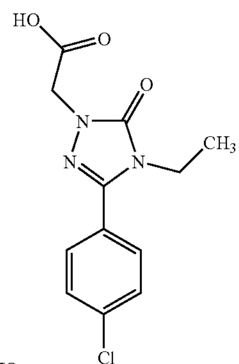 | $R_t$ = 1.69 min [5] | δ = 1.11 (t, 3H), 3.75 (q, 2H), 3.92 (s, 2H), 7.59, 7.61 (AA' part of an AA'BB' system, 2H), 7.65, 7.67 (BB' part of an AA'BB' system, 2H). |
| 99A | 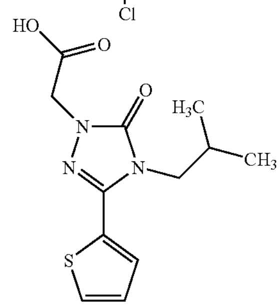 | $R_t$ = 1.55 min [7] | δ = 0.81 (d, 6H), 1.76-1.93 (m, 1H), 3.66 (d, 2H), 3.91 (s, 2H), 7.20 (dd, 1H), 7.52 (dd, 1H), 7.72 (dd, 1H). |
| 100A | 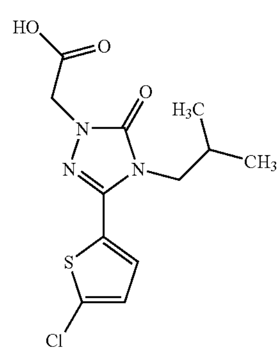 | $R_t$ = 2.32 min [8] | |

| Example No. | Structure | LC/MS $R_t$ [Method] | $^1$H-NMR (400 MHz, DMSO-$d_6$) |
|---|---|---|---|
| 101A | 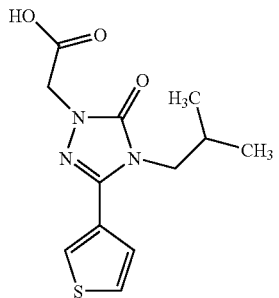 | $R_t$ = 1.72 min [5] | |
| 102A | 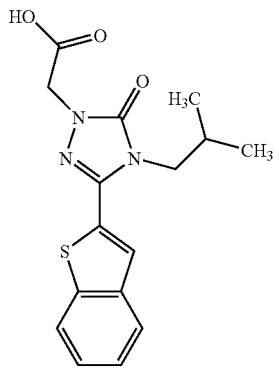 | $R_t$ = 2.14 min [5] | |
| 103A | 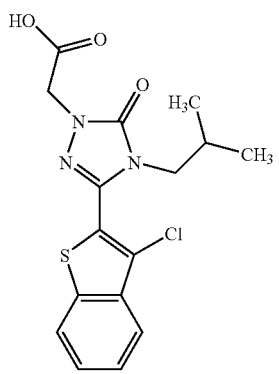 | $R_t$ = 2.58 min [8] | |

The following is obtained analogously to Example 88A/Method B:

Example 104A

[3-(3-chlorophenyl)-4-cyclopropyl-5-oxo-4,5-dihydro-1H-1,2,4-triazol-1-yl]acetic acid

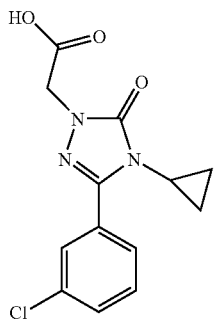

LC/MS [Method 8]: $R_t$=1.92 min
$^1$H-NMR (400 MHz, DMSO-$d_6$): δ=0.52-0.66 (m, 2H), 0.82-0.97 (m, 2H), 3.25 (dddd, 1H), 7.56 (t, 1H), 7.62 (br. d, 1H), 7.77 (d, 1H), 7.83 (br. s, 1H), 13.17 (br. s, 1H).

Example 105A rac-2-[3-(4-chlorophenyl)-4-cyclopropyl-5-oxo-4,5-dihydro-1H-1,2,4-triazol-1-yl]propionic acid

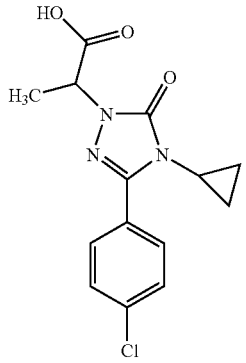

630 mg (1.88 mmol) of ethyl rac-2-[3-(4-chlorophenyl)-4-cyclopropyl-5-oxo-4,5-dihydro-1H-1,2,4-triazol-1-yl]-propionate from Example 85A are placed in 8 ml methanol, treated with 4 ml 20% aqueous potassium hydroxide and stirred for 2 hours at room temperature. The methanol is removed in vacuo, the aqueous residue acidified with 2 N hydrochloric acid, extracted with dichloromethane, and the organic phase dried over sodium sulphate and evaporated in vacuo. 463 mg (80% of theory) of the target compound are thus obtained.
HPLC [Method 2]: $R_t$=3.96 min
MS [ESIpos]: m/z=307 (M+H)$^+$
$^1$H-NMR (400 MHz, DMSO-$d_6$): δ=0.47-0.68 (m, 2H), 0.82-0.97 (m, 2H), 1.54 (d, 3H), 3.20 (dddd, 1H), 4.83 (q, 1H), 7.58, 7.60 (AA' part of an AA'BB' system, 2H), 7.81, 7.83 (BB' part of an AA'BB' system, 2H), 13.02 (s, 1H).

The following are obtained analogously:

Example 106A

2-[3-(4-chlorophenyl)-4-cyclopropyl-5-oxo-4,5-dihydro-1H-1,2,4-triazol-1-yl]-2-methylpropionic acid

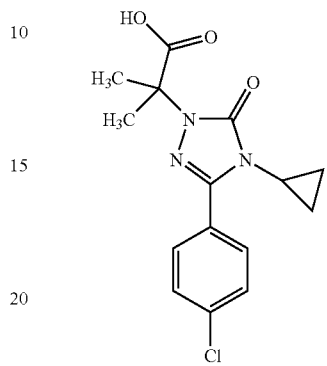

HPLC [Method 2]: $R_t$=4.17 min
MS [ESIpos]: m/z=322 (M+H)$^+$
$^1$H-NMR (400 MHz, DMSO-$d_6$): δ=0.48-0.61 (m, 2H), 0.81-0.95 (m, 2H), 1.64 (s, 6H), 3.17 (dddd, 1H), 7.58, 7.60 (AA' part of an AA'BB' system, 2H), 7.80, 7.83 (BB' part of an AA'BB' system, 2H), 12.88 (s, 1H).

Example 107A

3-[3-(4-chlorophenyl)-4-cyclopropyl-5-oxo-4,5-dihydro-1H-1,2,4-triazol-1-yl]propionic acid

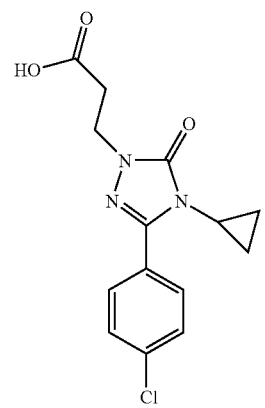

560 mg (1.67 mmol) of ethyl 3-[3-(4-chlorophenyl)-4-cyclopropyl-5-oxo-4,5-dihydro-1H-1,2,4-triazol-1-yl]-propionate from Example 87A are placed in 1.5 ml methanol, treated with 0.5 ml 20% aqueous potassium hydroxide and stirred for 2 hrs at room temperature. The methanol is removed in vacuo, the aqueous residue acidified to pH 1 with 2 N hydrochloric acid and the resulting precipitate isolated by filtration. 439 mg (73% of theory) of the target compound are thus obtained.
HPLC [Method 2]: $R_t$=3.81 min
MS [ESIpos]: m/z=308 (M+H)$^+$
$^1$H-NMR (400 MHz, DMSO-$d_6$): δ=0.50-0.63 (m, 2H), 0.80-0.97 (m, 2H), 2.66 (t, 2H), 3.15 (dddd, 1H), 3.92 (t, 2H), 7.58, 7.60 (AA' part of an AA'BB' system, 2H), 7.78, 7.80 (BB' part of an AA'BB' system, 2H), 12.36 (s, 1H).

Example 108A

Ethyl[3-(4-methoxyphenyl)-5-oxo-4,5-dihydro-1H-1,2,4-triazol-1-yl]acetate

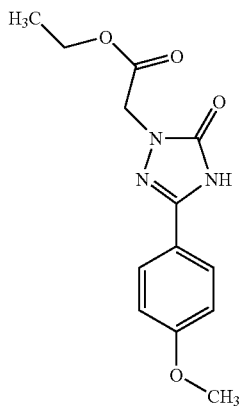

618 mg (4.00 mmol) of ethyl hydrazinoacetate hydrochloride are added to 479 mg (2.00 mmol) of N-(ethoxycarbonyl)-4-methoxyphenylcarboxylic acid thioamide [E. P. Papadopoulos, J. Org. Chem. 41 (6), 962-965 (1976)] in 10 ml ethanol and the mixture is heated under reflux for six hours. After cooling, the resulting suspension is stirred with diethyl ether and the precipitate isolated by filtration. Stirring this crude product with water, filtering again and drying in vacuo yields 167 mg (30% of theory) of the target compound.

LC/MS [Method 7]: $R_t$=1.54 min
$^1$H-NMR (400 MHz, DMSO-$d_6$): δ=1.21 (t, 3H), 3.81 (s, 3H), 4.16 (q, 2H), 4.57 (s, 2H), 7.04, 7.06 (AA' part of an AA'BB' system, 2H), 7.72, 7.74 (BB' part of an AA'BB' system, 2H), 12.20 (s, 1H).

Example 109A

Ethyl 4-ethyl-[3-(4-methoxyphenyl)-5-oxo-4,5-dihydro-1H-1,2,4-triazol-1-yl]acetate

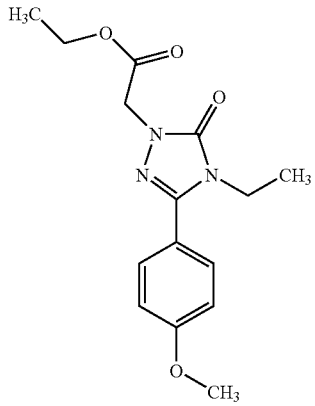

Method A:

6.1 mg (0.15 mmol) of sodium hydride (60% in mineral oil) are placed in 0.5 ml dimethyl-formamide and treated with 40 mg (0.14 mmol) of ethyl[3-(4-methoxyphenyl)-5-oxo-4,5-dihydro-1H-1,2,4-triazol-1-yl]-acetate from Example 108A in 2 ml dimethylformamide. This is stirred for 10 mins at room temperature, then 22 mg (0.012 ml, 0.14 mmol) of iodoethane are added and stirring continues overnight at room temperature. For the workup, the reaction mixture is treated with 2 ml of water, adjusted to pH 2 with 1 N hydrochloric acid and purified by preparative HPLC. 4.1 mg (9% of theory) of the target compound are thus obtained.

LC/MS [Method 4]: $R_t$=2.20 min
$^1$H-NMR (400 MHz, DMSO-$d_6$): δ=1.10 (t, 3H), 1.21 (t, 3H), 3.74 (q, 2H), 3.83 (s, 3H), 4.15 (q, 2H), 4.63 (s, 2H), 7.09, 7.11 (AA' part of an AA'BB' system, 2H), 7.72, 7.74 (BB' part of an AA'BB' system, 2H).

In addition, 3.8 mg (9% of theory) of ethyl[5-ethoxy-3-(4-methoxyphenyl)-1H-1,2,4-triazol-1-yl]-acetate are isolated:

LC/MS [Method 4]: $R_t$=2.59 min
$^1$H-NMR (400 MHz, DMSO-$d_6$): δ=1.21 (t, 3H), 1.36 (t, 3H), 3.79 (s, 3H), 4.17 (q, 2H), 4.49 (q, 2H), 4.87 (s, 2H), 6.98, 7.01 (AA' part of an AA'BB' system, 2H), 7.82, 7.85 (BB' part of an AA'BB' system, 2H).

Method B:

112 mg (0.912 mmol) of ethyl chloroacetate are added to 200 mg (0.912 mmol) of 4-ethyl-5-(4-methoxyphenyl)-2,4-dihydro-3H-1,2,4-triazol-3-one from Example 66A and 252 mg (1.82 mmol) potassium carbonate in 1.8 ml acetonitrile and the mixture is heated under reflux for 3 hours with stirring. After purification of the resulting crude product by preparative HPLC [Method 9], 212 mg (76% of theory) of the target compound are obtained.

Example 110A 4-ethyl-[3-(4-methoxyphenyl)-5-oxo-4,5-dihydro-1H-1,2,4-triazol-1-yl]acetic acid

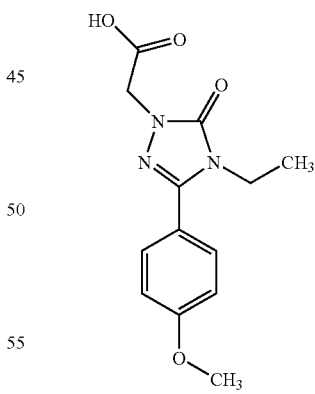

205 mg (0.67 mmol) of ethyl 4-ethyl-[3-(4-methoxyphenyl)-5-oxo-4,5-dihydro-1H-1,2,4-triazol-1-yl]-acetate from Example 109A are dissolved in 0.46 ml of methanol, treated with 0.18 ml 20% aqueous potassium hydroxide and stirred overnight. Next it is brought to a pH of 1 with 1 N hydrochloric acid, evaporated and the residue dried in vacuo. 207 mg of the target compound is thus obtained as crude product, which is further reacted as such.

LC/MS [Method 4]: $R_t$=1.65 min.

Example 111A 4-methyl-[3-(4-methylphenyl)-5-oxo-4,5-dihydro-1H-1,2,4-triazol-1-yl]acetic acid

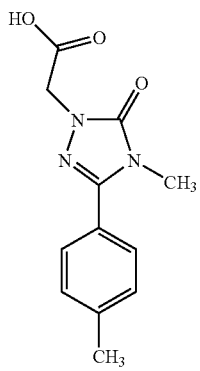

LC/MS [Method 4]: $R_t$=1.65 min.

Example 112A 2-bromo-1-(4-chlorophenyl)propan-1-one

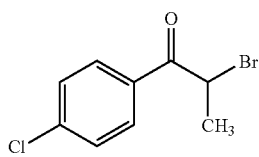

3000 mg (17.791 mmol) of 1-(4-chlorophenyl)propan-1-one are placed in 15 ml dichloromethane and treated with one drop of hydrobromic acid. The mixture is stirred at 35° C., then 2843 mg (17.791 mmol) of bromine are added dropwise so that the reaction solution decolorizes again after each addition. Three hours after the start of the reaction, the mixture is evaporated to dryness. 4490 mg (96% of theory) of the target compound are obtained.

HPLC [Method 2]: $R_t$=4.92 min $^1$H-NMR (400 MHz, DMSO-$d_6$): δ=1.78 (d, 3H), 5.82 (q, 1H), 7.64 (d, 2H), 8.05 (d, 2H).

Example 113A

N-[2-(4-chlorophenyl)-2-oxoethyl]-N'-cyclopropylurea

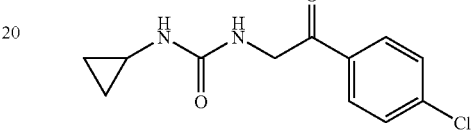

1000 mg (4.853 mmol) of 2-amino-1-(4-chlorophenyl)ethanone hydrochloride are placed in 20 ml dichloromethane, cooled to 0° C. and treated dropwise with a solution of 363 mg (4.367 mmol) of cyclopropyl isocyanate in 2 ml dichloromethane. It is stirred a further 10 mins at 0° C. and then a solution of 627 mg (4.853 mmol) of N,N-diisopropylethylamine in 4 ml dichloromethane is added dropwise. After two hours' stirring at room temperature the reaction mixture is evaporated and the crude product purified by flash chromatography on silica gel (eluent: dichloromethane/methanol 100:1). 1000 mg (73% of theory) of the target compound are obtained.

MS [CIpos]: m/z=270 (M+NH$_4$)$^+$

HPLC [Method 2]: $R_t$=3.99 min.

The following are prepared analogously:

| Example No. | Structure | LC/MS or HPLC, MS $R_t$ [Method] | $^1$H-NMR (400 MHz, DMSO-$d_6$) |
|---|---|---|---|
| 114A | ![structure] | $R_t$ = 1.64 min [4] | δ = 0.36 (m, 2H), 0.59 (m, 2H), 2.43 (m, 1H), 4.56 (d, 2H), 6.18 (br. t, 1H), 6.49 (br. d, 1H), 7.54 (t, 2H), 7.66 (t, 1H), 7.97 (d, 2H). |
| 115A | ![structure] | MS [EIpos]: m/z = 241 (M + H)$^+$; HPLC [2]: $R_t$ = 3.69 min | δ = 1.00 (t, 3H), 3.02 (dq, 2H), 4.53 (d, 2H), 6.15 (br. t, 1H), 6.22 (br. t, 1H), 7.61 (d, 2H), 7.98 (d, 2H). |
| 116A | ![structure] | $R_t$ = 1.94 min [4] | δ = 0.36 (m, 2H), 0.59 (m, 2H), 2.95 (m, 1H), 4.52 (d, 2H), 6.20 (br. t, 1H), 6.49 (br. d, 1H), 7.75 (d, 2H), 7.91 (d, 2H). |

Example 117A

N-[2-(4-chlorophenyl)-1-methyl-2-oxoethyl]-glycine ethyl ester

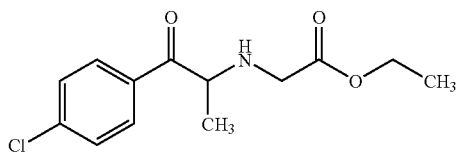

200 mg (0.808 mmol) of 2-bromo-1-(4-chlorophenyl)propan-1-one from Example 112A are dissolved in 1 ml acetonitrile and treated with 226 mg (1.616 mmol) of glycine ethyl ester hydrochloride and 209 mg (1.616 mmol) of N,N-diisopropylethylamine. After stirring overnight at room temperature, the reaction mixture is evaporated and the residue is partitioned between water and dichloromethane. The organic phase is separated, dried over sodium sulphate and concentrated. The crude product is purified by flash chromatography on silica gel (eluent: first dichloromethane, then dichloromethane/methanol 200:1). 91 mg (42% of theory) of the target compound are thus obtained.

MS [CIpos]: m/z=270 (M+H)$^+$

HPLC [Method 2]: $R_t$=3.77 min $^1$H-NMR (400 MHz, DMSO-d$_6$): δ=1.15 (t, 3H), 1.17 (d, 3H), 3.33 (s, 2H), 4.05 (q, 2H), 4.40 (q, 1H), 7.61 (d, 2H), 8.01 (d, 2H).

Example 118A 5-(4-chlorophenyl)-1-cyclopropyl-1,3-dihydro-2H-imidazol-2-one

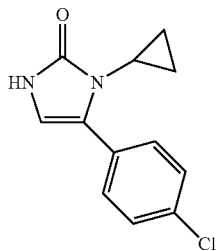

1525 mg (6.035 mmol) of N-[2-(4-chlorophenyl)-2-oxoethyl]-N'-cyclopropylurea from Example 113A are suspended in 25 ml of concentrated hydrochloric acid, treated with 25 ml methanol and stirred for one hour at room temperature. The reaction mixture is evaporated to dryness and the residue purified by flash chromatography on silica gel (eluent: dichloromethane/methanol 100:1, then 50:1). 1300 mg (90% of theory) of the target compound are obtained.

MS [CIpos]: m/z=252 (M+NH$_4$)$^+$

HPLC [Method 2]: $R_t$=3.92 min $^1$H-NMR (400 MHz, DMSO-d$_6$): δ=0.46 (m, 2H), 0.78 (m, 2H), 2.95 (tt, 1H), 6.62 (d, 1H), 7.44 (d, 2H), 7.54 (d, 2H), 10.17 (s, 1H).

The following are prepared analogously:

| Example No. | Structure | LC/MS or HPLC, MS $R_t$ [Method] | $^1$H-NMR (400 MHz, DMSO-d$_6$) |
|---|---|---|---|
| 119A | 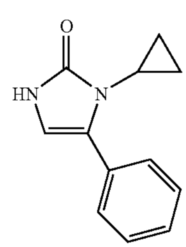 | MS [CIpos]: m/z = 218 (M + NH$_4$)$^+$ | δ = 0.46 (m, 2H), 0.76 (m, 2H), 2.95 (tt, 1H), 6.53 (d, 1H), 7.29 (t, 1H), 7.38 (t, 2H), 7.51 (d, 2H), 10.09 (s, 1H). |
| 120A | 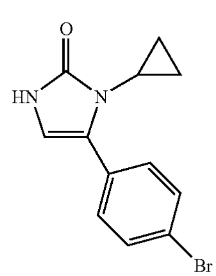 | MS [CIpos]: m/z = 296 and 298 (M + NH$_4$)$^+$; HPLC [2]: $R_t$ = 4.08 min | δ = 0.46 (m, 2H), 0.79 (m, 2H), 2.95 (tt, 1H), 6.63 (d, 1H), 7.47 (d, 2H), 7.57 (d, 2H), 10.17 (s, 1H). |

Example 121A 5-(4-chlorophenyl)-1-ethyl-1,3-dihydro-2H-imidazol-2-one

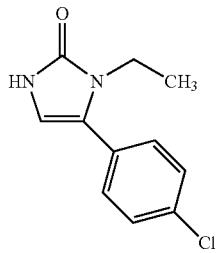

990 mg (4.113 mmol) of N-[2-(4-chlorophenyl)-2-oxoethyl]-N'-ethylurea from Example 115A are suspended in 16 ml concentrated hydrochloric acid, treated with 16 ml of methanol and stirred for one hour at room temperature. The reaction mixture is evaporated to dryness, the residue extracted with dichloromethane, and the organic phase dried over sodium sulphate and again concentrated. The crude product is purified by flash chromatography on silica gel (eluent: dichloromethane/methanol 100:1, then 50:1) and 701 mg (77% of theory) of the target compound are thus obtained.

MS [ESIpos]: m/z=223 (M+H)$^+$
HPLC [Method 2]: $R_t$=3.94 min
$^1$H-NMR (400 MHz, DMSO-d$_6$): δ=0.99 (t, 3H), 3.66 (q, 2H), 6.60 (d, 1H), 7.43 (d, 2H), 7.48 (d, 2H), 10.28 (s, 1H).

Example 122A

Ethyl[4-(4-chlorophenyl)-3-cyclopropyl-2-oxo-2,3-dihydro-1H-imidazol-1-yl]-acetate

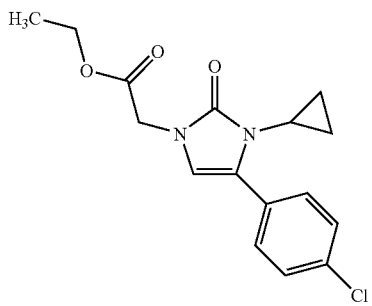

740 mg (3.15 mmol) of 5-(4-chlorophenyl)-1-cyclopropyl-1,3-dihydro-2H-imidazol-2-one from Example 118A are dissolved in 15 ml acetonitrile and treated with 386 mg (3.15 mmol) of ethyl chloroacetate and 872 mg (6.31 mmol) of potassium carbonate. The mixture is stirred overnight under reflux. It is then concentrated, the residue is partitioned between dichloromethane and water, the organic phase is separated, and this is dried over sodium sulphate and again concentrated. The crude product is purified by flash chromatography on silica gel (eluent: first dichloromethane, then dichloromethane/methanol 200:1→100:1) and thus yields 602 mg (57% of theory) of the target compound.

MS [ESIpos]: m/z=321 (M+H)$^+$
HPLC [Method 2]: $R_t$=4.33 min
$^1$H-NMR (400 MHz, DMSO-d$_6$): δ=0.47 (m, 2H), 0.81 (m, 2H), 1.21 (t, 3H), 3.04 (tt, 1H), 4.14 (q, 2H), 4.40 (s, 2H), 6.77 (s, 1H), 7.47 (d, 2H), 7.55 (d, 2H).

Example 123A

Ethyl(3-cyclopropyl-2-oxo-4-phenyl-2,3-dihydro-1H-imidazol-1-yl)-acetate

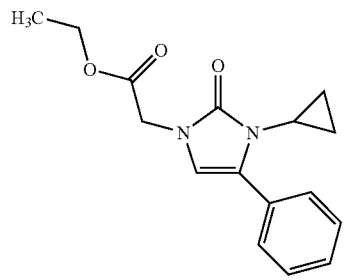

270 mg (1.35 mmol) of 1-cyclopropyl-5-phenyl-1,3-dihydro-2H-imidazol-2-one from Example 119A are dissolved in 5 ml acetonitrile and treated with 165 mg (1.35 mmol) of ethyl chloroacetate and 373 mg (2.70 mmol) of potassium carbonate. The mixture is stirred under reflux for 4 hrs, then a further 165 mg (1.35 mmol) of ethyl chloroacetate are added. After stirring overnight under reflux the reaction mixture is evaporated, the residue is partitioned between dichloromethane and water, the organic phase is separated, and this is dried over sodium sulphate and again concentrated. The crude product is purified by flash chromatography on silica gel (eluent: dichloromethane/methanol firstly 200:1, then 100:1) and thus yields 353 mg (91% of theory) of the target compound.

MS [ESIpos]: m/z=287 (M+H)$^+$
$^1$H-NMR (400 MHz, DMSO-d$_6$): δ=0.47 (m, 2H), 0.78 (m, 2H), 1.21 (t, 3H), 3.04 (tt, 1H), 4.14 (q, 2H), 4.40 (s, 2H), 6.70 (s, 1H), 7.32 (t, 2H), 7.42 (t, 2H), 7.51 (d, 2H).

Example 124A

Ethyl[4-(4-bromophenyl)-3-cyclopropyl-2-oxo-2,3-dihydro-1H-imidazol-1-yl]-acetate

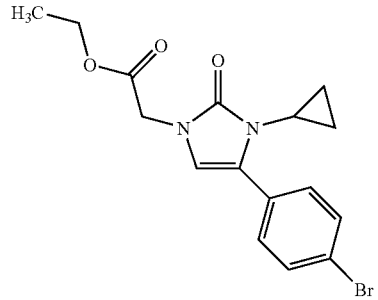

392 mg (1.40 mmol) of 5-(4-bromophenyl)-1-cyclopropyl-1,3-dihydro-2H-imidazol-2-one from Example 120A are dissolved in 7.7 ml acetonitrile, treated with 172 mg (1.40 mmol) of ethyl chloroacetate and 388 mg (2.81 mmol) of potassium carbonate and heated under reflux for two hours. After cooling, this is filtered, the filtrate evaporated, and the residue partitioned between ethyl acetate and water, the organic phase is separated, dried over sodium sulphate and again concentrated. 502 mg (98% of theory) of the target compound, which is reacted without further purification, are thus obtained.

LC/MS [Method 7]: $R_t$=2.07 min $^1$H-NMR (400 MHz, DMSO-$d_6$): δ=0.40-0.53 (m, 2H), 0.74-0.88 (m, 2H), 1.21 (t, 3H), 3.04 (dddd, 1H), 4.14 (q, 2H), 4.40 (s, 2H), 6.78 (s, 1H), 7.47, 7.49 (AA' part of an AA'BB' system, 2H), 7.59, 7.61 (BB' part of an AA'BB' system, 2H).

Example 125A

Ethyl 2-[4-(4-chlorophenyl)-3-cyclopropyl-2-oxo-2,3-dihydro-1H-imidazol-1-yl]-propionate

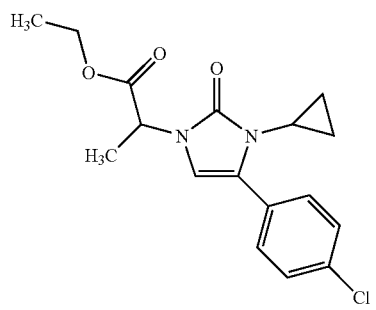

500 mg (2.13 mmol) of 5-(4-chlorophenyl)-1-cyclopropyl-1,3-dihydro-2H-imidazol-2-one from Example 118A are dissolved in 5 ml acetonitrile and treated with 386 mg (2.13 mmol) of ethyl 2-bromopropionate and 1388 mg (4.26 mmol) of caesium carbonate. The mixture is stirred under reflux overnight. It is then concentrated, the residue is partitioned between dichloromethane and water, the organic phase is separated, and this is dried over sodium sulphate and again concentrated. The crude product is purified by flash chromatography on silica gel (eluent: first dichloromethane, then dichloromethane/methanol 200:1→100:1) and thus yields 338 mg (45% of theory) of the target compound.

MS [ESIpos]: m/z=335 (M+H)$^+$

HPLC [Method 2]: $R_t$=4.50 min $^1$H-NMR (400 MHz, DMSO-$d_6$): δ=0.43 (m, 1H), 0.51 (m, 1H), 0.81 (m, 2H), 1.18 (t, 3H), 2.94 (d, 3H), 3.04 (tt, 1H), 4.12 (q, 2H), 4.74 (q, 1H), 6.92 (s, 1H), 7.47 (d, 2H), 7.58 (d, 2H).

Example 126A

Ethyl[4-(4-chlorophenyl)-3-cyclopropyl-5-methyl-2-oxo-2,3-dihydro-1H-imidazol-1-yl]-acetate

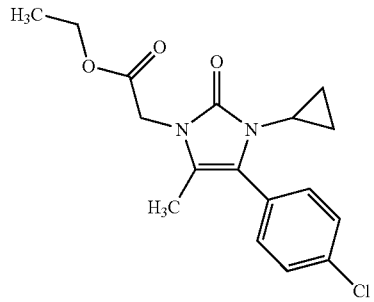

355 mg (1.32 mmol) of N-[2-(4-chlorophenyl)-1-methyl-2-oxoethyl]-glycine ethyl ester from Example 117A are placed in 5 ml tetrahydrofuran, treated with 109 mg (1.32 mmol) of cyclopropyl isocyanate and stirred overnight at room temperature. The reaction mixture is evaporated and the residue purified by flash chromatography on silica gel (eluent: first dichloromethane, then dichloromethane/methanol 200:1→100:1). 425 mg (91% of theory) of the target compound are thus obtained.

MS [ESIpos]: m/z=335 (M+H)$^+$

HPLC [Method 1]: $R_t$=4.49 min $^1$H-NMR (400 MHz, DMSO-$d_6$): δ=0.14 (m, 1H), 0.25 (m, 1H), 0.39 (m, 1H), 0.78 (m, 1H), 1.21 (t, 3H), 2.23 (tt, 1H), 2.50 (s, 3H), 3.32 (s, 2H), 4.11 (q, 2H), 7.45 (d, 2H), 7.51 (d, 2H).

Example 127A

[4-(4-chlorophenyl)-3-ethyl-2-oxo-2,3-dihydro-1H-imidazol-1-yl]-acetic acid

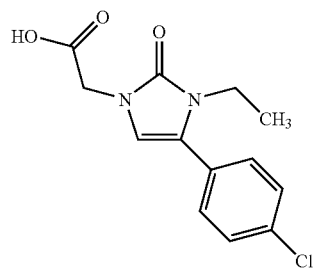

685 mg (3.076 mmol) of 5-(4-chlorophenyl)-1-ethyl-1,3-dihydro-2H-imidazol-2-one from Example 119A are placed in 10 ml acetonitrile, treated with 377 mg (3.076 mmol) of ethyl chloroacetate and 850 mg (6.152 mmol) of potassium carbonate and stirred under reflux overnight. The reaction mixture is evaporated, the residue is partitioned between dichloromethane and water, the organic phase is separated, and this is dried over sodium sulphate and again concentrated. The crude product is purified by flash chromatography on silica gel (eluent: first dichloromethane, then dichloromethane/methanol 100:1→50:1) and thus yields 226 mg (26% of theory) of the target compound.

MS [ESIpos]: m/z=281 (M+H)$^+$

HPLC [Method 2]: $R_t$=3.89 min $^1$H-NMR (400 MHz, DMSO-$d_6$): δ=1.02 (t, 3H), 3.69 (q, 2H), 4.13 (s, 2H), 6.70 (s, 1H), 7.41 (d, 2H), 7.49 (d, 2H), 10.30 (br. s, 1H).

Example 128A (3-cyclopropyl-2-oxo-4-phenyl-2,3-dihydro-1H-imidazol-1-yl)-acetic acid

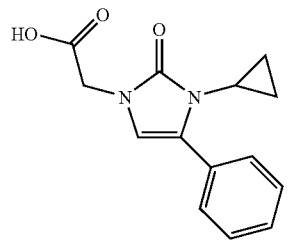

350 mg (1.222 mmol) of ethyl (3-cyclopropyl-2-oxo-4-phenyl-2,3-dihydro-1H-imidazol-1-yl)-acetate from Example 123A are placed in 2 ml methanol, treated with 0.5 ml 20% aqueous potassium hydroxide and stirred for two hours at room temperature. The methanol is removed on the rotary evaporator, and the residue acidified with 2 N hydrochloric acid and extracted with dichloromethane. The organic phase is separated, dried over sodium sulphate and concentrated. It is purified by flash chromatography on silica gel (eluent: dichloromethane/methanol first 50:1, then 25:1). 166 mg (53% of theory) of the target compound are thus obtained.

MS [ESIpos]: m/z=259 (M+H)+
HPLC [Method 2]: $R_t$=3.84 min
$^1$H-NMR (400 MHz, DMSO-d$_6$): δ=0.47 (m, 2H), 0.78 (m, 2H), 3.04 (tt, 1H), 4.30 (s, 2H), 6.69 (s, 1H), 7.32 (t, 1H), 7.41 (t, 2H), 7.51 (d, 2H), 12.96 (br. s, 1H).

Example 129A

[4-(4-bromophenyl)-3-cyclopropyl-2-oxo-2,3-dihydro-1H-imidazol-1-yl]-acetic acid

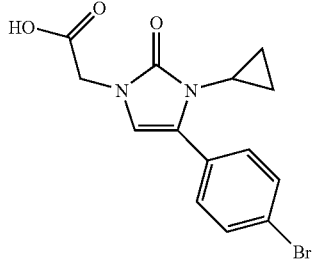

502 mg (1.28 mmol) of ethyl[4-(4-bromophenyl)-3-cyclopropyl-2-oxo-2,3-dihydro-1H-imidazol-1-yl]-acetate from Example 124A are placed in 0.94 ml methanol, treated with 0.34 ml 20% aqueous potassium hydroxide and stirred overnight at room temperature. It is adjusted to pH 3 with 1 N hydrochloric acid, the resulting precipitate recovered by filtration, and the product washed with water and dried in vacuo. 369 mg (80% of theory) of the target compound, which is reacted without further purification, are thus obtained.

LC/MS [Method 7]: $R_t$=1.71 min $^1$H-NMR (400 MHz, DMSO-d$_6$): δ=0.40-0.53 (m, 2H), 0.74-0.88 (m, 2H), 3.03 (dddd, 1H), 4.30 (s, 2H), 6.78 (s, 1H), 7.46, 7.49 (AA' part of an AA'BB' system, 2H), 7.59, 7.61 (BB' part of an AA'BB' system, 2H), 12.98 (br. s, 1H).

The following are prepared analogously:

| Example No. | Structure | LC/MS or HPLC, MS $R_t$ [Method] | $^1$H-NMR (400 MHz, DMSO-d$_6$) |
|---|---|---|---|
| 130A | 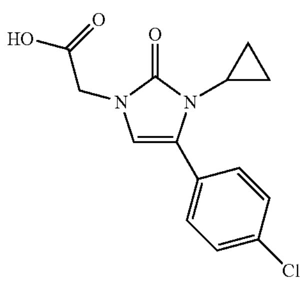 | $R_t$ = 2.42 min [4] | δ = 0.39-0.53 (m, 2H), 0.73-0.88 (m, 2H), 3.03 (dddd, 1H), 4.30 (s, 2H), 6.77 (s, 1H), 7.45, 7.48 (AA' part of an AA'BB' system, 2H), 7.53, 7.55 (BB' part of an AA'BB' system, 2H), 12.99 (br. s, 1H). |
| 131A | 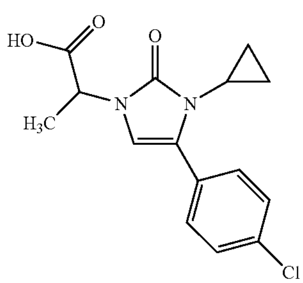 | MS [ESIpos]: m/z = 307 (M + H)+; HPLC [2]: $R_t$ = 4.02 min | δ = 0.42 (m, 1H), 0.52 (m, 1H), 0.81 (m, 2H), 1.51 (d, 3H), 3.04 (tt, 1H), 4.66 (q, 1H), 6.91 (s, 1H), 7.46 (d, 2H), 7.57 (d, 2H), 12.97 (br. s, 1H). |
| 132A | 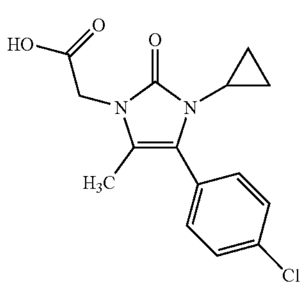 | MS [ESIpos]: m/z = 307 (M + H)+; HPLC [2]: $R_t$ = 4.02 min | δ = 0.40 (m, 2H), 0.67 (m, 2H), 1.96 (s, 3H), 2.89 (tt, 1H), 4.34 (s, 2H), 7.44 (d, 2H), 7.49 (d, 2H), 13.01 (br. s, 1H). |

Example 133A 2-chloro-N-{1-methyl-1-[3-(trifluoromethyl)phenyl]ethyl}acetamide

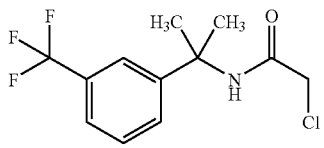

2.5 g (12.3 mmol) of the compound from Example 1A and 1.70 g (12.3 mmol) of potassium carbonate are placed in 30 ml dichloromethane and slowly treated at RT with a solution of 1.46 g (12.9 mmol) of chloroacetyl chloride in 5 ml dichloromethane. The mixture is stirred for 3 hrs at RT and then treated with 150 ml water and slowly with 30 ml 1 N hydrochloric acid. It is extracted three times with dichloromethane. The combined organic phases are dried over magnesium sulphate and freed of solvent on the rotary evaporator. 2.65 g (77% of theory) of the title compound are thus obtained.

LC/MS [Method 17]: $R_t$=3.37 min; m/z=280 (M+H)$^+$ $^1$H-NMR (400 MHz, DMSO-d$_6$): δ=1.59 (s, 6H), 4.05 (s, 2H), 7.50-7.67 (m, 4H), 8.60 (s, 1H).

Example 134A 2-chloro-N-[2-(trifluoromethyl)benzyl]acetamide

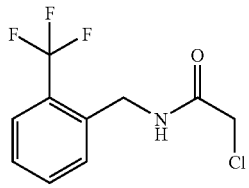

Analogously to Example 133A, 2.43 g (68% of theory) of the title compound are obtained from 2.5 g (14.3 mmol) 2-trifluoromethylbenzylamine and 1.69 g (15.0 mmol) of chloroacetyl chloride.

LC/MS [Method 18]: $R_t$=2.00 min; m/z=252 (M+H)$^+$ $^1$H-NMR (400 MHz, DMSO-d$_6$): δ=4.18 (s, 2H), 4.49 (d, J=6 Hz, 2H), 7.47-7.52 (m, 2H), 7.68 (t, J=7.5 Hz, 1H), 7.73 (d, J=7.8 Hz, 1H), 8.81 (br. t, 1H).

Example 135A 5-bromo-4-(2-fluorobenzyl)-2,4-dihydro-3H-1,2,4-triazol-3-one

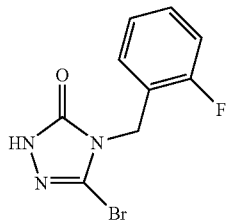

Step a): Preparation of N-(2-fluorobenzyl)-2-formylhydrazinecarboxamide

Under argon, 1.99 g (33 mmol) of formylhydrazine are placed in 80 ml THF. The solution is heated to 50° C., treated dropwise with a solution of 5.00 g (33 mmol) of 2-fluorobenzyl isocyanate in 50 ml THF and the resulting mixture stirred for 30 mins more at 50° C. It is then freed of solvent on the rotary evaporator. The residue is stirred with diethyl ether, the precipitate suction-filtered, then washed with diethyl ether and the white solid dried under high vacuum. 5.73 g (82% of theory) of the target product are obtained.

LC/MS [Method 7]: $R_t$=0.88 min; m/z=212 (M+H)$^+$.

Step b): Preparation of 4-(2-fluorobenzyl)-2,4-dihydro-3H-1,2,4-triazol-3-one The product from Step a (5.73 g, 27.1 mmol) is stirred under reflux in 60 ml 3 M aqueous sodium hydroxide for 5 hrs. The mixture is then cooled in an ice-bath and slowly acidified to pH 2 with 1 N hydrochloric acid. The precipitated solid is filtered off at the pump, then washed with water and dried under high vacuum. 3.38 g (64% of theory) of the target product are obtained.

LC/MS [Method 17]: $R_t$=1.35 min; m/z=194 (M+H)$^+$.

Step c): Preparation of 5-bromo-4-(2-fluorobenzyl)-2,4-dihydro-3H-1,2,4-triazol-3-one The product from Step b (3.35 g, 17.3 mmol) is placed in 37 ml water together with sodium hydroxide (970 mg, 24.2 mmol). Bromine (893 µl, 17.3 mmol) is added dropwise with stirring at RT. During the addition, a light brown solid precipitates. Stirring is continued overnight at RT. The precipitated solid is filtered off at the pump, washed with a little water and then dried under high vacuum. 4.25 g of the target product of adequate purity (ca. 83% by LC/MS) are obtained.

LC/MS [Method 8]: $R_t$=1.81 min; m/z=272 (M+H)$^+$ $^1$H-NMR (400 MHz, DMSO-d$_6$): δ=4.84 (s, 2H), 7.14-7.28 (m, 3H), 7.35-7.42 (m, 1H), 12.22 (s, 1H).

Example 136A 5-bromo-4-(2-methoxyethyl)-2,4-dihydro-3H-1,2,4-triazol-3-one

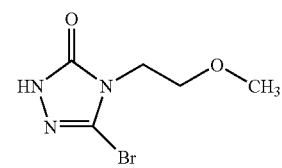

The title compound is prepared analogously to the synthetic sequence described for Example 135A, starting from 2-methoxyethyl isocyanate.

LC/MS [Method 3]: $R_t$=2.12 min; m/z=222 (M+H)$^+$ $^1$H-NMR (400 MHz, DMSO-d$_6$): δ=3.24 (s, 3H), 3.51 (d, J=5.5 Hz, 2H), 3.72 (d, J=5.5 Hz, 2H), 12.10 (s, 1H).

Example 137A 5-bromo-4-(3-fluorobenzyl)-2,4-dihydro-3H-1,2,4-triazol-3-one

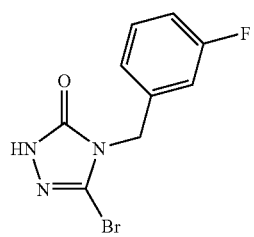

The title compound is prepared analogously to the synthetic sequence described for Example 135A, starting from 3-fluorobenzyl isocyanate.

LC/MS [Method 8]: $R_t$=1.79 min; m/z=272 (M+H)$^+$ $^1$H-NMR (400 MHz, DMSO-d$_6$): δ=4.81 (s, 2H), 7.04-7.12 (m, 2H), 7.15 (dt, 1H), 7.43 (q, 1H), 12.3 (s, 1H).

Example 138A

Methyl[3-bromo-4-(2-fluorobenzyl)-5-oxo-4,5-dihydro-1H-1,2,4-triazol-1-yl]-acetate

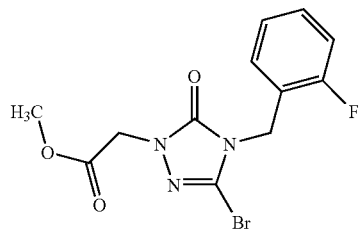

300 mg (1.1 mmol) of the compound from Example 135A are stirred under reflux for 2 hrs together with 150 mg (1.38 mmol) of methyl chloroacetate and 168 mg (1.21 mmol) of potassium carbonate in 10 ml acetonitrile. After cooling, the mixture is diluted with ethyl acetate and treated with 1 N hydrochloric acid. The organic phase is separated, washed with saturated sodium chloride solution, dried over sodium sulphate and freed of the volatile components on the rotary evaporator. The residue is dried under high vacuum. The product thus obtained (360 mg, purity ca. 73% by LC/MS) is used in the next synthetic step without further purification.

LC/MS [Method 17]: $R_t$=2.83 min; m/z=344 (M+H)$^+$ $^1$H-NMR (400 MHz, DMSO-d$_6$): δ=3.70 (s, 3H), 4.59 (s, 2H), 4.92 (s, 2H), 7.15-7.30 (m, 3H), 7.35-7.43 (m, 1H).

Example 139A

[3-bromo-4-(2-fluorobenzyl)-5-oxo-4,5-dihydro-1H-1,2,4-triazol-1-yl]-acetic acid

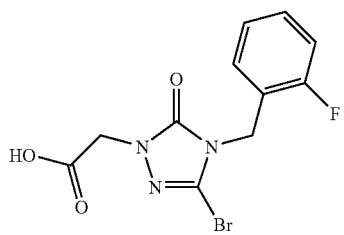

The compound from Example 138A (360 mg) is dissolved in 10 ml methanol and treated with 4.2 ml of a 1 M aqueous lithium hydroxide solution. The mixture is stirred overnight at RT and then freed of methanol on the rotary evaporator. The residue is diluted with 200 ml water and slowly acidified to pH 2 with 1 N hydrochloric acid. The aqueous phase is extracted three times with ethyl acetate, the combined organic phases dried over sodium sulphate and the solvent removed on the rotary evaporator. The residue is dissolved in a little DMSO and purified by preparative HPLC (Method 20). 246 mg (0.75 mmol) of the title compound are obtained.

LC/MS [Method 19]: $R_t$=2.00 min; m/z=330 (M+H)$^+$ $^1$H-NMR (400 MHz, DMSO-d$_6$): δ=4.53 (s, 2H), 4.91 (s, 2H), 7.15-7.30 (m, 3H), 7.35-7.45 (m, 1H), 13.10 (br. s, 1H).

Example 140A

2-[3-bromo-4-(2-fluorobenzyl)-5-oxo-4,5-dihydro-1H-1,2,4-triazol-1-yl]-N-{2-[(2-trifluoromethyl)-phenyl]ethyl}-acetamide

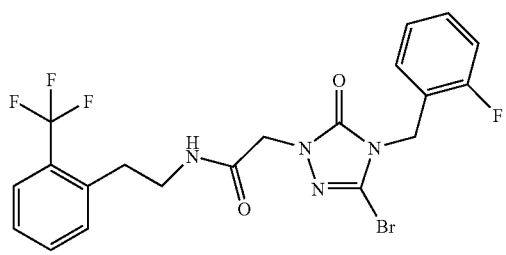

246 mg (0.64 mmol) of the compound from Example 139A and 121 mg of HOBt (0.90 mmol) are placed in 5 ml DMF and treated with 172 mg of EDC (0.90 mmol). After 20 mins stirring at RT, 2-(2-trifluoromethylphenyl)ethylamine (139 mg, 0.74 mmol) is added and the mixture stirred for 1 hr more at RT. Next the reaction mixture is directly separated by preparative HPLC (Method 20). 321 mg (99% of theory) of the title compound are isolated.

LC/MS [Method 17]: $R_t$=3.60 min; m/z=503 (M+H)$^+$ $^1$H-NMR (400 MHz, DMSO-d$_6$): δ=2.90 (t, 2H), 3.29-3.37 (m, 2H), 4.36 (s, 2H), 4.90 (s, 2H), 7.19-7.29 (m, 3H), 7.37-7.50 (m, 3H), 7.62 (t, 1H), 7.69 (d, 1H), 8.33 (t, 1H).

Example 141A

2-[3-bromo-4-(2-fluorobenzyl)-5-oxo-4,5-dihydro-1H-1,2,4-triazol-1-yl]-N-{1-methyl-1-[(3-trifluoromethyl)phenyl]ethyl}-acetamide

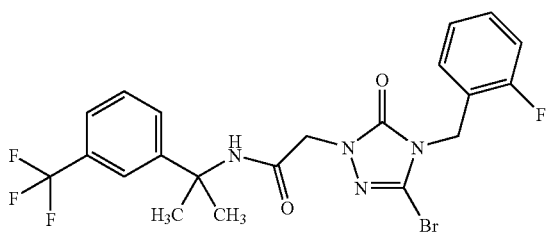

703 mg (2.15 mmol) of the compound from Example 135A are stirred under reflux overnight together with 600 mg (2.15 mmol) of 2-chloro-N-{1-methyl-1-[3-(trifluoromethyl)phenyl]ethyl}-acetamide (Example 133A) and 593 mg (4.29 mmol) of potassium carbonate in 15 ml acetonitrile. After cooling, the mixture is filtered and the filtrate directly purified by preparative HPLC (Method 20). 780 mg (71% of theory) of the title compound are obtained.

LC/MS [Method 17]: $R_t$=3.73 min; m/z=515 (M+H)$^+$ $^1$H-NMR (400 MHz, DMSO-d$_6$): δ=1.59 (s, 6H), 4.43 (s, 2H), 4.86 (s, 2H), 7.10-7.26 (m, 3H), 7.34-7.41 (m, 1H), 7.50-7.58 (m, 2H), 7.61 (s, 1H), 7.65 (br. d, J~6.8 Hz, 1H), 8.54 (s, 1H).

Example 142A

2-[3-bromo-4-(2-fluorobenzyl)-5-oxo-4,5-dihydro-1H-1,2,4-triazol-1-yl]-N-[(2-trifluoromethyl)-benzyl]-acetamide

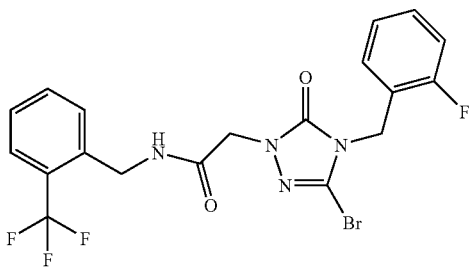

312 mg (0.95 mmol) of the compound from Example 135A are stirred under reflux overnight together with 240 mg (0.95 mmol) of 2-chloro-N-[2-(trifluoromethyl)benzyl]acetamide (Example 134A) and 264 mg (1.21 mmol) of potassium carbonate in 6 ml acetonitrile. After cooling, the mixture is treated with water and extracted three times with dichloromethane. The combined organic phases are dried over magnesium sulphate and freed of the volatile components on the rotary evaporator. The residue is purified by preparative HPLC (Method 20). 385 mg (79% of theory) of the title compound are obtained.

LC/MS [Method 8]: $R_t$=2.46 min; m/z=487 (M+H)$^+$ $^1$H-NMR (400 MHz, DMSO-d$_6$): δ=4.48 (d, J=5.6 Hz, 2H), 4.52 (s, 2H), 4.90 (s, 2H), 7.18-7.29 (m, 3H), 7.36-7.43 (m, 1H), 7.49 (t, J=7.6 Hz, 1H), 7.54 (d, J=7.6 Hz, 1H), 7.67 (t, J=7.6 Hz, 1H), 7.73 (d, J=7.6 Hz, 1H), 8.74 (t, J=5.8 Hz, 1H).

Example 143A

2-[3-bromo-4-(2-methoxyethyl)-5-oxo-4,5-dihydro-1H-1,2,4-triazol-1-yl]-N-{1-methyl-1-[(3-trifluoromethyl)phenyl]ethyl}-acetamide

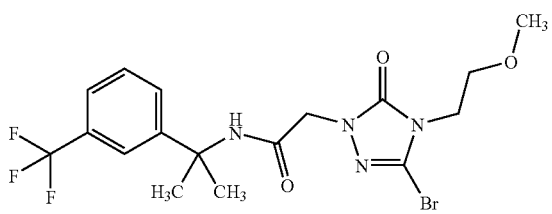

0.82 g of the compound from Example 136A (91% purity, 3.58 mmol) are stirred under reflux overnight together with 1.0 g (3.58 mmol) of 2-chloro-N-{1-methyl-1-[3-(trifluoromethyl)phenyl]-ethyl}-acetamide (Example 133A) and 0.99 g (7.15 mmol) of potassium carbonate in 25 ml acetonitrile. After cooling, the mixture is treated with water and extracted three times with dichloromethane. The combined organic phases are dried over sodium sulphate and freed of the volatile components on the rotary evaporator. The residue is dried under high vacuum. 1.47 g (88% of theory) of the title compound are obtained.

LC/MS [Method 17]: $R_t$=3.24 min; m/z=465 (M+H)$^+$ $^1$H-NMR (400 MHz, DMSO-d$_6$): δ=1.58 (s, 6H), 3.22 (s, 3H), 3.50 (t, 2H), 3.74 (t, 2H), 4.39 (s, 2H), 7.50-7.57 (m, 2H), 7.60 (s, 1H), 7.65 (br. d, 1H), 8.55 (s, 1H).

Example 144A 2-(3-bromo-4-cyclopropyl-5-oxo-4,5-dihydro-1H-1,2,4-triazol-1-yl)-N-{1-methyl-1-[(3-trifluoromethyl)phenyl]ethyl}-acetamide

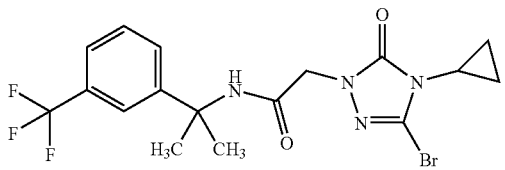

438 mg (2.15 mmol) of 5-bromo-4-cyclopropyl-2,4-dihydro-3H-1,2,4-triazol-3-one (for preparation see EP 0 425 948-A2, Example II-3) are stirred under reflux overnight together with 600 mg (2.15 mmol) of 2-chloro-N-{1-methyl-1-[3-(trifluoromethyl)phenyl]ethyl}-acetamide (Example 133A) and 593 mg (4.29 mmol) of potassium carbonate in 15 ml acetonitrile. After cooling, the mixture is treated with water and extracted three times with ethyl acetate. The combined organic phases are dried over magnesium sulphate and freed of the volatile components on the rotary evaporator. The residue is dried under high vacuum. 860 mg (90% of theory) of the title compound are obtained as a light brown solid.

LC/MS [Method 17]: $R_t$=3.35 min; m/z=447 (M+H)$^+$
$^1$H-NMR (400 MHz, DMSO-d$_6$): δ=0.86-0.92 (m, 2H), 0.92-1.01 (m, 2H), 1.58 (s, 6H), 2.80 (m, 1H), 4.33 (s, 2H), 7.50-7.57 (m, 2H), 7.59 (s, 1H), 7.65 (m, 1H), 8.50 (s, 1H).

Example 145A 2-(3-bromo-4-cyclopropyl-5-oxo-4,5-dihydro-1H-1,2,4-triazol-1-yl)-N-[(2-trifluoromethyl)benzyl]-acetamide

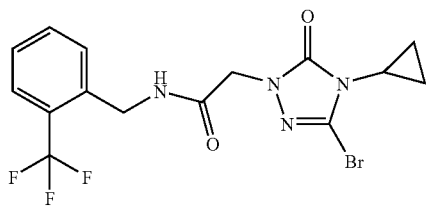

By the same method as described in Example 144A, starting from 487 mg (2.38 mmol) of 5-bromo-4-cyclopropyl-2,4-dihydro-3H-1,2,4-triazol-3-one (for preparation see EP 0 425 948-A2, Example II-3) and 600 mg (2.38 mmol) of 2-chloro-N-[2-(trifluoromethyl)benzyl]-acetamide (Example 134A), 900 mg (90% of theory) of the title compound are obtained as a light brown solid.

LC/MS [Method 17]: $R_t$=3.02 min; m/z=419 (M+H)$^+$
$^1$H-NMR (400 MHz, DMSO-d$_6$): δ=0.90-1.03 (m, 4H), 2.85 (m, 1H), 4.41 (s, 2H), 4.48 (d, 2H), 7.45-7.54 (m, 2H), 7.69 (t, 1H), 7.72 (d, 1H), 8.54 (t, 1H).

Example 146A

Methyl[3-bromo-4-(3-fluorobenzyl)-5-oxo-4,5-dihydro-1H-1,2,4-triazol-1-yl]-acetate

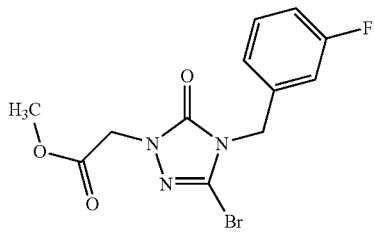

1.50 g (4.69 mmol) of the compound from Example 137A are stirred under reflux for 4 hrs together with 508 mg (4.69 mmol) of methyl chloroacetate and 1.30 g (9.4 mmol) of potassium carbonate in 33 ml acetonitrile. After cooling, the mixture is neutralized with 1 N hydrochloric acid and diluted with ethyl acetate. The organic phase is separated, washed with saturated sodium chloride solution, dried over sodium sulphate and freed of the volatile components on the rotary evaporator. The residue is dissolved in 20 ml dichloromethane and absorbed onto 3 g of diatomaceous earth. After removal of the solvent on the rotary evaporator the solid is transferred to a silica gel chromatography column and the product purified by elution with cyclohexane/ethyl acetate (gradient 5:1→1:1). 1.36 g (84% of theory) of the title compound are obtained.

LC/MS [Method 8]: $R_t$=2.07 min; m/z=344 (M+H)$^+$
$^1$H-NMR (400 MHz, DMSO-d$_6$): δ=3.70 (s, 3H), 4.69 (s, 2H), 4.90 (s, 2H), 7.08 (br. d, 2H), 7.17 (br. t, 1H), 7.45 (q, 1H).

Example 147A

Methyl[3-(4-chloro-2-methoxyphenyl)-4-(3-fluorobenzyl)-5-oxo-4,5-dihydro-1H-1,2,4-triazol-1-yl]-acetate

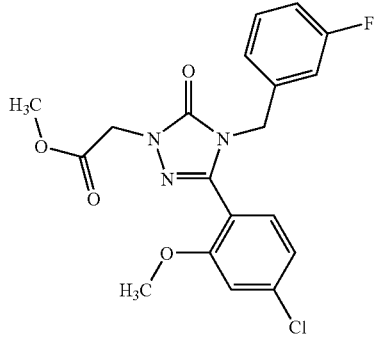

Under argon, 250 mg (0.73 mmol) of the compound from Example 146A and 190 mg (1.07 mmol) of 4-chloro-2-methoxyphenylboronic acid are dissolved in 7 ml degassed DMF. A previously degassed solution of sodium carbonate (2 N in water, 1.09 ml, 2.18 mmol) and 42 mg of tetrakis(triphenylphosphine)palladium (0.036 mmol) are added. The resulting mixture is heated and stirred for 8 hrs at 90° C. After cooling to RT it is acidified with 10% hydrochloric acid and the mixture filtered. The filtrate is purified by preparative HPLC (Method 20). 159 mg (54% of theory) of the title compound and 54 mg (18% of theory) of the corresponding acid formed by hydrolysis (see also Example 148A) are obtained.

LC/MS [Method 17]: $R_t$=3.54 min; m/z=406 (M+H)$^+$
$^1$H-NMR (400 MHz, DMSO-d$_6$): δ=3.69 (s, 3H), 3.72 (s, 3H), 4.72 (s, 4H), 6.78 (br. d, 1H), 6.82 (d, 1H), 7.05 (dt, 1H), 7.07 (dd, 1H), 7.23 (d, 1H), 7.25 (d, 1H), 7.31 (dt, 1H).

Example 148A

[3-(4-chloro-2-methoxyphenyl)-4-(3-fluorobenzyl)-5-oxo-4,5-dihydro-1H-1,2,4-triazol-1-yl]-acetic acid

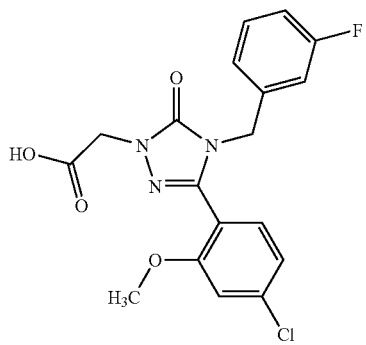

159 mg (0.39 mmol) of the compound from Example 147A in 4 ml methanol are treated with 1.57 ml of a 1 N solution of lithium hydroxide in water (1.57 mmol) and the resulting mixture is stirred overnight at RT. The methanol is removed on the rotary evaporator, the residue diluted with water and the resulting aqueous phase extracted twice with dichloromethane. These organic phases are discarded. The aqueous phase is then acidified with 1 N hydrochloric acid and extracted three times with dichloromethane. The extracts are combined, dried over magnesium sulphate, freed of solvent on the rotary evaporator and the residue dried under high vacuum. 144 mg (94% of theory) of the title compound are obtained.

LC/MS [Method 17]: $R_t$=3.20 min; m/z=392 (M+H)$^+$
$^1$H-NMR (400 MHz, DMSO-$d_6$): δ=3.69 (s, 3H), 4.57 (s, 2H), 4.71 (s, 2H), 6.76-6.84 (m, 2H), 7.05 (dt, 1H), 7.07 (dd, 1H), 7.23 (d, 1H), 7.24 (d, 1H), 7.29 (dt, 1H), 13.2 (br. s, 1H).

Example 149A

Methyl[4-(3-fluorobenzyl)-3-(2-hydroxyphenyl)-5-oxo-4,5-dihydro-1H-1,2,4-triazol-1-yl]-acetate

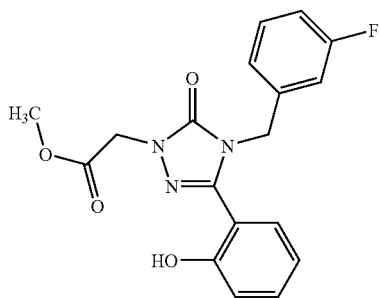

By the method described for Example 147A, starting from 250 mg (0.73 mmol) of the compound from Example 146A and 138 mg of (1.02 mmol) 2-hydroxyphenylboronic acid, 22 mg (8% of theory) of the title compound and 222 mg (85% of theory) of the corresponding acid formed by hydrolysis (see also Example 150A) are obtained.

LC/MS [Method 17]: $R_t$=2.94 min; m/z=358 (M+H)$^+$
$^1$H-NMR (400 MHz, DMSO-$d_6$): δ=3.72 (s, 3H), 4.70 (s, 2H), 4.82 (s, 2H), 6.73 (br. d, 1H), 6.79 (d, 1H), 6.83 (t, 1H), 6.98 (d, 1H), 7.03 (dt, 1H), 7.12 (dd, 1H), 7.28 (dt, 1H), 7.35 (ddd, 1H), 10.04 (s, 1H).

Example 150A

[4-(3-fluorobenzyl)-3-(2-hydroxyphenyl)-5-oxo-4,5-dihydro-1H-1,2,4-triazol-1-yl]-acetic acid

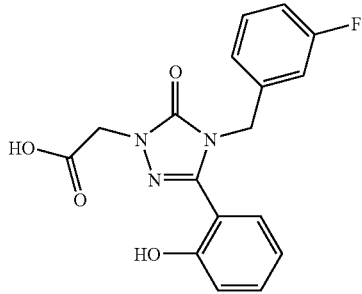

The title compound is either obtained directly as a side-component in the synthesis of Example 149A or can be produced by hydrolysis of the methyl ester from Example 149A by the same method as described in Example 148A.

LC/MS [Method 17]: $R_t$=3.20 min; m/z=392 (M+H)$^+$
$^1$H-NMR (400 MHz, DMSO-$d_6$): δ=4.55 (s, 2H), 4.82 (s, 2H), 6.75 (br. d, 1H), 6.79 (d, 1H), 6.83 (t, 1H), 6.98 (d, 1H), 7.02 (dt, 1H), 7.12 (dd, 1H), 7.26 (dt, 1H), 7.35 (ddd, 1H), 10.04 (s, 1H), 13.2 (br. s, 1H).

Example 151A

N-(2-fluorobenzyl)-2-(5-chlorthiophen-2-carbonyl)-hydrazinecarboxamide

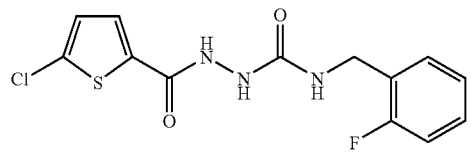

3.53 g (20 mmol) of 5-chloro-2-thiophenecarboxylic acid hydrazide are dissolved with heating in 100 ml THF and the solution then again cooled to RT. 3.08 g (20.4 mmol) of 2-fluorobenzyl isocyanate are rapidly added dropwise, during which a thick suspension forms. This is further stirred overnight at RT and then diluted with 100 ml diethyl ether. The precipitate is isolated by filtration, washed with diethyl ether and dried under high vacuum. 6.3 g of a solid (96% of theory), which is further reacted without additional purification, are obtained.

MS [DCI/NH$_3$]: m/z=328 (M+H)$^+$, 345 (M+NH$_4$)$^+$
$^1$H-NMR (400 MHz, DMSO-$d_6$): δ=4.27 (d, 2H), 7.12 (br. s, 1H), 7.12-7.19 (m, 2H), 7.23 (d, 1H), 7.25-7.31 (m, 1H), 7.35 (t, 1H), 7.70 (d, 1H), 8.12 (s, 1H).

Example 152A 5-(5-chlorothiophen-2-yl)-4-(2-fluorobenzyl)-2,4-dihydro-3H-1,2,4-triazol-3-one

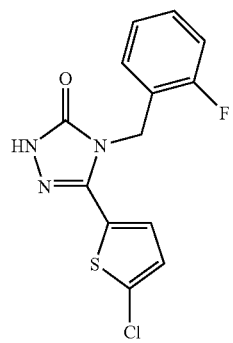

6.3 g (19.2 mmol) of the compound from Example 151A are heated overnight under reflux in 38.4 ml of 4 N aqueous sodium hydroxide. After cooling to RT, the mixture is diluted with water and adjusted to pH 10 by addition of 1 N hydrochloric acid. The product is extracted several times with ethyl acetate. The combined organic phases are washed with water to a neutral pH value, then washed with saturated sodium chloride solution and dried over sodium sulphate. After filtration, the solvent is removed on the rotary evaporator. 4.07 g (68% of theory) of the title compound are obtained.

MS [DCI/NH$_3$]: m/z=310 (M+H)$^+$, 327 (M+NH$_4$)$^+$
$^1$H-NMR (400 MHz, DMSO-d$_6$): δ=5.08 (s, 2H), 7.03 (t, 1H), 7.13-7.26 (m, 4H), 7.31-7.38 (m, 1H), 12.25 (br. s, 1H).

Example 153A

Methyl[3-(5-chlorothiophen-2-yl)-4-(2-fluorobenzyl)-5-oxo-4,5-dihydro-1H-1,2,4-triazol-1-yl]-acetate

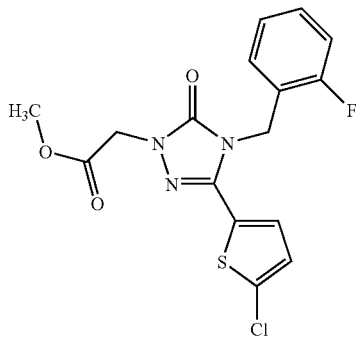

2.39 g (7.71 mmol) of the compound from Example 152A together with 1.05 g of methyl chloroacetate (9.6 mmol) and 1.17 g of potassium carbonate (8.5 mmol) in 79 ml acetonitrile are heated overnight under reflux. After cooling to RT, the mixture is diluted with ethyl acetate. The resulting organic phase is washed with 1 N hydrochloric acid, then with sat. sodium chloride solution, dried over sodium sulphate and freed of solvent on the rotary evaporator. The product is dried under high vacuum. 2.9 g (92% of theory) of the title compound are obtained.

LC/MS [Method 7]: R$_t$=2.30 min; m/z=382 (M+H)$^+$
$^1$H-NMR (400 MHz, DMSO-d$_6$): δ=3.71 (s, 3H), 4.75 (s, 2H), 5.15 (s, 2H), 7.02 (t, 1H), 7.13-7.28 (m, 4H), 7.32-7.39 (m, 1H).

Example 154A

[3-(5-chlorothiophen-2-yl)-4-(2-fluorobenzyl)-5-oxo-4,5-dihydro-1H-1,2,4-triazol-1-yl]-acetic acid

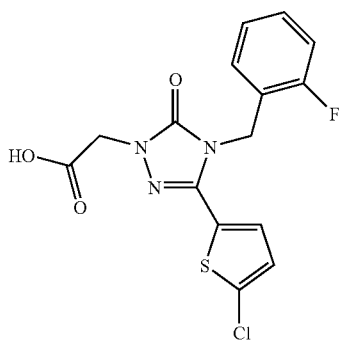

2.90 g (7.60 mmol) of the ester from Example 153A are dissolved in 77 ml methanol and treated with a 1 N solution of lithium hydroxide in water (30.3 ml, 30.4 mmol). The mixture is stirred overnight at RT, then freed of methanol on the rotary evaporator and diluted with 200 ml water. After addition of 1 N hydrochloric acid to a pH value of 2, the product precipitates out as a white solid, which is isolated by filtration and drying in high vacuum. 2.45 g (88% of theory) of the title compound are obtained.

LC/MS [Method 7]: R$_t$=1.93 min; m/z=368 (M+H)$^+$
$^1$H-NMR (400 MHz, DMSO-d$_6$): δ=4.60 (s, 2H), 5.13 (s, 2H), 7.03 (t, 1H), 7.12-7.28 (m, 4H), 7.32-7.38 (m, 1H), 13.23 (br. s, 1H).

Example 155A

Methyl[3-(4-chlorophenyl)-4-(2-fluorobenzyl)-5-oxo-4,5-dihydro-1H-1,2,4-triazol-1-yl]-acetate

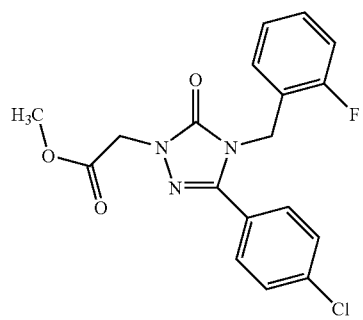

The title compound is obtained by the same method as described for Example 153A, starting from the compound from Example 40A and methyl chloroacetate.

LC/MS [Method 8]: R$_t$=2.45 min; m/z=375 (M+H)$^+$
$^1$H-NMR (400 MHz, DMSO-d$_6$): δ=3.71 (s, 3H), 4.75 (s, 2H), 5.05 (s, 2H), 7.03 (t, 1H), 7.11 (t, 1H), 7.16 (d, 1H), 7.50-7.60 (m, 4H).

Example 156A

[3-(4-chlorophenyl)-4-(2-fluorobenzyl)-5-oxo-4,5-dihydro-1H-1,2,4-triazol-1-yl]-acetic acid

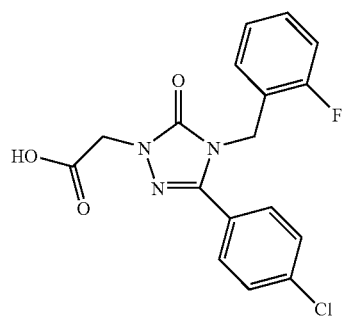

Analogously to Example 154A, the title compound is prepared by hydrolysis of the ester from Example 155A. By LC/MS and NMR, the purity is ca. 86%.

LC/MS [Method 17]: $R_t$=3.17 min; m/z=361 (M+H)$^+$
$^1$H-NMR (400 MHz, DMSO-d$_6$): δ=4.60 (s, 2H), 5.04 (s, 2H), 7.03 (t, 1H), 7.06-7.17 (m, 2H), 7.27-7.32 (m, 1H), 7.52-7.58 (m, 4H), 13.18 (br. s, 1H).

Example 157A

[5-chloro-2-(trifluoromethyl)phenyl]methylamine hydrochloride

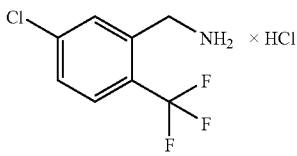

29.2 ml of borane-THF complex (29.2 mmol) are slowly added dropwise under argon to an ice-cooled solution of 5-chloro-2-(trifluoromethyl)benzonitrile (1.50 g, 7.3 mmol) in 45 ml of anhydrous THF. After the end of the addition, the mixture is heated under reflux for 1 hr, then stirred overnight at RT with cooling. 30 ml of 1 N hydrochloric acid are then added dropwise with ice-cooling. The THF is removed on the rotary evaporator. The precipitated solid is filtered off and discarded. The filtrate is diluted with water and extracted twice with dichloromethane. These organic phases are also discarded. The acidic aqueous phase is adjusted to pH 14 with 1 N aqueous sodium hydroxide and extracted three times with dichloromethane. The combined organic phases are dried over sodium sulphate and freed of solvent on the rotary evaporator. The residue is taken up in 20 ml diethyl ether and treated with 3 ml of a 4 N solution of hydrogen chloride in dioxan, during which the product precipitates. The solvent is completely removed on the rotary evaporator, then in high vacuum. 1.89 g (99% of theory) of the title compound are isolated.

LC/MS [Method 17]: $R_t$=1.02 min; m/z=210 (M+H)$^+$
$^1$H-NMR (400 MHz, DMSO-d$_6$): δ=4.17 (s, 2H), 7.85 (d, 1H), 7.89 (s, 1H), 7.92 (d, 1H), 8.70 (br. s, 3H).

Analogously to Example 157A, the following amines are obtained (as hydrochloride) from the corresponding nitriles by borane reduction:

| Example No. | Structure | Analytical Data |
| --- | --- | --- |
| 158A | 2,6-bis(trifluoromethyl)benzylamine · HCl | LC/MS [Method 17]: $R_t$ = 0.69 min; m/z = 210 (M + H)$^+$ <br> $^1$H-NMR (400 MHz, DMSO-d$_6$): δ = 4.24 (s, 2H), 7.92 (t, 1H), 8.20 (d, 2H), 8.51 (br. s, 3H). |
| 159A | 2-fluoro-6-(trifluoromethyl)benzylamine · HCl | LC/MS [Method 3]: $R_t$ = 1.77 min; m/z = 194 (M + H)$^+$ <br> $^1$H-NMR (400 MHz, DMSO-d$_6$): δ = 4.16 (s, 2H), 7.67-7.82 (m, 3H), 8.51 (br. s, 3H). |
| 160A | 3-fluoro-2-(trifluoromethyl)benzylamine · HCl | LC/MS [Method 3]: $R_t$ = 1.89 min; m/z = 194 (M + H)$^+$ <br> $^1$H-NMR (400 MHZ, DMSO-d$_6$): δ = 4.21 (s, 2H), 7.51-7.58 (m, 2H), 7.80-7.86 (m, 1H), 8.51 (br. s, 3H). |
| 161A | 2,3-bis(trifluoromethyl)benzylamine · HCl | HPLC [Method 2]: $R_t$ = 3.60 min; MS (DCI/NH$_3$): m/z = 244 (M + H)$^+$, 261 (M + NH$_4$)$^+$ <br> $^1$H-NMR (400 MHz, DMSO-d$_6$): δ = 4.24 (s, 2H), 7.92 (t, 1H), 8.20 (d, 2H), 8.51 (br. s, 3H). |

Example 162A

1-[2-(trifluoromethyl)benzyl]cyclopropanamine hydrochloride

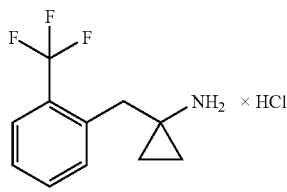

Under argon, 4.68 ml (14.0 mmol) of a 3 M solution of ethylmagnesium bromide in diethyl ether are added slowly dropwise at RT to a solution of 1.3 g of 2-(trifluoromethyl) phenylacetonitrile (7.2 mmol) and 2.20 g (7.7 mmol) of titanium(IV) isopropylate in 50 ml diethyl ether. This is stirred for 1 hr at RT, then treated with 1.78 ml of boron trifluoride-diethyl ether complex and stirred for a further 30 mins at RT. For the workup, 50 ml of 2 M aqueous sodium hydroxide are added and the mixture extracted three times with diethyl ether. The combined organic phases are extracted twice with 70 ml 1 N hydrochloric acid each time. The combined aqueous phases are then adjusted to pH 14 with 2 N aqueous sodium hydroxide and extracted three times with dichloromethane. These combined organic phases are dried over sodium sulphate and concentrated on the rotary evaporator to a volume of ca. 30 ml. This is treated with 4 ml of a 4 N solution of hydrogen chloride in dioxan. The precipitated solid is filtered off at the pump and dried under high vacuum. 670 mg (38% of theory) of the title compound are obtained.

LC/MS [Method 17]: $R_t$=1.02 min; m/z=210 (M+H)$^+$ $^1$H-NMR (400 MHz, DMSO-d$_6$): δ=0.64 (m, 2H), 1.01 (m, 2H), 3.27 (s, 2H), 7.50 (t, 1H), 7.61 (d, 2H), 7.68 (t, 1H), 7.72 (d, 1H), 8.50 (br. s, 3H).

Example 163A 2-methyl-2-[3-(trifluoromethyl)phenyl]-propanonitrile

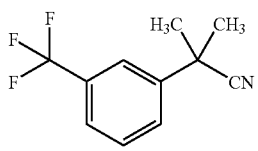

500 mg (2.7 mmol) of 3-(trifluoromethyl)phenylacetonitrile in 6 ml anhydrous diethyl ether are treated with 316 mg (8.1 mmol) of sodamide under argon with gentle cooling. Next the mixture is cooled to 0° C. and treated with 1.53 g (10.8 mmol) of iodomethane. After 30 mins, the ice-bath is removed and the reaction mixture further stirred overnight at RT. After this, 2 ml of a sat. ammonium chloride solution are added. The mixture is diluted with diethyl ether and washed twice with water. The organic phase is dried over magnesium sulphate and freed of solvent on the rotary evaporator. The residue (reddish liquid) corresponds to the pure title compound (545 mg, 95% of theory).

$^1$H-NMR (400 MHz, DMSO-d$_6$): δ=1.76 (s, 6H), 7.70 (t, 1H), 7.75 (d, 1H), 7.82 (s, 1H), 7.88 (d, 1H).

Example 164A 2-methyl-2-[3-(trifluoromethyl)phenyl]propanamine hydrochloride

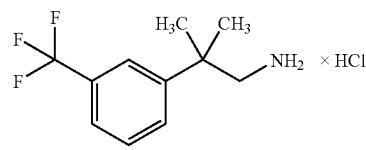

The title compound is obtained analogously to Example 157A by borane reduction of the nitrile from Example 163A.

LC/MS [Method 3]: $R_t$=2.59 min; m/z=218 (M+H)$^+$ $^1$H-NMR (400 MHz, DMSO-d$_6$): δ=1.49 (s, 6H), 3.11 (s, 2H), 7.59-7.68 (m, 2H), 7.71 (s, 1H), 7.76 (d, 1H), 7.78 (br. s, 3H).

Example 165A 2-methyl-2-[2-(trifluoromethyl)phenyl]-propanonitrile

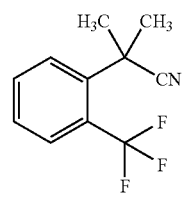

A solution of 2.0 g (10.8 mmol) of 2-(trifluoromethyl) phenylacetonitrile and 6.13 g (43 mmol) of iodomethane in 16 ml DMSO is slowly treated with 3.16 ml of 50% aqueous sodium hydroxide, so that the reaction temperature is kept between 40° C. and 45° C. After the addition is complete, the mixture is stirred overnight at RT. It is diluted with water and extracted three times with dichloromethane. The combined organic phases are washed with water, dried over sodium sulphate and freed of solvent on the rotary evaporator. The residue corresponds to the title compound (2.30 g, 100% of theory).

$^1$H-NMR (400 MHz, DMSO-d$_6$): δ=1.80 (s, 6H), 7.63 (t, 1H), 7.72-7.82 (m, 2H), 7.85 (d, 1H).

Example 166A 2-methyl-2-[2-(trifluoromethyl)phenyl]propanamine hydrochloride

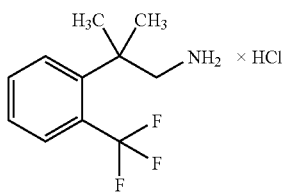

The title compound is obtained analogously to Example 157A by borane reduction of the nitrile from Example 165A.

LC/MS [Method 8]: $R_t$=1.10 min; m/z=218 (M+H)$^+$ $^1$H-NMR (400 MHz, DMSO-d$_6$): δ=1.50 (s, 6H), 3.15 (s, 2H), 7.53 (t, 1H), 7.65-7.74 (m, 2H), 7.85 (d, 1H), 7.90 (br. s, 3H).

Example 167A

2-[3-(trifluoromethyl)phenyl]propanonitrile

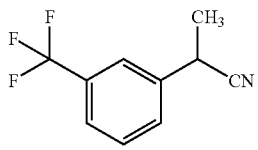

1.0 g (5.4 mmol) of 3-(trifluoromethyl)phenylacetonitrile and 767 mg of iodomethane (5.4 mmol) are placed in 5 ml toluene at 80° C. and slowly treated with a 50% suspension of sodamide in toluene. Next the mixture is stirred 1 hr more at 80° C., then cooled to RT and treated with water, then dichloromethane. The organic phase is separated, washed with water, dried over magnesium sulphate and freed of solvent on the rotary evaporator. The residue (1.7 g, 84% of theory) contains the title compound with a purity of ca. 53% by GC/MS and is used without purification for the next reaction.

GC/MS [Method 21]: $R_t$=3.42 min; m/z=199 (M)$^+$.

Example 168A

2-[3-(trifluoromethyl)phenyl]propanamine hydrochloride

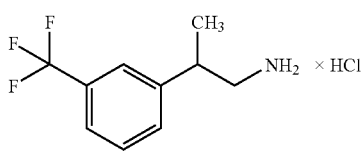

The title compound is obtained analogously to Example 157A by borane reduction of the nitrile from Example 167A (crude product) (yield 31% of theory).

LC/MS [Method 3]: $R_t$=2.52 min; m/z=204 (M+H)$^+$ $^1$H-NMR (400 MHz, DMSO-d$_6$): δ=1.29 (d, 3H), 3.00-3.11 (m, 2H), 3.13-3.25 (m, 1H), 7.55-7.69 (m, 4H), 7.98 (br. s, 3H).

Example 169A 2-amino-1-[2-(trifluoromethyl)phenyl]ethanone hydrochloride

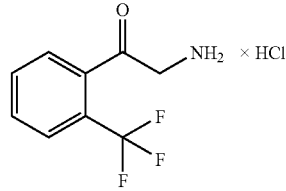

A solution of 1.0 g (3.75 mmol) of 2-bromo-1-[(2-trifluoromethyl)phenyl]ethanone in 4 ml of acetonitrile is treated at RT with 413 mg (4.34 mmol) of sodium diformylamide and stirred for 2.5 hrs. Next, the suspension is heated to 70° C. and filtered hot. The solid is washed with 2 ml of hot acetonitrile. The combined filtrates are freed of solvent on the rotary evaporator. According to LC/MS [Method 8; $R_t$=2.00 min; m/z=260 (M+H)$^+$], the dark oily residue corresponds to the diformyl intermediate stage. This residue is treated with 10 ml of a 5% ethanolic hydrogen chloride solution and stirred at RT for two days. The volatile components are removed on the rotary evaporator. The yellow solid obtained is stirred for 10 mins under reflux in 20 ml diethyl ether and the suspension is then cooled to RT. The white solid is filtered off at the pump, washed with diethyl ether and dried under high vacuum. 570 mg (64% of theory) of the title compound are obtained.

HPLC [Method 2]: $R_t$=3.19 min;

MS (DCI/NH$_3$): m/z=204 (M+H)$^+$, 221 (M+NH$_4$)$^+$ $^1$H-NMR (400 MHz, DMSO-d$_6$): δ=4.53 (s, 2H), 7.80-7.90 (m, 2H), 7.95 (d, 1H), 8.03 (d, 1H), 8.49 (br. s, 3H).

Example 170A

[2-chloro-3-(trifluoromethyl)phenyl]-methylammonium trifluoroacetate

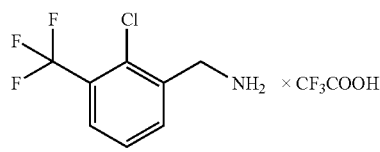

1.75 g of Rink-Amid® (0.96 mmol) is activated (FMOC cleavage) by stirring with 10 ml of a 25% solution of piperidine in DMF for 30 mins, then filtration of the resin and renewed treatment with 10 ml of a 25% solution of piperidine in DMF for 30 mins. The polymer is filtered off at the pump, washed successively three times each with DMF, methanol and dichloromethane and then allowed to swell in 10 ml of trimethyl orthoformate (TMOF). 400 mg (1.9 mmol) of 2-chloro-3-(trifluoromethyl)benzaldehyde are added and the suspension stirred for 5 hrs. The polymer is then filtered off, washed successively three times each with DMF, methanol and dichloromethane and dried on the rotary evaporator. The polymer is again allowed to preswell in 10 ml TMOF, then 987 mg (3.84 mmol) tetrabutylammonium borohydride are added and, slowly, 878 µl (15 mmol) of acetic acid. The suspension is stirred overnight at RT. The polymer is filtered off at the pump and washed successively five times each with DMF, methanol and dichloromethane. Next it is stirred with 20 ml trifluoroacetic acid/dichloromethane (1:1). After 1 hr, the polymer is filtered off at the pump and washed with dichloromethane. The filtrate is freed of the volatile components on the rotary evaporator and the residue briefly dried under high vacuum. 170 mg (27% of theory) of the title compound in acceptable purity (>50%), which is further used in this form, are obtained.

LC/MS [Method 3]: $R_t$=2.30 min; m/z=210 (M+H)$^+$ $^1$H-NMR (400 MHz, DMSO-d$_6$): δ=4.25 (q, 2H), 7.69 (t, 1H), 7.88 (d, 1H), 7.85 (d, 1H), 8.32 (br. s, 3H).

Example 171A

[2-methyl-3-(trifluoromethyl)phenyl]-methylammonium trifluoroacetate

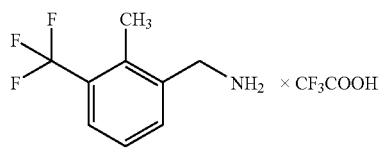

The title compound is produced from 2-methyl-3-(trifluoromethyl)benzaldehyde by the same method as described for Example 170A (yield: 49% of theory).

LC/MS [Method 3]: $R_t$=2.36 min; m/z=190 (M+H)$^+$ $^1$H-NMR (400 MHz, DMSO-d$_6$): δ=2.44 (s, 3H), 4.17 (q, 2H), 7.49 (t, 1H), 7.68 (d, 1H), 7.72 (d, 1H), 8.22 (br. s, 3H).

Example 172A

[2-(trifluoromethyl)phenyl]-glycine methyl ester hydrochloride

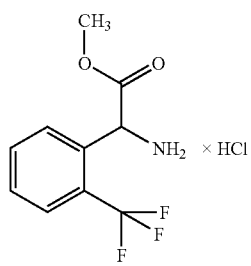

300 mg (1.37 mmol) of DL-[2-(trifluoromethyl)phenyl]-glycine are placed in 9 ml methanol and slowly treated at RT with 130 µl thionyl chloride. The solution is heated overnight under reflux, then cooled to RT and freed of the volatile components on the rotary evaporator. Since by LC/MS the residue still contains ca. 44% educt, it is reacted again under the conditions described above. After this, the conversion is complete. 371 mg (93% of theory) of the title compound are obtained.

LC/MS [Method 3]: $R_t$=2.14 min; m/z=233 (M+H)$^+$ $^1$H-NMR (400 MHz, DMSO-d$_6$): δ=3.72 (s, 3H), 5.27 (s, 1H), 7.66-7.78 (m, 2H), 7.84 (t, 1H), 7.89 (d, 1H), 9.21 (br. s, 3H).

Example 173A

N-tert.-butoxycarbonyl-[3-(trifluoromethyl)phenyl]-glycine

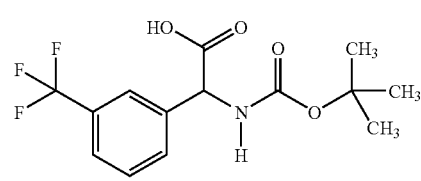

226 mg (1.03 mmol) of DL-[3-(trifluoromethyl)phenyl]-glycine are dissolved in 10 ml of an aqueous 5% sodium hydrogen carbonate solution and treated with 4 ml dioxan. 261 µl (1.13 mmol) of tert.-butyl dicarbonate are added and the mixture stirred overnight at RT. For the workup, the solution is carefully acidified to pH 2 with 1 N hydrochloric acid. The precipitated product is redissolved by addition of acetonitrile, and purified by preparative HPLC (Method 20). 135 mg (41% of theory) of the title compound are obtained.

LC/MS [Method 8]: $R_t$=2.53 min; m/z=319 (M+H)$^+$ $^1$H-NMR (400 MHz, DMSO-d$_6$): δ=1.39 (s, 9H), 5.28 (d, 1H), 7.59 (t, 1H), 7.68 (d, 1H), 7.72 (d, 1H), 7.79 (s, 1H), 7.80 (d, 1H), 12.99 (br. s, 1H).

Example 174A tert.-butyl {2-(dimethylamino)-2-oxo-1-[3-(trifluoromethyl)phenyl]ethyl}carbamate

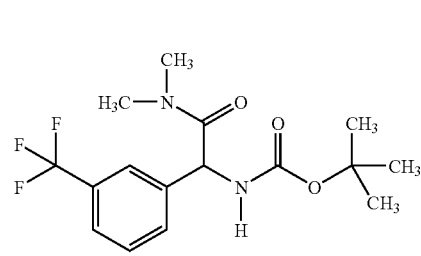

125 mg (392 µmol) of the compound from Example 173A and 95 mg of HOBt (705 µmol) are placed in 8 ml DMF and treated at RT with 135 mg (705 µmol) of EDC. After 20 mins, a 2 M solution of dimethylamine in THF (294 µl, 587 µmol) is added and the mixture stirred overnight at RT. After addition of 1 ml of 1 N hydrochloric acid, the mixture is separated directly by preparative HPLC (Method 20). 90 mg (64% of theory) of the title compound are obtained.

LC/MS [Method 17]: $R_t$=3.55 min; m/z=347 (M+H)$^+$.

Example 175A 2-dimethylamino-2-oxo-1-[3-(trifluoromethyl)phenyl]ethane hydrochloride

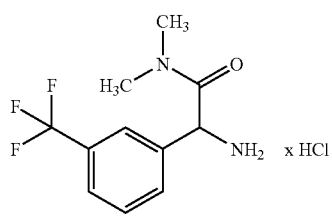

130 mg (375 μmol) of the compound from Example 174A are stirred at RT in 2 ml of a 4 M solution of hydrogen chloride in dioxan. After complete conversion, the volatile components are removed on the rotary evaporator and the residue dried under high vacuum. 105 mg (99% of theory) of the title compound are obtained.

LC/MS [Method 3]: $R_t$=2.42 min; m/z=247 (M+H)$^+$ $^1$H-NMR (400 MHz, DMSO-d$_6$): δ=5.70 (s, 1H), 7.72 (t, 1H), 7.80 (d, 1H), 7.83 (d, 1H), 7.95 (s, 1H), 8.75 (br. s, 3H).

Alternatively the cleavage of the tert.-butoxycarbonyl protective group can be effected by treatment of the compound from Example 174A with excess trifluoroacetic acid in dichloro-methane. After removal of the volatile components on the rotary evaporator, the product is obtained as the trifluoroacetate salt.

Example 176A

N-tert.-butoxycarbonyl-[2-(trifluoromethyl)phenyl]-glycine

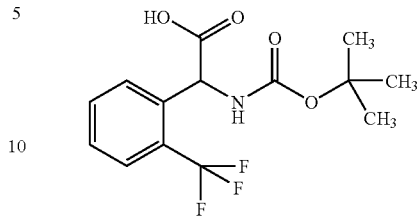

1.0 g (4.56 mmol) of DL-[2-(trifluoromethyl)phenyl]-glycine are dissolved in 30 ml of an aqueous 5% sodium hydrogen carbonate solution and treated with 4 ml dioxan. 1.15 ml (5.02 mmol) of di-tert.-butyl dicarbonate are added and the mixture is stirred overnight at RT. For the workup, the reaction mixture is poured into 100 ml of 1 N hydrochloric acid and extracted three times with dichloromethane. The combined organic phases are dried over sodium sulphate and freed of the volatile components on the rotary evaporator. The residue is dried under high vacuum. 1.26 g (86% of theory) of the title compound are obtained.

MS [DCI/NH$_3$]: m/z=337 (M+NH$_4$)$^+$ $^1$H-NMR (400 MHz, DMSO-d$_6$): δ=1.35 (s, 9H), 5.49 (d, 1H), 7.55 (t, 1H), 7.61 (d, 1H), 7.69 (t, 1H), 7.72 (d, 1H), 7.82 (d, 1H), 12.99 (br. s, 1H).

By the same amidation/Boc cleavage reaction sequence as described in Examples 174A and 175A, the following compounds are produced from Example 173A or Example 176A and the corresponding amines (here methylamine is used as a solution in ethanol; ammonia is used as a 33% solution in water):

| Example No. | Structure | Educt | Analytical Data |
|---|---|---|---|
| 177A | ![structure with morpholine amide, CF3, NH2, x CF3COOH] | 173A | LC/MS [Method 17]: $R_t$ = 1.12 min; m/z = 289 (M + H)$^+$. |
| 178A | ![structure with pyrrolidine amide, CF3, NH2, x CF3COOH] | 173A | LC/MS [Method 17]: $R_t$ = 1.44 min; m/z = 273 (M + H)$^+$. |
| 179A | ![structure with N-methyl amide, CF3, NH2, x CF3COOH] | 173A | LC/MS [Method 17]: $R_t$ = 0.81 min; m/z = 233 (M + H)$^+$. |

-continued

| Example No. | Structure | Educt | Analytical Data |
|---|---|---|---|
| 180A | (3-trifluoromethylphenyl)-CH(NH₂)-C(O)-N(azetidine) x CF₃COOH | 173A | LC/MS [Method 17]: R_t = 1.19 min; m/z = 259 (M + H)⁺. |
| 181A | (3-trifluoromethylphenyl)-CH(NH₂)-C(O)-NH-cyclopropyl x CF₃COOH | 173A | LC/MS [Method 17]: R_t = 1.25 min; m/z = 259 (M + H)⁺. |
| 182A | (2-trifluoromethylphenyl)-CH(NH₂)-C(O)-N(pyrrolidine) x CF₃COOH | 176A | LC/MS [Method 3]: R_t = 2.34 min; m/z = 273 (M + H)⁺. |
| 183A | (2-trifluoromethylphenyl)-CH(NH₂)-C(O)-NH-cyclopropyl x CF₃COOH | 176A | LC/MS [Method 3]: R_t = 2.14 min; m/z = 259 (M + H)⁺. |
| 184A | (3-trifluoromethylphenyl)-CH(NH₂)-C(O)-NH₂ x CF₃COOH | 173A | LC/MS [Method 3]: R_t = 1.65 min; m/z = 219 (M + H)⁺. |
| 185A | (2-trifluoromethylphenyl)-CH(NH₂)-C(O)-NH₂ x CF₃COOH | 176A | LC/MS [Method 3]: R_t = 0.95 min; m/z = 219 (M + H)⁺. |
| 186A | (2-trifluoromethylphenyl)-CH(NH₂)-C(O)-N(azetidine) x CF₃COOH | 176A | LC/MS [Method 3]: R_t = 2.20 min; m/z = 259 (M + H)⁺. |

Example 187A 2-(2,3-dichlorobenzyl)-2-methylpropanonitrile

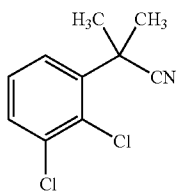

From 1.00 g of 2,3-dichlorophenylacetonitrile (5.37 mmol), 1.10 g of the title compound (96% of theory) are obtained by the method described in Example 165A.

GC/MS [Method 21]: $R_t$=5.56 min; m/z=213 (M)$^+$ $^1$H-NMR (400 MHz, DMSO-$d_6$): δ=1.81 (s, 6H), 7.46 (t, 1H), 7.55 (dd, 1H), 7.72 (dd, 1H).

Example 188A 2-(2,6-dichlorobenzyl)-2-methylpropanonitrile

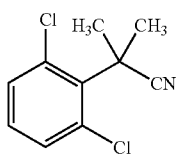

From 500 mg of 2,6-dichlorophenylacetonitrile (2.69 mmol), 262 mg of the title compound (46% of theory) and 135 mg (25% of theory) of the monomethylated derivative (see Example 189A) are obtained by the method described in Example 165A.

GC/MS [Method 21]: $R_t$=5.71 min; m/z=213 (M)$^+$ $^1$H-NMR (400 MHz, DMSO-$d_6$): δ=2.01 (s, 6H), 7.49 (t, 1H), 7.54 (d, 2H).

Example 189A 2-(2,3-dichlorobenzyl)propanonitrile

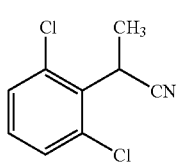

The title compound is obtained as a side-product in the preparation of Example 188A.

GC/MS [Method 21]: $R_t$=5.28 min; m/z=199 (M)$^+$ $^1$H-NMR (400 MHz, DMSO-$d_6$): δ=1.60 (d, 3H), 4.97 (q, 1H), 7.42 (t, 1H), 7.56 (d, 2H).

Example 190A

2-[2,3-dichlorophenyl]-2-methylpropanamine hydrochloride

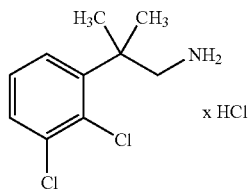

The title compound is obtained analogously to Example 157A by borane reduction of the nitrile from Example 187A.

LC/MS [Method 17]: $R_t$=1.71 min; m/z=218 (M+H)$^+$ $^1$H-NMR (400 MHz, DMSO-$d_6$): δ=1.51 (s, 6H), 3.40 (s, 2H), 7.38 (t, 1H), 7.42 (d, 1H), 7.63 (d, 1H), 7.80 (br. s, 3H).

Example 191A

2-[2,6-dichlorophenyl]-2-methylpropanamine hydrochloride

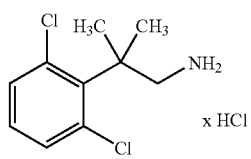

The title compound is obtained analogously to Example 157A by borane reduction of the nitrile from Example 188A.

LC/MS [Method 3]: $R_t$=2.48 min; m/z=218 (M+H)$^+$ $^1$H-NMR (400 MHz, DMSO-$d_6$): δ=1.72 (s, 6H), 3.50 (s, 2H), 7.29 (t, 1H), 7.47 (d, 2H), 8.00 (br. s, 3H).

Example 192A 2-(2,6-dichlorophenyl)-propanamine hydrochloride

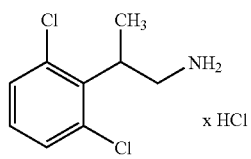

The title compound is obtained analogously to Example 157A by borane reduction of the nitrile from Example 189A.

LC/MS [Method 3]: $R_t$=2.39 min; m/z=204 (M+H)$^+$

¹H-NMR (400 MHz, DMSO-d₆): δ=1.40 (d, 3H), 3.25 (dd, 1H), 3.35 (dd, 1H), 3.93 (m, 1H), 7.32 (t, 1H), 7.45 (d, 1H), 7.51 (d, 1H), 8.07 (br. s, 3H).

Example 193A

Ethyl 3-{[(benzyloxy)carbonyl]amino}-2-[2-(trifluoromethyl)phenyl]propanoate

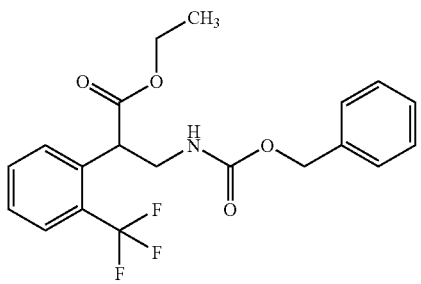

An LDA solution is prepared under argon by slow dropwise addition of an n-butyllithium solution (1.6 M in hexane, 2.6 ml, 4.13 mmol) to a solution of 591 µl of diisopropylamine (4.21 mmol) in 3 ml anhydrous THF at −15° C. and stirring for 10 mins at 0° C. This LDA solution is cooled to −70° C. and slowly treated with a solution of 500 mg of ethyl 2-(trifluoromethyl)phenylacetate (2.15 mmol) and N-methoxymethylbenzyl carbamate (350 mg, 1.79 mmol) in 3 ml THF. After 15 mins at −70° C., 1.17 ml (3.95 mmol) of titanium(IV) isopropylate are added. The mixture is stirred for 1 hr more at this temperature, then overnight at −60° C. Next it is allowed to warm to 0° C. within one hour and stirred for one hour more at this temperature. The mixture is treated with 20 ml of 1 N hydrochloric acid and extracted three times with dichloromethane. The combined organic phases are dried over magnesium sulphate and freed of the volatile components on the rotary evaporator. The residue is dried under high vacuum. 450 mg (49% of theory, purity ca. 92%) of the title compound are obtained.

MS [DCI/NH₃]: m/z=413 (M+NH₄)⁺

¹H-NMR (400 MHz, DMSO-d₆): =1.00 (t, 3H), 3.35 (m, 1H), 3.69 (m, 1H), 3.99-4.11 (m, 2H), 4.23 (t, 1H), 4.99 (s, 2H), 7.26-7.38 (m, 5H), 7.48-7.56 (m, 2H), 7.62-7.75 (m, 3H).

Example 194A

Ethyl 3-amino-2-[2-(trifluoromethyl)phenyl]propanoate hydrochloride

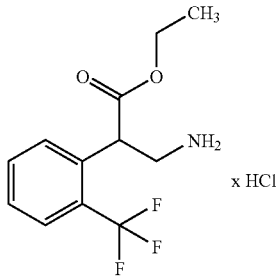

450 mg (1.05 mmol) of the compound from Example 193A are dissolved in 10 ml ethanol and hydrogenated under hydrogen (normal pressure) with 50 mg palladium (10% on charcoal) as catalyst. A reaction test after 18 hrs shows complete conversion. The catalyst is filtered off and the filtrate freed of the volatile components on the rotary evaporator. The residue is taken up in 10 ml diethyl ether and treated with 0.4 ml of a 4 M solution of hydrogen chloride in dioxan. The precipitated solid is filtered off at the pump and dried under high vacuum. 262 mg (84% of theory) of the title compound are obtained.

LC/MS [Method 3]: R$_t$=2.52 min; m/z=262 (M+H)⁺

¹H-NMR (400 MHz, DMSO-d₆): δ=1.11 (t, 3H), 3.06 (m, 1H), 3.51 (m, 1H), 4.07-4.18 (m, 2H), 4.31 (m, 1H), 7.53 (d, 1H), 7.59 (t, 1H), 7.22 (d, 1H), 7.80 (d, 1H), 8.18 (br. s, 3H).

Example 195A

Ethyl 3-{[(benzyloxy)carbonyl]amino}-2-[3-(trifluoromethyl)phenyl]propanoate

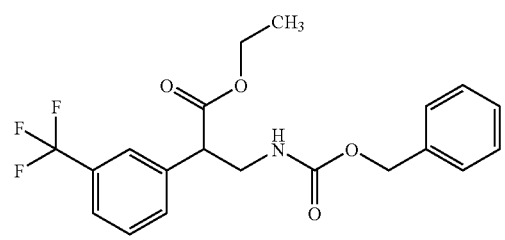

By the same method as described for Example 193A, 334 mg (28% of theory) of the title compound are obtained from 700 mg (3.02 mmol) of ethyl 3-(trifluoromethyl)phenylacetate.

LC/MS [Method 8]: R$_t$=2.83 min; m/z=396 (M+H)⁺

¹H-NMR (400 MHz, DMSO-d₆): δ=1.12 (t, 3H), 3.40 (m, 1H), 3.60 (m, 1H), 4.00 (t, 1H), 4.03-4.15 (m, 2H), 4.99 (s, 2H), 7.22-7.38 (m, 5H), 7.46 (t, 1H), 7.52-7.70 (m, 4H).

Example 196A

Ethyl 3-amino-2-[3-(trifluoromethyl)phenyl]propanoate hydrochloride

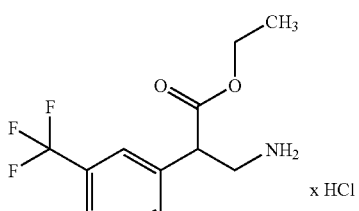

Analogously to the preparation of Example 194A, 220 mg of the title compound (purity ca. 87%, 81% of theory) are obtained from 315 mg of the compound from Example 195A. It is used without further purification.

LC/MS [Method 8]: R$_t$=1.27 min; m/z=262 (M+H)⁺

$^1$H-NMR (400 MHz, DMSO-d$_6$): δ=1.12 (t, 3H), 3.20 (m, 1H), 3.51 (m, 1H), 4.12 (q, 2H), 4.22 (t, 1H), 7.07-7.25 (m, 4H), 8.11 (br. s, 3H).

Example 197A 1-(2,3-dichlorobenzyl)cyclopropanamine hydrochloride

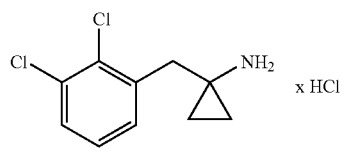

From 1.00 g of 2,3-dichlorophenylacetonitrile (5.37 mmol), 723 mg of the title compound (53% of theory) are obtained by the method described in Example 162A.

LC/MS [Method 3]: R$_t$=2.48 min; m/z=216 (M+H)$^+$ $^1$H-NMR (400 MHz, DMSO-d$_6$): δ=0.71 (m, 2H), 0.98 (m, 2H), 3.23 (s, 2H), 7.38 (t, 1H), 7.46 (d, 1H), 7.60 (d, 1H), 8.41 (br. s, 3H).

Example 198A 1-(2,6-dichlorobenzyl)cyclopropanamine hydrochloride

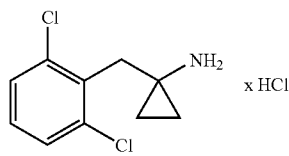

From 1.30 g of 2,6-dichlorophenylacetonitrile (6.99 mmol), 1.24 g of the title compound (62% of theory) are obtained by the method described in Example 162A.

LC/MS [Method 8]: R$_t$=0.94 min; m/z=216 (M+H)$^+$ $^1$H-NMR (400 MHz, DMSO-d$_6$): δ=0.35 (m, 2H), 0.91 (m, 2H), 3.52 (s, 2H), 7.36 (t, 1H), 7.50 (d, 2H), 8.59 (br. s, 3H).

Example 199A

1-[2,3-bis(trifluoromethyl)phenyl]ethaniminium chloride

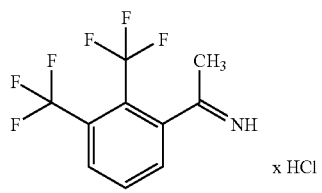

Under argon, a solution of 200 mg of (0.84 mmol) of 2,3-bis(trifluoromethyl)benzonitrile in 2.5 ml toluene is heated to reflux and treated with 3.59 ml of methylmagnesium bromide (1.4 M solution in toluene/THF 3:1; 5 mmol). It is stirred for 3 hrs more at reflux temperature, then cooled to RT. Next, 10 ml of a sat. sodium carbonate solution are added dropwise. The reaction mixture is diluted with water and extracted twice with ethyl acetate. The combined organic phases are extracted twice with 1 N hydrochloric acid. The combined aqueous phases are adjusted to pH 12 with 2 N aqueous sodium hydroxide and extracted twice with dichloromethane. These organic phases are combined, dried over sodium sulphate and filtered. The filtrate is treated with 1 ml of a 4 N solution of hydrogen chloride in dioxan and then freed of solvent on the rotary evaporator. 172 mg (67% of theory) of the title compound are obtained.

MS [DCI/NH$_3$]: m/z=256 (M+H)$^+$, 273 (M+NH$_4$)$^+$ $^1$H-NMR (400 MHz, DMSO-d$_6$): δ=2.82 (s, 3H), 8.11 (d, 1H), 8.17 (t, 1H), 8.31 (d, 1H), 13.35 (br. s, 2H).

Example 200A

1-[2,3-bis(trifluoromethyl)phenyl]ethanamine hydrochloride

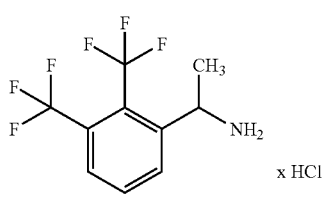

170 mg (0.58 mmol) of the compound from Example 199A are dissolved in 4 ml methanol and treated successively at RT with 147 mg (2.33 mmol) of sodium cyanoborohydride and 334 μl of acetic acid. The mixture is stirred overnight at RT, then diluted with water and extracted twice with dichloromethane. The acidic aqueous phase is adjusted to pH 14 with 2 N aqueous sodium hydroxide and extracted three times with dichloromethane. The combined organic phases are dried over sodium sulphate and filtered. The filtrate is treated with 1 ml of a 4 N solution of hydrogen chloride in dioxan and then freed of solvent on the rotary evaporator. The residue is dried under high vacuum and corresponds to the title compound (160 mg, 93% of theory).

MS [DCI/NH$_3$]: m/z=258 (M+H)$^+$, 275 (M+NH$_4$)$^+$ $^1$H-NMR (400 MHz, DMSO-d$_6$): δ=1.60 (d, 3H), 4.65 (q, 1H), 8.03-8.11 (m, 2H), 8.39 (d, 1H), 8.78 (br. s, 3H).

Example 201A

[3-(trifluoromethyl)phenyl]-p-toluenesulphonylhydrazone

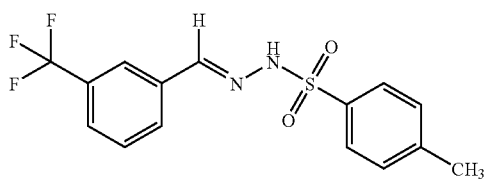

A solution of 2.35 g of (12.6 mmol) p-toluenesulphonylhydrazine in 5 ml methanol is treated slowly at RT with 2.00 g of 3-(trifluoromethyl)benzaldehyde. It is stirred overnight at RT and then the solvent is removed on the rotary evaporator. The residue is taken up in 40 ml cyclohexane/dichloromethane (5:1) and stirred overnight. The precipitated solid is filtered off at the pump, washed with a little cyclohexane/dichloromethane (5:1) washed and dried under high vacuum. 1.27 g of the title compound are thus obtained. Since the mother liquor still contains much product, it is concentrated on the rotary evaporator to a volume of ca. 10 ml. The precipitated solid is again suction-filtered, washed with a little cyclohexane/ethyl acetate (5:1) washed and dried under high vacuum. A further 2.02 g of the title compound (yield overall 84% of theory) are obtained.

LC/MS [Method 19]: $R_t$=3.62 min; m/z=343 (M+H)$^+$ $^1$H-NMR (400 MHz, DMSO-d$_6$): δ=3.36 (s, 3H), 7.40 (d, 2H), 7.63 (t, 1H), 7.72-7.79 (m, 3H), 7.85-7.90 (m, 2H), 8.00 (s, 1H), 11.70 (s, 1H).

Example 202A cis-N-{2-[3-(trifluoromethyl)phenyl]cyclopropyl}phthalimide

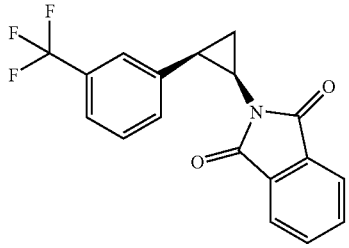

1.00 g (2.92 mmol) of the compound from Example 201A in 14 ml THF at −78° C. under argon is treated slowly with 4.38 ml LiHMDS (1 M solution in THF, 4.38 mmol). After 15 mins at this temperature, the reaction mixture is allowed to warm to RT. The THF is removed on the rotary evaporator. To the remaining lithium salt are added 67 mg of benzyltriethylammonium chloride (0.29 mmol), 13 mg of rhodium acetate dimer (29 μmol), 2.02 g of N-vinylphthalimide (11.68 mmol) and then 14 ml dioxan. The reaction mixture is stirred overnight at RT, then poured into water and extracted three times with dichloromethane. The combined organic phases are dried over sodium sulphate and the solvent removed on the rotary evaporator. The residue is purified by preparative HPLC (by Method 20, but with acetonitrile/0.3% hydrochloric acid instead of acetonitrile/formic acid). The product-containing fractions are freed of the volatile components on the rotary evaporator and the residue dried under high vacuum. 346 mg of the title compound (purity ca. 73%, 26% of theory) are obtained.

$^1$H-NMR (400 MHz, DMSO-d$_6$): δ=1.30 (t, 3H), 1.68 (m, 1H), 2.01 (m, 1H), 2.70 (q, 1H), 3.16 (m, 1H), 7.27 (s, 1H), 7.32-7.41 (m, 3H), 7.69-7.80 (m, 4H).

Example 203A cis-2-[3-(trifluoromethyl)phenyl]cyclopropylamine hydrochloride

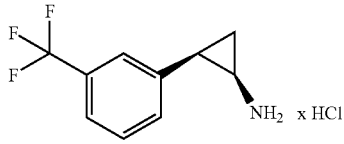

346 mg (0.76 mmol) of the compound from Example 202A are stirred in 3 ml ethanol with 185 μl (3.8 mmol) of hydrazine hydrate at 40° C. for 3 hrs and then freed of all volatile components on the rotary evaporator. The residue is treated with 3-4 ml of DMSO, filtered and the filtrate purified by preparative HPLC (Method 20). The product-containing fractions are treated with 3 ml of 1 N hydrochloric acid and freed of the volatile components on the rotary evaporator. The residue is dried under high vacuum and corresponds to the title compound (66 mg, 36% of theory).

LC/MS [Method 23]: $R_t$=0.65 min; m/z=202 (M+H)$^+$ $^1$H-NMR (400 MHz, DMSO-d$_6$): δ=1.31-1.37 (m, 2H), 2.49 (m, 1H), 2.89 (m, 1H), 7.56-7.73 (m, 4H), 8.14 (br. s, 3H).

Example 204A

Difluoro-[3-(trifluoromethyl)phenyl]-acetonitrile

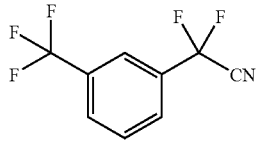

A solution of 500 mg of [3-(trifluoromethyl)phenyl]-acetonitrile (2.70 mmol) in 12 ml anhydrous THF is treated dropwise at −78° C. with 3.50 ml of a tert.-butyllithium solution (1.7 M in pentane, 5.94 mmol). The brown reaction mixture is stirred for 1 hr at −78° C., then a solution of 2.04 g (6.5 mmol) of N-fluorobenzenesulphonic acid imide in 12 ml THF is added. It is stirred for 2 hrs more at −78° C. and then the reaction is stopped by addition of 0.1 M hydrochloric acid. After warming to RT, the mixture is extracted twice with dichloromethane. The combined organic phases are washed with dilute sodium bicarbonate solution then with sat. sodium chloride solution, and then dried over sodium sulphate and freed of solvent on the rotary evaporator. The residue is purified by preparative HPLC (Method 20). The product-containing fractions are freed of acetonitrile on the rotary evaporator and the aqueous phase that remains is extracted with dichloromethane. The organic phases are dried over magnesium sulphate and the solvent removed on the rotary evaporator. 85 mg of the title compound in ca. 81% purity (12% of theory) are obtained.

GC/MS [Method 21]: $R_t$=1.49 min; m/z=221 (M)$^+$ $^1$H-NMR (400 MHz, DMSO-d$_6$): δ=7.35-7.43 (m, 2H), 7.63-7.70 (m, 2H).

Example 205A 2,2-difluoro-2-[3-(trifluoromethyl)phenyl]ethanamine hydrochloride

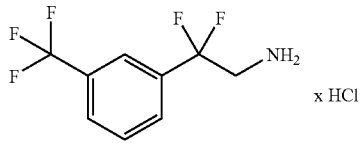

Borane reduction of the compound from Example 204A by the method described in Example 157A yields 73 mg (68% of theory) of the title compound.

LC/MS [Method 23]: $R_t$=0.69 min; m/z=226 (M+H)$^+$ $^1$H-NMR (400 MHz, DMSO-d$_6$): δ=3.37 (t, 2H), 7.81 (t, 1H), 7.94-8.03 (m, 3H), 8.71 (br. s, 3H).

Example 206A 2-(4-chlorobenzoyl)-N-allylhydrazinecarboxamide

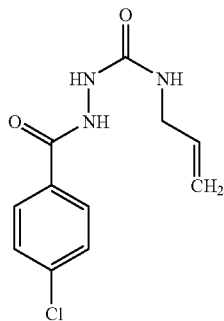

Under an argon atmosphere, 19.00 g (111.4 mmol) of 4-chlorobenzoic acid hydrazide are placed in 150 ml THF. 9.44 g (111.6 mmol) of allyl isocyanate, dissolved in 110 ml THF, are added dropwise at 50° C. and the mixture further stirred overnight at 50° C. The solvent is then evaporated in vacuo, diethyl ether is added to the residue and the solid formed is isolated and purified by filtration and further washing with diethyl ether. 26.80 g (95% of theory) of the target compound are thus obtained.

LC/MS [Method 18]: $R_t$=1.51 min; MS [ESIpos]: m/z=254 (M+H)$^+$ $^1$H-NMR (400 MHz, DMSO-d$_6$): δ=3.60-3.70 (m, 2H), 5.01 (d, 1H), 5.15 (d, 1H), 5.80 (m, 1H), 6.70 (s, 1H), 7.56 (d, 2H), 7.90 (d, 2H), 7.92 (s, 1H), 10.21 (s, 1H).

The following compounds are prepared analogously:

| Example No. | Structure | LC/MS or HPLC, MS $R_t$ [Method] |
|---|---|---|
| 207A | | LC/MS: $R_t$ = 1.66 min [8] [ESIpos]: m/z = 296 (M + H)$^+$ |
| 208A | 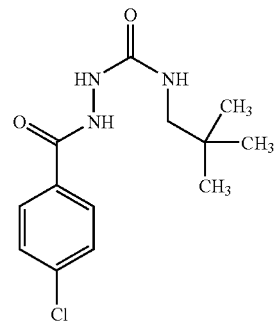 | LC/MS: $R_t$ = 2.75 min [17] [ESIpos]: m/z = 284 (M + H)$^+$ |
| 209A | 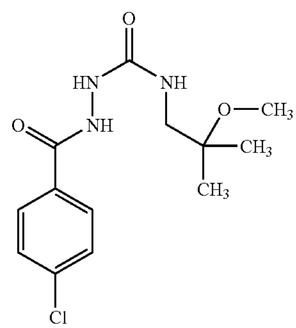 | LC/MS: $R_t$ = 2.07 min [17] [ESIpos]: m/z = 300 (M + H)$^+$ |

Example 210A 5-(4-chlorophenyl)-4-allyl-2,4-dihydro-3H-1,2,4-triazol-3-one

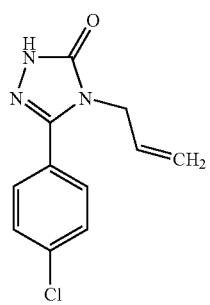

26.80 g (105.6 mmol) of 2-(4-chlorobenzoyl)-N-allylhydrazinecarboxamide from Example 206A are heated overnight under reflux in 211 ml 3 N aqueous sodium hydroxide. After cooling, it is adjusted to pH 10 with 6 N hydrochloric acid, during which the product almost completely precipitates. The precipitate is suction-filtered, washed with much water and then stirred with methanol. An insoluble white precipitate remains, which is filtered off. The filtrate is concentrated in vacuo and the residue that remains is dried under high vacuum. 21.5 g (86% of theory) of the target compound are thus obtained.

LC/MS [Method 18]: $R_t$=1.79 min; MS [ESIpos]: m/z=236 (M+H)$^+$ $^1$H-NMR (400 MHz, DMSO-d$_6$): δ=4.30-4.35 (m, 2H), 4.90 (d, 1H), 5.12 (d, 1H), 5.85 (m, 1H), 7.57 (d, 2H), 7.63 (d, 2H), 12.06 (s, 1H).

The following compounds are prepared analogously:

| Example No. | Structure | Educt | LC/MS or HPLC, MS $R_t$ [Method] |
|---|---|---|---|
| 211A | 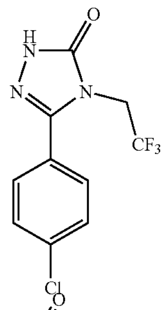 | 207A | LC/MS: $R_t$ = 2.66 min [19] [ESIpos]: m/z = 278 (M + H)+ |
| 212A | 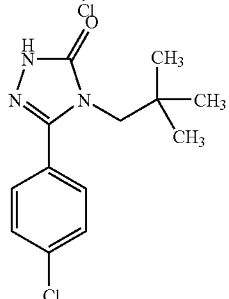 | 208A | LC/MS: $R_t$ = 2.98 min [19] [ESIpos]: m/z = 266 (M + H)+ |
| 213A | 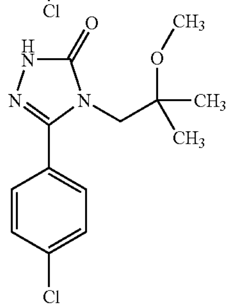 | 209A | LC/MS: $R_t$ = 1.91 min [8] [ESIpos]: m/z = 282 (M + H)+ |

Example 214A

Methyl[3-(4-chlorophenyl)-4-allyl-5-oxo-4,5-dihydro-1H-1,2,4-triazol-1-yl]-acetate

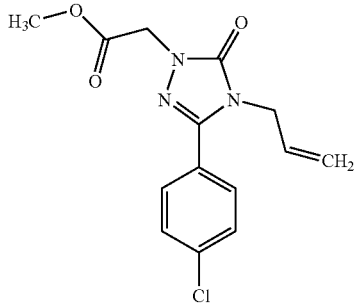

13.87 g (100.35 mmol) of potassium carbonate are added to 21.50 g (91.2 mmol) of 5-(4-chlorophenyl)-4-allyl-2,4-dihydro-3H-1,2,4-triazol-3-one from Example 210A and 11.88 g (109.5 mmol) of methyl chloroacetate in 350 ml acetonitrile and the mixture is heated under reflux for 5 hrs with stirring. It is then concentrated and the residue taken up in ethyl acetate is washed with 1 N hydrochloric acid and then with saturated sodium chloride solution. The organic phase is dried over sodium sulphate. After filtration, the filtrate is concentrated in vacuo. After purification by flash chromatography on silica gel (eluent: cyclohexane/ethyl acetate 2:1) 24.00 g (85% of theory) of the target compound are obtained.

$^1$H-NMR (400 MHz, DMSO-$d_6$): δ=3.70 (s, 3H), 4.36-4.43 (m, 2H), 4.72 (s, 2H), 4.93 (d, 1H), 5.15 (d, 1H), 5.86 (m, 1H), 7.60 (d, 2H), 7.66 (d, 2H).

The following compounds are prepared analogously:

| Example No. | Structure | Educt | LC/MS or HPLC, MS $R_t$ [Method] |
|---|---|---|---|
| 215A | 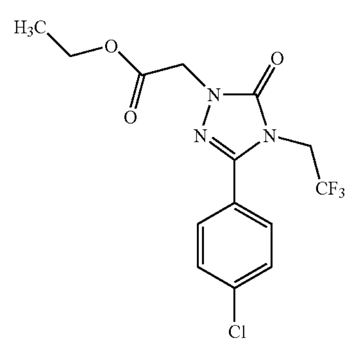 | 211A | LC/MS: $R_t$ = 2.39 min [8] [ESIpos]: m/z = 364 (M + H)+ |

-continued

| Example No. | Structure | Educt | LC/MS or HPLC, MS $R_t$ [Method] |
|---|---|---|---|
| 216A | H₃C-O-CH₂-C(=O)-N-N=C(-4-Cl-C₆H₄)-N(CH₂C(CH₃)₃)-C(=O) (triazolinone) | 212A | LC/MS: $R_t$ = 3.36 min [19] [ESIpos]: m/z = 338 (M + H)⁺ |
| 217A | H₃C-O-CH₂-C(=O)-N-N=C(-4-Cl-C₆H₄)-N(CH₂C(OCH₃)(CH₃)₂)-C(=O) (triazolinone) | 213A | LC/MS: $R_t$ = 2.19 min [8] [ESIpos]: m/z = 354 (M + H)⁺ |

Example 218A

[3-(4-chlorophenyl)-4-allyl-5-oxo-4,5-dihydro-1H-1,2,4-triazol-1-yl]-acetic acid

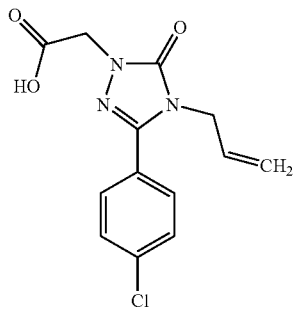

4.88 g (15.9 mmol) of ethyl[3-(4-chlorophenyl)-4-allyl-5-oxo-4,5-dihydro-1H-1,2,4-triazol-1-yl]-acetate from Example 214A are placed in 48 ml methanol and stirred with 5 ml 20% aqueous potassium hydroxide for 2 hrs at room temperature. The solution is concentrated to ca. one half, then diluted with water and extracted with ethyl acetate. The aqueous phase is acidified with ca. 2 ml of conc. hydrochloric acid and extracted twice with 100 ml ethyl acetate each time. The last organic extracts are combined, dried over sodium sulphate, filtered and concentrated in vacuo. After drying in high vacuum, 4.20 g (90% of theory) of the target compound are thus obtained.

LC/MS [Method 8]: $R_t$=2.93 min; MS [ESIpos]: m/z=294 (M+H)⁺

¹H-NMR (400 MHz, DMSO-d₆): δ=4.36-4.43 (m, 2H), 4.59 (s, 2H), 4.93 (d, 1H), 5.15 (d, 1H), 5.87 (m, 1H), 7.60 (d, 2H), 7.67 (d, 2H), 13.17 (s, 1H).

The following compounds are prepared analogously:

| Example No. | Structure | Educt | LC/MS or HPLC, MS $R_t$ [Method] |
|---|---|---|---|
| 219A | HO-CH₂-C(=O)-N-N=C(-4-Cl-C₆H₄)-N(CH₂CF₃)-C(=O) (triazolinone) | 215A | LC/MS: $R_t$ = 2.69 min [19] [ESIpos]: m/z = 336 (M + H)⁺ |

| Example No. | Structure | Educt | LC/MS or HPLC, MS $R_t$ [Method] |
|---|---|---|---|
| 220A | HO-C(=O)-CH2-N(N=C(-C6H4-Cl)-N(-CH2-C(CH3)3)-C(=O)) (triazolone with 4-chlorophenyl and neopentyl) | 216A | LC/MS: $R_t$ = 2.98 min [19] [ESIpos]: m/z = 324 (M + H)$^+$ |
| 221A | HO-C(=O)-CH2-N(N=C(-C6H4-Cl)-N(-CH2-C(CH3)2-OCH3)-C(=O)) | 217A | LC/MS: $R_t$ = 2.69 min [17] [ESIpos]: m/z = 340 (M + H)$^+$ |

Example 222A

Methyl[3-(4-chlorophenyl)-5-oxo-4,5-dihydro-1H-1,2,4-triazol-1-yl]-acetate

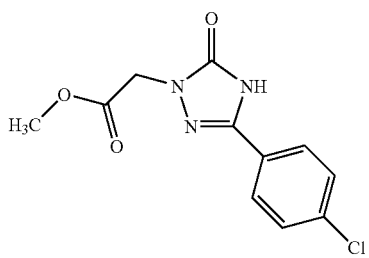

Under an argon atmosphere, 200 mg (0.65 mmol) of the compound from Example 214A, 49 µl of formic acid (1.3 mmol), 226 µl of triethylamine (1.63 mmol) and 38 mg of tetrakis(triphenylphosphine)palladium(0) (32 µmol) are dissolved in 2 ml degassed dioxan and stirred overnight at reflux temperature. To dissolve the precipitated solid, the reaction mixture is diluted with 20 ml of methanol after cooling to RT. The palladium catalyst is filtered off and the filtrate freed of the volatile components on the rotary evaporator. The residue is stirred with 5 ml acetonitrile and then suction-filtered. The solid is washed with acetonitrile and dried under high vacuum. It corresponds to the title compound with a purity of ca. 76% (130 mg, 57% of theory) and is used in the next reaction without further purification.

LC/MS [Method 19]: $R_t$=2.34 min; m/z=268 (M+H)$^+$
$^1$H-NMR (400 MHz, DMSO-d$_6$): δ=3.70 (s, 3H), 4.63 (s, 2H), 7.59 (d, 2H), 7.80 (d, 2H).

Example 223A

Methyl {4-[4-(tert.-butoxy)-4-oxo-n-butyl]-3-(4-chlorophenyl)-5-oxo-4,5-dihydro-1H-1,2,4-triazol-1-yl}-acetate

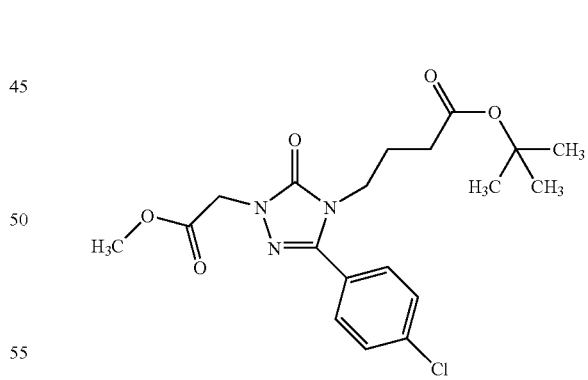

Under an argon atmosphere, a solution of 130 mg (0.38 mmol) of the compound from Example 222A in 1 ml DMF and 2 ml DME at 0° C. is treated with 505 µl of an LiHMDS solution (1 M in THF, 505 µmol). The cooling bath is removed and the mixture stirred for 15 mins at RT before addition of 113 mg (505 µmol) of tert.-butyl 4-bromobutanoate. The mixture is stirred overnight at 70° C. After cooling, 0.5 ml of 1 N hydrochloric acid are added. The reaction mixture is then directly separated by preparative HPLC (Method 20). 48 mg (30% of theory) of the title compound are obtained.

LC/MS [Method 17]: $R_t$=3.67 min; m/z=410 (M+H)$^+$
$^1$H-NMR (400 MHz, DMSO-$d_6$): δ=1.31 (s, 9H), 1.69 (quin, 2H), 2.12 (t, 2H), 3.70 (s, 3H), 3.79 (t, 2H), 4.69 (s, 2H), 7.52 (d, 2H), 7.70 (d, 2H).

Example 224A

{4-[4-(tert.-butoxy)-4-oxo-n-butyl]-3-(4-chlorophenyl)-5-oxo-4,5-dihydro-1H-1,2,4-triazol-1-yl}-acetic acid

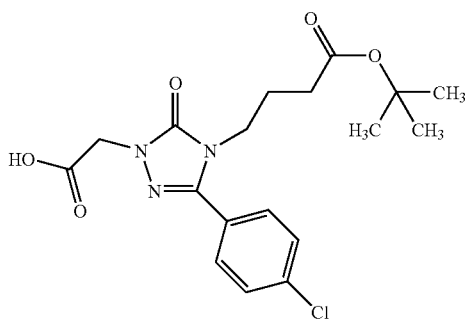

A solution of 48 mg (117 μmol) of the compound from Example 223A in 2 ml methanol is treated with a 1 N lithium hydroxide solution in water (470 μl, 470 μmol). After 1 hr at RT, the methanol is removed on the rotary evaporator. The residue is dissolved in DMSO and purified by preparative HPLC. 41 mg (88% of theory) of the title compound are obtained.

LC/MS [Method 8]: $R_t$=2.48 min; m/z=396 (M+H)$^+$
$^1$H-NMR (400 MHz, DMSO-$d_6$): δ=1.33 (s, 9H), 1.68 (quin, 2H), 2.14 (t, 2H), 3.77 (t, 2H), 4.54 (s, 2H), 7.61 (d, 2H), 7.70 (d, 2H), 13.14 (br. s, 1H).

Example 225A

Methyl[3-(4-chlorophenyl)-4-(2-oxoethyl)-5-oxo-4,5-dihydro-1H-1,2,4-triazol-1-yl]-acetate

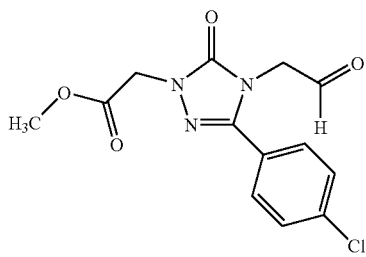

1.00 g (3.25 mmol) of the compound from Example 214A and 217 mg of OsEnCat 40 (micro-encapsulated osmium tetroxide, 0.3 mmol/g, 65 μmol) are placed in 20 ml dioxan and 9 ml water and slowly treated with 2.09 g (9.8 mmol) of sodium periodate at RT. This is allowed to react with vigorous stirring (1-4 days) until HPLC testing of the mixture shows adequate conversion. For the workup, the osmium catalyst is removed by filtration, then washed with dioxan and the total filtrate freed from the organic solvents on the rotary evaporator. The aqueous residue is diluted with more water and extracted three times with dichloromethane. The combined organic phases are dried over sodium sulphate and the solvent removed on the rotary evaporator. The oily residue is dried under high vacuum. 948 mg (purity ca. 84%, 79% of theory) of the title compound are obtained.

LC/MS [Method 17]: $R_t$=1.89 min; m/z=310 (M+H)$^+$
$^1$H-NMR (400 MHz, CDCl$_3$): δ=3.79 (s, 3H), 4.61 (s, 2H), 4.67 (s, 2H), 7.37-7.59 (m, 4H), 9.62 (s, 1H).

Example 226A

Methyl[3-(4-chlorophenyl)-5-oxo-4-(3,3,3-trifluoro-2-hydroxypropyl)-4,5-dihydro-1H-1,2,4-triazol-1-yl]-acetate (racemate)

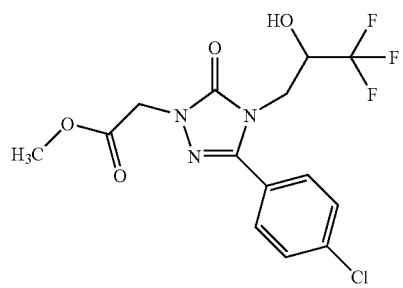

6.69 ml of a 0.5 M solution of (trifluoromethyl)trimethylsilane in THF (3.34 mmol) and 39 μl of a 1 M solution of tetra-n-butylammonium fluoride in THF (39 μmol) are successively added at 0° C. to a solution of 948 mg (2.57 mmol) of the compound from Example 225A in 17 ml THF. The temperature is allowed to rise to RT and the mixture stirred for 1 hr more. For the workup, the reaction mixture is treated with 8 ml of 1 N hydrochloric acid. It is stirred for 1 hr at RT, before the THF is removed on the rotary evaporator. The aqueous residue is extracted with ethyl acetate. The organic phase is washed twice with water and once with sat. sodium chloride solution, dried over magnesium sulphate and freed of solvent on the rotary evaporator. The residue is purified by silica gel chromatography (eluent: dichloromethane/methanol 100:1→100:2). 630 mg (65% of theory) of the title compound are obtained.

LC/MS [Method 8]: $R_t$=2.23 min; m/z=380 (M+H)$^+$
$^1$H-NMR (400 MHz, DMSO-$d_6$): δ=3.70 (s, 3H), 3.84 (dd, 1H), 4.00 (dd, 1H), 4.25 (m, 1H), 4.71 (s, 2H), 6.91 (d, 1H), 7.63 (d, 2H), 7.76 (d, 2H).

The racemate from Example 226A can be separated into the enantiomers by HPLC on chiral phase [Column: chiral silica gel phase based on the selector poly(N-methacryloyl-L-isoleucine-3-pentyl-amide, 430 mm×40 mm; Eluent: Step gradient iso-hexane/ethyl acetate 1:1→ethyl acetate→iso-

Example 227A

Methyl[3-(4-chlorophenyl)-5-oxo-4-(3,3,3-trifluoro-2-hydroxypropyl)-4,5-dihydro-1H-1,2,4-triazol-1-yl]-acetate (Enantiomer 1)

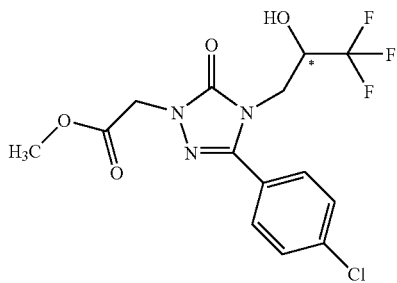

First eluting enantiomer from the racemate separation of Example 226A.

$R_t$=3.21 min [Column: chiral silica gel phase based on the selector poly(N-methacryloyl-L-isoleucine-3-pentylamide, 250 mm×4.6 mm; Eluent: iso-hexane/ethyl acetate 1:1; Flow rate: 1 mL/min; UV detection: 260 nm].

Example 228A

Methyl[3-(4-chlorophenyl)-5-oxo-4-(3,3,3-trifluoro-2-hydroxypropyl)-4,5-dihydro-1H-1,2,4-triazol-1-yl]-acetate (Enantiomer 2)

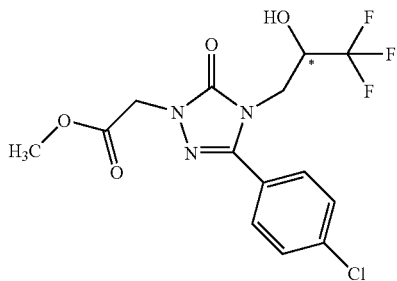

Last eluting enantiomer from the racemate separation of Example 226A.

$R_t$=4.48 min [Column: chiral silica gel phase based on the selector poly(N-methacryloyl-L-isoleucine-3-pentylamide, 250 mm×4.6 mm; Eluent: iso-hexane/ethyl acetate 1:1; Flow rate: 1 mL/min; UV detection: 260 nm].

Example 229A

[3-(4-chlorophenyl)-5-oxo-4-(3,3,3-trifluoro-2-hydroxypropyl)-4,5-dihydro-1H-1,2,4-triazol-1-yl]-acetic acid (Enantiomer 1)

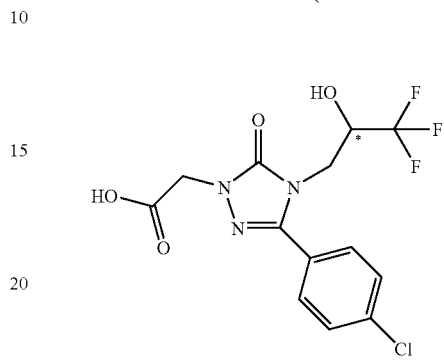

The enantiomerically pure ester from Example 227A (265 mg, 0.70 mmol) is dissolved in 14 ml methanol and treated with 2.8 ml of a 1 M solution of lithium hydroxide in water. The mixture is stirred for 1 hr at RT and then freed of methanol on the rotary evaporator. The residue is diluted with 200 ml water and extracted once with dichloromethane. This organic phase is discarded. The aqueous phase is slowly acidified to pH 2 with 1 N hydrochloric acid. The product is extracted three times with dichloromethane, the combined organic phases are dried over sodium sulphate and the solvent removed on the rotary evaporator. The residue is dried under high vacuum. 142 mg (56% of theory) of the title compound are thus obtained. Since the aqueous phase still contains more product, it is evaporated to dryness on the rotary evaporator, and the residue is dissolved in a little DMSO and purified by preparative HPLC (Method 20). A further 71 mg (28% of theory) of the pure title compound are obtained.

$[\alpha]_D^{20}$=+3.4° (methanol, c=0.37 g/100 ml)

LC/MS [Method 17]: $R_t$=2.83 min; m/z=366 (M+H)$^+$ $^1$H-NMR (400 MHz, DMSO-d$_6$): δ=3.84 (dd, 1H), 4.00 (dd, 1H), 4.25 (m, 1H), 4.58 (s, 2H), 6.91 (d, 1H), 7.63 (d, 2H), 7.78 (d, 2H), 13.20 (br. s, 1H).

Example 230A

[3-(4-chlorophenyl)-5-oxo-4-(3,3,3-trifluoro-2-hydroxypropyl)-4,5-dihydro-1H-1,2,4-triazol-1-yl]-acetic acid (Enantiomer 2)

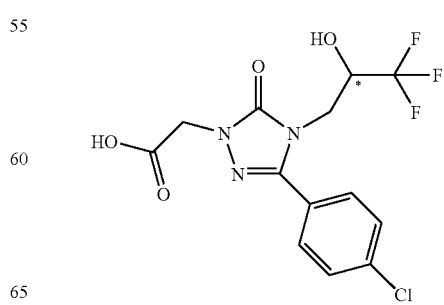

Analogously to Example 229A, 210 mg (80% of theory) of the title compound are obtained from 271 mg of the enantiomerically pure ester from Example 228A.

[α]$_D^{20}$=−4.6° (methanol, c=0.44 g/100 ml)

LC/MS [Method 17]: R$_t$=2.83 min; m/z=366 (M+H)$^+$ $^1$H-NMR (400 MHz, DMSO-d$_6$): δ=3.84 (dd, 1H), 4.00 (dd, 1H), 4.25 (m, 1H), 4.58 (s, 2H), 6.91 (d, 1H), 7.63 (d, 2H), 7.78 (d, 2H), 13.20 (br. s, 1H).

Example 231A

Methyl {[2-(4-chlorophenyl)-2-oxoethyl]amino}acetate

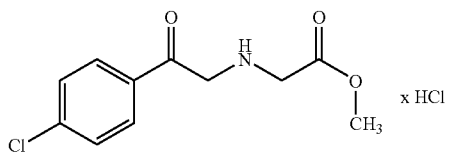

A solution of glycine methyl ester hydrochloride (5.00 g, 39.8 mmol) in 80 ml methyl isobutyl ketone is treated with 12.6 g of sodium carbonate and the mixture stirred overnight at RT. Next, a solution of 2-bromo-1-(4-chlorophenyl)ethanone (8.37 g, 35.8 mmol) in 40 ml methyl isobutyl ketone is added dropwise to this suspension. The mixture is stirred for 1 hr more at RT, then the solid is suction-filtered and washed with 55 ml methyl isobutyl ketone. The filtrate is acidified with 12 ml of 6 N hydrochloric acid, then treated with 6.4 ml isopropanol. The precipitated solid is filtered off at the pump, washed with a little methyl isobutyl ketone, then stirred in 240 ml of acetonitrile and again suction-filtered. 3.41 g (34% of theory) of the pure title compound are thus obtained.

LC/MS [Method 3]: R$_t$=2.20 min; m/z=242 (M+H)$^+$.

Example 232A

Methyl[4-(4-chlorophenyl)-2-oxo-2,3-dihydro-1H-imidazol-1-yl]-acetate

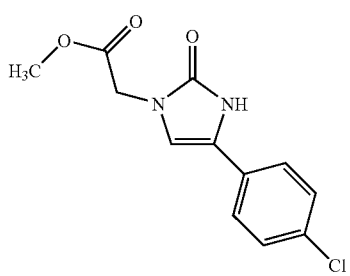

A solution of 3.41 g (12.27 mmol) of the compound from Example 231A in 14 ml methanol/water (7:3) is added dropwise to a solution of 995 mg (12.27 mmol) of potassium isocyanate in 11 ml methanol/water (7:3). This is stirred for 1 hr at RT. The thick suspension is diluted with 7.4 ml water and 39 ml methanol to facilitate stirring, then heated under reflux for 1 hr and then left to stand overnight at RT. After cooling to 0° C., the precipitate is filtered off, washed with ice-cold water and dried overnight in the drying cabinet at 60° C. 2.84 g (76% of theory) of the title compound are obtained.

LC/MS [Method 4]: R$_t$=2.03 min; m/z=267 (M+H)$^+$.

Example 233A

[4-(4-chlorophenyl)-2-oxo-2,3-dihydro-1H-imidazol-1-yl]-acetic acid

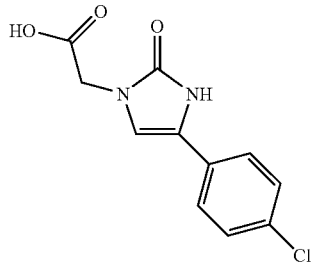

770 mg (2.89 mmol) of methyl[4-(4-chlorophenyl)-2-oxo-2,3-dihydro-1H-imidazol-1-yl]-acetate from Example 232A are placed in 20 ml methanol, treated with 5.8 ml of 1 M aqueous lithium hydroxide solution and stirred for 18 hrs at room temperature. The methanol is then removed on the rotary evaporator and the residue is acidified with 1 N hydrochloric acid. The resulting precipitate is filtered off at the pump, washed with water and dried under high vacuum. 690 mg (94% of theory) of the target compound are thus obtained.

LC/MS [Method 17]: R$_t$=2.19 min; MS [ESIpos]: m/z=253 (M+H)$^+$ $^1$H-NMR (400 MHz, DMSO-d$_6$): δ=4.30 (s, 2H), 7.08 (s, 1H), 7.41 (d, 2H), 7.51 (d, 2H), 10.08 (s, 1H), 13.01 (s, 1H).

Example 234A

2-[4-(4-chlorophenyl)-2-oxo-2,3-dihydro-1H-imidazol-1-yl]-N-{1-methyl-1-[3-(trifluoromethyl)-phenyl]ethyl}acetamide

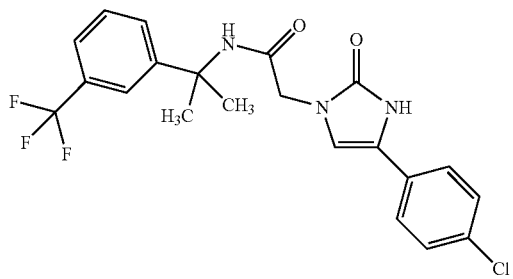

318 mg (1.26 mmol) of [4-(4-chlorophenyl)-2-oxo-2,3-dihydro-1H-imidazol-1-yl]-acetic acid from Example 233A are placed in 10 ml DMF and treated with 221 mg (1.64 mmol) of HOBt and 314 mg (1.64 mmol) of EDC hydrochloride. After 10 mins' stirring, 332 mg (1.64 mmol) of 1-methyl-1-[(3-trifluoromethyl)phenyl]ethylamine from Example 1A are added and the mixture is stirred overnight at room temperature. For the workup, the reaction mixture is stirred with 100 ml water. Next, the resulting precipitate is suction-filtered, washed with water and dried under high vacuum. Further purification is effected by preparative HPLC [Method 10]. 209 mg (38% of theory) of the target compound are thus obtained.

LC/MS [Method 17]: $R_t$=3.57 min; MS [ESIpos]: m/z=438 (M+H)$^+$ $^1$H-NMR (400 MHz, DMSO-d$_6$): δ=1.60 (s, 6H), 4.26 (s, 2H), 6.96 (s, 1H), 7.32-7.69 (m, 8H), 8.71 (s, 2H), 10.71 (s, 1H).

Example 235A

1-[2-(5-chloro-2-thienyl)-2-oxoethyl]-3-(2-fluorobenzyl)-urea

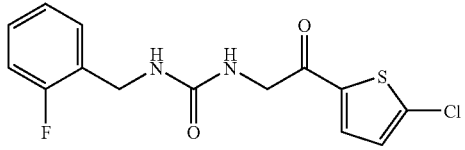

850 mg (4.007 mmol) of 2-amino-1-(4-chlor-2-thienyl) ethanone hydrochloride are placed in 26 ml dichloromethane, cooled to 0° C. and treated dropwise with a solution of 606 mg (4.007 mmol) of 2-fluorobenzyl isocyanate in 2 ml dichloromethane. It is stirred for 10 mins more at 0° C. and then a solution of 518 mg (4.007 mmol) of N,N-diisopropylethylamine in 4 ml dichloromethane is added dropwise. After two hours' stirring at room temperature the reaction mixture is evaporated and the crude product (1300 mg, 99% of theory) further reacted without purification.

LC/MS [Method 8]: $R_t$=2.11 min; MS [ESIpos]: m/z=327 (M+H)$^+$ $^1$H-NMR (400 MHz, DMSO-d$_6$): δ=1.60 (s, 6H), 4.26 (s, 2H), 6.96 (s, 1H), 7.32-7.69 (m, 8H), 8.71 (s, 2H), 10.71 (s, 1H).

Example 236A 5-(5-chloro-2-thienyl)-1-(2-fluorobenzyl)-1,3-dihydro-2H-imidazol-2-one

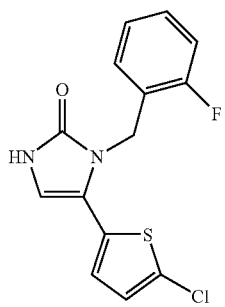

1300 mg (ca. 4.0 mmol) of 1-[2-(5-chloro-2-thienyl)-2-oxoethyl]-3-(2-fluorobenzyl)-urea (Example 235A) are suspended in 15 ml of concentrated hydrochloric acid, diluted with 15 ml of methanol diluted and stirred at RT for 2 hrs. The suspension is filtered, the filtrate concentrated in vacuo and the residue purified by preparative HPLC [Method 10]. 220 mg (18% of theory) of the target compound are thus obtained.

LC/MS [Method 7]: $R_t$=2.10 min; MS [ESIpos]: m/z=309 (M+H)$^+$ $^1$H-NMR (400 MHz, DMSO-d$_6$): δ=4.90 (s, 2H), 6.78-7.38 (m, 7H), 10.61 (s, 1H).

Example 237A

Ethyl[4-(5-chloro-2-thienyl)-3-(2-fluorobenzyl)-2-oxo-2,3-dihydro-1H-imidazol-1-yl]-acetate

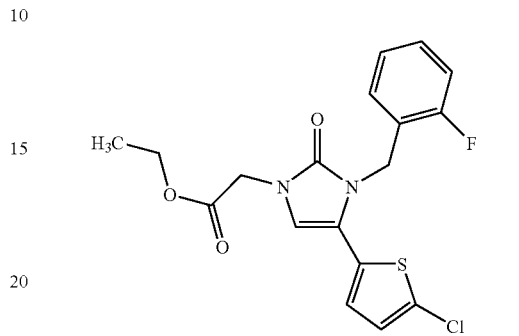

650 mg (2.15 mmol) of 5-(5-chloro-2-thienyl)-1-(2-fluorobenzyl)-1,3-dihydro-2H-imidazol-2-one from Example 236A, 516 mg (4.21 mmol) of ethyl chloroacetate and 582 mg (4.21 mmol) of potassium carbonate are stirred in 12 ml acetonitrile for 7 hrs at 80° C. The reaction solution is diluted with ethyl acetate and washed three times with saturated sodium chloride solution. The organic phase is dried over sodium sulphate. After filtration from the drying agent, the filtrate is concentrated in vacuo. After purification by flash chromatography over silica gel (eluent: cyclohexane/ethyl acetate first 5:1, then 1:1), 610 mg (74% of theory) of the target compound are obtained.

LC/MS [Method 17]: $R_t$=3.74 min; MS [ESIpos]: m/z=395 (M+H)$^+$ $^1$H-NMR (400 MHz, DMSO-d$_6$): δ=1.22 (t, 3H), 4.18 (q, 2H), 4.51 (s, 2H), 4.97 (s, 2H), 6.86-6.94 (m, 2H), 6.98 (s, 1H), 7.05 (d, 1H), 7.10-7.22 (m, 2H), 7.27-7.36 (m, 1H).

Example 238A

[4-(5-chloro-2-thienyl)-3-(2-fluorobenzyl)-2-oxo-2,3-dihydro-1H-imidazol-1-yl]-acetic acid

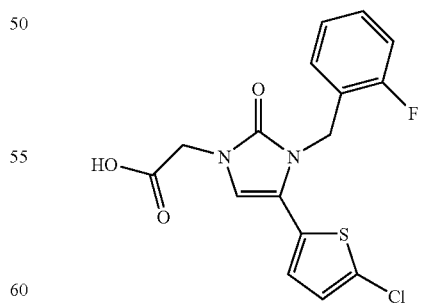

Analogously to the procedure of Example 129A, 150 mg (99% of theory) of the target compound are obtained from 165 mg (0.418 mmol) of the compound from Example 237A.

LC/MS [Method 7]: $R_t$=2.01 min; MS [ESIpos]: m/z=367 (M+H)$^+$ $^1$H-NMR (400 MHz, DMSO-d$_6$): δ=4.40 (s, 2H), 4.97 (s, 2H), 6.82-6.95 (m, 2H), 6.98 (s, 1H), 7.04-7.22 (m, 3H), 7.25-7.36 (m, 1H).

Example 239A

Methyl[4-(4-chlorophenyl)-3-(cyclopropylmethyl)-2-oxo-2,3-dihydro-1H-imidazol-1-yl]-acetate

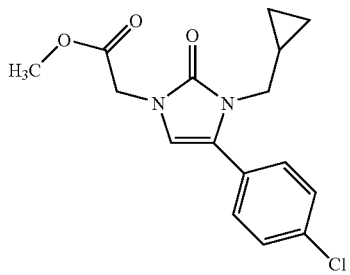

300 mg (1.13 mmol) of the compound from Example 232A together with 1.10 g (3.38 mmol) of caesium carbonate are placed in 12 ml acetone and treated with 456 mg (3.38 mmol) of bromo-methylcyclopropane. This is stirred for 2 hrs at 50° C. The reaction mixture is then diluted with 10 ml each of ethyl acetate and water and acidified with 1 N hydrochloric acid. The phases are separated and the aqueous phase is once again extracted with 10 ml ethyl acetate. The combined organic phases are dried over sodium sulphate, filtered and concentrated in vacuo. Further purification is effected by preparative HPLC [Method 10]. 60 mg (17% of theory) of the target compound are thus obtained.

LC/MS [Method 8]: R$_t$=2.28 min; MS [ESIpos]: m/z=321 (M+H)$^+$ $^1$H-NMR (400 MHz, DMSO-d$_6$): δ=0.05 (m, 2H), 0.39 (m, 2H), 0.76 (m, 1H), 3.60 (d, 2H), 3.70 (s, 3H), 4.46 (s, 2H), 6.73 (s, 1H), 7.40-7.55 (m, 4H).

Example 240A

[4-(4-chlorophenyl)-3-(cyclopropylmethyl)-2-oxo-2,3-dihydro-1H-imidazol-1-yl]-acetic acid

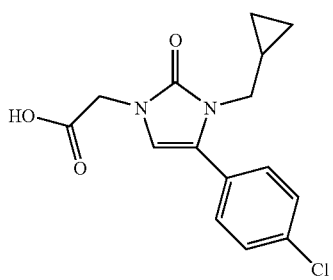

Analogously to the procedure of Example 129A, 84 mg (100% of theory) of the target compound are obtained starting from 87 mg (0.271 mmol) of methyl[4-(4-chlorophenyl)-3-(cyclopropyl-methyl)-2-oxo-2,3-dihydro-1H-imidazol-1-yl]-acetate from Example 239A.

LC/MS [Method 17]: R$_t$=2.86 min; MS [ESIpos]: m/z=307 (M+H)$^+$ $^1$H-NMR (500 MHz, DMSO-d$_6$): δ=0.05 (m, 2H), 0.28 (m, 2H), 0.65 (m, 1H), 3.60 (d, 2H), 4.33 (s, 2H), 6.73 (s, 1H), 7.40-7.55 (m, 4H), 13.03 (br. s, 1H).

Example 241A

2-[3-(4-chlorophenyl)-5-oxo-4,5-dihydro-1H-1,2,4-triazol-1-yl]-N-{1-methyl-1-[3-(trifluoromethyl)-phenyl]ethyl}-acetamide

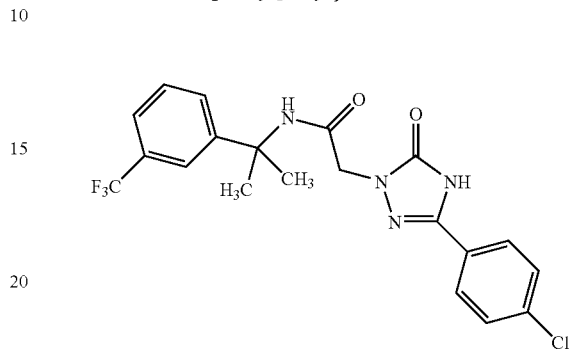

2.00 g (4.12 mmol) of 2-[3-(4-chlorophenyl)-4-allyl-5-oxo-4,5-dihydro-1H-1,2,4-triazol-1-yl]-N-{-methyl-1-[3-(trifluoromethyl)phenyl]ethyl}-acetamide from Example 371 are dissolved in 20 ml degassed dioxan and treated under argon with 97 mg of tetrakis(triphenylphosphine)-palladium (0) (0.084 mmol), 1.46 ml (10.44 mmol) of triethylamine and 0.32 ml (8.35 mmol) of formic acid and stirred for two hours at 85° C. The suspension is then allowed to cool to room temperature and the precipitated crystals are filtered off at the pump and washed with isopropanol. The mother liquor is concentrated in vacuo and treated with isopropanol, during which further crystals deposit, which are likewise suction-filtered and washed with isopropanol. Together 1.56 g (85% of theory) of the target compound are thus obtained.

LC/MS [Method 8]: R$_t$=2.47 min; MS [ESIpos]: m/z=439 (M+H)$^+$ $^1$H-NMR (400 MHz, DMSO-d$_6$): δ=1.60 (s, 6H), 4.61 (s, 2H), 7.50-7.70 (m, 6H), 7.78 (d, 2H), 8.55 (s, 1H), 12.27 (s, 1H).

The following compounds are obtained analogously:

| Example No. | Structure | LC/MS or HPLC, MS R$_t$ [Method] |
|---|---|---|
| 242A | 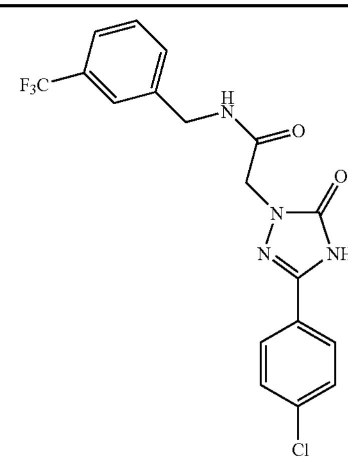 | LC/MS: R$_t$ = 2.09 min [7] [ESIpos]: m/z = 411 (M + H)$^+$ |

153
-continued

| Example No. | Structure | LC/MS or HPLC, MS R_t [Method] |
|---|---|---|
| 243A | 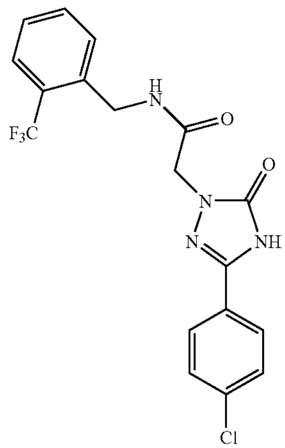 | LC/MS: R_t = 2.06 min [7] [ESIpos]: m/z = 411 (M + H)+ |
| 244A | 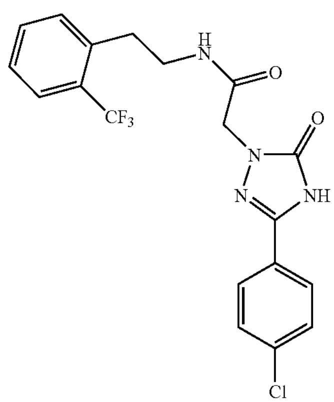 | LC/MS: R_t = 2.37 min [8] [ESIpos]: m/z = 425 (M + H)+ |
| 245A | 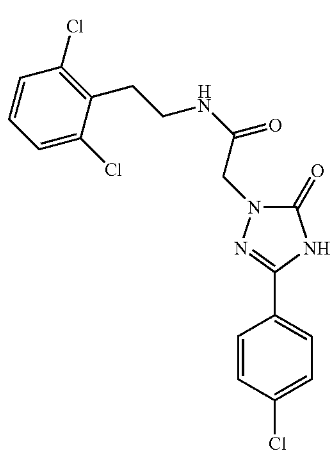 | LC/MS: R_t = 2.37 min [8] [ESIpos]: m/z = 424/426 (M + H)+ |

154

Example 246A

2-[(3-chloro-4-methyl-2-thienyl)carbonyl]-N-isobutylhydrazinecarboxamide

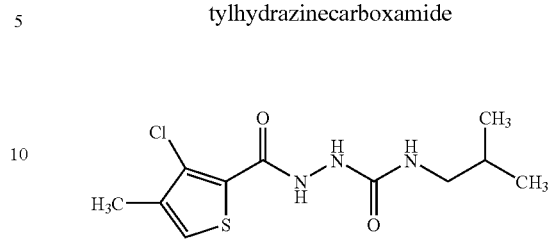

1.00 g (5.25 mmol) of 3-chloro-4-methylthien-2-ylcarboxylic acid hydrazide are placed in 10 ml THF at room temperature. 520 mg (5.25 mmol) of isobutyl isocyanate, dissolved in 2 ml THF, are rapidly added dropwise with stirring. The mixture is further stirred overnight at room temperature. For the workup, the reaction mixture is treated with 10 ml diethyl ether, cooled in the water/ice-bath to about 0° C., and the resulting precipitate recovered by filtration, washed with diethyl ether and dried in vacuo. 1.29 g (85% of theory) of the target compound are thus obtained.

LC/MS [Method 7]: R_t=1.63 min $^1$H-NMR (400 MHz, DMSO-$d_6$): δ=0.84 (d, 6H), 1.59-1.73 (m, 1H), 2.18 (s, 3H), 2.86 (t, 2H), 6.37 (t, 1H), 7.60 (s, 1H), 7.92 (s, 1H), 9.70 (s, 1H).

Example 247A 5-(3-chloro-4-methyl-2-thienyl)-4-isobutyl-2,4-dihydro-3H-1,2,4-triazol-3-one

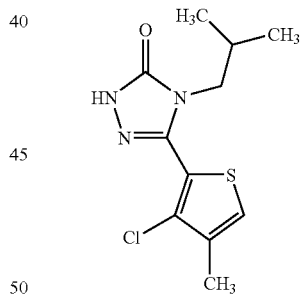

A suspension of 1.28 g (4.42 mmol) of 2-[(3-chloro-4-methyl-2-thienyl)carbonyl]-N-isobutyl-hydrazinecarboxamide from Example 246A in 12 ml 3 N aqueous sodium hydroxide is first heated overnight under reflux. After cooling, it is filtered. The filtrate contains impure product, while the solid filtered off mainly corresponds to the educt. This solid is taken up again in ca. 15 ml of 3 N ethanolic aqueous sodium hydroxide and again heated overnight under reflux. After neutralization with 1 N hydrochloric acid and concentration, the residue together with the concentrated filtrate from the aqueous reaction is purified by preparative HPLC [Method 12]. After evaporation and drying of the product fractions, 562 mg (47% of theory) of the target compound are thus obtained.

LC/MS [Method 8]: R_t=2.13 min.

Example 248A

Ethyl 2-[3-(3-chloro-4-methyl-2-thienyl)-4-isobutyl-5-oxo-4,5-dihydro-1H-1,2,4-triazol-1-yl]-acetate

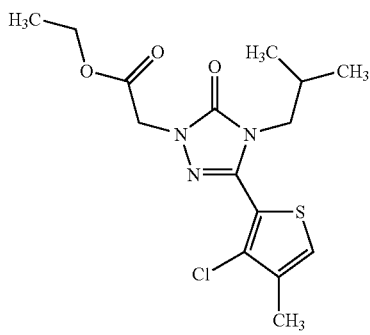

570 mg (4.12 mmol) of potassium carbonate are added to a suspension of 560 mg (2.06 mmol) of 5-(3-chloro-4-methyl-2-thienyl)-4-isobutyl-2,4-dihydro-3H-1,2,4-triazol-3-one from Example 247A and 253 mg (2.06 mmol) of ethyl chloroacetate in 10 ml acetonitrile and heated for 4 hrs under reflux. For the workup, this is concentrated, and the residue taken up in water and extracted three times with ethyl acetate. The combined organic phases are concentrated, and the crude product remaining as the residue is purified by preparative HPLC [Method 12]. 705 mg (96% of theory) of the target compound are thus obtained.

LC/MS [Method 5]: $R_t$=2.49 min.

Example 249A

2-[3-(3-chloro-4-methyl-2-thienyl)-4-isobutyl-5-oxo-4,5-dihydro-1H-1,2,4-triazol-1-yl]-acetic acid

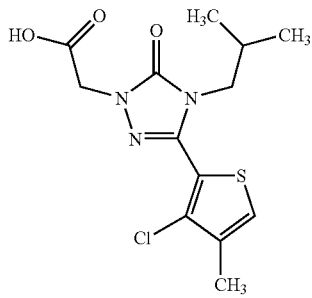

700 mg (1.96 mmol) of ethyl 2-[3-(3-chloro-4-methyl-2-thienyl)-4-isobutyl-5-oxo-4,5-dihydro-1H-1,2,4-triazol-1-yl]-acetate from Example 248A are placed in 10 ml methanol and treated with 1 ml of 20% aqueous potassium hydroxide. This is stirred overnight at room temperature, the reaction mixture is then adjusted to pH 6 with 1 N hydrochloric acid and directly purified by preparative HPLC [Method 12]. 555 mg (86% of theory) of the target compound are thus obtained.

LC/MS [Method 8]: $R_t$=2.17 min;

$^1$H-NMR (400 MHz, DMSO-$d_6$): δ=0.72 (d, 6H), 1.71-1.86 (m, 1H), 2.23 (s, 3H), 3.45 (d, 2H), 4.56 (s, 2H), 7.72 (s, 1H), 13.15 (br. s, 1H).

Example 250A

2-[3-(4-chlorophenyl)-5-oxo-4,5-dihydro-1H-1,2,4-triazol-1-yl]-N-[3-trifluoromethyl)phenylmethyl]-acetamide

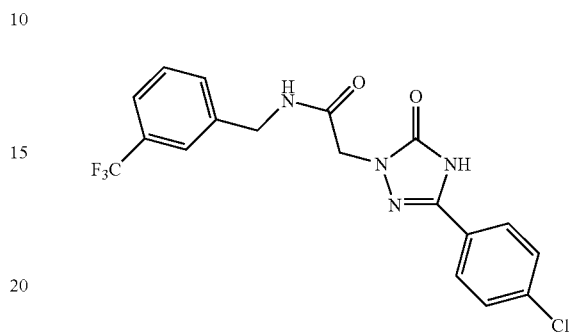

31.8 mg (0.294 mmol) of anisole are added to 780 mg (1.47 mmol) of 2-[3-(4-chlorophenyl)-4-(4-methoxyphenylmethyl)-5-oxo-4,5-dihydro-1H-1,2,4-triazol-1-yl]-N-[3-(trifluoromethyl)phenyl-methyl]-acetamide from Example 153 in 10 ml trifluoroacetic acid and stirred for 72 hrs under reflux. For the workup, the reaction mixture is added to water after cooling and the mixture extracted with ethyl acetate. The organic phase is concentrated, and the residue taken up in methanol and purified by preparative HPLC [Method 12]. In this manner, 360 mg (60% of theory) of the target compound are obtained.

LC/MS [Method 5]: $R_t$=2.22 min;

$^1$H-NMR (400 MHz, DMSO-$d_6$): δ=4.40 (d, 2H), 4.45 (s, 2H), 7.54-7.65 (m, 6H), 7.79, 7.81 (BB' part of an AA'BB' system, 2H), 8.70 (t, 1H), 12.35 (s, 1H).

Example 251A 3-(nitromethyl)-3-[3-(trifluoromethyl)phenyl]oxetane

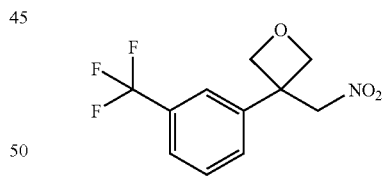

A solution of 103 mg of 1-bromo-3-(trifluoromethyl)benzene (0.46 mmol) in 4 ml anhydrous THF is treated slowly at −78° C. with an n-butyllithium solution (1.6 M in hexane, 312 µl, 0.50 mmol). After 15 mins' stirring at −78° C., a solution of 50 mg (0.43 mmol) of 3-nitromethylenoxetane [Herstellung: G. Wuitschik et al., Agnew. Chem. Int. Ed. 45 (46), 7736-7739 (2006)] in 2 ml THF is added. The mixture is stirred overnight at −78° C. and then the reaction is stopped by addition of 5 ml of saturated ammonium chloride solution at −78° C. After warming to RT, the mixture is diluted with water and extracted three times with dichloromethane. The combined organic phases are dried over sodium sulphate and freed of the volatile components on the rotary evaporator. The oily residue is briefly dried under high vacuum. 53 mg (33% of theory) of the title compound in ca. 70% purity are obtained.

GC/MS [Method 21]: $R_t$=5.44 min; m/z=201 [M-CH$_2$NO$_2$]$^+$ $^1$H-NMR (400 MHz, CDCl$_3$): δ=4.95 (d, 2H), 5.07 (s, 2H), 5.09 (d, 2H), 7.31 (d, 1H), 7.36 (s, 1H), 7.53 (t, 1H), 7.60 (d, 1H).

Example 252A

1-{3-[3-(trifluoromethyl)phenyl]oxetan-3-yl}-methanamine hydrochloride

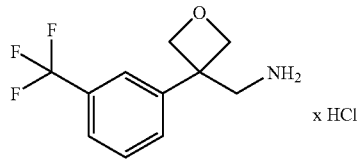

50 mg of the compound from Example 251A (0.134 mmol) in 2 ml ethanol are hydrogenated overnight under 1 atm hydrogen at RT in the presence of 15 mg (0.11 mmol) of palladium hydroxide (20% on charcoal). The catalyst is then filtered off, and the filtrate is diluted with water, adjusted to pH 1 with 1 N hydrochloric acid and washed twice with dichloromethane. The aqueous phase is adjusted to pH 13 with 2 N aqueous sodium hydroxide and extracted three times with dichloromethane. The latter organic phases are combined, dried over sodium sulphate and filtered. The filtrate is treated with 200 μl of a 4 N solution of hydrogen chloride in dioxan and concentrated on the rotary evaporator. The residue is dried under high vacuum. 20 mg of the title compound are obtained, which is further used as the crude product (purity ca. 60%).

LC/MS [Method 22]: $R_t$=0.47 min; m/z=231 [M+H]$^+$.

Practical Examples

Example 1

2-[3-(4-chlorophenyl)-4-cyclopropyl-5-oxo-4,5-dihydro-1H-1,2,4-triazol-1-yl]-N-[3-(trifluoro-methyl)phenylmethyl]-acetamide

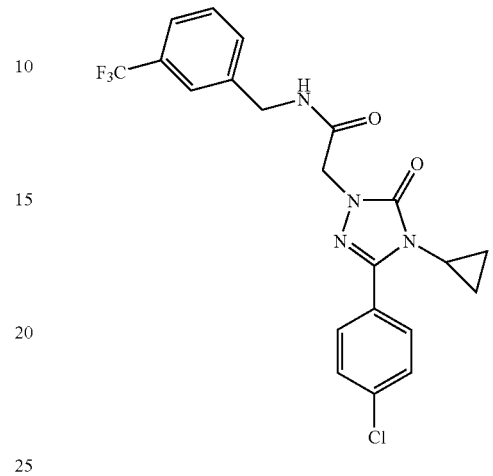

50.0 mg (0.170 mmol) of [3-(4-chlorophenyl)-4-cyclopropyl-5-oxo-4,5-dihydro-1H-1,2,4-triazol-1-yl]-acetic acid from Example 88A and 32.8 mg (0.187 mmol) of 3-trifluoromethylbenzylamine are placed in 2 ml dimethylformamide and treated with 27.6 mg (0.204 mmol) of HOBt. After 10 mins' stirring, 42.4 mg (0.221 mmol) of EDC hydrochloride are added and the mixture stirred overnight at room temperature. For the workup, the reaction mixture is partitioned between dichloromethane and water, and the organic phase is separated, dried over sodium sulphate and concentrated. The residue is purified by flash chromatography on silica gel (eluent: dichloromethane/methanol first 200:1, then 100:1) and thus yields 76 mg (99% of theory) of the target compound.

MS [ESIpos]: m/z=451 (M+H)$^+$

HPLC [Method 1]: $R_t$=4.74 min $^1$H-NMR (400 MHz, DMSO-d$_6$): δ=0.59 (m, 2H), 0.90 (m, 2H), 3.18 (tt, 1H), 4.40 (d, 2H), 4.44 (s, 2H), 7.53-7.66 (m, 6H), 7.80 (d, 2H), 8.67 (t, 1H).

The following compounds are prepared analogously:

| Example No. | Structure | LC/MS or HPLC, MS $R_t$ [Method] | $^1$H-NMR (400 MHz, DMSO-d$_6$) |
|---|---|---|---|
| 2 | 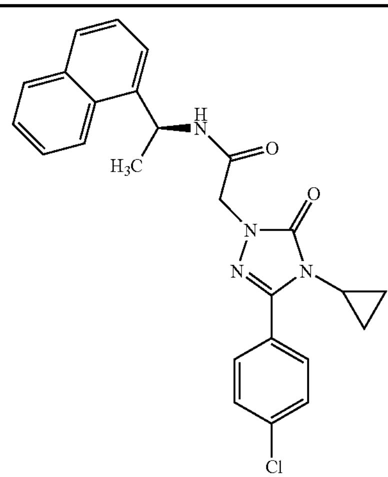 | MS [ESIpos]: m/z = 447 (M + H)$^+$; $R_t$ = 4.73 min [2] | δ = 0.56 (m, 2H), 0.89 (m, 2H), 1.51 (d, 3H), 3.16 (tt, 1H), 4.42 (s, 2H), 5.71 (dq, 1H), 7.46-7.56 (m, 4H), 7.58 (d, 2H), 7.78 (d, 2H), 7.83 (d, 1H), 7.94 (d, 1H), 8.09 (d, 1H), 8.75 (d, 1H). |

-continued

| Example No. | Structure | LC/MS or HPLC, MS R_t [Method] | $^1$H-NMR (400 MHz, DMSO-d_6) |
|---|---|---|---|
| 3 | 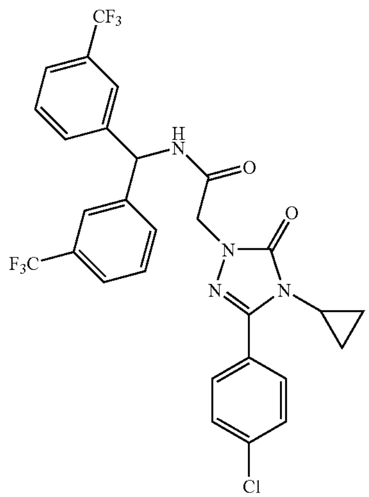 | MS [ESIpos]: m/z = 595 (M + H)+; R_t = 5.16 min [1] | δ = 0.57 (m, 2H), 0.89 (m, 2H), 3.17 (tt, 1H), 4.46 (s, 2H), 6.38 (d, 1H), 7.56-7.69 (m, 8H), 7.73 (br. s, 2H), 7.78 (d, 2H), 9.28 (d, 1H). |
| 4 | 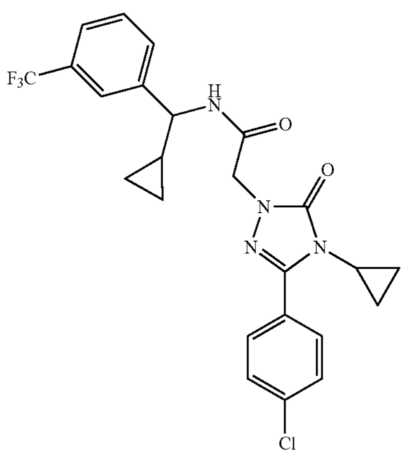 | MS [ESIpos]: m/z = 491 (M + H)+; R_t = 4.86 min [1] | δ = 0.32-0.60 (m, 6H), 0.89 (m, 2H), 1.17 (m, 1H), 3.17 (tt, 1H), 4.30 (m, 1H), 4.45 (s, 2H), 7.54-7.73 (m, 6H), 7.79 (d, 2H), 8.84 (d, 1H). |
| 5 | lp;1p | MS [ESIpos]: m/z = 495/497 (M + H)+; R_t = 4.69 min [1] | δ = 0.60 (m, 2H), 0.90 (m, 2H), 3.17 (tt, 1H), 4.41 (d, 2H), 4.45 (s, 2H), 7.53-7.64 (m, 4H), 7.73 (br. s, 4H), 8.66 (t, 1H). |

-continued

| Example No. | Structure | LC/MS or HPLC, MS $R_t$ [Method] | $^1$H-NMR (400 MHz, DMSO-$d_6$) |
|---|---|---|---|
| 6 | 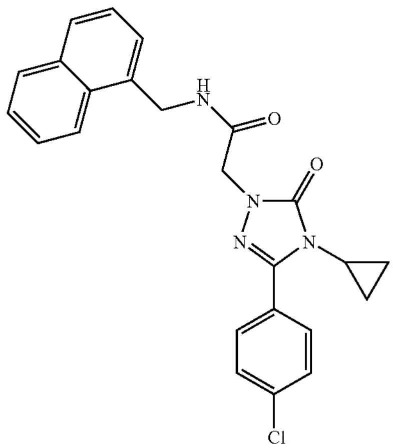 | MS [ESIpos]: m/z = 433 (M + H)$^+$; $R_t$ = 4.60 min [2] | δ = 0.60 (m, 2H), 0.91 (m, 2H), 3.18 (tt, 1H), 4.45 (s, 2H), 4.78 (d, 2H), 7.44-7.50 (m, 2H), 7.52-7.58 (m, 2H), 7.61 (d, 2H), 7.82 (d, 2H), 7.86 (m, 1H), 7.96 (m, 1H), 8.07 (m, 1H), 8.63 (t, 1H). |
| 7 | 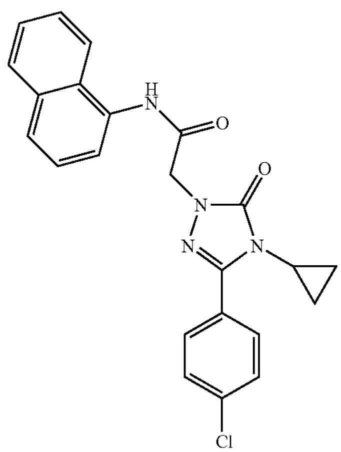 | MS [ESIpos]: m/z = 419 (M + H)$^+$; $R_t$ = 4.52 min [2] | δ = 0.62 (m, 2H), 0.92 (m, 2H), 3.21 (tt, 1H), 4.78 (s, 2H), 7.50 (t, 1H), 7.56 (t, 2H), 7.62 (d, 2H), 7.67 (d, 1H), 7.80 (d, 1H), 7.86 (d, 2H), 7.95 (t, 1H), 8.13 (m, 1H), 10.14 (s, 1H). |
| 8 | 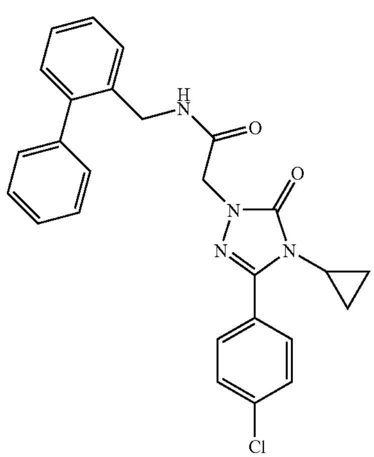 | MS (CIpos): m/z = 476 (M + NH$_4$)$^+$, 459 (M + H)$^+$; $R_t$ = 4.79 min [2] | δ = 0.58 (m, 2H), 0.90 (m, 2H), 3.17 (tt, 1H), 4.22 (d, 2H), 4.40 (s, 2H), 7.22 (m, 1H), 7.31-7.48 (m, 8H), 7.60 (d, 2H), 7.81 (d, 2H), 8.49 (t, 1H). |

-continued

| Example No. | Structure | LC/MS or HPLC, MS R$_t$ [Method] | $^1$H-NMR (400 MHz, DMSO-d$_6$) |
|---|---|---|---|
| 9 | 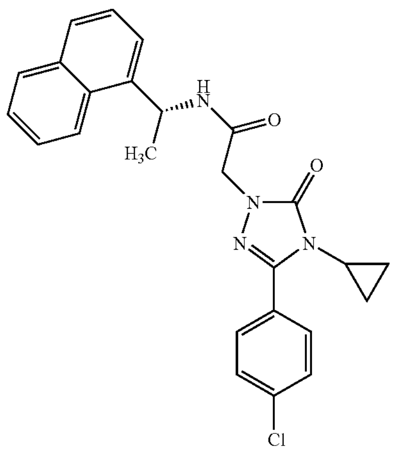 | MS [ESIpos]: m/z = 447 (M + H)$^+$; R$_t$ = 4.52 min [1] | δ = 0.57 (m, 2H), 0.89 (m, 2H), 1.52 (d, 3H), 3.16 (tt, 1H), 4.43 (s, 2H), 5.71 (dq, 1H), 7.46-7.61 (m, 6H), 7.78 (d, 2H), 7.84 (d, 1H), 7.94 (d, 1H), 8.09 (br. d, 1H), 8.75 (d, 1H). |
| 10 | 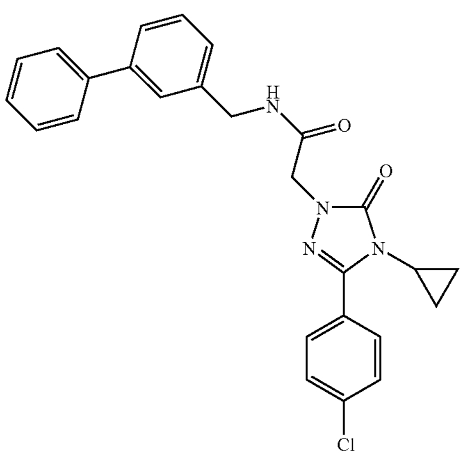 | MS [ESIpos]: m/z = 459 (M + H)$^+$ | δ = 0.60 (m, 2H), 0.90 (m, 2H), 3.17 (tt, 1H), 4.39 (d, 2H), 4.45 (s, 2H), 7.27 (br. d, 1H), 7.33-7.47 (m, 4H), 7.52-7.60 (m, 4H), 7.65 (d, 2H), 7.80 (d, 2H), 8.61 (t, 1H). |
| 11 | 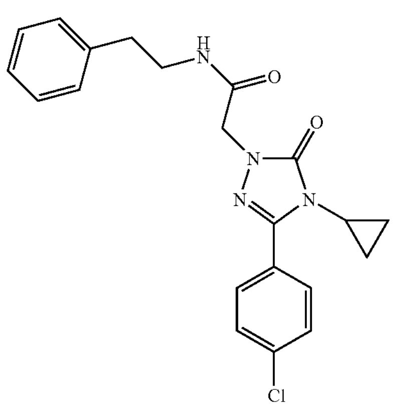 | R$_t$ = 2.28 min [5] | δ = 0.59 (m, 2H), 0.91 (m, 2H), 2.72 (t, 2H), 3.18 (tt, 1H), 4.33 (s, 2H), 7.17-7.31 (m, 5H), 7.60 (d, 2H), 7.81 (d, 2H), 8.14 (t, 1H). |

| Example No. | Structure | LC/MS or HPLC, MS $R_t$ [Method] | $^1$H-NMR (400 MHz, DMSO-$d_6$) |
|---|---|---|---|
| 12 | (4-CF₃-phenyl)-C(CH₃)₂-NH-C(O)-CH₂-[4-cyclopropyl-5-(4-chlorophenyl)-3-oxo-1,2,4-triazol-1-yl] | MS [ESIpos]: m/z = 479 (M + H)⁺; $R_t$ = 4.85 min [1] | δ = 0.55 (m, 2H), 0.88 (m, 2H), 1.57 (s, 6H), 3.15 (tt, 1H), 4.43 (s, 2H), 7.53-7.64 (m, 6H), 7.78 (d, 2H), 8.55 (s, 1H). |
| 13 | (3-F-benzyl)-NH-C(O)-CH₂-[4-cyclopropyl-5-(4-chlorophenyl)-3-oxo-1,2,4-triazol-1-yl] | MS [ESIpos]: m/z = 401 (M + H)⁺ | δ = 0.60 (m, 2H), 0.90 (m, 2H), 3.18 (tt, 1H), 4.33 (d, 2H), 4.45 (s, 2H), 7.03-7.14 (m, 3H), 7.36 (dd, 1H), 7.60 (d, 2H), 7.82 (d, 2H), 8.61 (t, 1H). |
| 14 | (phenyl)(CH₃)CH-NH-C(O)-CH₂-[4-cyclopropyl-5-(4-chlorophenyl)-3-oxo-1,2,4-triazol-1-yl] | MS [ESIpos]: m/z = 397 (M + H)⁺ | δ = 0.57 (m, 2H), 0.89 (m, 2H), 1.37 (d, 3H), 3.17 (tt, 1H), 4.41 (s, 2H), 4.91 (dq, 1H), 7.20-7.35 (m, 5H), 7.59 (d, 2H), 7.80 (d, 2H), 8.58 (d, 1H). |

| Example No. | Structure | LC/MS or HPLC, MS $R_t$ [Method] | $^1$H-NMR (400 MHz, DMSO-d$_6$) |
| --- | --- | --- | --- |
| 15 | 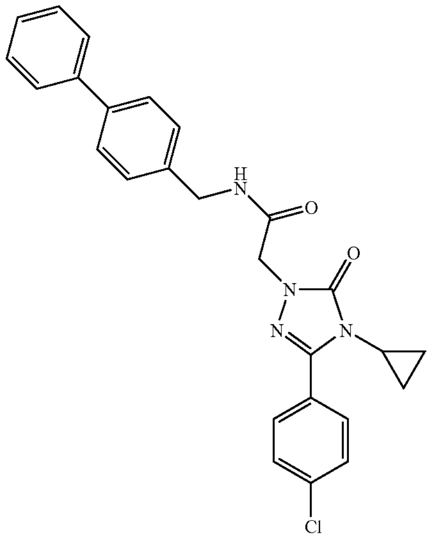 | MS [CIpos]: m/z = 476 (M + NH$_4$)$^+$, 459 (M + H)$^+$; $R_t$ = 4.79 min [2] | δ = 0.60 (m, 2H), 0.91 (m, 2H), 3.18 (tt, 1H), 4.35 (d, 2H), 4.44 (s, 2H), 7.33-7.49 (m, 5H), 7.58-7.68 (m, 6H), 7.82 (d, 2H), 8.60 (t, 1H). |
| 16 | 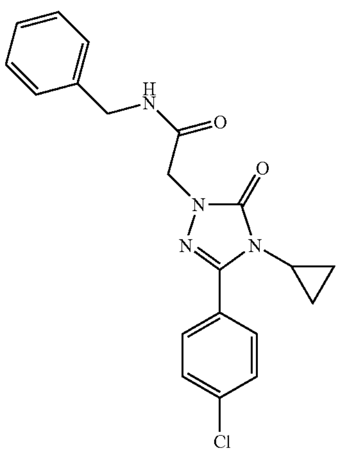 | $R_t$ = 2.20 min [5] | δ = 0.59 (m, 2H), 0.90 (m, 2H), 3.18 (tt, 1H), 4.31 (d, 2H), 4.43 (s, 2H), 7.21-7.36 (m, 5H), 7.60 (d, 2H), 7.81 (d, 2H), 8.56 (t, 1H). |
| 17 | 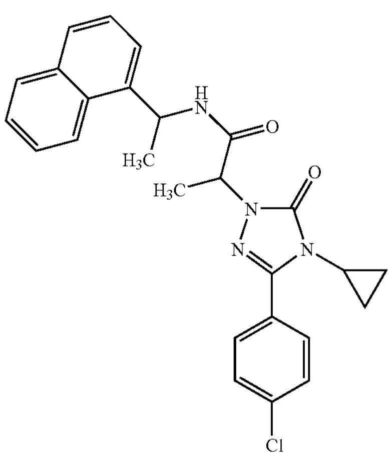 | MS [CIpos]: m/z = 478 (M + NH$_4$)$^+$, 461 (M + H)$^+$; $R_t$ = 4.88 min [2] | |

| Example No. | Structure | LC/MS or HPLC, MS R_t [Method] | $^1$H-NMR (400 MHz, DMSO-d$_6$) |
|---|---|---|---|
| 18 | 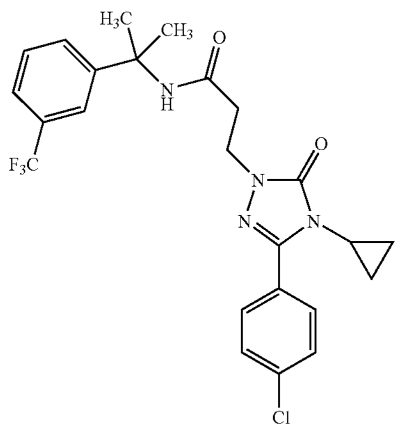 | MS [ESIpos]: m/z = 493 (M + H)$^+$; R_t = 4.80 min [1] | δ = 0.56 (m, 2H), 0.89 (m, 2H), 1.52 (s, 6H), 2.59 (t, 2H), 3.15 (tt, 1H), 3.87 (t, 2H), 7.43 (t, 1H), 7.49-7.64 (m, 5H), 7.81 (d, 2H), 8.32 (t, 1H). |
| 19 | 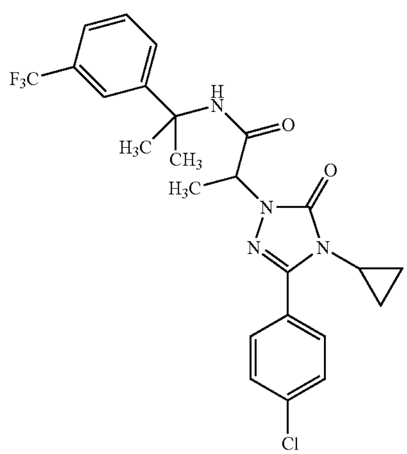 | MS [ESIpos]: m/z = 493 (M + H)$^+$; R_t = 4.96 min [1] | δ = 0.56 (m, 2H), 0.89 (m, 2H), 1.53 (d, 3H), 1.56 (s, 3H), 1.58 (s, 3H), 3.15 (tt, 1H), 4.81 (q, 1H), 7.47-7.60 (m, 5H), 7.64 (br. d, 1H), 7.78 (d, 2H), 8.43 (s, 1H). |
| 20 | 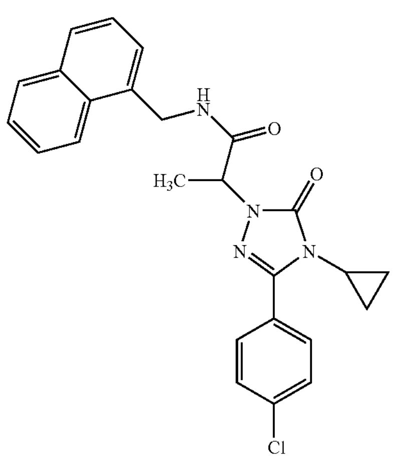 | MS [CIpos]: m/z = 464 (M + NH$_4$)$^+$, 447 (M + H)$^+$; R_t = 4.77 min [2] | δ = 0.58 (m, 2H), 0.89 (m, 2H), 1.55 (d, 3H), 3.16 (tt, 1H), 4.73 (dd, 1H), 4.79 (dd, 1H), 4.82 (q, 1H), 7.42-7.48 (m, 2H), 7.50-7.56 (m, 2H), 7.60 (d, 2H), 7.80 (d, 2H), 7.84 (m, 1H), 7.94 (m, 1H), 8.04 (m, 1H), 8.44 (t, 1H). |

| Example No. | Structure | LC/MS or HPLC, MS R$_t$ [Method] | $^1$H-NMR (400 MHz, DMSO-d$_6$) |
|---|---|---|---|
| 21 | 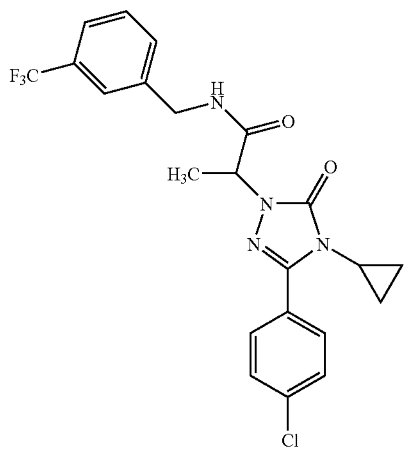 | MS [CIpos]: m/z = 482 (M + NH$_4$)$^+$, 465 (M + H)$^+$; R$_t$ = 4.78 min [2] | δ = 0.61 (m, 2H), 0.90 (m, 2H), 1.53 (d, 3H), 3.16 (tt, 1H), 4.34 (dd, 1H), 4.44 (dd, 1H), 4.80 (q, 1H), 7.51-7.63 (m, 6H), 7.80 (d, 2H), 8.48 (s, 1H). |
| 22 | 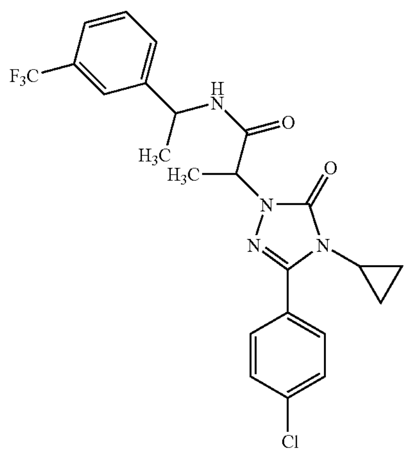 | MS [ESIpos]: m/z = 479 (M + H)$^+$; R$_t$ = 4.87 min [1] | |
| 23 | 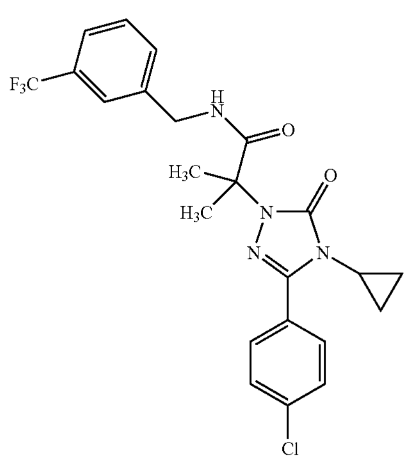 | MS [ESIpos]: m/z = 479 (M + H)$^+$; R$_t$ = 4.89 min [2] | δ = 0.56 (m, 2H), 0.87 (m, 2H), 1.64 (s, 6H), 3.13 (tt, 1H), 4.37 (d, 2H), 7.50-7.67 (m, 6H), 7.82 (d, 2H), 8.31 (s, 1H). |

-continued
| Example No. | Structure | LC/MS or HPLC, MS $R_t$ [Method] | $^1$H-NMR (400 MHz, DMSO-$d_6$) |
|---|---|---|---|
| 24 | 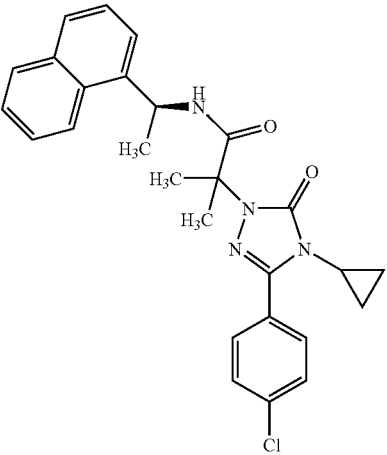 | MS [ESIpos]: m/z = 475 (M + H)$^+$; $R_t$ = 4.99 min [2] | δ = 0.55 (m, 2H), 0.89 (m, 2H), 1.49 (d, 3H), 1.62 (d, 6H), 3.13 (tt, 1H), 5.71 (dq, 1H), 7.42-7.61 (m, 6H), 7.80 (m, 3H), 7.93 (m, 1H), 8.08 (br. d, 1H), 8.17 (d, 1H). |
| 25 | 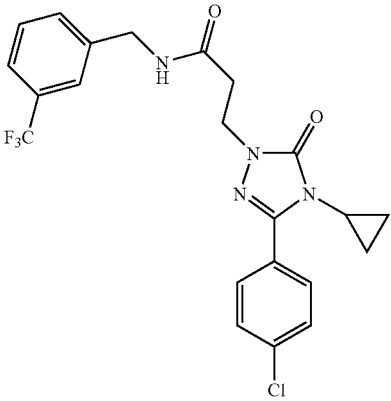 | MS [ESIpos]: m/z = 465 (M + H)$^+$; $R_t$ = 4.55 min [1] | δ = 0.56 (m, 2H), 0.88 (m, 2H), 2.62 (t, 2H), 3.13 (tt, 1H), 3.95 (t, 2H), 4.35 (d, 2H), 7.43-7.61 (m, 6H), 7.77 (d, 2H), 8.57 (t, 1H). |
| 26 | 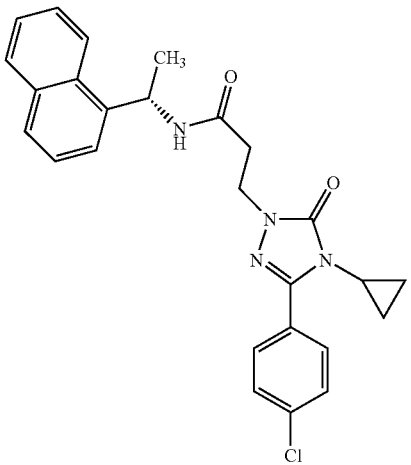 | MS [ESIpos]: m/z = 461 (M + H)$^+$; $R_t$ = 4.63 min [1] | δ = 0.54 (m, 2H), 0.87 (m, 2H), 1.45 (d, 3H), 2.60 (t, 2H), 3.12 (tt, 1H), 3.92 (m, 2H), 5.69 (dq, 1H), 7.39 (t, 1H), 7.47-7.55 (m, 3H), 7.58 (d, 2H), 7.75 (d, 2H), 7.80 (d, 1H), 7.93 (m, 1H), 8.07 (m, 1H), 8.56 (d, 1H). |

Example 27

2-[3-(4-chlorophenyl)-4-cyclopropyl-5-oxo-4,5-di-hydro-1H-1,2,4-triazol-1-yl]-N-{1-[3-(trifluoromethyl)phenyl]ethyl}acetamide

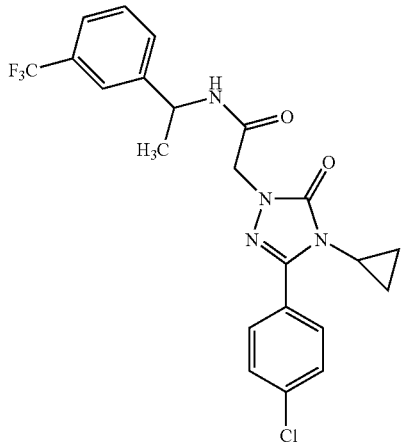

40.0 mg (0.136 mmol) of [3-(4-chlorophenyl)-4-cyclopropyl-5-oxo-4,5-dihydro-1H-1,2,4-triazol-1-yl]-acetic acid from Example 88A, 28.3 mg (0.150 mmol) of 1-[(3-trifluoromethyl)phenyl]-ethylamine and 22.1 mg (0.163 mmol) of HOBt are placed in 1 ml dimethylformamide and treated with 33.9 mg (0.177 mmol) of EDC hydrochloride. The mixture is stirred overnight at room temperature and then treated with 15 ml of water for the workup. The resulting precipitate is isolated by filtration and then purified by preparative HPLC [Method 9]. 20 mg (32% of theory) of the target compound are thus obtained.

LC/MS [Method 7]: $R_t$=2.34 min $^1$H-NMR (400 MHz, DMSO-$d_6$): δ=0.50-0.64 (m, 2H), 0.82-0.96 (m, 2H), 1.39 (d, 3H), 3.17 (dddd, 1H), 4.42 (s, 2H), 5.00 (dq, 1H), 7.52-7.69 (m, 4H), 7.57, 7.60 (AA' part of an AA'BB' system, 2H), 7.78, 7.80 (BB' part of an AA'BB' system, 2H), 8.71 (d, 1H).

The following compounds are prepared analogously:

| Example No. | Structure | LC/MS $R_t$ [Method] | $^1$H-NMR (400 MHz, DMSO-$d_6$) |
|---|---|---|---|
| 28 | 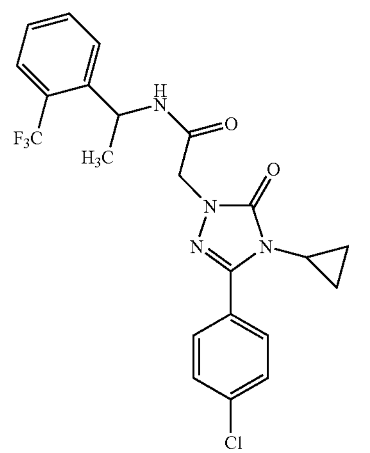 | $R_t$ = 2.48 min [5] | δ = 0.49-0.62 (m, 2 H), 0.81-0.96 (m, 2 H), 1.36 (d, 3 H), 3.16(dddd, 1 H), 4.41 (centre of an AB system, 2 H), 5.20 (dq, 1 H), 7.45 (t, 1 H), 7.57, 7.59 (AA' part of an AA'BB' system, 2 H), 7.64-7.73 (m, 3 H), 7.77, 7.79 (BB' part of an AA'BB' system, 2 H), 8.83 (d, 1 H). |
| 29 | 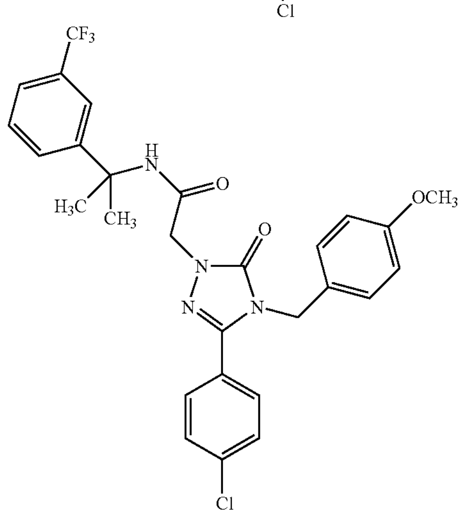 | $R_t$ = 2.68 min [7] | δ = 1.60 (s, 6 H), 3.68 (s, 3 H), 4.52 (s, 2 H), 4.89 (s, 2 H), 6.80, 6.82 (AA' part of an AA'BB' system, 2 H), 6.96, 6.98 (BB' part of an AA'BB' system, 2 H), 7.49-7.57 (m, 6 H), 7.63 (s, 1 H), 7.68 (d, 1 H), 8.59 (s, 1 H). |

| Example No. | Structure | LC/MS $R_t$ [Method] | $^1$H-NMR (400 MHz, DMSO-$d_6$) |
|---|---|---|---|
| 30 | 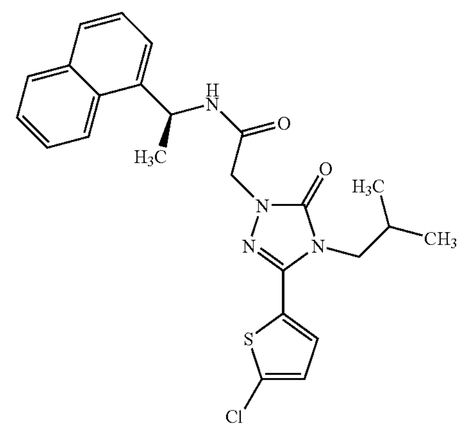 | $R_t$ = 2.62 min [7] | δ = 0.81 (d, 6 H), 1.51 (d, 3 H), 1.87 (m, 1 H), 3.67 (d, 2 H), 4.47 (s, 2 H), 5.70 (dq, 1 H), 7.26 (d, 1 H), 7.45-7.60 (m, 5 H), 7.84 (d, 1 H), 7.91-7.97 (m, 1 H), 8.09 (d, 1 H), 8.80 (d, 1 H). |
| 31 | 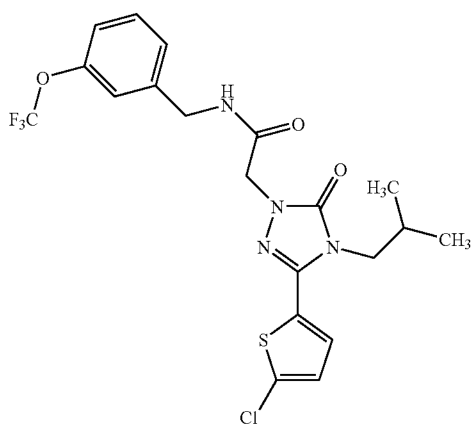 | $R_t$ = 2.58 min [7] | δ = 0.83 (d, 6 H), 1.90 (m, 1 H), 3.69 (d, 2 H), 4.36 (d, 2 H), 4.49 (s, 2 H), 7.21-7.34 (m, 4 H), 7.43-7.50 (m, 2 H), 8.70 (t, 1 H). |
| 32 | 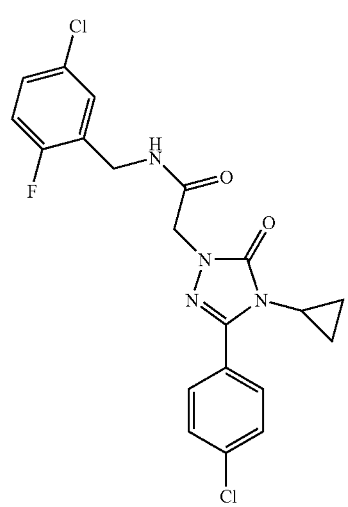 | $R_t$ = 2.36 min [5] | δ = 0.53-0.67 (m, 2 H), 0.83-0.97 (m, 2 H), 3.18 (dddd, 1 H), 4.33 (d, 2 H), 4.46 (s, 2 H), 7.21-7.28 (m, 1 H), 7.34-7.40 (m, 2 H), 7.59, 7.61 (AA' part of an AA'BB' system, 2 H), 7.81, 7.83 (BB' part of an AA'BB' system, 2 H), 8.62 (t, 1 H). |

| Example No. | Structure | LC/MS $R_t$ [Method] | $^1$H-NMR (400 MHz, DMSO-$d_6$) |
|---|---|---|---|
| 33 | (structure: 2-chloro-5-(trifluoromethyl)benzyl amide linked to CH$_2$-triazolone with 4-cyclopropyl and 5-(4-chlorophenyl)) | $R_t$ = 2.53 min [5] | δ = 0.56-0.63 (m, 2 H), 0.83-0.97 (m, 2 H), 3.18 (dddd, 1 H), 4.44 (d, 2 H), 4.49 (s, 2 H), 7.58, 7.60 (AA' part of an AA'BB' system, 2 H), 7.65-7.73 (m, 3 H), 7.80, 7.82 (BB' part of an AA'BB' system, 2 H), 8.71 (t, 1 H). |
| 34 | (structure: 2-fluoro-5-(trifluoromethyl)benzyl amide linked to CH$_2$-triazolone with 4-cyclopropyl and 5-(4-chlorophenyl)) | $R_t$ = 2.44 min [5] | δ = 0.53-0.66 (m, 2 H), 0.83-0.97 (m, 2 H), 3.17 (dddd, 1 H), 4.41 (d, 2 H), 4.45 (s, 2 H), 7.44 (t, 1 H), 7.58, 7.60 (AA' part of an AA'BB' system, 2 H), 7.68-7.75 (m, 2 H), 7.79, 7.81 (BB' part of an AA'BB' system, 2 H), 8.67 (t, 1 H). |
| 35 | (structure: 2,5-dichlorobenzyl amide linked to CH$_2$-triazolone with 4-cyclopropyl and 5-(4-chlorophenyl)) | $R_t$ = 2.46 min [5] | δ = 0.54-0.67 (m, 2 H), 0.84-0.98 (m, 2 H), 3.18 (dddd, 1 H), 4.36 (d, 2 H), 4.49 (s, 2 H), 7.35-7.43 (m, 2 H), 7.49 (d, 1 H0, 7.59, 7.61 (AA' part of an AA'BB' system, 2 H), 7.82, 7.84 (BB' part of an AA'BB' system, 2 H), 8.65 (t, 1 H). |

| Example No. | Structure | LC/MS $R_t$ [Method] | $^1$H-NMR (400 MHz, DMSO-$d_6$) |
|---|---|---|---|
| 36 | 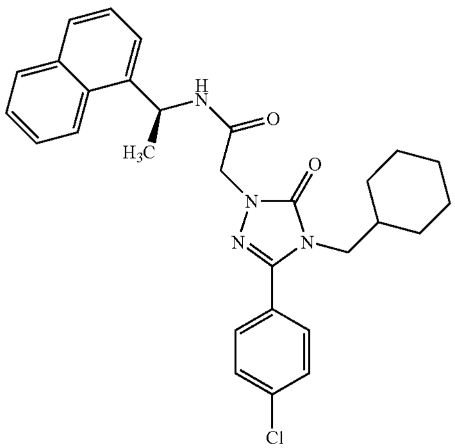 | $R_t$ = 2.99 min [5] | δ = 0.66-0.79 (m, 2 H), 0.92-1.09 (m, 3 H), 1.34-1.45 (m, 3 H), 1.46-1.57 (m, 3 H), 1.51 (d, 3 H), 3.62 (d, 2 H), 4.47 (s, 2 H), 5.70 (dq, 1 H), 7.46-7.67 (m, 8 H), 7.84 (d, 1 H), 7.92-7.97 (m, 1 H), 8.07-8.12 (m, 1 H), 8.78 (d, 1 H). |
| 37 | 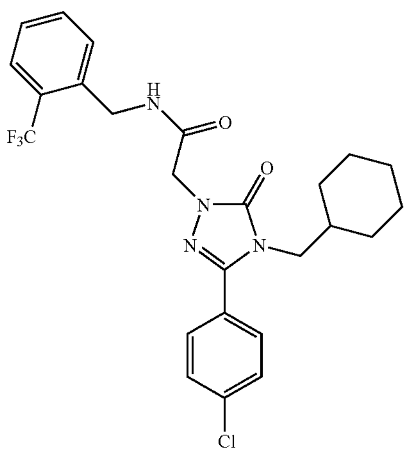 | $R_t$ = 2.91 min [5] | δ = 0.68-0.82 (m, 2 H), 0.94-1.10 (m, 3 H), 1.36-1.62 (m, 6 H), 3.63 (d, 2 H), 4.49 (d, 2 H), 4.54 (s, 2 H), 7.48 (t, 1 H), 7.56 (d, 1 H), 7.60-7.74 (m, 6 H), 8.70 (t, 1 H). |
| 38 | 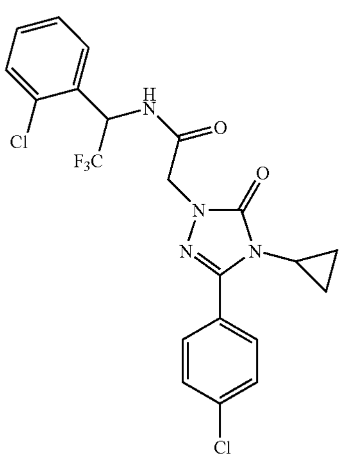 | $R_t$ = 2.68 min [4] | δ = 0.49-0.64 (m, 2 H), 0.81-0.96 (m, 2 H), 3.18 (dddd, 1 H), 4.57 (centre of an AB system, 2 H), 6.17-6.29 (m, 1 H), 7.44-7.54 (m, 2 H), 7.54-7.62 (m, 1 H), 7.57, 7.59 (AA' part of an AA'BB' system, 2 H), 7.74 (d, 1 H), 7.77, 7.80 (BB' part of an AA'BB' system, 2 H), 9.67 (d, 1 H). |

| Example No. | Structure | LC/MS $R_t$ [Method] | $^1$H-NMR (400 MHz, DMSO-$d_6$) |
|---|---|---|---|
| 39 | 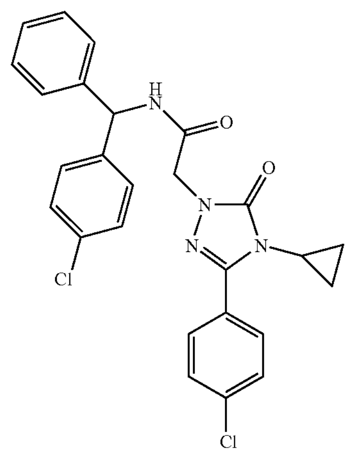 | $R_t$ = 2.83 min [4] | δ = 0.49-0.64 (m, 2 H), 0.82-0.97 (m, 2 H), 3.17 (dddd, 1 H), 4.52 (s, 2 H), 6.11 (d, 1 H), 7.23-7.43 (m, 9 H), 7.58, 7.60 (AA' part of an AA'BB' system, 2 H), 7.78, 7.81 (BB' part of an AA'BB' system, 2 H), 9.09 (d, 1 H). |
| 40 | 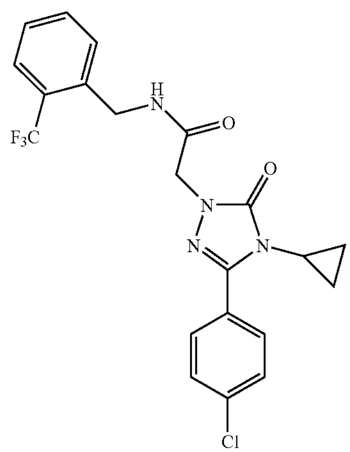 | $R_t$ = 2.55 min [4] | δ = 0.52-0.67 (m, 2 H), 0.83-0.98 (m, 2 H), 3.18 (dddd, 1 H), 4.49 (br. s, 4 H), 7.48 (t, 1 H), 7.56 (d, 1 H), 7.60, 7.62 (AA' part of an AA'BB' system, 2 H), 7.66 (t, 1 H), 7.72 (d, 1 H), 7.81, 7.83 (BB' part of an AA'BB' system, 2 H), 8.66 (t, 1 H). |
| 41 | 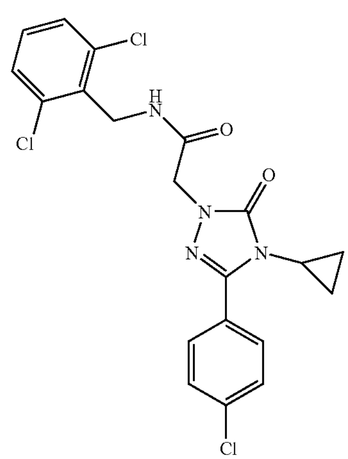 | $R_t$ = 2.51 min [4] | δ = 0.50-0.65 (m, 2 H), 0.82-0.97 (m, 2 H), 3.18 (dddd, 1 H), 4.37 (s, 2 H), 4.53 (d, 2 H), 7.38 (t, 1 H), 7.50 (d, 2 H), 7.58, 7.60 (AA' part of an AA'BB' system, 2 H), 7.80, 7.82 (BB' part of an AA'BB' system, 2 H), 8.39 (t, 1 H). |

-continued

| Example No. | Structure | LC/MS $R_t$ [Method] | $^1$H-NMR (400 MHz, DMSO-$d_6$) |
|---|---|---|---|
| 42 | (3-chlorophenyl)-CH(CH₃)-NH-C(O)-CH₂-[4-cyclopropyl-5-(4-chlorophenyl)-3-oxo-1,2,4-triazol-1-yl] | $R_t$ = 2.42 min [5] | δ = 0.50-0.64 (m, 2 H), 0.82-0.97 (m, 2 H), 1.37 (d, 3 H), 3.17 (dddd, 1 H), 4.42 (centre of an AB system, 2 H), 4.91 (dq, 1 H), 7.26-7.40 (m, 4 H), 7.58, 7.60 (AA' part of an AA'BB' system, 2 H), 7.79, 7.81 (BB' part of an AA'BB' system, 2 H), 8.63 (t, 1 H). |

Further, the following are obtained analogously:

| Example No. | Structure | LC/MS $R_t$ [Method] |
|---|---|---|
| 43 | (naphthalen-2-yl)-CH(CH₃)-NH-C(O)-CH₂-[4-cyclopropyl-5-(4-chlorophenyl)-3-oxo-1,2,4-triazol-1-yl] | $R_t$ = 2.67 min [4] |
| 44 | (naphthalen-1-yl)-CH(CH₃)-NH-C(O)-CH₂-[4-cyclopropyl-5-(4-chlorophenyl)-3-oxo-1,2,4-triazol-1-yl] | $R_t$ = 2.33 min [7] |

| Example No. | Structure | LC/MS $R_t$ [Method] |
|---|---|---|
| 45 | 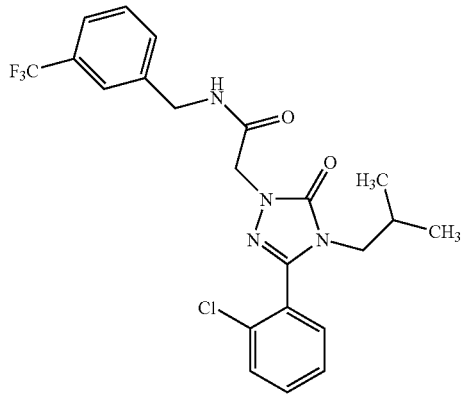 | $R_t$ = 2.37 min [7] |
| 46 | 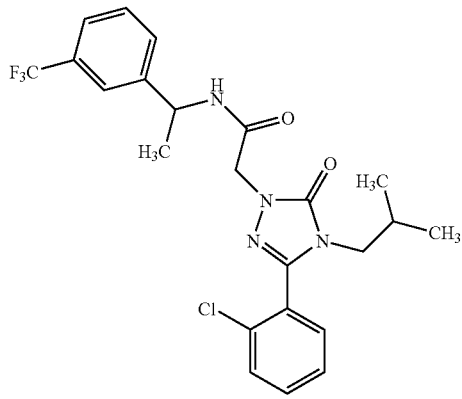 | $R_t$ = 2.45 min [7] |
| 47 | 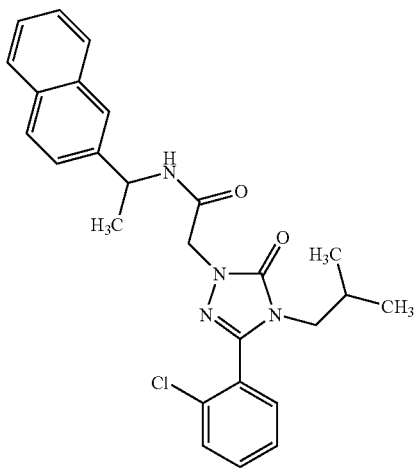 | $R_t$ = 2.45 min [7] |

-continued
| Example No. | Structure | LC/MS $R_t$ [Method] |
|---|---|---|
| 48 | 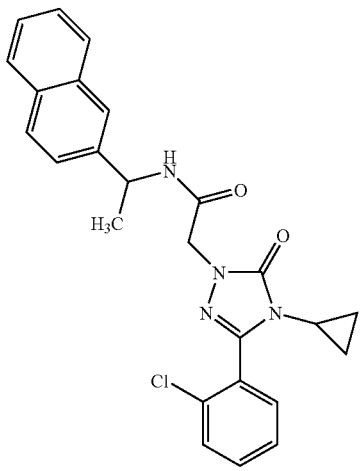 | $R_t$ = 2.22 min [7] |
| 49 | 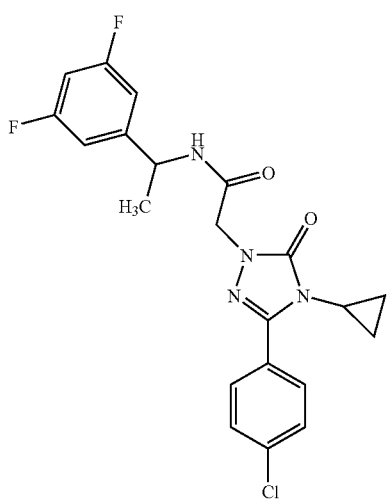 | $R_t$ = 2.20 min [7] |
| 50 | 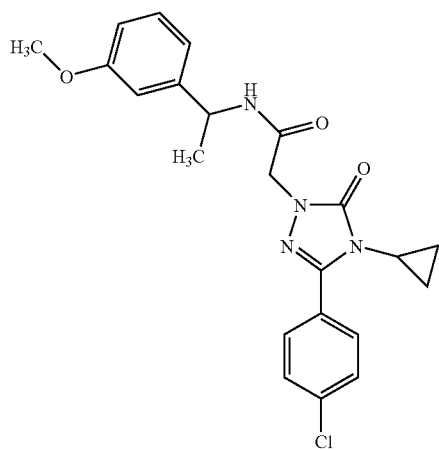 | $R_t$ = 2.42 min [4] |

-continued
| Example No. | Structure | LC/MS $R_t$ [Method] |
|---|---|---|
| 51 | 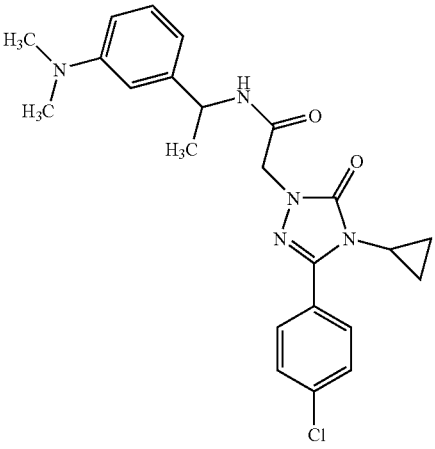 | $R_t$ = 1.76 min [7] |
| 52 | 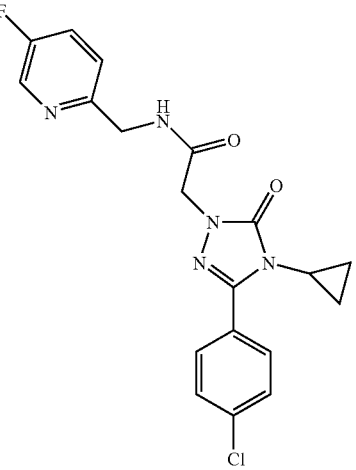 | $R_t$ = 1.75 min [7] |
| 53 | 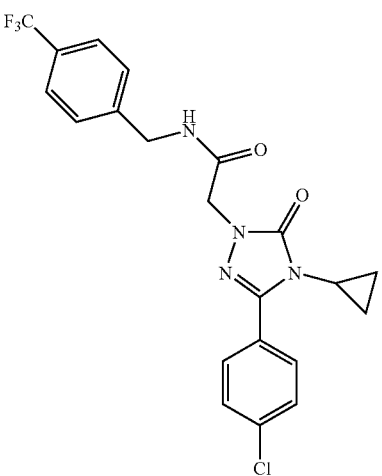 | $R_t$ = 2.62 min [4] |

-continued
| Example No. | Structure | LC/MS R_t [Method] |
|---|---|---|
| 54 | 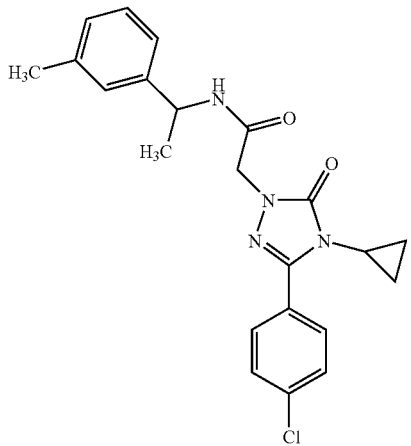 | R_t = 2.22 min [7] |
| 55 | 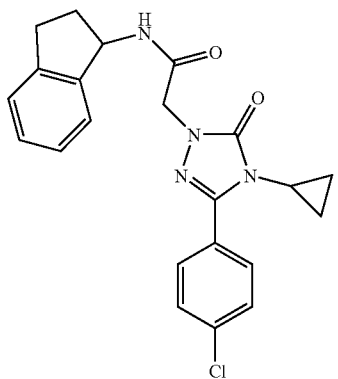 | R_t = 2.42 min [4] |
| 56 | 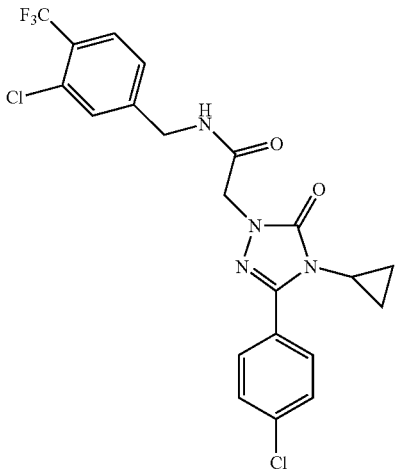 | R_t = 2.64 min [4] |

| Example No. | Structure | LC/MS $R_t$ [Method] |
|---|---|---|
| 57 | 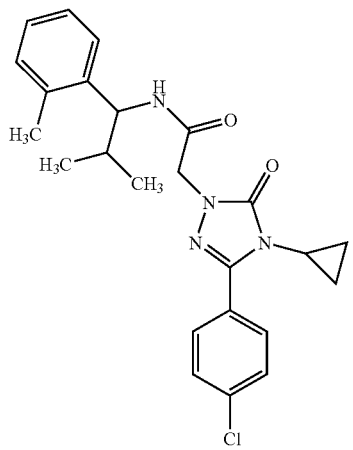 | $R_t$ = 2.70 min [4] |
| 58 | 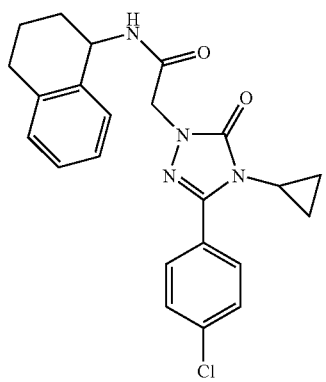 | $R_t$ = 2.51 min [4] |
| 59 | 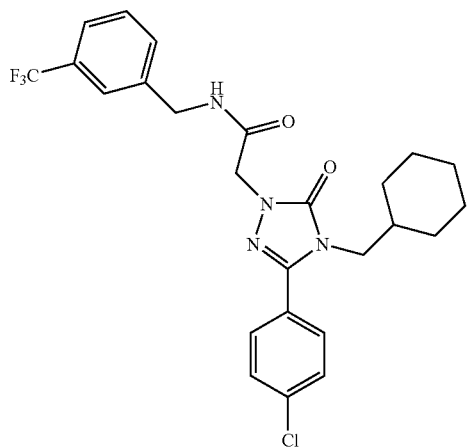 | $R_t$ = 2.91 min [5] |

| Example No. | Structure | LC/MS R_t [Method] |
|---|---|---|
| 60 | 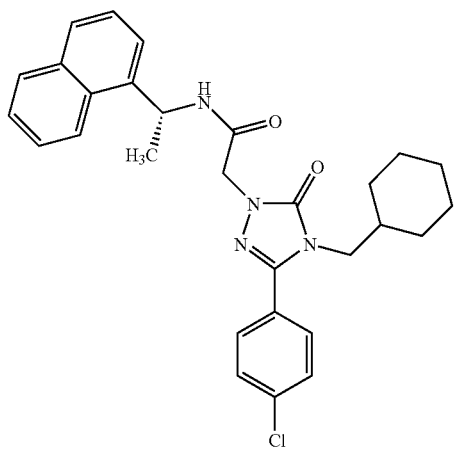 | R_t = 2.99 min [5] |
| 61 | 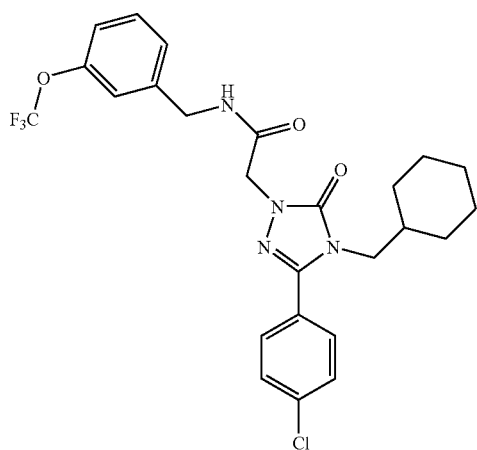 | R_t = 2.96 min [5] |
| 62 | 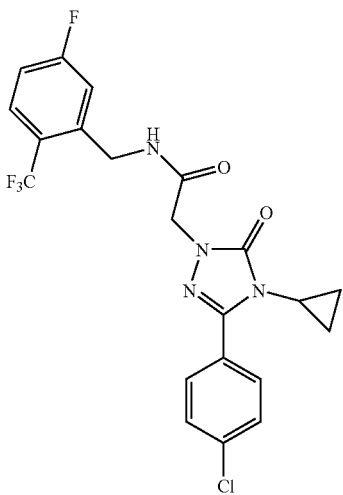 | R_t = 2.46 min [5] |

| Example No. | Structure | LC/MS $R_t$ [Method] |
|---|---|---|
| 63 | 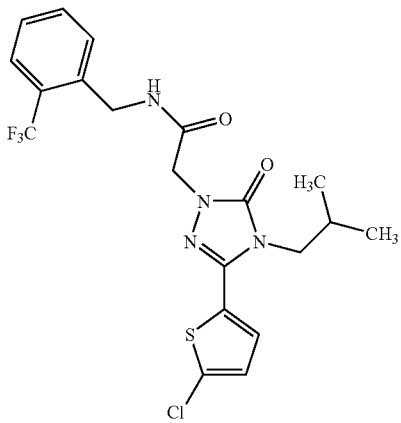 | $R_t$ = 2.68 min [5] |
| 64 | 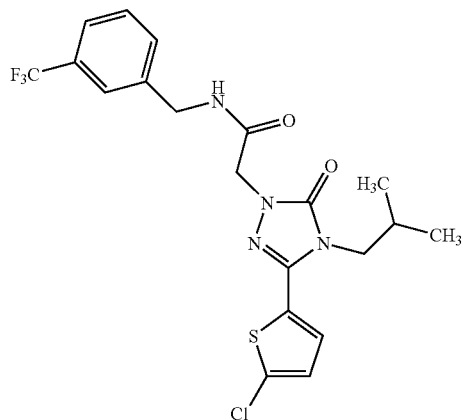 | $R_t$ = 2.53 min [7] |
| 65 | 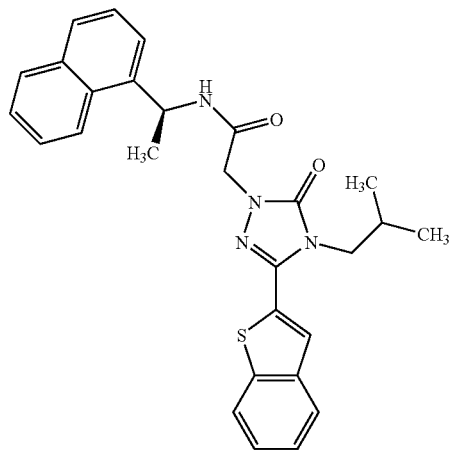 | $R_t$ = 2.67 min [7] |

-continued
| Example No. | Structure | LC/MS R_t [Method] |
|---|---|---|
| 66 | 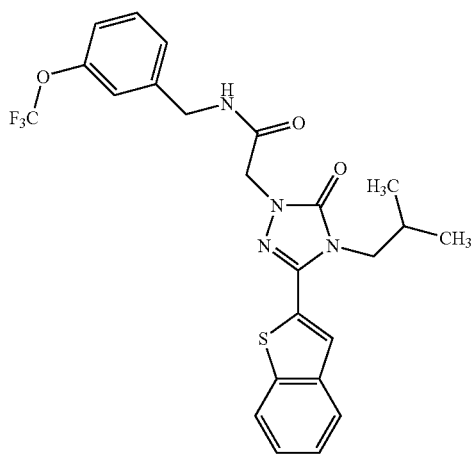 | $R_t$ = 2.64 min [7] |
| 67 | 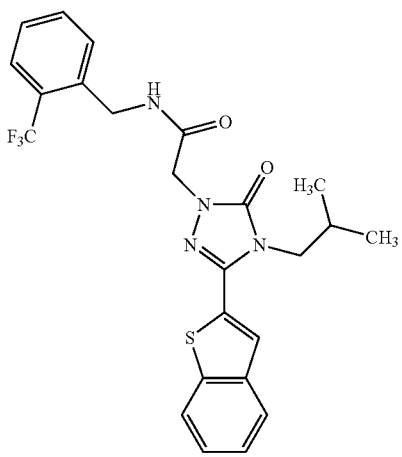 | $R_t$ = 2.59 min [7] |
| 68 | 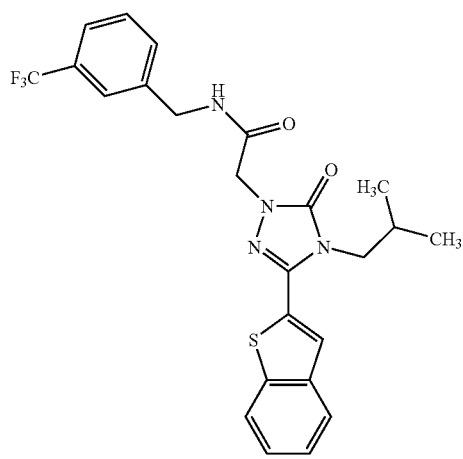 | $R_t$ = 2.58 min [7] |

| Example No. | Structure | LC/MS $R_t$ [Method] |
|---|---|---|
| 69 | 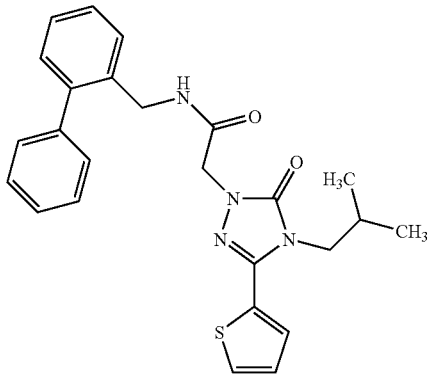 | $R_t$ = 2.42 min [7] |
| 70 | 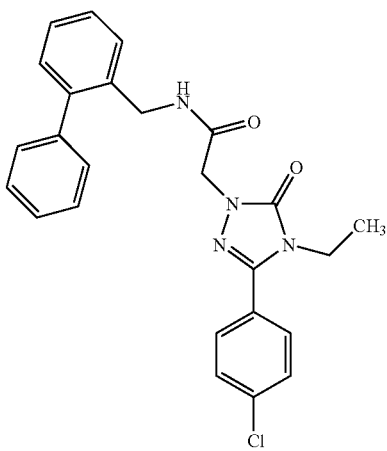 | $R_t$ = 2.56 min [5] |
| 71 | 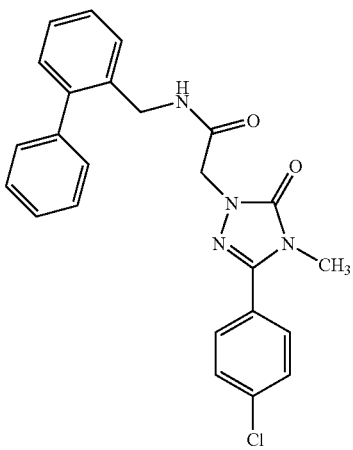 | $R_t$ = 2.46 min [5] |

| Example No. | Structure | LC/MS $R_t$ [Method] |
|---|---|---|
| 72 | 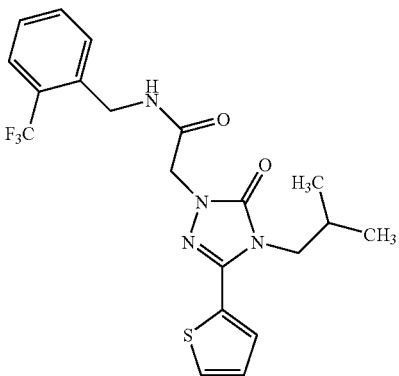 | $R_t$ = 2.27 min [7] |
| 73 | 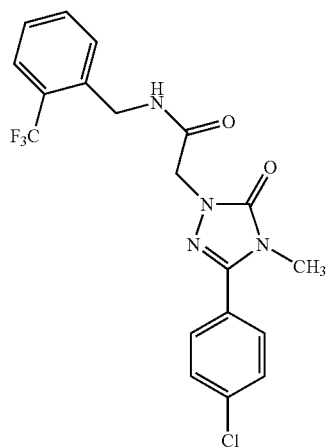 | $R_t$ = 2.27 min [7] |
| 74 | 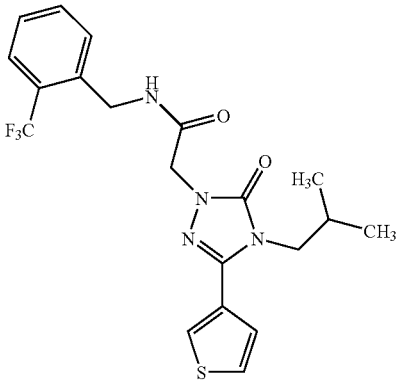 | $R_t$ = 2.45 min [8] |

Example 75

2-[3-(4-chlorophenyl)-4-cyclopropyl-5-oxo-4,5-dihydro-1H-1,2,4-triazol-1-yl]-N-{1-methyl-1-[3-(trifluoromethyl)phenyl]ethyl}acetamide

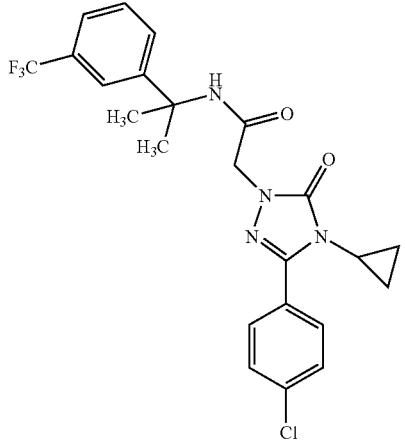

70.0 mg (0.238 mmol) of [3-(4-chlorophenyl)-4-cyclopropyl-5-oxo-4,5-dihydro-1H-1,2,4-triazol-1-yl]-acetic acid from Example 88A and 53.3 mg (0.262 mmol) of 1-methyl-1-[(3-trifluoromethyl)-phenyl]ethylamine from Example 1A are placed in 2 ml of dimethylformamide and treated with 38.6 mg (0.286 mmol) of HOBt. After 10 mins' stirring, 59.4 mg (0.310 mmol) of EDC hydrochloride are added and the mixture is stirred overnight at room temperature. For the workup, the reaction mixture is partitioned between dichloromethane and water, and the organic phase is separated, dried over sodium sulphate and concentrated. The residue is purified by flash chromatography on silica gel (eluent: dichloromethane/methanol first 200:1, then 100:1). 97 mg (85% of theory) of the target compound are thus obtained.

HPLC [Method 1]: $R_t$=4.79 min
MS [ESIpos]: m/z=479 (M+H)$^+$; [ESIneg]: m/z=477 (M−H)$^-$ $^1$H-NMR (400 MHz, DMSO-d$_6$): δ=0.48-0.61 (m, 2H), 0.81-0.95 (m, 2H), 1.59 (s, 6H), 3.15 (dddd, 1H), 4.42 (s, 2H), 7.48-7.69 (m, 4H), 7.57, 7.59 (AA' part of an AA'BB' system, 2H), 7.77, 7.79 (BB' part of an AA'BB' system, 2H), 8.55 (s, 1H).

Example 76

2-[3-(4-chlorophenyl)-4-cyclopropyl-5-oxo-4,5-dihydro-1H-1,2,4-triazol-1-yl]-N-[1-(3,5-dichlorophenyl)-1-methylethyl]acetamide

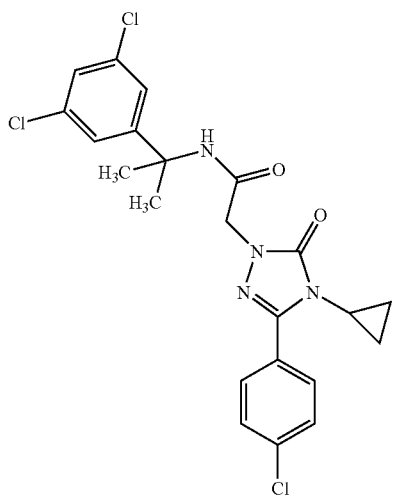

70.0 mg (0.238 mmol) of [3-(4-chlorophenyl)-4-cyclopropyl-5-oxo-4,5-dihydro-1H-1,2,4-triazol-1-yl]-acetic acid from Example 88A and 48.6 mg (0.238 mmol) of 2-(3,5-dichlorophenyl)propan-2-amine are placed in 2 ml of dimethylformamide and treated with 38.6 mg (0.286 mmol) of HOBt. After 10 mins' stirring, 59.4 mg (0.310 mmol) of EDC hydrochloride are added and the mixture is stirred overnight at room temperature. Without further workup, the mixture is purified directly by preparative HPLC [Method 10]. 70 mg (61% of theory) of the target compound are thus obtained.

MS [ESIpos]: m/z=479 (M+H)$^+$

HPLC [Method 1]: $R_t$=4.99 min $^1$H-NMR (400 MHz, DMSO-d$_6$): δ=0.57 (m, 2H), 0.89 (m, 2H), 1.54 (s, 6H), 3.16 (tt, 1H), 4.42 (s, 2H), 7.33 (d, 2H), 7.39 (t, 1H), 7.58 (d, 2H), 7.80 (d, 2H), 8.53 (s, 1H).

Example 77

2-[3-(4-chlorophenyl)-4-cyclopropyl-5-oxo-4,5-dihydro-1H-1,2,4-triazol-1-yl]-N-(1-methyl-1-phenylethyl)acetamide

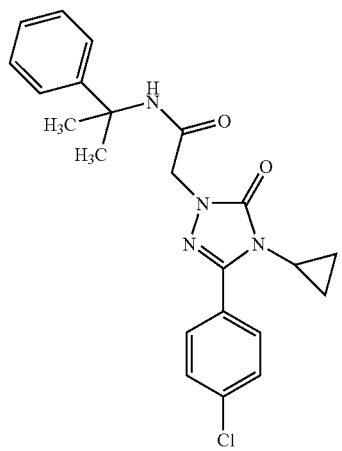

70.0 mg (0.238 mmol) of [3-(4-chlorophenyl)-4-cyclopropyl-5-oxo-4,5-dihydro-1H-1,2,4-triazol-1-yl]-acetic acid from Example 88A and 32.2 mg (0.238 mmol) of 2-phenylpropan-2-amine are placed in 2 ml of dimethylformamide and treated with 38.7 mg (0.286 mmol) of HOBt. After 10 mins' stirring, 59.4 mg (0.310 mmol) EDC hydrochloride are added and the mixture is stirred overnight at room temperature. After this, 32.2 mg (0.238 mmol) of 2-phenylpropan-2-amine, 38.7 mg (0.286 mmol) of HOBt and 59.4 mg (0.310 mmol) of EDC hydrochloride are again added to the reaction mixture and stirred for a further for two hours at room temperature. Without further workup, the mixture is purified directly by preparative HPLC [Method 10]. 44 mg (45% of theory) of the target compound are thus obtained.

MS [ESIpos]: m/z=411 (M+H)$^+$

HPLC [Method 1]: $R_t$=4.99 min $^1$H-NMR (400 MHz, DMSO-d$_6$): δ=0.55 (m, 2H), 0.89 (m, 2H), 1.56 (s, 6H), 3.15 (tt, 1H), 4.41 (s, 2H), 7.17 (t, 1H), 7.27 (t, 2H), 7.35 (d, 2H), 7.59 (d, 2H), 7.79 (d, 2H), 8.34 (s, 1H).

Example 78

N-[1-(3-chlorophenyl)cyclobutyl]-2-[3-(4-chlorophenyl)-4-cyclopropyl-5-oxo-4,5-dihydro-1H-1,2,4-triazol-1-yl]acetamide

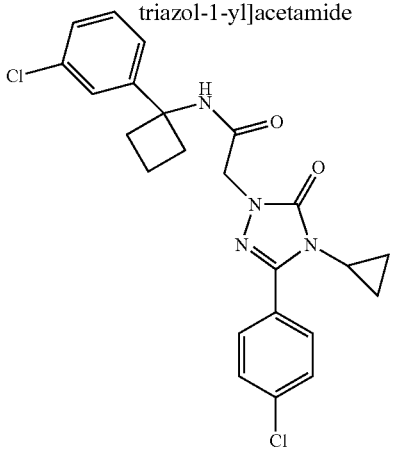

57.2 mg (0.262 mmol) of 1-(3-chlorophenyl)cyclobutanamine hydrochloride are placed in 2 ml of dimethylformamide and treated with 26.5 mg (0.262 mmol) of triethylamine. After 10 mins' stirring, 70.0 mg (0.238 mmol) of [3-(4-chlorophenyl)-4-cyclopropyl-5-oxo-4,5-dihydro-1H-1,2,4-triazol-1-yl]-acetic acid from Example 88A and 38.7 mg (0.286 mmol) of HOBt are added. After a further 10 mins' stirring, the mixture is treated with 59.4 mg (0.310 mmol) of EDC hydrochloride and stirred overnight at room temperature. For the workup, the reaction mixture is partitioned between dichloromethane and water, and the organic phase is separated, dried over sodium sulphate and concentrated. The residue is purified by flash chromatography on silica gel (eluent: dichloromethane/methanol first 200:1, then 100:1) and thus yields 66 mg (61% of theory) of the target compound.

MS [ESIpos]: m/z=457 (M+H)$^+$

HPLC [Method 2]: $R_t$=4.82 min $^1$H-NMR (400 MHz, DMSO-d$_6$): δ=0.57 (m, 2H), 0.89 (m, 2H), 1.83 (m, 1H), 2.02 (m, 1H), 2.44 (t, 4H), 3.16 (tt, 1H), 4.39 (s, 2H), 7.25 (br. d, 1H), 7.31-7.41 (m, 3H), 7.58 (d, 2H), 7.79 (d, 2H), 8.83 (s, 1H).

Example 79

N-[1-(3-chlorophenyl)cyclohexyl]-2-[3-(4-chlorophenyl)-4-cyclopropyl-5-oxo-4,5-dihydro-H-1,2,4-triazol-1-yl]acetamide

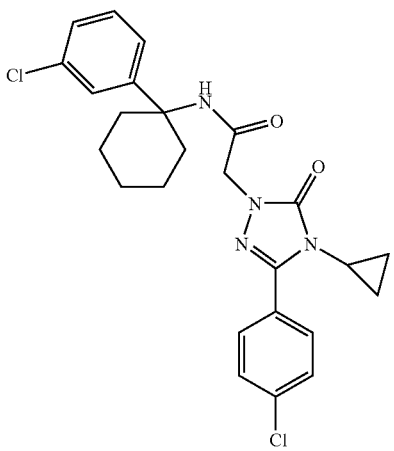

70.0 mg (0.238 mmol) of [3-(4-chlorophenyl)-4-cyclopropyl-5-oxo-4,5-dihydro-1H-1,2,4-triazol-1-yl]-acetic acid from Example 88A and 50.0 mg (0.238 mmol) of 1-(3-chlorophenyl)-cyclohexanamine are placed in 2 ml of dimethylformamide and treated with 38.7 mg (0.286 mmol) of HOBt. After 10 mins' stirring, 59.4 mg (0.310 mmol) of EDC hydrochloride are added and the mixture is stirred overnight at room temperature. After this, 50.0 mg (0.238 mmol) of 1-(3-chlorophenyl)cyclohexanamine, 38.7 mg (0.286 mmol) of HOBt and 59.4 mg (0.310 mmol) of EDC hydrochloride are again added to the reaction mixture and stirred first for two hours at room temperature, then overnight at 60° C. Stirring for a final two hours at 80° C. and direct purification of the mixture by preparative HPLC [Method 10] without further workup yield 6 mg (5% of theory) of the target compound.

LC/MS [Method 7]: $R_t$=2.64 min $^1$H-NMR (400 MHz, DMSO-d$_6$): δ=0.56 (m, 2H), 0.89 (m, 2H), 1.49-1.69 (m, 8H), 2.25 (m, 2H), 3.16 (tt, 1H), 4.49 (s, 2H), 7.22 (br. d, 1H), 7.27-7.38 (m, 3H), 7.59 (d, 2H), 7.79 (d, 2H), 8.11 (s, 1H).

Example 80

2-[3-(4-chlorophenyl)-4-cyclopropyl-5-oxo-4,5-dihydro-1H-1,2,4-triazol-1-yl]-N-{1-[3-(trifluoromethyl)phenyl]ethyl}acetamide (Enantiomer A)

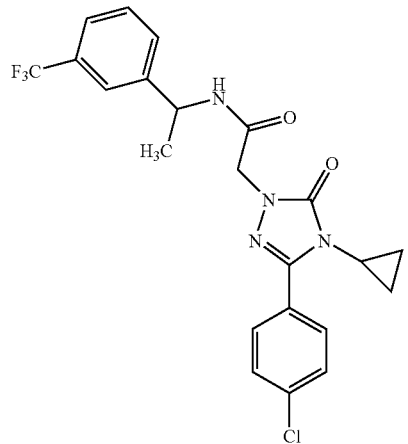

2000.0 mg (6.809 mmol) of [3-(4-chlorophenyl)-4-cyclopropyl-5-oxo-4,5-dihydro-1H-1,2,4-triazol-1-yl]-acetic acid from Example 88A and 1417.0 mg (7.490 mmol) of 1-[3-(trifluoromethyl)phenyl]-ethanamine are placed in 10 ml of dimethylformamide and treated with 1104.0 mg (8.171 mmol) of HOBt. After 10 mins' stirring, 1697.0 mg (8.852 mmol) of EDC hydrochloride are added and the mixture is stirred overnight at room temperature. For the workup, the reaction mixture is partitioned between dichloromethane and water, and the organic phase is separated, dried over sodium sulphate and concentrated. The residue is purified by flash chromatography on silica gel (eluent: dichloromethane/methanol first 200:1, then 100:1). A subsequent enantiomer separation by preparative HPLC on chiral phase [Method 14] yields 1460 mg (46% of theory) of the enantiomerically pure target compound (see also Example 81).

MS [ESIpos]: m/z=465 (M+H)$^+$

HPLC [Method 2]: $R_t$=4.74 min $^1$H-NMR (400 MHz, DMSO-d$_6$): δ=0.57 (m, 2H), 0.89 (m, 2H), 1.39 (d, 3H), 3.17 (tt, 1H), 4.42 (s, 2H), 5.00 (dq, 1H), 7.52-7.68 (m, 6H), 7.79 (d, 2H), 8.69 (d, 1H).

chiral HPLC [Method 14]: $R_t$=2.02 min.

Example 81

2-[3-(4-chlorophenyl)-4-cyclopropyl-5-oxo-4,5-dihydro-1H-1,2,4-triazol-1-yl]-N-{1-[3-(trifluoromethyl)phenyl]ethyl}acetamide (Enantiomer B)

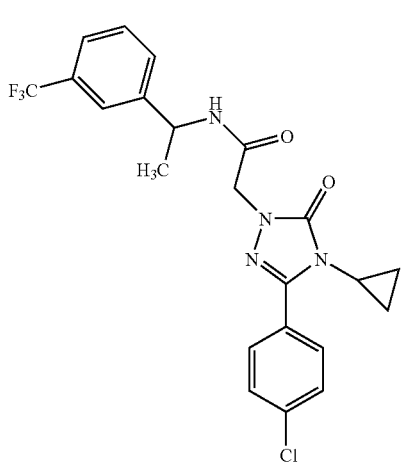

2000.0 mg (6.809 mmol) of [3-(4-chlorophenyl)-4-cyclopropyl-5-oxo-4,5-dihydro-1H-1,2,4-triazol-1-yl]-acetic acid from Example 88A and 1417.0 mg (7.490 mmol) of 1-[3-(trifluoromethyl)phenyl]-ethanamine are placed in 10 ml of dimethylformamide and treated with 1104.0 mg (8.171 mmol) of HOBt. After 10 mins' stirring, 1697.0 mg (8.852 mmol) of EDC hydrochloride are added and the mixture is stirred overnight at room temperature. For the workup, the reaction mixture is partitioned between dichloromethane and water, and the organic phase is separated, dried over sodium sulphate and concentrated. The residue is purified by flash chromatography on silica gel (eluent: dichloromethane/methanol first 200:1, then 100:1). A subsequent enantiomer separation by preparative HPLC on chiral phase [Method 14] yields 1260 mg (40% of theory) of the enantiomerically pure target compound (see also Example 80).

MS [ESIpos]: m/z=465 (M+H)$^+$

HPLC [Method 2]: $R_t$=4.74 min $^1$H-NMR (400 MHz, DMSO-d$_6$): δ=0.58 (m, 2H), 0.89 (m, 2H), 1.40 (d, 3H), 3.17 (tt, 1H), 4.43 (s, 2H), 5.01 (dq, 1H), 7.52-7.68 (m, 6H), 7.79 (d, 2H), 8.70 (d, 1H).

chiral HPLC [Method 14]: $R_t$=2.71 min.

Example 82

N-(5-bromo-2-fluorophenylmethyl)-2-[3-(4-chlorophenyl)-4-cyclopropyl-5-oxo-4,5-dihydro-1H-1,2,4-triazol-1-yl]acetamide

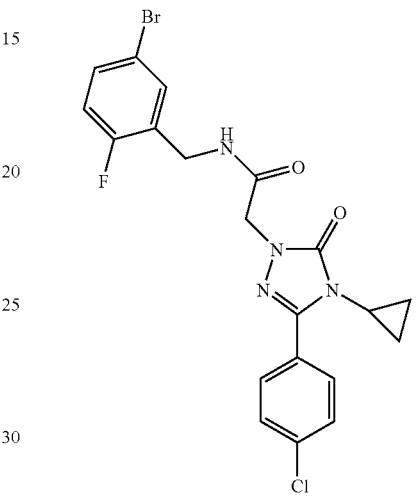

40.0 mg (0.144 mmol) of [3-(4-chlorophenyl)-4-cyclopropyl-5-oxo-4,5-dihydro-1H-1,2,4-triazol-1-yl]-acetic acid from Example 93A, 36.0 mg (0.150 mmol) of 5-bromo-2-fluorobenzylamine hydrochloride, 22.1 mg (0.163 mmol) of HOBt and 17.6 mg (0.136 mmol) of N,N-diisopropyl-ethylamine are placed in 1.5 ml of dimethylformamide and treated with 33.9 mg (0.177 mmol) of EDC hydrochloride. This is stirred overnight at room temperature, then diluted with 15 ml of water and extracted with ethyl acetate. After evaporation of the organic phase, the crude product is purified by preparative HPLC [Method 13]. 21 mg (32% of theory) of the target compound are thus obtained.

LC/MS [Method 5]: $R_t$=2.39 min $^1$H-NMR (400 MHz, DMSO-d$_6$): δ=0.53-0.67 (m, 2H), 0.83-0.98 (m, 2H), 3.18 (dddd, 1H), 4.34 (d, 2H), 4.45 (s, 2H), 7.15-7.23 (m, 1H), 7.47-7.53 (m, 2H), 7.59, 7.61 (AA' part of an AA'BB' system, 2H), 7.82, 7.84 (BB' part of an AA'BB' system, 2H), 8.62 (t, 1H).

Example 83

2-[3-(4-chlorophenyl)-4-(2-methoxyethyl)-5-oxo-4,5-dihydro-1H-1,2,4-triazol-1-yl]-N-[3-(trifluoromethyl)phenylmethyl]acetamide

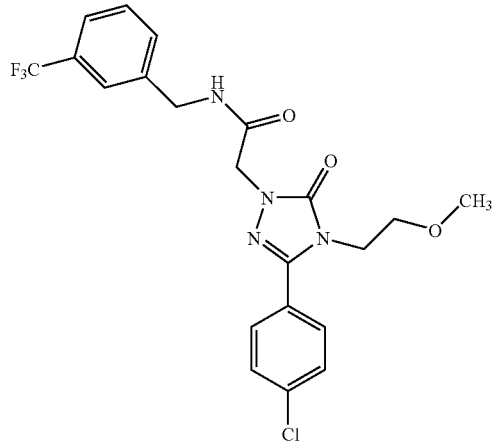

50.0 mg (0.160 mmol) of 2-[3-(4-chlorophenyl)-4-(2-methoxyethyl)-5-oxo-4,5-dihydro-1H-1,2,4-triazol-1-yl]-acetic acid from Example 90A, 30.9 mg (0.176 mmol) of 3-trifluoromethylbenzyl-amine and 40.0 mg (0.209 mmol) of HOBt are placed in 2 ml of dimethylformamide and treated with 26.0 mg (0.192 mmol) of EDC hydrochloride. This is stirred overnight at room temperature, then stirred with 15 ml of water and the resulting precipitate recovered by filtration. The crude product is washed with water and dried in vacuo. 66.9 mg (89% of theory) of the target compound are thus obtained.

LC/MS [Method 7]: $R_t$=2.24 min $^1$H-NMR (400 MHz, DMSO-$d_6$): δ=3.13 (s, 3H), 3.50 (t, 2H), 3.88 (t, 2H), 4.41 (d, 2H), 4.50 (s, 2H), 7.54-7.65 (m, 6H), 7.70-7.75 (m, 2H), 8.71 (t, 1H).

The following compounds are obtained analogously:

| Example No. | Structure | LC/MS $R_t$ [Method] | $^1$H-NMR (400 MHz, DMSO-$d_6$) |
|---|---|---|---|
| 84 | 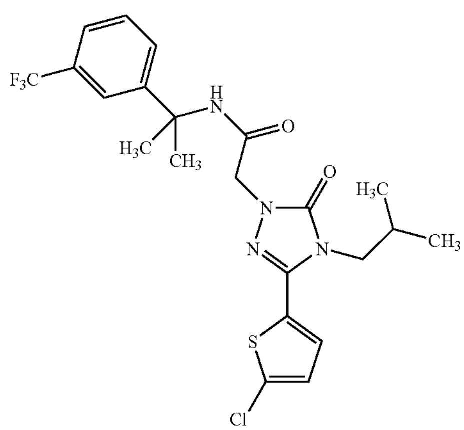 | $R_t$ = 2.71 min [7] | δ = 0.80 (d, 6 H), 1.58 (s, 6 H), 1.79-1.91 (m, 1 H), 3.65 (d, 2 H), 4.46 (s, 2 H), 7.25 (d, 1 H), 7.45 (d, 1 H), 7.48-7.56 (m, 2 H), 7.60 (s, 1 H), 7.66 (d, 1 H), 8.56 (s, 1 H). |
| 85 | 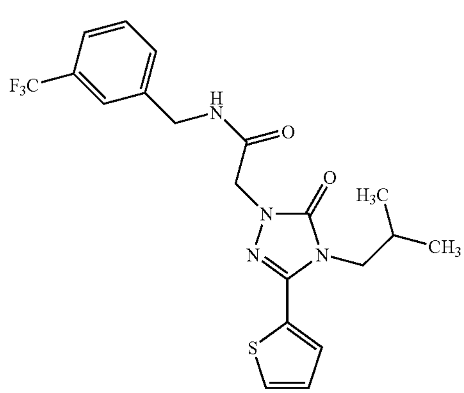 | $R_t$ = 2.43 min [5] | δ = 0.83 (d, 6 H), 1.83-1.95 (m, 1 H), 3.70 (d, 2 H), 4.41 (d, 2 H), 4.50 (s, 2 H), 7.23 (dd, 1 H), 7.54-7.64 (m, 5 H), 7.79 (dd, 1 H), 8.72 (t, 1 H). |

| Example No. | Structure | LC/MS R$_t$ [Method] | $^1$H-NMR (400 MHz, DMSO-d$_6$) |
|---|---|---|---|
| 86 | 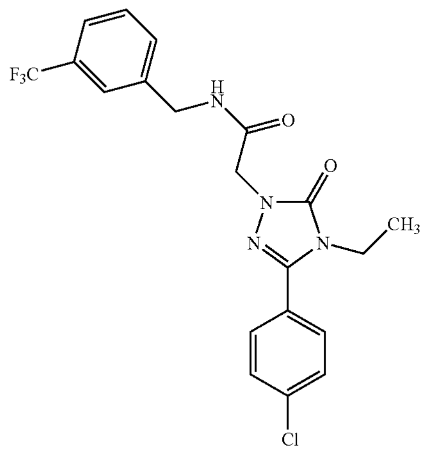 | R$_t$ = 2.41 min [5] | δ = 1.13 (t, 3 H), 3.76 (q, 2 H), 4.41 (d, 2 H), 4.49 (s, 2 H), 7.54-7.70 (m, 8 H), 8.70 (t, 1 H). |
| 87 | 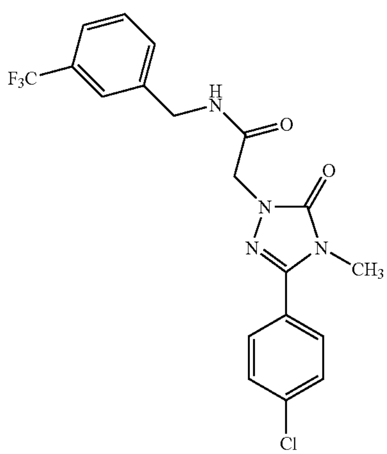 | R$_t$ = 2.31 min [5] | δ = 3.30 (s, 3 H), 4.41 (d, 2 H), 4.50 (s, 2 H), 7.54-7.65 (m, 6 H), 7.70-7.76 (m, 2 H), 8.68 (t, 1 H). |
| 88 | 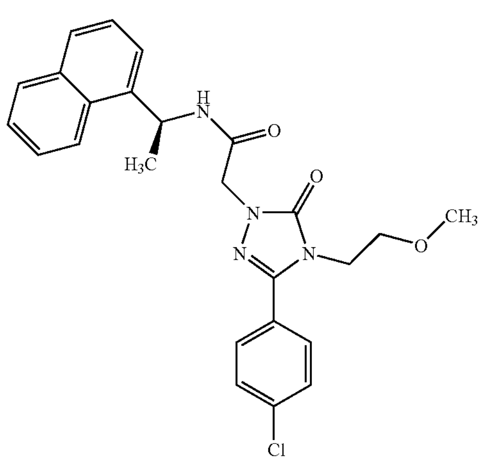 | R$_t$ = 2.30 min [7] | δ = 1.52 (d, 3 H), 3.11 (s, 3 H), 3.47 (t, 2 H), 3.86 (t, 2 H), 4.47 (centre of an AB system, 2 H), 5.71 (dq, 1 H), 7.47-7.63 (m, 6 H), 7.67-7.72 (m, 2 H), 7.84 (d, 1 H), 7.91-7.97 (m, 1 H), 8.10 (d, 1 H), 8.78 (d, 1 H). |

| Example No. | Structure | LC/MS R$_t$ [Method] | $^1$H-NMR (400 MHz, DMSO-d$_6$) |
|---|---|---|---|
| 89 | 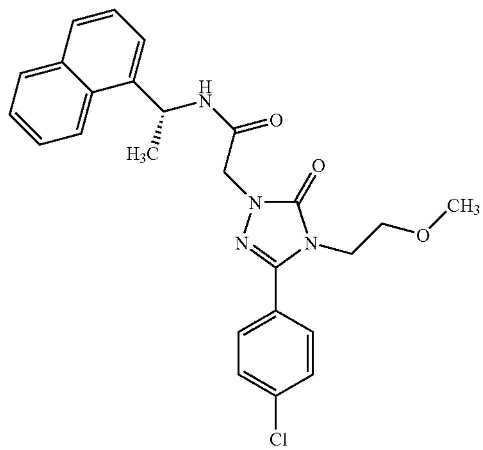 | R$_t$ = 2.30 min [7] | δ = 1.52 (d, 3 H), 3.11 (s, 3 H), 3.47 (t, 2 H), 3.86 (t, 2 H), 4.47 (centre of an AB system, 2 H), 5.71 (dq, 1 H), 7.47-7.63 (m, 6 H), 7.67-7.72 (m, 2 H), 7.84 (d, 1 H), 7.91-7.97 (m, 1 H), 8.10 (d, 1 H), 8.78 (d, 1 H). |
| 90 | 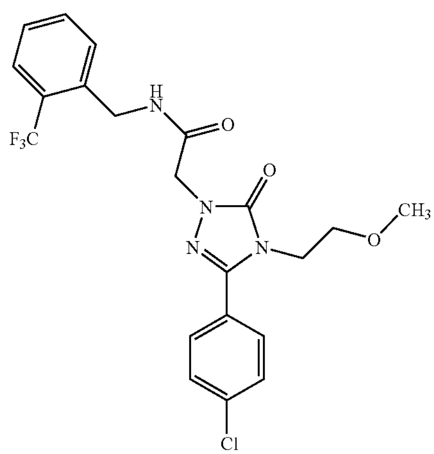 | R$_t$ = 2.23 min [7] | δ = 3.13 (s, 3 H), 3.50 (t, 2 H), 3.88 (t, 2 H), 4.49 (d, 2 H), 4.54 (s, 2 H), 7.48 (t, 1 H), 7.55-7.77 (m, 7 H), 8.71 (t, 1 H). |
| 91 | 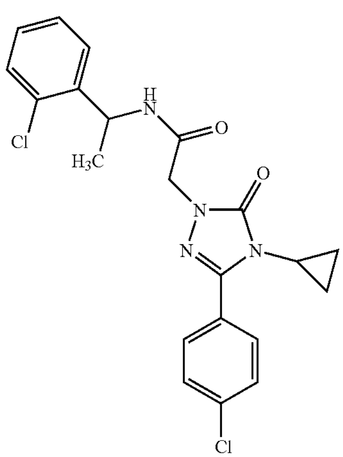 | R$_t$ = 2.44 min [5] | δ = 0.49-0.63 (m, 2 H), 0.81-0.97 (m, 2 H), 1.34 (d, 3 H), 3.16 (dddd, 1 H), 4.43 (s, 2 H), 5.20 (dq, 1 H), 7.26 (dt, 1 H), 7.33 (dt, 1 H), 7.40 dd, 1 H), 7.47 (dd, 1 H), 7.58, 7.60 (AA' part of an AA'BB' system, 2 H), 7.78, 7.80 (BB' part of an AA'BB' system, 2 H), 8.77 (d, 1 H). |

| Example No. | Structure | LC/MS R$_t$ [Method] | $^1$H-NMR (400 MHz, DMSO-d$_6$) |
|---|---|---|---|
| 92 | 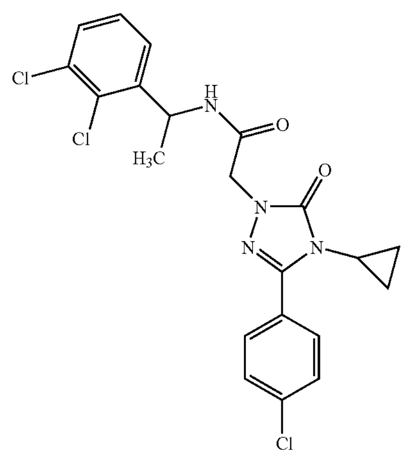 | R$_t$ = 2.57 min [5] | δ = 0.49-0.62 (m, 2 H), 0.81-0.96 (m, 2 H), 1.35 (d, 3 H), 3.16 (dddd, 1 H), 4.43 (s, 2 H), 5.20 (dq, 1 H), 7.36 (t, 1 H), 7.44 (dd, 1 H), 7.53 (dd, 1 H), 7.58, 7.60 (AA' part of an AA'BB' system, 2 H), 7.77, 7.80 (BB' part of an AA'BB' system, 2 H), 8.85 (d, 1 H). |
| 93 | 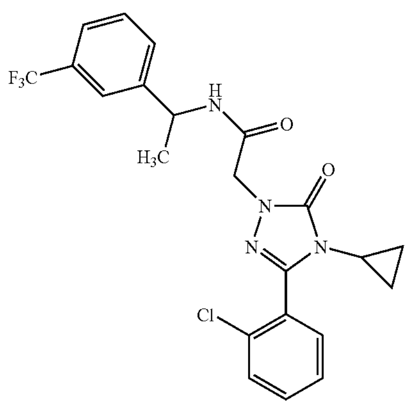 | R$_t$ = 2.23 min [7] | δ = 0.45-0.59 (m, 2 H), 0.59-0.74 (m, 2 H), 1.40 (d, 3 H), 2.87 (dddd, 1 H), 4.43 (s, 2 H), 5.01 (dq, 1 H), 7.37-7.69 (m, 8 H), 8.69 (d, 1 H). |
| 94 | 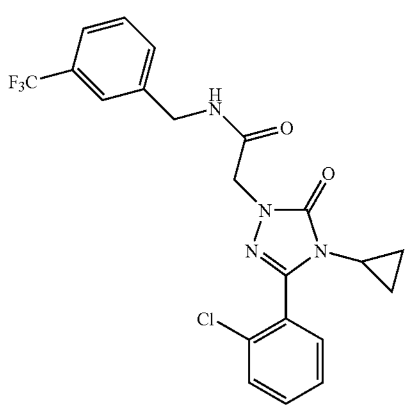 | R$_t$ = 2.15 min [7] | δ = 0.51-0.58 (m, 2 H), 0.64-0.71 (m, 2 H), 2.89 (dddd, 1 H), 4.42 (d, 2 H), 4.46 (s, 2 H), 7.48-7.69 (m, 8 H), 8.65 (t, 1 H). |

-continued

| Example No. | Structure | LC/MS $R_t$ [Method] | $^1$H-NMR (400 MHz, DMSO-$d_6$) |
|---|---|---|---|
| 95 | 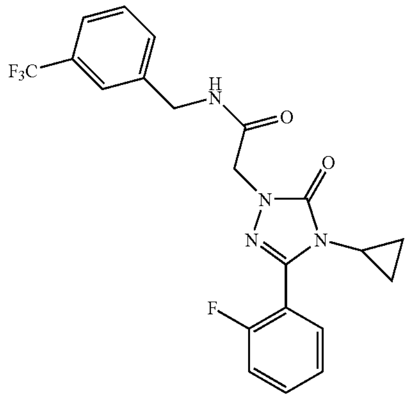 | $R_t$ = 2.08 min [7] | δ = 0.44-0.59 (m, 2 H), 0.67-0.81 (m, 2 H), 2.90-2.98 (m, 1 H), 4.41 (d, 2 H), 4.46 (s, 2 H), 7.37 (t, 1 H), 7.43 (dd, 1 H), 7.53-7.68 (m, 6 H), 8.69 (t, 1 H). |
| 96 | 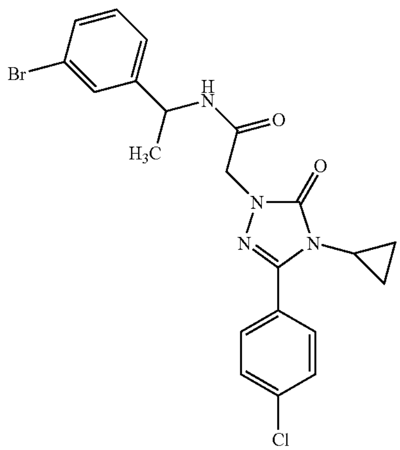 | $R_t$ = 2.48 min [5] | δ = 0.51-0.64 (m, 2 H), 0.82-0.97 (m, 2 H), 1.36 (d, 3 H), 3.17 (dddd, 1 H), 4.41 (centre of an AB system, 2 H), 4.90 (dq, 1 H), 7.25-7.35 (m, 2 H), 7.43 (dt, 1 H), 7.51 (t, 1 H), 7.58, 7.60 (AA' part of an AA'BB' system, 2 H), 7.79, 7.81 (BB' part of an AA'BB' system, 2 H), 8.62 (d, 1 H). |

Further, the following are obtained analogously:

| Example No. | Structure | LC/MS $R_t$ [Method] |
|---|---|---|
| 97 | 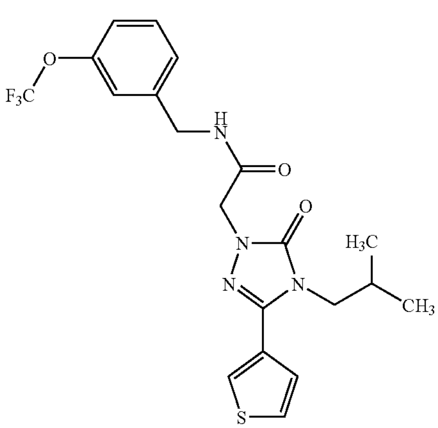 | $R_t$ = 2.49 min [5] |

| Example No. | Structure | LC/MS $R_t$ [Method] |
|---|---|---|
| 98 | 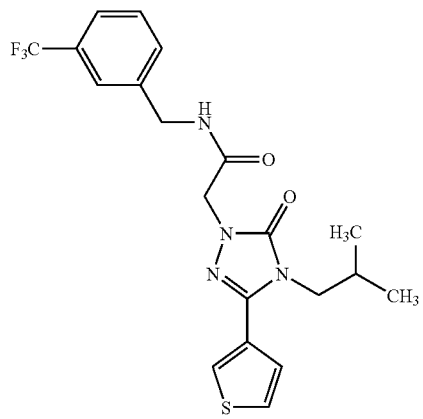 | $R_t$ = 2.43 min [5] |
| 99 | 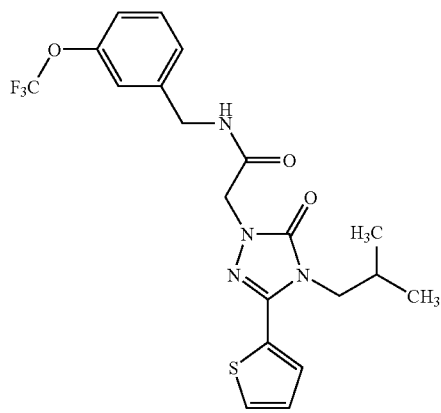 | $R_t$ = 2.48 min [5] |
| 100 | 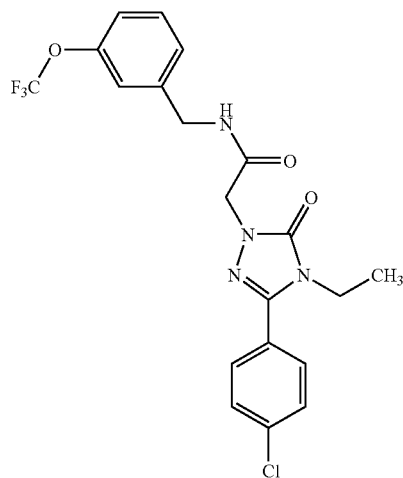 | $R_t$ = 2.46 min [5] |

-continued

| Example No. | Structure | LC/MS $R_t$ [Method] |
|---|---|---|
| 101 | 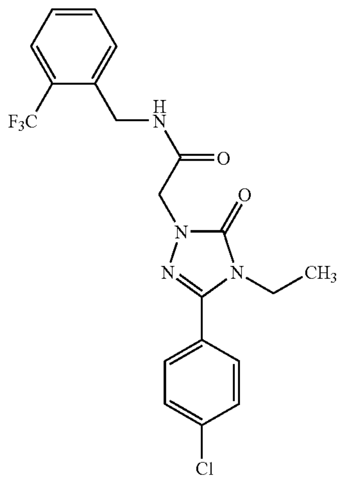 | $R_t$ = 2.40 min [5] |
| 102 | 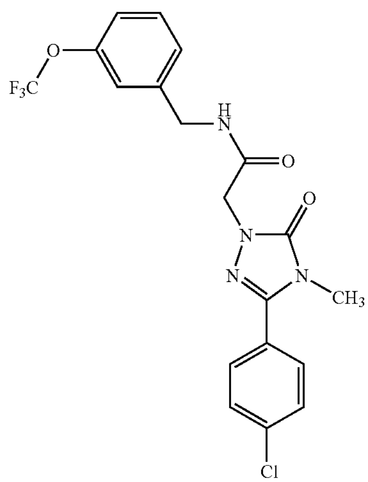 | $R_t$ = 2.22 min [7] |
| 103 | 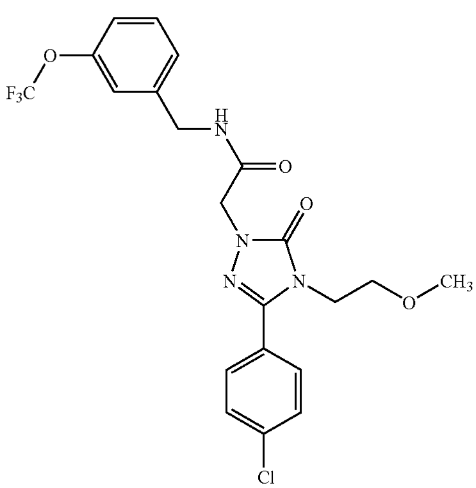 | $R_t$ = 2.29 min [7] |

| Example No. | Structure | LC/MS R$_t$ [Method] |
|---|---|---|
| 104 | 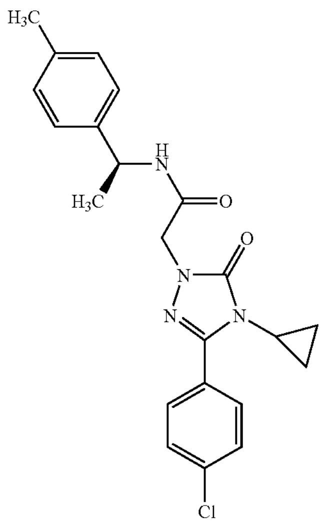 | R$_t$ = 2.42 min [5] |
| 105 | 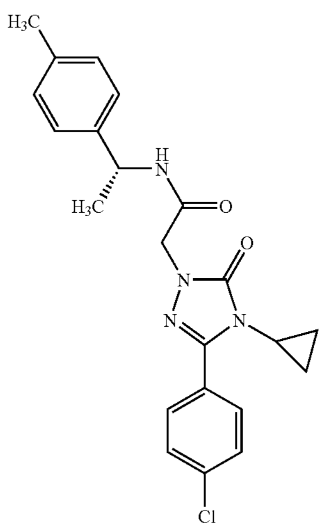 | R$_t$ = 2.42 min [5] |
| 106 | 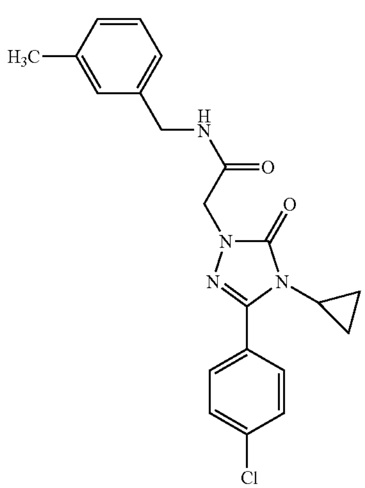 | R$_t$ = 2.40 min [4] |

-continued

| Example No. | Structure | LC/MS R$_t$ [Method] |
|---|---|---|
| 107 | 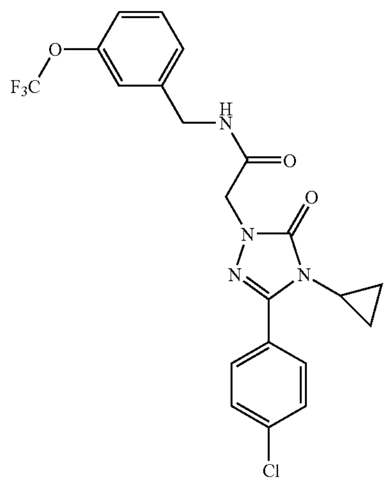 | R$_t$ = 2.57 min [4] |
| 108 | 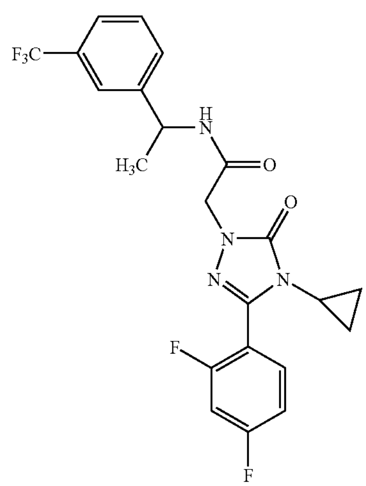 | R$_t$ = 2.22 min [7] |
| 109 | 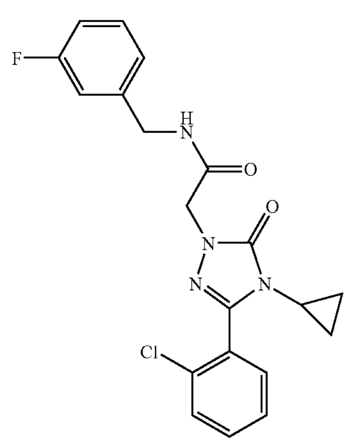 | R$_t$ = 1.94 min [7] |

-continued

| Example No. | Structure | LC/MS R$_t$ [Method] |
|---|---|---|
| 110 | 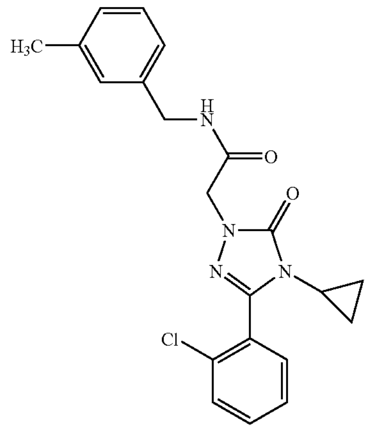 | R$_t$ = 2.02 min [7] |
| 111 | 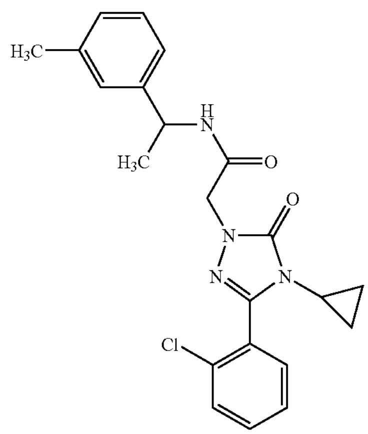 | R$_t$ = 2.10 min [7] |
| 112 | 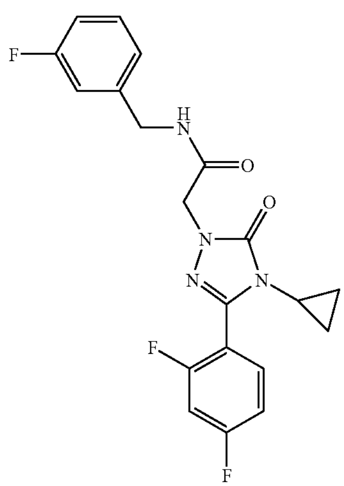 | R$_t$ = 1.93 min [7] |

-continued
| Example No. | Structure | LC/MS R_t [Method] |
|---|---|---|
| 113 | 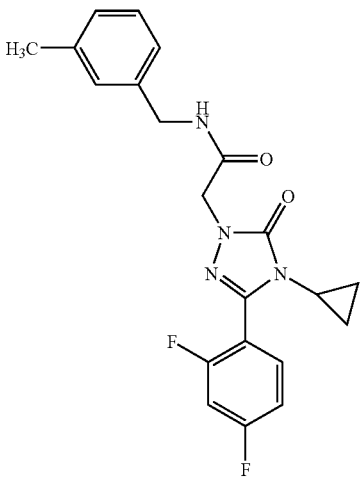 | R_t = 2.01 min [7] |
| 114 | 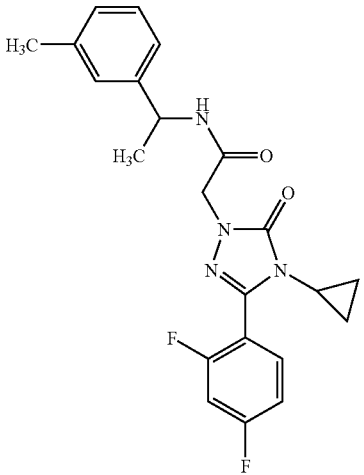 | R_t = 2.09 min [7] |
| 115 | 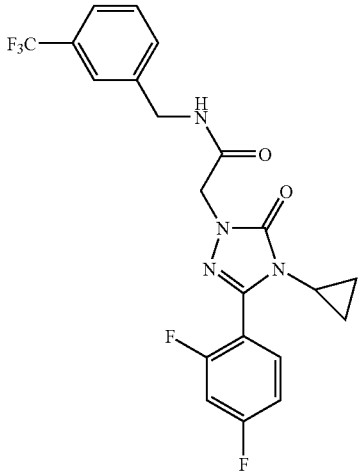 | R_t = 2.13 min [7] |

-continued

| Example No. | Structure | LC/MS $R_t$ [Method] |
|---|---|---|
| 116 | 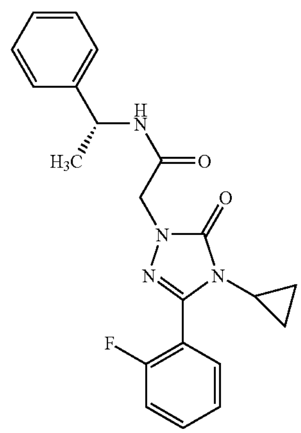 | $R_t$ = 1.88 min [7] |
| 117 | 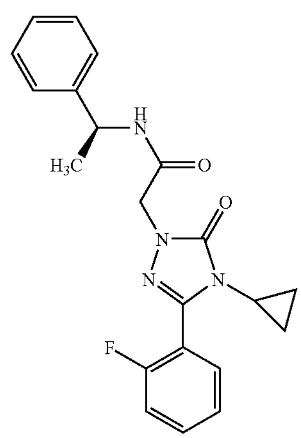 | $R_t$ = 1.89 min [7] |
| 118 | 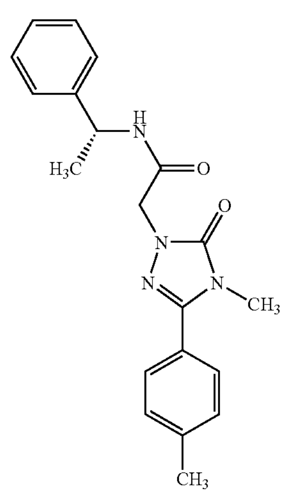 | $R_t$ = 2.13 min [5] |

-continued

| Example No. | Structure | LC/MS $R_t$ [Method] |
|---|---|---|
| 119 | 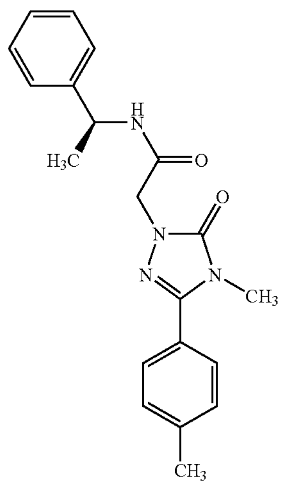 | $R_t$ = 2.12 min [5] |
| 120 | 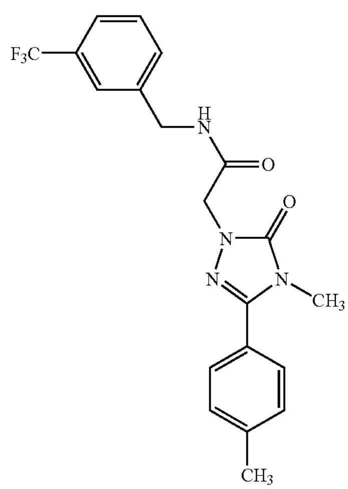 | $R_t$ = 2.30 min [5] |
| 121 | 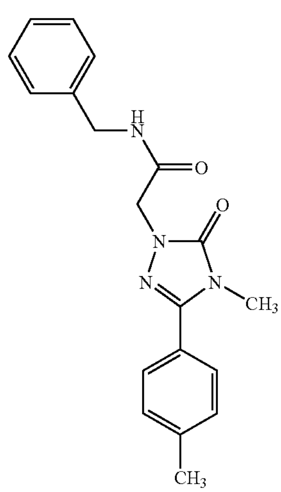 | $R_t$ = 2.03 min [5] |

-continued
| Example No. | Structure | LC/MS $R_t$ [Method] |
|---|---|---|
| 122 | 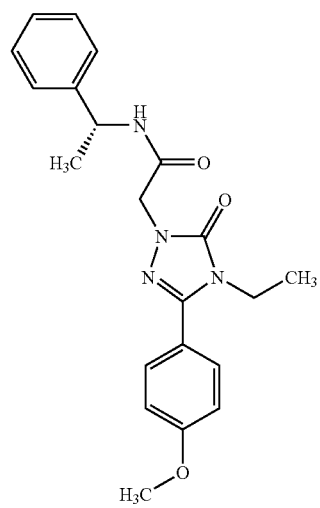 | $R_t$ = 2.09 min [5] |
| 123 | 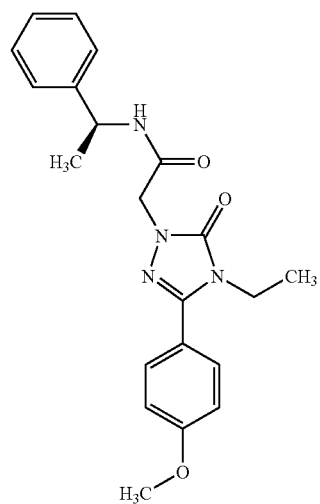 | $R_t$ = 2.09 min [5] |

| Example No. | Structure | LC/MS $R_t$ [Method] |
|---|---|---|
| 124 | 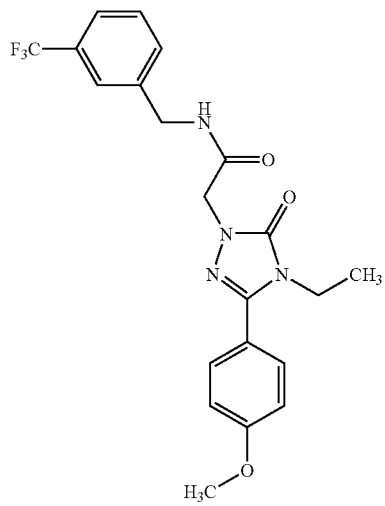 | $R_t$ = 2.28 min [5] |
| 125 | 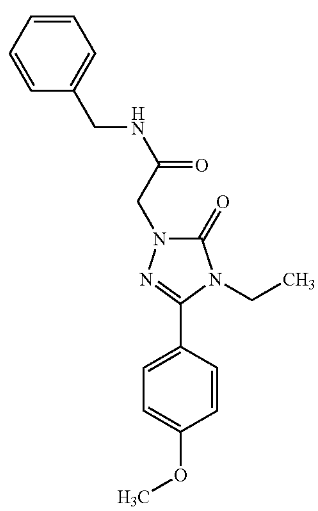 | $R_t$ = 2.01 min [5] |

Example 126

2-[4-cyclopropyl-3-(2-fluorophenyl)-5-oxo-4,5-dihydro-1H-1,2,4-triazol-1-yl]-N-(2-phenylethyl)-acetamide

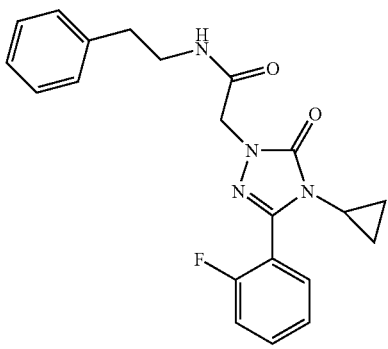

40.0 mg (0.144 mmol) of [4-cyclopropyl-3-(2-fluorophenyl)-2,4-dihydro-3H-1,2,4-triazol-3-yl]-acetic acid from Example 92A, 19.2 mg (0.159 mmol) of 2-phenylethylamine and 23.4 mg (0.173 mmol) of HOBt are placed in 2 ml of dimethylformamide and treated with 36.0 mg (0.188 mmol) of EDC hydrochloride. This is stirred overnight at room temperature, then diluted with 10 ml of water and extracted with ethyl acetate. After evaporation of the organic phase, the crude product is purified by preparative HPLC [Method 9]. 32.0 mg (58% of theory) of the target compound are thus obtained.

LC/MS [Method 4]: $R_t$=2.13 min $^1$H-NMR (400 MHz, DMSO-d$_6$): δ=0.45-0.58 (m, 2H), 0.68-0.82 (m, 2H), 2.72 (t, 2H), 2.90-2.98 (m, 1H), 3.29 (t, 2H), 4.34 (s, 2H), 7.17-7.24 (m, 3H), 7.24-7.31 (m, 2H), 7.35-7.47 (m, 2H), 7.57-7.69 (m, 2H), 8.17 (t, 1H).

The following are obtained analogously:

| Example No. | Structure | LC/MS $R_t$ [Method] |
|---|---|---|
| 127 | 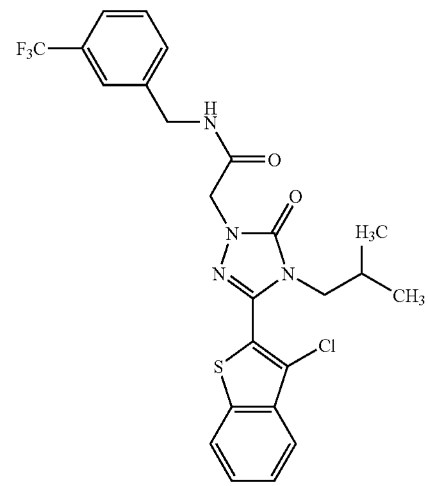 | $R_t$ = 2.87 min [8] |
| 128 | 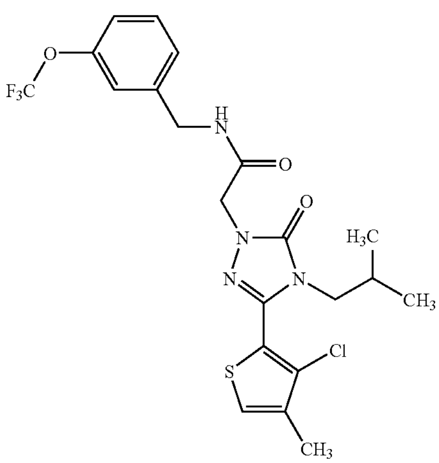 | $R_t$ = 2.73 min [8] |
| 129 | 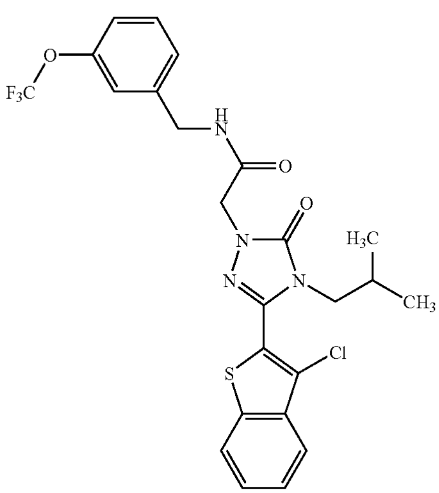 | $R_t$ = 2.92 min [8] |

| Example No. | Structure | LC/MS $R_t$ [Method] |
|---|---|---|
| 130 | 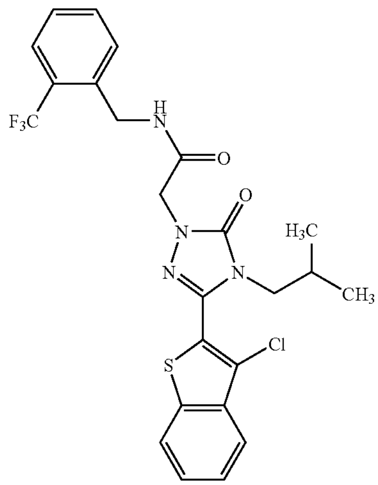 | $R_t$ = 2.88 min [8] |
| 131 | 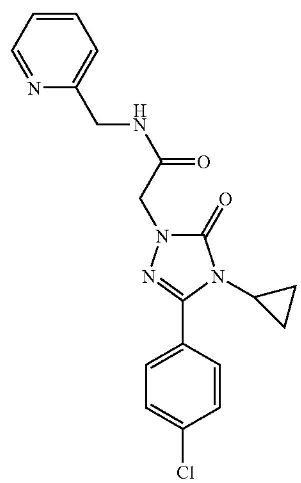 | $R_t$ = 1.63 min [5] |
| 132 | 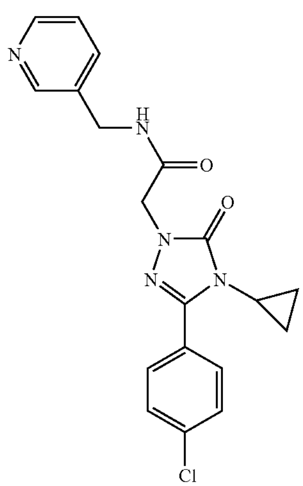 | $R_t$ = 1.45 min [5] |

-continued

| Example No. | Structure | LC/MS $R_t$ [Method] |
|---|---|---|
| 133 | 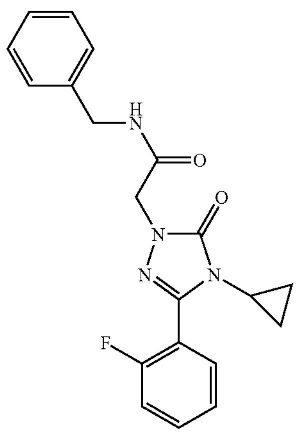 | $R_t$ = 2.06 min [4] |
| 134 | 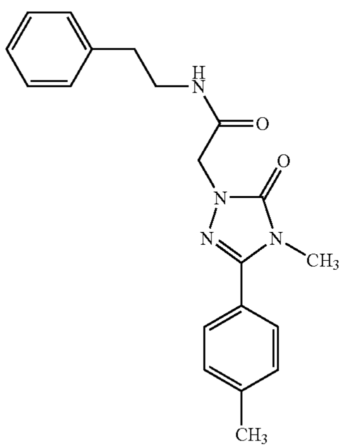 | $R_t$ = 2.15 min [4] |
| 135 | 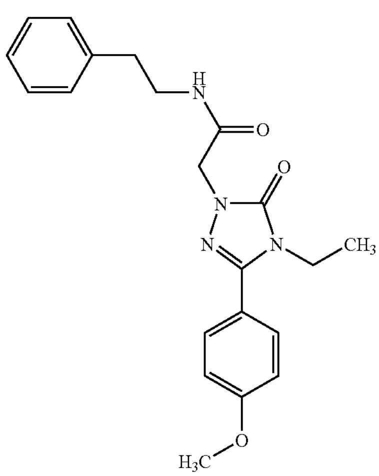 | $R_t$ = 1.88 min [7] |

Example 136

2-[4-cyclopropyl-3-(2-methoxyphenyl)-5-oxo-4,5-dihydro-1H-1,2,4-triazol-1-yl]-N-[3-(trifluoromethyl)phenylmethyl]acetamide

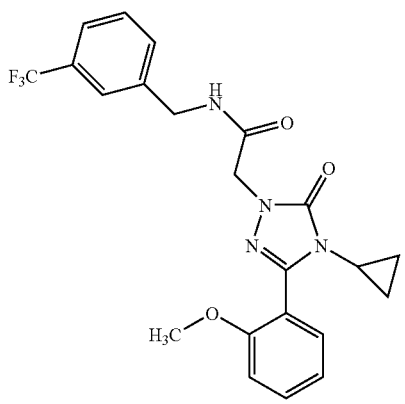

Method a):

76 mg (0.26 mmol) of [4-cyclopropyl-3-(2-methoxyphenyl)-5-oxo-4,5-dihydro-1H-1,2,4-triazol-1-yl]-acetic acid from Example 95A and 45 mg (0.28 mmol) of carbonyldiimidazole are stirred in 1 ml of 1,2-dichloroethane, until initial gas evolution has ended. A solution of 51 mg (0.29 mmol) of 3-trifluoromethylbenzylamine in 0.55 ml of 1,2-dichloroethane is added and stirred overnight at 70° C. For the workup, the solvent is removed in vacuo and the residue purified by preparative HPLC [Method 11]. 46 mg (39% of theory) of the target compound are thus obtained.

Method b):

150 mg (0.52 mmol) of [4-cyclopropyl-3-(2-methoxyphenyl)-5-oxo-4,5-dihydro-1H-1,2,4-triazol-1-yl]-acetic acid from Example 95A, 100 mg (0.57 mmol) of 3-trifluoromethylbenzylamine and 84 mg (0.62 mmol) of HOBt are placed in 3.2 ml of dimethylformamide and treated with 129 mg (0.67 mmol) of EDC hydrochloride. This is stirred overnight at room temperature and then purified directly by preparative HPLC [Method 11]. 222 mg (96% of theory) of the target compound are thus obtained.

LC/MS [Method 7]: $R_t$=2.05 min $^1$H-NMR (400 MHz, DMSO-$d_6$): δ=0.41-0.55 (m, 2H), 0.58-0.72 (m, 2H), 2.86 (dddd, 1H), 3.86 (s, 3H), 4.42 (d, 2H), 4.43 (s, 2H), 7.06 (t, 1H), 7.19 (d, 1H), 7.33 (dd, 1H), 7.52-7.65 (m, 5H), 8.65 (t, 1H).

Example 137

2-[3-(3-chlorophenyl)-4-cyclopropyl-5-oxo-4,5-dihydro-1H-1,2,4-triazol-1-yl]-N-[3-(trifluoromethyl)phenylmethyl]acetamide

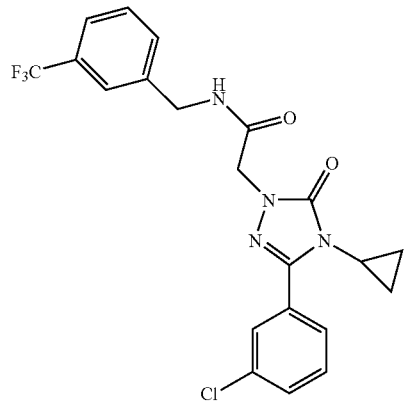

30.0 mg (0.102 mmol) of [3-(3-chlorophenyl)-4-cyclopropyl-5-oxo-4,5-dihydro-1H-1,2,4-triazol-1-yl]-acetic acid from Example 104A, 19.7 mg (0.112 mmol) of 3-trifluoromethylbenzylamine and 16.6 mg (0.123 mmol) of HOBt are placed in 0.75 ml of dimethylformamide and treated with 25.5 mg (0.133 mmol) of EDC hydrochloride. This is stirred overnight at room temperature and the reaction solution is purified directly by preparative HPLC [Method 9]. 20 mg (43% of theory) of the target compound are thus obtained.

LC/MS [Method 7]: $R_t$=2.27 min $^1$H-NMR (400 MHz, DMSO-$d_6$): δ=0.53-0.68 (m, 2H), 0.83-0.98 (m, 2H), 3.22 (dddd, 1H), 4.41 (d, 2H), 4.46 (s, 2H), 7.53-7.64 (m, 6H), 7.74-7.83 (m, 2H), 8.66 (t, 1H).

The following are obtained analogously:

| Example No. | Structure | LC/MS $R_t$ [Method] |
|---|---|---|
| 138 | ![structure] | $R_t$ = 2.42 min [7] |

-continued

| Example No. | Structure | LC/MS $R_t$ [Method] |
|---|---|---|
| 139 | 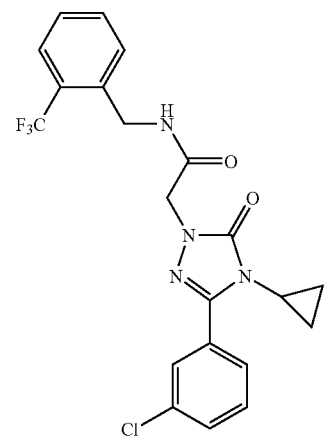 | $R_t$ = 2.25 min [7] |
| 140 | 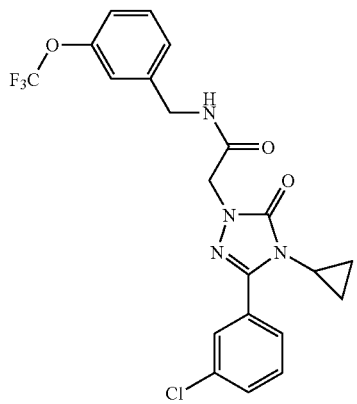 | $R_t$ = 2.32 min [7] |

Example 141

2-[3-(4-chlorophenyl)-4-(3-fluorophenylmethyl)-5-oxo-4,5-dihydro-1H-1,2,4-triazol-1-yl]-N-[3-(trifluoromethyl)phenylmethyl]acetamide

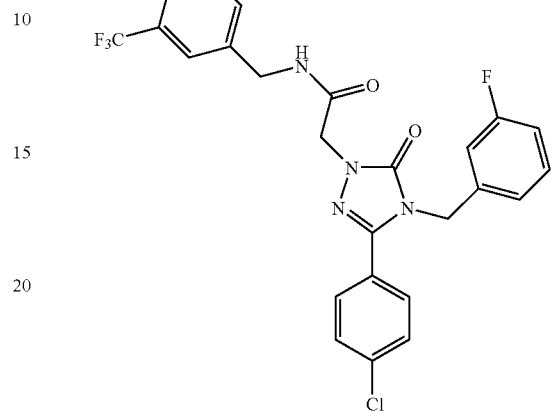

200 mg (0.66 mmol) of 5-(4-chlorophenyl)-4-(3-fluorophenylmethyl)-2,4-dihydro-3H-1,2,4-triazol-3-one from Example 41A, 193 mg (0.69 mmol) of 2-chloro-N-[3-(trifluoromethyl)phenylmethyl]-acetamide [preparable according to EP 0 163 607, Example 28] and 182 mg (1.32 mmol) of potassium carbonate are suspended in 2.5 ml of acetonitrile and heated under reflux overnight. After cooling, this is diluted with water, and purified by preparative HPLC [Method 9] and 219 mg (64% of theory) of the target compound are thus obtained.

LC/MS [Method 7]: $R_t$=2.57 min $^1$H-NMR (400 MHz, DMSO-$d_6$): δ=4.44 (d, 2H), 4.58 (s, 2H), 5.01 (s, 2H), 6.93-7.01 (m, 2H), 7.09 (td, 1H), 7.36 (dt, 1H), 7.49-7.67 (m, 8H), 8.76 (t, 1H).

The following are obtained analogously:

| Example No. | Structure | LC/MS $R_t$ [Method] | $^1$H-NMR (400 MHz, DMSO-$d_6$) |
|---|---|---|---|
| 142 | 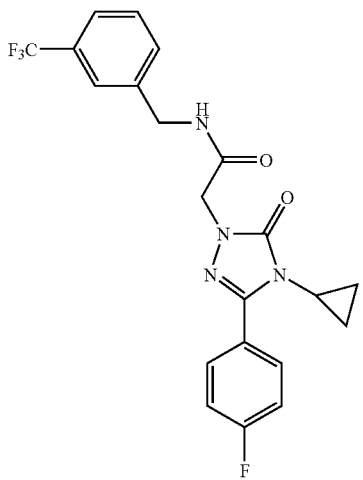 | $R_t$ = 2.16 min [7] | δ = 0.52-0.66 (m, 2 H), 0.81-0.96 (m, 2 H), 3.17 (dddd, 1 H), 4.41 (d, 2 H), 4.44 (s, 2 H), 7.37 (t, 2 H), 7.52-7.66 (m, 4 H), 7.79-7.88 (m, 2 H), 8.65 (t, 1 H). |

| Example No. | Structure | LC/MS $R_t$ [Method] | ¹H-NMR (400 MHz, DMSO-d₆) |
|---|---|---|---|
| 143 | 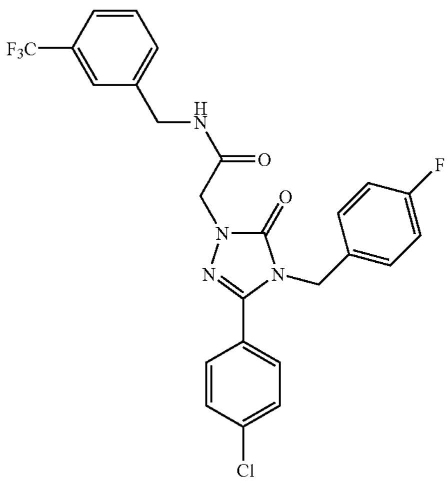 | $R_t$ = 2.58 min [7] | δ = 4.43 (d, 2 H), 4.57 (s, 2 H), 4.98 (s, 2 H), 7.09-7.20 (m, 4 H), 7.49-7.67 (m, 8 H), 8.75 (t, 1 H). |
| 144 | 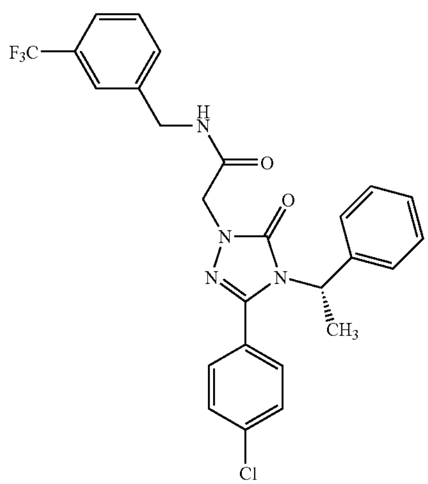 | $R_t$ = 2.82 min [8] | δ = 1.78 (d, 3 H), 4.43 (d, 2 H), 4.50 (s, 2 H), 5.26 (q, 1 H), 7.24-7.39 (m, 7 H), 7.51-7.66 (m, 6 H), 8.73 (t, 1 H). |
| 145 | 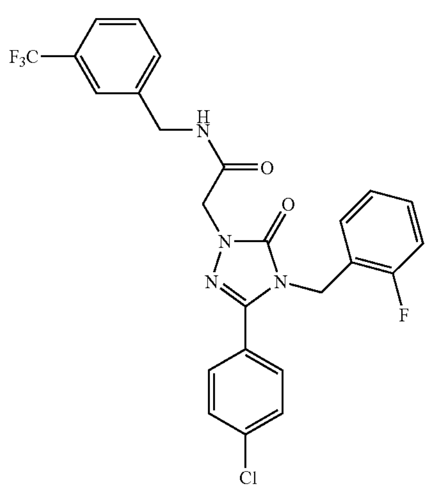 | $R_t$ = 2.55 min [7] | δ = 4.43 (d, 2 H), 4.56 (s, 2 H), 5.03 (s, 2 H), 7.06-7.19 (m, 3 H), 7.26-7.35 (m, 1 H), 7.51-7.66 (m, 8 H), 8.75 (t, 1 H). |

The following are also obtained analogously:
| Example No. | Structure | LC/MS $R_t$ [Method] |
|---|---|---|
| 146 | 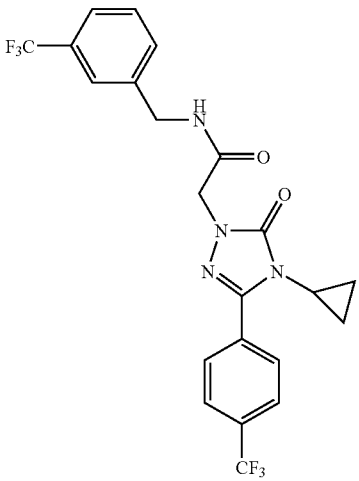 | $R_t$ = 2.53 min [5] |
| 147 | 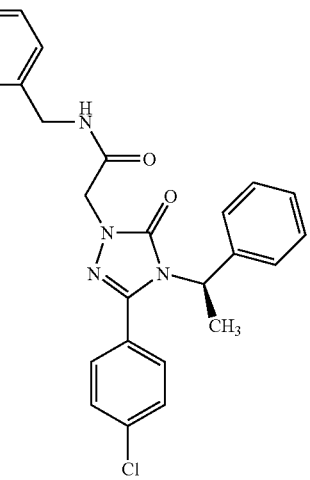 | $R_t$ = 2.65 min [7] |
| 148 | 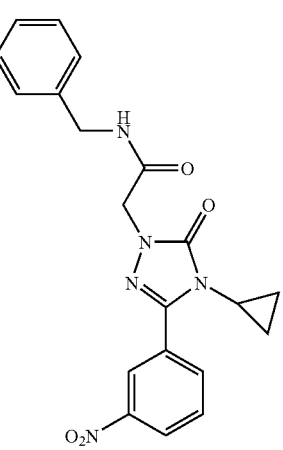 | $R_t$ = 2.27 min [5] |

-continued
| Example No. | Structure | LC/MS $R_t$ [Method] |
|---|---|---|
| 149 | 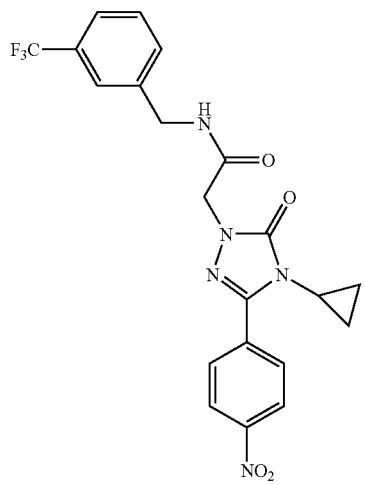 | $R_t$ = 2.29 min [5] |
| 150 | 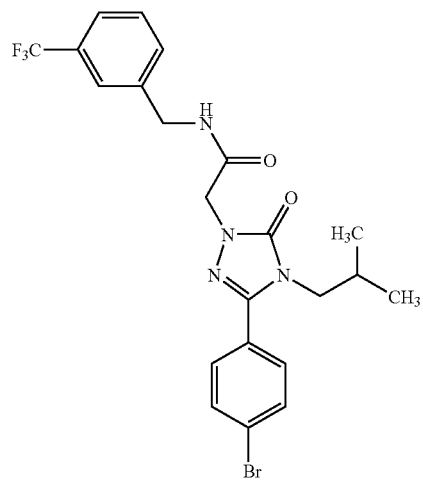 | $R_t$ = 2.69 min [5] |

| Example No. | Structure | LC/MS $R_t$ [Method] |
|---|---|---|
| 151 | (structure shown) | $R_t$ = 2.77 min [5] |
| 152 | (structure shown) | $R_t$ = 2.86 min [8] |

Example 153

2-[3-(4-chlorophenyl)-4-(4-methoxyphenylmethyl)-5-oxo-4,5-dihydro-1H-1,2,4-triazol-1-yl]-N-[3-(trifluoromethyl)phenylmethyl]acetamide

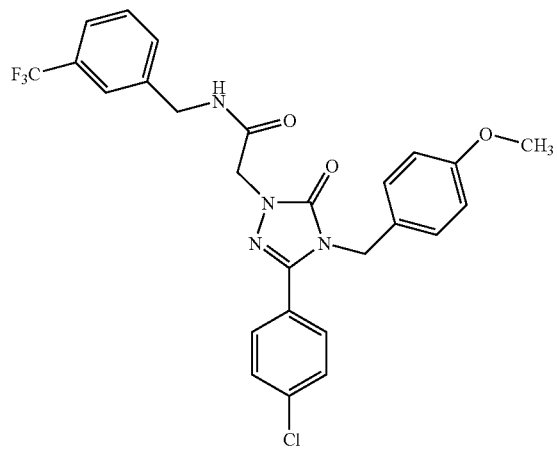

1.00 g (3.17 mmol) of 5-(4-chlorophenyl)-4-(4-methoxyphenylmethyl)-2,4-dihydro-3H-1,2,4-triazol-3-one from Example 55A, 0.80 g (3.17 mmol) of 2-chloro-N-[3-(trifluoromethyl)phenylmethyl]-acetamide and 0.88 g (6.33 mmol) of potassium carbonate are suspended in 20 ml of acetonitrile and heated under reflux for 8 hrs. The mixture is then concentrated in vacuo, and the residue taken up in water and extracted three times with ethyl acetate. The combined organic phases are concentrated and the residue purified by preparative HPLC [Method 12]. 1.07 g (64% of theory) of the target compound are thus obtained.

LC/MS [Method 5]: $R_t$=2.67 min $^1$H-NMR (400 MHz, DMSO-$d_6$): δ=3.70 (s, 3H), 4.43 (d, 2H), 4.6 (s, 2H), 4.92 (s, 2H), 6.83, 6.86 (AA' part of an AA'BB' system, 2H), 7.02, 7.04 (BB' part of an AA'BB' system, 2H), 7.51-7.66 (m, 8H), 8.75 (t, 1H).

The following are obtained analogously:

| Example No. | Structure | LC/MS $R_t$ [Method] | $^1$H-NMR (400 MHz, DMSO-$d_6$) |
|---|---|---|---|
| 154 | 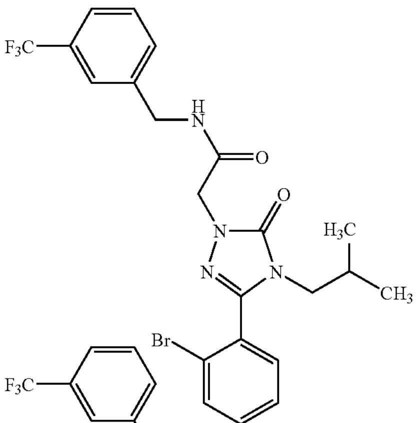 | $R_t$ = 2.42 min [7] | δ = 0.69 (d, 2 H), 1.59-1.75 (m, 1 H), 3.30 (d, 2 H), 4.42 (d, 2 H), 4.51 (s, 2 H), 7.50-7.65 (m, 7 H), 7.83 (br. d, 1 H), 8.69 (t, 1 H). |
| 155 | 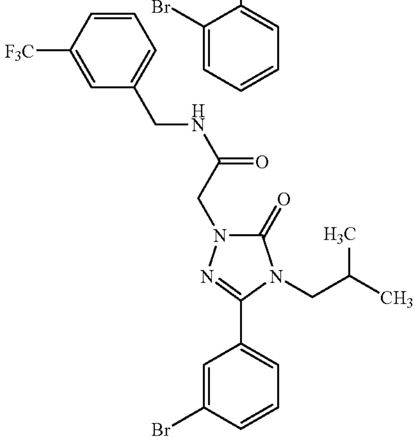 | $R_t$ = 2.80 min [8] | δ = 0.71 (d, 6 H), 1.62-1.76 (m, 1 H), 3.62 (d, 2 H), 4.42 (d, 2 H), 4.51 (s, 2 H), 7.51 (t, 1 H), 7.52-7.65 (m, 4 H), 7.69 (d, 1 H), 7.77 (d, 1 H), 7.83 (br. s, 1 H), 8.69 (t, 1 H). |

A library of further practical examples is prepared by parallel synthesis as follows:

0.12 mmol of the relevant amine and 0.10 mmol of the relevant triazolylacetic acid are dissolved in 0.6 ml of dimethylsulphoxide, treated with 25.8 mg (0.2 mmol) of N,N-diisopropylethylamine and 41.7 mg (0.130 mmol) of TBTU and shaken overnight at room temperature. The reaction solution is filtered and the filtrate purified by preparative LC/MS [Method 6]. The following are obtained in this manner:

| Example No. | Structure | LC/MS [Method 6] |
|---|---|---|
| 156 | 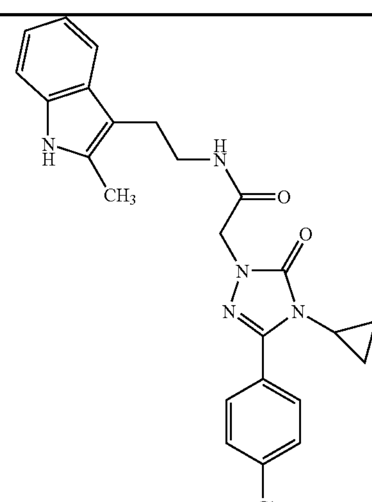 | $R_t$ = 2.01 min; MS [ESIpos]: m/z = 450 (M + H)$^+$ |

-continued
| Example No. | Structure | LC/MS [Method 6] |
|---|---|---|
| 157 | 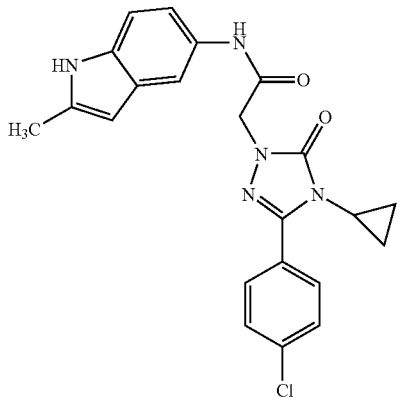 | $R_t$ = 1.93 min; MS [ESIpos]: m/z = 422 (M + H)$^+$ |
| 158 | 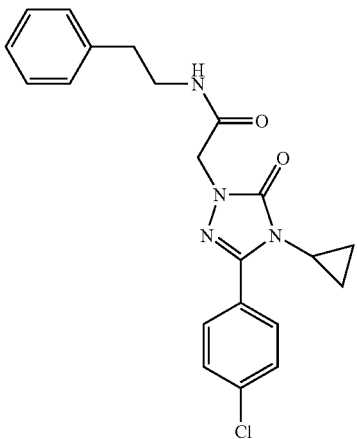 | $R_t$ = 2.00 min; MS [ESIpos]: m/z = 397 (M + H)$^+$ |
| 159 | 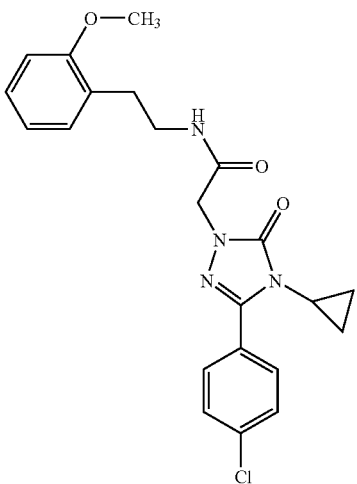 | $R_t$ = 2.02 min; MS [ESIpos]: m/z = 427 (M + H)$^+$ |

| Example No. | Structure | LC/MS [Method 6] |
|---|---|---|
| 160 | (3-methylpyrazol-1-yl-propyl)-NH-C(O)-CH2-triazolone(4-cyclopropyl)-(2-chlorophenyl) | R$_t$ = 1.73 min; MS [ESIpos]: m/z = 415 (M + H)$^+$ |
| 161 | (1H-indol-3-yl-ethyl)-NH-C(O)-CH2-triazolone(4-cyclopropyl)-(4-chlorophenyl) | R$_t$ = 1.97 min; MS [ESIpos]: m/z = 436 (M + H)$^+$ |
| 162 | (4-chlorophenyl-ethyl)-NH-C(O)-CH2-triazolone(4-cyclopropyl)-(4-chlorophenyl) | R$_t$ = 2.11 min; MS [ESIpos]: m/z = 431 (M + H)$^+$ |

-continued

| Example No. | Structure | LC/MS [Method 6] |
|---|---|---|
| 163 | 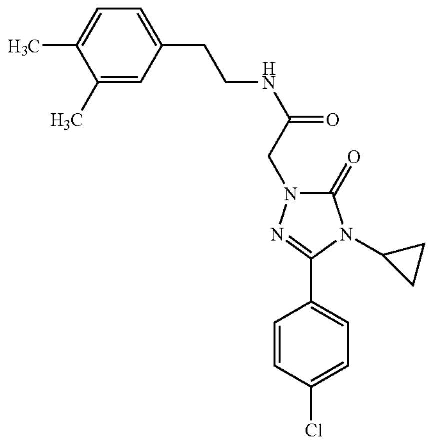 | $R_t$ = 2.14 min; MS [ESIpos]: m/z = 425 (M + H)$^+$ |
| 164 | 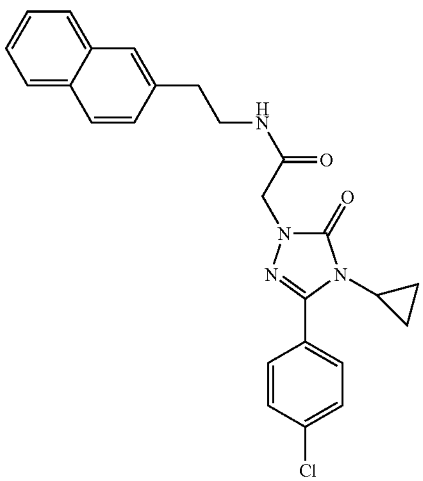 | $R_t$ = 2.15 min; MS [ESIpos]: m/z = 447 (M + H)$^+$ |
| 165 | 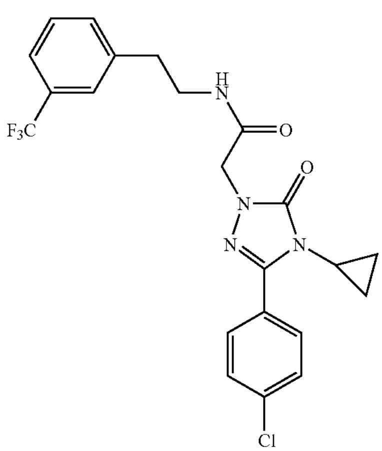 | $R_t$ = 2.12 min; MS [ESIpos]: m/z = 465 (M + H)$^+$ |

-continued
| Example No. | Structure | LC/MS [Method 6] |
|---|---|---|
| 166 | 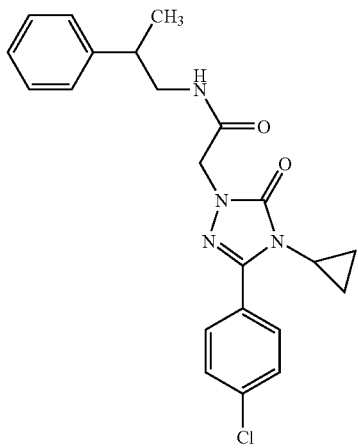 | R_t = 2.06 min; MS [ESIpos]: m/z = 411 (M + H)+ |
| 167 | 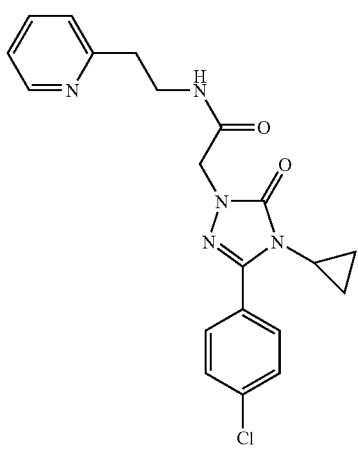 | R_t = 1.35 min; MS [ESIpos]: m/z = 398 (M + H)+ |
| 168 | 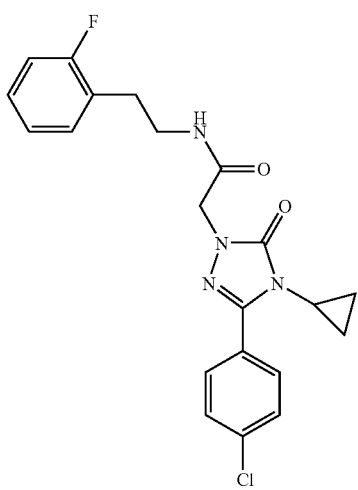 | R_t = 2.02 min; MS [ESIpos]: m/z = 415 (M + H)+ |

-continued
| Example No. | Structure | LC/MS [Method 6] |
|---|---|---|
| 169 | 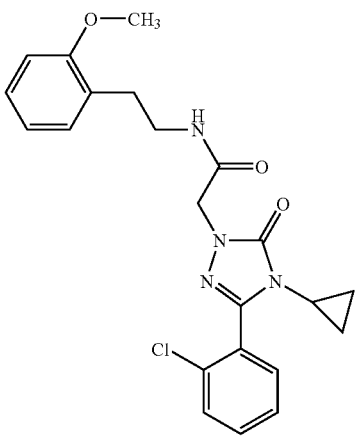 | $R_t$ = 1.97 min; MS [ESIpos]: m/z = 427 (M + H)$^+$ |
| 170 | 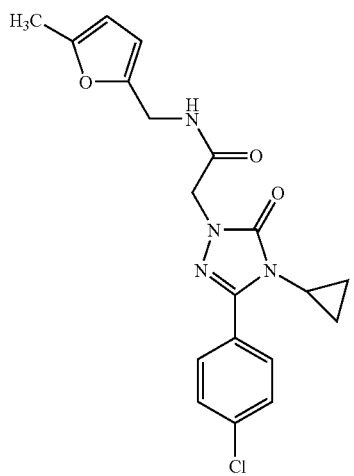 | $R_t$ = 1.93 min; MS [ESIpos]: m/z = 387 (M + H)$^+$ |
| 171 | 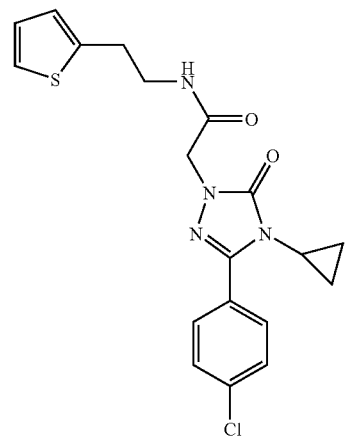 | $R_t$ = 1.97 min; MS [ESIpos]: m/z = 403 (M + H)$^+$ |

| Example No. | Structure | LC/MS [Method 6] |
|---|---|---|
| 172 | 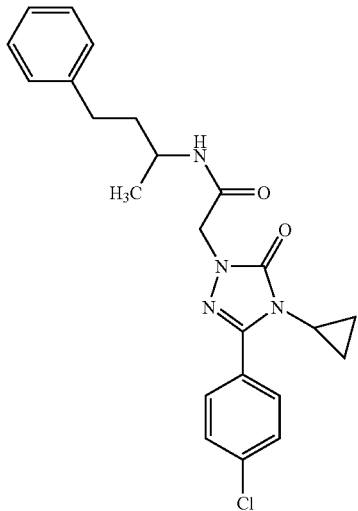 | $R_t$ = 2.11 min; MS [ESIpos]: m/z = 425 $(M + H)^+$ |
| 173 | 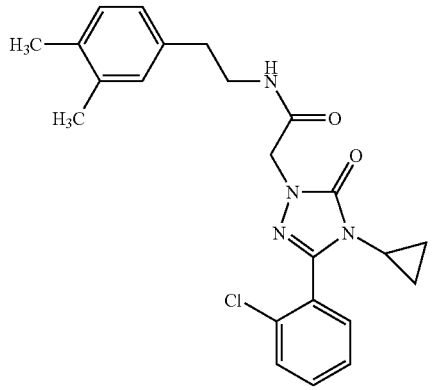 | $R_t$ = 2.08 min; MS [ESIpos]: m/z = 425 $(M + H)^+$ |
| 174 | 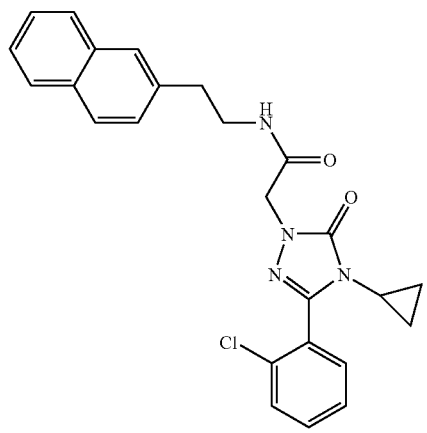 | $R_t$ = 2.09 min; MS [ESIpos]: m/z = 447 $(M + H)^+$ |

-continued
| Example No. | Structure | LC/MS [Method 6] |
|---|---|---|
| 175 | 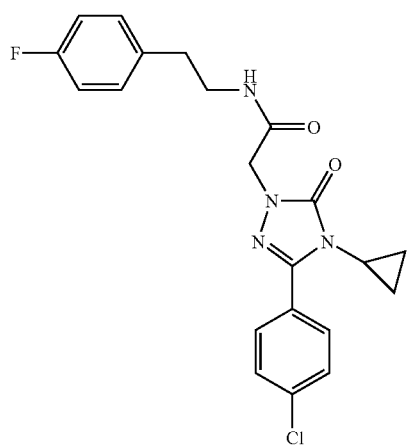 | $R_t$ = 2.01 min; MS [ESIpos]: m/z = 415 (M + H)$^+$ |
| 176 | 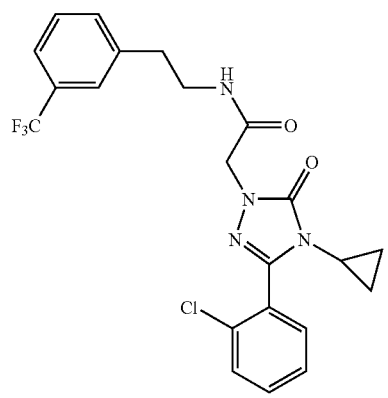 | $R_t$ = 2.07 min; MS [ESIpos]: m/z = 465 (M + H)$^+$ |
| 177 | 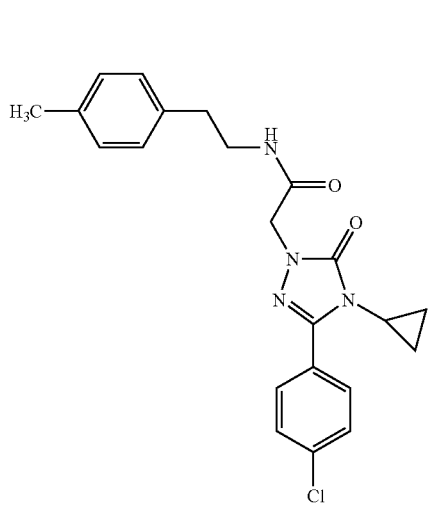 | $R_t$ = 2.08 min; MS [ESIpos]: m/z = 411 (M + H)$^+$ |

-continued

| Example No. | Structure | LC/MS [Method 6] |
|---|---|---|
| 178 | 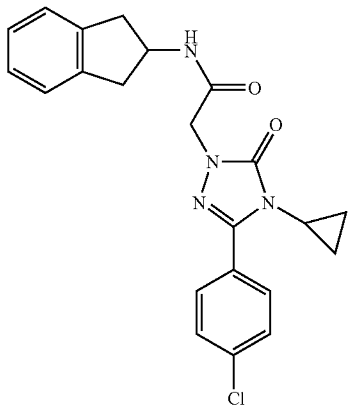 | $R_t$ = 2.03 min; MS [ESIpos]: m/z = 409 (M + H)$^+$ |
| 179 | 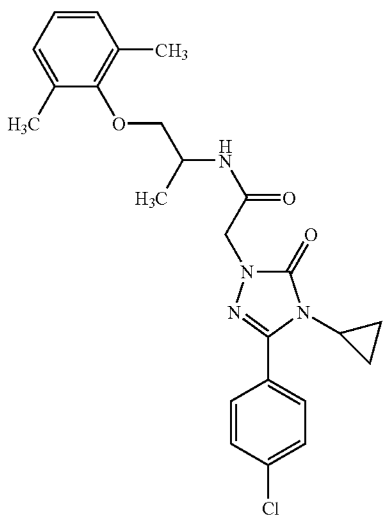 | $R_t$ = 2.18 min; MS [ESIpos]: m/z = 455 (M + H)$^+$ |
| 180 | 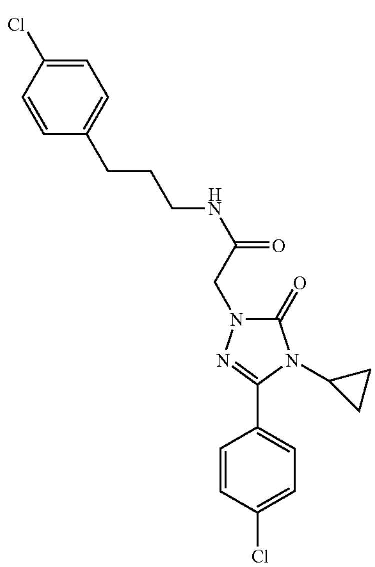 | $R_t$ = 2.14 min; MS [ESIpos]: m/z = 445 (M + H)$^+$ |

| Example No. | Structure | LC/MS [Method 6] |
|---|---|---|
| 181 | 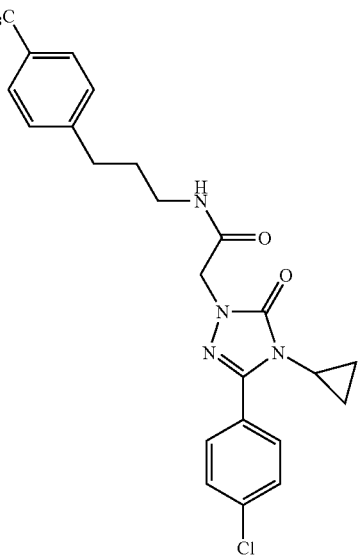 | $R_t$ = 2.19 min; MS [ESIpos]: m/z = 479 (M + H)$^+$ |
| 182 | 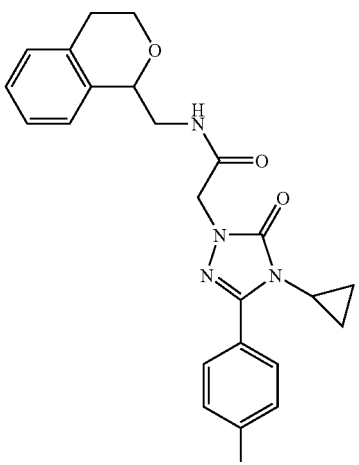 | $R_t$ = 2.00 min; MS [ESIpos]: m/z = 439 (M + H)$^+$ |
| 183 | 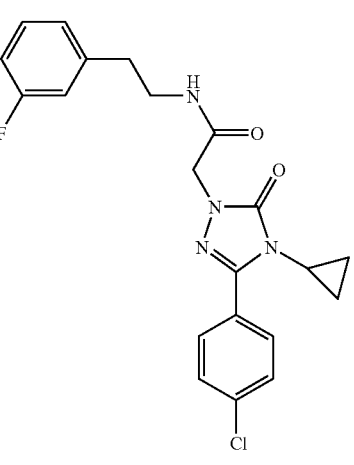 | $R_t$ = 2.03 min; MS [ESIpos]: m/z = 415 (M + H)$^+$ |

| Example No. | Structure | LC/MS [Method 6] |
|---|---|---|
| 184 | 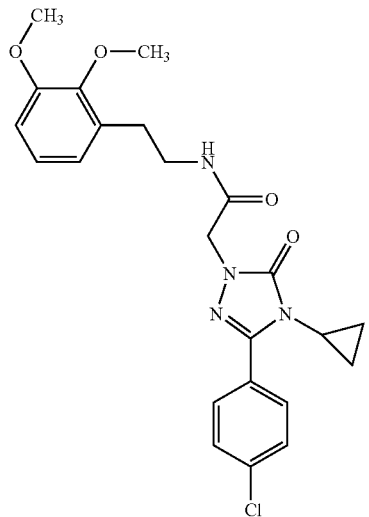 | $R_t$ = 2.02 min; MS [ESIpos]: m/z = 457 (M + H)$^+$ |
| 185 | 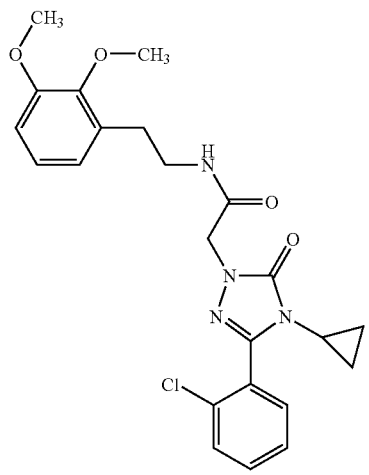 | $R_t$ = 1.94 min; MS [ESIpos]: m/z = 457 (M + H)$^+$ |

Example 186

2-[3-(4-chlorophenyl)-4-cyclopropyl-5-oxo-4,5-di-hydro-1H-1,2,4-triazol-1-yl]-N-[(1S)-1-(1-naphthyl)ethyl]propionamide (Diastereomer A)

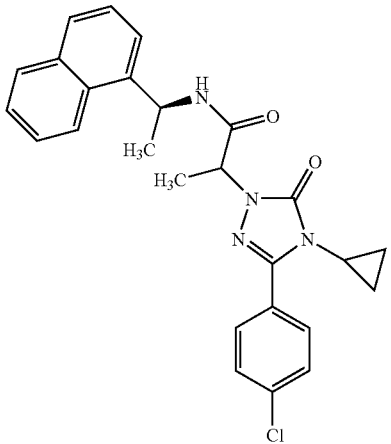

100.0 mg (0.325 mmol) of 2-[3-(4-chlorophenyl)-4-cyclo-propyl-5-oxo-4,5-dihydro-1H-1,2,4-triazol-1-yl]-propionic acid from Example 105A are placed in 2 ml of DMF and treated with 61.2 mg (0.357 mmol) of (1S)-1-(1-naphthyl)ethanamine, 52.7 mg (0.390 mmol) of HOBt and 81.0 mg (0.422 mmol) of EDC hydrochloride. The mixture is stirred overnight at room temperature, then partitioned between dichloromethane and water, and the organic phase is separated, dried over sodium sulphate and concentrated. The residue is purified by flash chromato-graphy on silica gel (eluent: first dichloromethane, then dichloromethane/methanol 100:1) and then further separated by preparative HPLC on chiral phase [Method 15]. 52 mg (35% of theory) of the diastereomerically pure target compound are thus obtained (see also Example 187).

MS [ESIpos]: m/z=461 (M+H)$^+$
HPLC [Method 2]: $R_t$=4.84 min
chiral HPLC [Method 15]: $R_t$=2.49 min
$^1$H-NMR (400 MHz, DMSO-$d_6$): δ=0.52 (m, 2H), 0.87 (m, 2H), 1.50 (d, 3H), 1.53 (d, 3H), 3.13 (tt, 1H), 4.80 (q, 1H), 5.68 (dq, 1H), 7.43 (t, 1H), 7.48-7.61 (m, 5H), 7.74 (d, 2H), 7.82 (d, 1H), 7.93 (m, 1H), 8.05 (m, 1H), 8.54 (d, 1H).

Example 187

2-[3-(4-chlorophenyl)-4-cyclopropyl-5-oxo-4,5-di-hydro-1H-1,2,4-triazol-1-yl]-N-[(1S)-1-(1-naphthyl)ethyl]propionamide (Diastereomer B)

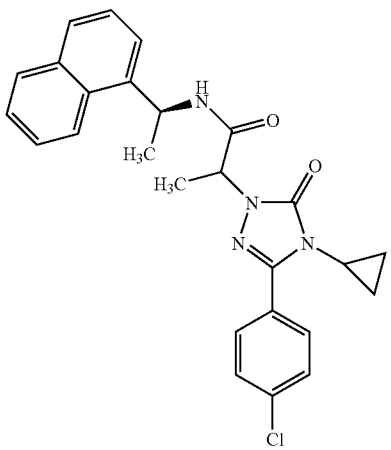

100.0 mg (0.325 mmol) of 2-[3-(4-chlorophenyl)-4-cyclo-propyl-5-oxo-4,5-dihydro-1H-1,2,4-triazol-1-yl]-propionic acid from Example 105A are placed in 2 ml of DMF and treated with 61.2 mg (0.357 mmol) of (1S)-1-(1-naphthyl)ethanamine, 52.7 mg (0.390 mmol) of HOBt and 81.0 mg (0.422 mmol) of EDC hydrochloride. The mixture is stirred overnight at room temperature, then partitioned between dichloromethane and water, and the organic is phase separated, dried over sodium sulphate and concentrated. The residue is purified by flash chromato-graphy on silica gel (eluent: first dichloromethane, then dichloromethane/methanol 100:1) and then further separated by preparative HPLC on chiral phase [Method 15]. 51 mg (34% of theory) of the diastereomerically pure target compound are thus obtained (see also Example 186).

MS [ESIpos]: m/z=461 (M+H)$^+$
HPLC [Method 2]: $R_t$=4.84 min
chiral HPLC [Method 15]: $R_t$=5.03 min
$^1$H-NMR (400 MHz, DMSO-$d_6$): δ=0.57 (m, 2H), 0.89 (m, 2H), 1.51 (br. d, 6H), 3.16 (tt, 1H), 4.78 (q, 1H), 5.67 (dq, 1H), 7.46-7.61 (m, 6H), 7.78 (d, 2H), 7.83 (d, 1H), 7.94 (br. d, 1H), 8.06 (br. d, 1H), 8.60 (d, 1H).

Example 188

2-[3-(4-chlorophenyl)-4-cyclopropyl-5-oxo-4,5-di-hydro-1H-1,2,4-triazol-1-yl]-N-[(1R)-1-(1-naphthyl)ethyl]propionamide (Diastereomer A)

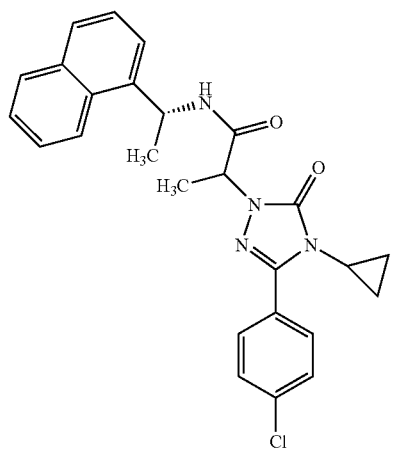

100.0 mg (0.325 mmol) of 2-[3-(4-chlorophenyl)-4-cyclo-propyl-5-oxo-4,5-dihydro-1H-1,2,4-triazol-1-yl]-propionic acid from Example 105A are placed in 2 ml of DMF and treated with 61.2 mg (0.357 mmol) of (1R)-1-(1-naphthyl)ethanamine, 52.7 mg (0.390 mmol) of HOBt and 81.0 mg (0.422 mmol) of EDC hydrochloride. The mixture is stirred overnight at room temperature, then partitioned between dichloromethane and water, and the organic phase is separated, dried over sodium sulphate and concentrated. The residue is purified by flash chromato-graphy on silica gel (eluent: first dichloromethane, then dichloromethane/methanol 100:1) and then further separated by preparative HPLC on chiral phase [Method 16]. 44 mg (29% of theory) of the diastereomerically pure target compound are thus obtained (see also Example 189).

MS [ESIpos]: m/z=461 (M+H)+

HPLC [Method 2]: $R_t$=4.84 min chiral HPLC [Method 16]: $R_t$=2.43 min $^1$H-NMR (400 MHz, DMSO-$d_6$): δ=0.52 (m, 2H), 0.87 (m, 2H), 1.50 (d, 3H), 1.53 (d, 3H), 3.13 (tt, 1H), 4.80 (q, 1H), 5.68 (dq, 1H), 7.43 (t, 1H), 7.47-7.61 (m, 5H), 7.74 (d, 2H), 7.82 (d, 1H), 7.93 (m, 1H), 8.05 (m, 1H), 8.53 (d, 1H).

Example 189

2-[3-(4-chlorophenyl)-4-cyclopropyl-5-oxo-4,5-di-hydro-1H-1,2,4-triazol-1-yl]-N-[(1R)-1-(1-naphthyl)ethyl]propionamide (Diastereomer B)

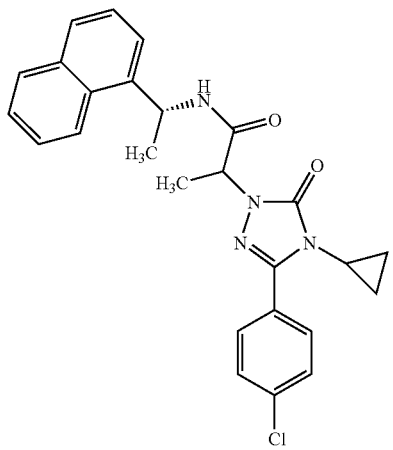

100.0 mg (0.325 mmol) of 2-[3-(4-chlorophenyl)-4-cyclo-propyl-5-oxo-4,5-dihydro-1H-1,2,4-triazol-1-yl]-propionic acid from Example 105A are placed in 2 ml of DMF and treated with 61.2 mg (0.357 mmol) of (1R)-1-(1-naphthyl)ethanamine, 52.7 mg (0.390 mmol) of HOBt and 81.0 mg (0.422 mmol) of EDC hydrochloride. The mixture is stirred overnight at room temperature, then partitioned between dichloromethane and water, and the organic phase is separated, dried over sodium sulphate and concentrated. The residue is purified by flash chromato-graphy on silica gel (eluent: first dichloromethane, then dichloromethane/methanol 100:1) and then further separated by preparative HPLC on chiral phase [Method 16]. 58 mg (39% of theory) of the diastereo-merically pure target compound are thus obtained (see also Example 188).

MS [ESIpos]: mm/z=461 (M+H)+

HPLC [Method 2]: $R_t$=4.84 min chiral HPLC [Method 16]: $R_t$=6.14 min $^1$H-NMR (400 MHz, DMSO-$d_6$): δ=0.57 (m, 2H), 0.89 (m, 2H), 1.51 (br. d, 6H), 3.16 (tt, 1H), 4.77 (q, 1H), 5.67 (dq, 1H), 7.46-7.61 (m, 6H), 7.78 (d, 2H), 7.83 (br. d, 1H), 7.94 (br. d, 1H), 8.06 (br. d, 1H), 8.60 (d, 1H).

Example 190 rac-2-(3-cyclopropyl-2-oxo-4-phenyl-2,3-dihydro-1H-imidazol-1-yl)-N-[1-(2-naphthyl)ethyl]-aceta-mide

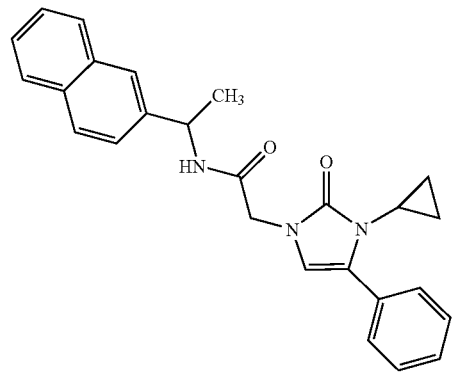

40 mg (0.155 mmol) of (3-cyclopropyl-2-oxo-4-phenyl-2,3-dihydro-1H-imidazol-1-yl)-acetic acid from Example 128A, 29.2 mg (0.17 mmol) of 1-(2-naphthyl)ethylamine, 38.6 mg (0.20 mmol) of EDC hydrochloride and 25.1 mg (0.19 mmol) of HOBt are dissolved in 1.5 ml of dry DMF and stirred overnight at RT. The crude product is purified by preparative HPLC [Method 10, with addition of 0.01 M hydrochloric acid in the water]. The target compound is obtained in a yield of 41 mg (63% of theory).

HPLC [Method 2]: $R_t$=4.44 min

MS [ESIpos]: m/z=412 (M+H)+

$^1$H-NMR (400 MHz, DMSO-$d_6$): δ=0.46 (m, 2H), 0.78 (m, 2H), 1.47 (d, 3H), 3.00 (m, 1H), 4.28 (s, 2H), 5.08 (m, 1H), 6.65 (s, 1H), 7.25-7.54 (m, 8H), 7.77-7.93 (m, 4H), 8.70 (d, 1H).

Example 191 rac-2-[4-(4-bromophenyl)-3-cyclopropyl-2-oxo-2,3-dihydro-1H-imidazol-1-yl]-N-{1-[3-(trifluorom-ethyl)phenyl]ethyl}acetamide

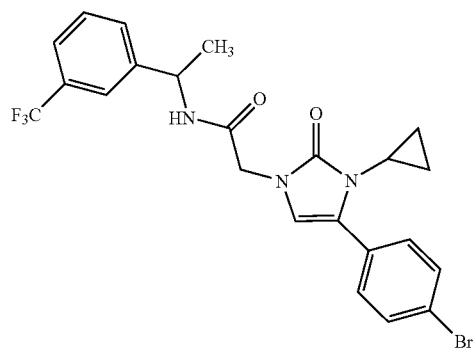

40.0 mg (0.119 mmol) of 4-(4-bromophenyl)-3-cyclopro-pyl-2-oxo-2,3-dihydro-1H-imidazol-1-yl]-acetic acid from Example 129A, 24.7 mg (0.130 mmol) of 1-[3-(trifluorom-ethyl)phenyl]ethylamine and 19.2 mg (0.142 mmol) of HOBt are placed in 1.5 ml of dimethylformamide and treated with 29.6 mg (0.154 mmol) of EDC hydrochloride. This is stirred overnight at room temperature, then stirred with 15 ml of water, and the resulting precipitate is isolated and this crude product purified by preparative HPLC [Method 13]. 23 mg (38% of theory) of the target compound are thus obtained.

LC/MS [Method 7]: $R_t$=2.43 min $^1$H-NMR (400 MHz, DMSO-$d_6$): δ=0.39-0.53 (m, 2H), 0.73-0.88 (m, 2H), 1.39 (d, 3H), 3.00 (dddd, 1H), 4.25 (centre of an AB system, 2H), 4.99 (dq, 1H), 6.72 (s, 1H), 7.44, 7.46 (AA' part of an AA'BB' system, 2H), 7.52-7.68 (m, 4H), 7.57, 7.59 (BB' part of an AA'BB' system, 2H), 8.71 (d, 1H).

The following are obtained analogously:

| Example No. | Structure | LC/MS $R_t$ [Method] | $^1$H-NMR (400 MHz, DMSO-$d_6$) |
|---|---|---|---|
| 192 | 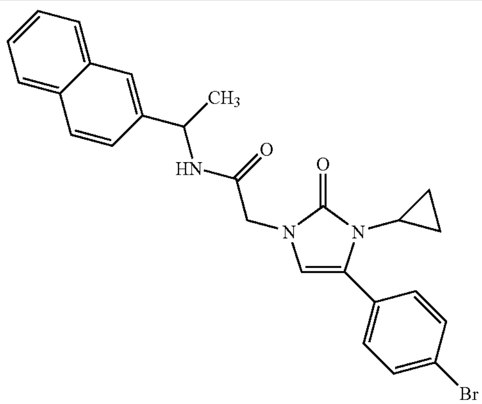 | $R_t$ = 2.42 min [7] | δ = 0.42-0.50 (m, 2 H), 0.77-0.84 (m, 2 H), 1.47 (d, 3 H), 3.00 (dddd, 1 H), 4.27 (s, 2 H), 5.07 (dq, 1 H), 6.73 (s, 1 H), 7.42-7.60 (m, 7 H), 7.81 (br. s, 1 H), 7.83-7.91 (m, 3 H), 8.70 (d, 1 H). |
| 193 | 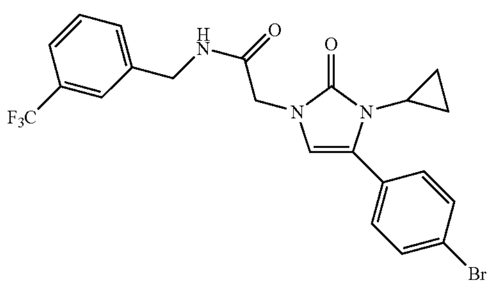 | $R_t$ = 2.34 min [7] | δ = 0.45-0.52 (m, 2 H), 0.78-0.85 (m, 2 H), 3.02 (dddd, 1 H), 4.27 (s, 2 H), 4.39 (d, 2 H), 6.78 (s, 1 H), 7.46, 7.48 (AA' part of an AA'BB' system, 2 H), 7.54-7.64 (m, 4 H), 7.58, 7.60 (BB' part of an AA'BB' system, 2 H), 8.66 (t, 1 H). |

Example 194

2-[4-(4-chlorophenyl)-3-cyclopropyl-2-oxo-2,3-dihydro-1H-imidazol-1-yl]-N-[3-(trifluoromethyl)-phenylmethyl]acetamide

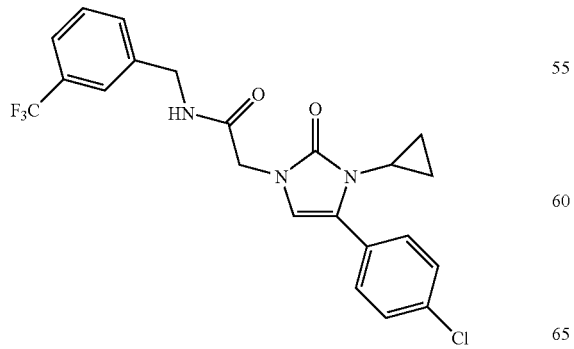

50.0 mg (0.171 mmol) of 4-(4-chlorophenyl)-3-cyclopropyl-2-oxo-2,3-dihydro-1H-imidazol-1-yl]-acetic acid from Example 130A, 32.9 mg (0.188 mmol) of 3-trifluoromethylbenzylamine and 27.7 mg (0.205 mmol) of HOBt are placed in 1.5 ml of dimethylformamide and treated with 42.6 mg (0.222 mmol) of EDC hydrochloride. This is stirred overnight at room temperature, then stirred with 19 ml of water and the resulting precipitate recovered by filtration. The crude product is washed with water and dried in vacuo. 65 mg (85% of theory) of the target compound are thus obtained.

LC/MS [Method 4]: $R_t$=2.59 min $^1$H-NMR (400 MHz, DMSO-$d_6$): δ=0.42-0.55 (m, 2H), 0.73-0.88 (m, 2H), 3.02 (dddd, 1H), 4.27 (s, 2H), 4.39 (d, 2H), 6.76 (s, 1H), 7.43-7.66 (m, 8H), 8.66 (t, 1H).

Example 195 rac-2-[4-(4-chlorophenyl)-3-cyclopropyl-2-oxo-2,3-dihydro-1H-imidazol-1-yl]-N-{1-[3-(trifluoromethyl)phenyl]ethyl}acetamide

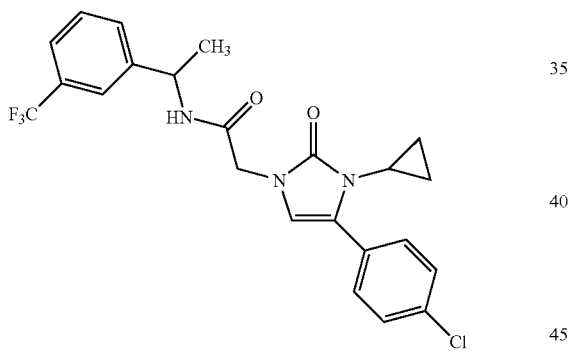

50.0 mg (0.171 mmol) of 4-(4-chlorophenyl)-3-cyclopropyl-2-oxo-2,3-dihydro-1H-imidazol-1-yl]-acetic acid from Example 130A, 35.5 mg (0.188 mmol) of 1-[3-(trifluoromethyl)phenyl]-ethylamine and 27.7 mg (0.205 mmol) of HOBt are placed in 1.5 ml of dimethylformamide and treated with 42.6 mg (0.222 mmol) of EDC hydrochloride. This is stirred overnight at room temperature, then stirred with 19 ml of water and the resulting precipitate recovered by filtration. The crude product is washed with water, dried in vacuo and purified by preparative HPLC [Method 9]. 14 mg (18% of theory) of the target compound are thus obtained.

LC/MS [Method 7]: $R_t$=2.38 min $^1$H-NMR (400 MHz, DMSO-$d_6$): δ=0.39-0.53 (m, 2H), 0.73-0.87 (m, 2H), 1.39 (d, 3H), 3.00 (dddd, 1H), 4.25 (centre of an AB system, 2H), 4.50 (dq, 1H), 6.72 (s, 1H), 7.44, 7.46 (AA' part of an AA'BB' system, 2H), 7.51, 7.53 (BB' part of an AA'BB' system, 2H), 7.54-7.69 (m, 4H), 8.71 (d, 1H).

The following is obtained analogously:

Example 196 rac-2-[4-(4-chlorophenyl)-3-cyclopropyl-2-oxo-2,3-dihydro-1H-imidazol-1-yl]-N-[1-(2-naphthyl)-ethyl]acetamide

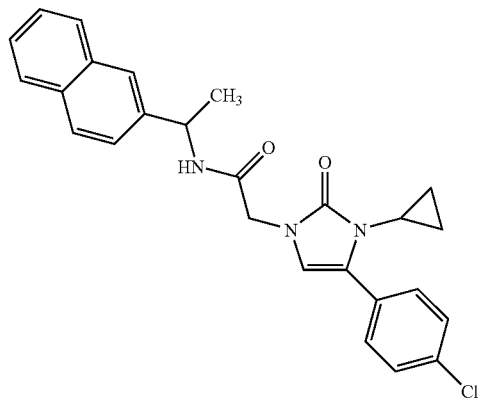

LC/MS [Method 7]: $R_t$=2.38 min $^1$H-NMR (400 MHz, DMSO-$d_6$): δ=0.39-0.53 (m, 2H), 0.73-0.88 (m, 2H), 1.47 (d, 3H), 3.01 (dddd, 1H), 4.27 (s, 2H), 5.07 (dq, 1H), 6.72 (s, 1H), 7.41-7.54 (m, 7H), 7.81 (s, 1H), 7.84-7.91 (m, 3H), 8.70 (d, 1H).

Example 197

2-[4-(4-chlorophenyl)-3-cyclopropyl-2-oxo-2,3-dihydro-1H-imidazol-1-yl]-N-[(1S)-1-(1-naphthyl)-ethyl]acetamide

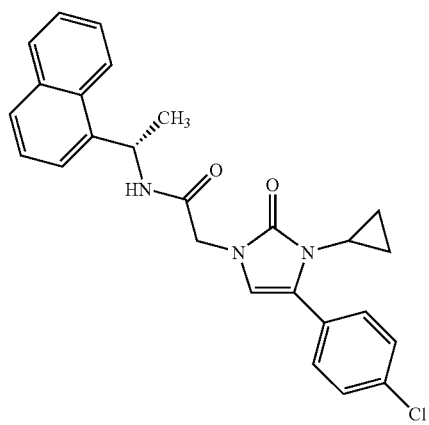

150 mg (0.512 mmol) of [4-(4-chlorophenyl)-3-cyclopropyl-2-oxo-2,3-dihydro-1H-imidazol-1-yl]-acetic acid from Example 130A, 96.5 mg (0.564 mmol) of (1R)-1-(1-naphthyl)ethylamine, 128 mg (0.67 mmol) of EDC hydrochloride and 83.1 mg (0.62 mmol) of HOBt are dissolved in 2 ml of dry DMF and stirred overnight at room temperature. The crude product is purified by flash chromatography on silica gel (eluent: first dichloromethane, then dichloromethane/methanol 100:1). The target compound is obtained in a yield of 172 mg (75% of theory).

HPLC [Method 2]: $R_t$=4.78 min

MS [ESIpos]: m/z=446 (M+H)$^+$ $^1$H-NMR (400 MHz, DMSO-d$_6$): δ=0.45 (m, 2H), 0.79 (m, 2H), 1.51 (d, 3H), 3.00 (m, 1H), 4.25 (d, 2H), 5.70 (m, 1H), 6.70 (s, 1H), 7.40-7.61 (m, 8H), 7.84 (d, 1H), 7.95 (d, 1H), 8.10 (d, 1H), 8.76 (d, 1H).

The following are obtained analogously to Examples 190 and 197:

| Example No. | Structure | LC/MS or HPLC, MS $R_t$ [Method] | $^1$H-NMR (400 MHz, DMSO-d$_6$) |
|---|---|---|---|
| 198 | 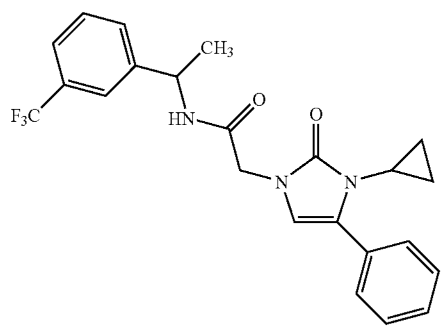 | MS [ESIpos]: m/z = 430 (M + H)$^+$; [ESIneg]: m/z = 428 (M − H)$^-$ $R_t$ = 4.44 min [2] | δ = 0.46 (m, 2 H), 0.77 (m, 2 H), 1.40 (d, 3 H), 3.00 (m, 1 H), 4.25 (s, 2 H), 5.00 (m, 1 H), 6.63 (s, 1 H), 7.26-7.73 (m, 9 H), 8.70 (d, 1 H). |
| 199 | 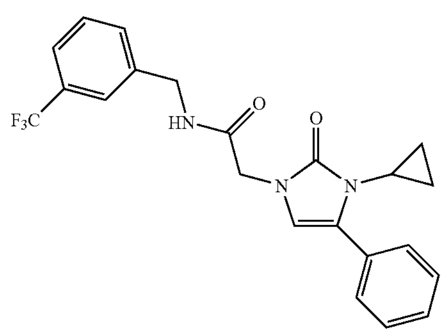 | MS [ESIpos]: m/z = 416 (M + H)$^+$; [ESIneg]: m/z = 414 (M − H)$^-$ $R_t$ = 4.38 min [2] | δ = 0.49 (m, 2 H), 0.78 (m, 2 H), 3.02 (m, 1 H), 4.28 (s, 2 H), 4.40 (d, 2 H), 6.69 (s, 1 H), 7.26-7.65 (m, 9 H), 8.66 (t, 1 H). |
| 200 | 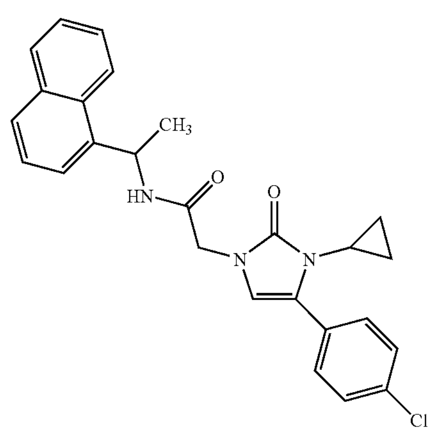 | MS [ESIpos]: m/z = 446 (M + H)$^+$; [ESIneg]: m/z = 444 (M − H)$^-$ $R_t$ = 4.78 min [2] | δ = 0.45 (m, 2 H), 0.79 (m, 2 H), 1.51 (d, 3 H), 3.00 (m, 1 H), 4.26 (d, 2 H), 5.70 (m, 1 H), 6.69 (s, 1 H), 7.40-7.60 (m, 8 H), 7.84 (d, 1 H), 7.94 (d, 1 H), 8.10 (d, 1 H), 8.75 (d, 1 H). |

| Example No. | Structure | LC/MS or HPLC, MS $R_t$ [Method] | $^1$H-NMR (400 MHz, DMSO-$d_6$) |
|---|---|---|---|
| 201 | 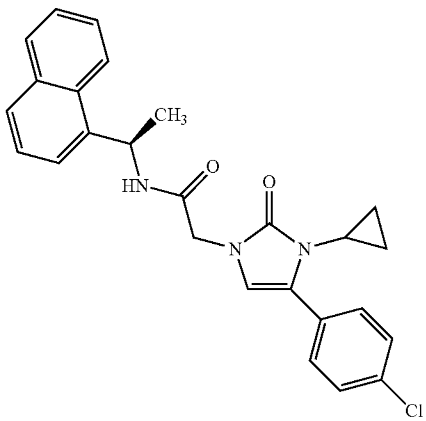 | MS [ESIpos]: m/z = 446 (M + H)$^+$; [ESIneg]: m/z = 444 (M − H)$^-$ $R_t$ = 4.77 min [2] | δ = 0.45 (m, 2 H), 0.79 (m, 2 H), 1.52 (d, 3 H), 3.00 (m, 1 H), 4.26 (d, 2 H), 5.70 (m, 1 H), 6.70 (s, 1 H), 7.40-7.60 (m, 8 H), 7.84 (d, 1 H), 7.94 (d, 1 H), 8.11 (d, 1 H), 8.76 (d, 1 H). |
| 202 | 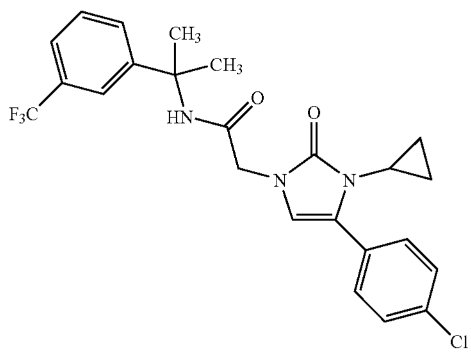 | MS [ESIpos]: m/z = 478 (M + H)$^+$; [ESIneg]: m/z = 476 (M − H)$^-$ $R_t$ = 4.88 min [2] | δ = 0.44 (m, 2 H), 0.79 (m, 2 H), 1.58 (s, 6 H), 2.99 (m, 1 H), 4.25 (s, 2 H), 6.65 (s, 1 H), 7.41-7.56 (m, 6 H), 7.60 (s, 1 H), 7.66 (d, 1 H), 8.54 (s, 1 H). |
| 203 | 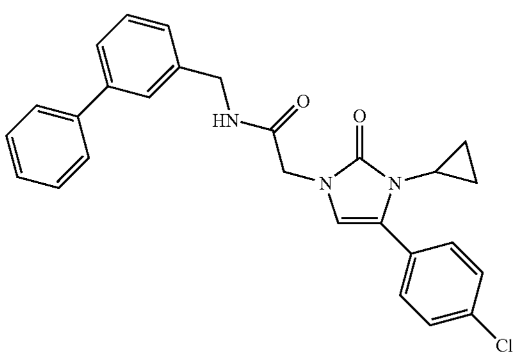 | MS [CI]: m/z = 458 (M + H)$^+$ $R_t$ = 4.84 min [2] | δ = 0.49 (m, 2 H), 0.81 (m, 2 H), 3.02 (m, 1 H), 4.28 (s, 2 H), 4.38 (d, 2 H), 6.77 (s, 1 H), 7.23-7.70 (m, 13 H), 8.63 (t, 1 H). |
| 204 | 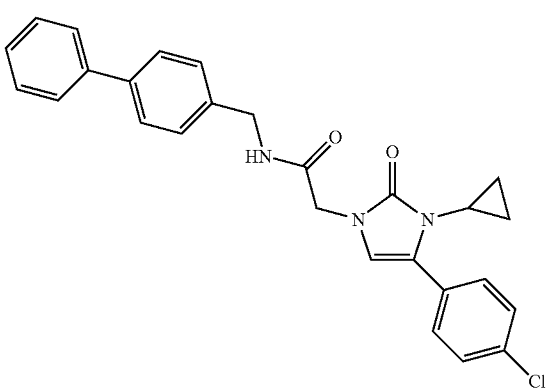 | MS [CI]: m/z = 458 (M + H)$^+$ $R_t$ = 4.84 min [2] | δ = 0.49 (m, 2 H), 0.82 (m, 2 H), 3.03 (m, 1 H), 4.28 (s, 2 H), 4.34 (d, 2 H), 6.78 (s, 1 H), 7.33-7.68 (m, 13 H), 8.61 (t, 1 H). |

| Example No. | Structure | LC/MS or HPLC, MS R$_t$ [Method] | $^1$H-NMR (400 MHz, DMSO-d$_6$) |
|---|---|---|---|
| 205 | 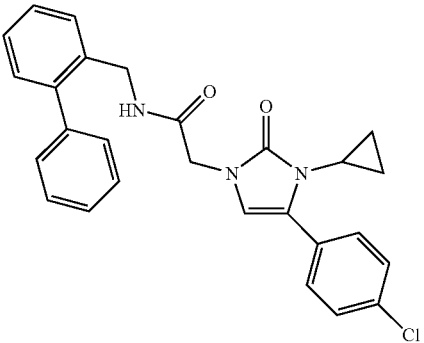 | R$_t$ = 2.44 min [7] | δ = 0.47 (m, 2 H), 0.81 (m, 2 H), 3.01 (m, 1 H), 4.17-4.27 (m, 4 H), 6.72 (s, 1 H), 7.22 (d, 1 H), 7.31-7.57 (m, 12 H), 8.50 (t, 1 H). |
| 206 | 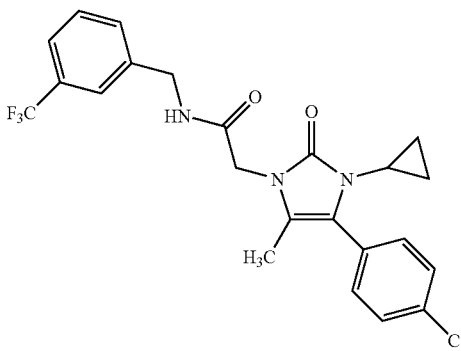 | MS [CI]: m/z = 464 (M + H)$^+$ R$_t$ = 4.78 min [2] | δ = 0.41 (m, 2 H), 0.67 (m, 2 H), 1.94 (s, 3 H), 2.87 (m, 1 H), 4.32 (s, 2 H), 4.40 (d, 2 H), 7.39-7.65 (m, 8 H), 8.72 (t, 1 H). |
| 207 | 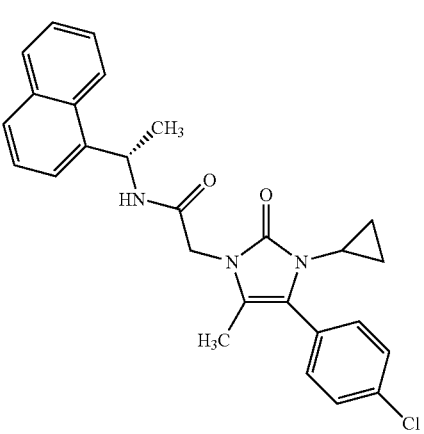 | MS [ESIpos]: m/z = 460 (M + H)$^+$; [ESIneg]: m/z = 458 (M − H)$^-$ R$_t$ = 4.87 min [2] | δ = 0.37 (m, 2 H), 0.66 (m, 2 H), 1.52 (d, 3 H), 1.91 (s, 3 H), 2.86 (m, 1 H), 4.29 (q, 2 H), 5.71 (m, 1 H), 7.37-7.60 (m, 8 H), 7.84 (d, 1 H), 7.95 (d, 1 H), 8.09 (d, 1 H), 8.78 (d, 1 H). |
| 208 | 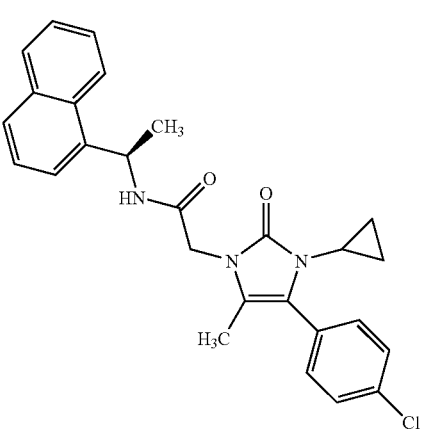 | MS [ESIpos]: m/z = 460 (M + H)$^+$; [ESIneg]: m/z = 458 (M − H)$^-$ R$_t$ = 4.87 min [2] | δ = 0.37 (m, 2 H), 0.66 (m, 2 H), 1.52 (d, 3 H), 1.90 (s, 3 H), 2.86 (m, 1 H), 4.29 (q, 2 H), 5.71 (m, 1 H), 7.37-7.60 (m, 8 H), 7.84 (d, 1 H), 7.95 (d, 1 H), 8.09 (d, 1 H), 8.78 (d, 1 H). |

| Example No. | Structure | LC/MS or HPLC, MS $R_t$ [Method] | $^1$H-NMR (400 MHz, DMSO-$d_6$) |
|---|---|---|---|
| 209 | 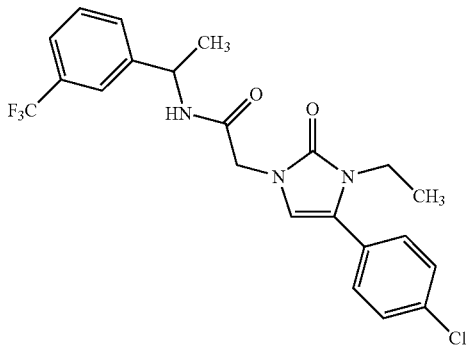 | MS [ESIpos]: m/z = 452 (M + H)$^+$; [ESIneg]: m/z = 450 (M − H)$^-$ $R_t$ = 4.78 min [2] | δ = 1.00 (s, 3 H), 1.40 (d, 3 H), 3.68 (q, 2 H), 4.29 (s, 2 H), 5.00 (m, 1 H), 6.68 (s, 1 H), 7.37-7.70 (m, 8 H), 8.72 (d, 1 H). |
| 210 | 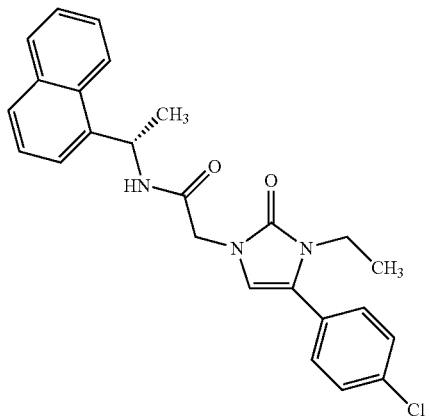 | MS [ESIpos]: m/z = 434 (M + H)$^+$; [ESIneg]: m/z = 432 (M − H)$^-$ $R_t$ = 4.78 min [2] | δ = 1.00 (t, 3 H), 1.52 (d, 3 H), 3.67 (q, 2 H), 4.30 (d, 2 H), 5.71 (m, 1 H), 6.67 (s, 1 H), 7.37-7.60 (m, 8 H), 7.84 (d, 1 H), 7.95 (d, 1 H), 8.10 (d, 1 H), 8.78 (d, 1 H). |
| 211 | 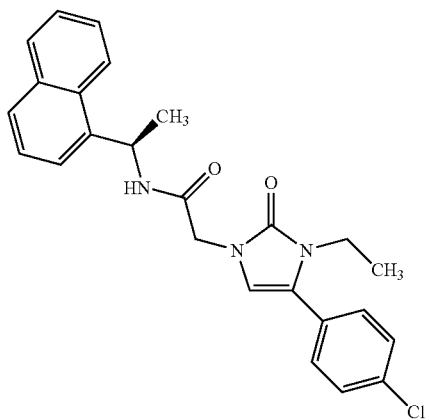 | MS [ESIpos]: m/z = 434 (M + H)$^+$; [ESIneg]: m/z = 432 (M − H)$^-$ $R_t$ = 4.78 min [2] | δ = 1.00 (t, 3 H), 1.52 (d, 3 H), 3.67 (q, 2 H), 4.30 (d, 2 H), 5.71 (m, 1 H), 6.67 (s, 1 H), 7.36-7.61 (m, 8 H), 7.84 (d, 1 H), 7.94 (d, 1 H), 8.10 (d, 1 H), 8.78 (d, 1 H). |

| Example No. | Structure | LC/MS or HPLC, MS $R_t$ [Method] | $^1$H-NMR (400 MHz, DMSO-d$_6$) |
|---|---|---|---|
| 212 | 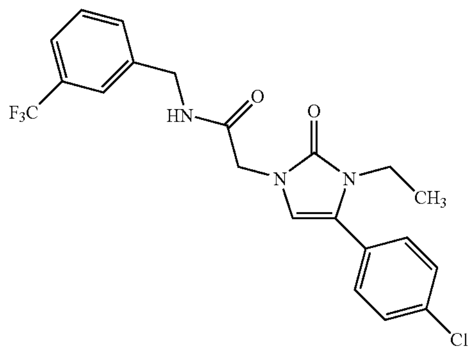 | MS [ESIpos]: m/z = 438 (M + H)$^+$; [ESIneg]: m/z = 436 (M – H)$^-$ $R_t$ = 4.69 min [2] | δ = 1.02 (t, 3 H), 3.69 (q, 2 H), 4.32 (s, 2 H), 4.40 (d, 2 H), 6.74 (s, 1 H), 7.39-7.66 (m, 8 H), 8.69 (t, 1 H). |

Example 213

2-[4-(4-chlorophenyl)-3-cyclopropyl-2-oxo-2,3-dihydro-1H-imidazol-1-yl]-N-[3-(trifluoromethyl)-phenylmethyl]propionamide

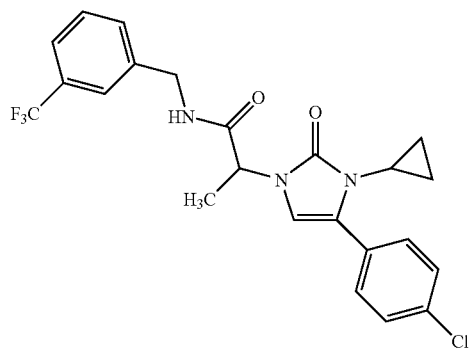

50 mg (0.163 mmol) of 2-(4-[4-chlorophenyl]-3-cyclopropyl-2-oxo-2,3-dihydro-1H-imidazol-1-yl)-propionic acid from Example 131A, 31.4 mg (0.179 mmol) of 3-trifluoromethylbenzylamine, 40.6 mg (0.212 mmol) of EDC hydrochloride and 26.4 mg (0.196 mmol) of HOBt are dissolved in 1 ml of dry dimethylformamide and stirred overnight at room temperature. The mixture is partitioned between water and dichloromethane, and the separated organic phase is dried over sodium sulphate and concentrated. The crude product that remains is purified by flash chromatography on silica gel (eluent: first dichloromethane, then dichloromethane/methanol 100:1→50:1). 42 mg (56% of theory) of the target compound are thus obtained.

MS [ESIpos]: m/z=464 (M+H)$^+$; [ESIneg]: m/z=462 (M–H)$^-$ $^1$H-NMR (400 MHz, DMSO-d$_6$): δ=0.42-0.54 (m, 2H), 0.75-0.87 (m, 2H), 1.47 (d, 3H), 3.02 (dddd, 1H), 4.37 (d, 2H), 4.74 (q, 1H), 6.91 (s, 1H), 7.44, 7.47 (AA' part of an AA'BB' system, 2H), 7.53-7.63 (m, 4H), 7.55, 7.57 (BB' part of an AA'BB' system, 2H), 8.75 (t, 1H).

The following are obtained analogously:

| Example No. | Structure | HPLC, MS $R_t$ [Method] |
|---|---|---|
| 214 | 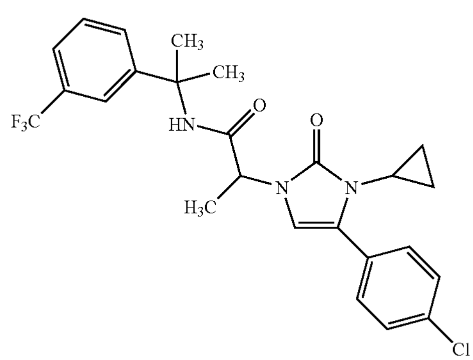 | MS [CIpos]: m/z = 509 (M + NH$_4$)$^+$, 492 (M + H)$^+$ $R_t$ = 5.06 min [1] |

| Example No. | Structure | HPLC, MS $R_t$ [Method] |
|---|---|---|
| 215 | (1:1 diastereomer mixture) | MS [CIpos]: m/z = 477 (M + NH$_4$)$^+$, 460 (M + H)$^+$ $R_t$ = 4.95 min [1] |

Example 216

2-[3-(4-chloro-2-methoxyphenyl)-4-(2-fluorobenzyl)-5-oxo-4,5-dihydro-1H-1,2,4-triazol-1-yl]-N-[1-methyl-1-(3-trifluoromethyl-phenyl)ethyl]-acetamide

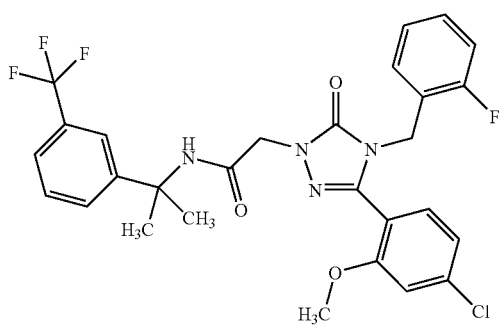

Under argon, 70 mg (0.14 mmol) of the bromide from Example 141A and 35.4 mg of (2-methoxy-4-chlorophenyl)boronic acid (0.19 mmol) are dissolved in 1.75 ml of degassed DMF and treated with 204 µl of a degassed 2 M sodium carbonate solution in water (0.41 mmol). Ca. 8 mg of tetrakis-(triphenylphosphine)palladium (ca. 7 µmol) are added and the mixture heated at 90° C. for 5 hrs. After cooling, it is filtered, the solid washed with a little DMSO and the total filtrate separated by preparative HPLC (Method 20). 65 mg (83% of theory) of the title compound are obtained.

LC/MS [Method 7]: $R_t$=2.63 min; m/z=577 (M+H)$^+$ $^1$H-NMR (400 MHz, DMSO-d$_6$): δ=1.60 (s, 6H), 3.68 (s, 3H), 4.49 (s, 2H), 4.71 (s, 2H), 6.96-7.08 (m, 4H), 7.16 (d, 1H), 7.19-7.28 (m, 2H), 7.48-7.57 (m, 2H), 7.62 (s, 1H), 7.67 (d, 1H), 8.51 (br. s, 1H).

By the same, method, the following examples are prepared from the corresponding boronic acids (all commercially available) and the stated educt bromides. In a few cases, the corresponding 4,4,5,5-tetramethyl-1,2,3-borolane derivative (cyclic pinacol boronate ester) is used instead of the boronic acid.

| Example No. | Structure | Educt; yield | LC/MS: $R_t$ [Method], m/z |
|---|---|---|---|
| 217 | 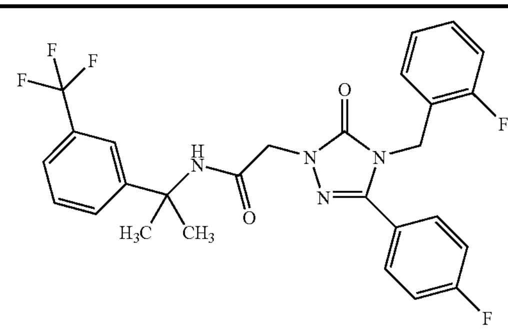 | 141A; 87% | $R_t$ = 2.81 min [8] m/z = 531 (M + H)$^+$ |

-continued
| Example No. | Structure | Educt; yield | LC/MS: $R_t$ [Method], m/z |
|---|---|---|---|
| 218 | 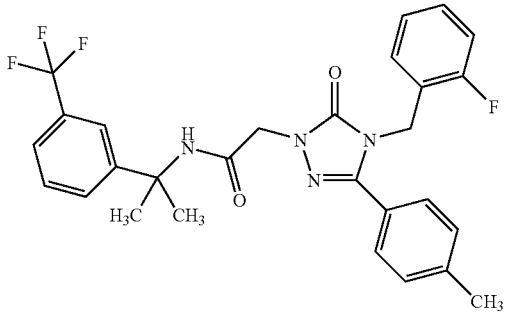 | 141A; 71% | $R_t$ = 2.90 min [8] m/z = 527 (M + H)$^+$ |
| 219 | 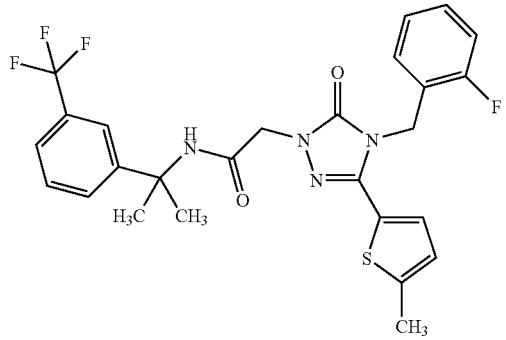 | 141A; 70% | $R_t$ = 2.58 min [7] m/z = 533 (M + H)$^+$ |
| 220 | 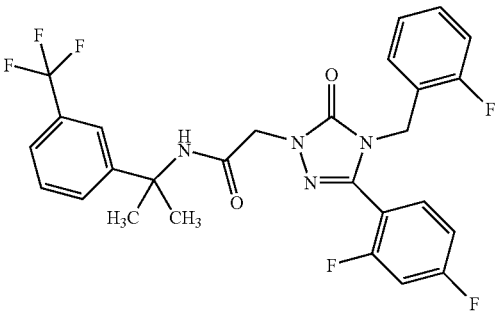 | 141A; 78% | $R_t$ = 2.53 min [7] m/z = 549 (M + H)$^+$ |
| 221 | 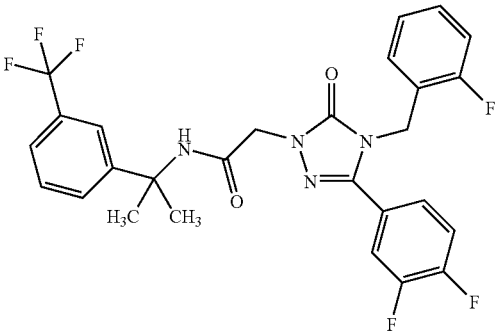 | 141A; 63% | $R_t$ = 2.58 min [7] m/z = 549 (M + H)$^+$ |

-continued
| Example No. | Structure | Educt; yield | LC/MS: $R_t$ [Method], m/z |
|---|---|---|---|
| 222 | 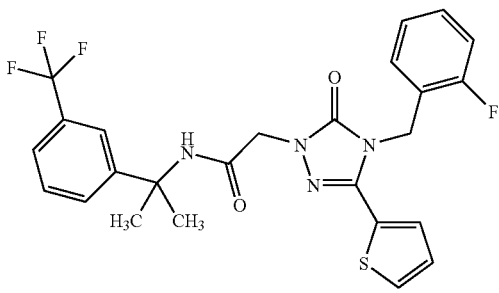 | 141A; 77% | $R_t$ = 2.66 min [8] m/z = 519 (M + H)⁺ |
| 223 | 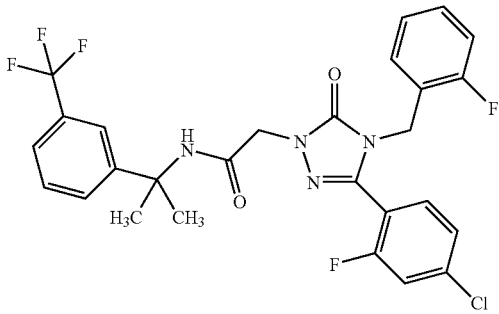 | 141A; 27% | $R_t$ = 2.94 min [8] m/z = 565 (M + H)⁺ |
| 224 | 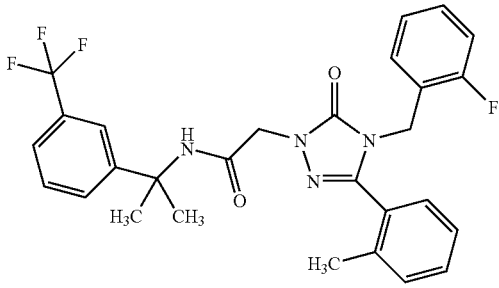 | 141A; 63% | $R_t$ = 2.85 min [8] m/z = 527 (M + H)⁺ |
| 225 | 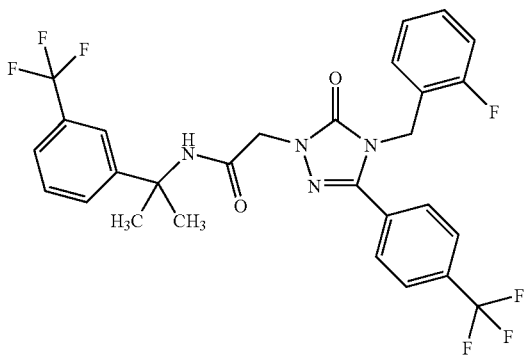 | 141A; 82% | $R_t$ = 4.15 min [17] m/z = 581 (M + H)⁺ |

-continued

| Example No. | Structure | Educt; yield | LC/MS: R$_t$ [Method], m/z |
|---|---|---|---|
| 226 | 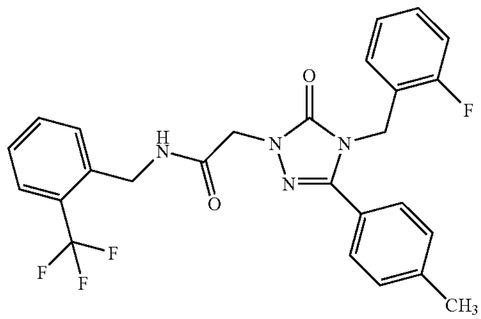 | 142A; 68% | R$_t$ = 2.45 min [7]<br>m/z = 499 (M + H)$^+$ |
| 227 | 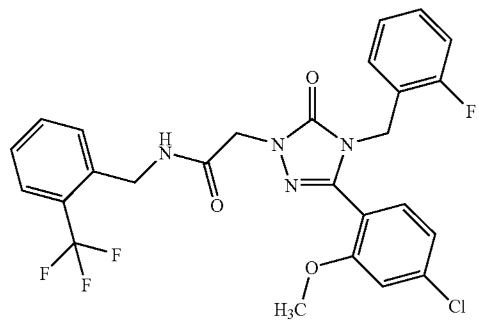 | 142A; 68% | R$_t$ = 2.47 min [7]<br>m/z = 549 (M + H)$^+$ |
| 228 | 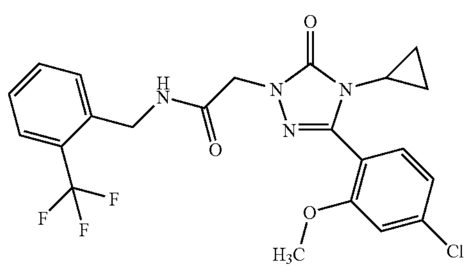 | 145A; 98% | R$_t$ = 2.39 min [18]<br>m/z = 481 (M + H)$^+$ |
| 229 | 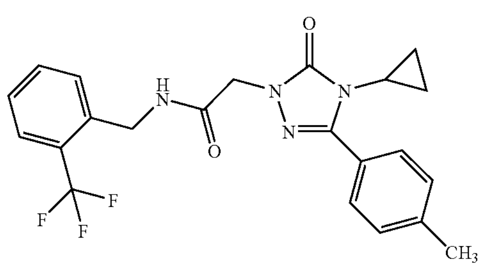 | 145A; 66% | R$_t$ = 2.21 min [7]<br>m/z = 431 (M + H)$^+$ |
| 230 | 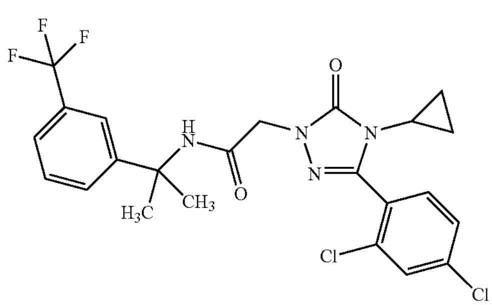 | 144A; 28% | R$_t$ = 2.63 min [18]<br>m/z = 513 (M + H)$^+$ |

| Example No. | Structure | Educt; yield | LC/MS: R_t [Method], m/z |
|---|---|---|---|
| 231 | 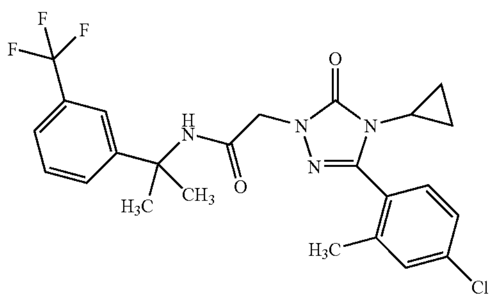 | 144A; 80% | R_t = 3.89 min [17]; m/z = 493 (M + H)⁺ |
| 232 | 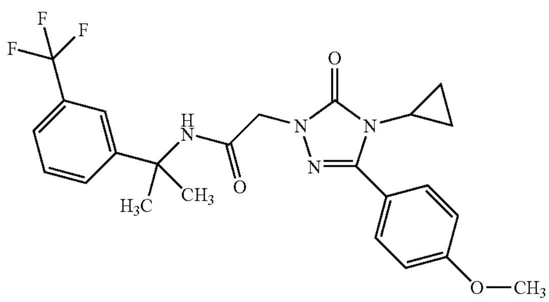 | 144A; 77% | R_t = 2.26 min [7]; m/z = 475 (M + H)⁺ |
| 233 | 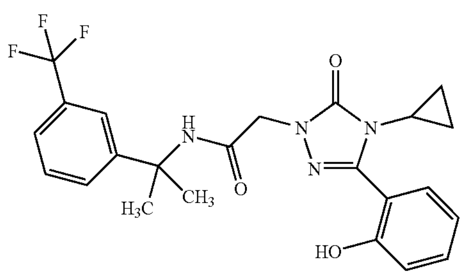 | 144A; 52% | R_t = 2.15 min [7]; m/z = 461 (M + H)⁺ |
| 234 | 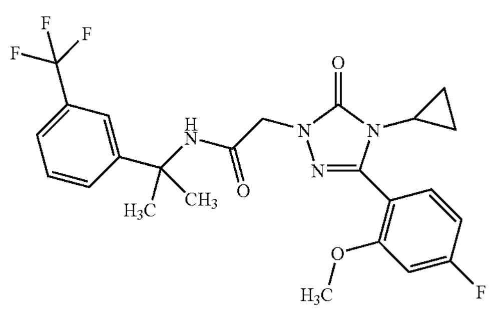 | 144A; 66% | R_t = 2.42 min [18]; m/z = 493 (M + H)⁺ |
| 235 | 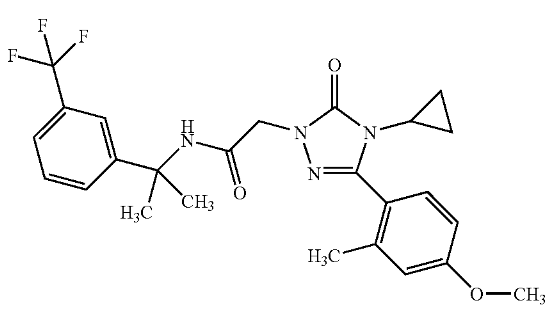 | 144A; 82% | R_t = 2.56 min [8]; m/z = 489 (M + H)⁺ |

-continued
| Example No. | Structure | Educt; yield | LC/MS: $R_t$ [Method], m/z |
|---|---|---|---|
| 236 | 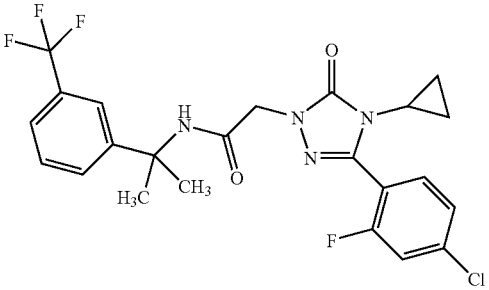 | 144A; 25% | $R_t$ = 2.56 min [18]<br>m/z = 497 (M + H)+ |
| 237 | 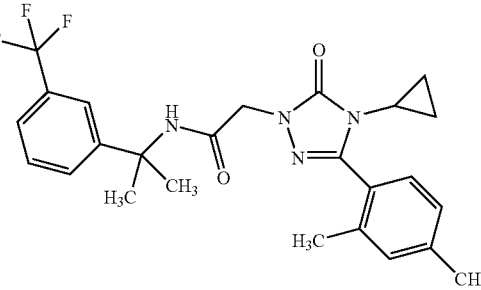 | 144A; 81% | $R_t$ = 3.70 min [8]<br>m/z = 473 (M + H)+ |
| 238 | 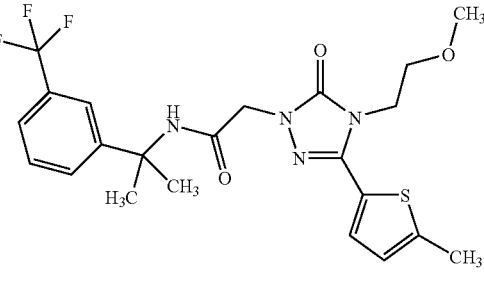 | 143A; 42% | $R_t$ = 2.32 min [7]<br>m/z = 483 (M + H)+ |
| 239 | 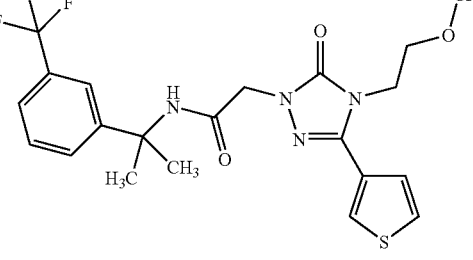 | 143A; 79% | $R_t$ = 2.17 min [7]<br>m/z = 469 (M + H)+ |
| 240 | 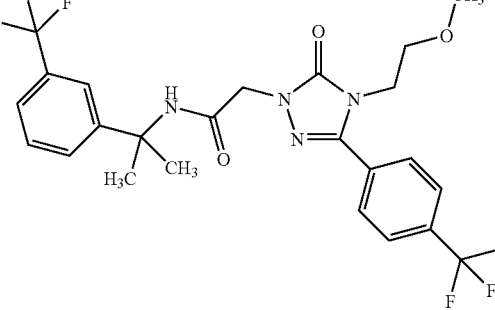 | 143A; 74% | $R_t$ = 3.85 min [17]<br>m/z = 531 (M + H)+ |

| Example No. | Structure | Educt; yield | LC/MS: R$_t$ [Method], m/z |
|---|---|---|---|
| 241 | 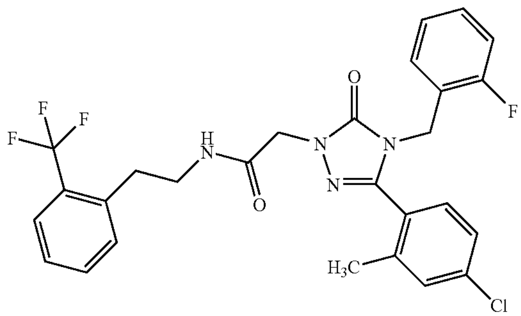 | 140A; 64% | R$_t$ = 2.68 min [8]<br>m/z = 547 (M + H)$^+$ |
| 242 | 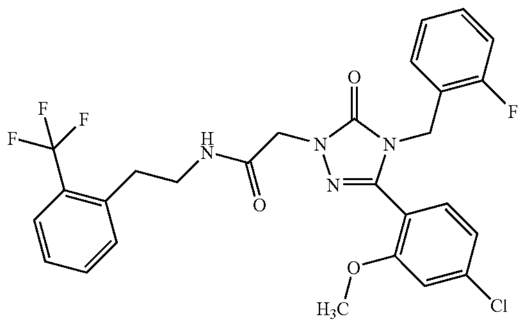 | 140A; 67% | R$_t$ = 3.93 min [17]<br>m/z = 563 (M + H)$^+$ |
| 243 | 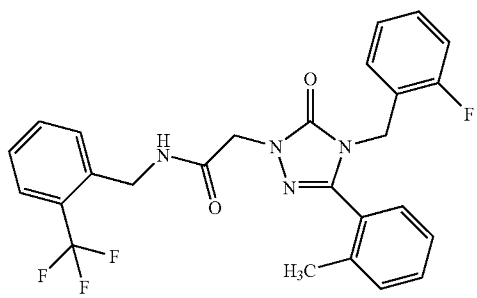 | 142A; 68% | R$_t$ = 2.61 min [8]<br>m/z = 499 (M + H)$^+$ |

Example 244

2-[3-(4-chloro-2-hydroxyphenyl)-4-(2-fluorobenzyl)-5-oxo-4,5-dihydro-1H-1,2,4-triazol-1-yl]-N-[1-methyl-1-(3-trifluoromethyl-phenyl)ethyl]-acetamide

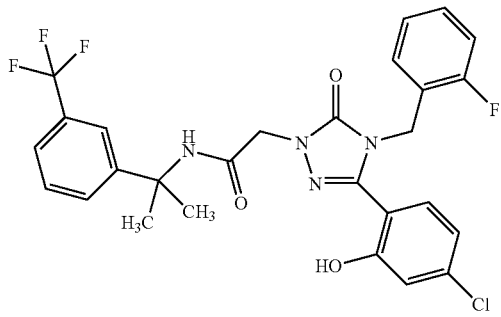

Under argon, a solution of 41 mg (71 µmol) of the compound from Example 216 is treated with 355 µl of a 1 M solution of boron tribromide in dichloromethane (355 µmol) at −20° C. The cooling bath is removed and the reaction mixture further stirred overnight at RT. The reaction is stopped by addition of 750 µl of methanol. The volatile components are removed on the rotary evaporator and the residue purified by preparative HPLC (Method 20). 15 mg (38% of theory) of the title compound are obtained.

LC/MS [Method 8]: R$_t$=2.72 min; m/z=563 (M+H)$^+$ $^1$H-NMR (400 MHz, DMSO-d$_6$): δ=1.60 (s, 6H), 4.49 (s, 2H), 4.71 (s, 2H), 6.86 (dd, 1H), 6.96 (d, 1H), 6.96-7.07 (m, 4H), 7.23 (m, 1H), 7.49-7.56 (m, 2H), 7.52 (s, 1H), 7.58 (d, 1H), 8.52 (s, 1H), 10.89 (br. s, 1H).

Example 245

2-[3-(4-chloro-2-hydroxyphenyl)-4-(2-fluorobenzyl)-5-oxo-4,5-dihydro-1H-1,2,4-triazol-1-yl]-N-[(2-trifluoromethyl-phenyl)methyl]-acetamide

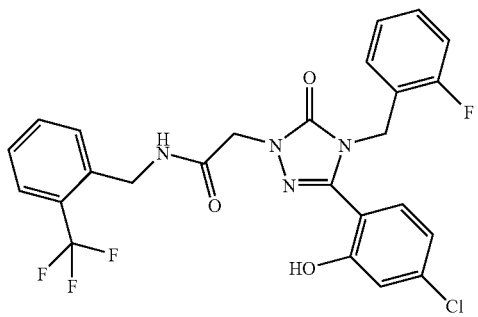

The title compound is prepared by the same method as described for Example 244, starting from Example 227.

LC/MS [Method 7]: $R_t$=2.33 min; m/z=535 (M+H)$^+$ $^1$H-NMR (400 MHz, DMSO-d$_6$): δ=4.50 (d, 2H), 4.55 (s, 2H), 4.86 (s, 2H), 6.89 (dd, 1H), 6.98 (d, 1H), 7.02-7.10 (m, 3H), 7.12 (d, 1H), 7.25 (m, 1H), 7.49 (t, 1H), 7.59 (d, 1H), 7.65 (t, 1H), 7.72 (d, 1H), 8.54 (t, 1H), 10.90 (br. s, 1H).

Example 246

2-[3-(5-chlorothiophen-2-yl)-4-(2-fluorobenzyl)-5-oxo-4,5-dihydro-1H-1,2,4-triazol-1-yl]-N-[1-methyl-1-(3-trifluoromethyl-phenyl)ethyl]-acetamide

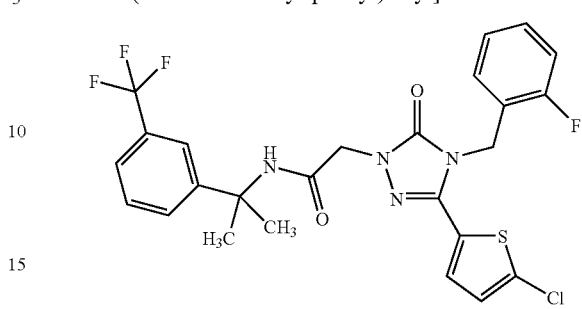

The carboxylic acid from Example 154A (150 mg, 0.41 mmol) and 1-methyl-1-(3-trifluoromethyl-phenyl)ethylamine (Example 1A, 91.2 mg, 0.45 mmol) are placed in 4 ml DMF and treated at RT with 66.1 mg (0.49 mmol) of HOBt. After 10 mins, 101.6 mg (0.53 mmol) of EDC are added and the mixture stirred overnight at RT. It is then treated with water and ethyl acetate. The phases are separated, and the aqueous phase is extracted with ethyl acetate. The combined organic phases are washed with water, then with sat. sodium chloride solution, dried by filtration through an Extrelut cartridge and freed of the volatile components on the rotary evaporator. The residue is purified by chromatography on silica gel (Biotage cartridge 25M, eluent: cyclohexane/ethyl acetate 1:1). 192 mg (85% of theory) of the title compound are thus obtained.

LC/MS [Method 8]: $R_t$=2.92 min; m/z=553 (M+H)$^+$ $^1$H-NMR (400 MHz, DMSO-d$_6$): δ=1.72 (s, 6H), 4.53 (s, 2H), 5.15 (s, 2H), 6.63 (s, 1H), 6.86 (d, 1H), 6.94 (d, 1H), 7.04-7.11 (m, 3H), 7.30 (m, 1H), 7.43 (t, 1H), 7.49 (d, 1H), 7.58 (d, 1H), 7.59 (s, 1H).

The compounds in the following table are prepared analogously. The amines used here are commercially available.

| Example No. | Structure | Educt; yield | LC/MS: $R_t$ [Method], m/z or $R_f$-value |
|---|---|---|---|
| 247 | 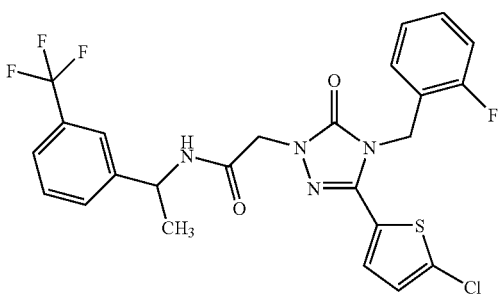 | 154A; 86% | $R_t$ = 2.86 min [8] m/z = 539 (M + H)$^+$ |

-continued

| Example No. | Structure | Educt; yield | LC/MS: R_t [Method], m/z or R_f value |
|---|---|---|---|
| 248 | 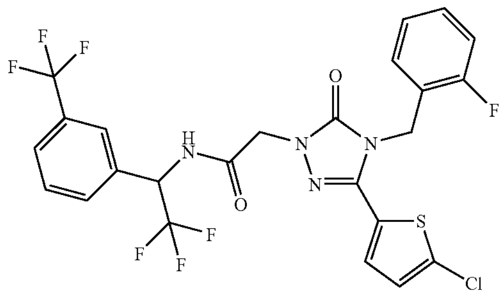 | 154A; 87% | R_t = 3.00 min [8] m/z = 593 (M + H)+ |
| 249 | 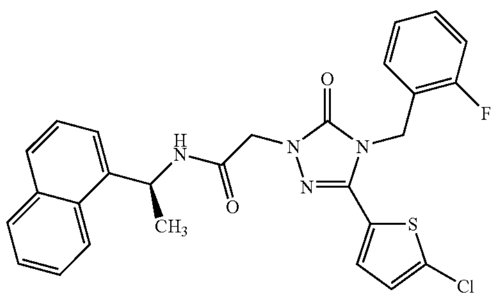 | 154A; 56% | R_t = 2.67 min [7] m/z = 521 (M + H)+ |
| 250 | 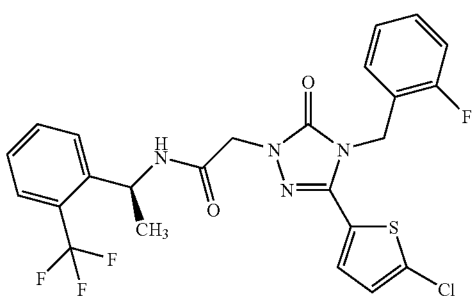 | 154A; 98% | R_f = 0.17 (cyclohexane/EA 1:1) MS [DCI]: m/z = 556 (M + NH_4)+ |
| 251 | 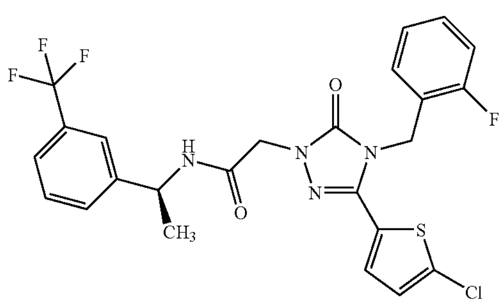 | 154A; 96% | R_f = 0.18 (cyclohexane/EA 1:1) MS [ESIpos]: m/z = 539 (M + H)+ |
| 252 | 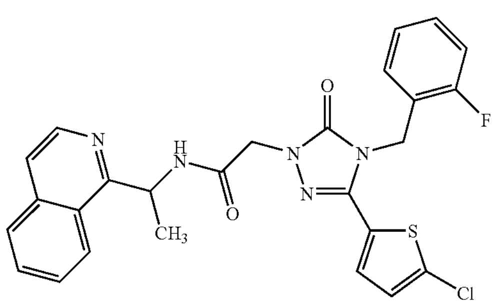 | 154A; 94% | R_f = 0.09 (cyclohexane/EA 1:1) MS [ESIpos]: m/z = 522 (M + H)+ |

Example 253

2-[4-(3-fluorobenzyl)-3-(2-hydroxyphenyl)-5-oxo-4,5-dihydro-1H-1,2,4-triazol-1-yl]-N-[1-methyl-1-(3-trifluoromethyl-phenyl)ethyl]-acetamide

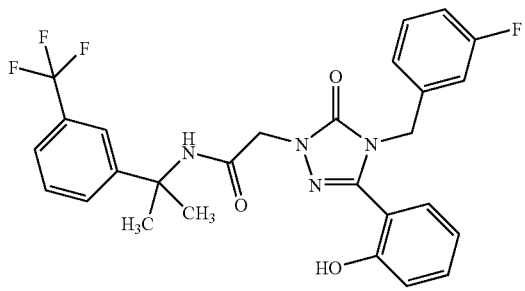

The carboxylic acid from Example 150A (50 mg, 0.15 mmol) and HOBt (35.4 mg, 0.26 mmol) are placed in 1 ml of DMF and treated at RT with 50.3 mg (0.26 mmol) of EDC. After 20 mins, 1-methyl-1-(3-trifluoromethyl-phenyl)ethylamine (Example 1A, 44.4 mg, 0.22 mmol) is added and the mixture stirred overnight at RT. The reaction mixture is then directly separated by preparative HPLC (Method 20). 24 mg (31% of theory) of the title compound are obtained.

LC/MS [Method 17]: $R_t$=3.68 min; m/z=529 (M+H)$^+$ $^1$H-NMR (400 MHz, DMSO-d$_6$): δ=1.59 (s, 6H), 4.48 (s, 2H), 4.78 (s, 2H), 6.72 (d, 1H), 6.76 (d, 1H), 6.82 (t, 1H), 6.94-7.03 (m, 2H), 7.08 (dd, 1H), 7.23 (dt, 1H), 7.33 (dt, 1H), 7.48-7.56 (m, 2H), 7.63 (s, 1H), 7.67 (d, 1H), 8.53 (s, 1H), 10.33 (s, 1H).

Workup Alternatives:

At the end of the reaction, the reaction mixture can be treated with 1 N hydrochloric acid (2-8 ml per mmol of carboxylic acid used), before the solution is then directly separated by preparative HPLC (Method 20). For larger quantities (>0.4 mmol of carboxylic acid used), an extractive workup, such as described in Example 246, is carried out before the crude product is purified by preparative HPLC.

Analogously to Example 253, the compounds in the following table are prepared. Unless otherwise stated, the amine educts are commercially available. When the amine educt is used as a salt (hydrochloride or trifluoroacetate), 1 eq. of N,N-diisopropylethylamine is added to the reaction mixture.

| Example No. | Structure | Educt(s); yield | LC/MS: $R_t$ [Method], m/z |
|---|---|---|---|
| 254 | 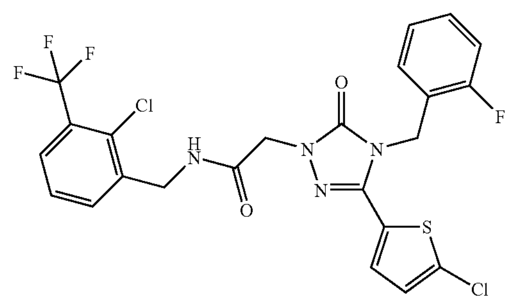 | 154A + 170A; 39% | $R_t$ = 2.66 min [7]; m/z = 559 (M + H)$^+$ |
| 255 | 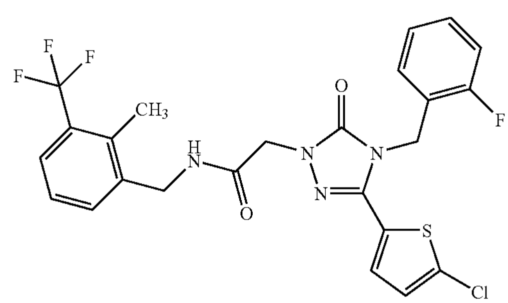 | 154A + 171A; 75% | $R_t$ = 2.65 min [7]; m/z = 539 (M + H)$^+$ |
| 256 | 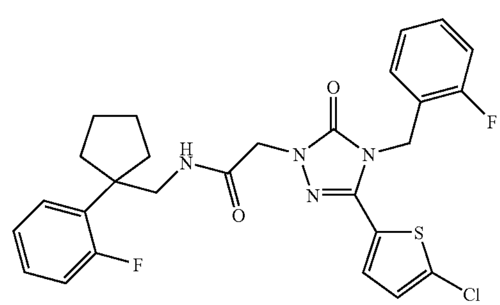 | 154A; 96% | $R_t$ = 2.80 min [7]; m/z = 543 (M + H)$^+$ |

-continued

| Example No. | Structure | Educt(s); yield | LC/MS: $R_t$ [Method], m/z |
|---|---|---|---|
| 257 | 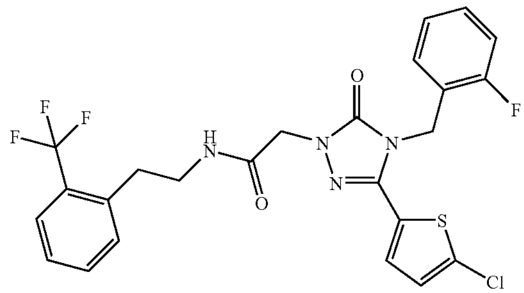 | 154A; 91% | $R_t$ = 2.60 min [7]; m/z = 539 (M + H)$^+$ |
| 258 | 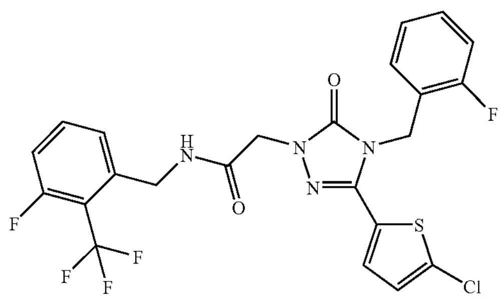 | 154A + 160A; 98% | $R_t$ = 2.56 min [7]; m/z = 534 (M + H)$^+$ |
| 259 | 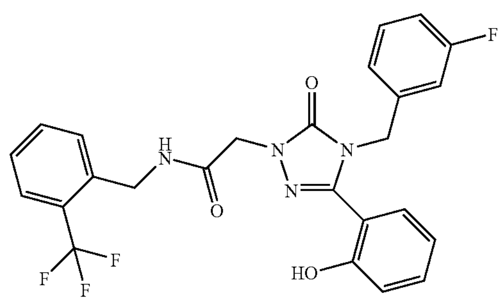 | 150A; 66% | $R_t$ = 3.31 min [19]; m/z = 501 (M + H)$^+$ |
| 260 | 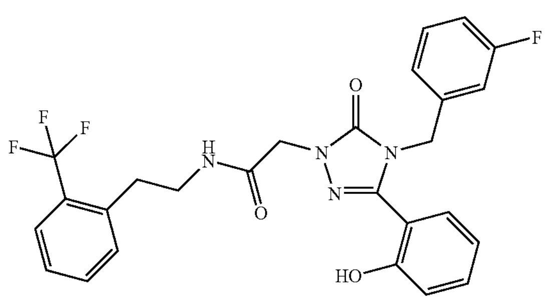 | 150A; 61% | $R_t$ = 3.37 min [19]; m/z = 515 (M + H)$^+$ |
| 261 | 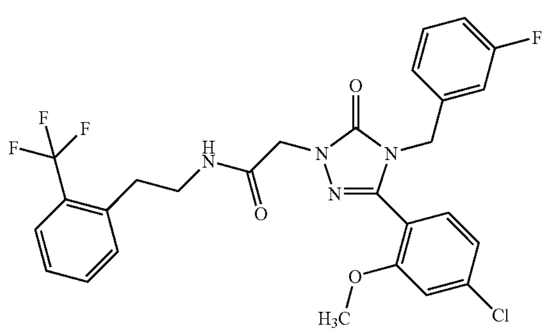 | 148A; 81% | $R_t$ = 3.76 min [19]; m/z = 563 (M + H)$^+$ |

| Example No. | Structure | Educt(s); yield | LC/MS: $R_t$ [Method], m/z |
|---|---|---|---|
| 262 | 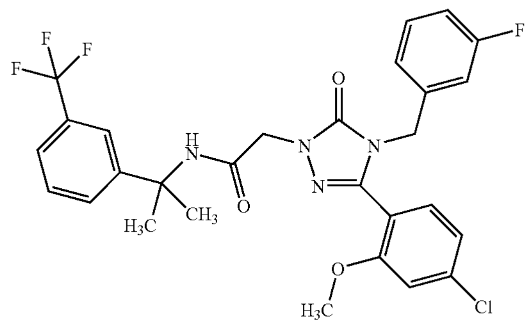 | 148A + 1A; 83% | $R_t$ = 4.06 min [17] m/z = 577 (M + H)⁺ |

Example 263

2-[3-(4-chlorophenyl)-4-(2-fluorobenzyl)-5-oxo-4,5-dihydro-1H-1,2,4-triazol-1-yl]-N-[1-methyl-1-(3-trifluoromethyl-phenyl)ethyl]-acetamide

Example 264

2-[3-(4-chlorophenyl)-4-(2-fluorobenzyl)-5-oxo-4,5-dihydro-1H-1,2,4-triazol-1-yl]-N-[2-(2-trifluoromethyl-phenyl)ethyl]-acetamide

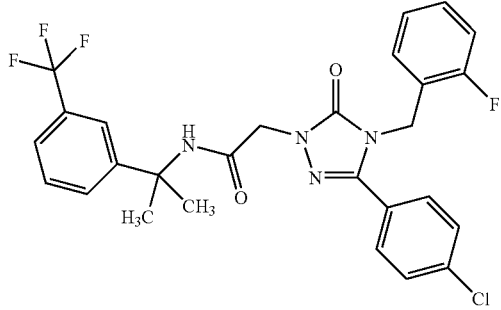

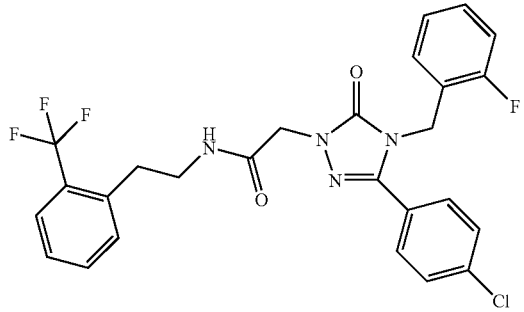

100 mg (0.36 mmol) of the compound from Example 133A, 108.6 mg (0.36 mmol) of the compound from Example 40A and 98.8 mg (0.72 mmol) of potassium carbonate are stirred overnight at reflux temperature in 2.7 ml of acetonitrile. After cooling, the mixture is diluted with water and extracted three times with ethyl acetate. The combined organic phases are dried over sodium sulphate and freed of the volatile components on the rotary evaporator. The residue is dried under high vacuum. 192 mg (98% of theory) of the title compound are obtained.

LC/MS [Method 7]: $R_t$=2.70 min; m/z=547 (M+H)⁺

¹H-NMR (400 MHz, DMSO-d₆): δ=1.60 (s, 6H), 4.52 (s, 2H), 5.00 (s, 2H), 6.98-7.16 (m, 3H), 7.25-7.32 (m, 1H), 7.48-7.56 (m, 6H), 7.62 (s, 1H), 7.67 (d, 1H), 8.58 (s, 1H).

The carboxylic acid from Example 156A (60 mg, 0.14 mmol) and HOBt (27.0 mg, 0.20 mmol) are placed in 0.86 ml DMF and treated at RT with 38.2 mg (0.20 mmol) of EDC. After 20 mins, 27 mg of 2-(2-trifluoromethyl-phenyl)ethylamine (0.14 mmol) are added and the mixture is stirred overnight at RT. The mixture is then directly separated by preparative HPLC (Method 20). 69 mg (91% of theory) of the title compound are obtained.

LC/MS [Method 7]: $R_t$=2.57 min; m/z=533 (M+H)⁺

¹H-NMR (400 MHz, DMSO-d₆): δ=2.92 (t, 2H), 3.35 (q, 2H), 4.44 (s, 2H), 5.03 (s, 2H), 7.06-7.19 (m, 3H), 7.28-7.35 (m, 1H), 7.43 (t, 1H), 7.49 (d, 1H), 7.60 (t, 1H), 7.68 (d, 1H), 8.32 (t, 1H).

The compounds in the following table are prepared analogously. Unless otherwise stated, the amine educts are commercially available. If the amine educt is used as a salt (hydrochloride or trifluoroacetate), 1 eq. of N,N-diisopropylethylamine is added to the reaction mixture.

| Example No. | Structure | Educt(s); yield | LC/MS: R$_t$ [Method], m/z |
|---|---|---|---|
| 265 | (structure) × HCOOH | 156A; 60% | R$_t$ = 1.63 min [8]<br>m/z = 542 (M + H)$^+$ |
| 266 | (structure) | 156A; 85% | R$_t$ = 2.93 min [8]<br>m/z = 537 (M + H)$^+$ |
| 267 | (structure) | 156A; 79% | R$_t$ = 3.79 min [17]<br>m/z = 533 (M + H)$^+$ |
| 268 | (structure) | 156A; 81% | R$_t$ = 3.90 min [17]<br>m/z = 499 (M + H)$^+$ |

| Example No. | Structure | Educt(s); yield | LC/MS: $R_t$ [Method], m/z |
|---|---|---|---|
| 269 | 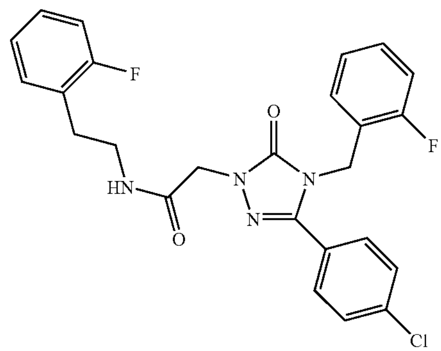 | 156A; 80% | $R_t$ = 3.76 min [17]<br>m/z = 483 (M + H)$^+$ |
| 270 | 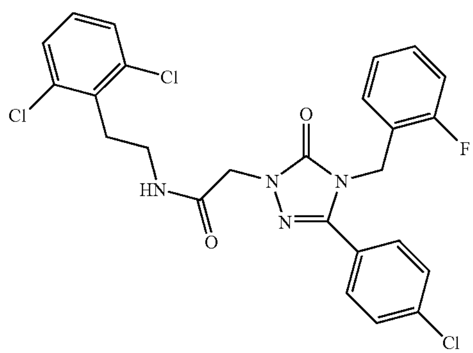 | 156A; 66% | $R_t$ = 3.98 min [17]<br>m/z = 533 (M + H)$^+$ |
| 271 | 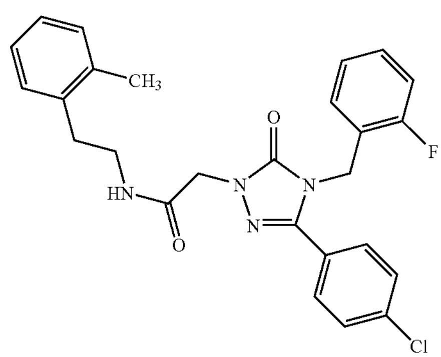 | 156A; 79% | $R_t$ = 3.68 min [17]<br>m/z = 479 (M + H)$^+$ |
| 272 | 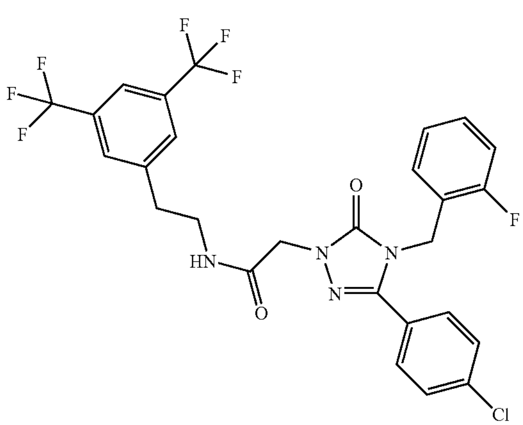 | 156A; 90% | $R_t$ = 4.02 min [17]<br>m/z = 601 (M + H)$^+$ |

| Example No. | Structure | Educt(s); yield | LC/MS: $R_t$ [Method], m/z |
|---|---|---|---|
| 273 | 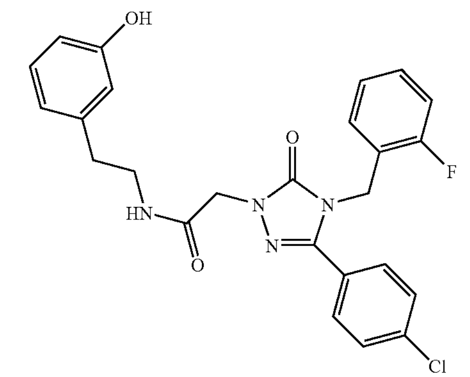 | 156A; 97% | $R_t$ = 2.34 min [8] m/z = 481 (M + H)⁺ |
| 274 | 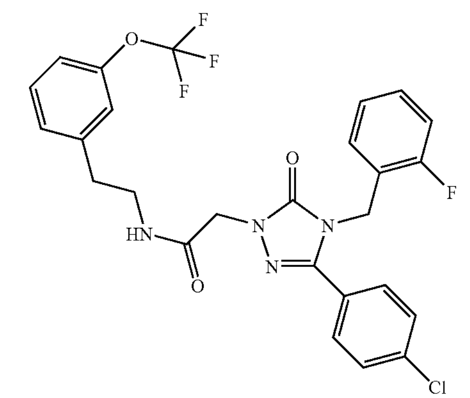 | 156A; 72% | $R_t$ = 2.81 min [8] m/z = 549 (M + H)⁺ |
| 275 | 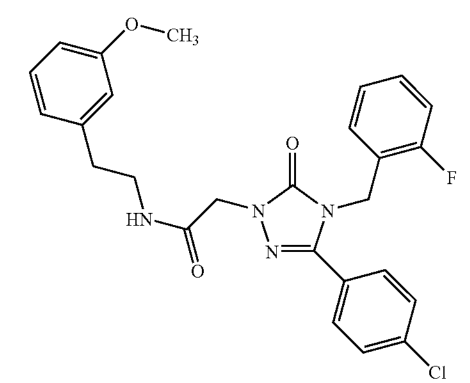 | 156A; 93% | $R_t$ = 3.56 min [19] m/z = 495 (M + H) |
| 276 | 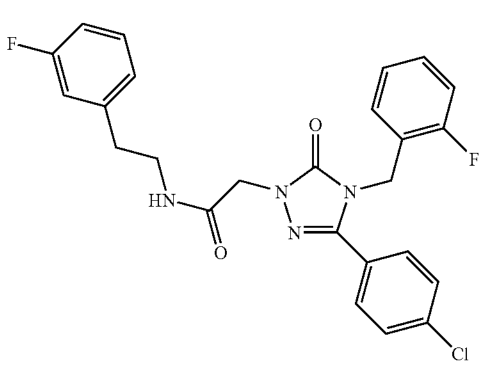 | 156A; 83% | $R_t$ = 3.60 min [19] m/z = 483 (M + H)⁺ |

-continued

| Example No. | Structure | Educt(s); yield | LC/MS: R$_t$ [Method], m/z |
|---|---|---|---|
| 277 | 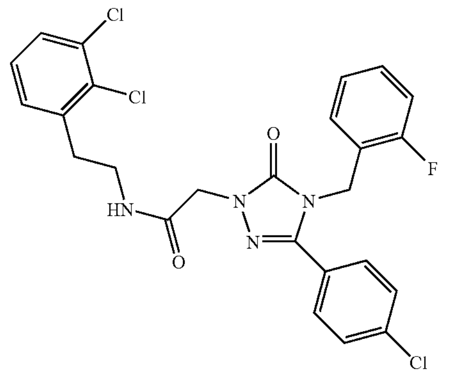 | 156A; 93% | R$_t$ = 4.04 min [17]  m/z = 533 (M + H)$^+$ |
| 278 | 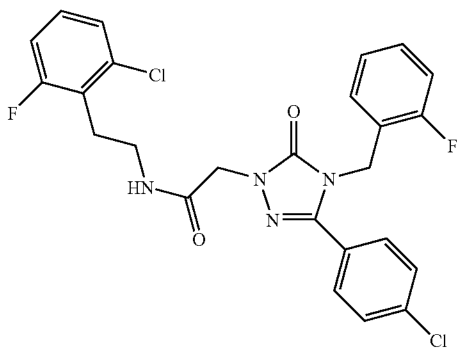 | 156A; 100% | R$_t$ = 3.70 min [19]  m/z = 517 (M + H)$^+$ |
| 279 | 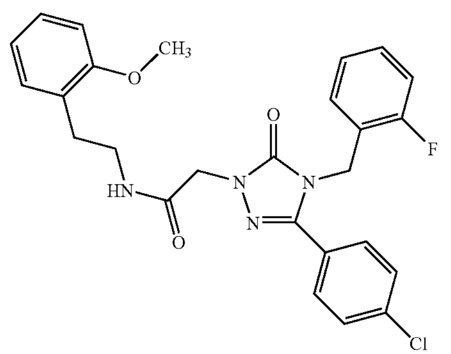 | 156A; 97% | R$_t$ = 3.81 min [17]  m/z = 495 (M + H)$^+$ |
| 280 | 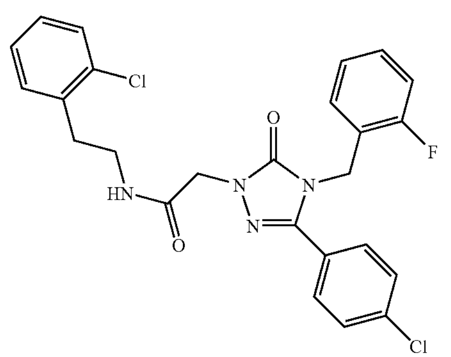 | 156A; 94% | R$_t$ = 2.77 min [8]  m/z = 499 (M + H)$^+$ |

-continued

| Example No. | Structure | Educt(s); yield | LC/MS: R_t [Method], m/z |
|---|---|---|---|
| 281 | 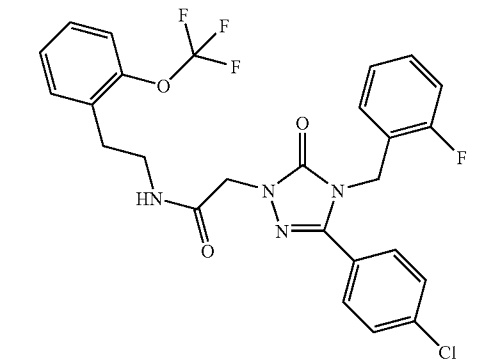 | 156A; 100% | $R_t$ = 2.86 min [17] m/z = 549 (M + H)$^+$ |
| 282 | 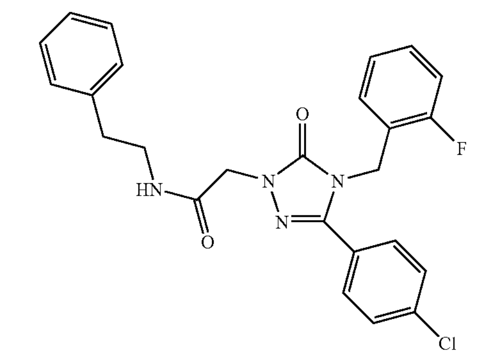 | 156A; 92% | $R_t$ = 3.76 min [17] m/z = 465 (M + H)$^+$ |
| 283 | 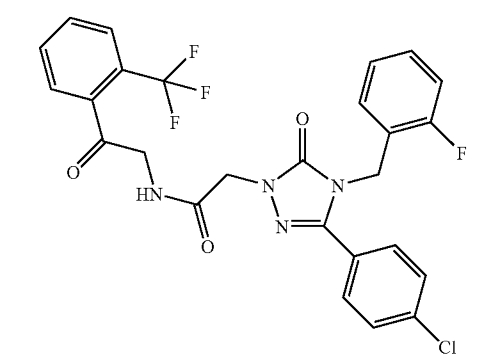 | 156A + 169A; 66% | $R_t$ = 2.67 min [8] m/z = 547 (M + H)$^+$ |
| 284 | 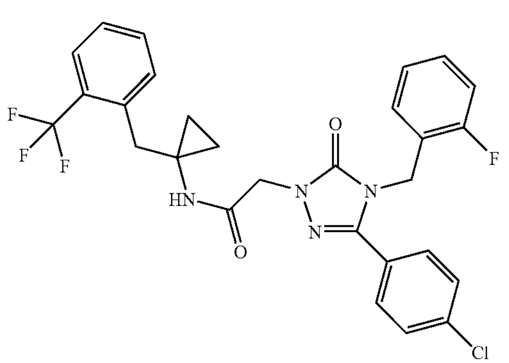 | 156A + 162A; 78% | $R_t$ = 2.86 min [8] m/z = 559 (M + H)$^+$ |

-continued

| Example No. | Structure | Educt(s); yield | LC/MS: $R_t$ [Method], m/z |
|---|---|---|---|
| 285 | 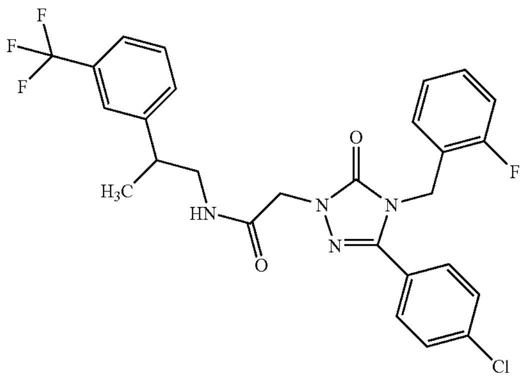 | 156A + 168A; 70% | $R_t$ = 2.91 min [8] m/z = 547 (M + H)$^+$ |
| 286 | 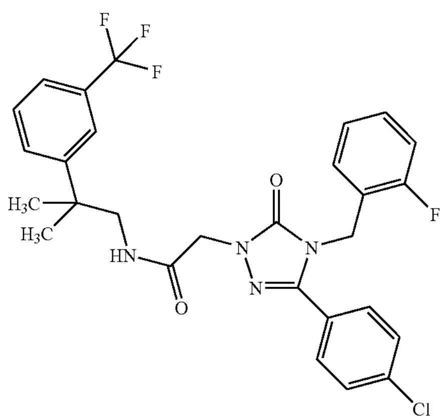 | 156A + 164A; 91% | $R_t$ = 3.00 min [8] m/z = 561 (M + H) |
| 287 | (R enantiomer) | 156A; 63% | $R_t$ = 4.01 min [17] m/z = 591 (M + H)$^+$ |
| 288 | 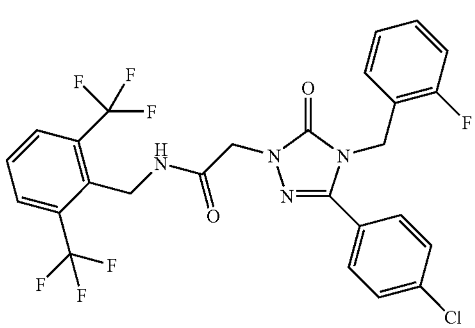 | 156A + 158A; 72% | $R_t$ = 2.58 min [7] m/z = 587 (M + H)$^+$ |

-continued

| Example No. | Structure | Educt(s); yield | LC/MS: R$_t$ [Method], m/z |
|---|---|---|---|
| 289 | 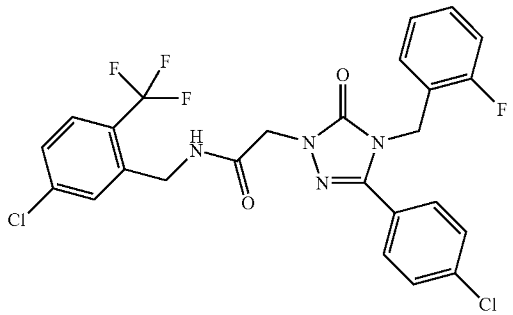 | 156A + 157A; 70% | R$_t$ = 2.66 min [7] m/z = 553 (M + H)$^+$ |
| 290 | 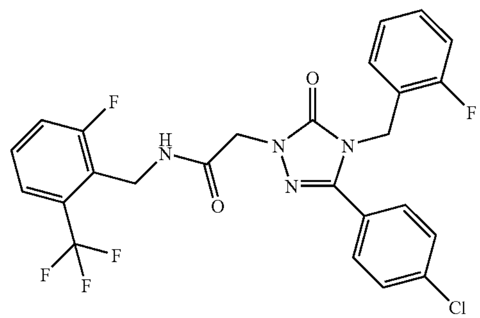 | 156A + 159A; 82% | R$_t$ = 2.48 min [7] m/z = 537 (M + H)$^+$ |
| 291 | 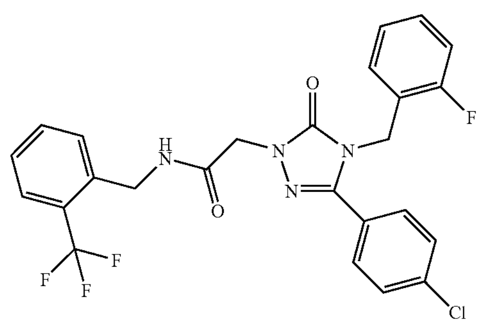 | 156A; 87% | R$_t$ = 2.53 min [7] m/z = 519 (M + H)$^+$ |
| 292 | 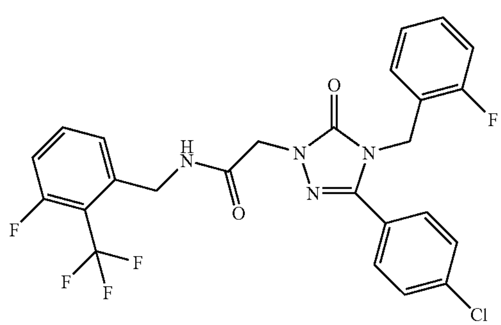 | 156A + 160A; 81% | R$_t$ = 3.91 min [17] m/z = 537 (M + H)$^+$ |

-continued

| Example No. | Structure | Educt(s); yield | LC/MS: R$_t$ [Method], m/z |
|---|---|---|---|
| 293 | 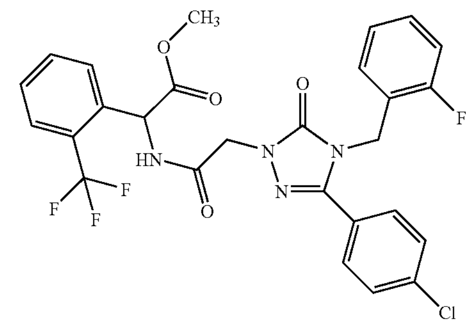 | 156A + 172A; 73% | R$_t$ = 2.77 min [8] m/z =577 (M + H)$^+$ |
| 294 | 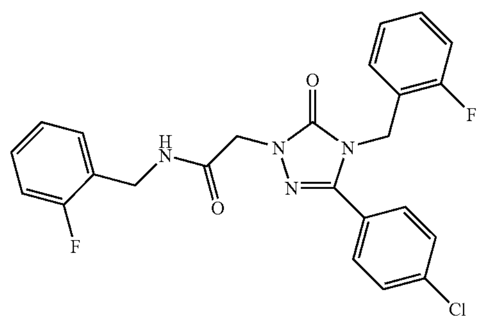 | 156A; 81% | R$_t$ = 3.70 min [17] m/z = 469 (M + H)$^+$ |
| 295 | 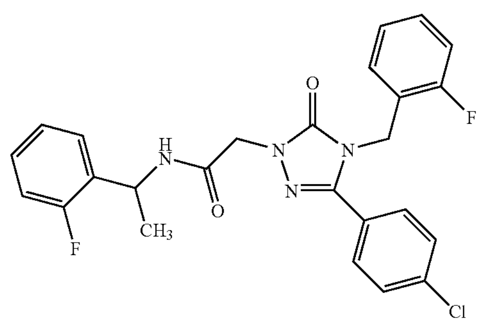 | 156A; 86% | R$_t$ = 2.67 min [8] m/z = 483 (M + H)$^+$ |
| 296 | 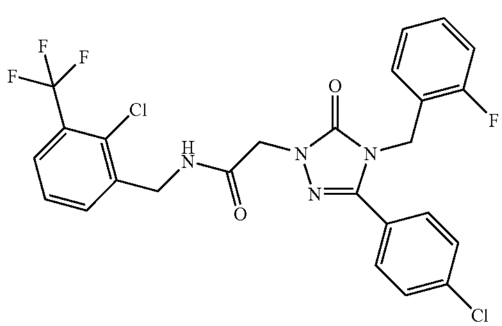 | 156A + 170A; 68% | R$_t$ = 4.03 min [17] m/z = 553 (M + H)$^+$ |

| Example No. | Structure | Educt(s); yield | LC/MS: $R_t$ [Method], m/z |
|---|---|---|---|
| 297 | 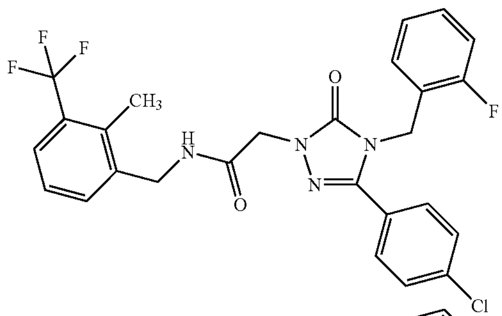 | 156A + 171A; 79% | $R_t$ = 3.84 min [19] m/z = 533 (M + H)⁺ |
| 298 | 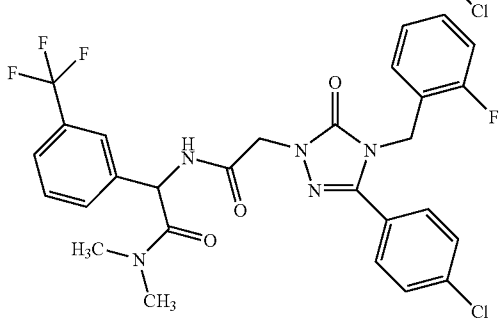 | 156A + 175A; 81% | $R_t$ = 3.70 min [17] m/z = 469 (M + H)⁺ |
| 299 | 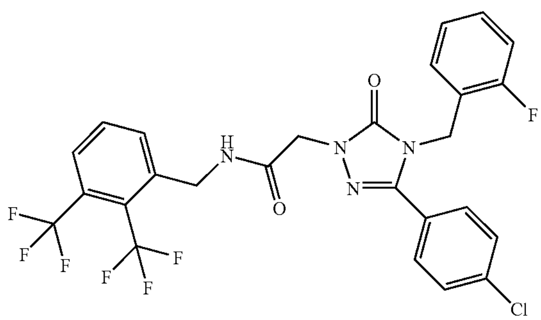 | 156A + 161A; 86% | $R_t$ = 2.93 min [8] m/z = 587 (M + H)⁺ |

Example 300

N-{[3-(4-chlorophenyl)-4-(2-fluorobenzyl)-5-oxo-4,5-dihydro-1H-1,2,4-triazol-1-yl]acetyl}-(2-trifluoromethyl)-D-phenylalanine

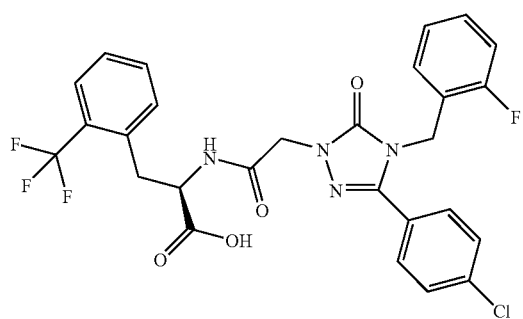

The compound from Example 287 (50 mg, 0.085 mmol) in 5 ml methanol is treated with 1 M aqueous lithium hydroxide solution (423 µl) and the mixture stirred overnight at RT. Then it is acidified to pH 1 with 1 N hydrochloric acid, treated with 30 ml of water and extracted three times with ethyl acetate. The combined organic phases are dried over sodium sulphate and freed of the volatile components on the rotary evaporator. The residue is dried under high vacuum. 44 mg (90% of theory) of the title compound are obtained.

LC/MS [Method 8]: $R_t$=2.76 min; m/z=577 (M+H)⁺.

Example 301

N$^\alpha$-{[3-(4-chlorophenyl)-4-(2-fluorobenzyl)-5-oxo-4,5-dihydro-1H-1,2,4-triazol-1-yl]acetyl}-N,N-dimethyl-2-trifluoromethyl-L-phenylalanine amide

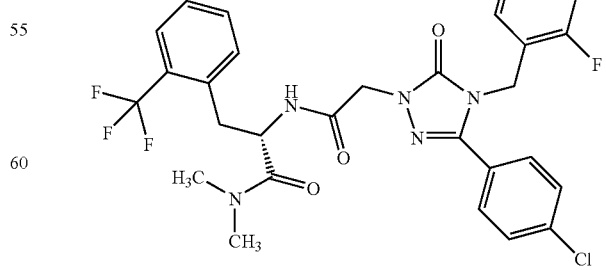

24 mg (42 µmol) of N-{[3-(4-chlorophenyl)-4-(2-fluorobenzyl)-5-oxo-4,5-dihydro-1H-1,2,4-triazol-1-yl]acetyl}-

(2-trifluoromethyl)-L-phenylalanine [preparation analogous to Example 287 starting from Example 156A and L-2-trifluoromethylphenylalanine methyl ester, followed by the hydrolysis of the methyl ester analogously to Example 300] and 8 mg of HOBt (58 µmol) are placed in 1 ml of DMF and treated and at RT with 11 mg (58 µmol) of EDC. After 20 mins, a 2 M solution of dimethylamine in THF (25 µl, 50 µmol) is added and the mixture stirred overnight at RT. After addition of 1 ml of 1 N hydrochloric acid, the mixture is separated directly by preparative HPLC (Method 20). 16 mg (64% of theory) of the title compound are obtained.

LC/MS [Method 19]: $R_t$=3.68 min; m/z=604 (M+H)$^+$.

Example 302

N-{2-amino-2-oxo-1-[2-(trifluoromethyl)phenyl]ethyl}-2-[3-(4-chlorophenyl)-4-(2-fluorobenzyl)-5-oxo-4,5-dihydro-1H-1,2,4-triazol-1-yl]-acetamide

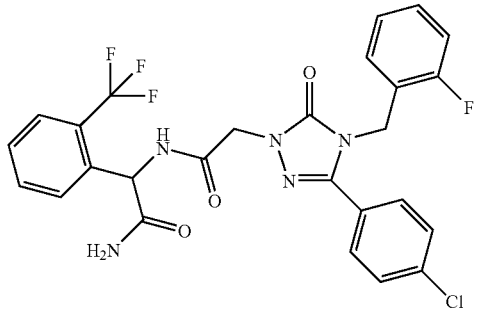

200 mg of the compound from Example 293 (347 µmol) are stirred in 36 ml of methanol with 3.47 ml of 1 N aqueous lithium hydroxide solution for 2 hrs at RT. Next the mixture is adjusted to pH 2 with 1 N hydrochloric acid. The methanol is removed on the rotary evaporator, and the mixture that remains is diluted with water and extracted three times with ethyl acetate. The combined organic phases are dried over sodium sulphate and freed of the volatile components on the rotary evaporator. The carboxylic acid thus obtained is dried under high vacuum [quantitative yield, LC/MS [Method 17]: $R_t$=3.67 min; m/z=563 (M+H)$^+$].

23 mg (41 µmol) of the carboxylic acid obtained above are placed with 10 mg of HOBt (74 µmol) in 0.9 ml of DMF and treated at RT with 14 mg (74 µmol) of EDC. After 20 mins, an aqueous ammonia solution (32%, 1.09 g, 20 mmol) is added and the mixture is stirred overnight at RT. After addition of 1 ml of 1 N hydrochloric acid, the mixture is directly separated by preparative HPLC (Method 20). 13 mg (57% of theory) of the title compound are obtained.

LC/MS [Method 22]: $R_t$=1.94 min; m/z=562 (M+H)$^+$ $^1$H-NMR (400 MHz, DMSO-d$_6$): δ=4.50 (d, 1H), 4.68 (d, 1H), 5.02 (s, 2H), 5.66 (d, 1H), 7.01-7.18 (m, 3H), 7.27-7.34 (m, 1H), 7.44 (s, 1H), 7.52 (s, 4H), 7.54 (t, 1H), 7.64 (d, 1H), 7.65 (s, 1H), 7.69-7.75 (m, 2H), 9.04 (d, 1H).

Example 303

2-[3-(4-chlorophenyl)-4-(cyclopropyl)-5-oxo-4,5-dihydro-1H-1,2,4-triazol-1-yl]-N-[2-(2-trifluoromethyl-phenyl)ethyl]-acetamide

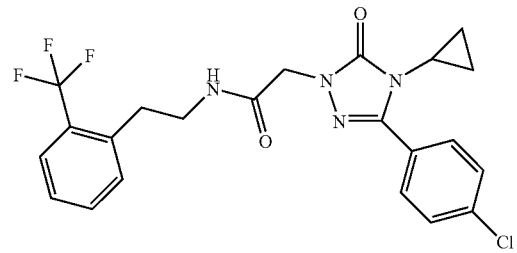

The carboxylic acid from Example 88A (50 mg, 0.14 mmol) and HOBt (35 mg, 0.26 mmol) are placed in 3 ml of DMF and treated at RT with 49 mg (0.26 mmol) of EDC. After 20 mins, 41 mg of 2-(2-trifluoromethyl-phenyl)ethylamine (0.21 mmol) are added and the mixture is stirred overnight at RT. After addition of 1 ml of 1 N hydrochloric acid, the mixture is directly separated by preparative HPLC (Method 20). 51 mg (77% of theory) of the title compound are obtained LC/MS [Method 19]: $R_t$=3.50 min; m/z=465 (M+H)$^+$ $^1$H-NMR (400 MHz, DMSO-d$_6$): δ=0.56-0.63 (m, 2H), 0.87-0.94 (m, 2H), 2.89 (t, 2H), 3.17 (m, 1H), 3.30-3.37 (m, 2H), 4.33 (s, 2H), 7.43 (t, 1H), 7.47 (d, 1H), 7.57-7.64 (m, 3H), 7.68 (d, 1H), 7.81 (d, 2H), 8.25 (t, 1H).

The compounds in the following table are prepared analogously. Unless otherwise stated, the amine educts are commercially available. If the amine educt is used as a salt (hydrochloride or trifluoroacetate), 1 eq. of N,N-diisopropylethylamine is added to the reaction mixture.

| Example No. | Structure | Educt(s); yield | LC/MS: $R_t$ [Method], m/z |
|---|---|---|---|
| 304 | ![structure] | 88A; 98% | $R_t$ = 2.75 min [8] m/z = 469 (M + H)$^+$ |

| Example No. | Structure | Educt(s); yield | LC/MS: $R_t$ [Method], m/z |
|---|---|---|---|
| 305 | 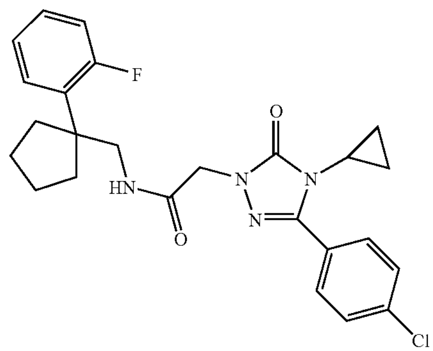 | 88A; 91% | $R_t$ = 2.74 min [8] m/z = 469 (M + H)$^+$ |
| 306 | 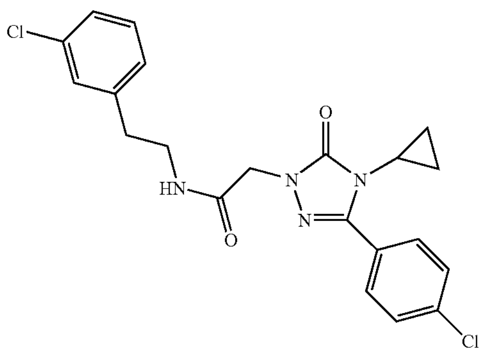 | 88A; 89% | $R_t$ = 2.47 min [8] m/z = 431 (M + H)$^+$ |
| 307 | 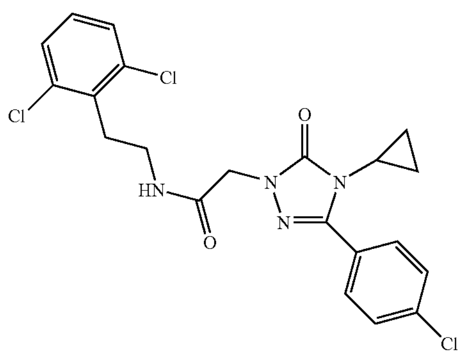 | 88A; 71% | $R_t$ = 2.56 min [8] m/z = 467 (M + H)$^+$ |
| 308 | 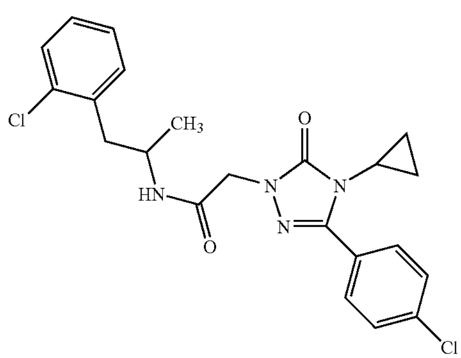 | 88A; 97% | $R_t$ = 3.62 min [17] m/z = 445 (M + H)$^+$ |

| Example No. | Structure | Educt(s); yield | LC/MS: $R_t$ [Method], m/z |
|---|---|---|---|
| 309 | 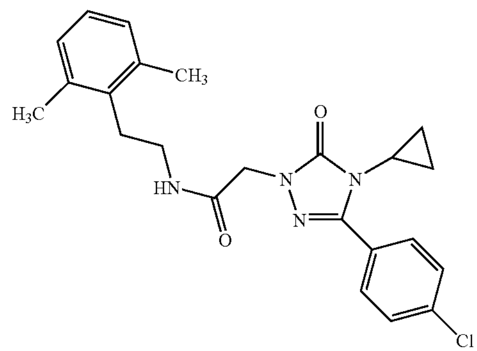 | 88A; 74% | $R_t$ = 3.51 min [19] m/z = 425 (M + H)$^+$ |
| 310 | 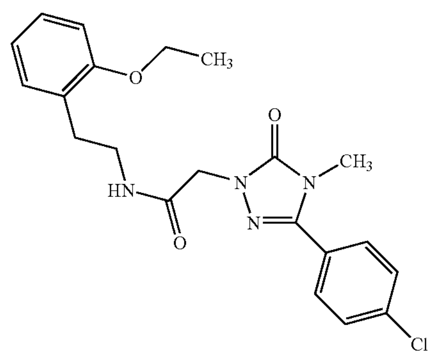 | 88A; 78% | $R_t$ = 2.53 min [8] m/z = 441 (M + H)$^+$ |
| 311 | 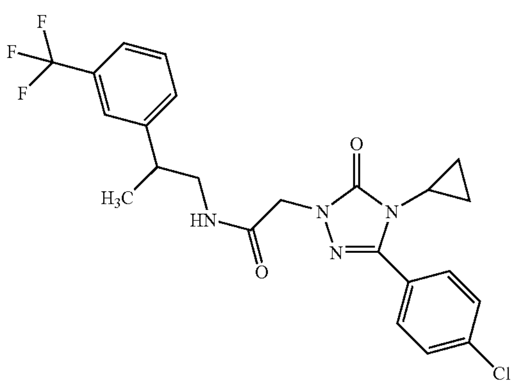 | 88A + 168A; 74% | $R_t$ = 3.76 min [17] m/z = 479 (M + H)$^+$ |
| 312 | 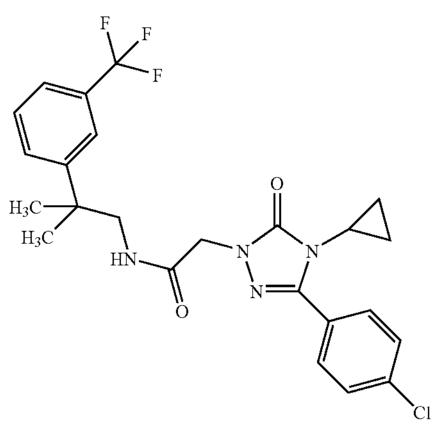 | 88A + 164A; 85% | $R_t$ = 3.88 min [17] m/z = 493 (M + H)$^+$ |

-continued

| Example No. | Structure | Educt(s); yield | LC/MS: R$_t$ [Method], m/z |
|---|---|---|---|
| 313 | 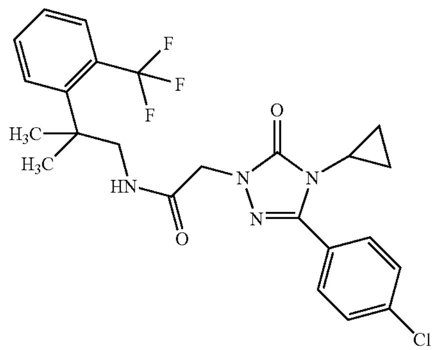 | 88A + 166A; 79% | R$_t$ = 3.86 min [17] m/z = 493 (M + H)$^+$ |
| 314 | 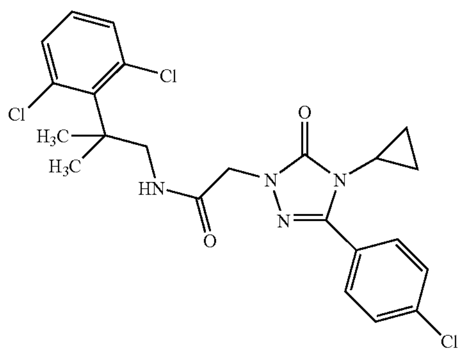 | 88A + 191A; 74% | R$_t$ = 3.76 min [19] m/z = 493 (M + H)$^+$ |
| 315 | 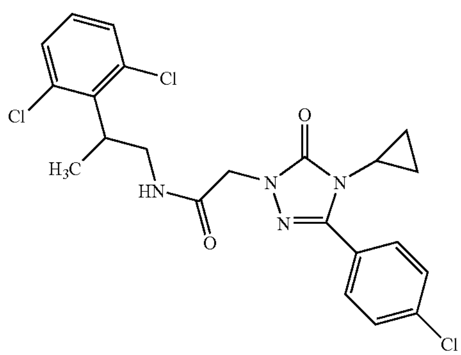 | 88A + 192A; 83% | R$_t$ = 3.60 min [19] m/z = 479 (M + H)$^+$ |
| 316 | 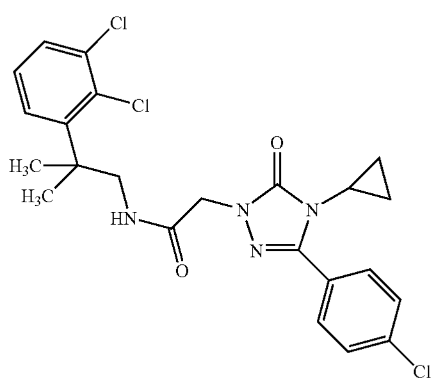 | 88A + 190A; 95% | R$_t$ = 2.42 min [23] m/z = 493 (M + H)$^+$ |

| Example No. | Structure | Educt(s); yield | LC/MS: $R_t$ [Method], m/z |
|---|---|---|---|
| 317 | 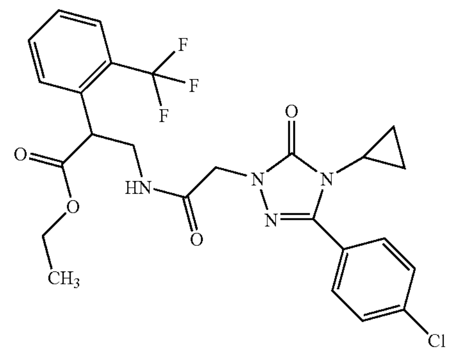 | 88A + 194A; 79% | $R_t$ = 3.63 min [8] m/z = 537 (M + H)$^+$ |
| 318 | 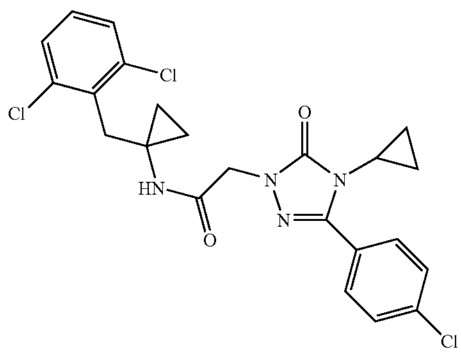 | 88A + 198A; 64% | $R_t$ = 3.72 min [17] m/z = 491 (M + H)$^+$ |
| 319 | 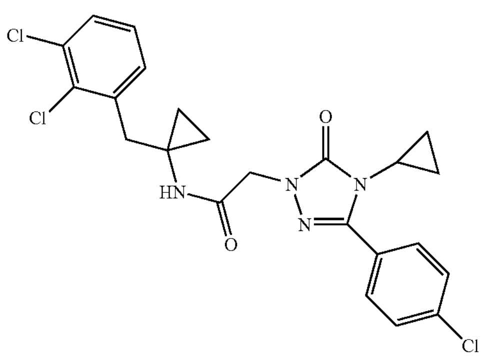 | 88A + 197A; 90% | $R_t$ = 2.29 min [23] m/z = 491 (M + H)$^+$ |
| 320 | 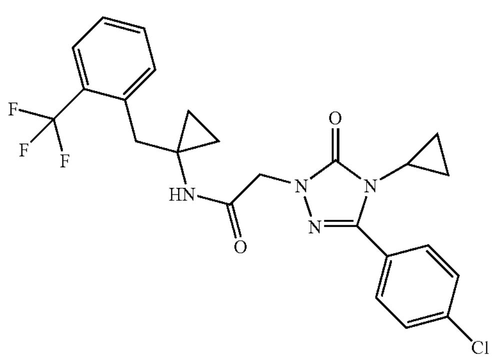 | 88A + 162A; 68% | $R_t$ = 2.60 min [8] m/z = 491 (M + H)$^+$ |

-continued

| Example No. | Structure | Educt(s); yield | LC/MS: R_t [Method], m/z |
|---|---|---|---|
| 321 | (R enantiomer) | 88A; 69% | R_t = 3.50 min [19]<br>m/z = 523 (M + H)+ |
| 322 | 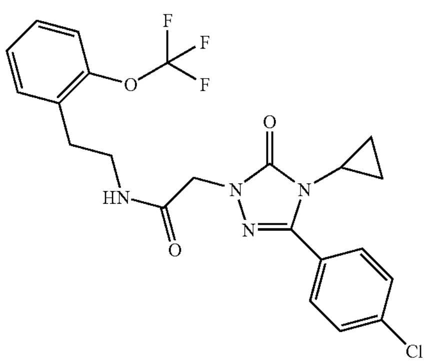 | 88A; 80% | R_t = 2.59 min [8]<br>m/z = 481 (M + H)+ |
| 323 | 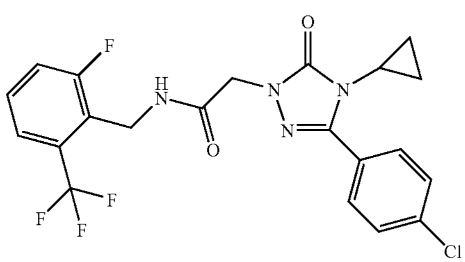 | 88A + 159A; 85% | R_t = 3.37 min [19]<br>m/z = 469 (M + H) |
| 324 | 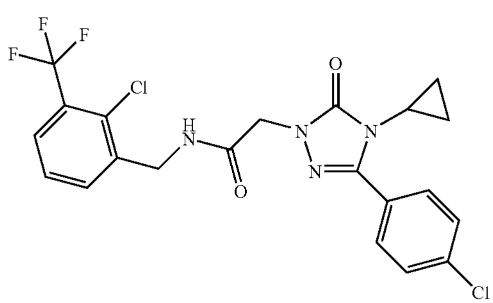 | 88A + 170A; 47% | R_t = 3.70 min [17]<br>m/z = 485 (M + H)+ |

| Example No. | Structure | Educt(s); yield | LC/MS: R_t [Method], m/z |
|---|---|---|---|
| 325 | 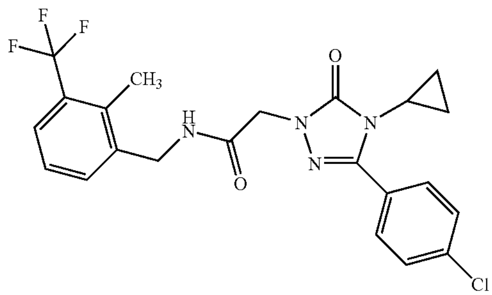 | 88A + 171A; 72% | $R_t$ = 3.69 min [17] m/z = 465 (M + H)$^+$ |
| 326 | 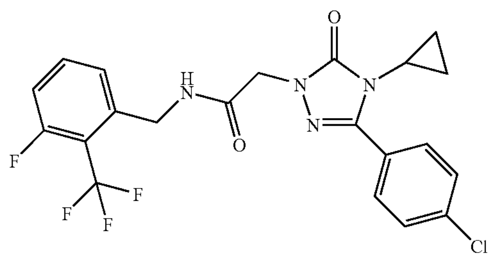 | 88A + 160A; 82% | $R_t$ = 3.58 min [17] m/z = 469 (M + H)$^+$ |
| 327 | 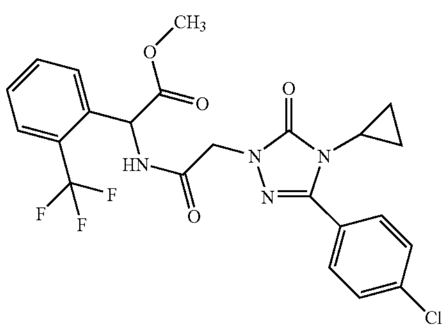 | 88A + 172A; 81% | $R_t$ = 3.58 min [17] m/z = 509 (M + H)$^+$ |
| 328 | 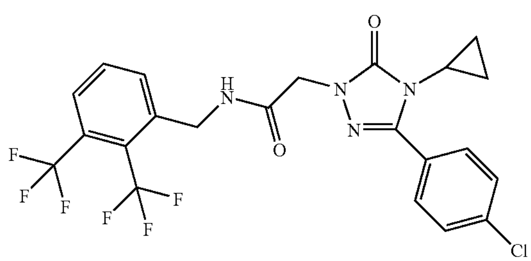 | 88A + 161A; 88% | $R_t$ = 3.79 min [17] m/z = 519 (M + H)$^+$ |
| 329 | 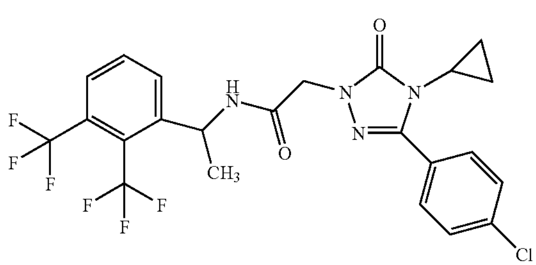 | 88A + 200A; 88% | $R_t$ = 2.74 min [8] m/z = 533 (M + H)$^+$ |

| Example No. | Structure | Educt(s); yield | LC/MS: R$_t$ [Method], m/z |
|---|---|---|---|
| 330 | 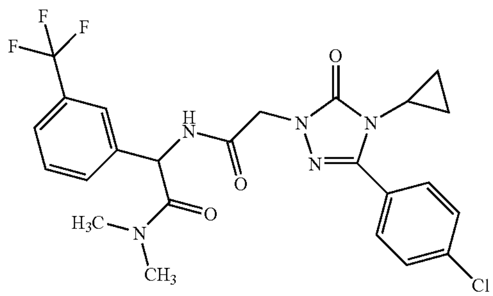 | 88A + 175A; 84% | R$_t$ = 3.37 min [19] m/z = 522 (M + H)$^+$ |
| 331 | 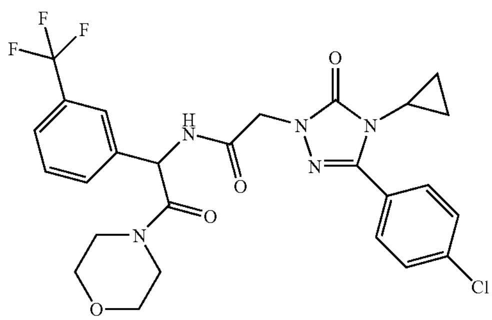 | 88A + 177A; 73% | R$_t$ = 2.47 min [8] m/z = 564 (M + H)$^+$ |
| 332 | 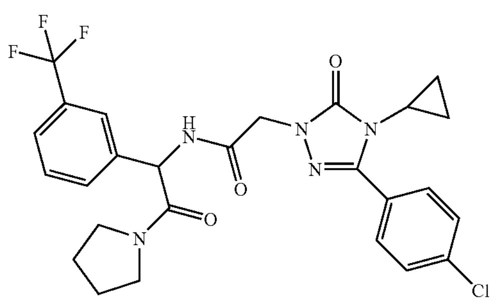 | 88A + 178A; 79% | R$_t$ = 2.19 min [23] m/z = 548 (M + H)$^+$ |
| 333 | 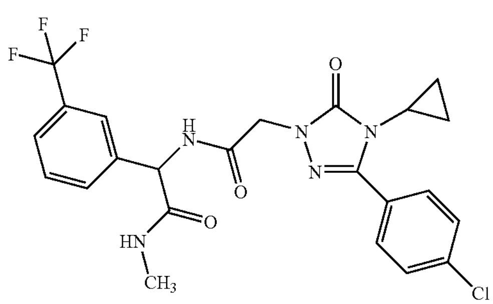 | 88A + 179A; 55% | R$_t$ = 1.99 min [23] m/z = 508 (M + H)$^+$ |
| 334 | 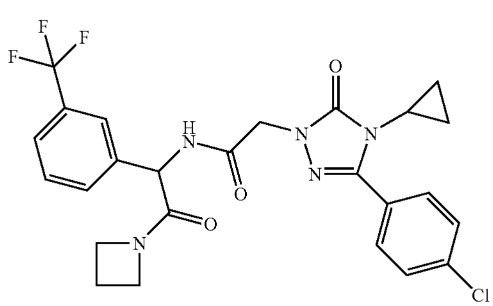 | 88A + 180A; 91% | R$_t$ = 2.08 min [23] m/z = 534 (M + H)$^+$ |

-continued

| Example No. | Structure | Educt(s); yield | LC/MS: R$_t$ [Method], m/z |
|---|---|---|---|
| 335 | 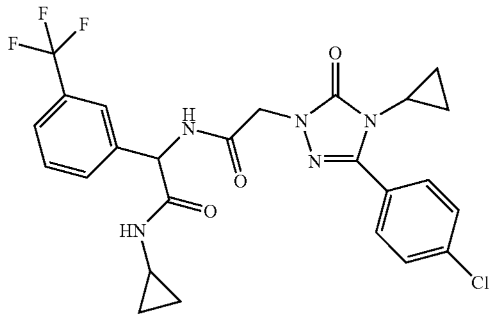 | 88A + 181A; 91% | R$_t$ = 2.54 min [8] m/z = 534 (M + H)$^+$ |
| 336 | 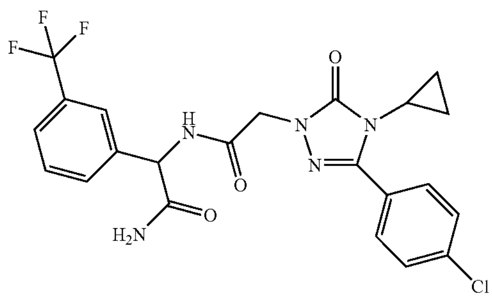 | 88A + 184A; 81% | R$_t$ = 1.92 min [22] m/z = 494 (M + H)$^+$ |
| 337 | 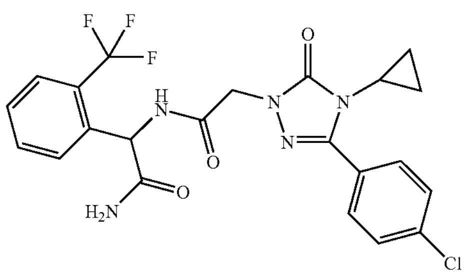 | 88A + 185A; 29% | R$_t$ = 1.66 min [22] m/z = 494 (M + H)$^+$ |
| 338 | 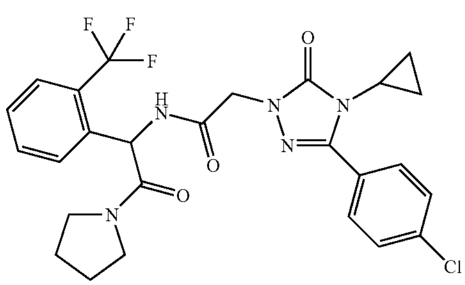 | 88A + 182A; 64% | R$_t$ = 1.93 min [23] m/z = 548 (M + H)$^+$ |
| 339 | 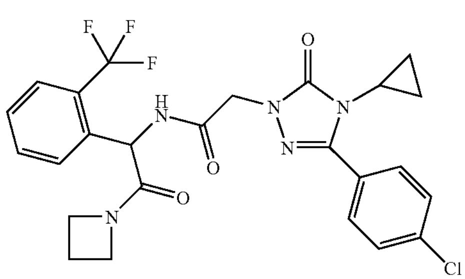 | 88A + 186A; 74% | R$_t$ = 1.85 min [23] m/z = 534 (M + H)$^+$ |

| Example No. | Structure | Educt(s); yield | LC/MS: $R_t$ [Method], m/z |
|---|---|---|---|
| 340 | 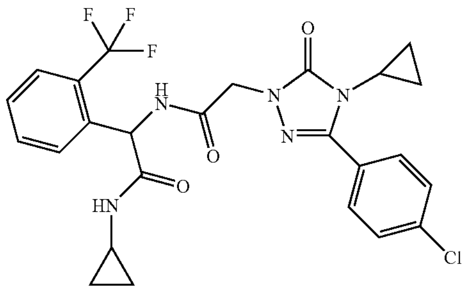 | 88A + 183A; 75% | $R_t$ = 1.86 min [23] m/z = 534 (M + H)⁺ |
| 341 | 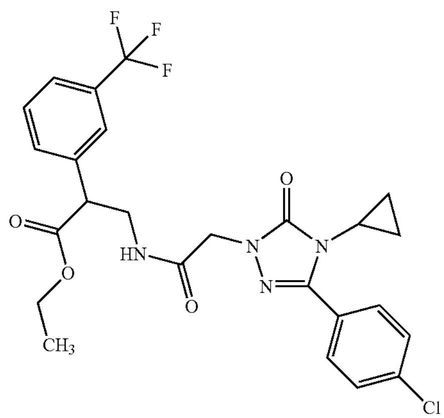 | 88A + 196A; 93% | $R_t$ = 2.70 min [8] m/z = 537 (M + H) |

Example 342

2-[3-(4-chlorophenyl)-4-(cyclopropyl)-5-oxo-4,5-dihydro-1H-1,2,4-triazol-1-yl]-N-[2-(2-chlorophenyl)-3-hydroxypropyl]-acetamide

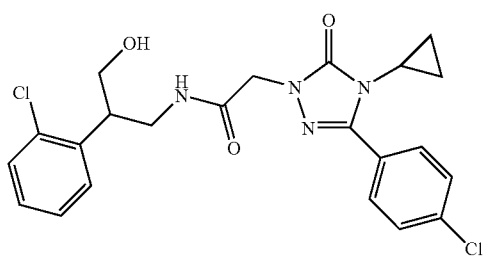

By the method described in Example 303, the title compound is obtained in 83% yield from the carboxylic acid from Example 88A and 2-(2-chlorophenyl)-3-hydroxypropylamine [preparation: see *Arch. Pharm.* 301, 750 (1968)].

LC/MS [Method 19]: $R_t$=2.99 min; m/z=461 (M+H)⁺.

Example 343

2-({[3-(4-chlorophenyl)-4-(2-methoxyethyl)-5-oxo-4,5-dihydro-1H-1,2,4-triazol-1-yl]acetyl}amino)-N-cyclopropyl-2-[3-(trifluoromethyl)phenyl]-acetamide

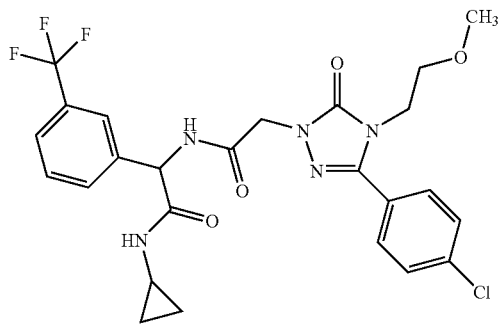

The carboxylic acid from Example 90A (25 mg, 81 μmol) and HOBt (20 mg, 145 μmol) are placed in 1.7 ml of DMF and treated at RT with 28 mg (145 μmol) of EDC. After 20 mins, 36 mg (97 μmol) of the amine trifluoroacetate from Example 181A and 28 μl (161 μmol) of N,N-diisopropylethylamine are added and the mixture is stirred overnight at RT. After addition of 1 ml of 1 N hydrochloric acid, the mixture is directly separated by preparative HPLC (Method 20). 30 mg (67% of theory) of the title compound are obtained.

LC/MS [Method 23]: $R_t$=2.09 min; m/z=552 (M+H)⁺

¹H-NMR (400 MHz, DMSO-d₆): δ=0.27-0.35 (m, 1H), 0.39-0.47 (m, 1H), 0.56-0.70 (m, 2H), 2.58-2.66 (m, 1H), 3.11 (s, 3H), 3.46 (t, 2H), 3.87 (t, 2H), 4.57 (m [AB], 2H), 5.48 (d, 1H), 7.57-7.63 (m, 3H), 7.65-7.73 (m, 4H), 7.76 (s, 1H), 8.53 (d, 1H), 9.05 (d, 1H).

The compounds in the following table are prepared analogously. Unless otherwise stated, the amine educts are commercially available.

| Example No. | Structure | Educt(s); yield | LC/MS: $R_t$ [Method], m/z |
|---|---|---|---|
| 344 | 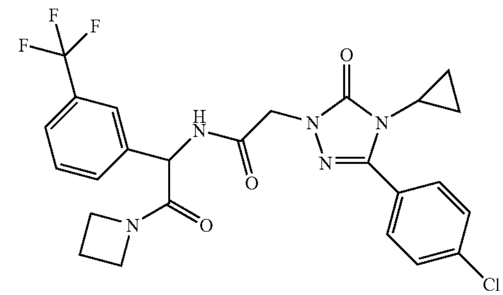 | 90A + 180A; 86% | $R_t$ = 2.07 min [23] m/z = 552 (M + H)$^+$ |
| 345 | 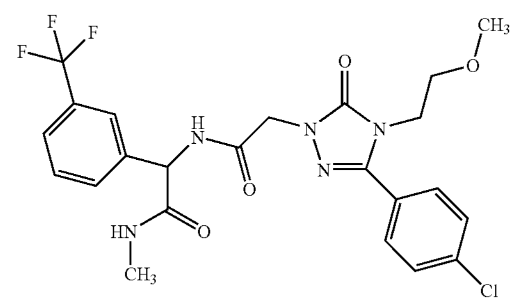 | 90A + 179A; 37% | $R_t$ = 1.98 min [23] m/z = 526 (M + H)$^+$ |
| 346 | 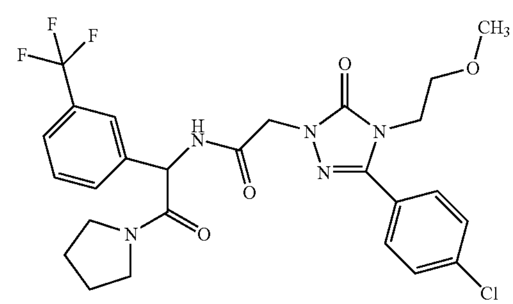 | 90A + 178A; 52% | $R_t$ = 3.46 min [19] m/z = 566 (M + H)$^+$ |
| 347 | 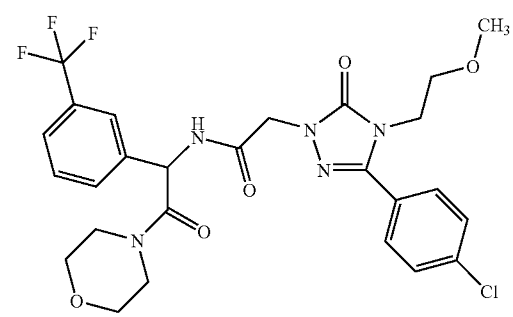 | 90A + 177A; 60% | $R_t$ = 2.46 min [8] m/z = 582 (M + H)$^+$ |

-continued

| Example No. | Structure | Educt(s); yield | LC/MS: $R_t$ [Method], m/z |
|---|---|---|---|
| 348 | 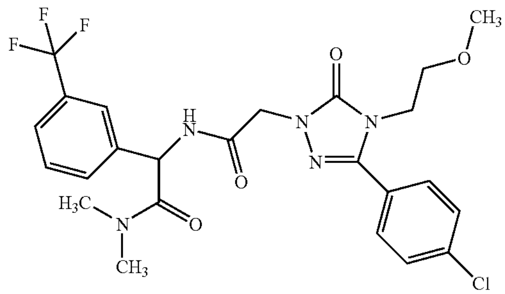 | 90A + 175A; 99% | $R_t$ = 2.43 min [8] m/z = 540 (M + H)$^+$ |
| 349 | 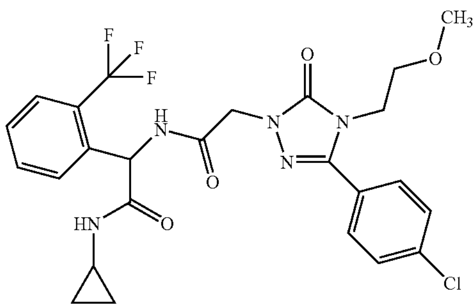 | 90A + 183A; 72% | $R_t$ = 1.99 min [23] m/z = 552 (M + H)$^+$ |
| 350 | 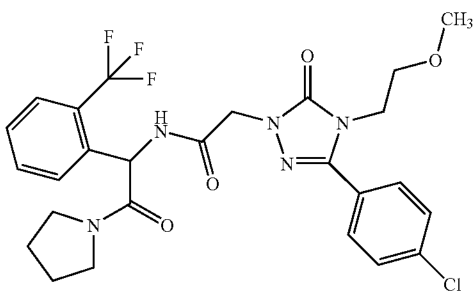 | 90A + 182A; 72% | $R_t$ = 1.91 min [22] m/z = 566 (M + H)$^+$ |
| 351 | 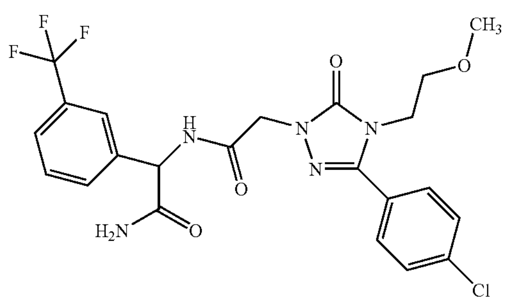 | 90A + 184A; 85% | $R_t$ = 1.73 min [22] m/z = 512 (M + H)$^+$ |
| 352 | 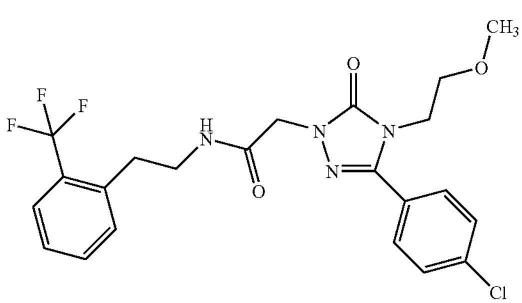 | 90A; 70% | $R_t$ = 2.30 min [7] m/z = 483 (M + H)$^+$ |

-continued

| Example No. | Structure | Educt(s); yield | LC/MS: $R_t$ [Method], m/z |
|---|---|---|---|
| 353 | 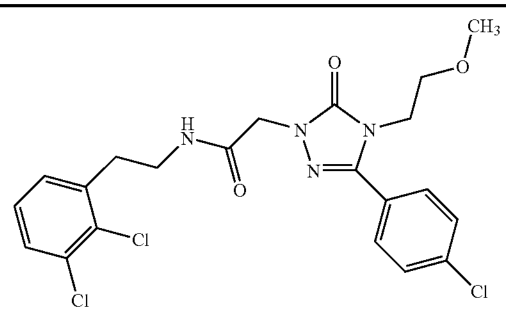 | 90A; 86% | $R_t$ = 3.48 min [19] m/z = 483 (M + H)+ |

Example 354

2-[3-(4-chlorophenyl)-4-(2-methoxyethyl)-5-oxo-4,5-dihydro-1H-1,2,4-triazol-1-yl]-N-[2,2-diethoxy-2-(pyridine-2-yl)ethyl)]-acetamide hydrochloride

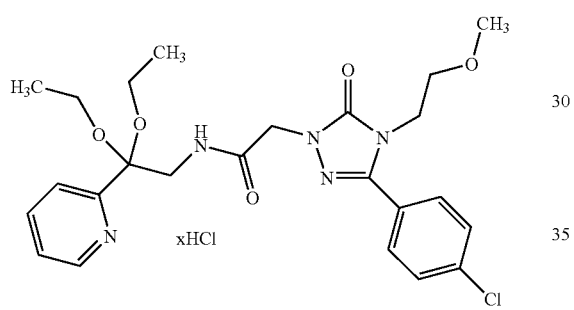

80 mg (92% of theory) of the title compound are obtained from the carboxylic acid from Example 90A (50 mg, 160 μmol) and 2,2-diethoxy-2-(pyridyl-2-yl)ethylamine dihydrochloride (68 mg, 240 μmol; for preparation see *Synthesis*, 1980 (4), 329), by the method described in Example 343.

LC/MS [Method 8]: $R_t$=2.09 min; m/z=504 (M+H)+.

Example 355

2-[3-(4-chlorophenyl)-4-(cyclopropyl)-5-oxo-4,5-dihydro-1H-1,2,4-triazol-1-yl]-N-{(1RS,2RS)-[2-(3-trifluoromethyl-phenyl)cyclopropyl]}-acetamide

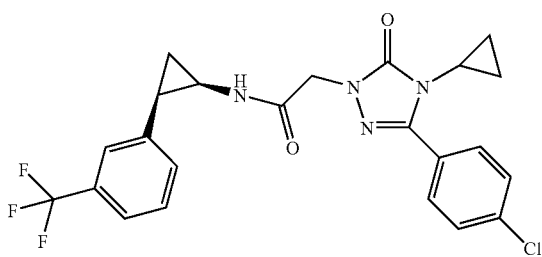

The carboxylic acid from Example 88A (28 mg, 96 μmol) and HOBt (19 mg, 0.14 mmol) are placed in 1 ml of DMF and treated at RT with 28 mg (0.14 mmol) of EDC. After 20 mins, 25 mg (0.11 mmol) of the compound from Example 203A and 23 μl of N,N-diisopropylethylamine (134 μmol) are added and the mixture is stirred for 5 hrs at RT. The mixture is then separated directly by preparative HPLC (Method 20). 39 mg (86% of theory) of the title compound are obtained.

LC/MS [Method 8]: $R_t$=2.57 min; m/z=477 (M+H)+

$^1$H-NMR (400 MHz, DMSO-d$_6$): δ=0.50-0.60 (m, 2H), 0.83-0.92 (m, 2H), 1.14 (m, 1H), 1.35 (m, 1H), 2.31 (m, 1H), 3.01 (m, 1H), 3.14 (m, 1H), 4.01 (d, 1H), 4.19 (d, 1H), 7.38-7.52 (m, 4H), 7.59 (d, 2H), 7.73 (d, 2H), 8.20 (d, 1H).

Example 356

2-[3-(4-chlorophenyl)-4-(cyclopropyl)-5-oxo-4,5-dihydro-1H-1,2,4-triazol-1-yl]-N-{2,2-difluoro-2-[3-(trifluoromethyl)phenyl]ethyl}-acetamide

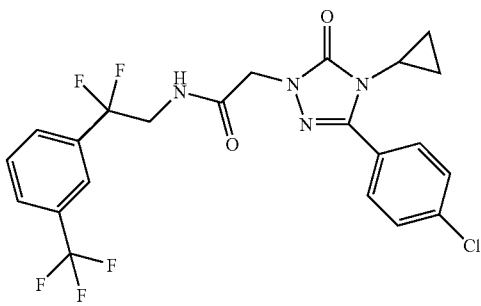

Starting from Example 88A and Example 205A, the title compound is obtained in 68% yield by the method described in Example 355.

LC/MS [Method 23]: $R_t$=2.30 min; m/z=501 (M+H)+

¹H-NMR (400 MHz, DMSO-d₆): δ=0.54-0.60 (m, 2H), 0.86-0.93 (m, 2H), 3.17 (m, 1H), 3.94 (dt, 2H), 4.36 (s, 2H), 7.59 (d, 2H), 7.71-7.81 (m, 3H), 7.82-7.88 (m, 2H), 7.91 (d, 1H), 8.59 (t, 1H).

Example 357

2-[3-(4-chlorophenyl)-5-oxo-4-(3,3,3-trifluoro-2-hydroxypropyl)-4,5-dihydro-1H-1,2,4-triazol-1-yl]-N-{(1RS,2RS)-[2-(3-trifluoromethyl-phenyl)cyclopropyl]}-acetamide

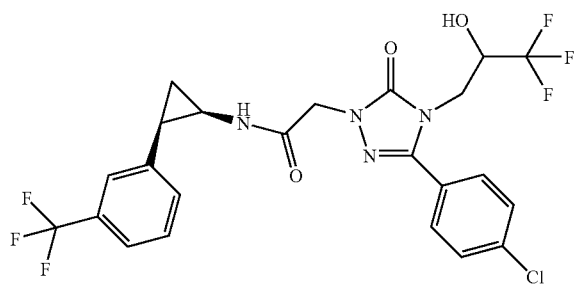

The carboxylic acid from Example 229A (enantiomer 1; 35 mg, 96 μmol) and HOBt (19 mg, 0.14 mmol) are placed in 1 ml of DMF and treated at RT with 28 mg (0.14 mmol) of EDC. After 20 mins, 25 mg (0.11 mmol) of the compound from Example 203A and 23 μl (0.13 mmol) of N,N-diisopropylethylamine are added and the mixture is stirred overnight at RT. The mixture is then separated directly by preparative HPLC (Method 20). 46 mg (88% of theory) of the title compound are obtained.

LC/MS [Method 8]: $R_t$=2.67 min; m/z=549 (M+H)⁺

¹H-NMR (400 MHz, DMSO-d₆): δ=1.15 (q, 1H), 1.37 (dt, 1H), 2.33 (q, 1H), 3.03 (m, 1H), 3.80 (dd, 1H), 3.93 (br. d, 1H), 4.06 (dd, 1H), 4.25 (m, 1H), 4.26 (dd, 1H), 6.89 (d, 1H), 7.40-7.52 (m, 4H), 7.60-7.65 (m, 2H), 7.66-7.72 (m, 2H), 8.25 (dd, 1H).

The compounds in the following table are prepared analogously. Unless otherwise stated, the amine educts are commercially available.

| Example No. | Structure | Educt; yield | LC/MS: $R_t$ [Method], m/z |
|---|---|---|---|
| 358 | (Enantiomer 1) | 229A; 85% | $R_t$ = 3.70 min [19] m/z = 553 (M + H)⁺ |
| 359 | (Enantiomer 2) | 230A; 83% | $R_t$ =3.70 min [19] m/z = 553 (M + H)⁺ |

-continued
| Example No. | Structure | Educt; yield | LC/MS: R$_t$ [Method], m/z |
|---|---|---|---|
| 360 | 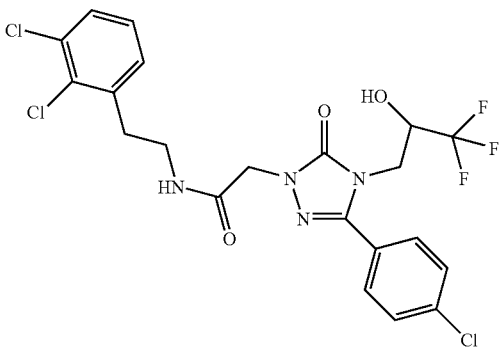<br>(Enantiomer 1) | 229A; 84% | R$_t$ = 3.69 min [19]<br>m/z = 537 (M + H)$^+$ |
| 361 | 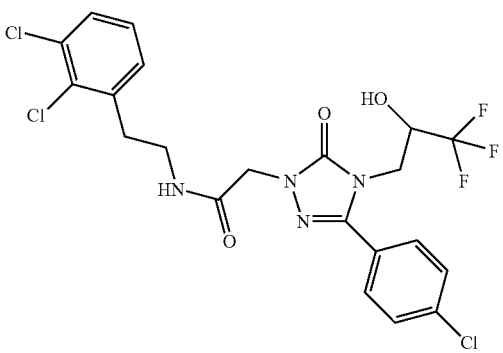<br>(Enantiomer 2) | 230A; 82% | R$_t$ = 3.70 min [19]<br>m/z = 537 (M + H)$^+$ |
| 362 | 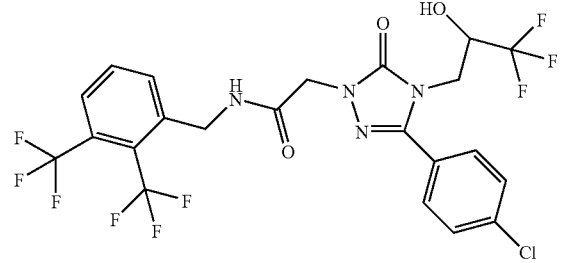<br>(Enantiomer 1) | 229A; 80% | R$_t$ = 3.79 min [19]<br>m/z = 591 (M + H)$^+$ |
| 363 | 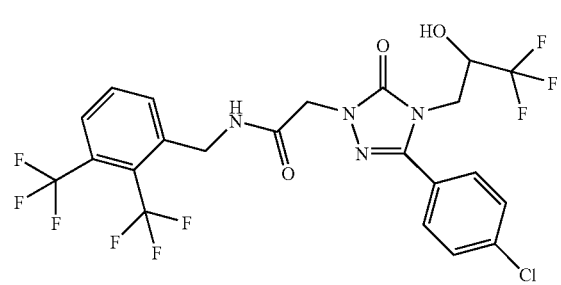<br>(Enantiomer 2) | 230A; 74% | R$_t$ = 3.78 min [19]<br>m/z = 591 (M + H)$^+$ |

-continued

| Example No. | Structure | Educt; yield | LC/MS: $R_t$ [Method], m/z |
|---|---|---|---|
| 364 | (Enantiomer 1) | 229A; 80% | $R_t$ = 2.39 min [23] m/z = 573 (M + H)$^+$ |

Example 365 tert.-butyl 4-{3-(4-chlorophenyl)-1-[2-({2-methyl-2-[2-(trifluoromethyl)phenyl]propyl}amino)-2-oxoethyl]-5-oxo-1,5-dihydro-4H-1,2,4-triazol-4-yl}-butanoate

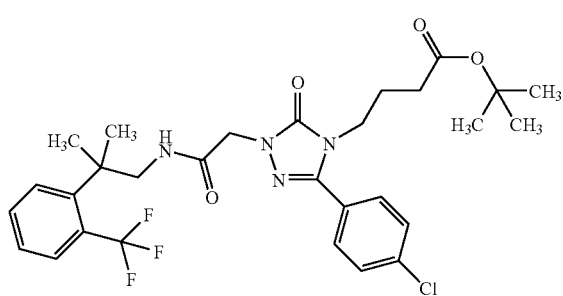

The carboxylic acid from Example 224A (20 mg, 51 μmol), HOBt (13 mg, 91 μmol) and N,N-diisopropylethylamine (13 μl, 76 μmol) are placed in 0.75 ml of DMF and treated at RT with 17.4 mg (91 μmol) of EDC. After 20 mins, 17 mg (66 μmol) of the compound from Example 166A are added and the mixture is stirred overnight at RT. The mixture is then separated directly by preparative HPLC (Method 20). 24 mg (80% of theory) of the title compound are obtained.

LC/MS [Method 22]: $R_t$=2.54 min; m/z=595 (M+H)$^+$ $^1$H-NMR (400 MHz, DMSO-d$_6$): δ=1.35 (s, 9H), 1.39 (s, 6H), 1.69 (quin, 2H), 2.14 (t, 2H), 3.45 (d, 2H), 3.75 (t, 2H), 4.45 (s, 2H), 7.45 (t, 1H), 7.56-7.69 (m, 6H), 7.75 (d, 1H), 7.91 (t, 1H).

Example 366 tert.-butyl 4-{3-(4-chlorophenyl)-1-[2-({2-(dimethylamino)-2-oxo-1-[3-(trifluoromethyl)phenyl]-ethyl}-amino)-2-oxoethyl]-5-oxo-1,5-dihydro-4H-1,2,4-triazol-4-yl}-butanoate

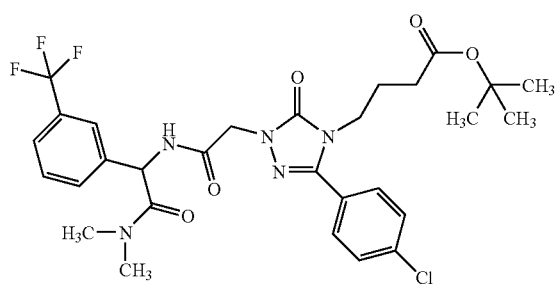

Starting from Example 224A and Example 175A (as the trifluoroacetate salt), the title compound is obtained analogously to Example 365.

LC/MS [Method 22]: $R_t$=2.32 min; m/z=624 (M+H)$^+$ $^1$H-NMR (400 MHz, DMSO-d$_6$): δ=1.32 (s, 9H), 1.69 (quin, 2H), 2.14 (t, 2H), 2.85 (s, 3H), 2.99 (s, 3H), 3.75 (t, 2H), 4.50 (m, 2H), 5.99 (d, 1H), 7.58-7.72 (m, 7H), 7.77 (s, 1H), 8.99 (d, 1H).

Example 367

4-{3-(4-chlorophenyl)-1-[2-({2-methyl-2-[2-(trifluoromethyl)phenyl]propyl}amino)-2-oxoethyl]-5-oxo-1,5-dihydro-4H-1,2,4-triazol-4-yl}-butanoic acid

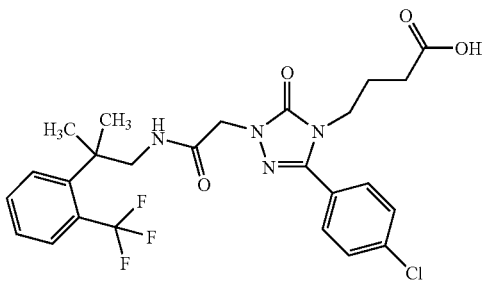

The compound from Example 365 (22 mg, 37 μmol) is stirred overnight at RT with 1 ml of a 4 M hydrogen chloride solution in dioxan. The solvent is then removed on the rotary evaporator. The residue is taken up in DMSO and purified by preparative HPLC (Method 20). 14 mg (70% of theory) of the title compound are obtained.

LC/MS [Method 22]: $R_t$=1.98 min, m/z=539 (M+H)$^+$ $^1$H-NMR (400 MHz, DMSO-d$_6$): δ=1.39 (s, 6H), 1.69 (quin, 2H), 2.18 (t, 2H), 3.45 (d, 2H), 3.74 (t, 2H), 4.35 (s, 2H), 7.44 (t, 1H), 7.56-7.63 (m, 3H), 7.63-7.68 (m, 3H), 7.77 (d, 1H), 7.91 (t, 1H), 12.12 (br. s, 1H).

Example 368

4-{3-(4-chlorophenyl)-1-[2-({2-(dimethylamino)-2-oxo-1-[3-(trifluoromethyl)phenyl]ethyl}-amino)-2-oxoethyl]-5-oxo-1,5-dihydro-4H-1,2,4-triazol-4-yl}-butanoic acid

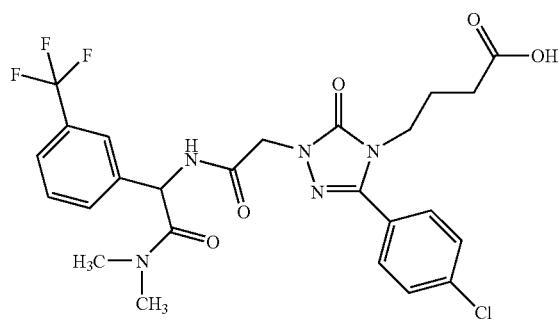

Starting from Example 366, the title compound is obtained analogously to Example 367.

LC/MS [Method 22]: R$_t$=1.80 min; m/z=568 (M+H)$^+$ $^1$H-NMR (400 MHz, DMSO-d$_6$): δ=1.69 (quin, 2H), 2.17 (t, 2H), 2.85 (s, 3H), 2.99 (s, 3H), 3.75 (t, 2H), 4.50 (m, 2H), 5.99 (d, 1H), 7.57-7.73 (m, 7H), 7.76 (s, 1H), 8.99 (d, 1H), 12.11 (br. s, 1H).

Example 369

2-[3-(4-chlorophenyl)-4-(2-fluorobenzyl)-5-oxo-4,5-dihydro-1H-1,2,4-triazol-1-yl]-N-[1-(isoquinoline-1-yl)ethyl]-acetamide

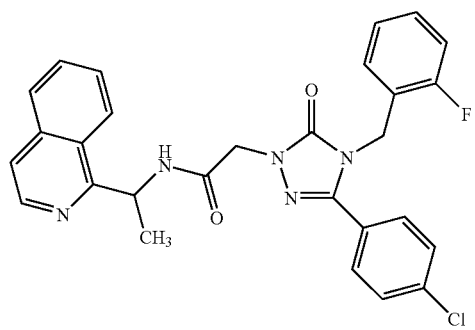

The title compound is prepared analogously to Example 264 from the carboxylic acid from Example 156A (40 mg, 0.11 mmol) and 26.7 mg (0.16 mmol) of 1-isoquinolin-1-ylethylamine [preparation: see *Chem. Ber.* 108, 3771-3778 (1975)]. Yield: 70% of theory LC/MS [Method 17]: R$_t$=3.47 min; m/z=516 (M+H)$^+$.

Example 370

2-[3-(4-chlorophenyl)-4-(cyclopropyl)-5-oxo-4,5-dihydro-1H-1,2,4-triazol-1-yl]-N-{3-dimethyl-amino-3-oxo-2-[2-(trifluoromethyl)phenyl]propyl}-acetamide

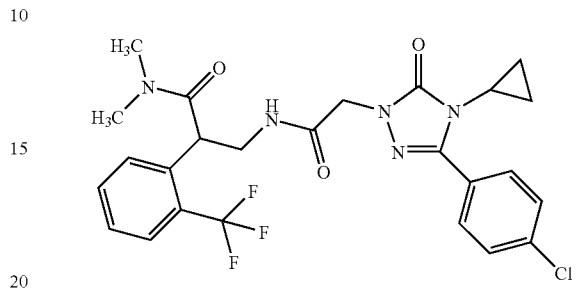

The compound from Example 317 (55 mg, 102 μmol) is hydrolysed to the corresponding carboxylic acid (52 mg) analogously to Example 300. 30 mg of this acid (59 μmol) are then reacted with dimethylamine analogously to Example 301 to give the title compound (31 mg, 98% of theory).

LC/MS [Method 22]: R$_t$=1.93 min; m/z=536 (M+H)$^+$.

Example 371

2-[3-(4-chlorophenyl)-4-allyl-5-oxo-4,5-dihydro-1H-1,2,4-triazol-1-yl]-N-{1-methyl-1-[3-(trifluoromethyl)phenyl]ethyl}-acetamide

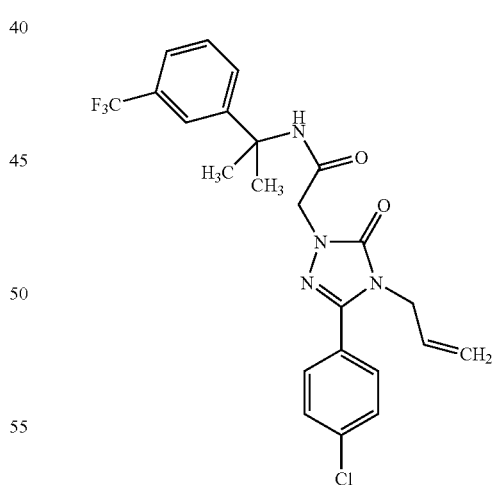

1.98 g (6.74 mmol) of [3-(4-chlorophenyl)-4-allyl-5-oxo-4,5-dihydro-1H-1,2,4-triazol-1-yl]-acetic acid from Example 218A and 1.51 g (7.42 mmol) of 1-methyl-1-[(3-trifluoromethyl)phenyl]-ethylamine from Example 1A are placed in 50 ml of DMF and treated with 1.09 g (8.09 mmol) of HOBt. After 10 mins' stirring, 1.68 g (8.76 mmol) of EDC hydrochloride are added and the mixture is stirred overnight at RT. For the workup, the reaction mixture is stirred with 500 ml of water. Next, the resulting precipitate is suction-filtered, washed with water and dried under high vacuum. 2.41 g (75% of theory) of the target compound are thus obtained.

LC/MS [Method 7]: R$_t$=2.49 min; MS [ESIpos]: m/z=479 (M+H)$^+$ $^1$H-NMR (400 MHz, DMSO-d$_6$): δ=1.60 (s, 6H), 4.30-4.38 (m, 4H), 4.50 (s, 2H), 4.92 (d, 1H), 5.11 (d, 1H), 5.82 (m, 1H), 7.50-7.70 (m, 8H), 8.55 (s, 1H).

The following compounds are prepared analogously:

| Example No. | Structure | LC/MS or HPLC, MS R$_t$ [Method] |
|---|---|---|
| 372 | 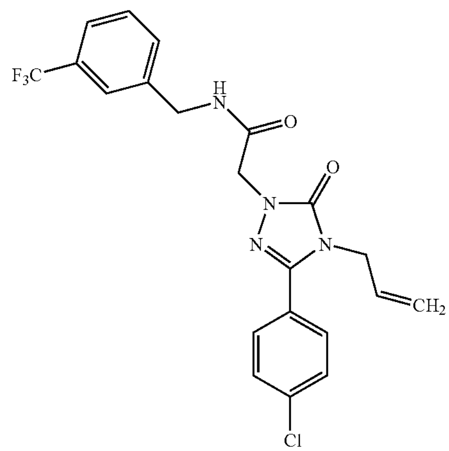 | LC/MS: R$_t$ = 2.55 min [8] [ESIpos]: m/z = 451 (M + H)$^+$ |
| 373 | 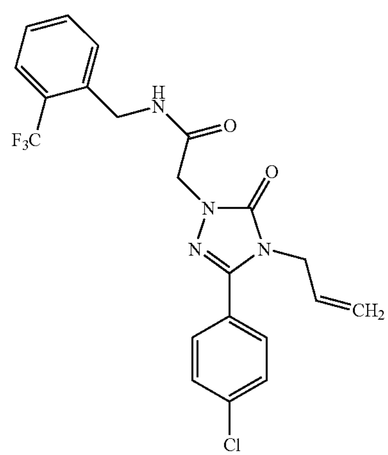 | LC/MS: R$_t$ = 2.60 min [8] [ESIpos]: m/z = 451 (M + H)$^+$ |
| 374 | 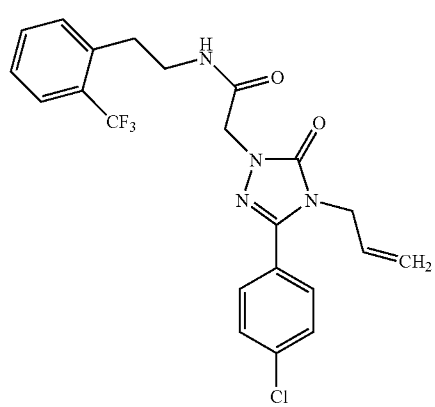 | LC/MS: R$_t$ = 3.72 min [17] [ESIpos]: m/z = 465 (M + H)$^+$ |

| Example No. | Structure | LC/MS or HPLC, MS $R_t$ [Method] |
|---|---|---|
| 375 | 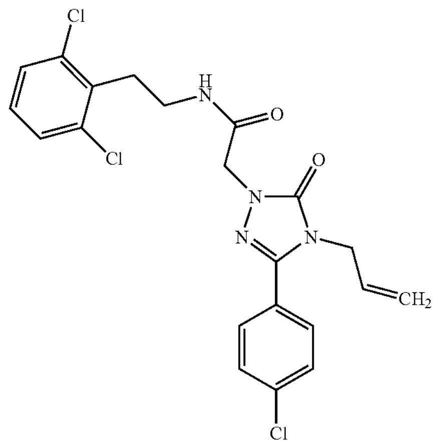 | LC/MS: $R_t$ = 3.72 min [17] [ESIpos]: m/z = 465 (M + H)$^+$ |
| 376 | 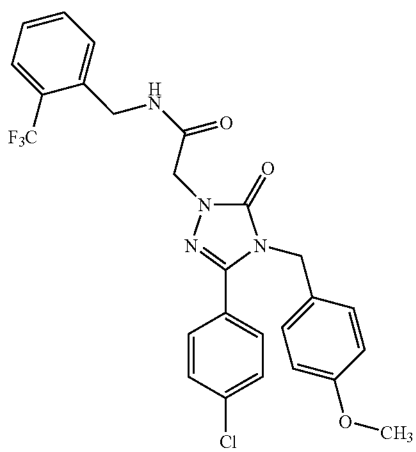 | LC/MS: $R_t$ = 2.51 min [7] [ESIpos]: m/z = 531 (M + H)$^+$ |
| 377 | 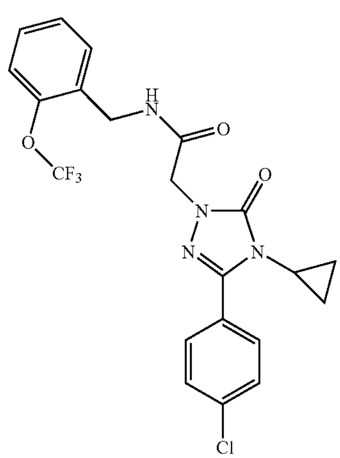 | [ESIpos]: m/z = 467 (M + H)$^+$ |

Example 378

2-[3-(4-chlorophenyl)-4-(2-methoxyethyl)-5-oxo-4,5-dihydro-1H-1,2,4-triazol-1-yl]-N-1-methyl-1-[3-(trifluoromethyl)phenyl]ethyl-acetamide

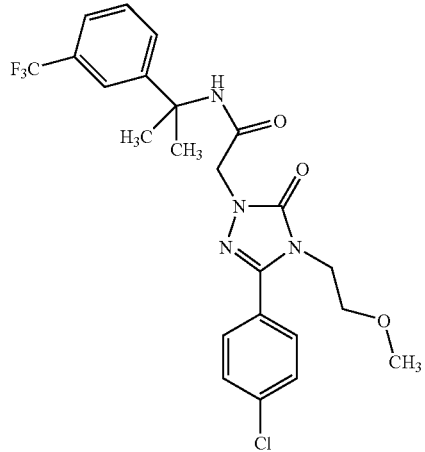

2.90 g (9.30 mmol) of [3-(4-chlorophenyl)-4-(2-methoxyethyl)-5-oxo-4,5-dihydro-1H-1,2,4-triazol-1-yl]-acetic acid from Example 90A and 2.08 g (10.23 mmol) of 1-methyl-1-[(3-trifluoromethyl)-phenyl]ethylamine from Example 1A are placed in 60 ml of DMF and treated with 1.51 g (11.2 mmol) of HOBt. After 10 mins' stirring, 2.32 g (12.1 mmol) of EDC hydrochloride are added and the mixture is stirred overnight at RT. For the workup, the reaction mixture is stirred with 500 ml of water. Next, the resulting precipitate is suction-filtered, washed with water and dried under high vacuum. 3.27 g (71% of theory) of the target compound are thus obtained.

LC/MS [Method 19]: $R_t$=3.60 min; MS [ESIpos]: m/z=497 (M+H)$^+$ $^1$H-NMR (400 MHz, DMSO-d$_6$): δ=1.60 (s, 6H), 3.10 (s, 3H), 3.45 (t, 2H), 3.84 (t, 2H), 4.47 (s, 2H), 7.48-7.72 (m, 8H), 8.56 (s, 1H).

The following compounds are prepared analogously:

| Example No. | Structure | LC/MS or HPLC, MS $R_t$ [Method] |
|---|---|---|
| 379 | 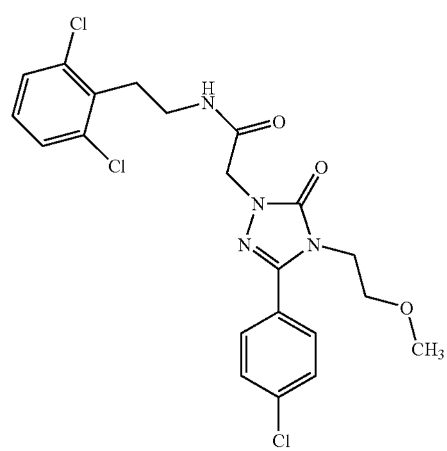 | LC/MS: $R_t$ = 2.56 min [8] [ESIpos]: m/z = 483/485 (M + H)$^+$ |
| 380 | 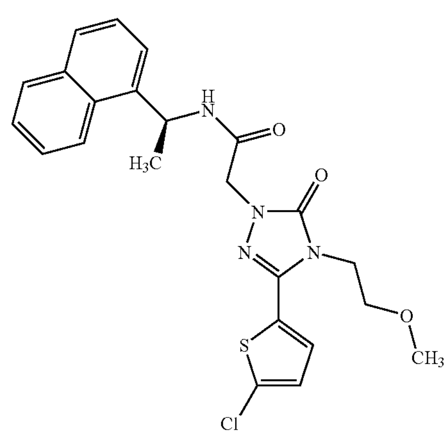 | LC/MS: $R_t$ = 2.36 min [7] [ESIpos]: m/z = 471 (M + H)$^+$ |

| Example No. | Structure | LC/MS or HPLC, MS $R_t$ [Method] |
|---|---|---|
| 381 | 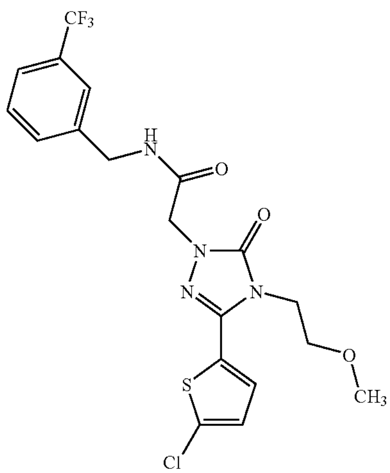 | LC/MS: $R_t$ = 2.51 min [8] [ESIpos]: m/z = 475 (M + H)$^+$ |
| 382 | 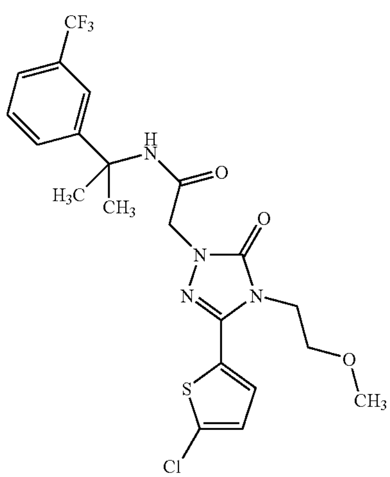 | LC/MS: $R_t$ = 3.02 min [8] [ESIpos]: m/z = 503 (M + H)$^+$ |
| 383 | 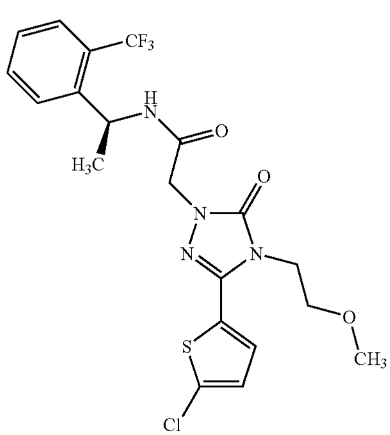 | LC/MS: $R_t$ = 3.66 min [17] [ESIpos]: m/z = 489 (M + H)$^+$ |

| Example No. | Structure | LC/MS or HPLC, MS $R_t$ [Method] |
|---|---|---|
| 384 | 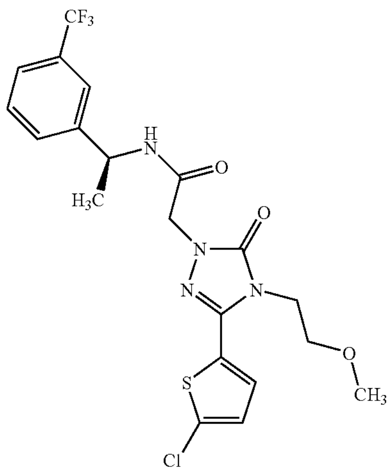 | LC/MS: $R_t$ = 3.66 min [8] [ESIpos]: m/z = 489 (M + H)$^+$ |
| 385 | 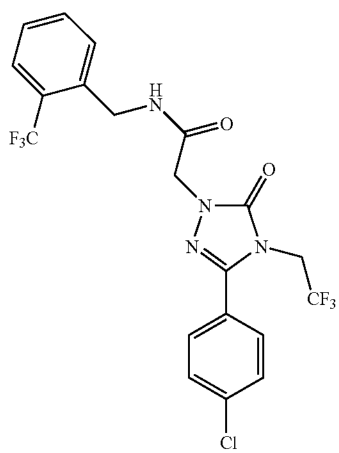 | LC/MS: $R_t$ = 2.59 min [8] [ESIpos]: m/z = 493 (M + H)$^+$ |
| 386 | 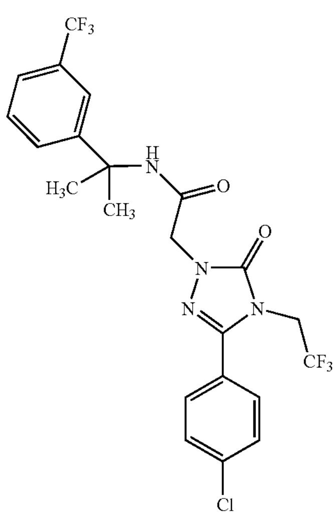 | LC/MS: $R_t$ = 3.95 min [17] [ESIpos]: m/z = 521 (M + H)$^+$ |

-continued
| Example No. | Structure | LC/MS or HPLC, MS $R_t$ [Method] |
|---|---|---|
| 387 | 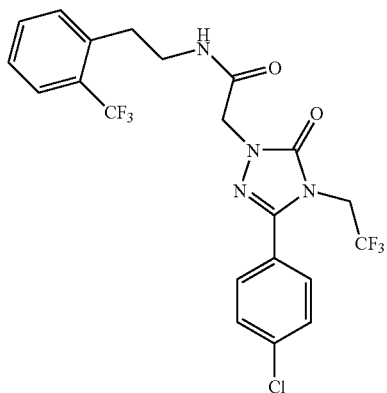 | LC/MS: $R_t$ = 3.82 min [17] [ESIpos]: m/z = 507 (M + H)+ |
| 388 | 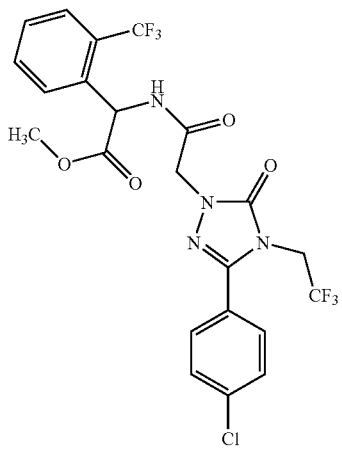 | LC/MS: $R_t$ = 3.60 min [19] [ESIpos]: m/z = 551 (M + H)+ |
| 389 | 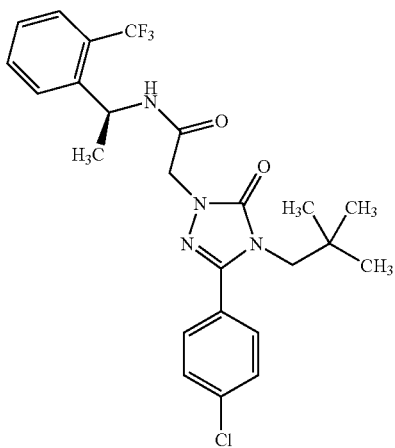 | LC/MS: $R_t$ = 4.02 min [17] [ESIpos]: m/z = 495 (M + H)+ |

| Example No. | Structure | LC/MS or HPLC, MS $R_t$ [Method] |
|---|---|---|
| 390 | 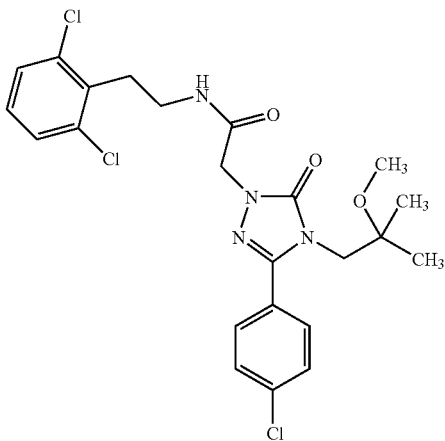 | LC/MS: $R_t$ = 3.78 min [17] [ESIpos]: m/z = 511/513 (M + H)$^+$ |
| 391 | 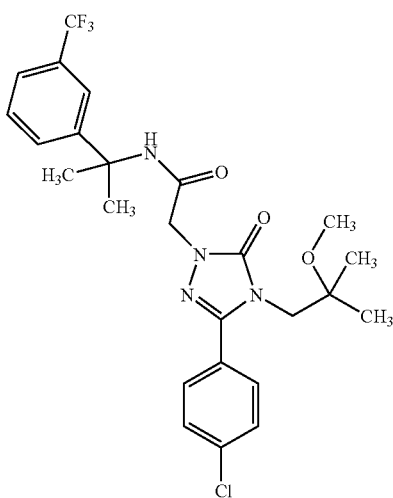 | LC/MS: $R_t$ = 3.91 min [17] [ESIpos]: m/z = 525 (M + H)$^+$ |
| 392 | 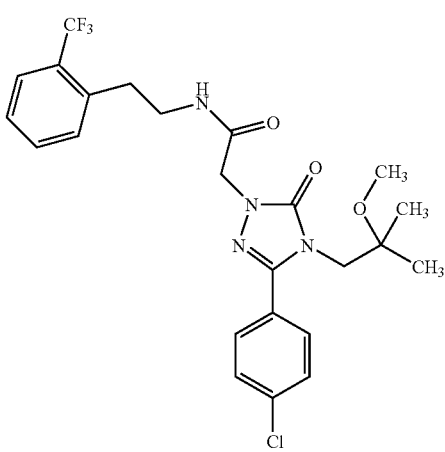 | LC/MS: $R_t$ = 3.77 min [17] [ESIpos]: m/z = 511 (M + H)$^+$ |

| Example No. | Structure | LC/MS or HPLC, MS $R_t$ [Method] |
|---|---|---|
| 393 | 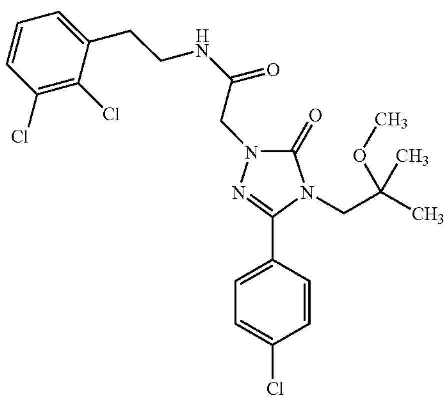 | LC/MS: $R_t$ = 3.64 min [19] [ESIpos]: m/z = 511/513 (M + H)⁺ |
| 394 | 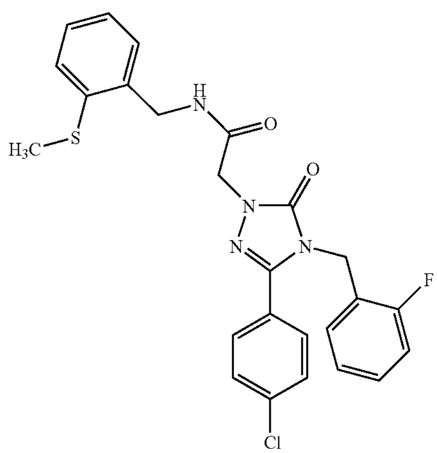 | LC/MS: $R_t$ = 2.16 min [22] [ESIpos]: m/z = 497 (M + H)⁺ |
| 395 | 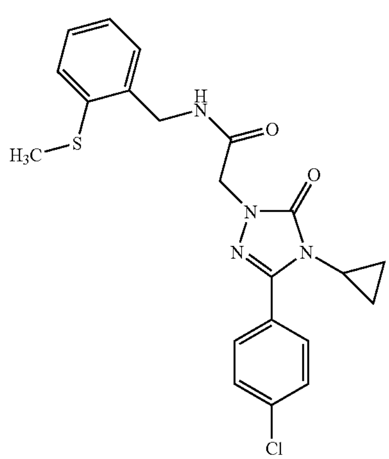 | MS [DCI]: m/z = 429 (M + H)⁺, 446 (M + NH₄)⁺ |

Example 396

2-[3-(4-chlorophenyl)-4-(2-hydroxyethyl)-5-oxo-4,5-dihydro-1H-1,2,4-triazol-1-yl]-N-1-methyl-1-[3-(trifluoromethyl)phenyl]ethyl-acetamide

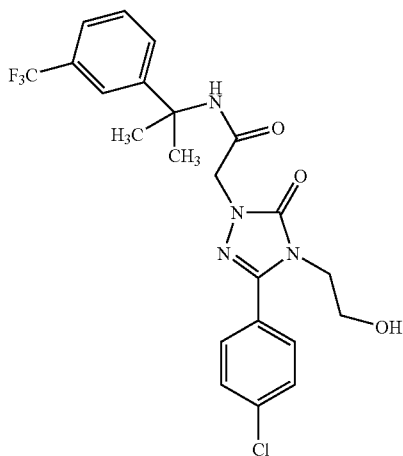

2.95 g (5.94 mmol) of 2-[3-(4-chlorophenyl)-4-(2-methoxyethyl)-5-oxo-4,5-dihydro-1H-1,2,4-triazol-1-yl]-N-1-methyl-1-[3-(trifluoromethyl)phenyl]ethyl-acetamide from Example 378 are dissolved in 40 ml of trichloromethane and treated at RT with 6.76 ml (47.5 mmol) of iodo-trimethylsilane. This is stirred for 1 hr at RT. Next, a mixture of 40 ml methanol and 5.99 g (47.5 mmol) of sodium sulphite is added with vigorous stirring with ice-cooling. The reaction solution is diluted with 100 ml water and extracted twice with 50 ml ethyl acetate each time. The combined organic phases are dried over sodium sulphate, filtered and concentrated in vacuo. The crude product is dissolved in 50 ml isopropanol. After addition of ca. 50 ml water, the desired product precipitates out. The mixture is stirred at RT for one hour. Next, the crystals are suction-filtered and washed with a little water and a little cyclohexane. After drying under high vacuum, 2.56 g (89% of theory) of the target compound are thus obtained.

LC/MS [Method 17]: $R_t$=3.45 min; MS [ESIpos]: m/z=483 $(M+H)^+$ $^1$H-NMR (400 MHz, DMSO-$d_6$): δ=1.60 (s, 6H), 3.54 (q, 2H), 3.75 (t, 2H), 4.47 (s, 2H), 5.00 (t, 1H), 7.48-7.78 (m, 8H), 8.55 (s, 1H).

The following compounds are prepared analogously:

| Example No. | Structure | LC/MS or HPLC, MS $R_t$ [Method] |
|---|---|---|
| 397 | 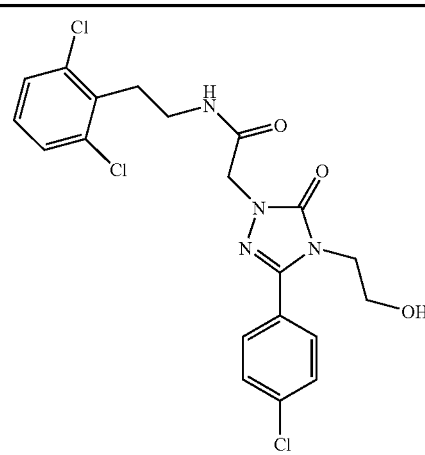 | LC/MS: $R_t$ = 3.12 min [19] [ESIpos]: m/z = 469/471 $(M + H)^+$ |
| 398 | 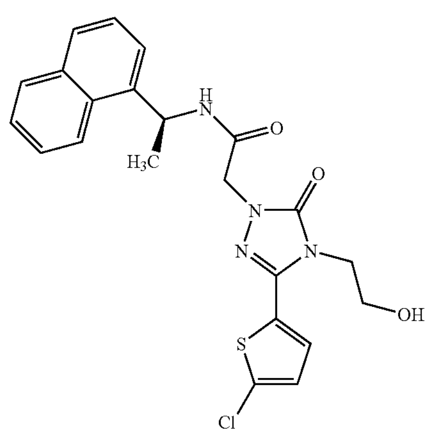 | LC/MS: $R_t$ = 2.09 min [7] [ESIpos]: m/z = 457 $(M + H)^+$ |

-continued

| Example No. | Structure | LC/MS or HPLC, MS $R_t$ [Method] |
|---|---|---|
| 399 | 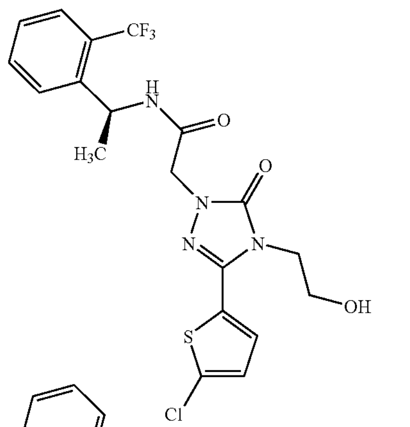 | LC/MS: $R_t$ = 2.07 min [7] [ESIpos]: m/z = 475 (M + H)$^+$ |
| 400 | 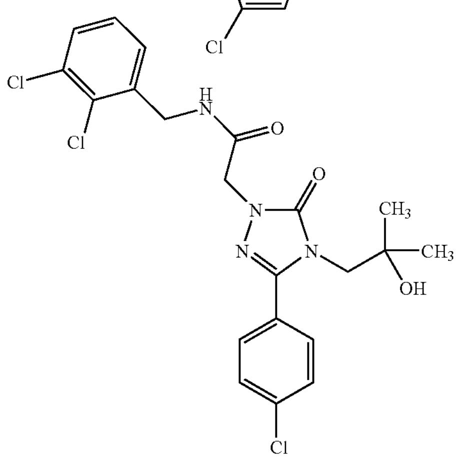 | LC/MS: $R_t$ = 3.52 min [17] [ESIpos]: m/z = 497/499 (M + H)$^+$ |

Example 401

2-[3-(4-chlorophenyl)-4-(2-oxoethyl)-5-oxo-4,5-dihydro-1H-1,2,4-triazol-1-yl]-N-1-methyl-1-[3-(trifluoromethyl)phenyl]ethyl-acetamide

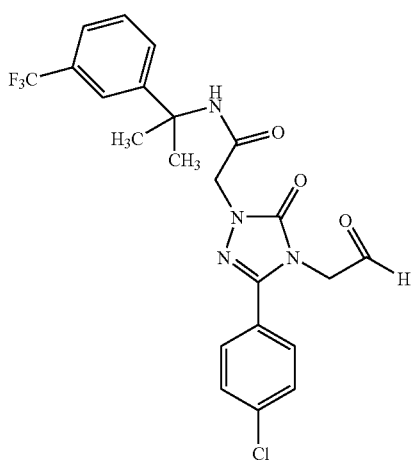

0.5 g (1.04 mmol) of 2-[3-(4-chlorophenyl)-4-(2-hydroxy-ethyl)-5-oxo-4,5-dihydro-1H-1,2,4-triazol-1-yl]-N-1-methyl-1-[3-(trifluoromethyl)phenyl]ethyl-acetamide from Example 396 are dissolved in 30 ml of dichloromethane and treated at 0° C. with 0.57 g (1.35 mmol) of 1,1,1-tris-(acetoxy)-1,1-dihydro-1,2-benziodoxol-3-(1H)-one (Dess-Martin periodinane). This is stirred at RT for 18 hrs. A further 0.38 g (0.90 mmol) of Dess-Martin periodinane are then added. After 3 hrs, the suspension is directly purified. by flash chromatography on silica gel (eluent: dichloromethane/ethyl acetate/methanol 100:100:1) The product thus obtained is taken up in 50 ml ethyl acetate and washed once with 50 ml of 0.05 N hydrochloric acid. The organic phase is dried over sodium sulphate, filtered and concentrated in vacuo. 0.32 g (64% of theory) of the target compound are thus obtained.

LC/MS [Method 19]: $R_t$=3.21 min; MS [ESIpos]: m/z=481 (M+H)$^+$ $^1$H-NMR (400 MHz, CDCl$_3$): δ=1.71 (s, 6H), 4.52 (s, 2H), 4.49 (s, 2H), 6.55 (s, 1H), 7.44-7.70 (m, 8H), 9.61 (s, 1H).

The following compound is prepared analogously:

| Example No. | Structure | LC/MS or HPLC, MS $R_t$ [Method] |
|---|---|---|
| 402 | 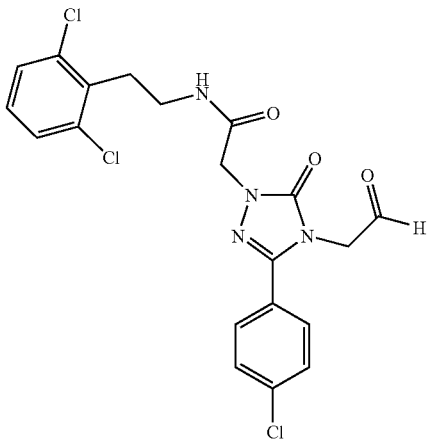 | LC/MS: $R_t$ = 2.20 min [8] [ESIpos]: m/z = 467/469 $(M + H)^+$ |

Example 403

2-[3-(4-chlorophenyl)-4-(3-methoxybenzyl)-5-oxo-4,5-dihydro-1H-1,2,4-triazol-1-yl]-N-1-methyl-1-[3-(trifluoromethyl)phenyl]ethyl-acetamide

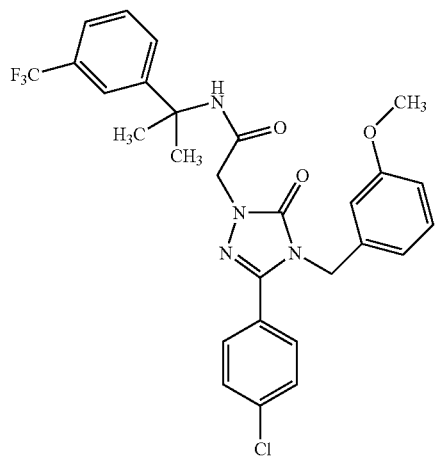

75 mg (0.17 mmol) of 2-[3-(4-chlorophenyl)-5-oxo-4,5-dihydro-1H-1,2,4-triazol-1-yl]-N-{1-methyl-1-[3-(trifluoromethyl)phenyl]ethyl}-acetamide from Example 241A are suspended in 2.5 ml of acetone with 84 mg (0.26 mmol) of caesium carbonate and treated with 45 mg (0.22 mmol) of 3-methoxybenzyl chloride. This is stirred for 6 hrs at 50° C. and then for 18 hrs at RT. The suspension is treated with 1 ml of water and extracted three times with ethyl acetate. The combined organic phases are dried over sodium sulphate and filtered. After evaporation of the organic phase, the crude product is purified by preparative HPLC [Method 10]. 55.6 mg (58% of theory) of the target compound are thus obtained.

LC/MS [Method 18]: $R_t$=2.78 min; MS [ESIpos]: m/z=559 $(M+H)^+$ $^1$H-NMR (400 MHz, DMSO-$d_6$): δ=1.60 (s, 6H), 3.60 (s, 3H), 4.54 (s, 2H), 4.95 (s, 2H), 6.59-6.64 (m, 2H), 6.75-6.80 (m, 1H), 7.18 (t, 1H), 7.46-7.72 (m, 8H), 8.58 (s, 1H).

The following compounds are prepared analogously:

| Example No. | Structure | LC/MS or HPLC, MS $R_t$ [Method] |
|---|---|---|
| 404 | 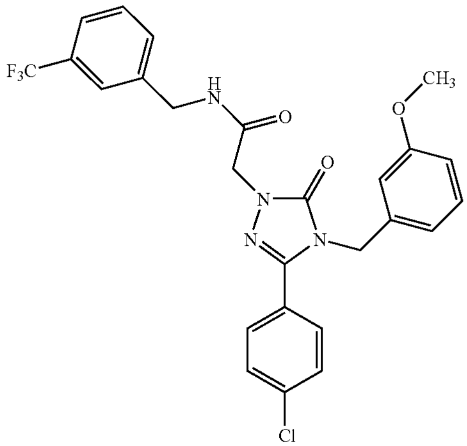 | LC/MS: $R_t$ = 2.66 min [18] [ESIpos]: m/z = 531 (M + H)$^+$ |
| 405 | 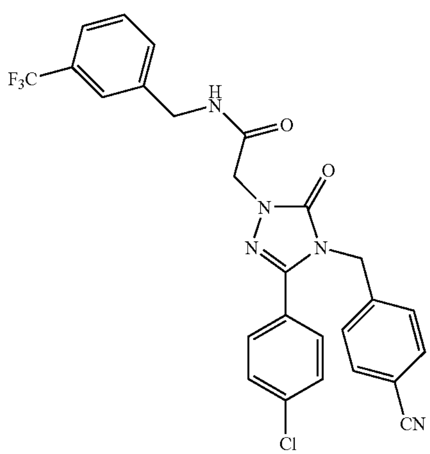 | LC/MS: $R_t$ = 2.43 min [7] [ESIpos]: m/z = 526 (M + H)$^+$ |
| 406 | 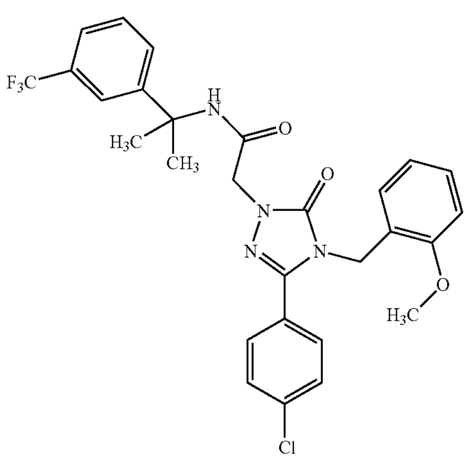 | LC/MS: $R_t$ = 2.73 min [7] [ESIpos]: m/z = 559 (M + H)$^+$ |

| Example No. | Structure | LC/MS or HPLC, MS R_t [Method] |
|---|---|---|
| 407 | 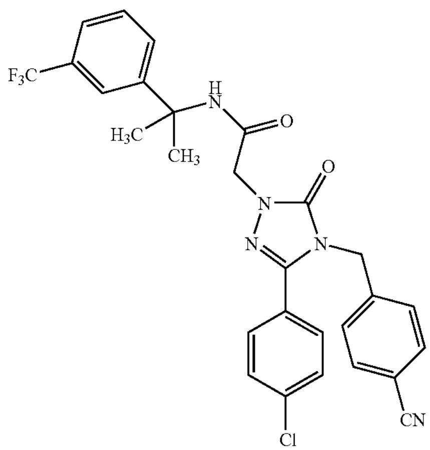 | LC/MS: $R_t$ = 2.67 min [18] [ESIpos]: m/z = 554 (M + H)$^+$ |
| 408 | 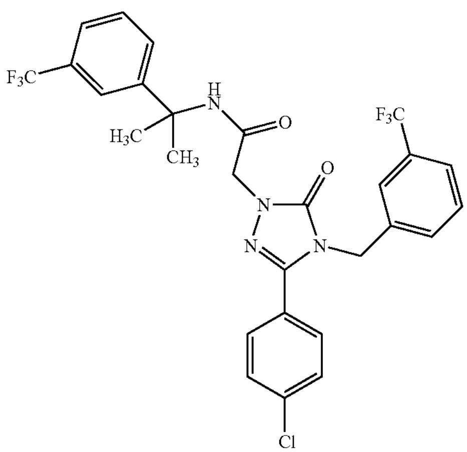 | LC/MS: $R_t$ = 2.91 min [18] [ESIpos]: m/z = 597 (M + H)$^+$ |
| 409 | 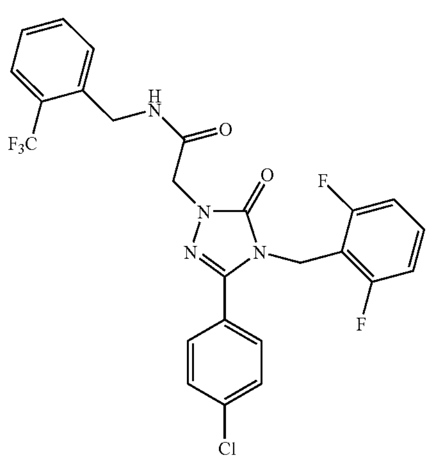 | LC/MS: $R_t$ = 2.47 min [7] [ESIpos]: m/z = 537 (M + H)$^+$ |

-continued

| Example No. | Structure | LC/MS or HPLC, MS R_t [Method] |
|---|---|---|
| 410 | 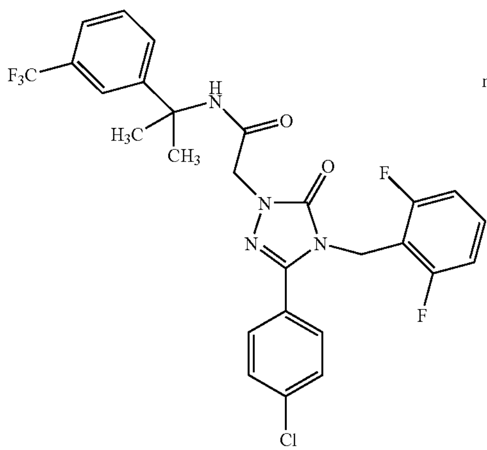 | LC/MS: $R_t$ = 2.63 min [7] [ESIpos]: m/z = 565 (M + H)$^+$ |
| 411 | 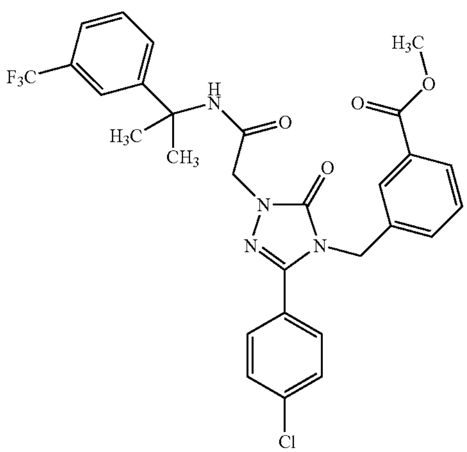 | LC/MS: $R_t$ = 3.86 min [19] [ESIpos]: m/z = 587 (M + H)$^+$ |
| 412 | 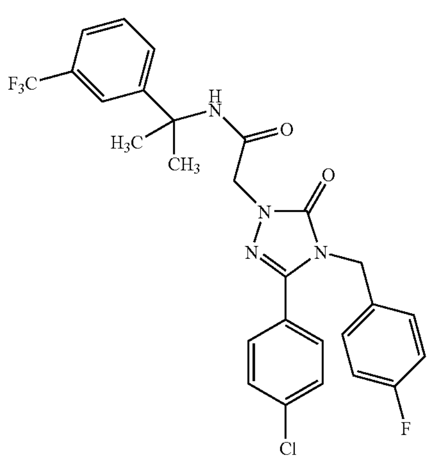 | LC/MS: $R_t$ = 2.91 min [8] [ESIpos]: m/z = 547 (M + H)$^+$ |

-continued

| Example No. | Structure | LC/MS or HPLC, MS R_t [Method] |
|---|---|---|
| 413 | 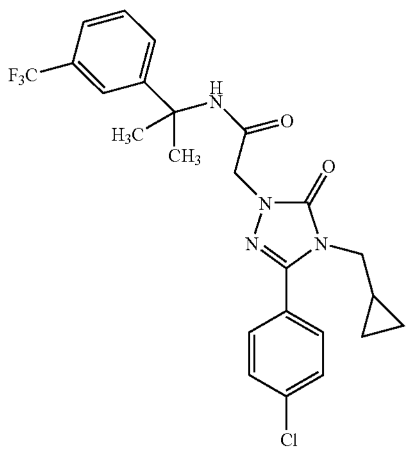 | LC/MS: $R_t$ = 2.55 min [7] [ESIpos]: m/z = 493 (M + H)$^+$ |
| 414 | 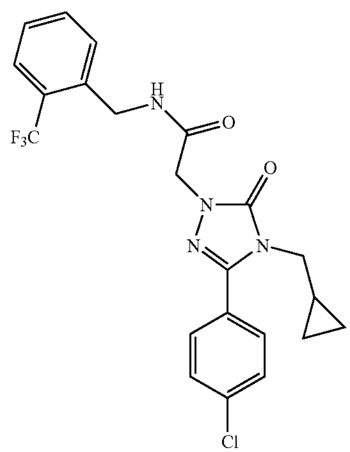 | LC/MS: $R_t$ = 3.58 min [19] [ESIpos]: m/z = 465 (M + H)$^+$ |
| 415 | 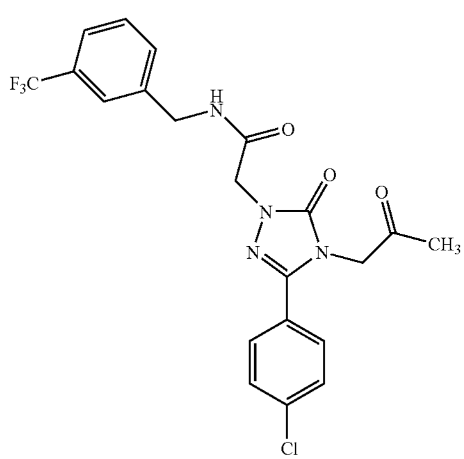 | LC/MS: $R_t$ = 2.45 min [8] [ESIpos]: m/z = 467 (M + H)$^+$ |

-continued

| Example No. | Structure | LC/MS or HPLC, MS $R_t$ [Method] |
|---|---|---|
| 416 | 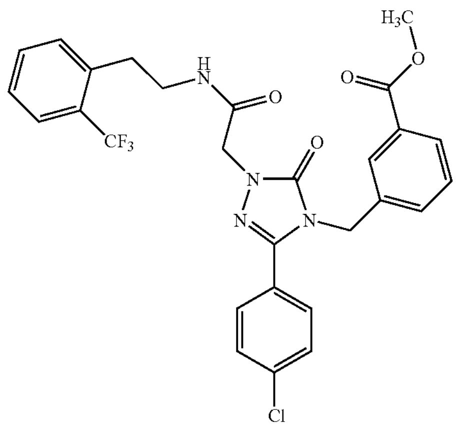 | LC/MS: $R_t$ = 3.73 min [19] [ESIpos]: m/z = 573 (M + H)$^+$ |
| 417 | 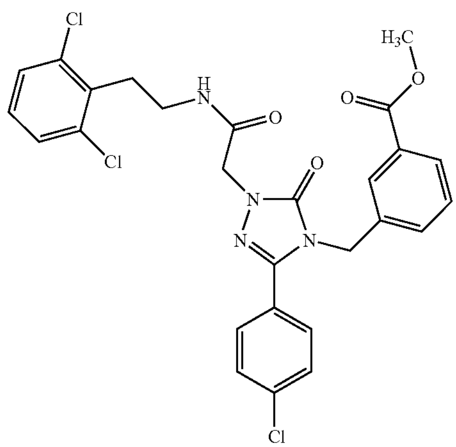 | LC/MS: $R_t$ = 3.94 min [19] [ESIpos]: m/z = 573/575 (M + H)$^+$ |
| 418 | 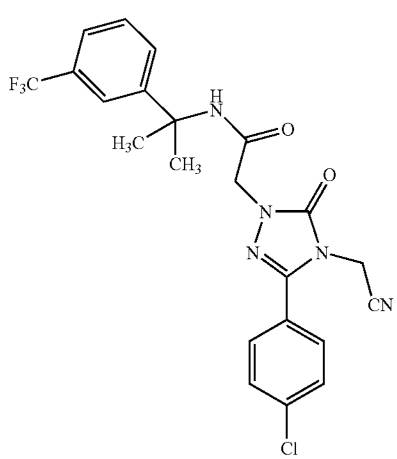 | LC/MS: $R_t$ = 2.61 min [8] [ESIpos]: m/z = 478 (M + H)$^+$ |

| Example No. | Structure | LC/MS or HPLC, MS $R_t$ [Method] |
|---|---|---|
| 419 | 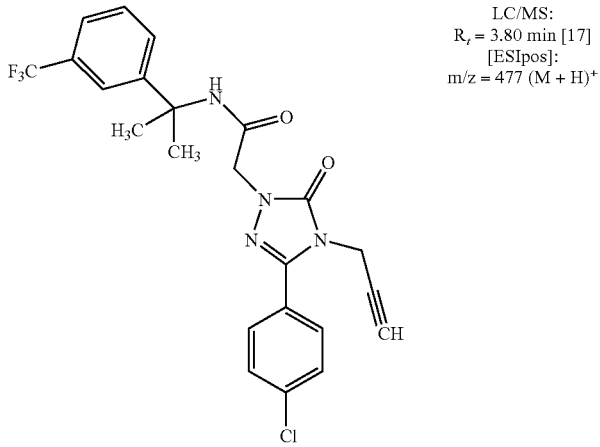 | LC/MS: $R_t$ = 3.80 min [17] [ESIpos]: m/z = 477 (M + H)$^+$ |
| 420 | 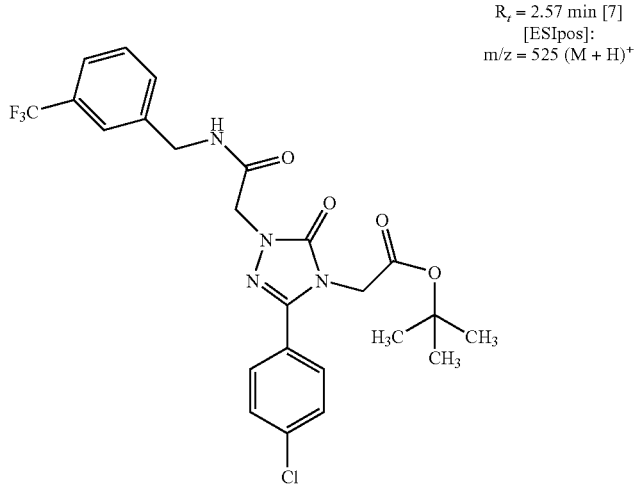 | LC/MS: $R_t$ = 2.57 min [7] [ESIpos]: m/z = 525 (M + H)$^+$ |
| 421 | 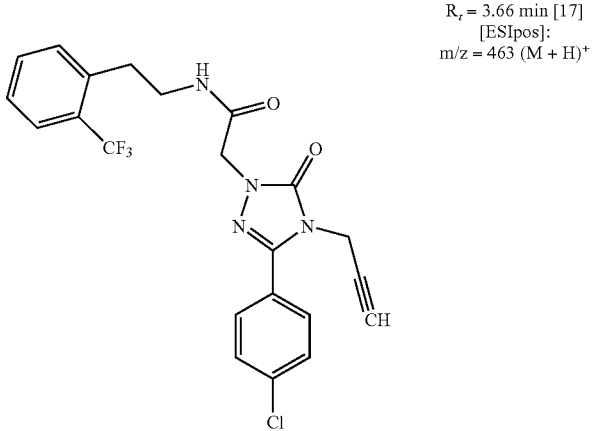 | LC/MS: $R_t$ = 3.66 min [17] [ESIpos]: m/z = 463 (M + H)$^+$ |

-continued

| Example No. | Structure | LC/MS or HPLC, MS $R_t$ [Method] |
|---|---|---|
| 422 | 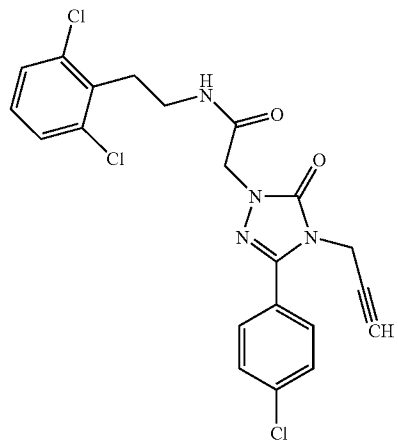 | LC/MS: $R_t$ = 3.67 min [17] [ESIpos]: m/z = 463/465 (M + H)⁺ |

Example 423

2-[3-(4-chlorophenyl)-4-(2-methylprop-2-en-1-yl)-5-oxo-4,5-dihydro-1H-1,2,4-triazol-1-yl]-N-1-methyl-1-[3-(trifluoromethyl)phenyl]ethyl-acetamide

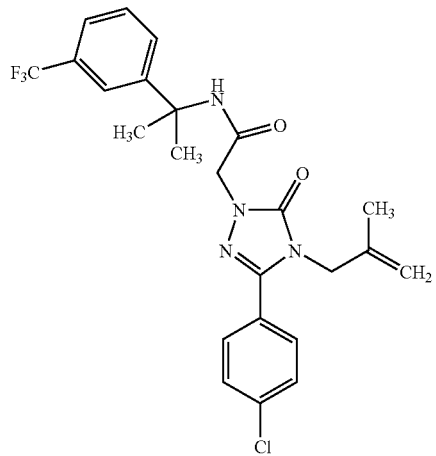

75 mg (0.17 mmol) of 2-[3-(4-chlorophenyl)-5-oxo-4,5-dihydro-1H-1,2,4-triazol-1-yl]-N-{1-methyl-1-[3-(trifluoromethyl)phenyl]ethyl}-acetamide from Example 241A are suspended in a mixture of 2.5 ml of acetone and 0.5 ml of DMF with 84 mg (0.26 mmol) of caesium carbonate and treated with 185 mg (1.12 mmol) of 1-bromo-2-fluoro-2-methylpropane. This is stirred for 18 hrs at 50° C. The suspension is then treated with 1 ml of water and extracted three times with ethyl acetate. The combined organic phases are dried over sodium sulphate and filtered. After evaporation, the crude product is purified by preparative HPLC [Method 10]. 37.3 mg (44% of theory) of the target compound are obtained.

LC/MS [Method 7]: $R_t$=2.56 min; MS [ESIpos]: m/z=493 (M+H)⁺

¹H-NMR (400 MHz, DMSO-d₆): δ=1.60 (s, 6H), 1.62 (s, 3H), 3.60 (s, 3H), 4.27 (s, 2H), 4.46 (s, 1H), 4.52 (s, 2H), 4.80 (s, 1H), 7.48-7.70 (m, 8H), 8.54 (s, 1H).

The following compound is prepared analogously:

| Example No. | Structure | LC/MS or HPLC, MS $R_t$ [Method] |
|---|---|---|
| 424 | 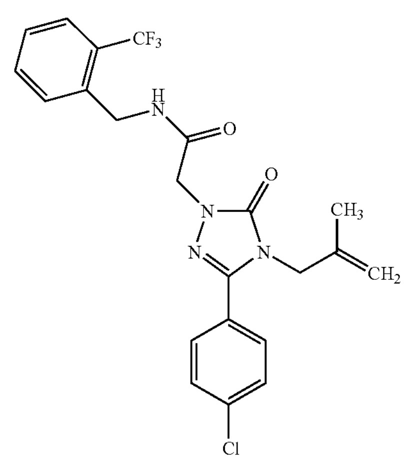 | LC/MS: $R_t$ = 3.77 min [17] [ESIpos]: m/z = 465 (M + H)⁺ |

Example 425

Ethyl(2)-3-3-(4-chlorophenyl)-1-[2-(1-methyl-1-[3-(trifluoromethyl)phenyl]ethylamino)-2-oxo-ethyl]-5-oxo-1,5-dihydro-4H-1,2,4-triazol-4-yl-acrylate

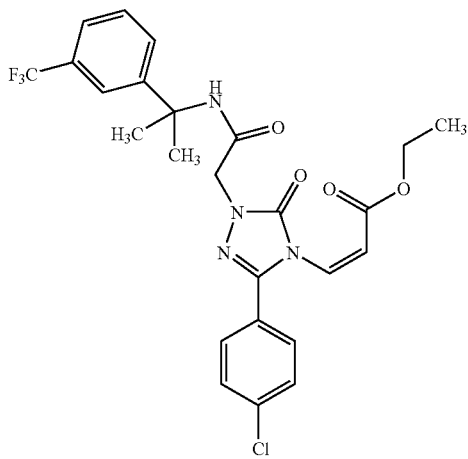

and

Example 426

Ethyl(2E)-3-3-(4-chlorophenyl)-1-[2-(1-methyl-1-[3-(trifluoromethyl)phenyl]ethylamino)-2-oxo-ethyl]-5-oxo-1,5-dihydro-4H-1,2,4-triazol-4-yl-acrylate

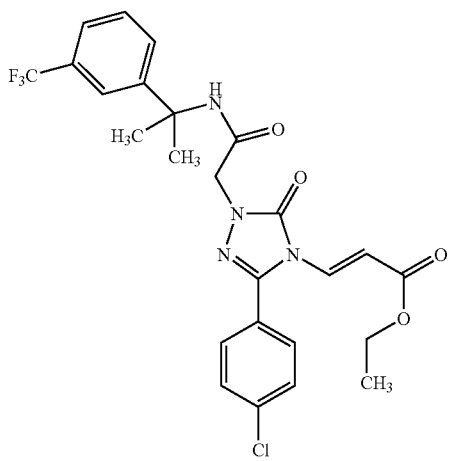

75 mg (0.17 mmol) of 2-[3-(4-chlorophenyl)-5-oxo-4,5-dihydro-1H-1,2,4-triazol-1-yl]-N-{1-methyl-1-[3-(trifluoromethyl)phenyl]ethyl}-acetamide from Example 241A are suspended in 2.5 ml of acetone with 84 mg (0.26 mmol) of caesium carbonate and treated with 40 mg (0.22 mmol) of ethyl cis-3-bromoacrylate. This is stirred for 18 hrs at 50° C. The suspension is then treated with 1 ml of water and extracted three times with ethyl acetate. The combined organic phases are dried over sodium sulphate and filtered. After evaporation, the crude product is purified by preparative HPLC [Method 10]. The Z- and the E-Isomer of the title compound are obtained in separated form.

Z-Isomer

Example 425

Yield: 32.1 mg (35% of theory)
LC/MS [Method 8]: $R_t$=2.79 min; MS [ESIpos]: m/z=537 (M+H)$^+$
$^1$H-NMR (400 MHz, DMSO-d$_6$): δ=1.01 (t, 3H), 1.60 (s, 6H), 3.90 (q, 2H), 4.50 (s, 2H), 6.09 (d, 1H), 6.90 (d, 1H), 7.48-7.70 (m, 8H), 8.56 (s, 1H).

E-Isomer

Example 426

Yield: 43.4 mg (49% of theory)
LC/MS [Method 8]: $R_t$=2.91 min; MS [ESIpos]: m/z=537 (M+H)$^+$
$^1$H-NMR (400 MHz, DMSO-d$_6$): δ=1.20 (t, 3H), 1.60 (s, 6H), 4.14 (q, 2H), 4.52 (s, 2H), 6.72 (d, 1H), 7.41 (d, 1H), 7.48-7.70 (m, 8H), 8.60 (s, 1H).

Example 427

Methyl 4-(3-(4-chlorophenyl)-1-[2-(1-methyl-1-[3-(trifluoromethyl)phenyl]ethylamino)-2-oxoethyl]-5-oxo-1,5-dihydro-4H-1,2,4-triazol-4-ylmethyl)-benzoate

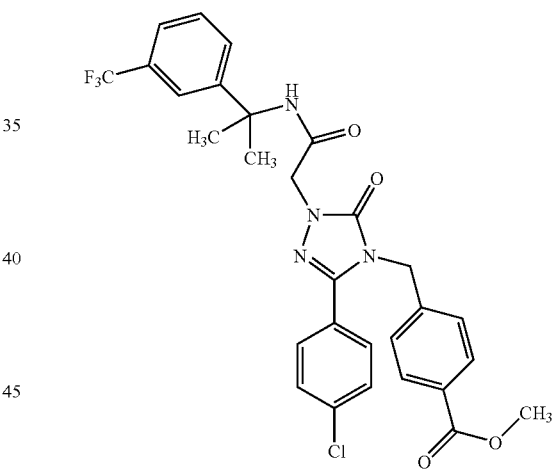

100 mg (0.23 mmol) of 2-[3-(4-chlorophenyl)-5-oxo-4,5-dihydro-1H-1,2,4-triazol-1-yl]-N-{-methyl-1-[3-(trifluoromethyl)phenyl]ethyl}-acetamide from Example 241A are suspended in 2.5 ml of acetone with 111 mg (0.34 mmol) of caesium carbonate and 34 mg (0.23 mmol) of sodium iodide and treated with 55 mg (0.30 mmol) of methyl 4-(chloromethyl)-benzoate. This is stirred for 4 hrs at 50° C. The suspension is then treated with 1.5 ml of water and extracted four times with 2 ml of ethyl acetate each time. The combined organic phases are dried over sodium sulphate and filtered. After evaporation, the crude product is purified by preparative HPLC [Method 10]. 56.6 mg (42% of theory) of the target compound are thus obtained.
LC/MS [Method 19]: $R_t$=3.84 min; MS [ESIpos]: m/z=587 (M+H)$^+$
$^1$H-NMR (400 MHz, DMSO-d$_6$): δ=1.60 (s, 6H), 3.81 (s, 3H), 4.54 (s, 2H), 5.07 (s, 2H), 7.21 (d, 2H), 7.43-7.71 (m, 8H), 7.86 (d, 2H), 8.60 (s, 1H).

The following compounds are prepared analogously:
| Example No. | Structure | LC/MS or HPLC, MS $R_t$ [Method] |
|---|---|---|
| 428 | 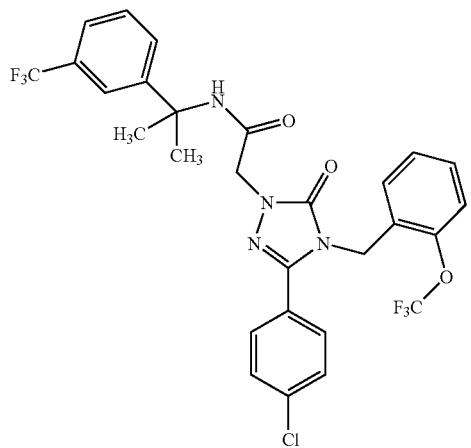 | LC/MS: $R_t$ = 4.14 min [19] [ESIpos]: m/z = 613 (M + H)$^+$ |
| 429 | 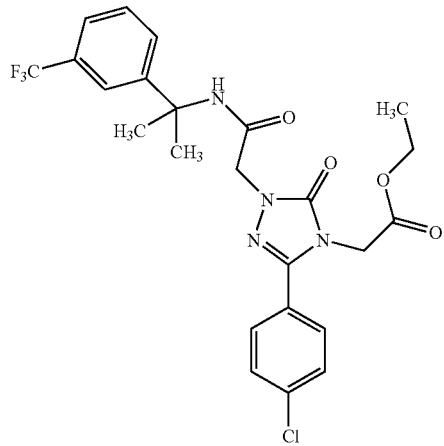 | LC/MS: $R_t$ = 3.72 min [19] [ESIpos]: m/z = 525 (M + H)$^+$ |

Example 430

2-[4-(4-tert.-butylbenzyl)-3-(4-chlorophenyl)-5-oxo-4,5-dihydro-1H-1,2,4-triazol-1-yl]-N-1-methyl-1-[3-(trifluoromethyl)phenyl]ethyl-acetamide

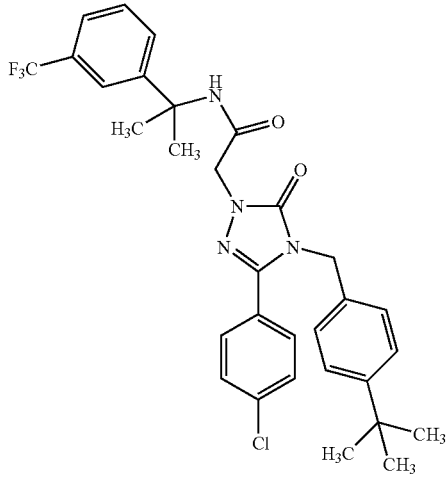

75 mg (0.17 mmol) of 2-[3-(4-chlorophenyl)-5-oxo-4,5-dihydro-1H-1,2,4-triazol-1-yl]-N-{1-methyl-1-[3-(trifluoromethyl)phenyl]ethyl}-acetamide from Example 241A are suspended in 2.5 ml of DMF with 84 mg (0.26 mmol) of caesium carbonate and 25 mg (0.17 mmol) of sodium iodide and treated with 50 mg (0.22 mmol) of 1-(bromomethyl)-4-tert.-butylbenzene. This is stirred for 1 hr at RT. After filtration through a Millipore filter, the suspension is directly purified by preparative HPLC [Method 9]. 44 mg (44% of theory) of the target compound are thus obtained.

LC/MS [Method 7]: $R_t$=3.09 min; MS [ESIpos]: m/z=585 (M+H)$^+$ $^1$H-NMR (400 MHz, DMSO-d$_6$): δ=1.21 (s, 9H), 1.60 (s, 6H), 4.52 (s, 2H), 4.94 (s, 2H), 6.99 (d, 2H), 7.29 (d, 2H), 7.50-7.70 (m, 8H), 8.59 (s, 1H).

The following compounds are prepared analogously:

| Example No. | Structure | LC/MS or HPLC, MS $R_t$ [Method] |
|---|---|---|
| 431 | 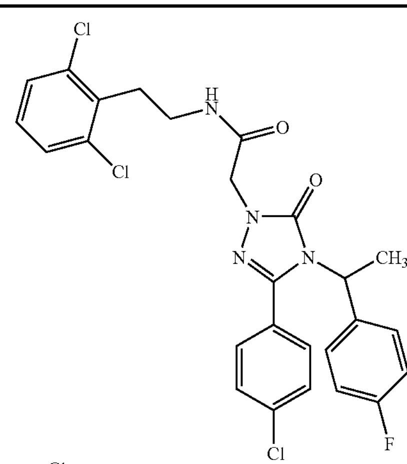 | LC/MS: $R_t$ = 3.97 min [19] [ESIpos]: m/z = 547/549 (M + H)$^+$ |
| 432 | 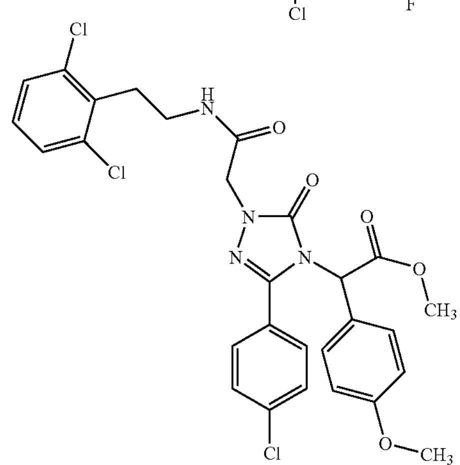 | LC/MS: $R_t$ = 3.97 min [17] [ESIpos]: m/z = 603/605 (M + H)$^+$ |

Example 433

2-[3-(4-chlorophenyl)-4-(3-fluorobenzyl)-5-oxo-4,5-dihydro-1H-1,2,4-triazol-1-yl]-N-1-methyl-1-[3-(trifluoromethyl)phenyl]ethyl-acetamide

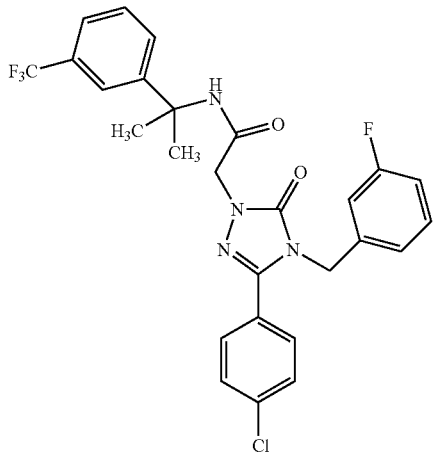

75 mg (0.17 mmol) of 2-[3-(4-chlorophenyl)-5-oxo-4,5-dihydro-1H-1,2,4-triazol-1-yl]-N-{1-methyl-1-[3-(trifluoromethyl)phenyl]ethyl}-acetamide from Example 241A are dissolved in a mixture of 0.6 ml of DMF and 1.1 ml of 1,2-dimethoxyethane (DME). This is cooled to 0° C. and treated with 9 mg (0.22 mmol) of sodium hydride. After 10 mins, 45 mg (0.51 mmol) of lithium bromide are added, and the mixture is then stirred for 15 mins at RT. Next, 42 mg (0.22 mmol) of 3-fluorobenzyl bromide, dissolved in 0.3 ml DME, are added, and the mixture is stirred for 5 hrs at 75° C. The reaction mixture is then diluted with ethyl acetate, filtered through a silica gel/Extrelut cartridge, then washed with ethyl acetate and concentrated in vacuo. The crude product is taken up in acetonitrile and purified by preparative HPLC [Method 10]. 68 mg (72% of theory) of the target compound are thus obtained.

LC/MS [Method 8]: $R_t$=2.91 min; MS [ESIpos]: m/z=547 (M+H)$^+$ $^1$H-NMR (400 MHz, DMSO-d$_6$): δ=1.60 (s, 6H), 4.54 (s, 2H), 4.99 (s, 2H), 6.85-6.95 (m, 2H), 7.02-7.11 (m, 1H), 7.28-7.36 (m, 1H), 7.45-7.72 (m, 8H), 8.60 (s, 1H).

The following compounds are prepared analogously:

| Example No. | Structure | LC/MS or HPLC, MS $R_t$ [Method] |
|---|---|---|
| 434 | 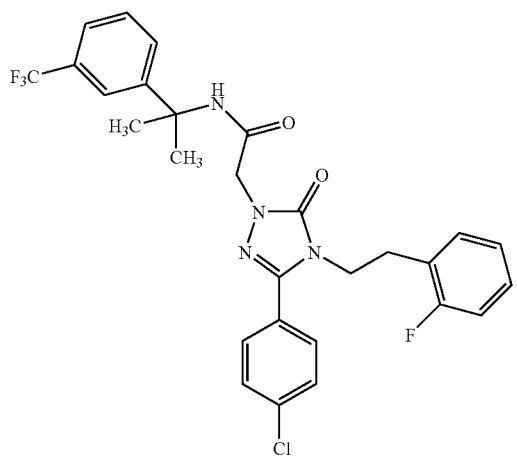 | LC/MS: $R_t$ = 4.15 min [17] [ESIpos]: m/z = 561 (M + H)$^+$ |

-continued

| Example No. | Structure | LC/MS or HPLC, MS R_t [Method] |
|---|---|---|
| 435 | 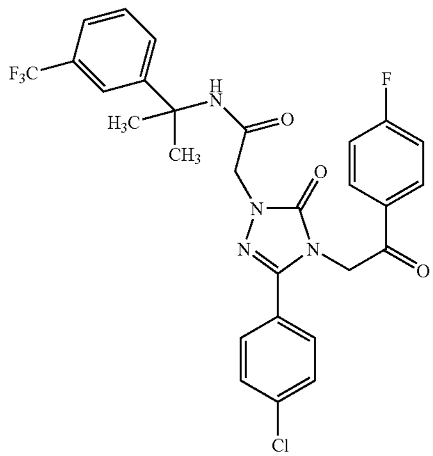 | LC/MS: $R_t = 3.90$ min [19] [ESIpos]: m/z = 575 (M + H)$^+$ |
| 436 | 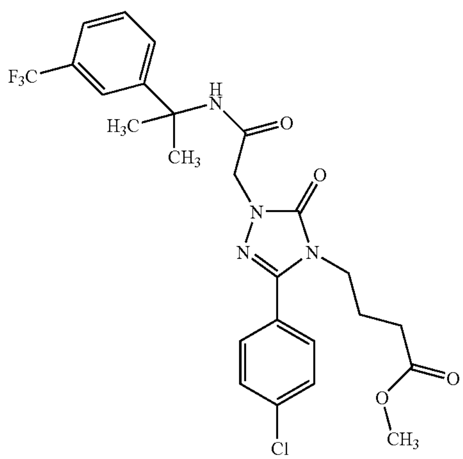 | LC/MS: $R_t = 2.66$ min [8] [ESIpos]: m/z = 539 (M + H)$^+$ |
| 437 | 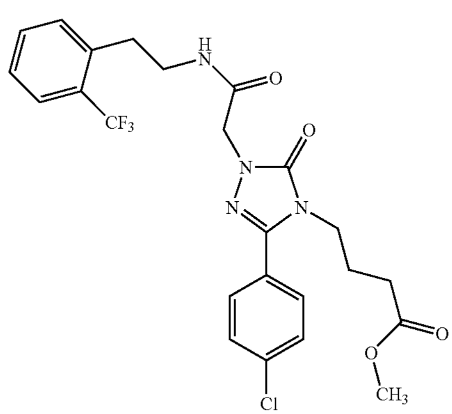 | LC/MS: $R_t = 3.65$ min [17] [ESIpos]: m/z = 525 (M + H)$^+$ |

| Example No. | Structure | LC/MS or HPLC, MS R_t [Method] |
|---|---|---|
| 438 | 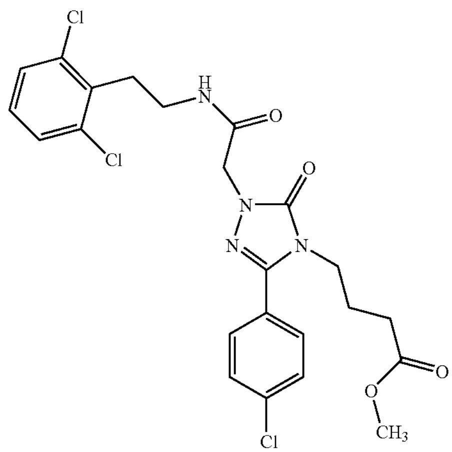 | LC/MS: R_t = 3.66 min [17] [ESIpos]: m/z = 525/527 (M + H)+ |
| 439 | 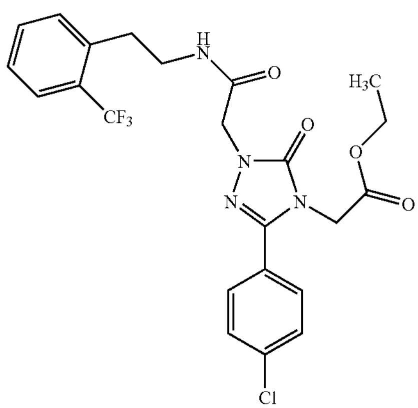 | LC/MS: R_t = 2.63 min [8] [ESIpos]: m/z = 511 (M + H)+ |
| 440 | 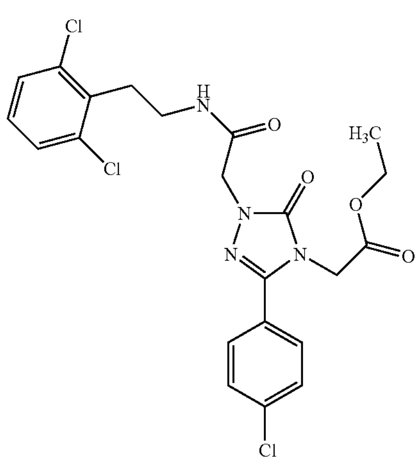 | LC/MS: R_t = 2.65 min [8] [ESIpos]: m/z = 511/513 (M + H)+ |

Example 441

2-[4-(2-chloroethyl)-3-(4-chlorophenyl)-5-oxo-4,5-dihydro-1H-1,2,4-triazol-1-yl]-N-[2-(trifluoromethyl)benzyl]-acetamide

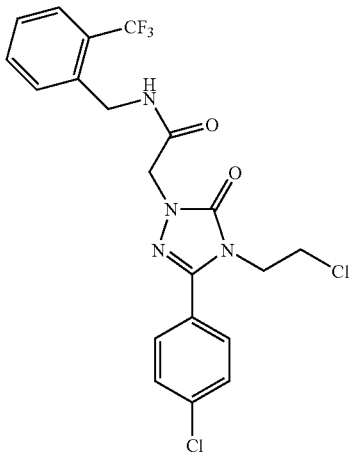

500 mg (1.01 mmol) of 2-[3-(4-chlorophenyl)-5-oxo-4,5-dihydro-1H-1,2,4-triazol-1-yl]-N-[2-(trifluoromethyl)benzyl]-acetamide from Example 243A are dissolved in 10 ml of toluene with 230 mg (1.01 mmol) of benzyltriethylammonium chloride. Next, a solution of 658 mg (2.02 mmol) of caesium carbonate, dissolved in 1.0 ml water, is added, and the mixture vigorously stirred at RT for 30 mins. After addition of 1.92 g (10.13 mmol) of 1-iodo-2-chloroethane, the mixture is heated for 7 hrs at 80° C. with vigorous stirring. The suspension is then diluted with ethyl acetate and washed once each with water, 10% sodium thiosulphate and saturated ammonium chloride solution. The organic phase is dried over sodium sulphate, filtered and concentrated in vacuo. The crude product is purified by preparative HPLC [Method 9]. 195 mg (41% of theory) of the target compound are thus obtained.

LC/MS [Method 7]: $R_t$=2.31 min; MS [ESIpos]: m/z=473/475 (M+H)$^+$ $^1$H-NMR (400 MHz, DMSO-d$_6$): δ=3.79 (t, 2H), 4.10 (t, 3H), 4.50 (d, 2H), 4.56 (d, 2H), 4.99 (s, 2H), 6.85-6.95 (m, 2H), 7.50 (t, 1H), 7.52-7.73 (m, 7H), 8.70 (t, 1H).

The following compound is prepared analogously:

| Example No. | Structure | LC/MS or HPLC, MS $R_t$ [Method] |
|---|---|---|
| 442 | 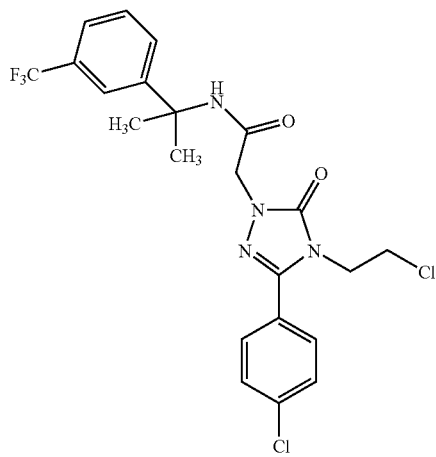 | LC/MS: $R_t$ = 2.64 min [8] [ESIpos]: m/z = 501/503 (M + H)$^+$ |

Example 443

2-[3-(4-chlorophenyl)-5-oxo-4-(2-oxobutyl)-4,5-dihydro-1H-1,2,4-triazol-1-yl]-N-1-methyl-1-[3-(trifluoromethyl)phenyl]ethyl-acetamide

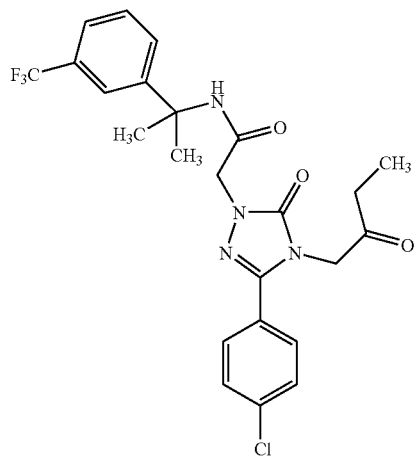

94 mg (0.21 mmol) of 2-[3-(4-chlorophenyl)-5-oxo-4,5-dihydro-1H-1,2,4-triazol-1-yl]-N-{1-methyl-1-[3-(trifluoromethyl)phenyl]ethyl}-acetamide from Example 241A are suspended in 2.5 ml DMF with 97.7 mg (0.30 mmol) of caesium carbonate and treated with 50 mg (0.30 mmol) of 1-bromo-2-butanone (90%). This is stirred for 3 hrs at 75° C. The suspension is then diluted with 10 ml ethyl acetate and washed twice with 5 ml of water each time and once with 5 ml of saturated sodium chloride solution. The organic phase is dried over sodium sulphate and filtered. After concentration, the crude product is purified by preparative thin layer chromatography on silica gel (eluent: dichloromethane/methanol 10:1). 64.8 mg (59% of theory) of the target compound are thus obtained.

LC/MS [Method 19]: $R_t$=3.66 min; MS [ESIpos]: m/z=509 (M+H)$^+$ $^1$H-NMR (400 MHz, DMSO-d$_6$): δ=0.88 (t, 3H), 1.60 (s, 6H), 2.50 (q, 2H), 4.49 (s, 2H), 4.77 (s, 2H), 6.59-6.64 (m, 2H), 6.75-6.80 (m, 1H), 7.18 (t, 1H), 7.46-7.72 (m, 8H), 8.55 (s, 1H).

Example 444

2-[3-(4-chlorophenyl)-5-oxo-4-(3,3,3-trifluoro-2-hydroxypropyl)-4,5-dihydro-1H-1,2,4-triazol-1-yl]-N-[2-(trifluoromethyl)benzyl]-acetamide

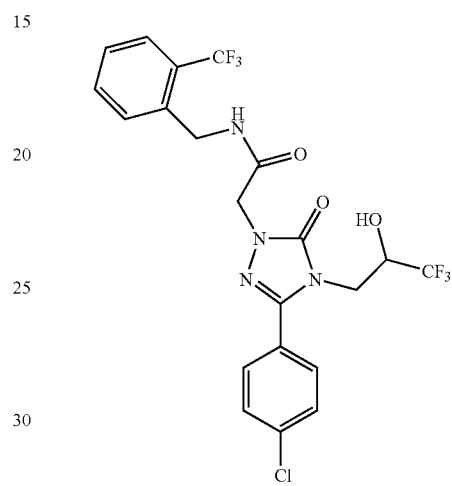

100 mg (0.24 mmol) of 2-[3-(4-chlorophenyl)-5-oxo-4,5-dihydro-1H-1,2,4-triazol-1-yl]-N-[2-(trifluoromethyl)benzyl]-acetamide from Example 243A are placed with 119 mg (0.37 mmol) of caesium carbonate in 0.6 ml of DMSO and treated with 137 mg (1.22 mmol) of 1,1,1-trifluoro-2,3-epoxypropane. This is stirred for 3 hrs at 120° C. Next, 137 mg (1.22 mmol) of 1,1,1-trifluoro-2,3-epoxypropane are again added and the mixture stirred for a further hour at 120° C. The suspension is then cooled to RT, diluted with ethyl acetate and washed three times with saturated ammonium chloride solution. The organic phase is dried over sodium sulphate, filtered and concentrated in vacuo. The crude product is purified by preparative HPLC [Method 10]. 30.6 mg (24% of theory) of the target compound are thus obtained.

LC/MS [Method 17]: $R_t$=3.69 min; MS [ESIpos]: m/z=523 (M+H)$^+$ $^1$H-NMR (400 MHz, DMSO-d$_6$): δ=3.83 (dd, 1H), 3.98 (dd, 1H), 4.30 (m, 1H), 4.47-4.60 (m, 4H), 6.90 (d, 1H), 7.46-7.81 (m, 8H), 8.70 (t, 1H).

The following compounds are prepared analogously:

| Example No. | Structure | LC/MS or HPLC, MS $R_t$ [Method] |
|---|---|---|
| 445 | 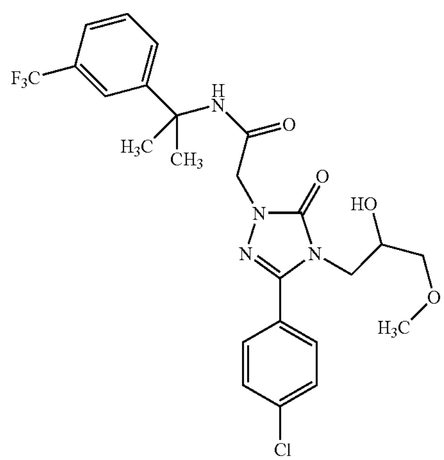 | LC/MS: $R_t$ = 3.54 min [17] [ESIpos]: m/z = 527 (M + H)⁺ |
| 446 | 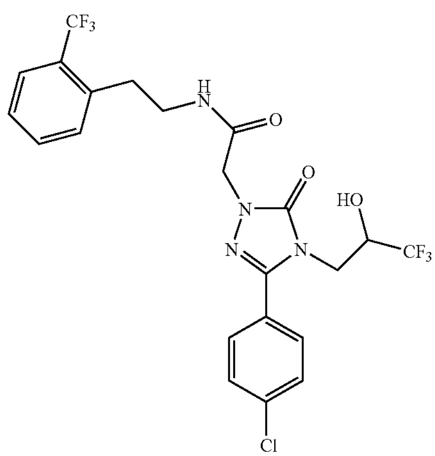 | LC/MS: $R_t$ = 3.78 min [17] [ESIpos]: m/z = 537 (M + H)⁺ |
| 447 | 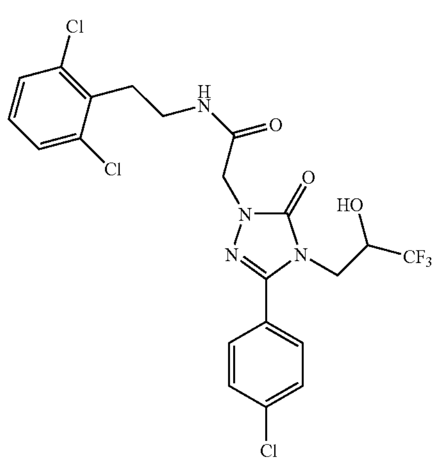 | LC/MS: $R_t$ = 2.67 min [8] [ESIpos]: m/z = 537/539 (M + H)⁺ |

By preparative HPLC on chiral phase [Daicel Chiralcel OD-H, 5 µm, 250 mm×20 mm; Eluent: isohexane/isopropanol 3:1; Flow rate: 15 mL/min; Temperature: 30° C.; UV detection: 220 nm] the racemate from Example 447 is separated into the enantiomers (see Examples 448 and 449). The specific rotation $α_D$ for the enantiomers is determined as follows [Perkin-Elmer Polarimeter 341; wavelength: 589 nm; solvent: methanol; layer thickness: 100 mm]:

| Example No. | Structure | Rotation α_D |
|---|---|---|
| 448 | 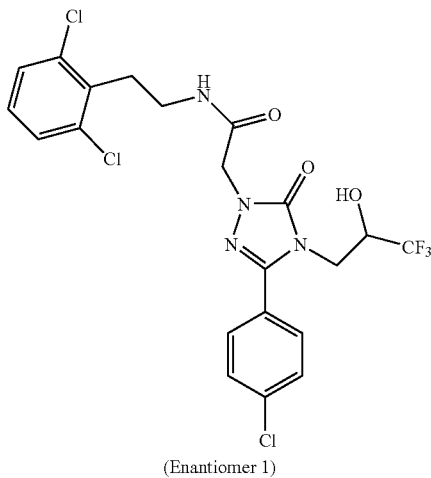<br>(Enantiomer 1) | −8.0°<br>(c = 0.16 mg/100 ml;<br>20.5° C.) |
| 449 | 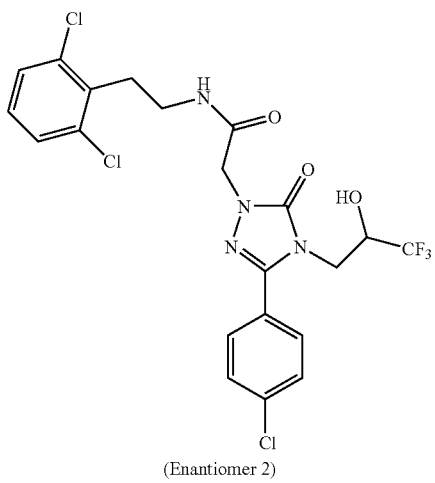<br>(Enantiomer 2) | +6.1°<br>(c = 0.315 mg/100 ml;<br>20.3° C.) |

Example 450

2-[3-(4-chlorophenyl)-5-oxo-4-(3,3,3-trifluoro-2-hydroxypropyl)-4,5-dihydro-1H-1,2,4-triazol-1-yl]-N-{1-methyl-1-[3-(trifluoromethyl)phenyl]ethyl}-acetamide (Racemate)

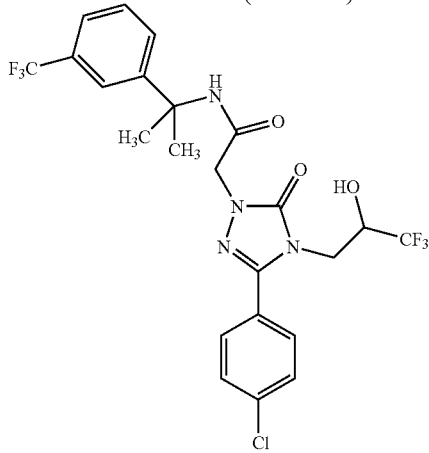

3.61 g (8.23 mmol) of 2-[3-(4-chlorophenyl)-5-oxo-4,5-dihydro-1H-1,2,4-triazol-1-yl]-N-{1-methyl-1-[3-(trifluoromethyl)phenyl]ethyl}-acetamide from Example 241A are dissolved in 20 ml of DMF with 3.75 g (11.52 mmol) of caesium carbonate and treated with 2.22 g (11.52 mmol) of 1,1,1-trifluoro-2,3-epoxypropane. This is stirred for 2.5 hrs at 75° C. The suspension is then diluted with 30 ml of ethyl acetate and washed twice with 20 ml water each time. The organic phase is dried over sodium sulphate and filtered. After concentration, the crude product is purified by flash chromatography on silica gel (eluent: cyclohexane/ethyl acetate first 5:1, then 1:1). 3.14 g (69% of theory) of the target compound are thus obtained.

LC/MS [Method 8]: $R_t$=2.75 min; MS [ESIpos]: m/z=551 (M+H)$^+$ $^1$H-NMR (400 MHz, CDCl$_3$): δ=1.72 (s, 6H), 3.99 (dd, 1H), 4.06 (dd, 1H), 4.41-4.58 (m, 3H), 4.85 (m, 1H), 6.45 (s, 1H), 7.40-7.63 (m, 8H).

By preparative HPLC on chiral phase [Daicel Chiralpak AD-H, 5 μm, 250 mm×20 mm; Eluent: isohexane/isopropanol 85:15; Flow rate: 15 mL/min; Temperature: 40° C.; UV detection: 220 nm], the racemate from Example 450 is separated into the enantiomers (see Examples 451 and 452):

Example 451

2-[3-(4-chlorophenyl)-5-oxo-4-(3,3,3-trifluoro-2-hydroxypropyl)-4,5-dihydro-1H-1,2,4-triazol-1-yl]-N-{1-methyl-1-[3-(trifluoromethyl)phenyl]ethyl}-acetamide (Enantiomer 1)

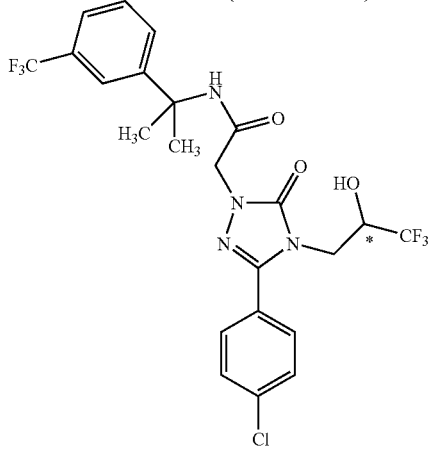

Yield: 1.31 g (29% of theory)

$R_t$=4.02 min [Daicel Chiralpak AD-H, 5 μm, 250 mm×4.6 mm; Eluent: isohexane/isopropanol 85:15; Flow rate: 1.0 ml/min; Temperature: 40° C.; UV detection: 220 nm].

Example 452

2-[3-(4-chlorophenyl)-5-oxo-4-(3,3,3-trifluoro-2-hydroxypropyl)-4,5-dihydro-1H-1,2,4-triazol-1-yl]-N-{1-methyl-1-[3-(trifluoromethyl)phenyl]ethyl}-acetamide (Enantiomer 2)

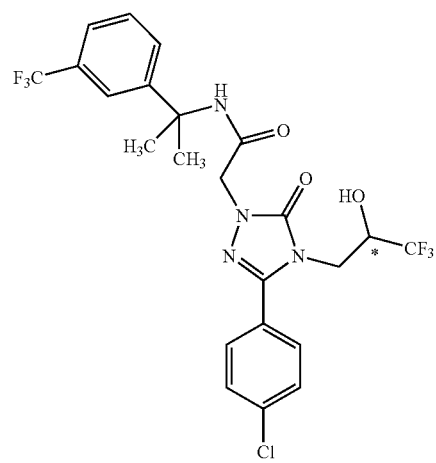

Yield: 1.20 g (26% of theory)

$R_t$=4.71 min [Daicel Chiralpak AD-H, 5 μm, 250 mm×4.6 mm; Eluent: isohexane/isopropanol 85:15; Flow rate: 1.0 ml/min; Temperature: 40° C.; UV detection: 220 nm].

Example 453

2-[3-(4-chlorophenyl)-4-(3-hydroxypropyl)-5-oxo-4,5-dihydro-1H-1,2,4-triazol-1-yl]-N-[3-(trifluoromethyl)benzyl]-acetamide

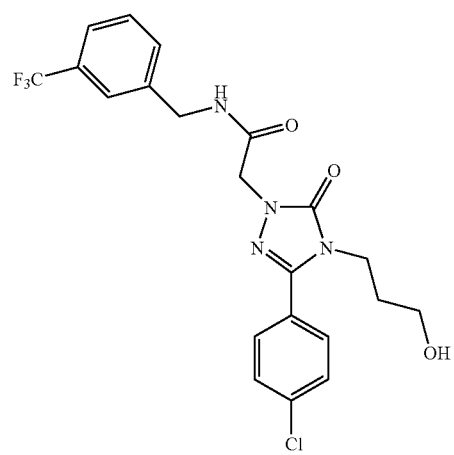

and

Example 454

2-[3-(4-chlorophenyl)-4-(2-hydroxypropyl)-5-oxo-4,5-dihydro-1H-1,2,4-triazol-1-yl]-N-[3-(trifluoromethyl)benzyl]-acetamide

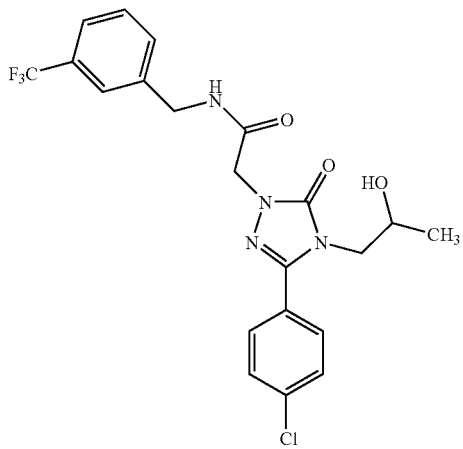

100 mg (0.22 mmol) of 2-[4-allyl-3-(4-chlorophenyl)-5-oxo-4,5-dihydro-1H-1,2,4-triazol-1-yl]-N-[3-(trifluoromethyl)benzyl]-acetamide from Example 372 are dissolved in 5 ml of THF and treated at 0° C. with 0.67 ml of a 1 M solution of borane-THF complex in THF. This is stirred for 18 hrs at RT. The reaction solution is then again cooled to 0° C., and 4.5 ml of a 10% aqueous sodium hydroxide and 4.5 ml of a 30% hydrogen peroxide solution are added. After 3 hrs' stirring, the mixture is poured into 10 ml water and extracted three times with 15 ml ethyl acetate each time. The combined organic phases are washed with 5 ml of 10% sodium thiosulphate solution and 5 ml of saturated sodium chloride solution, dried over sodium sulphate, and filtered and concentrated in vacuo. The crude product is purified by preparative HPLC [Method 10]. The two isomeric alcohols are obtained in separated form.

Example 453

Yield: 20 mg (19% of theory)

LC/MS [Method 18]: $R_t$=2.18 min; MS [ESIpos]: m/z=469 (M+H)$^+$ $^1$H-NMR (400 MHz, DMSO-d$_6$): δ=1.68 (quin, 2H), 3.27-3.40 (m, 2H), 3.80 (t, 2H), 4.41 (d, 2H), 4.45-4.56 (m, 3H), 7.52-7.73 (m, 8H), 8.68 (t, 1H).

Example 454

Yield: 13 mg (13% of theory)

LC/MS [Method 18]: $R_t$=2.18 min; MS [ESIpos]: m/z=469 (M+H)$^+$ $^1$H-NMR (400 MHz, DMSO-d$_6$): δ=1.0 (d, 3H), 3.52-3.68 (m, 2H), 3.86 (m, 1H), 4.36-4.56 (m, 4H), 5.04 (d, 1H), 7.51-7.67 (m, 6H), 7.80 (d, 2H), 8.68 (t, 1H).

The following compounds are prepared analogously:

| Example No. | Structure | LC/MS or HPLC, MS $R_t$ [Method] |
|---|---|---|
| 455 | ![structure] | LC/MS: $R_t$ = 2.28 min [8] [ESIpos]: m/z = 469 (M + H)$^+$ |
| 456 | ![structure] | LC/MS: $R_t$ = 2.33 min [8] [ESIpos]: m/z = 469 (M + H)$^+$ |

Example 457

2-{3-(4-chlorophenyl)-5-oxo-4-[(1E)-prop-1-en-1-yl]-4,5-dihydro-1H-1,2,4-triazol-1-yl}-N-[3-(trifluoromethyl)benzyl]-acetamide

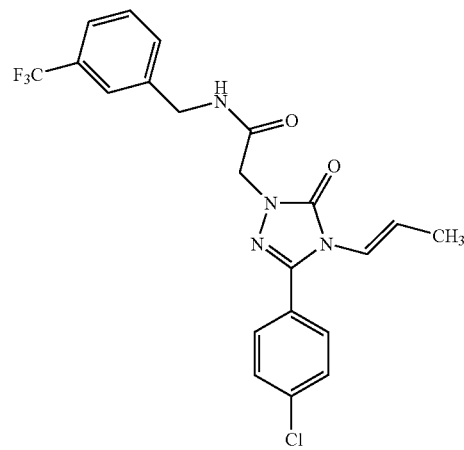

22 mg (0.047 mmol) of 2-[3-(4-chlorophenyl)-4-(2-hydroxypropyl)-5-oxo-4,5-dihydro-1H-1,2,4-triazol-1-yl]-N-[3-(trifluoromethyl)benzyl]-acetamide from Example 454 are dissolved in 1 ml of pyridine and treated at RT with 9.6 mg (0.084 mmol) of methanesulphonyl chloride. This is stirred for 2 hrs at RT. Next, it is diluted with 5 ml ethyl acetate and washed three times with 5 ml of 1 N hydrochloric acid each time. The organic phase is dried over sodium sulphate, filtered and concentrated in vacuo. The residue is dissolved in 1 ml of dry methanol, treated with 20 mg (0.94 mmol) of sodium methanolate, and stirred for 18 hrs at RT. To complete the reaction, a further 81 mg (0.38 mmol) of sodium methanolate are added, and the mixture is further stirred at RT for 48 hrs. The mixture is neutralised with 0.5 ml of 1 N hydrochloric acid and purified directly by preparative HPLC [Method 10]. 4.8 mg (23% of theory) of the target compound are thus obtained.

LC/MS [Method 8]: $R_t$=2.66 min; MS [ESIpos]: m/z=451 (M+H)$^+$ $^1$H-NMR (400 MHz, CDCl$_3$): δ=1.80 (d, 3H), 4.55 (d, 2H), 4.62 (s, 2H), 6.19-6.34 (m, 3H), 6.67 (m, 1H), 7.43-7.59 (m, 8H).

Example 458

2-{3-(4-chlorophenyl)-4-[2-(dimethylamino)ethyl]-5-oxo-4,5-dihydro-1H-1,2,4-triazol-1-yl}-N-{1-methyl-1-[3-(trifluoromethyl)phenyl]ethyl}-acetamide

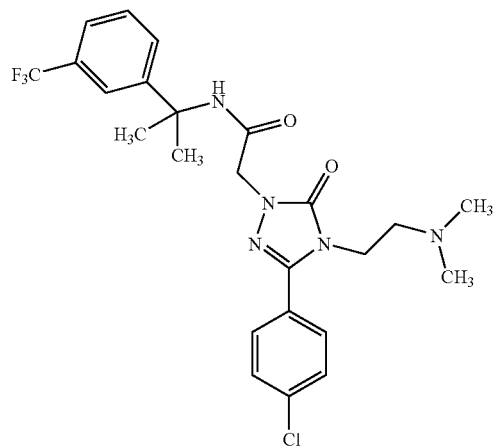

and

Example 459

2-[3-(4-chlorophenyl)-5-oxo-4-vinyl-4,5-dihydro-1H-1,2,4-triazol-1-yl]-N-{1-methyl-1-[3-(trifluoromethyl)phenyl]ethyl}-acetamide

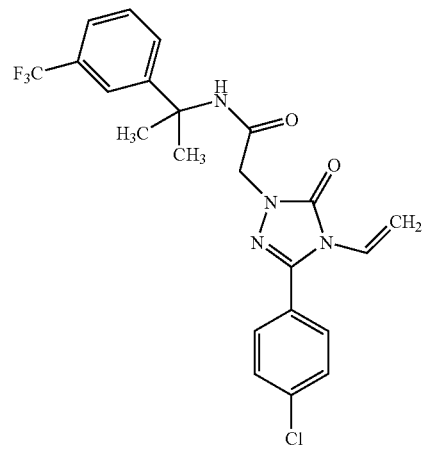

35 mg (0.07 mmol) of 2-[4-(2-chloroethyl)-3-(4-chlorophenyl)-5-oxo-4,5-dihydro-1H-1,2,4-triazol-1-yl]-N-{1-methyl-1-[3-(trifluoromethyl)phenyl]ethyl}-acetamide from Example 442 are dissolved in 0.7 ml of DMF and treated at RT with 127 mg (1.56 mmol) of dimethylamine hydrochloride, 10.5 mg (0.07 mmol) of sodium iodide and 106 mg (0.77 mmol) of potassium carbonate. This is stirred in the closed vessel for 24 hrs at 100° C. After cooling, it is diluted with 5 ml of water and extracted twice with 5 ml of ethyl acetate each time. The combined organic phases are dried over sodium sulphate, filtered and concentrated in vacuo. Purification by flash chromatography on silica gel (eluent: cyclohexane/ethyl acetate 1:1) first yields the 4-vinyl derivative (Example 459). By further elution with dichloromethane/7 N methanolic ammonia solution (10:1), the 4-[2-(dimethylamino)ethyl] derivative (Example 458) is obtained, which is further purified by preparative thick layer chromatography (eluent: dichloromethane/ethyl acetate/7 N methanolic ammonia solution 10:10:0.5).

Example 458

Yield: 7.6 mg (21% of theory)

LC/MS [Method 8]: $R_t$=1.60 min; MS [ESIpos]: m/z=510 (M+H)$^+$ $^1$H-NMR (400 MHz, DMSO-d$_6$): δ=1.60 (s, 6H), 1.98 (s, 6H), 2.29 (t, 2H), 3.79 (t, 2H), 4.46 (s, 2H), 7.48-7.70 (m, 8H), 8.54 (s, 1H).

Example 459

Yield: 6.8 mg (21% of theory)

LC/MS [Method 8]: $R_t$=2.62 min; MS [ESIpos]: m/z=465 (M+H)$^+$ $^1$H-NMR (400 MHz, DMSO-d$_6$): δ=1.60 (s, 6H), 4.50 (s, 2H), 5.10 (d, 1H), 5.74 (d, 1H), 6.61 (dd, 1H), 7.49-7.70 (m, 8H), 8.60 (s, 1H).

The following compounds are prepared analogously:
| Example No. | Structure | LC/MS or HPLC, MS $R_t$ [Method] |
|---|---|---|
| 460 | 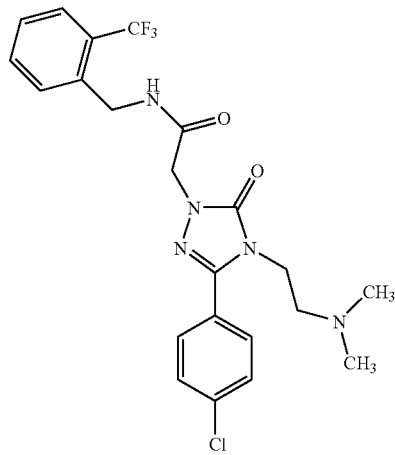 | LC/MS: $R_t$ = 2.14 min [19] [ESIpos]: m/z = 482 (M + H)$^+$ |
| 461 | 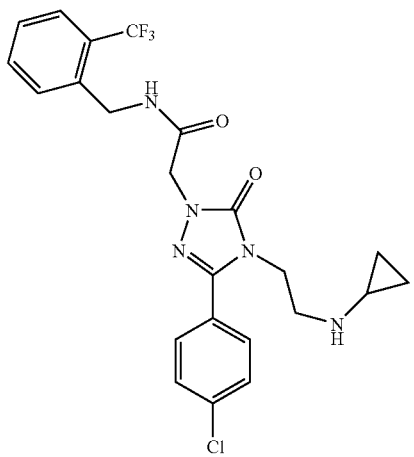 | LC/MS: $R_t$ = 1.59 min [8] [ESIpos]: m/z = 494 (M + H)$^+$ |

Example 462

2-[3-(4-chlorophenyl)-4-(2-morpholin-4-ylethyl)-5-oxo-4,5-dihydro-1H-1,2,4-triazol-1-yl]-N-{1-methyl-1-[3-(trifluoromethyl)phenyl]ethyl}-acetamide

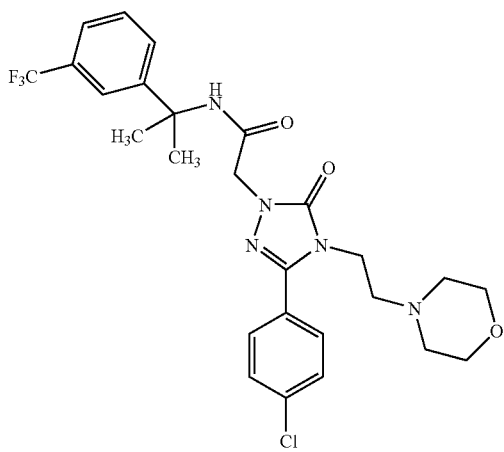

0.10 g (0.21 mmol) of 2-[3-(4-chlorophenyl)-4-(2-oxoethyl)-5-oxo-4,5-dihydro-1H-1,2,4-triazol-1-yl]-N-{1-methyl-1-[3-(trifluoromethyl)phenyl]ethyl}-acetamide from Example 401 are dissolved in 30 ml of dichloromethane and 0.4 ml of DMF and stirred with 22 mg (0.2 mmol) of morpholine for 1 hr at RT. Next, 66 mg (0.31 mmol) of sodium triacetoxyborohydride are added and the mixture is stirred for 18 hrs at RT. The reaction mixture is treated with 10 ml of saturated sodium hydrogen carbonate solution and extracted three times with 10 ml ethyl acetate each time. The combined organic phases are dried over sodium sulphate, filtered and concentrated in vacuo. The crude product is purified by preparative HPLC [Method 10]. 11.0 mg (10% of theory) of the target compound are obtained.

LC/MS [Method 17]: $R_t$=2.78 min; MS [ESIpos]: m/z=552 (M+H)$^+$ $^1$H-NMR (400 MHz, DMSO-d$_6$): δ=1.59 (s, 6H), 2.16 (m, 4H), 2.34 (t, 2H), 3.31 (m, 4H), 3.80 (t, 2H), 4.46 (s, 2H), 7.48-7.72 (m, 8H), 8.54 (s, 1H).

The following compounds are prepared analogously:

| Example No. | Structure | LC/MS or HPLC, MS $R_t$ [Method] |
|---|---|---|
| 463 | 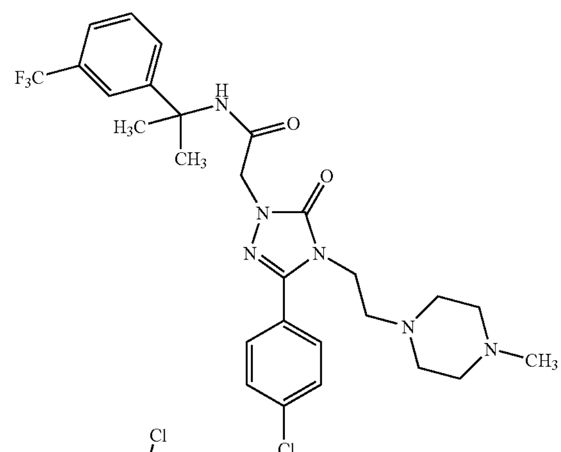 | LC/MS: $R_t$ = 2.65 min [19] [ESIpos]: m/z = 565 (M + H)$^+$ |
| 464 | 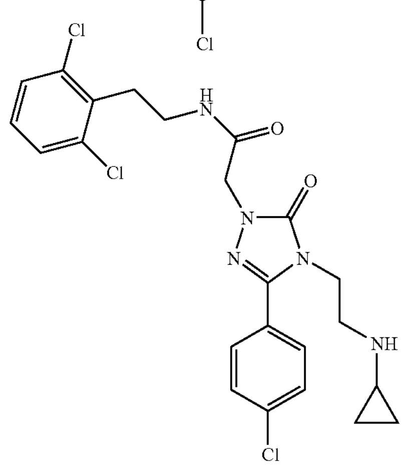 | LC/MS: $R_t$ = 2.43 min [19] [ESIpos]: m/z = 508 (M + H)$^+$ |

| Example No. | Structure | LC/MS or HPLC, MS $R_t$ [Method] |
|---|---|---|
| 465 | 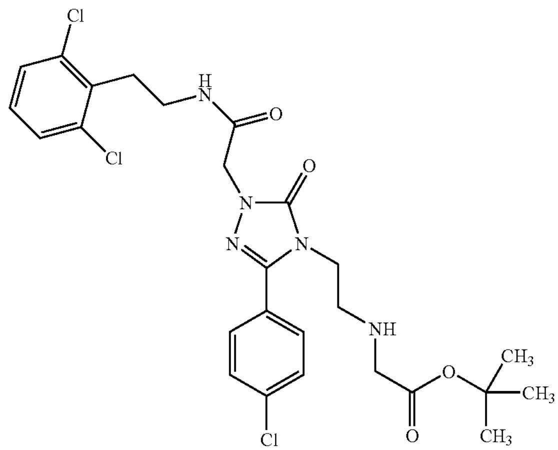 | LC/MS: $R_t$ = 2.79 min [19] [ESIpos]: m/z = 582/584 (M + H)+ |

Example 466

[3-(4-chlorophenyl)-5-oxo-1-(2-oxo-2-[3-(trifluoromethyl)benzyl]aminoethyl)-1,5-dihydro-4H-1,2,4-triazol-4-yl]-acetic acid

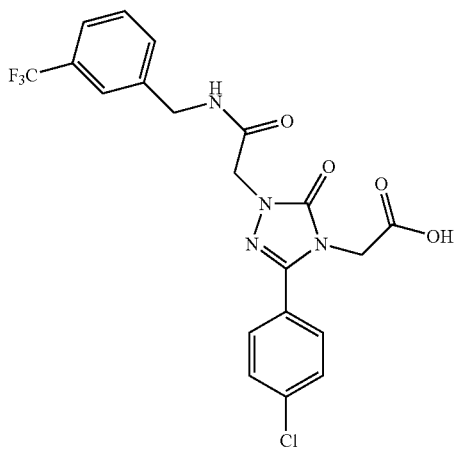

119 mg (0.23 mmol) of tert.-butyl[3-(4-chlorophenyl)-5-oxo-1-(2-oxo-2-{3-(trifluoromethyl)-benzyl]amino}ethyl)-1,5-dihydro-4H-1,2,4-triazol-4-yl]-acetate from Example 420 are dissolved in 9 ml of dichloromethane and treated with 3 ml of trifluoroacetic acid. This is stirred for 24 hrs at RT. The reaction mixture is then treated with 10 ml of toluene and concentrated under reduced pressure. A further 10 ml of toluene are added, and the mixture again evaporated. This procedure is repeated once again. The crude product is then freed of solvent residues under high vacuum. 110 mg (quantitative) of the target compound are thus obtained.

LC/MS [Method 7]: $R_t$=2.00 min; MS [ESIpos]: m/z=469 (M+H)+

$^1$H-NMR (500 MHz, DMSO-$d_6$): δ=4.41 (s, 2H), 4.52 (2s, 4H), 7.52-7.66 (m, 8H), 8.76 (t, 1H), 13.30 (br. s, 1H).

Example 467

3-(4-chlorophenyl)-1-[2-(1-methyl-1-[3-(trifluoromethyl)phenyl]ethylamino)-2-oxoethyl]-5-oxo-1,5-dihydro-4H-1,2,4-triazol-4-yl-acetic acid

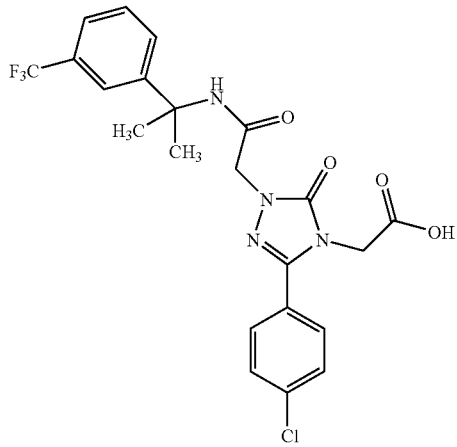

237 mg (0.45 mmol) of ethyl {3-(4-chlorophenyl)-1-[2-({1-methyl-1-[3-(trifluoromethyl)phenyl]-ethyl}amino)-2-oxoethyl]-5-oxo-1,5-dihydro-4H-1,2,4-triazol-4-yl}-acetate from Example 429 are dissolved in 3 ml of methanol and treated with 0.9 ml of 1 N aqueous lithium hydroxide solution. This is stirred for 24 hrs at RT. The reaction mixture is then concentrated under reduced pressure. 5 ml of water are added, and the mixture is acidified with 1 ml of 1 N hydrochloric acid and extracted twice with 10 ml of ethyl acetate each time. The combined organic phases are dried over sodium sulphate, filtered and concentrated in vacuo. The product that remains is freed from solvent residues under high vacuum. 220 mg (97% of theory) of the target compound are thus obtained.

LC/MS [Method 17]: $R_t$=3.49 min; MS [ESIpos]: m/z=497 (M+H)$^+$ $^1$H-NMR (400 MHz, DMSO-d$_6$): δ=1.60 (s, 6H), 4.50 (2s, 4H), 7.48-7.70 (m, 8H), 8.57 (s, 1H), 13.30 (br. s, 1H).

The following compounds are prepared analogously:

| Example No. | Structure | LC/MS or HPLC, MS $R_t$ [Method] |
|---|---|---|
| 468 | 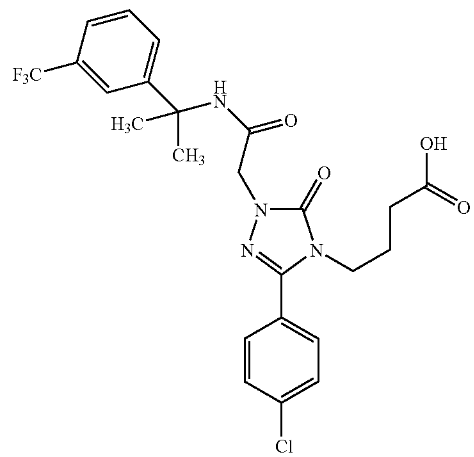 | LC/MS: $R_t$ = 3.35 min [19] [ESIpos]: m/z = 525 (M + H)$^+$ |
| 469 | 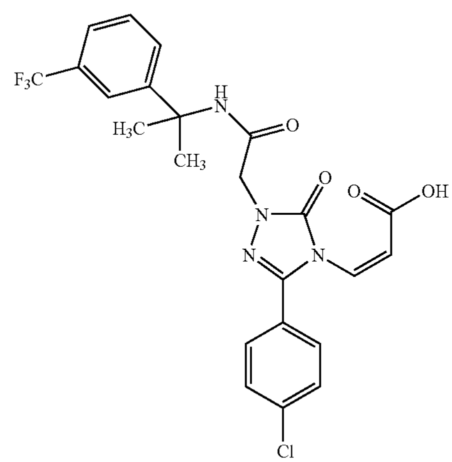 | LC/MS: $R_t$ = 3.53 min [17] [ESIpos]: m/z = 509 (M + H)$^+$ |
| 470 | 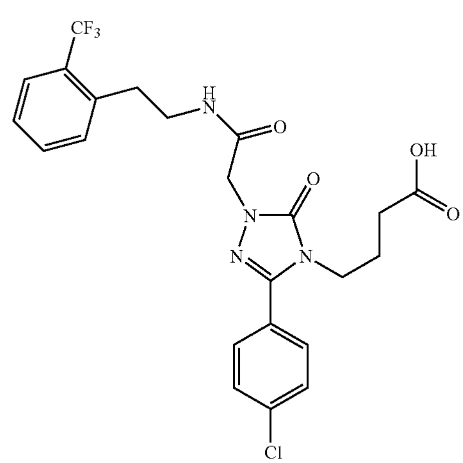 | LC/MS: $R_t$ = 3.37 min [17] [ESIpos]: m/z = 511 (M + H)$^+$ |

Example 471

3-(3-(4-chlorophenyl)-1-[2-(1-methyl-1-[3-(trifluoromethyl)phenyl]ethylamino)-2-oxoethyl]-5-oxo-1,5-dihydro-4H-1,2,4-triazol-4-ylmethyl)-benzoic acid

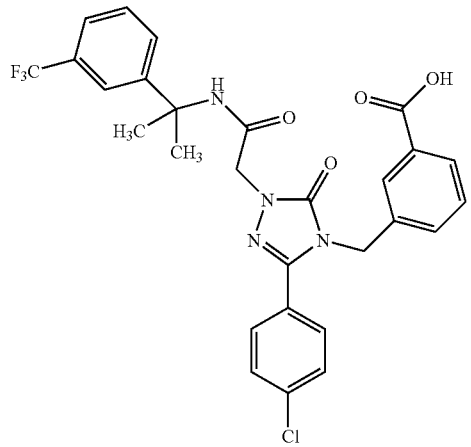

180 mg (0.31 mmol) of methyl 3-(3-(4-chlorophenyl)-1-[2-(1-methyl-1-[3-(trifluoromethyl)phenyl]-ethylamino)-2-oxoethyl]-5-oxo-1,5-dihydro-4H-1,2,4-triazol-4-ylmethyl)-benzoate (Example 411) are dissolved in 3 ml of methanol and 3 ml of THF, treated with 0.3 ml of 2 N aqueous sodium hydroxide and stirred for 1 hr at 70° C. The reaction mixture is then introduced into ca. of 10 ml water, brought to pH 4 with 1 N hydrochloric acid, and stirred for 2 hrs at RT. The resulting precipitate is filtered off at the pump, washed with water and freed of solvent residues under high vacuum. 154 mg (88% of theory) of the target compound are obtained.

LC/MS [Method 17]: $R_t$=3.69 min; MS [ESIpos]: m/z=573 (M+H)$^+$ $^1$H-NMR (400 MHz, DMSO-d$_6$): δ=1.60 (s, 6H), 4.52 (s, 2H), 5.05 (s, 2H), 7.28 (d, 1H), 7.40 (t, 1H), 7.47-7.72 (m, 6H), 7.80 (d, 2H), 8.60 (s, 1H), 13.02 (br. s, 1H).

The following compounds are prepared analogously:

| Example No. | Structure | LC/MS or HPLC, MS $R_t$ [Method] |
|---|---|---|
| 472 | 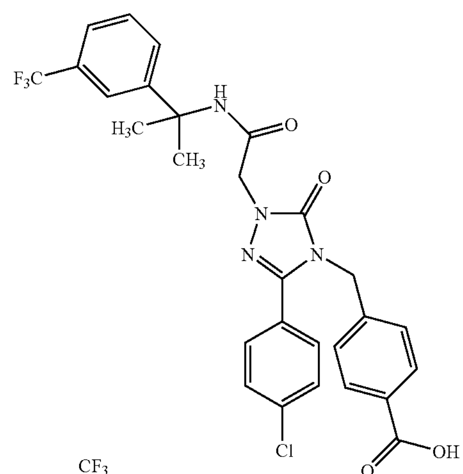 | LC/MS: $R_t$ = 3.68 min [17] [ESIpos]: m/z = 573 (M + H)$^+$ |
| 473 | 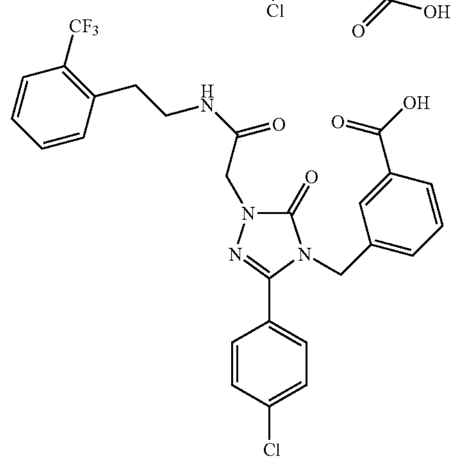 | LC/MS: $R_t$ = 2.51 min [8] [ESIpos]: m/z = 559 (M + H)$^+$ |

| Example No. | Structure | LC/MS or HPLC, MS $R_t$ [Method] |
|---|---|---|
| 474 | 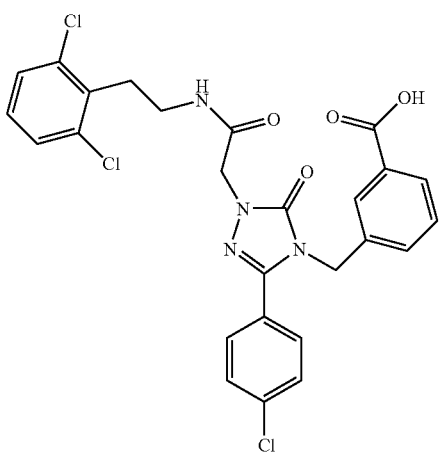 | LC/MS: $R_t$ = 3.58 min [17] [ESIpos]: m/z = 559/561 $(M + H)^+$ |

Example 475

3-(3-(4-chlorophenyl)-1-[2-(1-methyl-1-[3-(trifluoromethyl)phenyl]ethylamino)-2-oxoethyl]-5-oxo-1,5-dihydro-4H-1,2,4-triazol-4-ylmethyl)-N,N-dimethylbenzamide

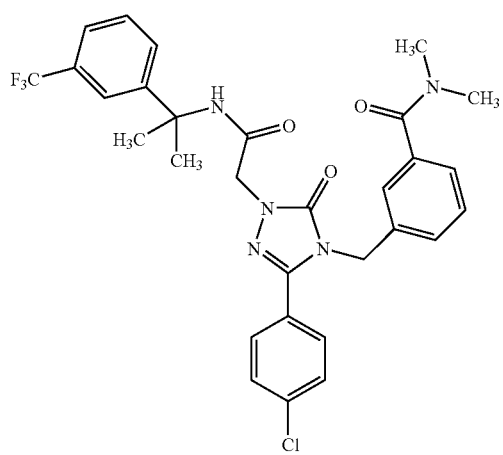

30 mg (0.052 mmol) of 3-(3-(4-chlorophenyl)-1-[2-(1-methyl-1-[3-(trifluoromethyl)phenyl]ethylamino)-2-oxoethyl]-5-oxo-1,5-dihydro-4H-1,2,4-triazol-4-ylmethyl)-benzoic acid (Example 471) are placed in 0.5 ml of DMF and treated with 9.2 mg (0.068 mmol) of HOBt and 13.0 mg (0.068 mmol) of EDC hydrochloride. After 10 mins' stirring, 6.0 mg (0.073 mmol) of dimethylamine hydrochloride and 10.2 mg (0.079 mmol) of N,N-diisopropylethylamine are added and the mixture is stirred overnight at RT. Without further workup, the crude product is purified directly by preparative HPLC [Method 10]. 29.8 mg (95% of theory) of the target compound are thus obtained.

LC/MS [Method 8]: $R_t$=2.59 min; MS [ESIpos]: m/z=600 $(M+H)^+$ $^1$H-NMR (400 MHz, DMSO-$d_6$): δ=1.60 (s, 6H), 2.66 (s, 3H), 2.85 (s, 3H), 4.55 (s, 2H), 5.02 (s, 2H), 7.04 (s, 1H), 7.12 (d, 1H), 7.23 (d, 1H), 7.33 (t, 1H), 7.45-7.75 (m, 8H), 8.60 (s, 1H).

The following compounds are prepared analogously:

| Example No. | Structure | LC/MS or HPLC, MS $R_t$ [Method] |
|---|---|---|
| 476 | 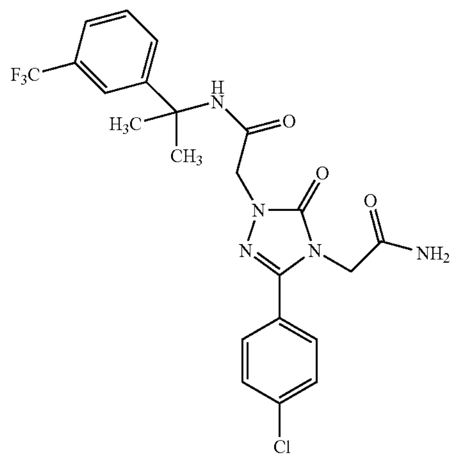 | LC/MS: $R_t$ = 2.31 min [8] [ESIpos]: m/z = 496 (M + H)⁺ |
| 477 | 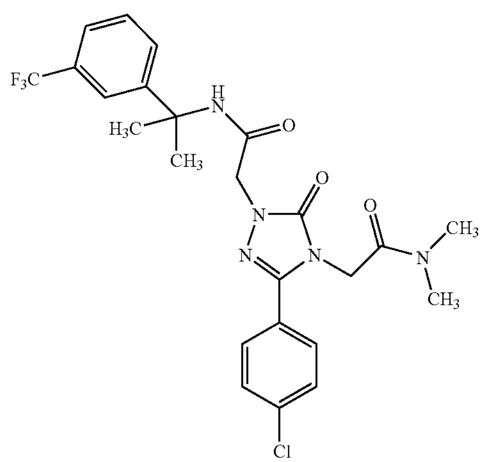 | LC/MS: $R_t$ = 2.47 min [8] [ESIpos]: m/z = 524 (M + H)⁺ |
| 478 | 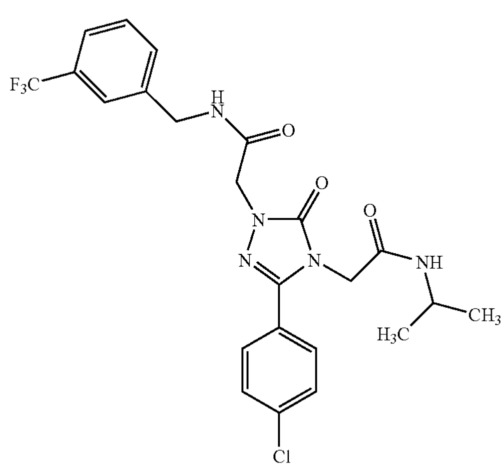 | LC/MS: $R_t$ = 2.44 min [8] [ESIpos]: m/z = 510 (M + H)⁺ |

Example 479

2-{3-(4-chlorophenyl)-4-[3-(hydroxymethyl)benzyl]-5-oxo-4,5-dihydro-1H-1,2,4-triazol-1-yl}-N-{1-methyl-1-[3-(trifluoromethyl)phenyl]ethyl}-acetamide

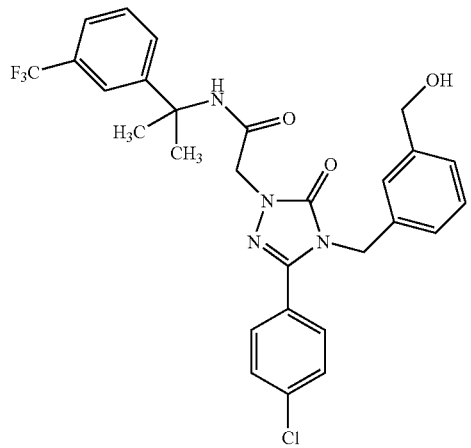

30 mg (0.052 mmol) of 3-(3-(4-chlorophenyl)-1-[2-(1-methyl-1-[3-(trifluoromethyl)phenyl]ethylamino)-2-oxoethyl]-5-oxo-1,5-dihydro-4H-1,2,4-triazol-4-ylmethyl)-benzoic acid (Example 471) are dissolved in 2 ml of THF and treated with 24 mg (0.24 mmol) of triethylamine and 33 mg (0.24 mmol) of isobutyl chloroformate. This is stirred for 1 hr at RT. Next, a solution of 24 mg (0.63 mmol) of sodium borohydride in 0.05 ml water is added slowly. After 1 hr, the mixture is treated with 0.06 ml (1.05 mmol) of acetic acid and then concentrated in vacuo. The residue is taken up in 10 ml of ethyl acetate, and washed with 10 ml of water. The aqueous phase is back-extracted once with 10 ml of ethyl acetate. The combined organic phases are dried over sodium sulphate, filtered and concentrated in vacuo. The crude product is purified by preparative HPLC [Method 10]. 23 mg (79% of theory) of the target compound are thus obtained.

LC/MS [Method 19]: $R_t$=3.53 min; MS [ESIpos]: m/z=559 (M+H)$^+$ $^1$H-NMR (400 MHz, DMSO-d$_6$): δ=1.60 (s, 6H), 4.40 (d, 2H), 4.52 (s, 2H), 4.96 (s, 2H), 5.15 (t, 1H), 6.89 (d, 1H), 7.04 (s, 1H), 7.14-7.26 (m, 2H), 7.47-7.59 (m, 6H), 7.65 (s, 1H), 7.69 (d, 1H), 8.60 (s, 1H).

Example 480

2-[3-(4-chlorophenyl)-4-(2-fluoroethyl)-5-oxo-4,5-dihydro-1H-1,2,4-triazol-1-yl]-N-{1-methyl-1-[3-(trifluoromethyl)phenyl]ethyl}-acetamide

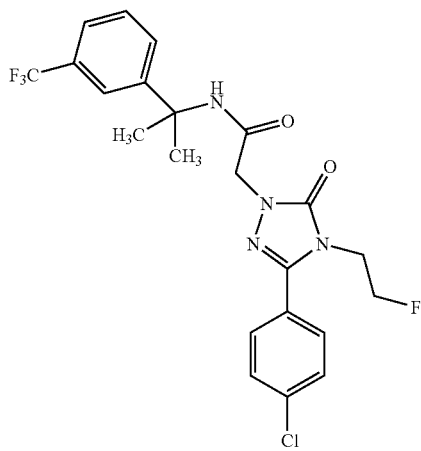

50 mg (0.10 mmol) of 2-[3-(4-chlorophenyl)-4-(2-hydroxyethyl)-5-oxo-4,5-dihydro-1H-1,2,4-triazol-1-yl]-N-{1-methyl-1-[3-(trifluoromethyl)phenyl]ethyl}-acetamide from Example 396 are dissolved in 1.5 ml of dichloromethane and treated at −10° C. with 20.5 µl (0.155 mmol) of diethylaminosulphur trifluoride. This is warmed to RT within 1 hr. Next, the reaction solution is treated with 5 ml of water and extracted twice with 5 ml of ethyl acetate each time. The combined organic phases are dried over sodium sulphate, filtered and concentrated in vacuo. The crude product is purified by preparative HPLC [Method 10]. 37 mg (73% of theory) of the target compound are thus obtained.

LC/MS [Method 8]: $R_t$=2.63 min; MS [ESIpos]: m/z=485 (M+H)$^+$ $^1$H-NMR (400 MHz, DMSO-d$_6$): δ=1.60 (s, 6H), 4.00 (t, 1H), 4.07 (t, 1H), 4.43 (s, 2H), 4.44 (t, 1H), 4.62 (t, 1H), 7.48-7.70 (m, 8H), 8.59 (s, 1H).

The following compound is prepared analogously:

| Example No. | Structure | LC/MS or HPLC, MS R_t [Method] |
|---|---|---|
| 481 | 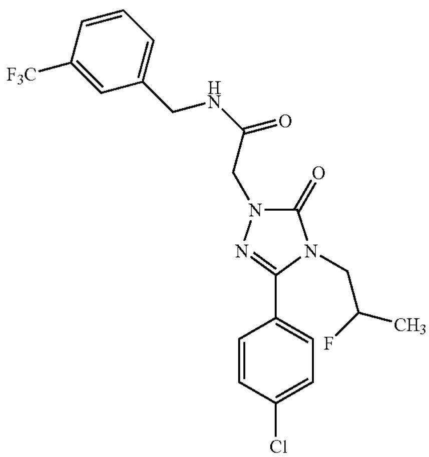 | LC/MS: R_t = 3.68 min [17] [ESIpos]: m/z = 471 (M + H)+ |

Example 482

2-[3-(4-chlorophenyl)-4-(2-fluorobenzyl)-5-oxo-4,5-dihydro-1H-1,2,4-triazol-1-yl]-N-[2-(methylsulphonyl)benzyl]-acetamide

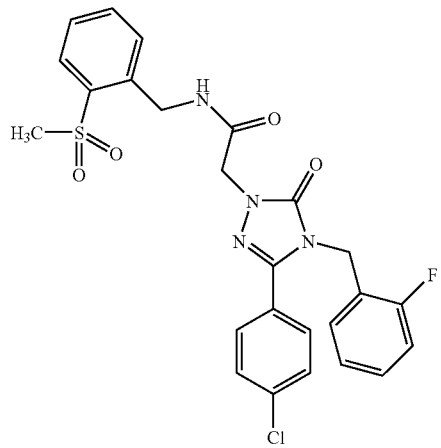

55 mg (0.11 mmol) of 2-[3-(4-chlorophenyl)-4-(2-fluorobenzyl)-5-oxo-4,5-dihydro-1H-1,2,4-triazol-1-yl]-N-[2-(methylthio)benzyl]-acetamide from Example 394 are dissolved in 3 ml of trichloromethane and treated at RT with 82 mg (0.33 mmol) of meta-chloroperbenzoic acid. After 1 hr, the reaction solution is diluted with 10 ml of dichloromethane and washed with 5 ml of saturated sodium hydrogen carbonate solution. The aqueous phase is extracted once with 10 ml of dichloromethane. The combined organic phases are dried over sodium sulphate, filtered and concentrated in vacuo. The crude product is purified by preparative thick layer chromatography (eluent: dichloromethane/methanol 20:1). 18 mg (30% of theory) of the target compound are thus obtained.

LC/MS [Method 23]: R_t=2.08 min; MS [ESIpos]: m/z=529 (M+H)+

$^1$H-NMR (400 MHz, DMSO-d$_6$): δ=3.32 (s, 3H), 4.60 (s, 2H), 4.77 (d, 2H), 5.04 (s, 2H), 7.03-7.20 (m, 3H), 7.25-7.49 (m, 1H), 7.48-7.72 (m, 7H), 7.93 (d, 1H), 8.80 (t, 1H).

Example 483

2-[3-(4-chlorophenyl)-5-oxo-4-(2-hydroxybutyl)-4,5-dihydro-1H-1,2,4-triazol-1-yl]-N-{1-methyl-1-[3-(trifluoromethyl)phenyl]ethyl}-acetamide (Racemate)

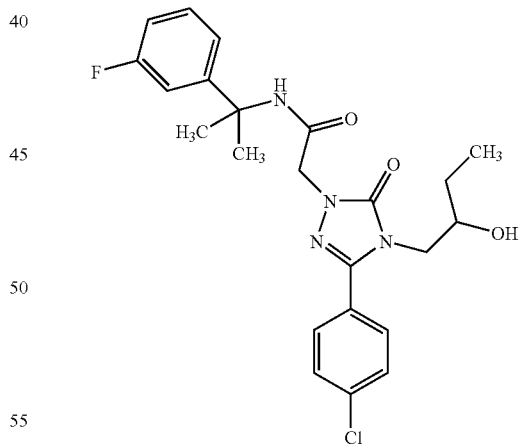

62 mg (0.12 mmol) of 2-[3-(4-chlorophenyl)-5-oxo-4-(2-oxobutyl)-4,5-dihydro-1H-1,2,4-triazol-1-yl]-N-{1-methyl-1-[3-(trifluoromethyl)phenyl]ethyl}-acetamide from Example 443 are dissolved in 2 ml of methanol and treated at RT with 4.7 mg (0.12 mmol) of sodium borohydride. This is stirred for 1 hr at RT. It is then treated with saturated ammonium chloride solution and extracted with 10 ml of ethyl acetate. The organic phase is dried over sodium sulphate, filtered and concentrated. 57 mg (92% of theory) of the target compound are thus obtained.

LC/MS [Method 23]: $R_t$=2.26 min; MS [ESIpos]: m/z=511 (M+H)$^+$.

By preparative HPLC on chiral phase [Sepaserve Sepapak-2, 5 μm, 250 mm×20 mm; Eluent: isohexane/ethanol 70:30; Flow rate: 15 mL/min; Temperature: 35° C.; UV detection: 220 nm] the racemate from Example 483 is separated into the enantiomers (see Examples 484 and 485):

Example 484

2-[3-(4-chlorophenyl)-5-oxo-4-(2-hydroxybutyl)-4,5-dihydro-1H-1,2,4-triazol-1-yl]-N-{1-methyl-1-[3-(trifluoromethyl)phenyl]ethyl}-acetamide (Enantiomer 1)

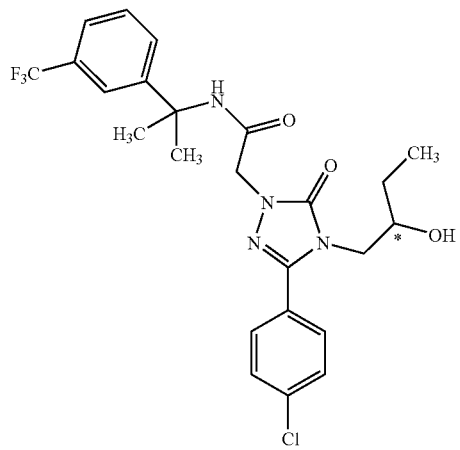

Yield: 19 mg (31% of theory)

$R_t$=5.55 min [Sepaserve Sepapak-2, 5 μm, 250 mm×4.6 mm; Eluent: isohexane/ethanol 70:30. Flow rate: 1 ml/min; Temperature: 35° C.; UV detection: 220 nm].

$^1$H-NMR (400 MHz, CDCl$_3$): δ=0.95 (t, 3H), 1.40-1.52 (m, 2H), 1.72 (s, 6H), 1.90 (br. s, 1H), 3.67-3.87 (m, 2H), 3.93 (m, 1H), 4.50 (s, 2H), 6.63 (s, 1H), 7.35-7.65 (m, 8H).

Example 485

2-[3-(4-chlorophenyl)-5-oxo-4-(2-hydroxybutyl)-4,5-dihydro-1H-1,2,4-triazol-1-yl]-N-{1-methyl-1-[3-(trifluoromethyl)phenyl]ethyl}-acetamide (Enantiomer 2)

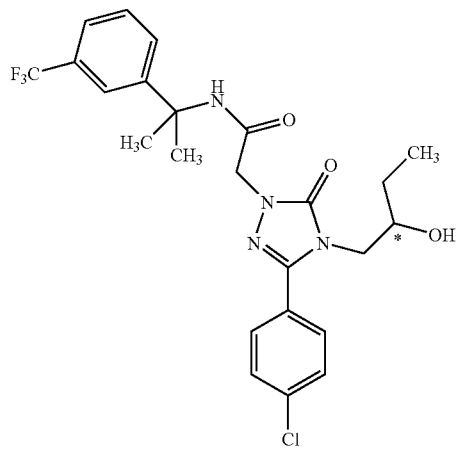

Yield: 21 mg (33% of theory)

$R_t$=7.44 min [Sepaserve Sepapak-2, 5 μm, 250 mm×4.6 mm; Eluent: isohexane/ethanol 70:30; Flow rate: 1 ml/min; Temperature: 35° C.; UV detection: 220 nm].

Example 486

2-[3-(4-chlorophenyl)-4-(2-cyclopropyl-2-hydroxyethyl)-5-oxo-4,5-dihydro-1H-1,2,4-triazol-1-yl]-N-{1-methyl-1-[3-(trifluoromethyl)phenyl]ethyl}-acetamide

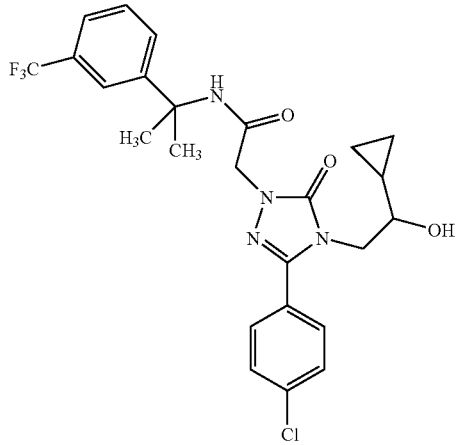

103 mg (0.21 mmol) of 2-[3-(4-chlorophenyl)-4-(2-oxoethyl)-5-oxo-4,5-dihydro-1H-1,2,4-triazol-1-yl]-N-{1-methyl-1-[3-(trifluoromethyl)phenyl]ethyl}-acetamide from Example 401 are dissolved in 1 ml of THF and treated at −78° C. with 1.1 ml (0.54 mmol) of cyclopropylmagnesium bromide (0.5 M solution in THF). This is stirred for 3 hrs at RT and then for a further 2 hrs at 50° C. For the workup, it is treated with saturated ammonium chloride solution and extracted twice with 10 ml of ethyl acetate each time. The combined organic phases are dried over sodium sulphate, filtered and concentrated in vacuo. The crude product is purified by preparative HPLC [Method 10]. 12 mg (11% of theory) of the target compound are thus obtained.

LC/MS [Method 8]: $R_t$=2.61 min; MS [ESIpos]: m/z=523 (M+H)$^+$ $^1$H-NMR (400 MHz, CDCl$_3$): δ=0.22 (m, 1H), 0.33 (m, 1H), 0.50 (m, 2H), 0.71 (m, 1H), 1.72 (s, 6H), 2.68 (d, 1H), 3.34 (m, 1H), 3.91 (dd, 1H), 3.99 (dd, 1H), 4.50 (s, 2H), 6.62 (s, 1H), 7.37-7.65 (m, 8H).

| Example No. | Structure | LC/MS or HPLC, MS $R_t$ [Method] |
|---|---|---|
| 487 | 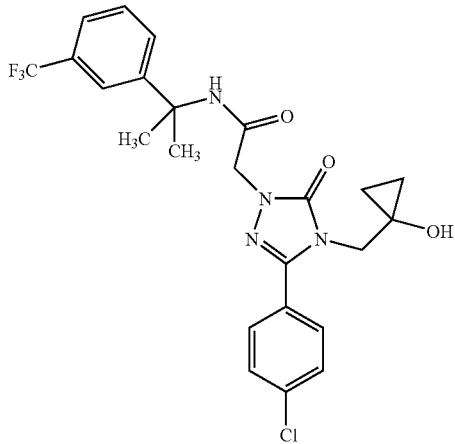 | LC/MS: $R_t$ = 4.02 min [17] [ESIpos]: m/z = 539 (M + H)⁺ |

Example 488

2-{3-(4-chlorophenyl)-4-[(1-hydroxycyclopropyl)methyl]-5-oxo-4,5-dihydro-1H-1,2,4-triazol-1-yl}-N-{1-methyl-1-[3-(trifluoromethyl)phenyl]ethyl}-acetamide 72 mg (0.14 mmol) of 2-[3-(4-chlorophenyl)-4-(2-oxoethyl)-5-oxo-4,5-dihydro-1H-1,2,4-triazol-1-yl]-N-{-methyl-1-[3-(trifluoromethyl)phenyl]ethyl}-acetamide from Example 401 together with 4 mg (0.014 mmol) of titanium (IV) isopropylate are dissolved in 0.45 ml of diethyl ether and 0.3 ml of THF and treated at RT within 1 hr with 108 µl (0.32 mmol) of ethylmagnesium bromide (3 M solution in diethyl ether), diluted with 0.4 ml diethyl ether. This is stirred for a further 10 mins at RT. For the workup, the mixture is poured into 10 ml of ice-cold 10% sulphuric acid and extracted twice with 10 ml of ethyl acetate each time. The combined organic phases are dried over sodium sulphate, filtered and concentrated in vacuo. The crude product is purified by preparative HPLC [Method 10]. 5 mg (7% of theory) of the target compound are thus obtained LC/MS [Method 8]: $R_t$=2.54 min; MS [ESIpos]: m/z=509 (M+H)⁺

¹H-NMR (400 MHz, CDCl₃): δ=0.51 (m, 2H), 0.81 (m, 2H), 1.72 (s, 6H), 3.82 (br. s, 1H), 3.95 (d, 2H), 4.52 (s, 2H), 6.62 (s, 1H), 7.37-7.62 (m, 8H).

Example 489

2-[3-(4-chlorophenyl)-5-oxo-4-(3,3,3-trifluoro-2-oxopropyl)-4,5-dihydro-1H-1,2,4-triazol-1-yl]-N-{1-methyl-1-[3-(trifluoromethyl)phenyl]ethyl}-acetamide 1.2 g (2.18 mmol) of 2-[3-(4-chlorophenyl)-5-oxo-4-(3,3,3-trifluoro-2-hydroxypropyl)-4,5-dihydro-1H-1,2,4-triazol-1-yl]-N-{1-methyl-1-[3-(trifluoromethyl)phenyl]ethyl}-acetamide from Example 452 are dissolved in 30 ml of dichloromethane and treated at 0° C. with 1.2 g (2.83 mmol) of 1,1,1-tris(acetoxy)-1,1-dihydro-1,2-benziodoxol-3-(1H)-one (Dess-Martin periodinane). This is stirred for 3 hrs at RT. The reaction solution is then diluted with 30 ml of ethyl acetate and washed three times with 15 ml of 1 N aqueous sodium hydroxide each time. The organic phase is dried over sodium sulphate, filtered and concentrated in vacuo. The crude product is purified by flash chromatography on silica gel (eluent: cyclohexane/ethyl acetate first 4:1, then 1:1). 0.90 g (75% of theory) of the target compound are obtained.

LC/MS [Method 22]: $R_t$=2.25 min; MS [ESIpos]: m/z=549 (M+H)$^+$ $^1$H-NMR (400 MHz, DMSO-d$_6$): δ=1.60 (s, 6H), 4.08 (s, 2H), 4.48 (s, 2H), 7.44-7.71 (m, 8H), 8.54 (s, 1H).

Further practical examples are prepared as follows by parallel synthesis:

0.10 mmol of the corresponding amine component are placed in 0.2 ml DMSO and treated with 0.10 mmol of the triazolylacetic acid from Example 90A, dissolved in 0.2 ml of DMSO. Next, this is treated with 25.8 mg (0.2 mmol) of N,N-diisopropylethylamine and 41.7 mg (0.130 mmol) of TBTU and the mixture shaken overnight at RT. The reaction solution is then filtered and the filtrate purified by preparative LC/MS [Method 24]. The following are obtained in this manner:

| Example No. | Structure | LC/MS or HPLC, MS $R_t$ [Method] |
|---|---|---|
| 490 | 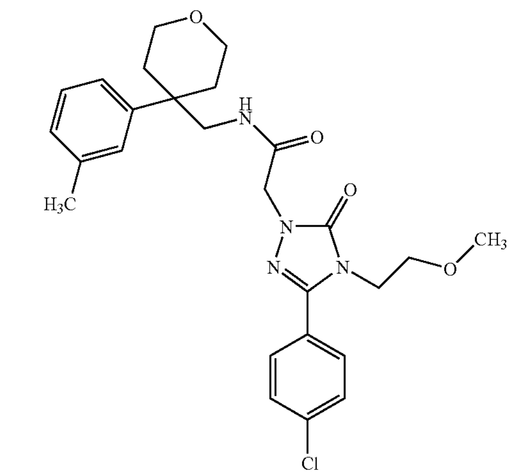 | LC/MS: $R_t$ = 2.21 min [24] [ESIpos]: m/z = 500 (M + H)$^+$ |
| 491 | 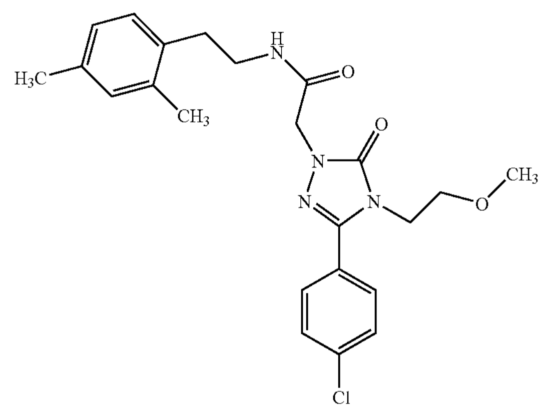 | LC/MS: $R_t$ = 2.28 min [24] [ESIpos]: m/z = 443 (M + H)$^+$ |
| 492 | 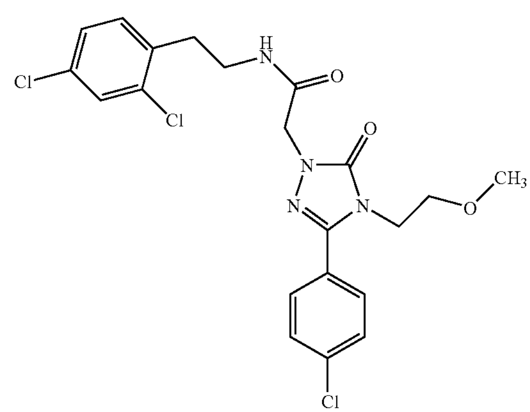 | LC/MS: $R_t$ = 2.31 min [24] [ESIpos]: m/z = 484 (M + H)$^+$ |

-continued
| Example No. | Structure | LC/MS or HPLC, MS $R_t$ [Method] |
|---|---|---|
| 493 | 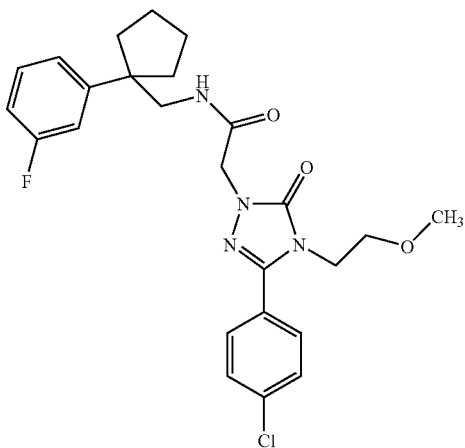 | LC/MS: $R_t$ = 2.36 min [24] [ESIpos]: m/z = 487 (M + H)$^+$ |
| 494 | 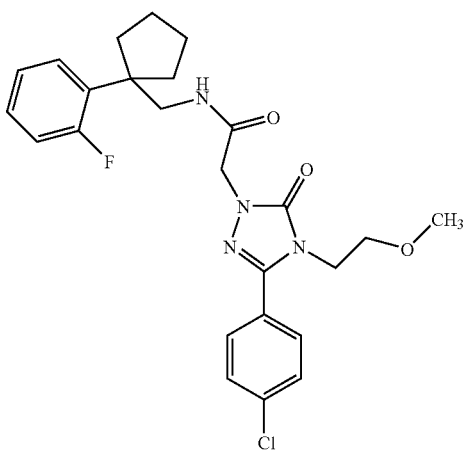 | LC/MS: $R_t$ = 2.36 min [24] [ESIpos]: m/z = 487 (M + H)$^+$ |
| 495 | 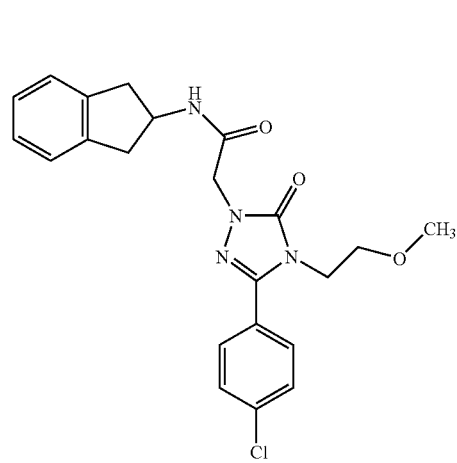 | LC/MS: $R_t$ = 2.01 min [24] [ESIpos]: m/z = 427 (M + H)$^+$ |

Example 496

2-[3-(3-chloro-4-methyl-2-thienyl)-4-isobutyl-5-oxo-4,5-dihydro-1H-1,2,4-triazol-1-yl]-N-[3-(trifluoromethyl)phenylmethyl]-acetamide

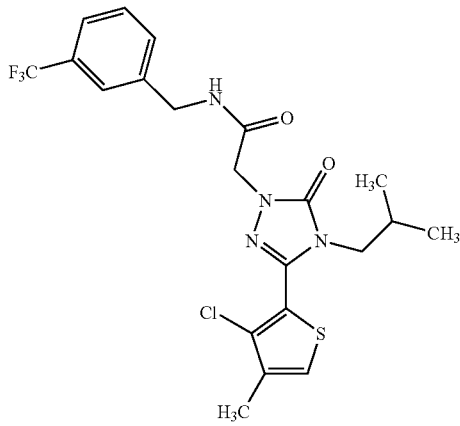

40.0 mg (0.121 mmol) of 2-[3-(3-chloro-4-methyl-2-thienyl)-4-isobutyl-5-oxo-4,5-dihydro-1H-1,2,4-triazol-1-yl]-acetic acid from Example 249A and 23.4 mg (0.133 mmol) of 3-trifluoromethyl-benzylamine are placed in 1.5 ml of DMF and treated with 19.7 mg (0.146 mmol) of HOBt. 30.2 mg (0.158 mmol) of EDC hydrochloride are added and the mixture is stirred overnight at RT. For the workup, the reaction mixture is stirred with about 15 ml of water and the resulting precipitate filtered off, washed with water and dried in vacuo. 43 mg (73% of theory) of the target compound are thus obtained.

LC/MS [Method 7]: $R_t$=2.52 min;
$^1$H-NMR (400 MHz, DMSO-$d_6$): δ=0.73 (d, 6H), 1.73-1.85 (m, 1H), 2.23 (s, 3H), 3.45 (d, 2H), 4.41 (d, 2H), 4.52 (s, 2H), 7.52-7.65 (m, 4H), 7.72 (s, 1H), 8.73 (t, 1H).

Example 497

2-[3-(3-chloro-4-methyl-2-thienyl)-4-isobutyl-5-oxo-4,5-dihydro-1H-1,2,4-triazol-1-yl]-N-[2-(trifluoromethyl)phenylmethyl]-acetamide

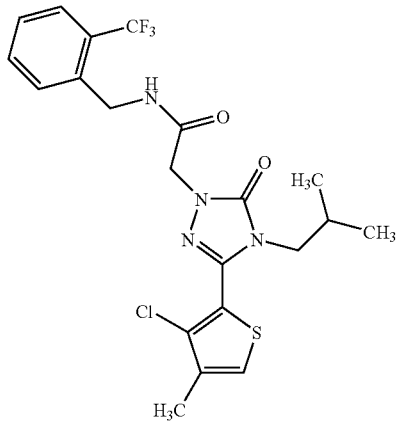

40.0 mg (0.121 mmol) of 2-[3-(3-chloro-4-methyl-2-thienyl)-4-isobutyl-5-oxo-4,5-dihydro-1H-1,2,4-triazol-1-yl]-acetic acid from Example 249A and 23.4 mg (0.133 mmol) of 2-trifluoromethyl-benzylamine are placed 1.5 ml of DMF and treated with 19.7 mg (0.146 mmol) of HOBt. 30.2 mg (0.158 mmol) of EDC hydrochloride are added and the mixture is stirred overnight at RT. For the workup, the reaction mixture is stirred with about 15 ml of water, saturated with sodium chloride and extracted with ethyl acetate. The organic phase is separated and concentrated, and the residue is dissolved in methanol and purified by preparative HPLC [Method 12]. 26 mg (44% of theory) of the target compound are thus obtained.

LC/MS [Method 7]: $R_t$=2.52 min;
$^1$H-NMR (400 MHz, DMSO-$d_6$): δ=0.73 (d, 6H), 1.72-1.87 (m, 1H), 2.23 (s, 3H), 3.45 (d, 2H), 4.49 (d, 2H), 4.57 (s, 2H), 7.49 (t, 1H), 7.56 (d, 1H), 7.65 (t, 1H), 7.69-7.75 (m, 2H), 8.73 (t, 1H).

Example 498 tert.-butyl[3-(4-chlorophenyl)-5-oxo-1-(2-oxo-2-{[3-(trifluoromethyl)phenylmethyl]amino}ethyl)-1,5-dihydro-4H-1,2,4-triazol-4-yl]-acetate

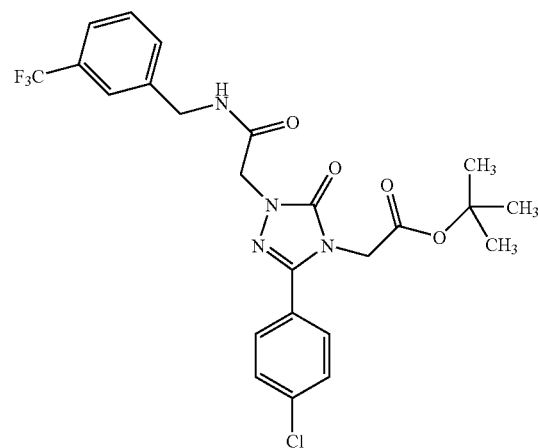

92.6 mg (0.475 mmol) of tert.-butyl bromoacetate are added to 150.0 mg of (0.365 mmol) 2-[3-(4-chlorophenyl)-5-oxo-4,5-dihydro-1H-1,2,4-triazol-1-yl]-N-[3-(trifluoromethyl)phenylmethyl]-acetamide from Example 242A and 178.5 mg (0.548 mmol) of caesium carbonate in 5.0 ml of acetone and heated for 5 hrs under reflux. For the workup, the reaction mixture is concentrated after cooling, the residue is partitioned between water and ethyl acetate, the organic phase separated and the aqueous phase extracted several times more with ethyl acetate. The combined organic phases are concentrated and the residue purified by preparative HPLC [Method 12]. 139 mg (73% of theory) of the target compound are thus obtained.

LC/MS [Method 7]: $R_t$=2.56 min;
$^1$H-NMR (400 MHz, DMSO-$d_6$): δ=1.28 (s, 9H), 4.41 (d, 2H), 4.54 (d, 4H), 7.53-7.65 (m, 8H), 8.75 (t, 1H).

Example 499

2-[4-(4-chlorophenyl)-2-oxo-3-(3,3,3-trifluoro-2-hydroxypropyl)-2,3-dihydro-1H-imidazol-1-yl]-N-{1-methyl-1-[3-(trifluoromethyl)phenyl]ethyl}-acetamide (Racemate)

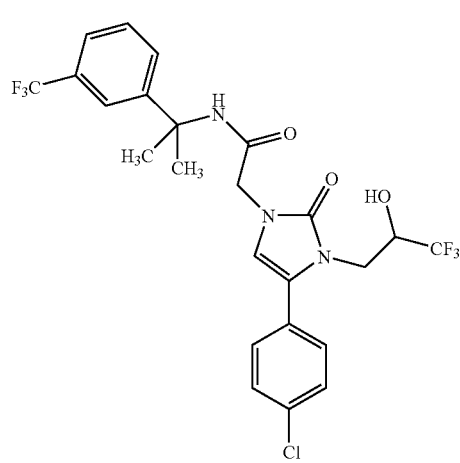

174 mg (0.397 mmol) of 2-[4-(4-chlorophenyl)-2-oxo-2,3-dihydro-1H-imidazol-1-yl]-N-{1-methyl-1-[3-(trifluoromethyl)phenyl]ethyl}-acetamide from Example 234A, 12.8 mg (0.04 mmol) of tetra-n-butylammonium bromide and 37.5 mg (0.199 mmol) of potassium carbonate are placed in 0.45 ml of DMF and treated with 49.0 mg (0.437 mmol) of 1,1,1-trifluoro-2,3-epoxypropane. This is stirred for 1 hr at 130° C. The suspension is diluted with 5 ml of ethyl acetate and washed twice with 5 ml of water each time. The organic phase is dried over sodium sulphate and filtered. After evaporation the crude product is purified by preparative HPLC [Method 10]. 48 mg (22% of theory) of the target compound are obtained.

LC/MS [Method 19]: $R_t$=3.76 min; MS [ESIpos]: m/z=550 (M+H)$^+$ $^1$H-NMR (400 MHz, DMSO-d$_6$): δ=1.60 (s, 6H), 3.73 (dd, 1H), 3.87 (dd, 1H), 4.23 (m, 1H), 4.31 (s, 2H), 6.15 (s, 1H), 6.20 (d, 1H), 7.45-7.70 (m, 8H), 8.56 (s, 1H).

By preparative HPLC on chiral phase [Daicel Chiralpak AD-H, 5 μm, 250 mm×20 mm; Eluent: isohexane/isopropanol 85:15; Flow rate: 15 ml/min; Temperature: 40° C.; UV detection: 220 nm], the racemate from Example 499 is separated into the enantiomers (see Examples 500 and 501):

Example 500

2-[4-(4-chlorophenyl)-2-oxo-3-(3,3,3-trifluoro-2-hydroxypropyl)-2,3-dihydro-1H-imidazol-1-yl]-N-{1-methyl-1-[3-(trifluoromethyl)phenyl]ethyl}-acetamide (Enantiomer 1)

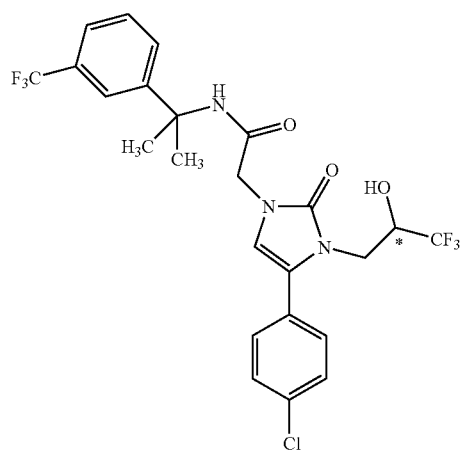

$R_t$=7.23 min [Daicel Chiralpak AD-H, 5 μm, 250 mm×4.6 mm; Eluent: isohexane/isopropanol 85:15; Flow rate: 1.0 ml/min; Temperature: 40° C.; UV detection: 220 nm].

Example 501

2-[4-(4-chlorophenyl)-2-oxo-3-(3,3,3-trifluoro-2-hydroxypropyl)-2,3-dihydro-1H-imidazol-1-yl]-N-{1-methyl-1-[3-(trifluoromethyl)phenyl]ethyl}-acetamide (Enantiomer 2)

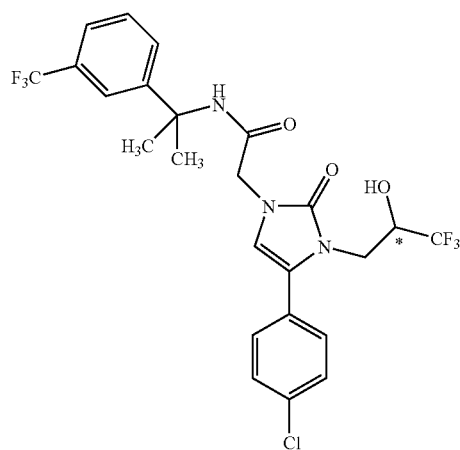

$R_t$=5.43 min [Daicel Chiralpak AD-H, 5 μm, 250 mm×4.6 mm; Eluent: isohexane/isopropanol 85:15; Flow rate: 1.0 ml/min; Temperature: 40° C.; UV detection: 220 nm].

Example 502

2-[4-(5-chloro-2-thienyl)-3-(2-fluorobenzyl)-2-oxo-2,3-dihydro-1H-imidazol-1-yl]-N-{1-methyl-1-[3-(trifluoromethyl)phenyl]ethyl}-acetamide

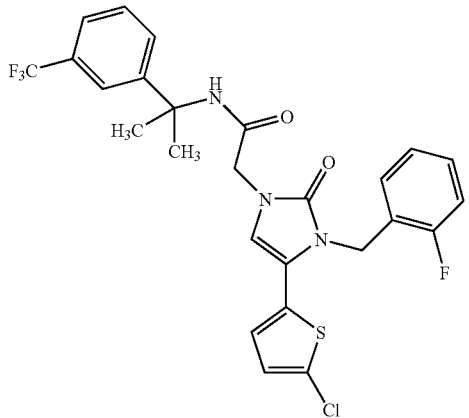

45 mg (0.123 mmol) of [4-(5-chloro-2-thienyl)-3-(2-fluorobenzyl)-2-oxo-2,3-dihydro-1H-imidazol-1-yl]-acetic acid from Example 238A, 20 mg (0.147 mmol) of HOBt and 31 mg (0.159 mmol) of EDC hydrochloride are placed in 1.5 ml of DMF and stirred for 10 mins. Next, 30 mg (0.147 mmol) of 1-methyl-1-[(3-trifluoromethyl)phenyl]ethylamine from Example 1A are added and the mixture is stirred overnight at RT. For the workup, the reaction mixture is stirred with 2 ml of water and extracted twice with 5 ml of ethyl acetate each time. The combined organic phases are dried over sodium sulphate, filtered and concentrated in vacuo. The crude product is purified by preparative HPLC [Method 10]. 50 mg (74% of theory) of the target compound are thus obtained.

LC/MS [Method 8]: $R_t$=3.00 min; MS [ESIpos]: m/z=552 (M+H)$^+$ $^1$H-NMR (400 MHz, DMSO-d$_6$): δ=1.60 (s, 6H), 4.36 (s, 2H), 4.93 (s, 2H), 6.82 (d, 1H), 6.84 (s, 1H), 6.88 (t, 1H), 7.05 (d, 1H), 7.07 (t, 1H), 7.16 (t, 1H), 7.30 (m, 1H), 7.48-7.58 (m, 2H), 7.63 (s, 1H), 7.67 (d, 1H), 8.56 (s, 1H).

The following compounds are prepared analogously:

| Example No. | Structure | LC/MS or HPLC, MS $R_t$ [Method] |
|---|---|---|
| 503 | 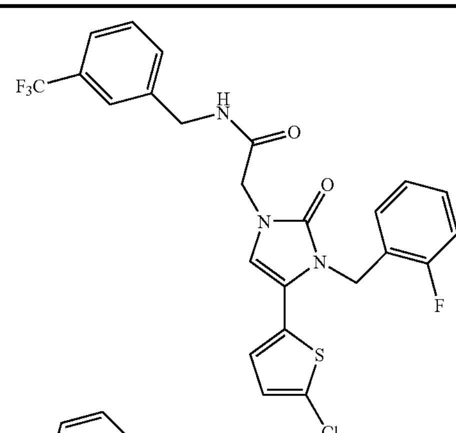 | LC/MS: $R_t$ = 3.97 min [17] [ESIpos]: m/z = 524 (M + H)$^+$ |
| 504 | 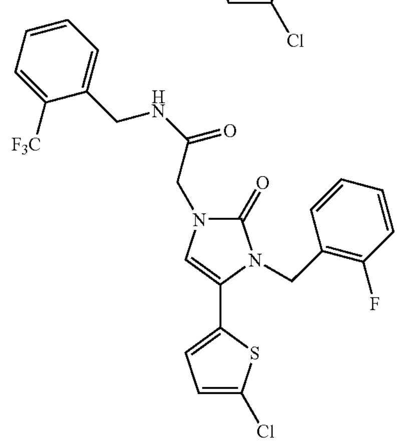 | LC/MS: $R_t$ = 3.96 min [17] [ESIpos]: m/z = 524 (M + H)$^+$ |

| Example No. | Structure | LC/MS or HPLC, MS $R_t$ [Method] |
|---|---|---|
| 505 | 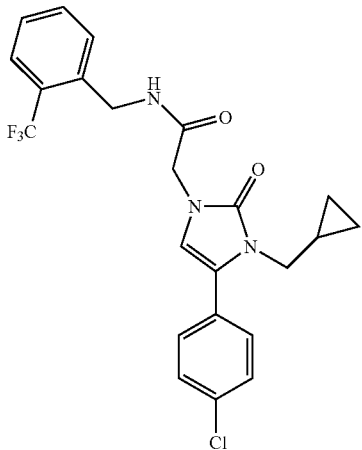 | LC/MS: $R_t$ = 2.63 min [8] [ESIpos]: m/z = 464 (M + H)$^+$ |
| 506 | 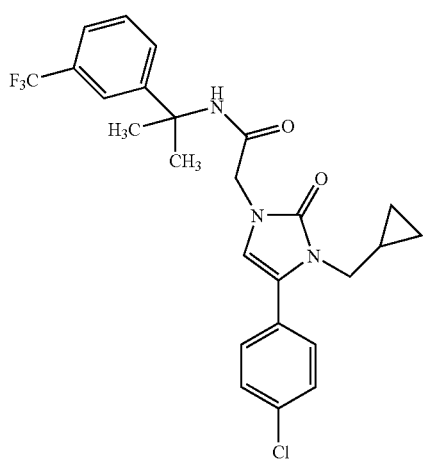 | LC/MS: $R_t$ = 2.80 min [8] [ESIpos]: m/z = 492 (M + H)$^+$ |
| 507 | 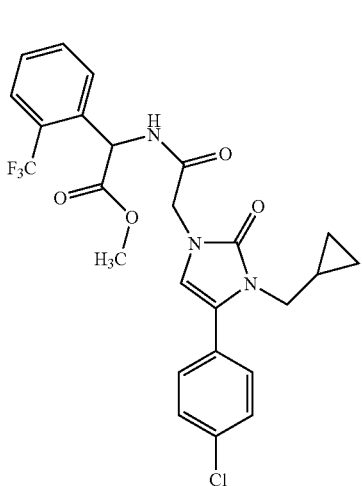 | LC/MS: $R_t$ = 2.66 min [8] [ESIpos]: m/z = 522 (M + H)$^+$ |

| Example No. | Structure | LC/MS or HPLC, MS $R_t$ [Method] |
|---|---|---|
| 508 | 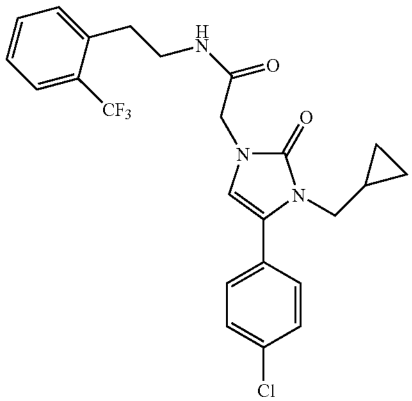 | LC/MS: $R_t$ = 2.68 min [8] [ESIpos]: m/z = 478 (M + H)⁺ |

Example 509

2-[3-(4-chlorophenyl)-5-oxo-4-(3,3,3-trifluoro-2-hydroxypropyl)-4,5-dihydro-1H-1,2,4-triazol-1-yl]-N-{2-amino-2-oxo-1-[3-(trifluoromethyl)phenyl]ethyl}-acetamide

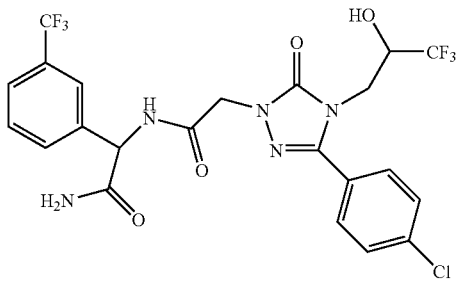

The carboxylic acid from Example 229A (enantiomer 1; 23 mg, 63 µmol) and HOBt (13 mg, 94 µmol) are placed in 0.91 ml of DMF and treated at RT with 18 mg (94 µmol) of EDC. After 20 mins, 25 mg (0.11 mmol) of the compound from Example 184A and 22 µl (0.13 mmol) of N,N-diisopropyl-ethylamine are added and the mixture is stirred overnight at RT. 1 ml of 1 N hydrochloric acid is then added and the mixture is directly separated by preparative HPLC (Method 20). 26 mg (73% of theory) of the title compound are obtained.

LC/MS [Method 23]: $R_t$=2.06 min; m/z=566 (M+H)⁺

¹H-NMR (400 MHz, DMSO-d₆): δ=3.82 (dd, 1H), 3.96 (br. d, 1H), 4.26 (m, 1H), 4.50-4.70 (m, 2H [ABM system]), 5.51 (d, 1H), 6.89 (t, 1H), 7.33 (s, 1H), 7.57-7.65 (m, 3H), 7.68 (d, 1H), 7.70-7.77 (m, 3H), 7.81 (s, 1H), 7.88 (s, 1H), 9.99 (d, 1H).

Example 510

2-([3-(4-chlorophenyl)-5-oxo-4-(3,3,3-trifluoro-2-hydroxypropyl)-4,5-dihydro-1H-1,2,4-triazol-1-yl]acetylamino)-N-cyclopropyl-2-[3-(trifluoromethyl)phenyl]-acetamide

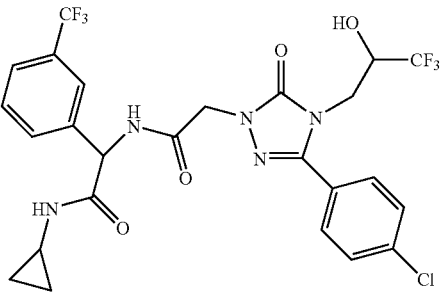

Analogously to the preparation of Example 509, 27 mg (65% of theory) of the title compound are obtained from 25 mg (69 µmol) of the carboxylic acid from Example 229A and 31 mg (82 µmol) of the compound from Example 181A.

LC/MS [Method 23]: $R_t$=2.24 min; m/z=606 (M+H)⁺

¹H-NMR (400 MHz, DMSO-d₆): δ=0.25-0.35 (m, 1H), 0.39-0.48 (m, 1H), 0.55-0.71 (m, 2H), 2.58-2.69 (m, 1H), 3.82 (dd, 1H), 3.96 (br. d, 1H), 4.26 (m, 1H), 4.53-4.65 (m, 2H [ABM system]), 5.48 (d, 1H), 6.89 (t, 1H), 7.57-7.79 (m, 8H), 8.53 (d, 1H), 9.06 (d, 1H).

Example 511

2-[3-(4-chlorophenyl)-5-oxo-4-(3,3,3-trifluoro-2-hydroxypropyl)-4,5-dihydro-1H-1,2,4-triazol-1-yl]-N-{2-morpholin-4-yl-2-oxo-1-[3-(trifluoromethyl)phenyl]ethyl}-acetamide

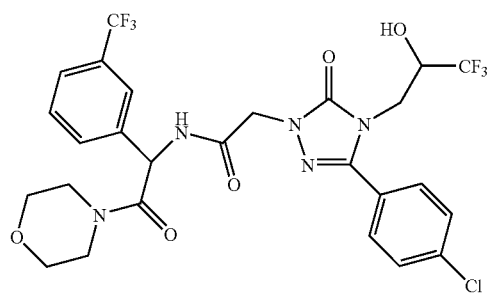

Analogously to the preparation of Example 509, 36 mg (97% of theory) of the title compound are obtained from 21 mg (58 µmol) of the carboxylic acid from Example 229A and 28 mg (70 µmol) of the compound from Example 177A.

LC/MS [Method 8]: $R_t$=2.57 min; m/z=636 (M+H)$^+$ $^1$H-NMR (400 MHz, DMSO-d$_6$): δ=3.18-3.39 (m, 2H), 3.40-3.66 (m, 6H), 3.83 (dd, 1H), 3.97 (br. d, 1H), 4.26 (m, 1H), 4.49-4.59 (m, 2H [ABM system]), 6.03 (d, 1H), 6.90 (dd, 1H), 7.59-7.79 (m, 8H), 8.53 (d, 1H), 9.07 (d, 1H).

Example 512

2-[3-(4-chlorophenyl)-5-oxo-4-(3,3,3-trifluoro-2-hydroxypropyl)-4,5-dihydro-1H-1,2,4-triazol-1-yl]-N-({3-[3-(trifluoromethyl)phenyl]oxetan-3-yl}methyl)-acetamide

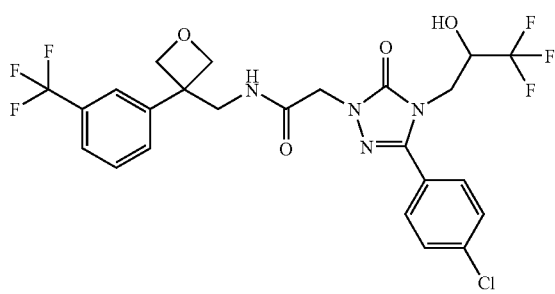

24.8 mg (68 µmol) of the carboxylic acid from Example 229A (enantiomer 1) in 710 µl DMF are successively treated with 14 mg (102 µmol) of HOBt, 20 mg (102 µmol) of EDC, 20 mg (75 µmol) of the compound from Example 252A and 17 µl of N,N-diisopropylethylamine (95 mmol). The reaction mixture is stirred overnight at RT and then directly separated by preparative HPLC (Method 20). The product-containing fractions are combined and concentrated on the rotary evaporator. The residue contains the title compound and side-products and is further purified by silica gel chromatography (eluent: cyclohexane/ethyl acetate 7:1). 9 mg (23% of theory) of the title compound are thus obtained.

LC/MS [Method 22]: $R_t$=2.07 min; m/z=579 [M+H]$^+$ $^1$H-NMR (400 MHz, DMSO-d$_6$): δ=3.65-3.75 (m, 2H), 3.82 (dd, 1H), 3.95 (dd, 1H), 4.26 (m, 1H), 4.36 (m, 2H [AB system]), 4.75 (m, 4H [AB system]), 6.90 (d, 1H), 7.46 (d, 1H), 7.50 (s, 1H), 7.55-7.65 (m, 4H), 7.73 (d, 2H), 8.29 (t, 1H).

B. ASSESSMENT OF PHARMACOLOGICAL ACTIVITY

The pharmacological activity of the compounds according to the invention can be demonstrated in the following assays:

Abbreviations:

EDTA Ethylendiaminetetraacetic acid

DMEM Dulbecco's Modified Eagle Medium

FCS Foetal calf serum

HEPES 4-(2-hydroxyethyl)-1-piperazineethanesulphonic acid

SmGM Smooth Muscle Cell Growth Media

Tris-HCl 2-amino-2-(hydroxymethyl)-1,3-propanediol hydrochloride

UtSMC Uterine Smooth Muscle Cells

B-1. Cellular In Vitro Test for Determination of the Vasopressin Receptor Activity The identification of agonists and antagonists of the V1a- and V2-vasopressin receptors in man and the rat and the quantification of the activity of the compounds according to the invention are effected by means of recombinant cell lines. These cells are originally derived from the ovarian epithelial cells of the hamster (Chinese Hamster Ovary, CHO K1, ATCC: American Type Culture Collection, Manassas, Va. 20108, USA). The test cell lines constitutively express a modified form of the calcium-sensitive photoprotein aequorin, which after reconstitution with the cofactor coelenterazine emits light on an increase in the free calcium concentrations [Rizzuto R, Simpson A W, Brini M, Pozzan T, *Nature* 358, 325-327 (1992)]. In addition, the cells are stably transfected with human or rat V1a- or V2 receptors. In the case of the Gs-coupled V2 receptors, the cells are stably transfected with a further gene which codes for the promiscuous G$_{\alpha 16}$-Protein [Amatruda T T, Steele D A, Slepak V Z, Simon M I, *Proceedings of the National Academy of Science USA* 88, 5587-5591 (1991)]. The resulting vasopressin receptor test cells react to stimulation of the recombinantly expressed vasopressin receptors with an intracellular release of calcium ions, which can be quantified by the resulting aequorin luminescence with a suitable luminometer [Milligan G, Marshall F, Rees S, *Trends in Pharmacological Sciences* 17, 235-237 (1996)].

Test Procedure:

On the day before the text, the cells are plated out in culture medium (DMEM, 10% FCS, 2 mM glutamine, 10 mM HEPES) in 384-well microtitre plates and kept in a cell incubator (96% atmospheric humidity, 5% v/v CO$_2$, 37° C.). On the test day, the culture medium is replaced by a Tyrode solution (140 mM NaCl, 5 mM KCl, 1 mM MgCl$_2$, 2 mM CaCl$_2$, 20 mM glucose, 20 mM HEPES) which in addition contains the cofactor coelenterazine (50 µM), and the microtitre plate is then incubated for a further 3-4 hours. The test substances in various concentrations are placed beforehand in the wells of the microtitre plate for 10 to 20 minutes, before the agonist [Arg$^8$]-vasopressin is added and the resulting light signal immediately measured in the luminometer. The IC$_{50}$ values are calculated by means of the computer program GraphPad PRISM (Version 3.02).

The following table shows representative $IC_{50}$ values for the compounds according to the invention in the cell line transfected with the human V1a- or V2 receptor:

TABLE

| Example No. | $IC_{50}$ hV1a [µM] | $IC_{50}$ hV2 [µM] |
|---|---|---|
| 25 | 6.3 | 0.18 |
| 28 | 0.030 | 0.18 |
| 29 | 0.17 | 0.009 |
| 59 | 1.1 | 0.009 |
| 63 | 0.038 | >10 |
| 75 | 0.39 | 0.026 |
| 84 | 0.32 | 0.008 |
| 101 | 0.094 | 1.1 |
| 143 | 0.96 | 0.006 |
| 145 | 0.095 | 0.007 |
| 151 | 3.4 | 0.93 |
| 153 | 0.042 | 0.012 |
| 159 | 0.44 | 0.42 |
| 207 | 0.23 | 0.063 |
| 209 | 0.14 | 0.26 |
| 214 | 6.3 | 0.18 |
| 216 | 0.073 | 0.006 |
| 219 | 0.090 | 0.009 |
| 221 | 0.165 | 0.030 |
| 227 | 0.008 | 0.037 |
| 230 | 0.783 | 0.083 |
| 241 | 0.076 | 0.271 |
| 251 | 0.037 | 0.013 |
| 252 | 0.018 | 0.447 |
| 260 | 0.030 | 0.154 |
| 262 | 0.157 | 0.005 |
| 265 | 0.028 | 0.749 |
| 284 | 0.009 | 0.191 |
| 288 | 0.761 | 0.666 |
| 296 | 0.054 | 0.009 |
| 305 | 0.093 | 0.784 |
| 313 | 0.003 | 1.025 |
| 320 | 0.024 | 1.517 |
| 321 | 0.050 | 0.51 |
| 325 | 0.107 | 0.028 |
| 340 | 0.039 | 1.149 |
| 348 | 0.004 | 0.217 |
| 357 | 0.338 | 0.005 |
| 359 | 0.019 | 0.009 |
| 364 | 0.022 | 0.008 |
| 386 | 0.611 | 0.023 |
| 394 | 0.019 | 0.019 |
| 415 | 0.870 | 0.026 |
| 421 | 0.032 | 0.088 |
| 423 | 0.157 | 0.015 |
| 433 | 0.199 | 0.009 |
| 439 | 0.058 | 0.077 |
| 443 | 0.093 | 0.023 |
| 451 | 0.012 | 0.002 |
| 457 | 0.043 | 0.029 |
| 462 | 0.373 | 0.046 |
| 467 | 0.439 | 0.026 |
| 471 | 0.039 | 0.002 |
| 475 | 0.328 | 0.020 |
| 476 | 1.229 | 0.094 |
| 482 | 0.009 | 0.25 |
| 485 | 0.012 | 0.002 |
| 489 | 0.035 | 0.002 |
| 494 | 0.049 | 0.257 |
| 496 | 0.166 | 0.576 |
| 501 | 0.012 | 0.003 |
| 503 | 0.025 | 0.221 |
| 508 | 0.005 | 0.336 |
| 509 | 0.008 | 0.004 |
| 510 | 0.004 | 0.007 |
| 511 | 0.004 | 0.011 |

B-2. Binding Studies on Membrane Preparations of Human Smooth Muscle Cells of the Uterus for the Determination of the Oxytocin Receptor Affinity Human smooth muscle cells of the uterus (UtSMC; Cambrex Bio Science Co., Walkersville, USA) are cultured in SmGM-2 medium (Cambrex Bio Science Co.). After attainment of 80% confluence, the cells are suspended in 10 ml of ice-cold homogenization buffer (10 mM Tris-HCl, 5 mM EDTA, pH 7.4) per 175 cm² cell culture bottle and homogenized by means of an Ultra-Turrax device. The homogenates are centrifuged for 10 minutes at 1000 g and 4° C. The supernatant is removed and centrifuged for 20 minutes at 35000 g and 4° C. The membrane sediment with the oxytocin receptors is taken up in 10 ml of binding buffer (50 mM Tris-HCl, 10 mM $MgCl_2$, pH 7.4) and stored at −80° C. For the binding experiment, 100 µg of the membrane preparation are mixed with the radio-ligand [³H]-oxytocin (0.5 nM) and incubated at room temperature for 60 minutes with increasing concentrations of the test compounds in binding buffer with 0.1% bovine serum albumin. The incubation is stopped by 10-minute centrifugation at 10000 g followed by washing with 0.1% bovine serum albumin in binding buffer at 4° C. A further centrifugation is performed for 10 minutes at 10000 g and 4° C. The sediment is resuspended in 0.1 ml of 1 N aqueous sodium hydroxide and transferred into scintillation tubes. After addition of 4 ml of Ultima Gold scintillator, the radioactivity bound on the membranes is quantified by means of an LS6000 IC scintillation counter (Beckman Coulter Co.). The radioactivity in the presence of 1 µM oxytocin is defined as non-specific binding. The $IC_{50}$ values are calculated by means of the computer program GraphPad PRISM (Version 3.02).

B-3. In Vivo Test for Detection of Cardiovascular Action; Blood Pressure Measurement on Narcotized Rats In male Wistar rats (350-450 g body weight) under isoflurane narcosis (2% isoflurane, 33% oxygen and 65% nitrous oxide) polyethylene tubes (PE-50; Intramedic®), which are prefilled with heparin-containing (500 I.E./ml) isotonic sodium chloride solution, are introduced into the femoral artery and femoral vein and then bound in. The test substances are administered via the venous access by means of a syringe. The arterial catheter is connected to a pressure transducer, which feeds its signals into a measurement computer equipped with suitable recording software. On the basis of the continuously recorded pressure curve, systolic and diastolic blood pressure are determined and the arterial mean pressure calculated therefrom and the heart rate determined. In a further modification of the experimental set-up, the abdominal cavity is also opened, the urinary bladder presented and a plastic tube through which the urine is continuously collected is inserted into the urinary bladder via a small cut, and fixed by suturing.

In a typical experiment, a bolus injection with a defined quantity of Arg-vasopressin in isotonic sodium chloride solution is administered to the test animal and, after the blood pressure has again reached starting values, the substance to be tested is administered as a bolus in a suitable solvent. After this, the same quantity of Arg-vasopressin as at the start is again administered at defined intervals. On the basis of the blood pressure values, it is determined how far and for how long the test substance counteracts the blood pressure-increasing action of the Arg-vasopressin. Control animals are given only solvent instead of the test substance.

In comparison to the solvent controls, after intravenous administration the compounds according to the invention cause inhibition of the blood pressure increase caused by Arg-vasopressin.

B-4. In Vivo Test for Detection of Cardiovascular Action: Diuresis Studies on Conscious Rats in Metabolic Cages Wistar rats (300-450 g body weight) are kept with free access to food (Altromin) and drinking water. During the experiment, the animals are kept separately for 4 to 6 hours in metabolic cages suitable for rats in this weight class (Tecniplast Deutschland GmbH, D-82383 Hohenpeißenberg) with free access to drinking water. At the start of the experiment, the test substance in a volume of 3 ml/kg body weight of a suitable solvent is administered to the animals into the stomach by means of a gastric feeding tube. Animals serving as controls are given only solvent. Controls and substance tests are carried out in parallel on the same day. Control groups and substance dose groups each consist of 3 to 6 animals. During the experiment, urine excreted by the animals is continuously collected in a collecting container on the cage floor. For each animal, the urine volume per unit time is separately determined and the concentration of the sodium and potassium ions excreted in the urine measured by standard flame photometry methods. In order to obtain an adequate quantity of urine, a defined quantity of water is administered to the animals by gastric feeding tube at the start of the experiment (typically 10 ml per kg body weight). Before the start of the experiment and after the end of the experiment, the body weight of the individual animals is determined.

In comparison to the control administrations of solvent, after oral administration the compounds according to the invention cause increased excretion of urine, which is essentially due to increased water excretion (aquaresis).

C. PRACTICAL EXAMPLES OF PHARMACEUTICAL COMPOSITIONS

The compounds according to the invention can be converted into pharmaceutical preparations as follows:
Tablet:
Composition:
  100 mg of the compound according to the invention, 50 mg of lactose (monohydrate), 50 mg of maize starch (native), 10 mg of polyvinylpyrrolidone (PVP 25) (BASF Co., Ludwigshafen, Germany) and 2 mg of magnesium stearate.
  Tablet weight 212 mg, diameter 8 mm, radius of curvature 12 mm.
Production:
  The mixture of compound according to the invention, lactose and starch is granulated with a 5% solution (w/w) of the PVP in water. After drying, the granulate is mixed with the magnesium stearate for 5 minutes. This mixture is compressed with a normal tablet press (tablet format: see above). As a guideline, a compression force of 15 kN is used for the compression.
Orally Dosable Suspension:
Composition:
  1000 mg of the compound according to the invention, 1000 mg of ethanol (96%), 400 mg of Rhodigel® (xanthan gum from FMC Co., Pennsylvania, USA) and 99 g water.
  10 ml of oral suspension correspond to a single dose of 100 mg of the compound according to the invention.
Production:
  The Rhodigel is suspended in ethanol, and the compound according to the invention is added to the suspension. The water is added with stirring. The mixture is stirred for ca. 6 hrs until completion of the swelling of the Rhodigel.
Orally Dosable Solution:
Composition:
  500 mg of the compound according to the invention, 2.5 g of polysorbate and 97 g of polyethylene glycol 400. 20 g of oral solution correspond to a single dose of 100 mg of the compound according to the invention.

Production:
  The compound according to the invention is suspended with stirring in the mixture of polyethylene glycol and polysorbate. The stirring process is continued until the complete dissolution of the compound according to the invention.
I.V. Solution:
  The compound according to the invention is dissolved in a physiologically compatible solvent (e.g. isotonic sodium chloride solution, 5% glucose solution and/or 30% PEG 400 solution) at a concentration below the saturation solubility. The solution is sterile-filtered and filled into sterile and pyrogen-free injection containers.

The invention claimed is:
1. A compound of the formula (I)

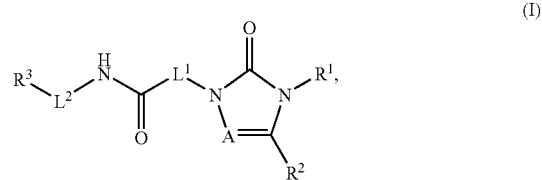

in which
A stands for N or C—$R^4$, wherein
  $R^4$ means hydrogen or ($C_1$-$C_4$) alkyl,
$R^1$ stands for ($C_1$-$C_6$) alkyl, ($C_2$-$C_6$) alkenyl or ($C_2$-$C_6$) alkynyl, which can each be singly to triply, similarly or differently, substituted with residues selected from the range halogen, cyano, oxo, trifluoromethyl, ($C_3$-$C_7$) cycloalkyl, phenyl, —$OR^{10}$, —$NR^{11}R^{12}$, —C(=O)—$OR^{13}$ and —C(=O)—$NR^{14}R^{15}$, wherein
  (i) ($C_3$-$C_7$) cycloalkyl can be up to doubly, similarly or differently, substituted with ($C_1$-$C_4$) alkyl, oxo, hydroxy, ($C_1$-$C_4$) alkoxy and/or amino,
  (ii) phenyl can be up to triply, similarly or differently, substituted with residues selected from the range halogen, cyano, nitro, ($C_1$-$C_4$) alkyl, trifluoromethyl, hydroxy, hydroxymethyl, ($C_1$-$C_4$) alkoxy, trifluoromethoxy, ($C_1$-$C_4$) alkoxymethyl, hydroxycarbonyl, ($C_1$-$C_4$) alkoxycarbonyl, aminocarbonyl, mono-($C_1$-$C_4$) alkylaminocarbonyl and di-($C_1$-$C_4$) alkylaminocarbonyl,
  (iii) $R^{10}$, $R^{11}$, $R^{12}$, $R^{13}$, $R^{14}$ and $R^{15}$ mutually independently on each single occurrence mean hydrogen, ($C_1$-$C_6$) alkyl or ($C_3$-$C_7$) cycloalkyl, wherein ($C_1$-$C_6$) alkyl can itself be up to doubly, similarly or differently, substituted with amino, hydroxy, ($C_1$-$C_4$) alkoxy, hydroxycarbonyl and/or ($C_1$-$C_4$) alkoxycarbonyl
  and
  ($C_3$-$C_7$) cycloalkyl can itself be up to doubly, similarly or differently, substituted with ($C_1$-$C_4$) alkyl, oxo, hydroxy, ($C_1$-$C_4$) alkoxy and/or amino,
  and/or
  (iv) $R^{11}$ and $R^{12}$ and also $R^{14}$ and $R^{15}$ respectively in pairs together with the nitrogen atom to which they are bound form a 4 to 7-membered heterocycle, which can contain a further hetero atom from the range N, O and S and be up to doubly, similarly or differently, substituted with ($C_1$-$C_4$) alkyl, oxo, hydroxy, ($C_1$-$C_4$) alkoxy and/or amino, or
$R^1$ stands for $(C_3-C_7)$ cycloalkyl, which can be up to doubly, similarly or differently, substituted with $(C_1-C_4)$ alkyl, $(C_1-C_4)$ alkoxy, hydroxy, amino and/or oxo, $R^2$ stands for phenyl, naphthyl, thienyl, benzothienyl, furyl or benzofuryl, which can each be singly to triply, similarly or differently, substituted with residues selected from the range halogen, cyano, nitro, $(C_1-C_4)$ alkyl, trifluoromethyl, hydroxy, $(C_1-C_4)$ alkoxy, trifluoromethoxy and phenyl,
  wherein the last-named phenyl residue can itself be up to doubly, similarly or differently, substituted with residues selected from the range halogen, cyano, nitro, $(C_1-C_4)$ alkyl, trifluoromethyl, hydroxy, $(C_1-C_4)$ alkoxy, trifluoromethoxy, hydroxy-$(C_1-C_4)$ alkyl and $(C_1-C_4)$ alkylthio, $L^1$ stands for a group of the formula $-(CR^{5A}R^{5B})_m-$,
  wherein
  m means the number 1, 2 or 3
  and
  $R^{5A}$ and $R^{5B}$ mutually independently mean hydrogen or $(C_1-C_4)$ alkyl
  or
  two residues $R^{5A}$ and $R^{5B}$ bound to the same carbon atom are linked to one another and together form a $-(CH_2)_n$ bridge, wherein
  n means the number 2, 3, 4 or 5,
  or, in the event that m stands for the number 2 or 3,
  two residues bound to adjacent (1,2- or 1,3-) or non-adjacent (1,3-) carbon atoms $R^{5A}$ and/or $R^{5B}$ are linked to one another and together form a $-(CH_2)_p$ bridge, wherein
  p means the number 1, 2, 3 or 4,
  where, in the event that the group $-CR^{5A}R^{5B}-$ occurs several times, the individual meanings of $R^{5A}$ and $R^{5B}$ can in each case be the same or different,
or
$L^1$ stands for a group of the formula

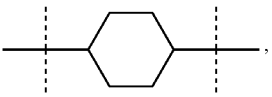

$L^2$ stands for a group of the formula $*-CR^{6A}R^{6B}-(CR^{7A}R^{7B})_q-$ or $*-CR^{6A}R^{6B}-CR^{7A}R^{7B}-O-$,
  wherein
  * means the binding site with the N atom of the amide group,
  q means the number 0, 1 or 2,
  $R^{6A}$ means hydrogen or $(C_1-C_4)$ alkyl,
  $R^{6B}$ means hydrogen, $(C_1-C_4)$ alkyl, trifluoromethyl, $(C_3-C_6)$ cycloalkyl or phenyl, which can be up to doubly, similarly or differently substituted with halogen, $(C_1-C_4)$ alkyl and/or trifluoromethyl, or a residue of the formula $-C(=O)-OR^{16}$ or $-C(=O)-NR^{17}R^{18}$, wherein
    $R^{16}$, $R^{17}$ and $R^{18}$ mutually independently represent hydrogen, $(C_1-C_4)$ alkyl or $(C_3-C_6)$ cycloalkyl
    or
    $R^{17}$ and $R^{18}$ together with the nitrogen atom to which they are bound form a 4 to 6-membered heterocycle, which can contain a further hetero atom from the range N, O and S and be up to doubly, similarly or differently, substituted with $(C_1-C_4)$ alkyl, hydroxy and/or $(C_1-C_4)$ alkoxy,
or
$R^{6A}$ and $R^{6B}$ are linked to one another and together form a $-(CH_2)_r$ bridge, wherein
  r means the number 2, 3, 4 or 5
  and one $CH_2$ group of the bridge can be exchanged for $-O-$, $-S-$ or $-N-R^{19}$, wherein
    $R^{19}$ represents hydrogen or $(C_1-C_4)$ alkyl,
$R^{7A}$ means hydrogen, fluorine, $(C_1-C_4)$ alkyl or $(C_1-C_4)$ alkoxy,
$R^{7B}$ means hydrogen, fluorine, $(C_1-C_4)$ alkyl, hydroxy-$(C_1-C_4)$ alkyl or a residue of the formula $-OR^{20}$, $-NR^{21}R^{22}$, $-C(=O)-OR^{23}$ or $-C(=O)-NR^{24}R^{25}$, wherein
  $R^{20}$, $R^{21}$, $R^{22}$, $R^{23}$, $R^{24}$ and $R^{25}$ mutually independently represent hydrogen, $(C_1-C_4)$ alkyl or $(C_3-C_6)$ cycloalkyl
  or
  $R^{21}$ and $R^{22}$ and also $R^{24}$ and $R^{25}$ respectively in pairs together with the nitrogen atom to which they are bound form a 4 to 6-membered heterocycle, which can contain a further hetero atom from the range N, O and S and be up to doubly, similarly or differently, substituted with $(C_1-C_4)$ alkyl, hydroxy and/or $(C_1-C_4)$ alkoxy,
or
$R^{7A}$ and $R^{7B}$ together form an oxo group
or
$R^{7A}$ and $R^{7B}$ are linked to one another and together form a $-(CH_2)_s$ bridge, wherein
  s means the number 2, 3, 4 or 5
  and one $CH_2$ group of the bridge can be exchanged for $-O-$, $-S-$ or $-N-R^{26}$, wherein
    $R^{26}$ represents hydrogen or $(C_1-C_4)$ alkyl,
  where, in the event that the group $-CR^{7A}R^{7B}-$ occurs several times, the individual meanings of $R^{7A}$ and $R^{7B}$ can in each case be the same or different,
or
$L^2$ stands for a group of the formula

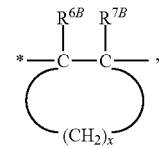

wherein
  * means the binding site with the N atom of the amide group,
  x means the number 1, 2, 3 or 4,
    where one $CH_2$ group of the ring can be exchanged for $-O-$, $-S-$ or $-N-R^{27}$, wherein
      $R^{27}$ represents hydrogen or $(C_1-C_4)$ alkyl,
  and
  $R^{6B}$ and $R^{7B}$ each have the aforesaid meanings,
$R^3$ stands for phenyl, naphthyl or 5 to 10-membered heteroaryl with up to three hetero atoms from the range N, O and/or S, which can each be singly to triply, similarly or differently, substituted with residues selected from the range halogen, cyano, nitro, $(C_1-C_4)$ alkyl, trifluoromethyl, hydroxy, $(C_1-C_4)$ alkoxy, trifluoromethoxy, $(C_1-C_4)$ alkylthio, $(C_1-C_4)$ alkylsulfinyl, $(C_1-C_4)$ alkylsulphonyl, di-$(C_1-C_4)$ alkylamino and phenyl, wherein the last-named phenyl residue can itself be up to doubly, similarly or differently, substituted with halogen, cyano, nitro, $(C_1-C_4)$ alkyl, $(C_1-C_4)$ alkoxy, trifluoromethyl and/or trifluoromethoxy, or the grouping $L^2-R^3$ together forms a group of the formula

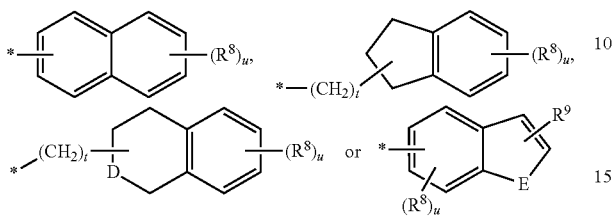

wherein

* means the binding site with the N atom of the amide group,

D means $CH_2$ or O,

E means NH, N—$CH_3$, O or S, t means the number 0 or 1, $R^8$ means a substituent selected from the range halogen, cyano, nitro, $(C_1-C_4)$ alkyl, $(C_1-C_4)$ alkoxy, trifluoromethyl and trifluoromethoxy, u means the number 0, 1 or 2, where, in the event that the substituent $R^8$ occurs several times, its meanings can be the same or different, and $R^9$ means hydrogen or $(C_1-C_4)$ alkyl, and salts thereof.

2. The compound of the formula (I) according to claim 1, in which

A stands for N or C—$R^4$, wherein $R^4$ means hydrogen or $(C_1-C_4)$ alkyl, $R^1$ stands for $(C_1-C_6)$ alkyl, which can be substituted with hydroxy, $(C_1-C_6)$ alkoxy, $(C_3-C_7)$ cycloalkyl or phenyl, or for $(C_3-C_7)$ cycloalkyl, wherein the said cycloalkyl residues can themselves be up to doubly, similarly or differently, substituted with $(C_1-C_4)$ alkyl, $(C_1-C_4)$ alkoxy, hydroxy, amino and/or oxo and the phenyl residue up to triply, similarly or differently, with halogen, cyano, nitro, $(C_1-C_4)$ alkyl, $(C_1-C_4)$ alkoxy, trifluoromethyl and/or trifluoromethoxy, $R^2$ stands for phenyl, naphthyl, thienyl, benzothienyl, furyl or benzofuryl, which can each be substituted up to triply, similarly or differently, with halogen, cyano, nitro, $(C_1-C_4)$ alkyl, $(C_1-C_4)$ alkoxy, trifluoromethyl, trifluoromethoxy and/or phenyl, wherein the last-named phenyl residue can itself be up to doubly, similarly or differently, substituted with halogen, cyano, nitro, $(C_1-C_4)$ alkyl, $(C_1-C_4)$ alkoxy, trifluoromethyl and/or trifluoromethoxy, $L^1$ stands for a group of the formula —$(CR^{5A}R^{5B})_m$—, wherein m means the number 1, 2 or 3 and $R^{5A}$ and $R^{5B}$ mutually independently mean hydrogen or $(C_1-C_4)$ alkyl or two residues $R^{5A}$ and $R^{5B}$ bound to the same carbon atom are linked to one another and together form a —$(CH_2)_n$ bridge, wherein n means the number 2, 3, 4 or 5, or, in the event that m stands for the number 2 or 3, two residues bound to adjacent (1,2- or 2,3-) or non-adjacent (1,3-) carbon atoms $R^{5A}$ and/or $R^{5B}$ are linked to one another and together form a —$(CH_2)_p$ bridge, wherein p means the number 1, 2, 3 or 4, where, in the event that the group —$CR^{5A}R^{5B}$— occurs several times, the individual meanings of $R^{5A}$ and $R^{5B}$ can in each case be the same or different, or $L^1$ stands for a group of the formula

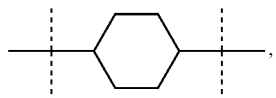

$L^2$ stands for a group of the formula *—$CR^{6A}R^{6B}$—$(CR^{7A}R^{7B})_q$— or *—$CR^{6A}R^{6B}$—$CR^{7A}R^{7B}$—O—, wherein

* means the binding site with the N atom of the amide group, q means the number 0, 1 or 2, $R^{6A}$ means hydrogen or $(C_1-C_4)$ alkyl, $R^{6B}$ means hydrogen, $(C_1-C_4)$ alkyl, trifluoromethyl, $(C_3-C_6)$ cycloalkyl or phenyl, which can be up to doubly, similarly or differently, substituted with halogen, $(C_1-C_4)$ alkyl and/or trifluoromethyl or $R^{6A}$ and $R^{6B}$ are linked to one another and together form a —$(CH_2)_r$ bridge, wherein r means the number 2, 3, 4 or 5, and $R^{7A}$ and $R^{7B}$ mutually independently mean hydrogen or $(C_1-C_4)$ alkyl, where, in the event that the group —$CR^{7A}R^{7B}$— occurs several times, the individual meanings of $R^{7A}$ and $R^{7B}$ can in each case be the same or different, $R^3$ stands for phenyl, naphthyl or 5 to 10-membered heteroaryl with up to three hetero atoms from the range N, O and/or S, which can each be substituted up to triply, similarly or differently, with halogen, cyano, nitro, $(C_1-C_4)$ alkyl, $(C_1-C_4)$ alkoxy, trifluoromethyl, trifluoromethoxy, di-$(C_1-C_4)$ alkylamino and/or phenyl, wherein the last-named phenyl residue can itself be up to doubly, similarly or differently, substituted with halogen, cyano, nitro, $(C_1-C_4)$ alkyl, $(C_1-C_4)$ alkoxy, trifluoromethyl and/or trifluoromethoxy, or the grouping $L^2-R^3$ together forms a group of the formula

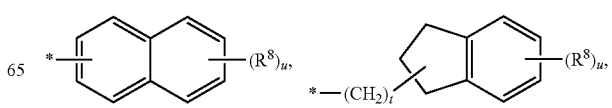

-continued

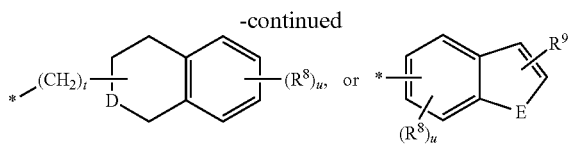

wherein
* means the binding site with the N atom of the amide group,
D means CH$_2$ or O,
E means NH, N—CH$_3$, O or S,
t means the number 0 or 1,
R$^8$ means a substituent selected from the range halogen, cyano, nitro, (C$_1$-C$_4$) alkyl, (C$_1$-C$_4$) alkoxy, trifluoromethyl and trifluoromethoxy,
u means the number 0, 1 or 2,
where, in the event that the substituent R$^8$ occurs several times, its meanings can be the same or different,
and
R$^9$ means hydrogen or (C$_1$-C$_4$) alkyl,
and salts thereof.

3. The compound of the formula (I) according to claim 1, in which
A stands for N or C—R$^4$, wherein
R$^4$ means hydrogen or (C$_1$-C$_4$) alkyl,
R$^1$ stands for (C$_1$-C$_6$) alkyl, which can be singly to triply, similarly or differently, substituted with residues selected from the range fluorine, chlorine, cyano, oxo, trifluoromethyl, (C$_3$-C$_6$) cycloalkyl, phenyl, —OR$^{10}$, —NR$^{11}$R$^{12}$, —C(=O)—OR$^{13}$ and —C(=O)—NR$^{14}$R$^{15}$, wherein
(i) (C$_3$-C$_6$) cycloalkyl can be up to doubly, similarly or differently, substituted with (C$_1$-C$_4$) alkyl, oxo, hydroxy, (C$_1$-C$_4$) alkoxy and/or amino,
(ii) phenyl can be up to triply, similarly or differently, substituted with residues selected from the range fluorine, chlorine, cyano, (C$_1$-C$_4$) alkyl, trifluoro-methyl, hydroxy, hydroxymethyl, (C$_1$-C$_4$) alkoxy, trifluoromethoxy, (C$_1$-C$_4$) alkoxymethyl, hydroxycarbonyl, (C$_1$-C$_4$) alkoxycarbonyl, aminocarbonyl, mono-(C$_1$-C$_4$) alkylaminocarbonyl and di-(C$_1$-C$_4$) alkylaminocarbonyl,
(iii) R$^{10}$, R$^{11}$, R$^{12}$, R$^{13}$, R$^{14}$ and R$^{15}$ mutually independently on each single occurrence mean hydrogen, (C$_1$-C$_4$) alkyl or (C$_3$-C$_6$) cycloalkyl, wherein
(C$_1$-C$_4$) alkyl can itself be up to doubly, similarly or differently, substituted with amino, hydroxy, (C$_1$-C$_4$) alkoxy, hydroxycarbonyl and/or (C$_1$-C$_4$) alkoxycarbonyl
and
(C$_3$-C$_6$) cycloalkyl can itself be up to doubly, similarly or differently, substituted with (C$_1$-C$_4$) alkyl, oxo, hydroxy, (C$_1$-C$_4$) alkoxy and/or amino,
and/or
(iv) R$^{11}$ and R$^{12}$ and also R$^{14}$ and R$^{15}$ respectively in pairs together with the nitrogen atom to which they are bound form a 4 to 6-membered heterocycle, which can contain a further hetero atom from the range N and O and be up to doubly, similarly or differently, substituted with (C$_1$-C$_4$) alkyl, oxo, hydroxy, (C$_1$-C$_4$) alkoxy and/or amino,
or
R$^1$ stands for (C$_2$-C$_6$) alkenyl, which can be substituted with hydroxy, (C$_1$-C$_4$) alkoxy, hydroxycarbonyl or (C$_1$-C$_4$) alkoxycarbonyl,
or
for (C$_3$-C$_6$) cycloalkyl, which can be up to doubly, similarly or differently, substituted with (C$_1$-C$_4$) alkyl, (C$_1$-C$_4$) alkoxy, hydroxy, amino and/or oxo,
R$^2$ stands for phenyl or thienyl, which can be singly to triply, similarly or differently, substituted with residues selected from the range fluorine, chlorine, cyano, (C$_1$-C$_4$) alkyl, trifluoromethyl, hydroxy, (C$_1$-C$_4$) alkoxy, trifluoromethoxy and phenyl,
wherein the last-named phenyl residue can itself be up to doubly, similarly or differently, substituted with residues selected from the range fluorine, chlorine, cyano, (C$_1$-C$_4$) alkyl, trifluoromethyl, (C$_1$-C$_4$) alkoxy and trifluoromethoxy,
L$^1$ stands for a group of the formula —CR$^{5A}$R$^{5B}$—, wherein
R$^{5A}$ and R$^{5B}$ mutually independently mean hydrogen or (C$_1$-C$_4$) alkyl,
L$^2$ stands for a group of the formula *—CR$^{6A}$R$^{6B}$—(CR$^{7A}$R$^{7B}$)$_q$—, wherein
* means the binding site with the N atom of the amide group,
q means the number 0 or 1,
R$^{6A}$ means hydrogen or (C$_1$-C$_4$) alkyl,
R$^{6B}$ means hydrogen, (C$_1$-C$_4$) alkyl, trifluoromethyl, (C$_3$-C$_6$) cycloalkyl or phenyl, which can be up to doubly, similarly or differently, substituted with fluorine, chlorine, (C$_1$-C$_4$) alkyl and/or trifluoromethyl, or a residue of the formula —C(=O)—OR$^{16}$ or —C(=O)—NR$^{17}$R$^{18}$, wherein
R$^{16}$, R$^{17}$ and R$^{18}$ mutually independently represent hydrogen, (C$_1$-C$_4$) alkyl or (C$_3$-C$_6$) cycloalkyl
or
R$^{17}$ and R$^{18}$ together with the nitrogen atom to which they are bound form a 4 to 6-membered heterocycle, which can contain a further hetero atom from the range N and O and be up to doubly, similarly or differently, substituted with (C$_1$-C$_4$) alkyl, hydroxy and/or (C$_1$-C$_4$) alkoxy,
or
R$^{6A}$ and R$^{6B}$ are linked to one another and together form a —(CH$_2$)$_r$ bridge, wherein
r means the number 2, 3, 4 or 5
and one CH$_2$ group of the bridge can be exchanged for —O—,
R$^{7A}$ means hydrogen, fluorine or (C$_1$-C$_4$),
R$^{7B}$ means hydrogen, fluorine, (C$_1$-C$_4$) alkyl, hydroxy-(C$_1$-C$_4$) alkyl or a residue of the formula —OR$^{20}$, —NR$^{21}$R$^{22}$, —C(=O)—OR$^{23}$ or —C(=O)—NR$^{24}$R$^{25}$, wherein
R$^{20}$, R$^{21}$, R$^{22}$, R$^{23}$, R$^{24}$ and R$^{25}$ mutually independently represent hydrogen, (C$_1$-C$_4$) alkyl or (C$_3$-C$_6$) cycloalkyl
or
R$^{21}$ and R$^{22}$ and also R$^{24}$ and R$^{25}$ respectively in pairs together with the nitrogen atom to which they are bound form a 4 to 6-membered heterocycle, which can contain a further hetero atom from the range N and O and be up to doubly, similarly or differently, substituted with (C$_1$-C$_4$) alkyl, hydroxy and/or (C$_1$-C$_4$) alkoxy,
or
R$^{7A}$ and R$^{7B}$ together form an oxo group
or
R$^{7A}$ and R$^{7B}$ are linked to one another and together form a —(CH$_2$)$_s$ bridge, wherein s means the number 2, 3, 4 or 5
and one CH$_2$ group of the bridge can be exchanged for —O—,
or
L$^2$ stands for a group of the formula

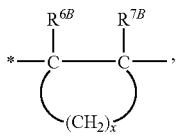

wherein
* means the binding site with the N atom of the amide group,
x means the number 1, 2, 3 or 4,
where one CH$_2$ group of the ring can be exchanged for —O—,
and
R$^{6B}$ and R$^{7B}$ each have the aforesaid meanings,
and
R$^3$ stands for phenyl, naphthyl or 5 to 10-membered heteroaryl with up to two hetero atoms from the range N, O and/or S, which can each be singly to triply, similarly or differently, substituted with residues selected from the range fluorine, chlorine, cyano, (C$_1$-C$_4$) alkyl, trifluoromethyl, hydroxy, (C$_1$-C$_4$) alkoxy, trifluoromethoxy, (C$_1$-C$_4$) alkylthio, (C$_1$-C$_4$) alkylsulphonyl, di-(C$_1$-C$_4$) alkylamino and phenyl,
wherein the last-named phenyl residue can itself be up to doubly, similarly or differently, substituted with fluorine, chlorine, cyano, (C$_1$-C$_4$) alkyl, (C$_1$-C$_4$) alkoxy, trifluoromethyl and/or trifluoromethoxy,
and salts thereof.

4. The compound of the formula (I) according to claim 1, in which
A stands for N or C—R$^4$, wherein
R$^4$ means hydrogen or (C$_1$-C$_4$) alkyl,
R$^1$ stands for (C$_1$-C$_6$) alkyl, which can be substituted with hydroxy, (C$_1$-C$_4$) alkoxy, (C$_3$-C$_6$) cycloalkyl or phenyl, or for (C$_3$-C$_6$) cycloalkyl,
wherein the said cycloalkyl residues can themselves be up to doubly, similarly or differently, substituted with (C$_1$-C$_4$) alkyl, (C$_1$-C$_4$) alkoxy, hydroxy and/or amino
and
the phenyl residue can be up to doubly, similarly or differently, substituted with halogen, cyano, nitro, (C$_1$-C$_4$) alkyl, (C$_1$-C$_4$) alkoxy, trifluoromethyl and/or trifluoromethoxy,
R$^2$ stands for phenyl, naphthyl, thienyl or benzothienyl, which can each be up to triply, similarly or differently, substituted with halogen, cyano, nitro, (C$_1$-C$_4$) alkyl, (C$_1$-C$_4$) alkoxy, trifluoromethyl, trifluoromethoxy and/or phenyl,
wherein the last-named phenyl residue can itself be up to doubly, similarly or differently, substituted with halogen, cyano, nitro, (C$_1$-C$_4$) alkyl, (C$_1$-C$_4$) alkoxy, trifluoromethyl and/or trifluoromethoxy,
L$^1$ stands for a group of the formula —(CR$^{5A}$R$^{5B}$)$_m$—, wherein
m means the number 1, 2 or 3
and
R$^{5A}$ and R$^{5B}$ mutually independently mean hydrogen or methyl or
two residues R$^{5A}$ and R$^{5B}$ bound to the same carbon atom are linked to one another and together form a —(CH$_2$)$_n$ bridge, wherein
n means the number 2, 3, 4 or 5,
or, in the event that m stands for the number 2 or 3,
two residues bound to adjacent (1,2- or 2,3-) or non-adjacent (1,3-) carbon atoms R$^{5A}$ and/or R$^{5B}$ are linked to one another and together form a —(CH$_2$)$_p$ bridge, wherein
p means the number 1, 2, 3 or 4,
where, in the event that the group —CR$^{5A}$R$^{5B}$— occurs several times, the individual meanings of R$^{5A}$ and R$^{5B}$ can in each case be the same or different,
or
L$^1$ stands for a group of the formula

L$^2$ stands for a group of the formula *—CR$^{6A}$R$^{6B}$—(CH$_2$)$_q$—, wherein
* means the binding site with the N atom of the amide group,
q means the number 0 or 1,
R$^{6A}$ means hydrogen or methyl,
R$^{6B}$ means hydrogen, (C$_1$-C$_4$) alkyl, trifluoromethyl or (C$_3$-C$_6$) cycloalkyl
or
R$^{6A}$ and R$^{6B}$ are linked to one another and together form a —(CH$_2$)$_r$ bridge, wherein
r means the number 2, 3, 4 or 5,
and
R$^3$ stands for phenyl, naphthyl or 5 to 10-membered heteroaryl with up to two hetero atoms from the range N, O and/or S, which can each be substituted up to triply, similarly or differently, with halogen, cyano, nitro, (C$_1$-C$_4$) alkyl, (C$_1$-C$_4$) alkoxy, trifluoromethyl, trifluoromethoxy and/or phenyl,
wherein the last-named phenyl residue can itself be up to doubly, similarly or differently, substituted with halogen, cyano, nitro, (C$_1$-C$_4$) alkyl, (C$_1$-C$_4$) alkoxy, trifluoromethyl and/or trifluoromethoxy,
and salts thereof.

5. The compound of the formula (I) according to claim 1, in which
A stands for N or C—R$^4$, wherein
R$^4$ means hydrogen or methyl,
R$^1$ stands for (C$_1$-C$_6$) alkyl, which can be singly or doubly, similarly or differently, substituted with residues selected from the range fluorine, oxo, trifluoromethyl, (C$_3$-C$_6$) cycloalkyl, phenyl, —OR$^{10}$, —C(=O)—OR$^{13}$ and —C(=O)—NR$^{14}$R$^{15}$, wherein
(i) (C$_3$-C$_6$) cycloalkyl can be up to doubly, similarly or differently, substituted with (C$_1$-C$_4$) alkyl, hydroxy and/or (C$_1$-C$_4$) alkoxy,
(ii) phenyl can be up to doubly, similarly or differently, substituted with residues selected from the range fluorine, chlorine, cyano, (C$_1$-C$_4$) alkyl, trifluoromethyl, hydroxymethyl, (C$_1$-C$_4$) alkoxy, hydroxycarbonyl, (C$_1$-C$_4$) alkoxycarbonyl, aminocarbonyl, mono-(C$_1$-C$_4$) alkylaminocarbonyl and di-(C$_1$-C$_4$) alkylaminocarbonyl, and
(iii) $R^{10}$, $R^{13}$, $R^{14}$ and $R^{15}$ mutually independently on each single occurrence mean hydrogen, $(C_1-C_4)$ alkyl or $(C_3-C_6)$ cycloalkyl, wherein
$(C_1-C_4)$ alkyl can itself be up to doubly, similarly or differently, substituted with hydroxy, $(C_1-C_4)$ alkoxy, hydroxycarbonyl and/or $(C_1-C_4)$ alkoxycarbonyl
and
$(C_3-C_6)$ cycloalkyl can itself be up to doubly, similarly or differently, substituted with $(C_1-C_4)$ alkyl, hydroxy and/or $(C_1-C_4)$ alkoxy,
or
$R^1$ stands for $(C_2-C_6)$ alkenyl, which can be substituted with hydroxycarbonyl or $(C_1-C_4)$ alkoxycarbonyl,
or
for $(C_3-C_6)$ cycloalkyl, which can be up to doubly, similarly or differently, substituted with $(C_1-C_4)$ alkyl, $(C_1-C_4)$ alkoxy and/or hydroxy,
$R^2$ stands for phenyl or thienyl, which can be singly to doubly, similarly or differently, substituted with residues selected from the range fluorine, chlorine, $(C_1-C_4)$ alkyl, trifluoromethyl, $(C_1-C_4)$ alkoxy and trifluoromethoxy,
$L^1$ stands for a group of the formula $—CR^{5A}R^{5B}—$, wherein
$R^{5A}$ and $R^{5B}$ mutually independently mean hydrogen or methyl,
$L^2$ stands for a group of the formula $*—CR^{6A}R^{6B}—(CR^{7A}R^{7B})_q—$, wherein
* means the binding site with the N atom of the amide group,
q means the number 0 or 1,
$R^{6A}$ means hydrogen or methyl,
$R^{6B}$ means hydrogen, methyl, trifluoromethyl or a residue of the formula $—C(=O)—OR^{16}$ or $—C(=O)—NR^{17}R^{18}$, wherein
$R^{16}$, $R^{17}$ and $R^{18}$ mutually independently represent hydrogen, $(C_1-C_4)$ alkyl or $(C_3-C_6)$ cycloalkyl
or
$R^{17}$ and $R^{18}$ together with the nitrogen atom to which they are bound form a 4 to 6-membered heterocycle, which can contain an O atom as a further hetero atom,
or
$R^{6A}$ and $R^{6B}$ are linked to one another and together form a $—(CH_2)_r$ bridge, wherein
r means the number 2, 3, 4 or 5
and one $CH_2$ group of the bridge can be exchanged for —O—,
$R^{7A}$ means hydrogen, fluorine or methyl,
$R^{7B}$ means hydrogen, fluorine, methyl or a residue of the formula $—C(=O)—OR^{23}$ or $—C(=O)—NR^{24}R^{25}$, wherein
$R^{23}$, $R^{24}$ and $R^{25}$ mutually independently represent hydrogen, $(C_1-C_4)$ alkyl or $(C_3-C_6)$ cycloalkyl
or
$R^{24}$ and $R^{25}$ together with the nitrogen atom to which they are bound form a 4 to 6-membered heterocycle, which can contain an O atom as a further hetero atom,
or
$R^{7A}$ and $R^{7B}$ together form an oxo group
or
$R^{7A}$ and $R^{7B}$ are linked to one another and together form a $—(CH_2)_s$ bridge, wherein s means the number 2, 3, 4 or 5
and one $CH_2$ group of the bridge can be exchanged for —O—,
or
$L^2$ stands for a group of the formula

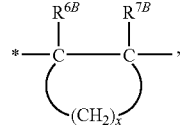

wherein
* means the binding site with the N atom of the amide group,
x means the number 1, 2, 3 or 4,
where one $CH_2$ group of the ring can be exchanged for —O—,
and
$R^{6B}$ and $R^{7B}$ each have the aforesaid meanings,
and
$R^3$ stands for phenyl, naphthyl, pyridyl, quinolinyl or isoquinolinyl, which can each be singly to doubly, similarly or differently, substituted with residues selected from the range fluorine, chlorine, cyano, $(C_1-C_4)$ alkyl, trifluoromethyl, $(C_1-C_4)$ alkoxy, trifluoromethoxy, $(C_1-C_4)$ alkylthio and phenyl,
wherein the last-named phenyl residue can itself be up to doubly, similarly or differently, substituted with fluorine, chlorine, cyano, $(C_1-C_4)$ alkyl, $(C_1-C_4)$ alkoxy, trifluoromethyl and/or trifluoromethoxy,
and salts thereof.

6. The compound of the formula (I) according to one of claim 1, in which
A stands for N or CH,
$R^1$ stands for $(C_1-C_6)$ alkyl, which can be singly or doubly, similarly or differently, substituted with residues selected from the range fluorine, oxo, hydroxy, $(C_1-C_4)$ alkoxy, trifluoromethyl, $(C_3-C_6)$ cycloalkyl and phenyl, where phenyl can itself be up to doubly, similarly or differently, substituted with residues selected from the range fluorine, chlorine, cyano, $(C_1-C_4)$ alkyl, trifluoromethyl, hydroxymethyl, $(C_1-C_4)$ alkoxy, trifluoromethoxy, hydroxycarbonyl, aminocarbonyl and di-$(C_1-C_4)$ alkylaminocarbonyl,
or
$R^1$ stands for $(C_2-C_4)$ alkenyl or $(C_3-C_6)$ cycloalkyl,
$R^2$ stands for phenyl or thienyl, which can be singly to doubly, similarly or differently, substituted with residues selected from the range fluorine, chlorine, bromine, $(C_1-C_4)$ alkyl and $(C_1-C_4)$ alkoxy,
$L^1$ stands for $—CH_2—$, $—CH(CH_3)—$ or $—CH_2CH_2—$,
$L^2$ stands for a group of the formula $*—CR^{6A}R^{6B}—(CR^{7A}R^{7B})_q—$, wherein
* means the binding site with the N atom of the amide group,
q means the number 0 or 1,
$R^{6A}$ means hydrogen or methyl,
$R^{6B}$ means hydrogen, methyl, trifluoromethyl or a residue of the formula $—C(=O)—NR^{17}R^{18}$, wherein
$R^{17}$ and $R^{18}$ mutually independently represent hydrogen, $(C_1-C_4)$ alkyl or $(C_3-C_6)$ cycloalkyl
or
$R^{17}$ and $R^{18}$ together with the nitrogen atom to which they are bound form a 4 to 6-membered heterocycle, which can contain an O atom as a further hetero atom, or
$R^{6A}$ and $R^{6B}$ are linked to one another and together form a —$(CH_2)_r$— bridge, wherein
r means the number 2, 3, 4 or 5
and one $CH_2$ group of the bridge can be exchanged for —O—,
$R^{7A}$ means hydrogen, fluorine or methyl,
$R^{7B}$ means hydrogen, fluorine, methyl or a residue of the formula —C(=O)—$OR^{23}$ or —C(=O)—$NR^{24}R^{25}$, wherein
$R^{23}$, $R^{24}$ and $R^{25}$ mutually independently represent hydrogen or ($C_1$-$C_4$) alkyl
or
$R^{24}$ and $R^{25}$ together with the nitrogen atom to which they are bound form a 4 to 6-membered heterocycle, which can contain an O atom as a further hetero atom,
or
$R^{7A}$ and $R^{7B}$ together form an oxo group
or
$R^{7A}$ and $R^{7B}$ are linked to one another and together form a —$(CH_2)_s$— bridge, wherein
s means the number 2, 3, 4 or 5
and one $CH_2$ group of the bridge can be exchanged for —O—,
or
$L^2$ stands for a group of the formula

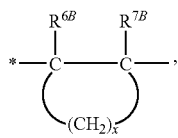

wherein
* means the binding site with the N atom of the amide group,
x means the number 1, 2, 3 or 4
and
$R^{6B}$ and $R^{7B}$ each have the aforesaid meanings,
and
$R^3$ stands for phenyl or pyridyl, which can be singly to doubly, similarly or differently, substituted with residues selected from the range fluorine, chlorine, ($C_1$-$C_4$) alkyl, trifluoromethyl, ($C_1$-$C_4$) alkoxy and trifluoromethoxy, or for naphthyl,
and salts thereof.

7. The compound of the formula (I) according to claim 1, in which
A stands for N or CH,
$R^1$ stands for ($C_1$-$C_6$) alkyl, which can be singly or doubly, similarly or differently, substituted with residues selected from the range fluorine, oxo, hydroxy, methoxy, ethoxy, trifluoromethyl, cyclopropyl and phenyl,
where phenyl can itself be up to doubly, similarly or differently, substituted with residues selected from the range fluorine, chlorine, cyano, methyl, hydroxymethyl, methoxy, hydroxycarbonyl, aminocarbonyl and dimethylaminocarbonyl,
or
$R^1$ stands for vinyl, allyl or cyclopropyl,
$R^2$ stands for phenyl or thienyl, which can be singly to doubly, similarly or differently, substituted with residues selected from the range fluorine, chlorine, methyl and methoxy $L^1$ stands for —$CH_2$—,
$L^2$ stands for a group of the formula *—$CR^{6A}R^{6B}$—$(CR^{7A}R^{7B})_q$—, wherein
* means the binding site with the N atom of the amide group,
q means the number 0 or 1,
$R^{6A}$ means hydrogen or methyl,
$R^{6B}$ means hydrogen, methyl, trifluoromethyl or a residue of the formula —C(=O)—$NR^{17}R^{18}$, wherein
$R^{17}$ and $R^{18}$ mutually independently represent hydrogen, methyl, ethyl or cyclopropyl
or
$R^{17}$ and $R^{18}$ together with the nitrogen atom to which they are bound form an azetidine, pyrrolidine, piperidine or morpholine ring,
or
$R^{6A}$ and $R^{6B}$ are linked together and together with the carbon atom to which they are bound form a group of the formula

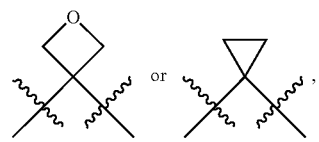

$R^{7A}$ means hydrogen, fluorine or methyl,
$R^{7B}$ means hydrogen, fluorine, methyl or a residue of the formula —C(=O)—$OR^{23}$ or —C(=O)—$NR^{24}R^{25}$, wherein
$R^{23}$, $R^{24}$ and $R^{25}$ mutually independently represent hydrogen, methyl or ethyl
or
$R^{24}$ and $R^{25}$ together with the nitrogen atom to which they are bound form an azetidine, pyrrolidine, piperidine or morpholine ring,
or
$R^{7A}$ and $R^{7B}$ together form an oxo group
or
$R^{7A}$ and $R^{7B}$ are linked to one another and together form a —$(CH_2)_s$— bridge, wherein
s means the number 2, 3, 4 or 5
and one $CH_2$ group of the bridge can be exchanged for —O—,
or
$L^2$ stands for a group of the formula

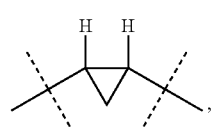

and
$R^3$ stands for phenyl, which can be singly or doubly, similarly or differently, substituted with fluorine, chlorine, trifluoromethyl and/or trifluoromethoxy, or for 1-naphthyl,
and salts thereof.

8. The compound of the formula (I) according to claim 1, in which

A stands for N or CH,

R¹ stands for ($C_1$-$C_4$) alkyl, 2-methoxyethyl, cyclopropyl, cyclohexylmethyl, benzyl or 1-phenethyl, where the phenyl ring in the said benzyl- and 1-phenethyl residues can be substituted with fluorine, chlorine, methyl, trifluoromethyl, methoxy or trifluoromethoxy, R² stands for phenyl or thienyl, which are each singly or doubly, similarly or differently, substituted with fluorine, chlorine, bromine, methyl and/or methoxy, L¹ stands for —$CH_2$—, —$CH_2CH_2$— or —$CH(CH_3)$—, L² stands for —$CH_2$—, —$CH(CH_3)$— or —$C(CH_3)_2$— and R³ stands for phenyl, which is singly or doubly, similarly or differently, substituted with fluorine, chlorine, trifluoromethyl and/or trifluoromethoxy, or for 1-naphthyl, and salts thereof.

9. A method of making compounds of the formula (I), as defined in claim 1, characterized in that

[A] a compound of the formula (II)

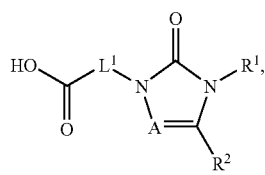

(II)

in which A, L¹, R¹ and R² each have the meanings stated in claims 1 to 8, is coupled with a compound of the formula (III)

$R^3$-$L^2$-$NH_2$     (III), in which L² and R³ have the meanings stated in claims 1 to 8, in an inert solvent with activation of the carboxylic acid function or

[B] a compound of the formula (IV)

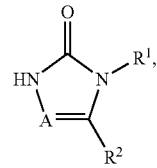

(IV)

in which A, R¹ and R² each have the meanings stated in claims 1 to 8, is reacted with a compound of the formula (V)

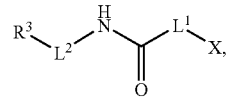

(V)

in which L¹, L² and R³ each have the meanings stated in claims 1 to 8 and

X stands for a leaving group, such as for example halogen, mesylate or tosylate, in an inert solvent in the presence of a base and the resulting compounds of the formula (I) are optionally converted into their solvates, salts and/or solvates of the salts with the appropriate (i) solvents and/or (ii) bases or acids.

10. A pharmaceutical composition comprising a compound of the formula (I) of claim 1, in combination with an inert, non-toxic, pharmaceutically suitable additive.

11. The pharmaceutical composition of claim 10, further comprising one or more further active substances selected from the group consisting of diuretics, angiotensin AII antagonists, ACE inhibitors, beta receptor blockers, mineralocorticoid receptor antagonists, organic nitrates, NO donors and substances with positive inotropic action.

* * * * *